US010246464B2

(12) United States Patent
Grembecka et al.

(10) Patent No.: US 10,246,464 B2
(45) Date of Patent: Apr. 2, 2019

(54) THIENOPYRIMIDINE AND THIENOPYRIDINE COMPOUNDS AND METHODS OF USE THEREOF

(71) Applicants: The Regents of the University of Michigan, Ann Arbor, MI (US); Kura Oncology, Inc, La Jolla, CA (US)

(72) Inventors: Jolanta Grembecka, Ann Arbor, MI (US); Tomasz Cierpicki, Ann Arbor, MI (US); Dmitry Borkin, Ann Arbor, MI (US); Jonathan Pollock, Ann Arbor, MI (US); Hongzhi Miao, Ann Arbor, MI (US); Duxin Sun, Ann Arbor, MI (US); Liansheng Li, La Jolla, CA (US); Tao Wu, La Jolla, CA (US); Jun Feng, La Jolla, CA (US); Pingda Ren, La Jolla, CA (US); Yi Liu, La Jolla, CA (US)

(73) Assignees: THE REGENTS OF THE UNIVERSITY OF MICHIGAN, Ann Arbor, MI (US); KURA ONCOLOGY, INC., La Jolla, CA (US)

( * ) Notice: Subject to any disclaimer, the term of this patent is extended or adjusted under 35 U.S.C. 154(b) by 0 days.

(21) Appl. No.: 15/509,989

(22) PCT Filed: Sep. 8, 2015

(86) PCT No.: PCT/US2015/048957
§ 371 (c)(1),
(2) Date: Mar. 9, 2017

(87) PCT Pub. No.: WO2016/040330
PCT Pub. Date: Mar. 17, 2016

(65) Prior Publication Data
US 2017/0247391 A1    Aug. 31, 2017

Related U.S. Application Data

(60) Provisional application No. 62/214,681, filed on Sep. 4, 2015, provisional application No. 62/171,124, filed on Jun. 4, 2015, provisional application No. 62/095,588, filed on Dec. 22, 2014, provisional application No. 62/048,036, filed on Sep. 9, 2014.

(51) Int. Cl.
*C07D 495/04* (2006.01)
*C07D 519/00* (2006.01)
*C07F 9/53* (2006.01)
*C07F 9/6558* (2006.01)

(52) U.S. Cl.
CPC ......... *C07D 495/04* (2013.01); *C07D 519/00* (2013.01); *C07F 9/5325* (2013.01); *C07F 9/65583* (2013.01)

(58) Field of Classification Search
None
See application file for complete search history.

(56) References Cited

U.S. PATENT DOCUMENTS

| 6,849,638 B2 | 2/2005 | Stolle et al. |
| 7,030,240 B2 | 4/2006 | Dhanoa et al. |
| 8,207,174 B2 | 6/2012 | Tasler et al. |
| 8,993,552 B2 | 3/2015 | Grembecka et al. |
| 9,216,993 B2 | 12/2015 | Grembecka et al. |
| 9,505,781 B2 | 11/2016 | Grembecka et al. |
| 9,505,782 B2 | 11/2016 | Grembecka et al. |
| 2003/0119829 A1 | 6/2003 | Stolle et al. |
| 2003/0153556 A1 | 8/2003 | Levy et al. |
| 2005/0123906 A1 | 6/2005 | Rana |
| 2005/0222175 A1 | 10/2005 | Dhanoa et al. |
| 2005/0222176 A1 | 10/2005 | Dhanoa et al. |
| 2006/0025406 A1 | 2/2006 | Zembower et al. |
| 2006/0281769 A1 | 12/2006 | Baumann et al. |
| 2006/0281771 A1 | 12/2006 | Baumann et al. |
| 2007/0078133 A1 | 4/2007 | Liu et al. |
| 2008/0249114 A1 | 10/2008 | Tasler et al. |
| 2008/0293699 A1 | 11/2008 | Reed et al. |
| 2009/0163545 A1 | 6/2009 | Goldfarb |
| 2009/0298772 A1 | 12/2009 | Thirman |
| 2010/0063047 A1 | 3/2010 | Borchardt et al. |
| 2011/0065690 A1 | 3/2011 | Grembecka et al. |
| 2012/0322742 A1 | 12/2012 | Thirman |
| 2014/0275070 A1 | 9/2014 | Grembecka et al. |
| 2014/0371239 A1 | 12/2014 | Grembecka et al. |
| 2016/0045504 A1 | 2/2016 | Grembecka et al. |
| 2016/0046647 A1 | 2/2016 | Grembecka et al. |
| 2017/0253611 A1 | 9/2017 | Grembecka et al. |
| 2018/0105531 A1 | 4/2018 | Grembecka et al. |

FOREIGN PATENT DOCUMENTS

| EP | 1382603 A1 | 1/2004 |
| JP | H10330377 A | 12/1998 |
| JP | 2013503906 A | 2/2013 |
| WO | WO-9965909 A1 | 12/1999 |
| WO | WO-02088138 A1 | 11/2002 |
| WO | WO-03022214 A2 | 3/2003 |
| WO | WO-2004030671 A2 | 4/2004 |
| WO | WO-2004030672 A1 | 4/2004 |
| WO | WO-2005020897 A2 | 3/2005 |
| WO | WO-2006135630 A1 | 12/2006 |
| WO | WO-2006135636 A2 | 12/2006 |

(Continued)

OTHER PUBLICATIONS

Agarwal et al. Menin molecular interactions: insights into normal functions and tumorigenesis. Horm Matab Res, 37(6), pp. 369-374 (2005).

(Continued)

*Primary Examiner* — Samantha L Shterengarts
(74) *Attorney, Agent, or Firm* — Casimir Jones SC; David W. Staple

(57) ABSTRACT

The present disclosure provides compounds and methods for inhibiting the interaction of menin with its upstream or downstream signaling molecules including but not limited to MLL1, MLL2 and MLL-fusion oncoproteins. Compounds of the disclosure may be used in methods for the treatment of a wide variety of cancers and other diseases associated with one or more of MLL1, MLL2, MLL fusion proteins, and menin.

20 Claims, 10 Drawing Sheets

Specification includes a Sequence Listing.

(56) References Cited

FOREIGN PATENT DOCUMENTS

| | | |
|---|---|---|
| WO | WO-2007026024 A2 | 3/2007 |
| WO | WO-2007115822 A1 | 10/2007 |
| WO | WO-2008070303 A2 | 6/2008 |
| WO | WO-2008090140 A1 | 7/2008 |
| WO | WO-2008099019 A1 | 8/2008 |
| WO | WO-2008107320 A1 | 9/2008 |
| WO | WO-2008114275 A2 | 9/2008 |
| WO | WO-2009017838 A2 | 2/2009 |
| WO | WO-2009064388 A2 | 5/2009 |
| WO | WO-2010030757 A2 | 3/2010 |
| WO | WO-2011003418 A1 | 1/2011 |
| WO | WO-2011029054 A1 | 3/2011 |
| WO | WO-2013024291 A2 | 2/2013 |
| WO | WO-2013072694 A1 | 5/2013 |
| WO | WO-2014164543 A1 | 10/2014 |
| WO | WO-2015154039 A2 | 10/2015 |
| WO | WO-2015191701 A1 | 12/2015 |
| WO | WO-2016040330 A1 | 3/2016 |
| WO | WO-2016195776 A1 | 12/2016 |
| WO | WO-2016197027 A1 | 12/2016 |
| WO | WO-2017112768 A1 | 6/2017 |
| WO | WO-2017132398 A1 | 8/2017 |
| WO | WO-2017161002 A1 | 9/2017 |
| WO | WO-2017161028 A1 | 9/2017 |
| WO | WO-2017192543 A1 | 11/2017 |
| WO | WO-2017207387 A1 | 12/2017 |
| WO | WO-2017214367 A1 | 12/2017 |
| WO | WO-2018024602 A1 | 2/2018 |
| WO | WO-2018050684 A1 | 3/2018 |
| WO | WO-2018050686 A1 | 3/2018 |
| WO | WO-2018053267 A1 | 3/2018 |

OTHER PUBLICATIONS

Arkin et al. Small-molecule inhibitors of protein-protein interactions: progressing toward the reality. Chem Biol. 21(9):1102-1114 (2014).

Bhaskar et al. Synthesis, Antimicrobial and Antihyperlipidemic Activities of Some 4-Substituted-5,6,7,8-tetrhydrol. Asian J Chemistry 2007, 19(7):5187-5194.

Borkin et al. Pharmacologic inhibition of the Menin-MLL interaction blocks progression of MLL leukemia in vivo. Cancer Cell. Apr. 13, 2015;27(4):589-602. doi: 10.1016/j.ccell.2015.02.016. Epub Mar. 26, 2015.

Borkin et al. Property Focused Structure-Based Optimization of Small Molecule Inhibitors of the Protein-Protein Interaction between Menin and Mixed Lineage Leukemia (MLL). J Med Chem. Feb. 11, 2016;59(3):892-913.

Chen et al. The tumor suppressor menin regulates hematopoiesis and myeloid transformation by influencing Hox gene expression. Proc Natl Acad Sci USA, 103(4), pp. 1018-1023 (2006).

Cox et al. Chromosomal aberration of the 11q23 locus in acute leukemia and frequency of MLL gene translocation: results in 378 adult patients. Am J Clin Pathol, 122(2), pp. 298-306 (2004).

Eguchi et al. The role of the MLL gene in infant leukemia. Int J Hematol, 78(5), pp. 390-401 (2003).

Grembecka et al. Menin-MLL inhibitors reverse oncogenic activity of MLL fusion proteins in leukemia. Nature Chemical Biology. 2012 No. 8. pp. 277-284.

Kim et al. Chemical Biology Investigation of Cell Death Pathways Activated by Endoplasmic Reticulum Stress Cytoprotective Modulators of ASK1. J Biological Chemistry Jan. 2009, 284(3):1593-1603.

Marx, Stephen J. Molecular genetics of multiple endocrine neoplasia types 1 and 2. Nat Rev Cancer, 5(5), pp. 367-75 (2005).

Mayer et al. Group epitope mapping by saturation transfer difference NMR to identify segments of a ligand in direct contact with a protein receptor. J Am Chem Soc, 123(25), pp. 6108-6117 (2001).

Mosmann et al. Rapid colorimetric assay for cellular growth and survival: application to proliferation and cytotoxicity assays. J Immunol Methods, 65, (1-2), pp. 55-63 (1983).

Nairn, J.G. Solutions, Emulsions, Suspensions and Extracts. Chapter 83 of Remington's Pharmaceutical Sciences. 18th Ed. Gennaro, Alfonso R. Mack Publishing Company, Pennsylvania. 1990. 35 pages.

Pollock et al. Rational Design of Orthogonal Multipolar Interactions with Fluorine in Protein-Ligand Complexes. J Med Chem. Sep. 24, 2015;58(18):7465-74.

PubChem SID 25433807, retrieved from https://pubchem.ncbi.nlm.nih.gov/substance/25433807, deposit date Jul. 30, 2007, 5 pages.

Pubchem CID 88912571. Create Date: Feb. 13, 2015. Date Accessed: Jul. 10, 2017; p. 4, compound listed.

Pubchem CID F1174-09147, retrieved from http://pubchem.ncbi.nlm.nih.govisummary/summary.cgi?cid=711090, 2007, 13 pages.

Pubchem CID SMR00018765, retrieved from http://pubchem.ncbi.nlm.nih.gov/summary/summary.cgi?cid=1323703, 2007, 16 pages.

Sharma et al. Synthesis of Thienopyrimidines and their Antipsychotic Activity. E Journal of Chemistry. 2010. 7(2):655-664.

Shi et al. Structural insights into inhibition of the bivalent menin-MLL interaction by small molecules in leukemia. Blood. Nov. 29, 2012;120(23):4461-9.

Slany, Robert K. The molecular biology of mixed lineage leukemia. Haematologica. 94(7), pp. 984-993 (2009).

Slany, Robert K. When epigenetics kills: MLL fusion proteins in leukemia. Hematol Oncol, 23(1), pp. 1-9 (2005).

Sorensen et al. Molecular rearrangements of the MLL gene are present in most cases of infant acute myeloid leukemia and are strongly correlated with monocytic or myelomonocytic phenotypes. J Clin Invest, 93(1), pp. 429-437 (1994).

Yokoyama et al. The menin tumor suppressor protein is an essential oncogenic cofactor for MLL-associated leukemogenesis. Cell, 123(2), pp. 207-218 (2005).

International Search Report and Written Opinion dated Dec. 8, 2015 for International PCT Patent Application No. PCT/US2015/048957.

Co-pending U.S. Appl. No. 15/578,837, filed Dec. 1, 2017.

FIG. 5

| | Comp. 91 | Comp. 98 | Comp. 100 | Comp. 101 | Comp. 112 | Comp. 115 | Comp. 232 |
|---|---|---|---|---|---|---|---|
| $IC_{50}$ [nM] | 19 | 16 | 18 | 16 | 28 | 37 | 33 |
| $GI_{50}$ MLL-AF9 BMC [nM] | 40 | 40 | 25 | 20 | 10 | 15 | 25 |
| $GI_{50}$ MV4;11 (MLL-AF4) [nM] | 80 | ND | 75 | 30 | 10 | 20 | 70 |
| $GI_{50}$ KOPN-8 (MLL-ENL) [nM] | 50 | 75 | 100 | 50 | 30 | ND | ND |
| $GI_{50}$ MOLM13 (MLL-AF9) [nM] | 200 | ND | 150 | 75 | 50 | ND | ND |
| $GI_{50}$ HM-2 (non-MLL) [nM] | 1700 | 800 | 600 | 2000 | 3000 | 3000 | ND |
| $GI_{50}$ REH (non-MLL) [nM] | 1500 | 750 | 750 | 1200 | 400 | ND | ND |

FIG. 8

Amino acid sequence of human menin, isoform 1 (SEQ ID NO: 1):

```
MGLKAAQKTLFPLRSIDDVVRLFAAELGREEPDLVLLSLVLGFVEHFLAVNRVIPTNVPE
LTFQPSPAPDPPGGLTYFPVADLSIIAALYARFTAQIRGAVDLSLYPREGGVSSRELVKK
VSDVIWNSLSRSYFKDRAHIQSLFSFITGWSPVGTKLDSSGVAFAVVGACQALGLRDVHL
ALSEDHAWVVFGPNGEQTAEVTWHGKGNEDRRGQTVNAGVAERSWLYLKGSYMRCDRKME
VAFMVCAINPSIDLHTDSLELLQLQQKLLWLLYDLGHLERYPMALGNLADLEELEPTPGR
PDPLTLYHKGIASAKTYYRDEHIYPYMYLAGYHCRNRNVREALQAWADTATVIQDYNYCR
EDEEIYKEFFEVANDVIPNLLKEAASLLEAGEERPGEQSQGTQSQGSALQDPECFAHLLR
FYDGICKWEEGSPTPVLHVGWATFLVQSLGRFEGQVRQKVRIVSREAEAAEAEEPWGEEA
REGRRRGPRRESKPEEPPPPKKPALDKGLGTGQGAVSGPPRKPPGTVAGTARGPEGGSTA
QVPAPTASPPPEGPVLTFQSEKMKGMKELLVATKINSSAIKLQLTAQSQVQMKKQKVSTP
SDYTLSFLKRQRKGL
```

FIG. 9

Amino acid sequence of human menin, isoform 2 (SEQ ID NO: 2):

MGLKAAQKTLFPLRSIDDVVRLFAAELGREEPDLVLLSLVLGFVEHFLAVNRVIPTNVPE
LTFQPSPAPDPPGGLTYFPVADLSIIAALYARFTAQIRGAVDLSLYPREGGVSSRELVKK
VSDVIWNSLSRSYFKDRAHIQSLFSFITGTKLDSSGVAFAVVGACQALGLRDVHLALSED
HAWVVFGPNGEQTAEVTWHGKGNEDRRGQTVNAGVAERSWLYLKGSYMRCDRKMEVAFMV
CAINPSIDLHTDSLELLQLQQKLLWLLYDLGHLERYPMALGNLADLEELEPTPGRPDPLT
LYHKGIASAKTYYRDEHIYPYMYLAGYHCRNRNVREALQAWADTATVIQDYNYCREDEEI
YKEFFEVANDVIPNLLKEAASLLEAGEERPGEQSQGTQSQGSALQDPECFAHLLRFYDGI
CKWEEGSPTPVLHVGWATFLVQSLGRFEGQVRQKVRIVSREAEAAEAEEPWGEEAREGRR
RGPRRESKPEEPPPPKKPALDKGLGTGQGAVSGPPRKPPGTVAGTARGPEGGSTAQVPAP
TASPPPEGPVLTFQSEKMKGMKELLVATKINSSAIKLQLTAQSQVQMKKQKVSTPSDYTL
SFLKRQRKGL

FIG. 10

Amino acid sequence of human menin, isoform 3 (SEQ ID NO: 3):

```
MGLKAAQKTLFPLRSIDDVVRLFAAELGREEPDLVLLSLVLGFVEHFLAVNRVIPTNVPE
LTFQPSPAPDPPGGLTYFPVADLSIIAALYARFTAQIRGAVDLSLYPREGGVSSRELVKK
VSDVIWNSLSRSYFKDRAHIQSLFSFITGTKLDSSGVAFAVVGACQALGLRDVHLALSED
HAWSWLYLKGSYMRCDRKMEVAFMVCAINPSIDLHTDSLELLQLQQKLLWLLYDLGHLER
YPMALGNLADLEELEPTPGRPDPLTLYHKGIASAKTYYRDEHIYPYMYLAGYHCRNRNVR
EALQAWADTATVIQDYNYCREDEEIYKEFFEVANDVIPNLLKEAASLLEAGEERPGEQSQ
GTQSQGSALQDPECFAHLLRFYDGICKWEEGSPTPVLHVGWATFLVQSLGRFEGQVRQKV
RIVSREAEAAEAEEPWGEEAREGRRRGPRRESKPEEPPPPKKPALDKGLGTGQGAVSGPP
RKPPGTVAGTARGPEGGSTAQVPAPTASPPPEGPVLTFQSEKMKGMKELLVATKINSSAI
KLQLTAQSQVQMKKQKVSTPSDYTLSFLKRQRKGL
```

THIENOPYRIMIDINE AND THIENOPYRIDINE COMPOUNDS AND METHODS OF USE THEREOF

CROSS-REFERENCE

This application claims the benefit of U.S. provisional application No. 62/048,036, filed Sep. 9, 2014, U.S. provisional application No. 62/095,588, filed Dec. 22, 2014, U.S. provisional application No. 62/171,124, filed Jun. 4, 2015, and U.S. provisional application No. 62/214,681, filed Sep. 4, 2015, each of which is incorporated by reference in its entirety.

STATEMENT REGARDING FEDERALLY SPONSORED RESEARCH OR DEVELOPMENT

This invention was made with government support under R01 CA160467 awarded by the National Institutes of Health. The government has certain rights in the invention.

BACKGROUND OF THE INVENTION

Chromosomal translocations that affect the proto-oncogene Mixed Lineage Leukemia (MLL) occur in aggressive human acute leukemias, both in children and adults (Sorensen et al., J Clin Invest., 1994.93(1): p. 429-37., Cox, et al., Am J Clin Pathol., 2004. 122(2): p. 298-306., herein incorporated by reference in their entireties). They are particularly common in infants with acute myeloblastic leukemia (AML) and acute lymphoblastic leukemia (ALL) and constitute up to 80% of all infant acute leukemia cases. Fusion of MLL with one of 60 partner genes forms a chimeric oncogene which upregulates HOX genes resulting in a blockage of blood cell differentiation that ultimately leads to acute leukemia (Eguchi et al. Int J Hematol., 2003. 78(5): p. 390-401., herein incorporated by reference in its entirety). Patients with leukemias harboring MLL translocations have a very poor prognosis (35% five year survival) and it is clear that novel therapeutic strategies are urgently needed to treat these leukemias (Slany. Hematol Oncol., 2005. 23(1): p. 1-9., herein incorporated by reference in its entirety). Menin is a critical cofactor in MLL-associated leukemias. Menin is a tumor-suppressor protein encoded by the Multiple Endocrine Neoplasia (MEN) gene. Menin is a ubiquitously expressed nuclear protein that is engaged in interactions with a cohort of transcription factors, chromatin modifying proteins, and DNA processing and repair proteins (Agarwal et al. Horm Metab Res., 2005. 37(6): p. 369-74., herein incorporated by reference in its entirety). The biological function of menin remains unclear and is context dependent. It functions as a tumor suppressor in endocrine organs (Marx. Nat Rev Cancer., 2005. 5(5): p. 367-75., herein incorporated by reference in its entirety) but has an oncogenic role in myeloid cells (Yokoyama et al., Cell., 2005.123(2): p. 207-18., herein incorporated by reference in its entirety). Association of menin with oncogenic MLL fusion proteins constitutively upregulates expression of HOX genes and impairs proliferation and differentiation of hematopoietic cells leading to leukemia development. Myeloid cells transformed with oncogenic MLL-AF9 fusion protein require menin for efficient proliferation (Chen et al., Proc Natl Acad Sci USA., 2006.103(4): p. 1018-23., herein incorporated by reference in its entirety). Menin is also required to maintain oncogenic transformation induced by other MLL translocations, including MLL-ENL, MLL-GAS7 and MLL-AF6 (Yokoyama et al., Cell., 2005.123(2): p. 207-18., herein incorporated by reference in its entirety), demonstrating that menin functions as a general oncogenic cofactor in MLL-related leukemias and implies the interaction of menin with MLL fusions and MLL is a valuable target for molecular therapy. The leukemogenic activity of MLL fusion oncoproteins is dependent on association with menin. Therefore, selective targeting of this interaction could provide an attractive therapeutic approach to develop novel drugs for leukemias with translocations of MLL gene and other leukemias with upregulation of HOX genes.

SUMMARY OF THE INVENTION

The present disclosure provides compounds and methods for inhibiting the interaction of menin with its upstream or downstream signaling molecules including but not limited to MLL1, MLL2 and MLL-fusion oncoproteins. Compounds of the disclosure may be used in methods for the treatment of a wide variety of cancers and other diseases associated with one or more of MLL1, MLL2, MLL fusion proteins, and menin. In certain embodiments, a compound of the disclosure covalently binds menin and inhibits the interaction of menin with MLL. In certain embodiments, a compound of the disclosure interacts non-covalently with menin and inhibits the interaction of menin with MLL.

In certain embodiments, the compounds of the disclosure are represented by a structure of Formula (1) or (2):

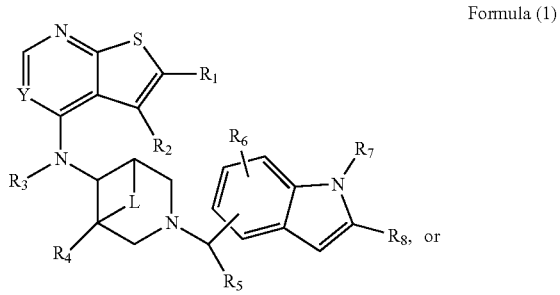

Formula (1)

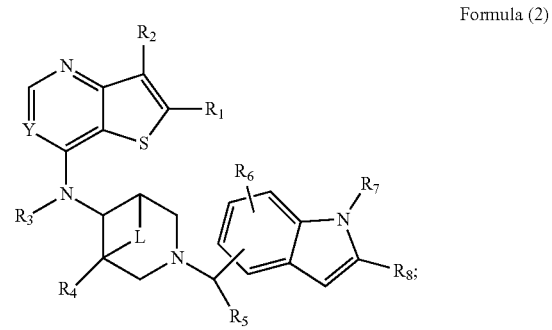

Formula (2)

or a salt thereof, wherein:

R1, R2, R4, R5, R6, and R8 are each independently selected from H, alkyl, substituted alkyl, hydroxy, alkoxy, amine, thioalkyl, halogen, ketone, amide, cyano, sulfonyl, a carbocyclic ring, an aromatic ring, a substituted aromatic ring, a heterocyclic aromatic ring, a substituted heterocyclic aromatic ring, a substituted or non-substituted heterocyclic non-aromatic ring, carbocyclic or heterocyclic aromatic ring fused to another aromatic ring, a hydrogen bond donor, a hydrogen bond acceptor, and combinations thereof; wherein R6 can be present at one or more of the positions of the benzyl and/or pyrrole portion of the indole ring that are not otherwise occupied by a substituent;

R3 is selected from H, alkyl, substituted alkyl, hydroxy, alkoxy, thioalkyl, ketone, amide, sulfonyl, a carbocyclic ring, an aromatic ring, a substituted aromatic ring, a heterocyclic aromatic ring, a substituted heterocyclic aromatic ring, a substituted or non-substituted heterocyclic non-aromatic ring, carbocyclic or heterocyclic aromatic ring fused to another aromatic ring, a hydrogen bond donor, a hydrogen bond acceptor, and combinations thereof;

Y is N or C($R^a$), wherein $R^a$ is selected from hydrogen, alkyl, heteroalkyl, substituted aryl, substituted alkyl, alcohol, alkoxy, amino, cyano, sulfonyl, aldehyde, non-aromatic heterocycle, and aromatic ring;

L is present or absent, and if present it is selected from alkylene, oxalkylene and aminoalkylene; and R7 comprises a functional group that covalently reacts with one or more residues on menin.

In certain embodiments, for a compound or salt of Formula (1), or (2), $R_1$ and $R_2$ are independently selected from hydrogen, halogen, hydroxy, alkoxy, cyano, nitro, amino, alkyl, substituted alkyl, alkenyl, substituted alkenyl, alkynyl, and substituted alkynyl. In certain embodiments, $R_1$ is selected from halogen, alkyl, substituted alkyl, alkenyl, substituted alkenyl, alkynyl, and substituted alkynyl, for example, $R_1$ is selected from halogen, haloalkyl, haloalkenyl, and haloalkynyl. In particular embodiments, $R_1$ is selected from —$CH_2CF_3$ and —$CH_2CHF_2$. In certain embodiments, for a compound or salt of Formula (1), or (2), $R_2$ is selected from hydrogen, hydroxy, nitro, cyano, halogen, alkyl, and alkoxy. In particular embodiments, $R_2$ is hydrogen.

In certain embodiments, for a compound or salt of Formula (1), or (2), $R_3$ is selected from hydrogen, alkyl, and substituted alkyl. In particular embodiments, $R_3$ is hydrogen.

In certain embodiments, for a compound or salt of Formula (1), or (2), $R_4$ is selected from hydrogen, halogen, hydroxy, alkoxy, cyano, nitro, amino, alkyl, substituted alkyl, alkenyl, substituted alkenyl, alkynyl, and substituted alkynyl. In particular embodiments, $R_4$ is selected from hydrogen and halogen, for example, $R_4$ is hydrogen.

In certain embodiments, for a compound or salt of Formula (1), or (2), $R_5$ is selected from hydrogen, halogen, hydroxy, alkoxy, cyano, nitro, amino, alkyl, substituted alkyl, alkenyl, substituted alkenyl, alkynyl, and substituted alkynyl. In particular embodiments, $R_5$ is hydrogen.

In certain embodiments, for a compound or salt of Formula (1), or (2), $R_6$, at each occurrence, is independently selected from halogen, hydroxy, alkoxy, cyano, nitro, amino, alkyl, substituted alkyl, alkenyl, substituted alkenyl, alkynyl, and substituted alkynyl, such as from halogen, hydroxy, alkoxy, and alkyl. In particular embodiments, $R_6$, at each occurrence, is selected from halogen, methyl, hydroxy and methoxy, for example, $R_6$, at each occurrence, is selected from methyl, hydroxy and methoxy. In certain embodiments, s is 0. In certain embodiments, s is 1.

In certain embodiments, for a compound or salt of Formula (1), or (2), $R_8$ is selected from hydrogen, halogen, hydroxy, alkoxy, cyano, nitro, amino, alkyl, substituted alkyl, alkenyl, substituted alkenyl, alkynyl, and substituted alkynyl. In particular embodiments, $R_8$ is cyano.

In certain embodiments, for a compound or salt of Formula (1), or (2), Y is N.

In certain embodiments, for a compound or salt of Formula (1), or (2), Y is C($R^a$) and $R^a$ is selected from hydrogen, halogen, nitro, amino, cyano, alkyl, alcohol, heteroalkyl, and substituted alkyl, such as $R^a$ is selected from hydrogen, alkyl, halogen, and substituted alkyl. In particular embodiments, $R^a$ is selected from hydrogen, substituted alkyl, e.g., —$CH_2OH$, and cyano.

In certain embodiments, the compounds of the disclosure are represented by a structure of Formula (3B):

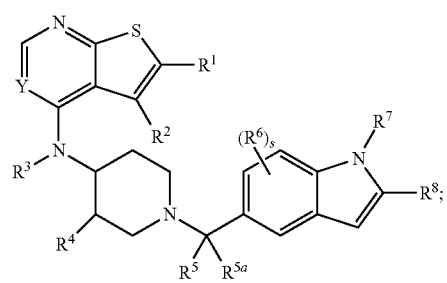

Formula (3B)

or a salt thereof, wherein:

$R^1$, $R^2$, $R^4$, $R^5$, $R^{5a}$, $R^8$, and $R^a$ are independently selected from hydrogen, halogen, —$OR^{20}$, —$SR^{20}$, —$N(R^{20})_2$, —$N(R^{20})C(O)R^{20}$, —$C(O)R^{20}$, —$C(O)OR^{20}$, —$C(O)N(R^{20})_2$, —$OC(O)R^{20}$, —$S(O)_2R^{20}$, —$S(O)_2N(R^{20})_2$, —$N(R^{20})S(O)_2R^{20}$, —$NO_2$, —$P(O)(OR^{20})_2$, —$P(O)(R^{20})_2$, —$OP(O)(OR^{20})_2$, and —CN; $C_{1-6}$ alkyl, $C_{2-6}$ alkenyl, and $C_{2-6}$ alkynyl, each of which is independently optionally substituted at each occurrence with one or more substituents selected from halogen, —$OR^{20}$, —$SR^{20}$, —$N(R^{20})_2$, —$N(R^{20})C(O)R^{20}$, —$C(O)R^{20}$, —$C(O)OR^{20}$, —$C(O)N(R^{20})_2$, —$OC(O)R^{20}$, —$S(O)_2R^{20}$, —$S(O)_2N(R^{20})_2$, —$N(R^{20})S(O)_2R^{20}$, —$NO_2$, =O, =S, =$N(R^{20})$, —$P(O)(OR^{20})_2$, —$P(O)(R^{20})_2$, —$OP(O)(OR^{20})_2$, —CN, $C_{3-10}$ carbocycle, and 3- to 10-membered heterocycle, or two substituents on the same carbon atom of an $C_{1-6}$ alkyl, $C_{2-6}$ alkenyl, or $C_{2-6}$ alkynyl come together to form a $C_{3-10}$ carbocycle or 3- to 10-membered heterocycle; and $C_{3-10}$ carbocycle and 3- to 10-membered heterocycle; or $R^5$ and $R^{5a}$ together with the carbon atom to which they are attached, come together to form a $C_{3-10}$ carbocycle or a 3- to 10-membered heterocycle; wherein any $C_{3-10}$ carbocycle and 3- to 10-membered heterocycle of $R^1$, $R^2$, $R^4$, $R^5$, $R^{5a}$, $R^8$, and $R^a$ is independently optionally substituted with one or more substituents selected from halogen, —$OR^{20}$, —$SR^{20}$, —$N(R^{20})_2$, —$N(R^{20})C(O)R^{20}$, —$C(O)R^{20}$, —$C(O)OR^{20}$, —$C(O)N(R^{20})_2$, —$OC(O)R^{20}$, —$S(O)_2R^{20}$, —$S(O)_2N(R^{20})_2$, —$N(R^{20})S(O)_2R^{20}$, —$NO_2$, =O, =S, =$N(R^{20})$, —$P(O)(OR^{20})_2$, —$P(O)(R^{20})_2$, —$OP(O)(OR^{20})_2$, —CN, $C_{1-6}$ alkyl, $C_{2-6}$ alkenyl, and $C_{2-6}$ alkynyl;

$R^3$ is selected from selected from hydrogen, —$C(O)R^{20}$, —$C(O)OR^{20}$, —$C(O)N(R^{20})_2$, —$S(O)_2R^{20}$, and —$S(O)_2N(R^{20})_2$; $C_{1-6}$ alkyl, $C_{2-6}$ alkenyl, and $C_{2-6}$ alkynyl, each of which is independently optionally substituted at each occurrence with one or more substituents selected from halogen, —$OR^{20}$, —$SR^{20}$, —$N(R^{20})_2$, —$N(R^{20})C(O)R^{20}$, —$C(O)R^{20}$, —$C(O)OR^{20}$, —$C(O)N(R^{20})_2$, —$OC(O)R^{20}$, —$S(O)_2R^{20}$, —$S(O)_2N(R^{20})_2$, —$N(R^{20})S(O)_2R^{20}$, —$NO_2$, =O, =S, =$N(R^{20})$, —$P(O)(OR^{20})_2$, —$P(O)(R^{20})_2$, —$OP(O)(OR^{20})_2$, —CN, $C_{3-10}$ carbocycle, and 3- to 10-membered heterocycle, or two substituents on the same carbon atom of an $C_{1-6}$ alkyl, $C_{2-6}$ alkenyl, or $C_{2-6}$ alkynyl come together to form a $C_{3-10}$ carbocycle or 3- to 10-membered heterocycle; and $C_{3-10}$ carbocycle and 3- to 10-membered heterocycle; wherein any $C_{3-10}$ carbocycle and 3- to 10-membered heterocycle of $R^3$ is independently optionally substituted with one or more substituents selected from halogen, —$OR^{20}$, —$SR^{20}$, —$N(R^{20})_2$, —$N(R^{20})C(O)R^{20}$, —$C(O)R^{20}$, —$C(O)$ $OR^{20}$, —C(O)N($R^{20}$)$_2$, —OC(O)$R^{20}$, —S(O)$_2R^{20}$, —S(O)$_2$N($R^{20}$)$_2$, —N($R^{20}$)S(O)$_2R^{20}$, —NO$_2$, =O, =S, =N($R^{20}$), —P(O)(O$R^{20}$)$_2$, —P(O)($R^{20}$)$_2$, —OP(O)(O$R^{20}$)$_2$, —CN, $C_{1-6}$ alkyl, $C_{2-6}$ alkenyl, and $C_{2-6}$ alkynyl;

$R^6$ is independently selected at each occurrence from halogen, —O$R^{20}$, —S$R^{20}$, —N($R^{20}$)$_2$, —N($R^{20}$)C(O)$R^{20}$, —C(O)$R^{20}$, —C(O)O$R^{20}$, —C(O)N($R^{20}$)$_2$, —OC(O)$R^{20}$, —S(O)$_2R^{20}$, —S(O)$_2$N($R^{20}$)$_2$, —N($R^{20}$)S(O)$_2R^{20}$, —NO$_2$, —P(O)(O$R^{20}$)$_2$, —P(O)($R^{20}$)$_2$, —OP(O)(O$R^{20}$)$_2$, and —CN; $C_{1-6}$ alkyl, $C_{2-6}$ alkenyl, and $C_{2-6}$ alkynyl, each of which is independently optionally substituted at each occurrence with one or more substituents selected from halogen, —O$R^{20}$, —S$R^{20}$, —N($R^{20}$)$_2$, —N($R^{20}$)C(O)$R^{20}$, —C(O)$R^{20}$, —C(O)O$R^{20}$, —C(O)N($R^{20}$)$_2$, —OC(O)$R^{20}$, —S(O)$_2R^{20}$, —S(O)$_2$N($R^{20}$)$_2$, —N($R^{20}$)S(O)$_2R^{20}$, —NO$_2$, =O, =S, =N($R^{20}$), —P(O)(O$R^{20}$)$_2$, —P(O)($R^{20}$)$_2$, —OP(O)(O$R^{20}$)$_2$, —CN, $C_{3-10}$ carbocycle, and 3- to 10-membered heterocycle, or two substituents on the same carbon atom of an $C_{1-6}$ alkyl, $C_{2-6}$ alkenyl, or $C_{2-6}$ alkynyl come together to form a $C_{3-10}$ carbocycle or 3- to 10-membered heterocycle; and $C_{3-10}$ carbocycle and 3- to 10-membered heterocycle; wherein any $C_{3-10}$ carbocycle and 3- to 10-membered heterocycle of $R^6$ is independently optionally substituted with one or more substituents selected from halogen, —O$R^{20}$, —S$R^{20}$, —N($R^{20}$)$_2$, —N($R^{20}$)C(O)$R^{20}$, —C(O)$R^{20}$, —C(O)O$R^{20}$, —C(O)N($R^{20}$)$_2$, —OC(O)$R^{20}$, —S(O)$_2R^{20}$, —S(O)$_2$N($R^{20}$)$_2$, —N($R^{20}$)S(O)$_2R^{20}$, —NO$_2$, =O, =S, =N($R^{20}$), —P(O)(O$R^{20}$)$_2$, —P(O)($R^{20}$)$_2$, —OP(O)(O$R^{20}$)$_2$, —CN, $C_{1-6}$ alkyl, $C_{2-6}$ alkenyl, and $C_{2-6}$ alkynyl;

$R^{20}$ at each occurrence is independently selected from hydrogen; $C_{1-6}$ alkyl, $C_{2-6}$ alkenyl, and $C_{2-6}$ alkynyl, each of which is independently optionally substituted at each occurrence with one or more substituents selected from halogen, —O$R^{30}$, —S$R^{30}$, —N($R^{30}$)$_2$, —N($R^{30}$)C(O)$R^{30}$, —C(O)$R^{30}$, —C(O)O$R^{30}$, —C(O)N($R^{30}$)$_2$, —OC(O)$R^{30}$, —S(O)$_2R^{30}$, —S(O)$_2$N($R^{30}$)$_2$, —N($R^{30}$)S(O)$_2R^{30}$, —NO$_2$, —P(O)(O$R^{30}$)$_2$, —P(O)($R^{30}$)$_2$, —OP(O)(O$R^{30}$)$_2$, and —CN; and 3- to 10-membered heterocycle and $C_{3-10}$ carbocycle;

$R^{30}$ at each occurrence is independently selected from hydrogen, $C_{1-6}$ alkyl, $C_{2-6}$ alkenyl, and $C_{2-6}$ alkynyl;

Y is N or C($R^a$);

s is selected from 0, 1, 2, 3, and 4; and $R^7$ comprises a functional group that covalently reacts with one or more residues on menin.

In certain embodiments, for a compound or salt of any one of Formulas (1), (2), and (3B), the functional group of $R^7$ covalently reacts with one or more cysteine residues on menin, such as cysteine 329 or cysteine 334. In certain embodiments, for a compound or salt of any one of Formulas (1), (2), and (3B), the compound is capable of (a) binding covalently to menin and (b) inhibiting the interaction of menin and MLL.

In certain embodiments, for a compound or salt of Formula (3B), $R^5$ is hydrogen. In certain embodiments, for a compound or salt of Formula (3B), $R^5$ and $R^{5a}$ are not hydrogen. $R^{5a}$ may be selected from hydrogen, halogen, —O$R^{20}$, —S$R^{20}$, —N($R^{20}$)$_2$, —NO$_2$, —P(O)(O$R^{20}$)$_2$, —P(O)($R^{20}$)$_2$, —OP(O)(O$R^{20}$)$_2$, and —CN; and $C_{1-6}$ alkyl, $C_{2-6}$ alkenyl, and $C_{2-6}$ alkynyl, each of which is optionally substituted with one or more substituents selected from halogen, —O$R^{20}$, —S$R^{20}$, —N($R^{20}$)$_2$, —N($R^{20}$)C(O)$R^{20}$, —C(O)$R^{20}$, —C(O)O$R^{20}$, —C(O)N($R^{20}$)$_2$, —OC(O)$R^{20}$, —S(O)$_2R^{20}$, —S(O)$_2$N($R^{20}$)$_2$, —N($R^{20}$)S(O)$_2R^{20}$, —NO$_2$, =O, =S, =N($R^{20}$), —P(O)(O$R^{20}$)$_2$, —P(O)($R^{20}$)$_2$, —OP(O)(O$R^{20}$)$_2$, —CN, $C_{3-10}$ carbocycle, and 3- to 10-membered heterocycle, or two substituents on the same carbon atom of an $C_{1-6}$ alkyl, $C_{2-6}$ alkenyl, or $C_{2-6}$ alkynyl come together to form a $C_{3-10}$ carbocycle or 3- to 10-membered heterocycle.

In certain embodiments, for a compound or salt of Formula (3B), s is 0, 1, or 2, for example, s is 0 or 1.

In certain embodiments, for a compound or salt of Formula (3B), $R^1$ and $R^2$ are independently selected from hydrogen, halogen, —O$R^{20}$, —S$R^{20}$, —N($R^{20}$)$_2$, —NO$_2$, and —CN; and $C_{1-6}$ alkyl, $C_{2-6}$ alkenyl, and $C_{2-6}$ alkynyl, each of which is independently optionally substituted at each occurrence with one or more substituents selected from halogen, —O$R^{20}$, —S$R^{20}$, —N($R^{20}$)$_2$, —N($R^{20}$)C(O)$R^{20}$, —C(O)$R^{20}$, —C(O)O$R^{20}$, —C(O)N($R^{20}$)$_2$, —OC(O)$R^{20}$, —S(O)$_2R^{20}$, —S(O)$_2$N($R^{20}$)$_2$, —N($R^{20}$)S(O)$_2R^{20}$, —NO$_2$, =O, =S, =N($R^{20}$), —P(O)(O$R^{20}$)$_2$, —P(O)($R^{20}$)$_2$, —OP(O)(O$R^{20}$)$_2$, —CN, $C_{3-10}$ carbocycle, and 3- to 10-membered heterocycle, for example, $R^1$ is selected from $C_{1-6}$ alkyl, $C_{2-6}$ alkenyl, and $C_{2-6}$ alkynyl, optionally substituted with one or more substituents selected from halogen, —O$R^{20}$, —S$R^{20}$, —N($R^{20}$)$_2$, —N($R^{20}$)C(O)$R^{20}$, —C(O)$R^{20}$, —C(O)O$R^{20}$, —C(O)N($R^{20}$)$_2$, —OC(O)$R^{20}$, —S(O)$_2R^{20}$, —S(O)$_2$N($R^{20}$)$_2$, —N($R^{20}$)S(O)$_2R^{20}$, —NO$_2$, =O, =S, =N($R^{20}$), and —CN. In particular embodiments, $R^1$ is selected from $C_{1-6}$ alkyl, $C_{2-6}$ alkenyl, and $C_{2-6}$ alkynyl, optionally substituted with one or more halogen atoms, for example, $R^1$ is selected from —CH$_2$CF$_3$ and —CH$_2$CHF$_2$.

In certain embodiments, for a compound or salt of Formula (3B), $R^2$ is selected from hydrogen halogen, —O$R^{20}$, —S$R^{20}$, —N($R^{20}$)$_2$, —NO$_2$, and —CN; and $C_{1-6}$ alkyl optionally substituted with one or more substituents selected from halogen, —O$R^{20}$, —S$R^{20}$, —N($R^{20}$)$_2$, —N($R^{20}$)C(O)$R^{20}$, —C(O)$R^{20}$, —C(O)O$R^{20}$, —C(O)N($R^{20}$)$_2$, —OC(O)$R^{20}$, —S(O)$_2R^{20}$, —S(O)$_2$N($R^{20}$)$_2$, —N($R^{20}$)S(O)$_2R^{20}$, —NO$_2$, =O, =S, =N($R^{20}$), and —CN, for example, $R^2$ is hydrogen.

In certain embodiments, for a compound or salt of Formula (3B), $R^3$ is selected from hydrogen, —C(O)$R^{20}$, —C(O)O$R^{20}$, and —C(O)N($R^{20}$)$_2$; and $C_{1-6}$ alkyl, $C_{2-6}$ alkenyl, and $C_{2-6}$ alkynyl, each of which is optionally substituted with one or more substituents selected from halogen, —O$R^{20}$, —S$R^{20}$, —N($R^{20}$)$_2$, —N($R^{20}$)C(O)$R^{20}$, —C(O)$R^{20}$, —C(O)O$R^{20}$, —C(O)N($R^{20}$)$_2$, —OC(O)$R^{20}$, —S(O)$_2R^{20}$, —S(O)$_2$N($R^{20}$)$_2$, —N($R^{20}$)S(O)$_2R^{20}$, —NO$_2$, =O, =S, =N($R^{20}$), —P(O)(O$R^{20}$)$_2$, —P(O)($R^{20}$)$_2$, —OP(O)(O$R^{20}$)$_2$, —CN, for example, $R^3$ is hydrogen.

In certain embodiments, for a compound or salt of Formula (3B), $R^4$ is selected from hydrogen, halogen, —O$R^{20}$, —S$R^{20}$, —N($R^{20}$)$_2$, —NO$_2$, —P(O)(O$R^{20}$)$_2$, —P(O)($R^{20}$)$_2$, —OP(O)(O$R^{20}$)$_2$, and —CN; and $C_{1-6}$ alkyl, $C_{2-6}$ alkenyl, and $C_{2-6}$ alkynyl, optionally substituted with one or more substituents selected from halogen, —O$R^{20}$, —S$R^{20}$, —N($R^{20}$)$_2$, —N($R^{20}$)C(O)$R^{20}$, —C(O)$R^{20}$, —C(O)O$R^{20}$, —C(O)N($R^{20}$)$_2$, —OC(O)$R^{20}$, —S(O)$_2R^{20}$, —S(O)$_2$N($R^{20}$)$_2$, —N($R^{20}$)S(O)$_2R^{20}$, —NO$_2$, =O, =S, =N($R^{20}$), —P(O)(O$R^{20}$)$_2$, —P(O)($R^{20}$)$_2$, —OP(O)(O$R^{20}$)$_2$, —CN, $C_{3-10}$ carbocycle, and 3- to 10-membered heterocycle, for example, $R^4$ is selected from hydrogen and halogen.

In certain embodiments, for a compound or salt of Formula (3B), $R^6$, at each occurrence, is independently selected from hydrogen, halogen, —O$R^{20}$, —S$R^{20}$, —N($R^{20}$)$_2$, —NO$_2$, —P(O)(O$R^{20}$)$_2$, —P(O)($R^{20}$)$_2$, —OP(O)(O$R^{20}$)$_2$, and —CN; and $C_{1-6}$ alkyl, $C_{2-6}$ alkenyl, and $C_{2-6}$ alkynyl, optionally substituted with one or more substituents selected from halogen, —O$R^{20}$, —S$R^{20}$, —N($R^{20}$)$_2$, —N($R^{20}$)C(O)$R^{20}$, —C(O)$R^{20}$, —C(O)O$R^{20}$, —C(O)N($R^{20}$)$_2$, —OC(O)$R^{20}$, —S(O)$_2R^{20}$, —S(O)$_2$N($R^{20}$)$_2$, —N($R^{20}$)S(O)$_2R^{20}$, —NO$_2$, =O, =S, =N($R^{20}$), —P(O)(O$R^{20}$)$_2$, —P(O)

($R^{20}$)$_2$, —OP(O)(O$R^{20}$)$_2$, —CN, $C_{3-10}$ carbocycle, and 3- to 10-membered heterocycle, for example, $R^6$, at each occurrence, is independently selected from halogen, —O$R^{20}$, and $C_{1-6}$ alkyl optionally substituted with one or more substituents selected from halogen, —O$R^{20}$, —S$R^{20}$, —N($R^{20}$)$_2$, —NO$_2$, =O, =S, =N($R^{20}$), and —CN.

In certain embodiments, for a compound or salt of Formula (3B), $R^8$ is selected from hydrogen, halogen, —O$R^{20}$, —S$R^{20}$, —N($R^{20}$)$_2$, —NO$_2$, and —CN; and $C_{1-6}$ alkyl, $C_{2-6}$ alkenyl, and $C_{2-6}$ alkynyl, optionally substituted with one or more substituents selected from halogen, —O$R^{20}$, —S$R^{20}$, —N($R^{20}$)$_2$, —N($R^{20}$)C(O)$R^{20}$, —C(O)$R^{20}$, —C(O)O$R^{20}$, —C(O)N($R^{20}$)$_2$, —OC(O)$R^{20}$, —S(O)$_2$$R^{20}$, —S(O)$_2$N($R^{20}$)$_2$, —N($R^{20}$)S(O)$_2$$R^{20}$, —NO$_2$, =O, =S, =N($R^{20}$), and —CN, for example $R^8$ is —CN.

In certain embodiments, for a compound or salt of Formula (3B), Y is N. In certain embodiments, for a compound or salt of Formula (3B), Y is C($R^a$) and $R^a$ is selected from hydrogen, halogen, —O$R^{20}$, —S$R^{20}$, —N($R^{20}$)$_2$, —NO$_2$, and —CN; and $C_{1-6}$ alkyl, $C_{2-6}$ alkenyl, and $C_{2-6}$ alkynyl, each of which is optionally substituted with one or more substituents selected from halogen, —O$R^{20}$, —S$R^{20}$, —N($R^{20}$)$_2$, —N($R^{20}$)C(O)$R^{20}$, —C(O)$R^{20}$, —C(O)O$R^{20}$, —C(O)N($R^{20}$)$_2$, —OC(O)$R^{20}$, —S(O)$_2$$R^{20}$, —S(O)$_2$N($R^{20}$)$_2$, —N($R^{20}$)S(O)$_2$$R^{20}$, —NO$_2$, =O, =S, =N($R^{20}$), —P(O)(O$R^{20}$)$_2$, —P(O)($R^{20}$)$_2$, —OP(O)(O$R^{20}$)$_2$, —CN, $C_{3-10}$ carbocycle, and 3- to 10-membered heterocycle, for example, Y is C($R^a$) and $R^a$ is selected from hydrogen, halogen, and $C_{1-6}$ alkyl optionally substituted with one or more substituents selected from halogen, —O$R^{20}$, —S$R^{20}$, —N($R^{20}$)$_2$, —N($R^{20}$)C(O)$R^{20}$, —C(O)$R^{20}$, —C(O)O$R^{20}$, —C(O)N($R^{20}$)$_2$, —OC(O)$R^{20}$, —S(O)$_2$$R^{20}$, —S(O)$_2$N($R^{20}$)$_2$, —N($R^{20}$)S(O)$_2$$R^{20}$, —NO$_2$, =O, =S, =N($R^{20}$), —P(O)(O$R^{20}$)$_2$, —P(O)($R^{20}$)$_2$, —OP(O)(O$R^{20}$)$_2$, —CN, $C_{3-10}$ carbocycle, and 3- to 10-membered heterocycle, for example, $R^a$ is hydrogen.

In certain embodiments, for a compound or salt of Formula (3B), $R^{20}$, at each occurrence, is independently selected from hydrogen, $C_{1-6}$ alkyl, $C_{2-6}$ alkenyl, and $C_{2-6}$ alkynyl, 3- to 10-membered heterocycle and $C_{3-10}$ carbocycle.

In certain embodiments, for a compound or salt of any of Formulas (1), (2), and (3B), $R^7$ is selected from:

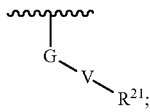

wherein:

G is selected from a bond, alkylene, heteroalkylene, $C_{3-12}$ carbocycle, 3- to 12-membered heterocycle, and combinations thereof, wherein G is optionally substituted with one or more $R^{32}$ groups;

V is absent or selected from a $C_{3-12}$ carbocycle, and 3- to 12-membered heterocycle; wherein V is optionally substituted with one or more $R^{32}$ groups;

$R^{32}$ at each occurrence is selected from halogen, —O$R^{20}$, —S$R^{20}$, —N($R^{20}$)$_2$, —N($R^{20}$)C(O)$R^{20}$, —C(O)$R^{20}$, —C(O)O$R^{20}$, —C(O)N($R^{20}$)$_2$, —OC(O)$R^{20}$, —S(O)$_2$$R^{20}$, —S(O)$_2$N($R^{20}$)$_2$, —N($R^{20}$)S(O)$_2$$R^{20}$, —NO$_2$, =O, =S, =N($R^{20}$), —P(O)(O$R^{20}$)$_2$, —P(O)($R^{20}$)$_2$, —OP(O)(O$R^{20}$)$_2$, and —CN; $C_{1-6}$ alkyl, $C_{2-6}$ alkenyl, and $C_{2-6}$ alkynyl, each of which is independently optionally substituted at each occurrence with one or more substituents selected from halogen, —O$R^{20}$, —S$R^{20}$, —N($R^{20}$)$_2$, —N($R^{20}$)C(O)$R^{20}$, —C(O)$R^{20}$, —C(O)O$R^{20}$, —C(O)N($R^{20}$)$_2$, —OC(O)$R^{20}$, —S(O)$_2$$R^{20}$, —S(O)$_2$N($R^{20}$)$_2$, —N($R^{20}$)S(O)$_2$$R^{20}$, —NO$_2$, =O, =S, =N($R^{20}$), —P(O)(O$R^{20}$)$_2$, —P(O)($R^{20}$)$_2$, —OP(O)(O$R^{20}$)$_2$, —CN, $C_{3-10}$ carbocycle, and 3- to 10-membered heterocycle; $C_{3-10}$ carbocycle and 3- to 10-membered heterocycle; or two $R^{32}$ on the same carbon atom can come together to form a $C_{3-10}$ carbocycle or 3- to 10-membered heterocycle, wherein each $C_{3-10}$ carbocycle and 3- to 10-membered heterocycle of $R^{32}$ is independently optionally substituted with one or more substituents selected from halogen, —O$R^{20}$, —S$R^{20}$, —N($R^{20}$)$_2$, —N($R^{20}$)C(O)$R^{20}$, —C(O)$R^{20}$, —C(O)O$R^{20}$, —C(O)N($R^{20}$)$_2$, —OC(O)$R^{20}$, —S(O)$_2$$R^{20}$, —S(O)$_2$N($R^{20}$)$_2$, —N($R^{20}$)S(O)$_2$$R^{20}$, —NO$_2$, =O, =S, =N($R^{20}$), —P(O)(O$R^{20}$)$_2$, —P(O)($R^{20}$)$_2$, —OP(O)(O$R^{20}$)$_2$, —CN, $C_{1-6}$ alkyl, $C_{2-6}$ alkenyl, and $C_{2-6}$ alkynyl;

$R^{20}$ at each occurrence is independently selected from hydrogen; $C_{1-6}$ alkyl, $C_{2-6}$ alkenyl, and $C_{2-6}$ alkynyl, each of which is independently optionally substituted at each occurrence with one or more substituents selected from halogen, —O$R^{30}$, —S$R^{30}$, —N($R^{30}$)$_2$, —N($R^{30}$)C(O)$R^{30}$, —C(O)$R^{30}$, —C(O)O$R^{30}$, —C(O)N($R^{30}$)$_2$, —OC(O)$R^{30}$, —S(O)$_2$$R^{30}$, —S(O)$_2$N($R^{30}$)$_2$, —N($R^{30}$)S(O)$_2$$R^{30}$, —NO$_2$, —P(O)(O$R^{30}$)$_2$, —P(O)($R^{30}$)$_2$, —OP(O)(O$R^{30}$)$_2$, and —CN; and 3- to 10-membered heterocycle and $C_{3-10}$ carbocycle;

$R^{30}$ at each occurrence is independently selected from hydrogen, $C_{1-6}$ alkyl, $C_{2-6}$ alkenyl, and $C_{2-6}$ alkynyl; and $R^{21}$ is a moiety comprising an alpha, beta-unsaturated carbonyl; an alpha, beta-unsaturated sulfonyl; an epoxide; an aldehyde; sulfonyl fluoride; a halomethylcarbonyl, a dihalomethylcarbonyl, or a trihalomethylcarbonyl.

In certain embodiments, for a compound or salt of any of Formulas (1), (2), and (3B), $R^{21}$ is selected from:

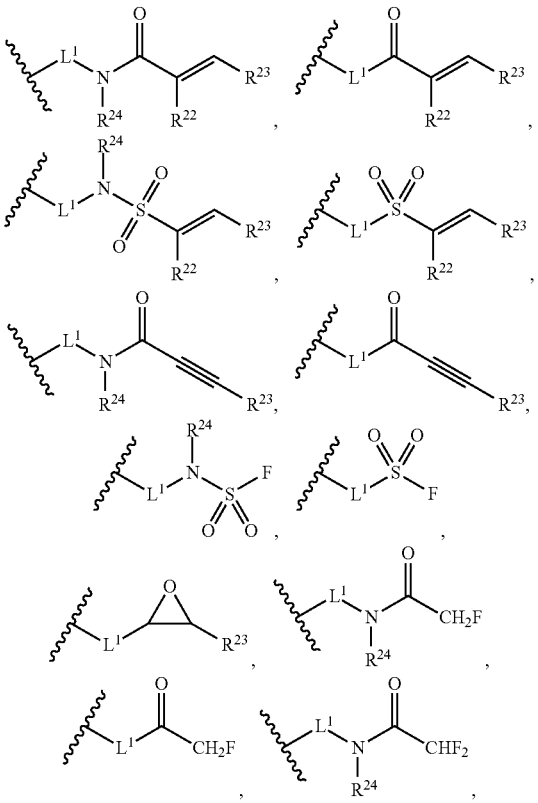

-continued

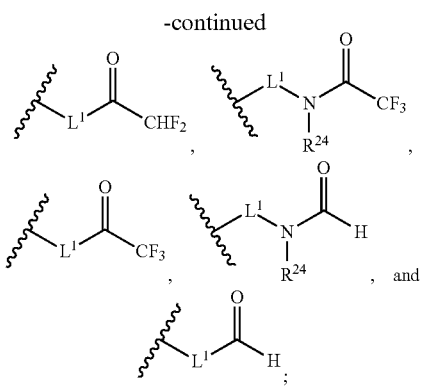

wherein:

L¹ is selected from a bond; and $C_{1-6}$ alkylene, $C_{1-6}$ heteroalkylene, $C_{2-6}$ alkenylene, and $C_{2-6}$ alkynylene, each of which may be optionally substituted with one or more $R^{32}$ groups;

$R^{22}$ and $R^{23}$ are selected from hydrogen, halogen, —$OR^{20}$, —$SR^{20}$, —$N(R^{20})_2$, —$N(R^{20})C(O)R^{20}$, —$C(O)R^{20}$, —$C(O)OR^{20}$, —$C(O)N(R^{20})_2$, —$OC(O)R^{20}$, —$S(O)_2R^{20}$, —$S(O)_2N(R^{20})_2$, —$N(R^{20})S(O)_2R^{20}$, —$NO_2$, $=O$, $=S$, $=N(R^{20})$, —$P(O)(OR^{20})_2$, —$P(O)(R^{20})_2$, —$OP(O)(OR^{20})_2$, and —$CN$; $C_{1-6}$ alkyl, $C_{2-6}$ alkenyl, and $C_{2-6}$ alkynyl, each of which is independently optionally substituted at each occurrence with one or more substituents selected from halogen, —$OR^{20}$, —$SR^{20}$, —$N(R^{20})_2$, —$N(R^{20})C(O)R^{20}$, —$C(O)R^{20}$, —$C(O)OR^{20}$, —$C(O)N(R^{20})_2$, —$OC(O)R^{20}$, —$S(O)_2R^{20}$, —$S(O)_2N(R^{20})_2$, —$N(R^{20})S(O)_2R^{20}$, —$NO_2$, $=O$, $=S$, $=N(R^{20})$, —$P(O)(OR^{20})_2$, —$P(O)(R^{20})_2$, —$OP(O)(OR^{20})_2$, —$CN$, $C_{3-10}$ carbocycle, and 3- to 10-membered heterocycle; and $C_{3-10}$ carbocycle and 3- to 10-membered heterocycle, wherein each $C_{3-10}$ carbocycle and 3- to 10-membered heterocycle of $R^{22}$ and $R^{23}$ is independently optionally substituted with one or more substituents selected from halogen, —$OR^{20}$, —$SR^{20}$, —$N(R^{20})_2$, —$N(R^{20})C(O)R^{20}$, —$C(O)R^{20}$, —$C(O)OR^{20}$, —$C(O)N(R^{20})_2$, —$OC(O)R^{20}$, —$S(O)_2R^{20}$, —$S(O)_2N(R^{20})_2$, —$N(R^{20})S(O)_2R^{20}$, —$NO_2$, $=O$, $=S$, $=N(R^{20})$, —$P(O)(OR^{20})_2$, —$P(O)(R^{20})_2$, —$OP(O)(OR^{20})_2$, —$CN$, $C_{1-6}$ alkyl, $C_{2-6}$ alkenyl, and $C_{2-6}$ alkynyl; or $R^{22}$ and $R^{23}$, together with the carbon atoms to which they are attached, form a carbocyclic ring;

$R^{24}$ is selected from hydrogen, —$C(O)R^{20}$, —$C(O)OR^{20}$, —$C(O)N(R^{20})_2$, —$OC(O)R^{20}$, —$S(O)_2R^{20}$, and —$S(O)_2N(R^{20})_2$; $C_{1-6}$ alkyl, $C_{2-6}$ alkenyl, and $C_{2-6}$ alkynyl, each of which is independently optionally substituted at each occurrence with one or more substituents selected from halogen, —$OR^{20}$, —$SR^{20}$, —$N(R^{20})_2$, —$N(R^{20})C(O)R^{20}$, —$C(O)R^{20}$, —$C(O)OR^{20}$, —$C(O)N(R^{20})_2$, —$OC(O)R^{20}$, —$S(O)_2R^{20}$, —$S(O)_2N(R^{20})_2$, —$N(R^{20})S(O)_2R^{20}$, —$NO_2$, $=O$, $=S$, $=N(R^{20})$, —$P(O)(OR^{20})_2$, —$P(O)(R^{20})_2$, —$OP(O)(OR^{20})_2$, —$CN$, $C_{3-10}$ carbocycle, and 3- to 10-membered heterocycle; and $C_{3-10}$ carbocycle and 3- to 10-membered heterocycle, wherein each $C_{3-10}$ carbocycle and 3- to 10-membered heterocycle of $R^{24}$ is independently optionally substituted with one or more substituents selected from halogen, —$OR^{20}$, —$SR^{20}$, —$N(R^{20})_2$, —$N(R^{20})C(O)R^{20}$, —$C(O)R^{20}$, —$C(O)OR^{20}$, —$C(O)N(R^{20})_2$, —$OC(O)R^{20}$, —$S(O)_2R^{20}$, —$S(O)_2N(R^{20})_2$, —$N(R^{20})S(O)_2R^{20}$, —$NO_2$, $=O$, $=S$, $=N(R^{20})$, —$P(O)(OR^{20})_2$, —$P(O)(R^{20})_2$, —$OP(O)(OR^{20})_2$, —$CN$, $C_{1-6}$ alkyl, $C_{2-6}$ alkenyl, and $C_{2-6}$ alkynyl; and $R^{32}$ is as described above.

In certain embodiments, for a compound or salt of any of Formulas (1), (2), and (3B), $L^1$ is selected from a bond, optionally substituted $C_{1-6}$ alkylene, such as methylene, ethylene or propylene; wherein $L^1$ is optionally substituted with one or more substituents selected from halogen, —$NO_2$, $=O$, $=S$, —$OR^{20}$, —$SR^{20}$, and —$N(R^{20})_2$.

In certain embodiments, for a compound or salt of any of Formulas (1), (2), and (3B), $R^{23}$ is selected from hydrogen; and $C_{1-6}$ alkyl, $C_{2-6}$ alkenyl, and $C_{2-6}$ alkynyl, each of which is independently optionally substituted at each occurrence with one or more substituents selected from halogen, —$OR^{20}$, —$SR^{20}$, —$N(R^{20})_2$, —$N(R^{20})C(O)R^{20}$, —$C(O)R^{20}$, —$C(O)OR^{20}$, —$C(O)N(R^{20})_2$, —$OC(O)R^{20}$, —$S(O)_2R^{20}$, —$S(O)_2N(R^{20})_2$, —$N(R^{20})S(O)_2R^{20}$, —$NO_2$, $=O$, $=S$, $=N(R^{20})$, —$P(O)(OR^{20})_2$, —$P(O)(R^{20})_2$, —$OP(O)(OR^{20})_2$, —$CN$, $C_{3-10}$ carbocycle and 3- to 10-membered heterocycle; and $C_{3-10}$ carbocycle, and 3- to 10-membered heterocycle, wherein each $C_{3-10}$ carbocycle and 3- to 10-membered heterocycle of $R^{23}$ is independently optionally substituted with one or more substituents selected from halogen, —$OR^{20}$, —$SR^{20}$, —$N(R^{20})_2$, —$N(R^{20})C(O)R^{20}$, —$C(O)R^{20}$, —$C(O)OR^{20}$, —$C(O)N(R^{20})_2$, —$OC(O)R^{20}$, —$S(O)_2R^{20}$, —$S(O)_2N(R^{20})_2$, —$N(R^{20})S(O)_2R^{20}$, —$NO_2$, $=O$, $=S$, $=N(R^{20})$, —$P(O)(OR^{20})_2$, —$P(O)(R^{20})_2$, —$OP(O)(OR^{20})_2$, —$CN$, $C_{1-6}$ alkyl, $C_{2-6}$ alkenyl, and $C_{2-6}$ alkynyl.

In certain embodiments, for a compound or salt of any of Formulas (1), (2), and (3B), $R^{22}$ is selected from hydrogen, and —$CN$; $C_{1-6}$ alkyl, $C_{2-6}$ alkenyl, and $C_{2-6}$ alkynyl, each of which is independently optionally substituted at each occurrence with one or more substituents selected from halogen, —$OR^{20}$, —$SR^{20}$, —$N(R^{20})_2$, —$N(R^{20})C(O)R^{20}$, —$C(O)R^{20}$, —$C(O)OR^{20}$, —$C(O)N(R^{20})_2$, —$OC(O)R^{20}$, —$S(O)_2R^{20}$, —$S(O)_2N(R^{20})_2$, —$N(R^{20})S(O)_2R^{20}$, —$NO_2$, $=O$, $=S$, $=N(R^{20})$, —$P(O)(OR^{20})_2$, —$P(O)(R^{20})_2$, —$OP(O)(OR^{20})_2$, —$CN$, $C_{3-10}$ carbocycle and 3- to 10-membered heterocycle; and $C_{3-10}$ carbocycle and 3- to 10-membered heterocycle, wherein each $C_{3-10}$ carbocycle and 3- to 10-membered heterocycle of $R^{22}$ is independently optionally substituted with one or more substituents selected from halogen, —$OR^{20}$, —$SR^{20}$, —$N(R^{20})_2$, —$N(R^{20})C(O)R^{20}$, —$C(O)R^{20}$, —$C(O)OR^{20}$, —$C(O)N(R^{20})_2$, —$OC(O)R^{20}$, —$S(O)_2R^{20}$, —$S(O)_2N(R^{20})_2$, —$N(R^{20})S(O)_2R^{20}$, —$NO_2$, $=O$, $=S$, $=N(R^{20})$, —$P(O)(OR^{20})_2$, —$P(O)(R^{20})_2$, —$OP(O)(OR^{20})_2$, —$CN$, $C_{1-6}$ alkyl, $C_{2-6}$ alkenyl, and $C_{2-6}$ alkynyl. In particular embodiments, $R^{22}$ is selected from hydrogen, —$CN$; and $C_{1-6}$ alkyl optionally substituted with one or more substituents selected from halogen, —$OR^{20}$, —$SR^{20}$, and —$N(R^{20})_2$.

In certain embodiments, for a compound or salt of any of Formulas (1), (2), and (3B), $R^{24}$ is selected from hydrogen and $C_{1-6}$ alkyl optionally substituted with one or more substituents selected from halogen, —$OR^{20}$, —$SR^{20}$, —$N(R^{20})_2$, —$NO_2$, $=O$, and —$CN$.

In certain embodiments, for a compound or salt of any of Formulas (1), (2), and (3B), $R^{21}$ is selected from:

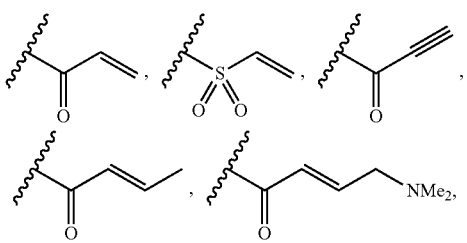

-continued
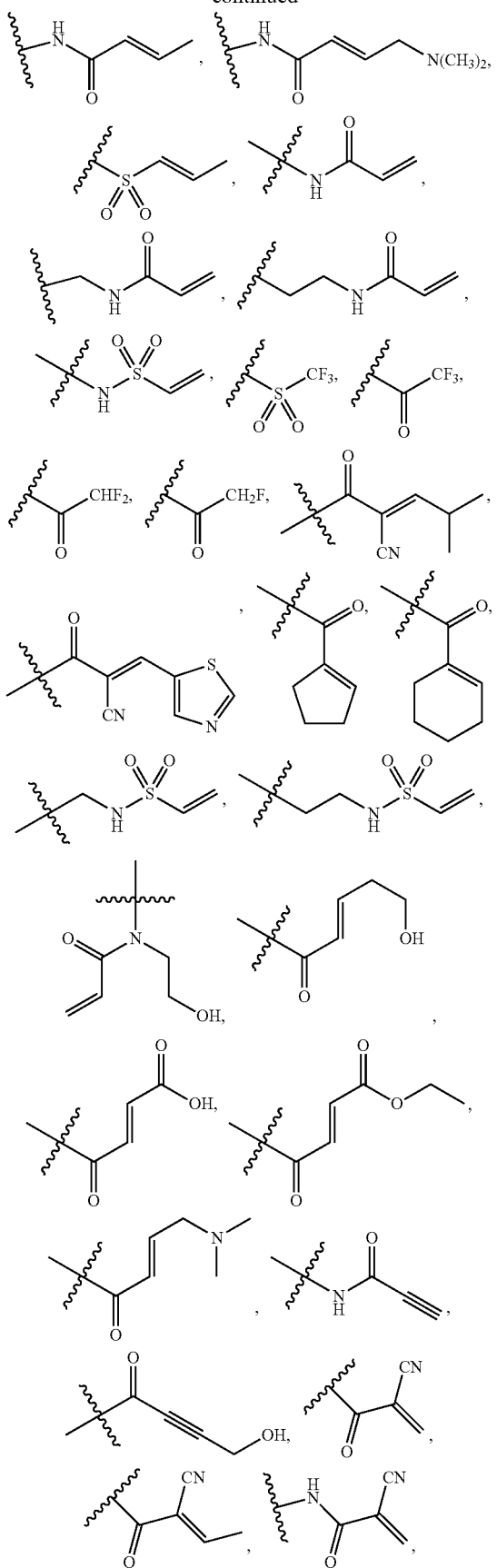
-continued
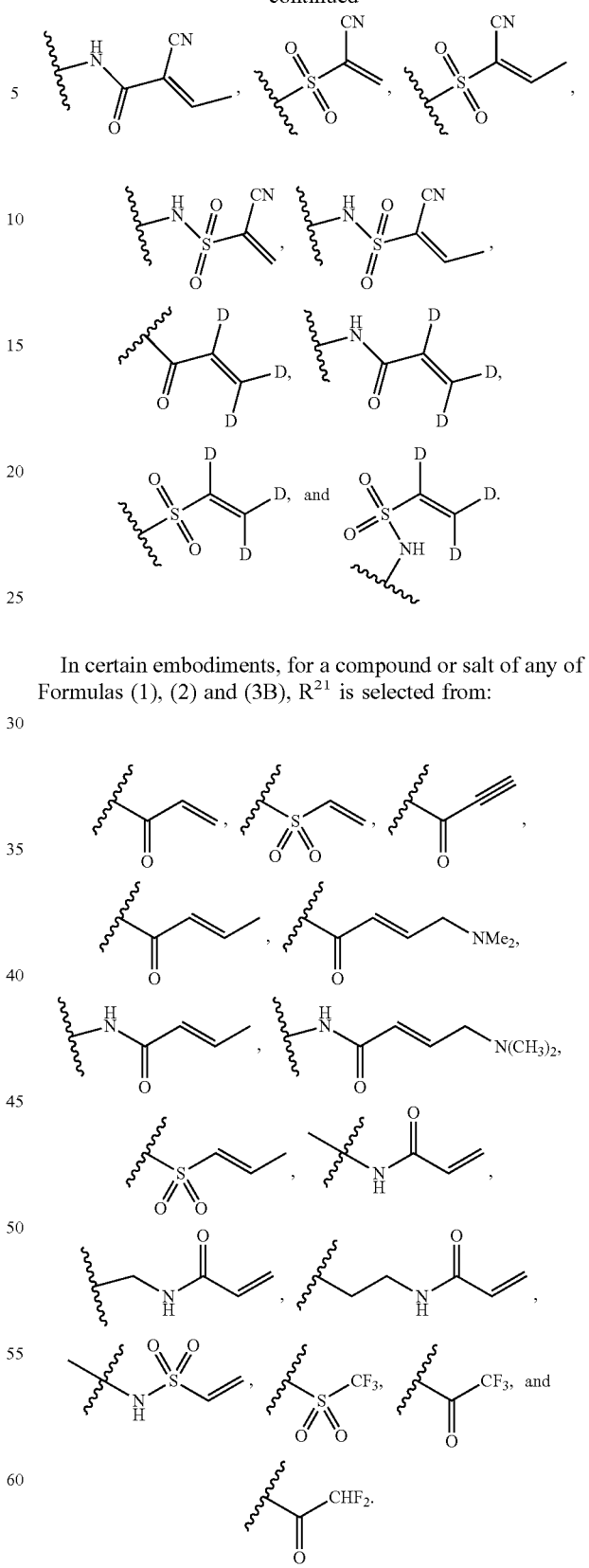
In certain embodiments, for a compound or salt of any of Formulas (1), (2) and (3B), $R^{21}$ is selected from:
In certain embodiments, for a compound or salt of any of Formulas (1), (2) and (3B), $R^{21}$ is selected from:

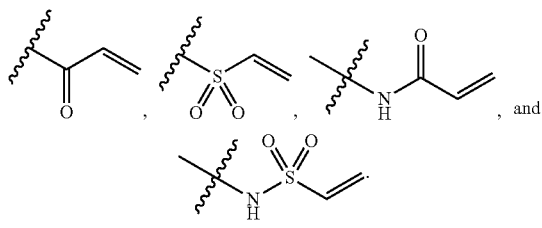

In certain embodiments, for a compound or salt of any of Formulas (1), (2), and (3B), G is selected from a bond, alkylene, heteroalkylene, $C_{3-12}$ carbocycle, and 3- to 12-membered heterocycle, wherein G is optionally substituted with one or more $R^{32}$ groups.

In certain embodiments, for a compound or salt of any of Formulas (1), (2), and (3B), G is selected from a bond; or alkylene optionally substituted with one or more $R^{32}$ groups. In certain embodiments, $R^{32}$ at each occurrence on G is selected from halogen, —$OR^{20}$, —$SR^{20}$, —$N(R^{20})_2$, —$N(R^{20})C(O)R^{20}$, —$C(O)R^{20}$, —$C(O)OR^{20}$, —$C(O)N(R^{20})_2$, —$OC(O)R^{20}$, —$S(O)_2R^{20}$, —$S(O)_2N(R^{20})_2$, —$N(R^{20})S(O)_2R^{20}$, —$NO_2$, =O, =S, =$N(R^{20})$, —$P(O)(OR^{20})_2$, —$P(O)(R^{20})_2$, —$OP(O)(OR^{20})_2$, and —CN; $C_{1-6}$ alkyl, $C_{2-6}$ alkenyl, and $C_{2-6}$ alkynyl, each of which is independently optionally substituted at each occurrence with one or more substituents selected from halogen, —$OR^{20}$, —$SR^{20}$, —$N(R^{20})_2$, —$N(R^{20})C(O)R^{20}$, —$C(O)R^{20}$, —$C(O)OR^{20}$, —$C(O)N(R^{20})_2$, —$OC(O)R^{20}$, —$S(O)_2R^{20}$, —$S(O)_2N(R^{20})_2$, —$N(R^{20})S(O)_2R^{20}$, —$NO_2$, =O, =S, =$N(R^{20})$, —$P(O)(OR^{20})_2$, —$P(O)(R^{20})_2$, —$OP(O)(OR^{20})_2$, —CN, $C_{3-10}$ carbocycle, and 3- to 10-membered heterocycle; $C_{3-10}$ carbocycle and 3- to 10-membered heterocycle; or two $R^{32}$ on the same carbon atom can come together to form a $C_{3-10}$ carbocycle or 3- to 10-membered heterocycle, wherein each $C_{3-10}$ carbocycle and 3- to 10-membered heterocycle of $R^{32}$ is independently optionally substituted with one or more substituents selected from halogen, —$OR^{20}$, —$SR^{20}$, —$N(R^{20})_2$, —$N(R^{20})C(O)R^{20}$, —$C(O)R^{20}$, —$C(O)OR^{20}$, —$C(O)N(R^{20})_2$, —$OC(O)R^{20}$, —$S(O)_2R^{20}$, —$S(O)_2N(R^{20})_2$, —$N(R^{20})S(O)_2R^{20}$, —$NO_2$, =O, =S, =$N(R^{20})$, —$P(O)(OR^{20})_2$, —$P(O)(R^{20})_2$, —$OP(O)(OR^{20})_2$, —CN, $C_{1-6}$ alkyl, $C_{2-6}$ alkenyl, and $C_{2-6}$ alkynyl;

$R^{20}$ at each occurrence is independently selected from hydrogen; $C_{1-6}$ alkyl, $C_{2-6}$ alkenyl, and $C_{2-6}$ alkynyl, each of which is independently optionally substituted at each occurrence with one or more substituents selected from halogen, —$OR^{30}$, —$SR^{30}$, —$N(R^{30})_2$, —$N(R^{30})C(O)R^{30}$, —$C(O)R^{30}$, —$C(O)OR^{30}$, —$C(O)N(R^{30})_2$, —$OC(O)R^{30}$, —$S(O)_2R^{30}$, —$S(O)_2N(R^{30})_2$, —$N(R^{30})S(O)_2R^{30}$, —$NO_2$, —$P(O)(OR^{30})_2$, —$P(O)(R^{30})_2$, —$OP(O)(OR^{30})_2$, and —CN; and 3- to 10-membered heterocycle and $C_{3-10}$ carbocycle; and $R^{30}$ at each occurrence is independently selected from hydrogen, $C_{1-6}$ alkyl, $C_{2-6}$ alkenyl, and $C_{2-6}$ alkynyl.

In certain embodiments, for a compound or salt of any of Formulas (1), (2), and (3B), G is alkylene optionally substituted with one or more $R^{32}$ groups. In certain embodiments, G is selected from optionally substituted $C_{1-10}$ alkylene. In particular embodiments, G is selected from methylene, ethylene, propylene, and butylene, any one of which is optionally substituted with one or more $R^{32}$ groups, for example, G is selected from:

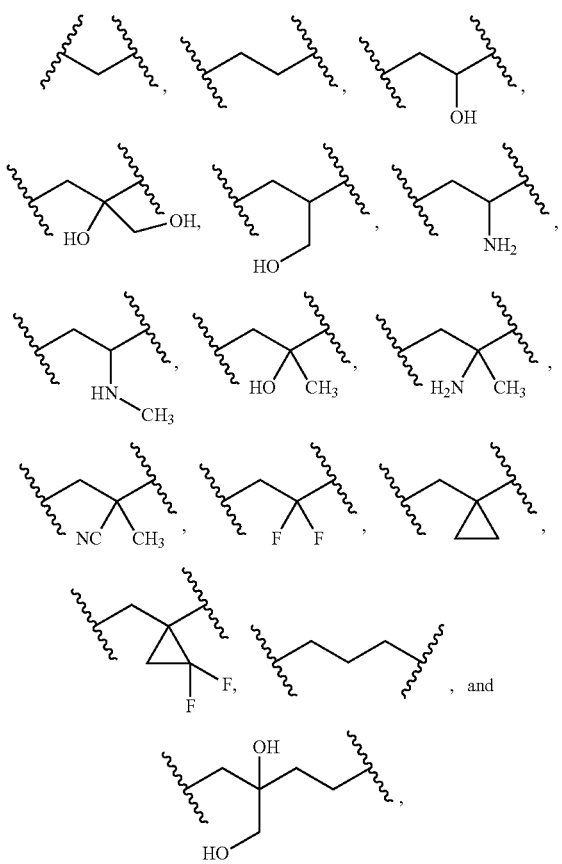

wherein any one of which is optionally substituted with one or more $R^{32}$ groups.

In certain embodiments, for a compound or salt of any of Formulas (1), (2), and (3B), G is heteroalkylene optionally substituted with one or more $R^{32}$ groups.

In certain embodiments, for a compound or salt of any of Formulas (1), (2), and (3B), G is $C_{3-10}$ carbocycle or 3- to 10-membered heterocycle, any one of which is optionally substituted with one or more $R^{32}$ groups. In particular embodiments, for a compound or salt of any of Formulas (1), (2), and (3B), G is a saturated $C_{3-10}$ carbocycle or saturated 3- to 10-membered heterocycle, any one of which is optionally substituted with one or more $R^{32}$ groups, for example, G is selected from:

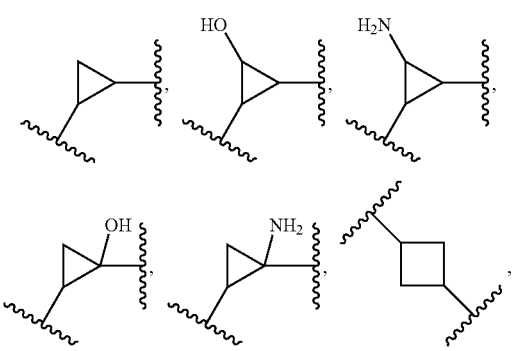

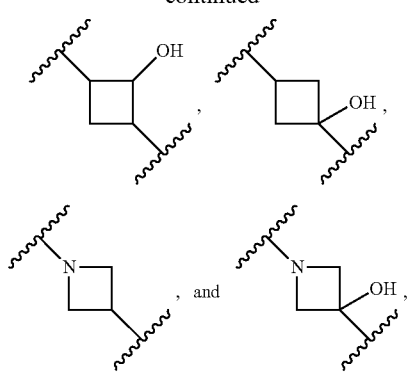

wherein any one of which is optionally substituted with one or more $R^{32}$ groups.

In certain embodiments, for a compound or salt of any of Formulas (1), (2), and (3B), V is selected from a 3-8 membered saturated carbocyclic or heterocyclic ring optionally substituted with one or more $R^{32}$ groups. In certain embodiments, V is a 3-, 4-, 5-, 6- or 7-membered saturated carbocycle, any one of which is optionally substituted with one or more $R^{32}$ groups. In particular embodiments, V is selected from:

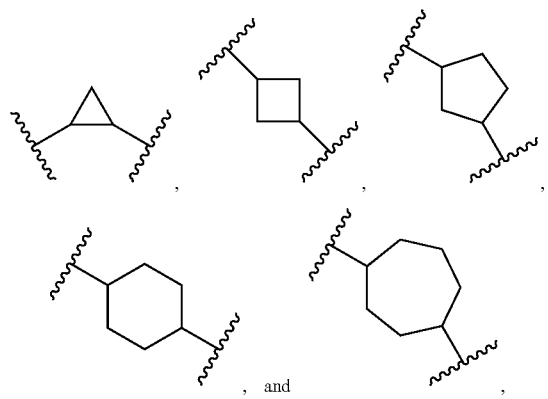

and any one of which is optionally substituted with one or more $R^{32}$ groups. In certain embodiments, V is a 4-, 5-, 6-, 7- or 8-membered saturated heterocycle, any one of which is optionally substituted with one or more $R^{32}$ groups. In particular embodiments, V is selected from azetidine, oxetane, piperidine, oxane, piperazine, pyrrolidine, tetrahydrofuran, thiolane, imidazolidine, morpholine, thiomorpholine, azepane, and homopiperazine, any one of which is optionally substituted with one or more $R^{32}$ groups. In particular embodiments, V is selected from:

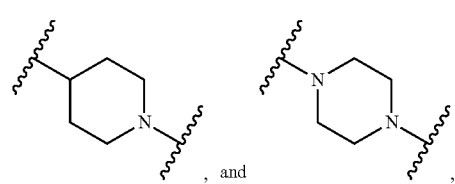

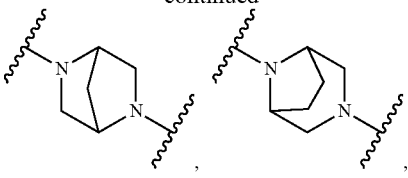

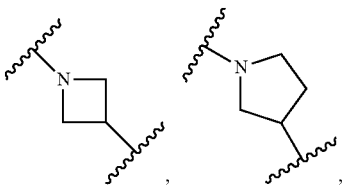

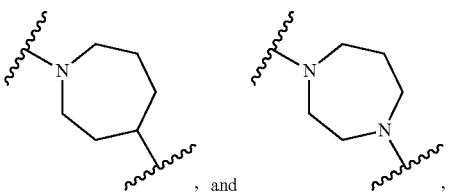

any one of which is optionally substituted with one or more $R^{32}$ groups.

In certain embodiments, for a compound or salt of any of Formulas (1), (2), and (3B), V is selected from an unsaturated, aromatic, or heteroaromatic ring. In particular embodiments, V is selected from phenyl, pyridine, pyrazine, pyrimidine, pyridazine, naphthalene, anthracene, quinoline, isoquinoline, quinoxaline, acridine, quinazoline, cinnoline, phthalazine, furan, dihydrofuran, thiophene, dihydrothiophene, imidazole, imidazoline, oxazole, oxazoline, pyrrole, dihydropyrrole, thiazole, dihydrothiazole, pyrazole, dihydropyrazole, isoxazole, dihydroisoxazole, isothiazole, dihydroisothiazole, benzofuran, isobenzofuran, indole, isoindole, benzothiophene, benzimidazole, purine, indazole, benzoxazole, benzisoxazole, and benzothiazole, any one of which is optionally substituted with one or more $R^{32}$ groups. In more particular embodiments, V is phenyl, optionally substituted with one or more $R^{32}$ groups. In certain embodiments, V is a heteroaromatic ring optionally substituted with one or more $R^{32}$ groups. In particular embodiments, V is selected from pyridine, pyrazine, pyrimidine, pyridazine, naphthalene, anthracene, quinoline, isoquinoline, quinoxaline, acridine, quinazoline, cinnoline, phthalazine, furan, thiophene, imidazole, oxazole, pyrrole, thiazole, pyrazole, isoxazole, isothiazole, benzofuran, isobenzofuran, indole, isoindole, benzothiophene, benzimidazole, purine, indazole, benzoxazole, benzisoxazole, and benzothiazole, any one of which is optionally substituted with one or more $R^{32}$ groups, such as V is selected from

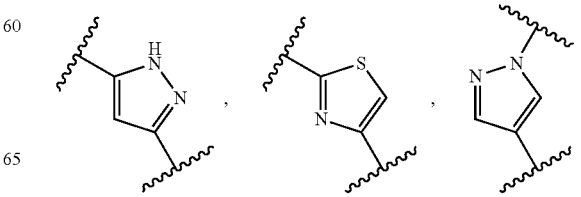

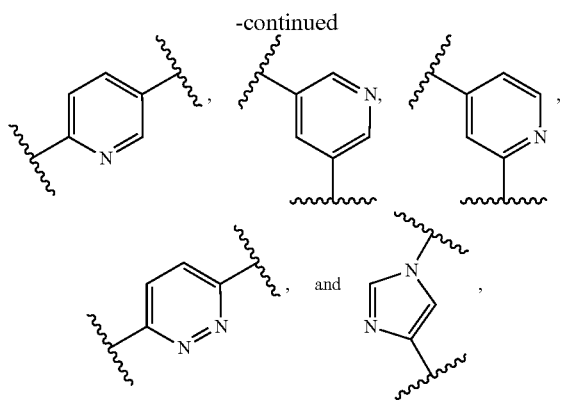

wherein any one of which is optionally substituted with one or more $R^{32}$ groups.

In certain embodiments, for a compound or salt of any of Formulas (1), (2), and (3B), V is absent.

In some embodiments, the compounds of the disclosure are selected from Scaffold 1 or Scaffold 2:

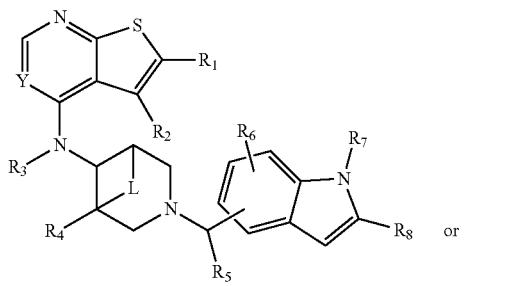

(Scaffold 1)

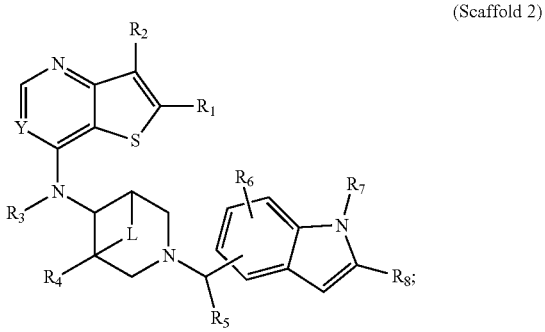

(Scaffold 2)

wherein R1, R2, R3, R4, R5, R6, and R8, each independently comprise or consist of: H, alkyl group (e.g., straight-chain alkyl (e.g., methane, ethane, propane, butane, pentane, hexane, etc.), branched alkyl group (e.g., iso-propyl, 2-methyl-hexane, 3-methyl, 2-propyl-octane, etc.), cycloalkyl (e.g., cyclopropane, cyclobutane, cyclopentane, cyclohexane, cyclooctane, etc.), branched cyclic alkyl (e.g., methylcyclohexane, ethylcyclobutane, propylcyclohexane, etc.)), a substituted alkyl group (e.g., halogen-substituted alkyl group (e.g., trihaloethane (e.g., trifluoroethane), dihaloethane (e.g. difluroethane), haloethane (e.g. fluoroethane), halomethane (e.g., fluoromethane), dihalomethane (e.g., difluoromethane), trihalomethane (e.g., trifluoromethane), etc.), alkene (e.g., $CH=CH_2$, $CH_2CH=CH_2$, $CH=CHCH_3$, etc.), alkyne (e.g., $C\equiv CH$, $C\equiv CCH_3$, $CH_2C\equiv CH$, etc.), hydroxyl, alkoxy group (e.g., ether, etc.), amine, alkylamine (e.g., primary amine (e.g., ethylamine, iso-butylamine, n-propylamine, sec-butylamine, iso-pro-pylamine, iso-amylamine, methylamine, dimethylamine, n-amylamine, etc.), secondary amines (e.g., dimethylamine, methylethanolamine, diphenylamine, etc.), tertiary amine (e.g., trimethylamine, triphenylamine, etc.), thioalkyl, combinations thereof, etc.), a substituted cycloalkyl group (e.g., halogen-substituted cycloalkyl group, cycloalkoxy group, cycloalkylamine, etc.), a halogen (e.g., F, Cl, Br, I, and At), a ketone, an amide, an alkylamide, a cyano group, methyl carbonitrile (e.g. $CH_2CN$), $—SO_2CH_3$ group, $—SO_2NH_2$ group, sulfonyl group, dialkylphosphine oxide (e.g., $—PO(CH_3)_2$), a carbocyclic ring, an aromatic ring, a substituted aromatic ring (e.g., branched aromatic ring (e.g., ethylbenzene, methyl benzene, etc.), halobenzene (e.g., chlorobenzene, fluorobenzene, etc.)), a heterocyclic aromatic ring (e.g., comprising one or more nitrogen, oxygen and/or sulfur members which may be non-substituted or substituted with alkyl, aryl, halogen, hydrogen bond donor or acceptor), a substituted or non-substituted heterocyclic non-aromatic ring (e.g., comprising carbon and one or more nitrogen, oxygen and/or sulfur members), carbocyclic or heterocyclic aromatic ring comprising carbon atoms and one or more nitrogen, oxygen and/or sulfur members fused to another aromatic ring, a multi-ring system comprising a combination of elements selected from aromatic rings, cycloalkane, heterocyclic rings, alkyl chains, and suitable C-, N-, O-, S-, and/or halogen-containing substituents, or a hydrogen bond donor or a hydrogen bond acceptor, and/or combinations thereof; and wherein any of the H atoms, R6, and R8 on the indole of the scaffold may be replaced with one of: halogen (e.g., F, Cl, Br, I, etc.), hydroxyl, alcohol (e.g., methanol, ethanol, etc.), alkyl ($C_1$-$C_5$), alkoxy (e.g. methoxy, ethoxy, etc), amine (e.g. $NH_2$, methylamine, ethylamine, etc), cyano group (e.g., CN, methyl carbonitrile, ethyl carbonitrile, etc.), an amide (e.g. $CONH_2$, acetamide, etc), $—SO_2CH_3$ group, and dialkylphosphine oxide (e.g., $—PO(CH_3)_2$); wherein R6 can be present on either the benzyl and/or pyrrole portion of the indole ring and wherein R6 can be present at one or more of the positions of the benzyl and/or pyrrole portion of the indole ring that are not otherwise occupied by a substituent; and wherein Y is N or C, and wherein when Y is C the Y position may be substituted with $R^a$, with $R^a$ consisting of or comprising a hydrogen, an alkyl (e.g., branched (e.g., iso-propyl), straight chain (e.g., propyl), cycloalkyl (e.g., cyclopropyl)), heteroalkyl (e.g., methyl propyl ether), alkyl-substituted aryl (e.g., ethylbenzene), substituted alkyl (e.g., halo-substituted alkyl (e.g., trihalomethyl group (e.g., trifluoromethyl group), monohaloalkyl group (e.g. monofluoroethyl group), dihaloalkyl group (e.g. difluoroethyl group), trihaloethyl group (e.g., trifluoroethyl group), trihalopropyl (e.g., trifluoropropyl ($(CH_2)_2CF_3$), trihalobutyl group (e.g., trifluorobutyl group ($(CH_2)_3CF_3$)), trihaloisopropyl (e.g., trifluoroisopropyl, 1-fluoro, 2-trifluoro, ethane, 1-trifluoro, 2-ethanol), alcohol (e.g., $(CH_2)_nOH$, wherein n=0-10), alkoxy (e.g., $(CH_2)_n$—OR, wherein n=0-10, wherein R is alkyl, $(CH_2)_n$-aryl, $(CH_2)_n$-aromatic, $(CH_2)_n$-non-aromatic heterocycle, substituted or non-substituted aryl, aromatic or non-aromatic heterocycle with one or more N, S, O, etc.), amino (e.g., alkyl amine, amino alkyl, etc.), cyano, sulfonyl, methoxy, aldehyde, non-aromatic heterocycle, aromatic, combinations thereof, etc.;

wherein L is present or absent, and if present it comprises alkylene (e.g. methylene, $—CH_2—$, ethylene, $—CH_2—CH_2—$, propylene, $—CH_2—CH_2—CH_2—$, etc), aminoalkylene (e.g. $—NH—$, $—CH_2—NH—CH_2$) or oxalkylene (e.g. $—O—$, $—CH_2—O—CH_2$) groups; and wherein R7 comprises:

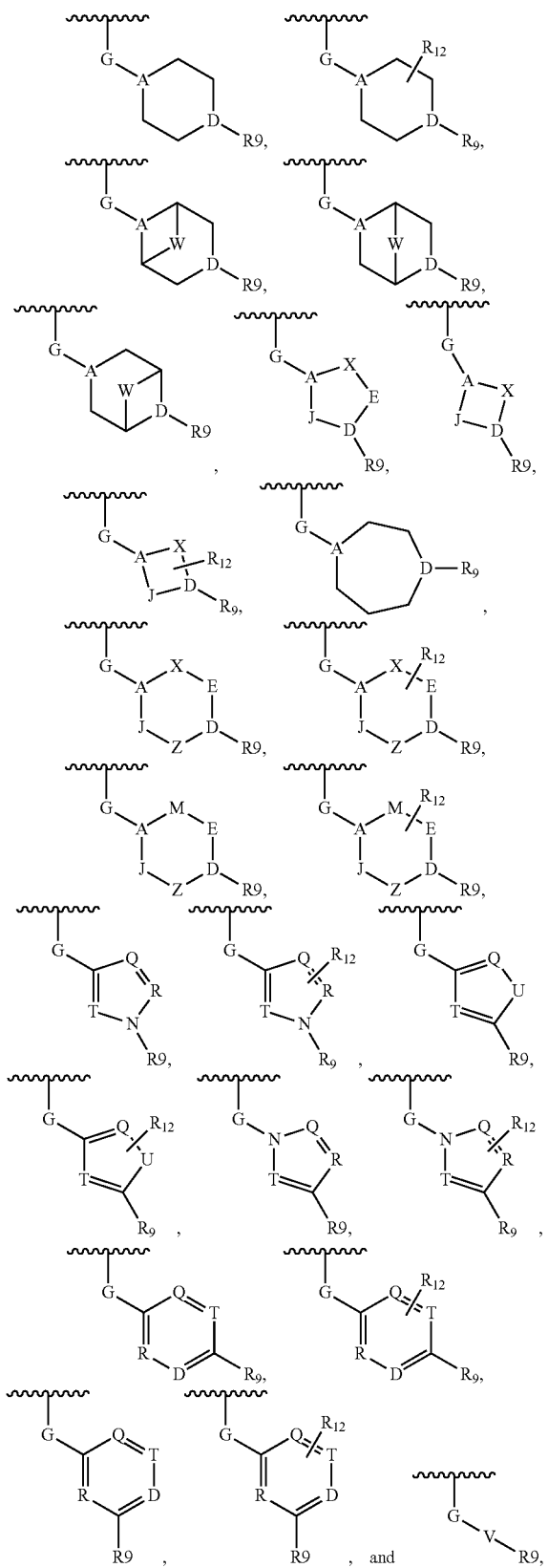

H, alkyl group (e.g., straight-chain alkyl (e.g., methane, ethane, propane, butane, pentane, hexane, etc.), branched alkyl group (e.g., iso-propyl, 2-methyl-hexane, 3-methyl, 2-propyl-octane, etc.), cycloalkyl (e.g., cyclopropane, cyclobutane, cyclopentane, cyclohexane, cyclooctane, etc.), branched cyclic alkyl (e.g., methylcyclohexane, ethylcyclobutane, propylcyclohexane, etc.)), a substituted alkyl group (e.g., halogen-substituted alkyl group (e.g., trihaloethane (e.g., trifluoroethane), halomethane (e.g., fluoromethane), dihalomethane (e.g., difluoromethane), trihalomethane (e.g., trifluoromethane), etc.), alkene (e.g., $CH=CH_2$, $CH_2CH=CH_2$, $CH=CHCH_3$, etc.), alkyne (e.g., $C\equiv CH$, $C\equiv CCH_3$, $CH_2C\equiv CH$, etc.), alkoxy group (e.g., ether, etc.), amine, alkylamine (e.g., primary amine (e.g., ethylamine, iso-butylamine, n-propylamine, sec-butylamine, iso-propylamine, iso-amylamine, methylamine, dimethylamine, n-amylamine, etc.), secondary amines (e.g., dimethylamine, methylethanolamine, diphenylamine, etc.), tertiary amine (e.g., trimethylamine, triphenylamine, etc.), thioalkyl, combinations thereof, etc.), a substituted cycloalkyl group (e.g., halogen-substituted cycloalkyl group, cycloalkoxy group, cycloalkylamine, etc.), a ketone, an amide, an alkylamide, a cyano group, methyl carbonitrile (e.g. $CH_2CN$), $-SO_2CH_3$ group, sulfonyl group, a carbocyclic ring, an aromatic ring, a substituted aromatic ring (e.g., branched aromatic ring (e.g., ethylbenzene, methyl benzene, etc.), halobenzene (e.g., chlorobenzene, fluorobenzene, etc.)), a heterocyclic aromatic ring (e.g., comprising one or more nitrogen, oxygen and/or sulfur members which may be non-substituted or substituted with alkyl, aryl, halogen, hydrogen bond donor or acceptor) connected directly or through a linker (e.g. methyl, ethyl, propyl) with the indole nitrogen, a substituted or non-substituted heterocyclic non-aromatic ring (e.g., comprising carbon and one or more nitrogen, oxygen and/or sulfur members, e.g. piperazine, piperidine, azetidine, pyrrolidine, azepane, etc.) connected directly or through a linker (e.g. methyl, ethyl, propyl) with the indole nitrogen, carbocyclic or heterocyclic aromatic ring comprising carbon atoms and one or more nitrogen, oxygen and/or sulfur members fused to another aromatic ring, a multi-ring system comprising a combination of elements selected from aromatic rings, cycloalkane, heterocyclic rings, alkyl chains, and suitable C-, N-, O-, S-, and/or halogen-containing substituents, or a hydrogen bond donor or a hydrogen bond acceptor, an electrophilic group such as any electrophilic group capable of covalently and/or irreversible binding to cysteine sulfhydryl groups, and/or combinations thereof;

wherein G, when present, comprises alkylene (e.g. methylene, $-CH_2-$, ethylene, $-CH_2-CH_2-$, propylene, $-CH_2-CH_2-CH_2-$, etc), branched alkylene (e.g. $-CH(CH_3)-CH_2-$, $-CH_2-CH(CH_3)-$, etc.), aminoalkylene (e.g. $-NH-$, $-CH_2-NH-CH_2$), oxalkylene (e.g. $-O-$, $-CH_2-O-CH_2$), haloalkylene groups; heteroalkyl; hydroxyalkyl (e.g. $-CH(OH)-$, $-CH(OH)-CH_2-$, $-CH(OH)-CH_2-$, $CH_2-CH(OH)-$, $-CH_2-CH(OH)-CH_2$, $-CH(OH)-CH_2-CH_2-$, $-CH_2-CH_2-CH(OH)-$, etc.), alkylhydroxyalkyl (e.g. $-CH_2-CH(CH_2OH)$, etc.), alkoxyalkyl (e.g. $-CH_2-CH(OCH_3)$, etc.), aminoalkyl or alkylamine (e.g. $-CH(NH_2)-$, $-CH(NH_2)-CH_2-$, $-CH_2-CH(NH_2)-$, etc.), alkylaminoalkyl (e.g. $-CH_2-CH(NHCH_2)$, etc.)-, etc.), carbocycle (cyclopropane, cyclobutane, cyclopentane, etc.), alkylcycloalkyl (e.g. methylcyclopropyl, methylcyclobuthyl, methylcyclopenthyl, etc.), hydoxycycloalkyl (e.g. hydroxycyclopropyl, dihydroxycyclopropyl, hydroxycyclobuthyl, dihydroxycyclobuthyl, hydroxycyclopenthyl, etc), alcoxycycloalkyl, hydroxalkylycycloalkyl (e.g. hydroxymethylcyclopropyl, hydroxymethylcyclobuthyl), disubstituted cycloalkyl (e.g. methyl-hydroxy-substituted cycloaklyl), aminocycloalkyl (e.g. aminocyclopropyl, diaminocyclopenthyl, aminocycclobuthyl, diaminocyclobuthyl, aminocyclopenthyl, etc.), alkylaminocycloalkyl (e.g. methylaminocyclopropyl, methylaminocyclobuthyl, etc.), substituted carbocycle, heterocycle (e.g., aziridine, azetidine, pyrrole, etc); substituted non-aromatic heterocycle (e.g., hydroxy azetidine, etc), and/or combinations thereof;

wherein V is selected from a 3-7 membered saturated ring, 3-7 membered unsaturated ring, 4-10 membered fused bicyclic ring, and 5-11 membered spiro bicyclic ring; wherein V may be optionally substituted with one or more R12 groups;

wherein R12, when present, comprises H, alkyl group (e.g., straight-chain alkyl (e.g., methane, ethane, propane, butane, pentane, hexane, etc.)), branched alkyl group (e.g., iso-propyl, 2-methyl-hexane, 3-methyl, 2-propyl-octane, etc.), cycloalkyl (e.g., cyclopropane, cyclobutane, cyclopentane, cyclohexane, cyclooctane, etc.), branched cyclic alkyl (e.g., methylcyclohexane, ethylcyclobutane, propylcyclohexane, etc.)), a substituted alkyl group (e.g., halogen-substituted alkyl group (e.g., trihaloethane (e.g., trifluoroethane), dihaloethane (e.g. difluroethane), haloethane (e.g. fluoroethane), halomethane (e.g., fluoromethane), dihalomethane (e.g., difluoromethane), trihalomethane (e.g., trifluoromethane), etc.), alkene (e.g., CH=CH$_2$, CH$_2$CH=CH$_2$, CH=CHCH$_3$, etc.), alkyne (e.g., C≡CH, C≡CCH$_3$, CH$_2$C≡CH, etc.), hydroxyl (e.g. —OH), hydroxyalkyl (e.g. —CH$_2$OH, etc), alkoxy group (e.g., ether, —CH$_2$—O-alky, CH$_2$—O-cycloalkyl (e.g., —CH$_2$—O-cyclopropyl, etc.), etc.), amine, alkylamine (e.g., primary amine (e.g., ethylamine, iso-butylamine, n-propylamine, sec-butylamine, iso-propylamine, iso-amylamine, methylamine, dimethylamine, n-amylamine, etc.), secondary amines (e.g., dimethylamine, methylethanolamine, diphenylamine, etc.), tertiary amine (e.g., trimethylamine, triphenylamine, etc.), thioalkyl, combinations thereof, etc.), a substituted cycloalkyl group (e.g., halogen-substituted cycloalkyl group, cycloalkoxy group, cycloalkylamine, etc.), a halogen (e.g., F, Cl, Br, I, and At), a ketone, an amide, an alkylamide, a cyano group, methyl carbonitrile (e.g. CH$_2$CN), —SO$_2$alkyl (e.g., —SO$_2$CH$_3$, —SO$_2$ethyl, —SO$_2$propyl, —SO$_2$cyclopropyl, etc.,), —SO$_2$NH$_2$ (e.g., —SO$_2$NHalkyl (e.g., —SO$_2$NHmethyl, —SO$_2$NHethyl, —SO$_2$NHpropyl, —SO$_2$NHcyclopropyl, etc.), SO$_2$Ndialkyl (e.g., —SO$_2$N-nm, wherein n and m are independently selected from methyl, ethyl, propyl, cyclopropyl, etc.), sulfonyl group, dialkylphosphine oxide (e.g., —PO(CH$_3$)$_2$), a carbocyclic ring, an aromatic ring, a substituted aromatic ring (e.g., branched aromatic ring (e.g., ethylbenzene, methyl benzene, etc.), halobenzene (e.g., chlorobenzene, fluorobenzene, etc.)), a heterocyclic aromatic ring (e.g., comprising one or more nitrogen, oxygen and/or sulfur members which may be non-substituted or substituted with alkyl, aryl, halogen, hydrogen bond donor or acceptor), a substituted or non-substituted heterocyclic non-aromatic ring (e.g., comprising carbon and one or more nitrogen, oxygen and/or sulfur members), carbocyclic or heterocyclic aromatic ring comprising carbon atoms and one or more nitrogen, oxygen and/or sulfur members fused to another aromatic ring, a multi-ring system comprising a combination of elements selected from aromatic rings, cycloalkane, heterocyclic rings, alkyl chains, and suitable C-, N-, O-, S-, and/or halogen-containing substituents, or a hydrogen bond donor or a hydrogen bond acceptor, and/or combinations thereof;

wherein A and D, when present, independently comprise C (CH) or N;

wherein E, J, X, and Z, when present, independently comprise C (CH), N, S, or O;

wherein M, when present, independently comprises (—CH$_2$—)$_n$, with n=0-4 wherein Q, R, T when present, independently comprises C (CH) or N wherein U when present independently comprises O, N or S wherein W, when present, comprises alkylene (e.g. methylene, —CH$_2$—, ethylene, —CH$_2$—CH$_2$—, propylene, —CH$_2$—CH$_2$—CH$_2$—, etc), aminoalkylene (e.g. —NH—, —CH$_2$—NH—CH$_2$), oxalkylene (e.g. —O—, —CH$_2$—O—CH$_2$) groups;

wherein one or more of any H atoms of R7 (e.g., H atoms on the R7 ring structure), when present, may independently be replaced with a halogen (e.g., F, Cl, Br, I, etc.), alcohol (e.g., OH, methanol, ethanol, etc.), alkyl (C1-C5), cycloalkyl (C1-C7), haloalkyl, alkene (C1-C5), alkyne (C1-C5), alkoxy (e.g. methoxy, ethoxy, etc), amine (e.g. NH$_2$, methylamine, ethylamine, etc), ester (methyl carboxylate, ethyl carboxylate etc.) cyano group (e.g., CN, methyl carbonitrile, ethyl carbonitrile, etc.), an amide (e.g. CONH$_2$, acetamide, etc), —SO$_2$CH$_3$ group, —SO$_2$alkyl, sulfonamide (e.g. SO$_2$NH$_2$, SO$_2$NHCH$_3$, SO$_2$NHCH$_2$CH$_3$ etc.) —COOH, etc.;

wherein R9, when present, comprises:

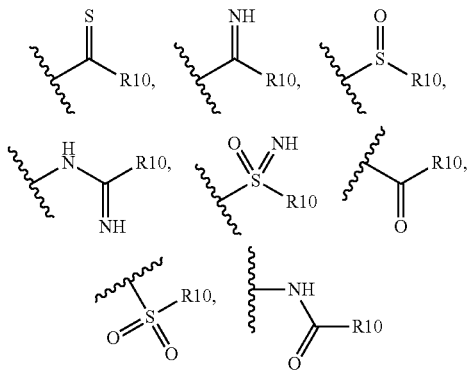

or

H, alkyl group (e.g., straight-chain alkyl (e.g., methane, ethane, propane, butane, pentane, hexane, etc.), branched alkyl group (e.g., iso-propyl, 2-methyl-hexane, 3-methyl, 2-propyl-octane, etc.), cycloalkyl (e.g., cyclopropane, cyclobutane, cyclopentane, cyclohexane, cyclooctane, etc.), branched cyclic alkyl (e.g., methylcyclohexane, ethylcyclobutane, propylcyclohexane, etc.)), a substituted alkyl group (e.g., halogen-substituted alkyl group (e.g., trihaloethane (e.g., trifluoroethane), halomethane (e.g., fluoromethane), dihalomethane (e.g., difluoromethane), trihalomethane (e.g., trifluoromethane), etc.), alkene (e.g., CH=CH$_2$, CH$_2$CH=CH$_2$, CH=CHCH$_3$, etc.), substituted alkene (e.g. halogen-substituted alkene group, e.g. chloroalkene, fluoroalkene) alkyne (e.g., C≡CH, C≡CCH$_3$, CH$_2$C≡CH, etc.), alkoxy group (e.g., ether, etc.), amine, alkylamine (e.g., primary amine (e.g., ethylamine, iso-butylamine, n-propylamine, sec-butylamine, iso-propylamine, iso-amylamine, methylamine, dimethylamine, n-amylamine, etc.), secondary amines (e.g., dimethylamine, methylethanolamine, diphenylamine, etc.), tertiary amine (e.g., trimethylamine, triphenylamine, etc.), thioalkyl, combinations thereof, etc.), a substituted cycloalkyl group (e.g., halogen-substituted cycloalkyl group, cycloalkoxy group, cycloalkylamine, etc.), a halogen (e.g., F, Cl, Br, I, and At), a ketone, an amide, an alkylamide, a cyano group, methyl carbonitrile (e.g. $CH_2CN$), —$SO_2CH_3$ group, sulfonyl group, amide group, a carbocyclic ring, an aromatic ring, a substituted aromatic ring (e.g., branched aromatic ring (e.g., ethylbenzene, methyl benzene, etc.), halobenzene (e.g., chlorobenzene, fluorobenzene, etc.)), a heterocyclic aromatic ring (e.g., comprising one or more nitrogen, oxygen and/or sulfur members which may be non-substituted or substituted with alkyl, aryl, halogen, hydrogen bond donor or acceptor), a substituted or non-substituted heterocyclic non-aromatic ring (e.g., comprising carbon and one or more nitrogen, oxygen and/or sulfur members), carbocyclic or heterocyclic aromatic ring comprising carbon atoms and one or more nitrogen, oxygen and/or sulfur members fused to another aromatic ring, a multi-ring system comprising a combination of elements selected from aromatic rings, cycloalkane, heterocyclic rings, alkyl chains, and suitable C-, N-, O-, S-, and/or halogen-containing substituents, or a hydrogen bond donor or a hydrogen bond acceptor, an electrophilic group such as any electrophilic group capable of covalent and/or irreversible binding to cysteine sulfhydryl groups, and/or combinations thereof;

wherein R10, when present, is selected from: H atom, halogen (e.g., Cl, Br, F, I), alkyl (e.g., methyl, ethyl, propyl, butyl, etc.), alkene (e.g., $CH=CH_2$, $CH_2CH=CH_2$, $CH=CHCH_3$, etc.), alkyne (e.g., $C≡CH$, $C≡CCH_3$, $CH_2C≡CH$, etc.), amine (e.g., $NH_2$, $CH_2NH_2$, $CH_2NHMe$, $CH_2NMe_2$, $CH_2NHEt$, $CH_2NEt_2$, etc.), alcohol (e.g., OH, $CH_2OH$, $CH_2CH_2OH$, etc.), thiol (e.g., SH, CH2SH, CH2CH2SH, etc.), O-alkyl (e.g., O-methyl, O-ethyl, O-propyl), N-alkyl (e.g., NH-methyl, NH-ethyl, NH-propyl), S-alkyl (e.g., S-methyl, S-ethyl, S-propyl), alkyl halides (e.g., $CH_2F$, $CHF_2$, $CF_3$, $CH_2CH_2F$, $CH_2CHF_2$, $CH_2CF_3$, or the same substituents with Cl, Br, or I in place of F, etc.), substituted alkene (e.g. halogen-substituted alkene group, e.g. chloroalkene, fluoroalkene, etc., alkyl substituted alkene, amino substituted alkene, etc.), substituted alkyne (e.g. halogen substituted alkyne group, e.g. chloroalkyne, fluoroalkyne, etc., alkyl substituted alkyne, amino substituted alkyne, etc.), nitrile (e.g., CN, $CH_2CN$, $CH_2CH_2CN$, etc.), aromatic ring (e.g., C3-C6), heteroaryl (e.g., C3-C6), non-aromatic heterocycle (e.g., C3-C6), carbocycle (e.g., C3-C7), $CH=CHCH_2N(CH_3)_n$ with n=0-3, an electrophilic group such as any electrophilic group capable of covalent and/or irreversible binding to cysteine sulfhydryl groups, any suitable hydrocarbon (e.g., alkane, alkene, alkyne, and combinations thereof) capped by R11 (e.g., $CH=CHCH_2R11$, $C≡CCH_2R11$), and any suitable combinations thereof (e.g., $CH=CHCH_2NMe_2$, $CH=CHCH_2NHCH_2$-furan, $C≡CCH_2OH$, $CH=CHCF_3$, $CH=CHCH_2N(CH_3)_2$, etc.);

wherein R11, when present, is selected from H, alkyl group (e.g., straight-chain alkyl (e.g., methane, ethane, propane, butane, pentane, hexane, etc.), branched alkyl group (e.g., iso-propyl, 2-methyl-hexane, 3-methyl, 2-propyl-octane, etc.), cycloalkyl (e.g., cyclopropane, cyclobutane, cyclopentane, cyclohexane, cyclooctane, etc.), branched cyclic alkyl (e.g., methylcyclohexane, ethylcyclobutane, propylcyclohexane, etc.)), a substituted alkyl group (e.g., halogen-substituted alkyl group (e.g., trihaloethane (e.g., trifluoroethane), halomethane (e.g., fluoromethane), dihalomethane (e.g., difluoromethane), trihalomethane (e.g., trifluoromethane), etc.), alkoxy group (e.g., ether, etc.), amine, alkylamine (e.g., primary amine (e.g., ethylamine, iso-butylamine, n-propylamine, sec-butylamine, iso-propylamine, iso-amylamine, methylamine, dimethylamine, n-amylamine, etc.), secondary amines (e.g., dimethylamine, methylethanolamine, diphenylamine, etc.), tertiary amine (e.g., trimethylamine, triphenylamine, etc.), thioalkyl, combinations thereof, etc.), a substituted cycloalkyl group (e.g., halogen-substituted cycloalkyl group, cycloalkoxy group, cycloalkylamine, etc.), a halogen (e.g., F, Cl, Br, I, and At), a ketone, an amide, an alkylamide, a cyano group, methyl carbonitrile (e.g. $CH_2CN$), —$SO_2CH_3$ group, sulfonyl group, a carbocyclic ring, an aromatic ring, a substituted aromatic ring (e.g., branched aromatic ring (e.g., ethylbenzene, methyl benzene, etc.), halobenzene (e.g., chlorobenzene, fluorobenzene, etc.)), a heterocyclic aromatic ring (e.g., comprising one or more nitrogen, oxygen and/or sulfur members which may be non-substituted or substituted with alkyl, aryl, halogen, hydrogen bond donor or acceptor), a substituted or non-substituted heterocyclic non-aromatic ring (e.g., comprising carbon and one or more nitrogen, oxygen and/or sulfur members), carbocyclic or heterocyclic aromatic ring comprising carbon atoms and one or more nitrogen, oxygen and/or sulfur members fused to another aromatic ring, a multi-ring system comprising a combination of elements selected from aromatic rings, cycloalkane, heterocyclic rings, alkyl chains, and suitable C-, N-, O-, S-, and/or halogen-containing substituents, or a hydrogen bond donor or a hydrogen bond acceptor, and/or combinations thereof.

In certain embodiments, $R_1$-$R_8$, L, and Y on compounds of Scaffold 1 and Scaffold 2 of the disclosure include one or more functional groups or a combination of two or more functional groups. Functional groups of the disclosure include, for example, halogens, alkanes, alkenes, alkynes, cycloalkanes, aromatic rings, heteroaromatic rings, non-aromatic rings, haloalkanes, alcohols, ketones, aldehydes, carboxylates, carboxylic acids, ethers, amides, primary amines, secondary amines, tertiary amines, azides, cyanates, cyano, nitriles, thiols, sulfides, sulfoxides, sulfones, sulfonamides, sulfinic acids, thiocyanate, and phosphates. Examples of alcohols include hydroxy, methanol, ethanol, propanol, butanol, pentanol, hexanol, cyclic alcohols (e.g., cyclohexanol), and aromatic alcohols (e.g., phenol). Examples of aldehydes include methanal, ethanal, propanal, butanal, pentanal, and hexanal. Examples of ketones include methyl methyl ketone (acetone), methyl ethyl ketone (butanone), and propyl ethyl ketone (pentanone). Examples of carboxylates include methanoate, ethanoate, propanote, butanoate, pentanoate, and hexanoate. Examples of Carboxylic acids include methanoic acid, ethanoic acid, propanoic acid, butanoic acid, pentanoic acid, and hexanoic acid. Examples of ethers include methoxymethyl, i.e., —$CH_2$—O—$CH_3$, and ethylmethoxy, i.e., —$CH_2$—$CH_2$—O—$CH_3$. Examples of amides include —$C(O)NH_2$, —$CH_2C(O)NH_2$, —$(CH_2)_2CONH_2$, —$(CH_2)_nC(O)NH_2$, —$(CH_2)_nC(O)NHCH_3$, —$(CH_2)_nNHC(O)CH_3$, —$(CH_2)_nC(O)NH(CH_2)_mCH_3$, —$(CH_2)_nNHC(O)(CH_2)_mCH_3$, where n and m are independently selected from 0-10. Examples of primary amines include —$NH_2$, —$CH_2$—$NH_2$, —$CH_2$—$CH_2$—$NH_2$, —$CH_2$—$CH_2$—$CH_2$—$NH_2$ and cyclopropyl-$NH_2$. Examples of secondary amines include —NH—$CH_3$, —NHCH$_2$—$CH_3$, —$CH_2$—NH—$CH_3$, and —$(CH_2)_n$—NH—$CH_3$, where n is 0-10. Examples of tertiary amines include —$N(CH_3)_2$, —$N(CH_2$—$CH_3)_2$, —$N(CH_3)CH_2CH_3$, and —$CH_2N(CH_2CH_3)_2$. Examples of azides include —$CH_2N_3$, —$(CH_2)_2N_3$, and —$(CH_2)_nN_3$, where n is selected from 0-10. Examples of cyanates include —$CH_2OCN$, —$(CH_2)_2OCN$, and —$(CH_2)_nOCN$, where n is selected from 0-10. Examplary cyano or nitrile groups include —CN, —$CH_2CN$), —$(CH_2)_2CN$, and $(CH_2)_nCN$, wherein n is selected from 0 to 10. Examples of thiols include —CH₂SH, —(CH₂)₂SH, and —(CH₂)ₙSH, where n is selected from 0 to 10. Examples of sulfides include —CH₂—S—CH₃, —CH₂—S—CH₂CH₃, and —(CH₂)ₙ—S—(CH₂)ₘCH₃, where n and m are independently selected from 0-10. Examples of sulfoxides include —CH₂S(O)CH₃, —CH₂S(O)CH₂CH₃, —(CH₂)ₙS(O)(CH₂)ₘCH₃, where n and m are independently selected from 0-10. Examples of sulfones include —CH₂SO₂CH₃, —CH₂SO₂CH₂CH₃, and —(CH₂)ₙSO₂ (CH₂)ₘCH₃, where n and m are independently selected from 0-10. Examples of sulfonamides include —SO₂NH₂, —CH₂SO₂NH₂, —(CH₂)₂SO₂NH₂, —(CH₂)ₙSO₂NH₂, —CH₂SO₂NHCH₃, —(CH₂)ₙSO₂NH(CH₂)ₘCH₃, where n and m are independently selected from 0-10. Examples of sulfinic acids include —SO₂H, —CH₂SO₂H, —(CH₂)₂SO₂H, and —(CH₂)ₙSO₂H, wherein n is selected from 0 to 10. Examples of thiocyanates include —SCN, —CH₂SCN, —(CH₂)₂SCN, and —(CH₂)ₙSCN, wherein n is selected from 0 to 10. Examples of phosphates include —OP(=O)(OH)₂, —CH₂OP(=O)(OH)₂, —(CH₂)₂OP(=O)(OH)₂, and —(CH₂)ₙOP(=O)(OH)₂, wherein n is selected from 0 to 10.

In certain embodiments, a compound or salt of Scaffold (1) or Scaffold (2) is selected from Formulas (1), (1A), (1B), (1C), (1D), (1E), (1F), (1G), (1H), (1I), and (1J):

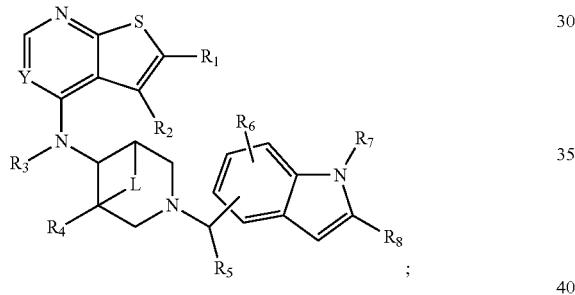

Formula (1)

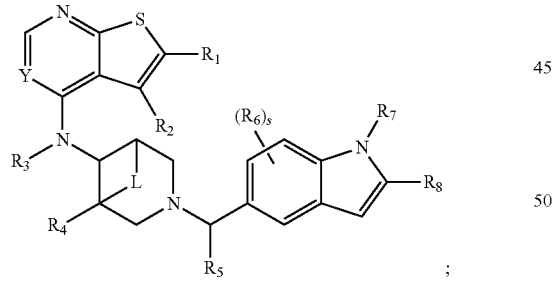

Formula (1A)

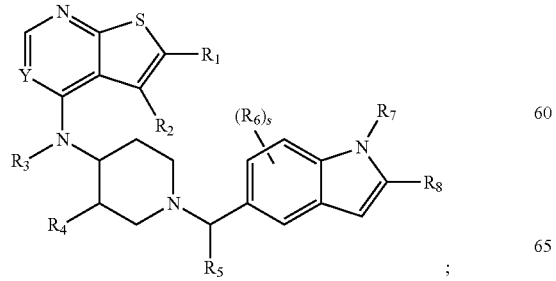

Formula (1B)

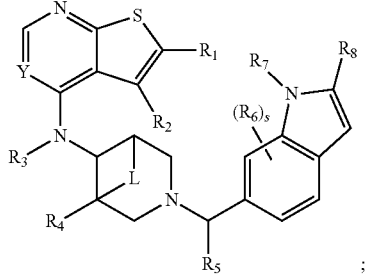

Formula (1C)

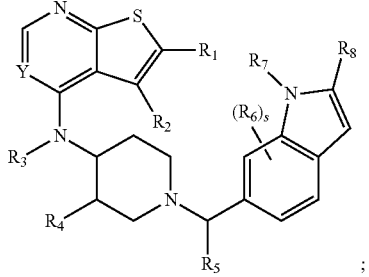

Formula (1D)

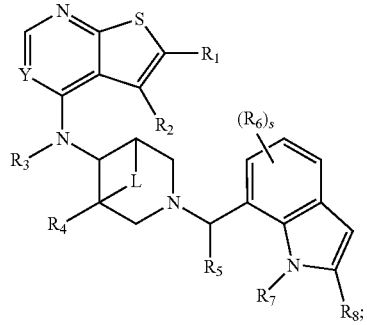

Formula (1E)

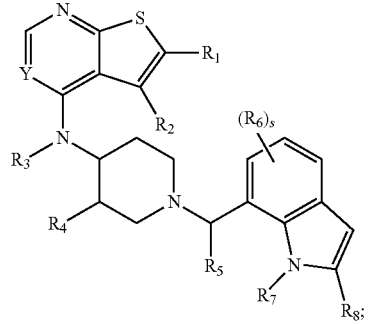

Formula (1F)

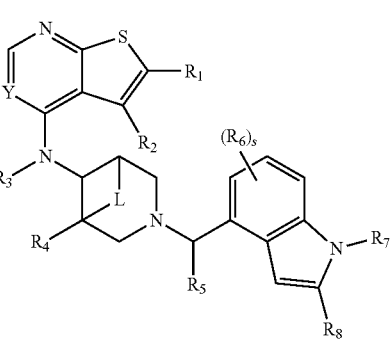

Formula (1G)

Formula (1H)

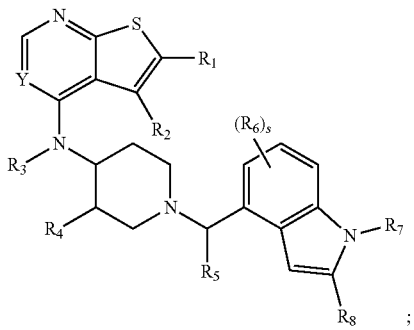

Formula (1I)

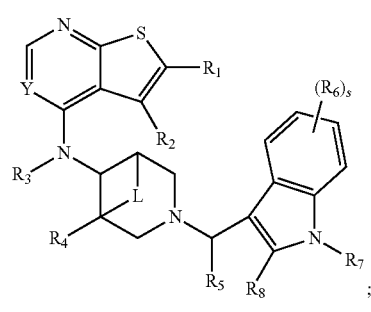

Formula (1J)

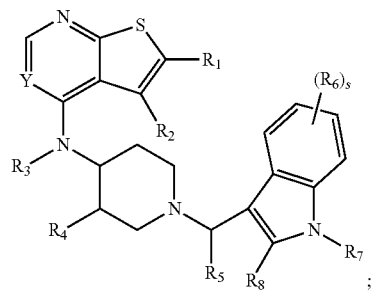

wherein R1, R2, R3, R4, R5, R6, R7, R8, and Y are as defined above with respect to Scaffold 1 and Scaffold 2 and s is selected from 0, 1, 2, 3, or 4.

In certain embodiments, Y of a compound or salt of any of Scaffold 1, Scaffold 2, and Formulas (1), (1A), (1B), (1C), (1D), (1E), (1F), (1G), (1H), (1I), and (1J) is N.

In certain embodiments, Y of a compound or salt of any of Scaffold 1, Scaffold 2, and Formulas (1), (1A), (1B), (1C), (1D), (1E), (1F), (1G), (1H), (1I), and (1J) is $C(R^a)$ and $R^a$ is selected from hydrogen, halogen, nitro, amino, cyano, alkyl, alcohol, heteroalkyl, and substituted alkyl, such as $R^a$ is selected from hydrogen, halogen, alkyl, and substituted alkyl.

In certain embodiments, R1 and R2 of a compound or salt of any of Scaffold 1, Scaffold 2, and Formulas (1), (1A), (1B), (1C), (1D), (1E), (1F), (1G), (1H), (1I), and (1J) are independently selected from hydrogen, halogen, hydroxy, alkoxy, cyano, nitro, amino, alkyl, substituted alkyl, alkenyl, substituted alkenyl, alkynyl, and substituted alkynyl. In certain embodiments, $R_1$ is selected from halogen, alkyl, substituted alkyl, alkenyl, substituted alkenyl, alkynyl, and substituted alkynyl, such as $R_1$ is selected from halogen, haloalkyl, haloalkenyl, and haloalkynyl, such as $R_1$ is —$CH_2CF_3$ or —$CH_2CHF_2$.

In some embodiments, R1 comprises or consists of mono-haloethane, dihaloethane or trihaloethane (e.g., monofluoroethane, difluoroethane and trifluoroethane) group.

In certain embodiments, R2 of a compound or salt of any of Scaffold 1, Scaffold 2, and Formulas (1), (1A), (1B), (1C), (1D), (1E), (1F), (1G), (1H), (1I), and (1J) is selected from hydrogen, hydroxy, nitro, cyano, halogen, alkyl, and alkoxy, such as R2 is hydrogen.

In some embodiments, R2 is H or another R2 substituent described herein.

In certain embodiments, R3 of a compound or salt of any of Scaffold 1, Scaffold 2, and Formulas (1), (1A), (1B), (1C), (1D), (1E), (1F), (1G), (1H), (1I), and (1J) is selected from hydrogen, alkyl, and substituted alkyl, such as $R_3$ is hydrogen.

In some embodiments R3 comprises or consists of an alkyl (e.g., methane, ethane, propane, butane, etc.), amine (e.g., $NH_2$, NH-alkyl (e.g., NH-methyl, NH-ethyl, NH—$CH_2$-Ph, etc.), NH-alcohol (e.g., NH—$CH_2$—$CH_2$—OH), etc.), an alcohol (e.g., methanol, ethanol, butanol, propanol, $CH_2CHOHCH_2OH$, etc.), a heterocyclic ring, or an alkyl-heterocyclic ring (e.g., ethyl-morpholine, propyl-indole, etc.). In some embodiments, R3 is fused in a ring with R2.

In certain embodiments, R4 of a compound or salt of any of Scaffold 1, Scaffold 2, and Formulas (1), (1A), (1B), (1C), (1D), (1E), (1F), (1G), (1H), (1I), and (1J) is selected from hydrogen, halogen, hydroxy, alkoxy, cyano, nitro, amino, alkyl, substituted alkyl, alkenyl, substituted alkenyl, alkynyl, and substituted alkynyl, such as R4 is selected from hydrogen and halogen.

In some embodiments R4 comprises or consists of amine (e.g. —$NH_2$), NH—$(CH_2)_{1-6}$-phenyl, NH—$(CH_2)_{1-6}$-(substituted aromatic ring), aminomethyl, aminoakyl N-formylpyrrolidine, aminoakyl N-sulfonylpyrrolidine, or —$CH_2$—OH.

In certain embodiments, R5 of a compound or salt of any of Scaffold 1, Scaffold 2, and Formulas (1), (1A), (1B), (1C), (1D), (1E), (1F), (1G), (1H), (1I), and (1J) is selected from hydrogen, halogen, hydroxy, alkoxy, cyano, nitro, amino, alkyl, substituted alkyl, alkenyl, substituted alkenyl, alkynyl, and substituted alkynyl, such as R5 is hydrogen.

In some embodiments, R5 is —$CH_2$—OH.

In certain embodiments, R6 of a compound or salt of any of Scaffold 1, Scaffold 2, and Formulas (1), (1A), (1B), (1C), (1D), (1E), (1F), (1G), (1H), (1I), and (1J) is independently selected, at each occurrence, from halogen, hydroxy, alkoxy, cyano, nitro, amino, alkyl, substituted alkyl, alkenyl, substituted alkenyl, alkynyl, and substituted alkynyl, such as R6 is independently selected, at each occurrence, from halogen, hydroxy, alkoxy, and alkyl.

In some embodiments, R6 is an alkyl (e.g., methane, ethane, propane, butane, etc.), cycloalkane (e.g., cyclopropane, cyclobutane, cyclopentane, cyclohexane, etc.), halogen (e.g., Br, F, Cl, I, etc.), haloalkane (e.g., monohaloalkane, dihaloalkane (e.g., difluoromethane), trihaloalkane (e.g., trichloroethane)), alkene (e.g. CH=$CH_2$, etc.), alkyne (e.g. C≡CH, etc), amine (e.g., $NH_2$, NH-alkyl (e.g., NH-methyl, NH-ethyl, NH—$CH_2$-Ph, etc.) alkyl-amine (e.g., $(CH_2)_{1-6}$—$NH_2$)), O-alkyl (e.g., $OCH_3$, $OCH_2CH_3$, etc.), NH-alcohol (e.g., NH—$CH_2$—$CH_2$—OH), etc.), hydroxy (e.g. —OH), an alcohol (e.g., methanol, ethanol, butanol, propanol, $CH_2CHOHCH_2OH$, etc.), or dialkylphosphine oxide (e.g., —$PO(CH_3)_2$). In some embodiments, R6 is present on either the benzyl and/or pyrrole portions of the indole ring. In some embodiments R6 on indole ring is present at more than one position on the benzyl and/or pyrrole portions of the indole ring. In some embodiments, R7 comprises a non-aromatic or aromatic heterocyclic ring (e.g., 3-, 4-, 5-, or 6-member ring). In some embodiments R7 comprises a linker between the heterocyclic ring of R7 and the scaffold (e.g., Scaffold 1, Scaffold 2, etc.). In some embodiments, the linker of R7 is an alkyl group (e.g., methyl, ethyl, propyl, butyl, etc.) or heteroalkyl group (e.g., methyl, ethyl, propyl, butyl, etc. with one or more hydrogen and/or carbons replaced by O, S, or N) attached to the rest of the compound through an alkyl (e.g. ethyl, propyl, etc) linker.

In some embodiments R7 comprises an electrophilic group capable of covalent and/or irreversible binding to cysteine sulfhydryl groups.

In some embodiments, R7 comprises a 4-member, 5-member or 6-member heterocyclic ring. In some embodiments, R7 comprises a 1,4-substituted, heterocyclic, 6-member ring (e.g., attached to the rest of the compound at the 1 position and substituted at the 4 position). In some embodiments, the 1,4-substituted, heterocyclic ring comprises N or C at the 1 position. In some embodiments, the 1,4-substituted, heterocyclic ring comprises N or C at the 4 position. In some embodiments, R7 comprises a pyridine ring (e.g., with the N of the pyridine ring at the 1 or 4 position), or pyrazine (e.g., with the N at the 1 and 4 positions). In some embodiments, R7 comprises a piperidine ring (e.g., with the N of the pyridine ring at the 1 or 4 position), or piperazine (e.g., with the N at the 1 and 4 positions). In some embodiments, the heterocyclic ring is bridged (e.g., linker moiety (e.g., alkylene (e.g., methylene ethylene, etc.), heteroalkyl (e.g., O-methyl, NH-methyl, S-methyl, etc.), 0, NH, S, etc.) bridging between positions 2 and 5, 2 and 6, 3 and 5, or 3 and 6 of a six-membered heterocyclic ring). In some embodiments, R7 comprises a linker between the aromatic or non-aromatic heterocycle of R7 and the scaffold (e.g., Scaffold 1, Scaffold 2, etc.). In some embodiments, the linker of R7 is an alkyl group (e.g., methyl, ethyl, propyl, butyl, etc.) or heteroalkyl group (e.g., methyl, ethyl, propyl, butyl, etc. with one or more hydrogen and/or carbons replaced by O, S, or N). In some embodiments, R7 comprises a substituent on the aromatic or non-aromatic heterocycle of R7.

In some embodiments, R7 comprises a 5-member heterocyclic ring (See, e.g., Compounds 26, 29, 30, etc.) with O and/or S at any of the 2, 3, 4, and/or 5 positions and C and N present at the 1, 2, 3, 4, and/or 5 positions. In some embodiments, R7 comprises a 3- or 4-substituted heterocyclic 5-member ring (e.g., attached to the rest of the compound at the 1 position and substituted at the 3 or 4 positions). In some embodiments, R7 comprises a 2,4-substituted heterocyclic 5-member ring (e.g., attached to the rest of the compound at the 1 position and substituted at the 2 and 4 positions; See, e.g., Compound 30). In some embodiments, heterocyclic ring comprises N or C at the 1 position. In some embodiments, R7 comprises a linker between the aromatic or non-aromatic heterocycle of R7 and the scaffold (e.g., Scaffold 1, Scaffold 2, etc.). In some embodiments, the linker of R7 is an alkyl group (e.g., methyl, ethyl, propyl, butyl, etc.) or heteroalkyl group (e.g., methyl, ethyl, propyl, butyl, etc. with one or more carbons replaced by O, S, or N). In some embodiments, R7 comprises a substituent on the aromatic or non-aromatic heterocycle of R7. In some embodiments substituents at the R7 5-membered aromatic or non-aromatic heterocycle include: NHC(O)CH=CH$_2$, C(O)CH=CH$_2$, etc., an alkyl group (e.g., methyl, ethyl, propyl, butyl, etc.), heteroalkyl group (e.g., methyl, ethyl, propyl, butyl, etc. with one or more carbons replaced by O, S, or N), haloalkane, alkene (e.g., CH=CH$_2$, CH$_2$CH=CH$_2$, CH=CHCH$_3$, etc.), substituted alkene (e.g. halogen-substituted alkene group, e.g. chloro-alkene, fluoroalkene, etc., alkyl substituted alkene, amino substituted alkene, etc.), alkyne (e.g., C≡CH, C≡CCH$_3$, CH$_2$C≡CH, etc.), substituted alkyne (e.g. halogen substituted alkyne group, e.g. chloroalkyne, fluoroalkyne, etc., alkyl substituted alkyne, amino substituted alkyne, etc.)

In some embodiments, R7 comprises a 4-member heterocyclic ring (See, e.g., Compound 28) with O and/or S at any of the 2, 3, and/or 4 positions and C or N at the 1, 2, 3, and/or 4 positions. In some embodiments, heterocyclic ring comprises N or C at the 1 or 3 positions. In some embodiments, R7 comprises a linker between the aromatic or non-aromatic heterocycle of R7 and the scaffold (e.g., Scaffold 1, Scaffold 2, etc.). In some embodiments, the linker of R7 is an alkyl group (e.g., methyl, ethyl, propyl, butyl, etc.) or heteroalkyl group (e.g., methyl, ethyl, propyl, butyl, etc. with one or more carbons replaced by O, S, or N). In some embodiments, R7 comprises a substituent on the aromatic or non-aromatic heterocycle of R7 (See, e.g., Compound 28). In some embodiments substituents at the R7 4-membered aromatic or non-aromatic heterocycle include: NHC(O)CH=CH$_2$, C(O)CH=CH$_2$, an alkyl group (e.g., methyl, ethyl, propyl, butyl, etc.) or heteroalkyl group (e.g., methyl, ethyl, propyl, butyl, etc. with one or more carbons replaced by O, S, or N, etc.), halogen substituted alkane (choloroalkane, fluoroalkane), alkene (e.g., CH=CH$_2$, CH$_2$CH=CH$_2$, CH=CHCH$_3$, etc.), substituted alkene (e.g. halogen-substituted alkene group, e.g. chloroalkene, fluoroalkene, etc., alkyl substituted alkene, amino substituted alkene, etc.), alkyne (e.g., C≡CH, C≡CCH$_3$, CH$_2$C≡CH, etc.), substituted alkyne (e.g. halogen substituted alkyne group, e.g. chloroalkyne, fluoroalkyne, etc., alkyl substituted alkyne, amino substituted alkyne, etc.).

In some embodiments, R7 comprises a substituent (e.g., R9) at the 4-position of the 6-member heterocyclic ring. In some embodiments R9 comprises an electrophilic group capable of irreversible binding to cysteine sulfhydryl groups. Suitable substituents (e.g., at the 4-position of the 6-member heterocyclic ring (e.g., R9)) comprise COR$^{10}$, SO$_2$R$^{10}$, NHCOR10, NHSO$_2$R10 wherein R10 is selected from the functional groups: alkyl (e.g., methyl, ethyl, propyl, butyl, etc.), alkene (e.g., ethylene, methylethylene, ethylenemethyl, etc.), substituted alkene (e.g. halogen substituted alkene, amino substituted alkene, etc), alkyne (e.g., acetylene, methylacetylene, acetylenemethyl, etc.), substituted alkyne (e.g. halogen substituted alkyne, amino substituted alkyne, etc), O-alkyl (e.g., O-methyl, O-ethyl, O-propyl), N-alkyl (e.g., NH-methyl, NH-ethyl, NH-propyl), S-alkyl (e.g., S-methyl, S-ethyl, S-propyl), alcohol (e.g., OH, CH$_2$OH, CH$_2$CH$_2$OH, etc.), thiol (e.g., SH, CH$_2$SH, CH$_2$CH$_2$SH, etc.), amine (e.g., NH$_2$, CH$_2$NH$_2$, CH$_2$CH$_2$NH$_2$, etc.), halogen (e.g., Br, Cl, F, I), alkyl halides (e.g., CH$_2$F, CHF$_2$, CF$_3$, CH$_2$CH$_2$F, CH$_2$CHF$_2$, CH$_2$CF$_3$, or the same substituents with Cl, Br, or I in place of F, etc.), nitrile (e.g., CN, CH$_2$CN, CH$_2$CH$_2$CN, etc.), aromatic ring (e.g., C$_3$-C$_6$), heteroaryl (e.g., C$_3$-C$_6$), non-aromatic heterocycle (e.g., C$_3$-C$_6$), carbocycle (e.g., C$_3$-C$_6$), an electrophilic group such as any electrophilic group capable of covalent and/or irreversible binding to cysteine sulfhydryl groups, any suitable hydrocarbon (e.g., alkane, alkene, alkyne, and combinations thereof) capped by R11 (e.g., CHCHCH$_2$R11), and any suitable combinations thereof.

In some embodiments, when present, R11 is selected from H, alkyl group (e.g., straight-chain alkyl (e.g., methane, ethane, propane, butane, pentane, hexane, etc.), branched alkyl group (e.g., iso-propyl, 2-methyl-hexane, 3-methyl, 2-propyl-octane, etc.), cycloalkyl (e.g., cyclopropane, cyclobutane, cyclopentane, cyclohexane, cyclooctane, etc.), branched cyclic alkyl (e.g., methylcyclohexane, ethylcyclobutane, propylcyclohexane, etc.)), a substituted alkyl group (e.g., halogen-substituted alkyl group (e.g., trihaloethane (e.g., trifluoroethane), halomethane (e.g., fluoromethane), dihalomethane (e.g., difluoromethane), trihalomethane (e.g., trifluoromethane), etc.), alkoxy group (e.g., ether, etc.), amine, alkylamine (e.g., primary amine (e.g., ethylamine, iso-butylamine, n-propylamine, sec-butylamine, iso-propylamine, iso-amylamine, methylamine, dimethylamine, n-amylamine, etc.), secondary amines (e.g., dimethylamine, methylethanolamine, diphenylamine, etc.), tertiary amine (e.g., trimethylamine, triphenylamine, etc.), thioalkyl, combinations thereof, etc.), a substituted cycloalkyl group (e.g., halogen-substituted cycloalkyl group, cycloalkoxy group, cycloalkylamine, etc.), a halogen (e.g., F, Cl, Br, I, and At), a ketone, an amide, an alkylamide, a cyano group, methyl carbonitrile (e.g. $CH_2CN$), —$SO_2CH_3$ group, sulfonyl group, a carbocyclic ring, an aromatic ring, a substituted aromatic ring (e.g., branched aromatic ring (e.g., ethylbenzene, methyl benzene, etc.), halobenzene (e.g., chlorobenzene, fluorobenzene, etc.)), a heterocyclic aromatic ring (e.g., comprising one or more nitrogen, oxygen and/or sulfur members which may be non-substituted or substituted with alkyl, aryl, halogen, hydrogen bond donor or acceptor), a substituted or non-substituted heterocyclic non-aromatic ring (e.g., comprising carbon and one or more nitrogen, oxygen and/or sulfur members), carbocyclic or heterocyclic aromatic ring comprising carbon atoms and one or more nitrogen, oxygen and/or sulfur members fused to another aromatic ring, a multi-ring system comprising a combination of elements selected from aromatic rings, cycloalkane, heterocyclic rings, alkyl chains, and suitable C-, N-, O-, S-, and/or halogen-containing substituents, or a hydrogen bond donor or a hydrogen bond acceptor, an electrophilic group such as any electrophilic group capable of covalent and/or irreversible binding to cysteine sulfhydryl groups, and/or combinations thereof.

In some embodiments, the aromatic or non-aromatic heterocycle of R7 (e.g., 4-member ring, 5-member ring, 6-member ring, etc.) is further substituted (e.g., at the 2, 3, 5, and/or 6 positions). Additional substituents substituted (e.g., at the 2, 3, 5, and/or 6 positions) may comprise: alkyl groups (e.g. methyl, ethyl, propyl, butyl, etc.), CN, halogens (e.g., F, Cl, Br, I), alcohols (e.g., OH, $CH_2OH$, $CH_2CH_2OH$, etc.), carboxylic acids (e.g., COOH, $CH_2COOH$, etc.), amides ($CONH_2$, $CH_2CONH_2$, NHCO-alkyl, NHCO-alkene (e.g., NHCOCH=CH2), NHCOCH=$CHCH_2N(CH_3)_2$ (See, e.g., Compound 27), etc.), amines (e.g., $NH_2$, $CH_2NH_2$, $CH_2CH_2NH_2$, etc.), alkyl halides (e.g., $CH_2F$, $CHF_2$, $CF_3$, $CH_2CH_2F$, $CH_2CHF_2$, $CH_2CF_3$, or the same substituents with Cl, Br, or I in place of F, etc.), and suitable combinations thereof.

In certain embodiments, R8 of a compound or salt of any of Scaffold 1, Scaffold 2, and Formulas (1), (1A), (1B), (1C), (1D), (1E), (1F), (1G), (1H), (1I), and (1J) is selected from hydrogen, halogen, hydroxy, alkoxy, cyano, nitro, amino, alkyl, substituted alkyl, alkenyl, substituted alkenyl, alkynyl, and substituted alkynyl, such as R8 is cyano.

In some embodiments, R8 comprises or consists of: H, alkyl (e.g., methyl, ethyl, propyl, butyl, etc.), cycloalkyl (e.g., cyclopropane (e.g., methyl cyclopropane), cyclobutane, cyclopentane, cyclohexane, etc.), a primary alcohol (e.g., OH, methanol, ethanol, propanol, butanol, etc.), a secondary alcohol, a substituted or non-substituted heteroaromatic ring (e.g., pyrazole, triazole (e.g., 1,2,4 triazole, 1,2,3 triazole (e.g., alkyl-substituted triazole)), isoxazole), isopropylisopropanolamine ($CH_2CHOHCH_2NHCH$ ($CH_3)_2$), sulfonamide, a cyano group (e.g., CN, methyl carbonitrile, ethyl carbonitrile, propyl carbonitrile, etc.), amide (e.g., $CONH_2$, methylcarboxamido (e.g., $CH_2CONH_2$, $CH_2CONH$—$C_{1-6}$), ethyl carboxamido ($CH_2CH_2CONH_2$), carboxyamido-methane (e.g., $CONHCH_3$ or $NHCOCH_3$), etc.), $CH_2CHOHCH_2OH$, methylsulfonyl, dialkylphosphine oxide (e.g., —$PO(CH_3)_2$), or ketone (e.g., =O).

In certain embodiments, for a compound or salt of any of Scaffold 1, Scaffold 2, and Formulas (1), (1A), (1B), (1C), (1D), (1E), (1F), (1G), (1H), (1I), and (1J), a substituted alkyl, substituted aromatic ring, substituted heterocyclic aromatic ring or substituted heterocyclic non-aromatic ring of any of R1, R2, R3, R4, R5, R6, R7, R8, and Y has one or more substituents independently selected from: halogen, —$OR^{20}$, —$SR^{20}$, —$N(R^{20})_2$, —$N(R^{20})C(O)R^{20}$, —$C(O)R^{20}$, —$C(O)OR^{20}$, —$C(O)N(R^{20})_2$, —$OC(O)R^{20}$, —$S(O)_2R^{20}$, —$S(O)_2N(R^{20})_2$, —$N(R^{20})S(O)_2R^{20}$, —$NO_2$, =O, =S, =$N(R^{20})$, —$P(O)(OR^{20})_2$, —$P(O)(R^{20})_2$, —$OP(O)(OR^{20})_2$, and —CN; $C_{1-6}$ alkyl, $C_{2-6}$ alkenyl, and $C_{2-6}$ alkynyl, each of which is independently optionally substituted at each occurrence with one or more substituents selected from halogen, —$OR^{20}$, —$SR^{20}$, —$N(R^{20})_2$, —$N(R^{20})C(O)R^{20}$, —$C(O)R^{20}$, —$C(O)OR^{20}$, —$C(O)N(R^{20})_2$, —$OC(O)R^{20}$, —$S(O)_2R^{20}$, —$S(O)_2N(R^{20})_2$, —$N(R^{20})S(O)_2R^{20}$, —$NO_2$, =O, =S, =$N(R^{20})$, —$P(O)(OR^{20})_2$, —$P(O)(R^{20})_2$, —$OP(O)(OR^{20})_2$, —CN, $C_{3-10}$ carbocycle, and 3- to 10-membered heterocycle or two substituents on the same carbon atom of an $C_{1-6}$ alkyl, $C_{2-6}$ alkenyl, or $C_{2-6}$ alkynyl come together to form a $C_{3-10}$ carbocycle or 3- to 10-membered heterocycle; and $C_{3-10}$ carbocycle and 3- to 10-membered heterocycle; wherein any $C_{3-10}$ carbocycle and 3- to 10-membered heterocycle is independently optionally substituted with one or more substituents selected from halogen, —$OR^{20}$, —$SR^{20}$, —$N(R^{20})_2$, —$N(R^{20})C(O)R^{20}$, —$C(O)R^{20}$, —$C(O)OR^{20}$, —$C(O)N(R^{20})_2$, —$OC(O)R^{20}$, —$S(O)_2R^{20}$, —$S(O)_2N(R^{20})_2$, —$N(R^{20})S(O)_2R^{20}$, —$NO_2$, =O, =S, =$N(R^{20})$, —$P(O)(OR^{20})_2$, —$P(O)(R^{20})_2$, —$OP(O)(OR^{20})_2$, —CN, $C_{1-6}$ alkyl, $C_{2-6}$ alkenyl, and $C_{2-6}$ alkynyl;

$R^{20}$ at each occurrence is independently selected from hydrogen; $C_{1-6}$ alkyl, $C_{2-6}$ alkenyl, and $C_{2-6}$ alkynyl, each of which is independently optionally substituted at each occurrence with one or more substituents selected from halogen, —$OR^{30}$, —$SR^{30}$, —$N(R^{30})_2$, —$N(R^{30})C(O)R^{30}$, —$C(O)R^{30}$, —$C(O)OR^{30}$, —$C(O)N(R^{30})_2$, —$OC(O)R^{30}$, —$S(O)_2R^{30}$, —$S(O)_2N(R^{30})_2$, —$N(R^{30})S(O)_2R^{30}$, —$NO_2$, —$P(O)(OR^{30})_2$, —$P(O)(R^{30})_2$, —$OP(O)(OR^{30})_2$, and —CN; and 3- to 10-membered heterocycle and $C_{3-10}$ carbocycle; and $R^{30}$ at each occurrence is independently selected from hydrogen, $C_{1-6}$ alkyl, $C_{2-6}$ alkenyl, and $C_{2-6}$ alkynyl.

In some embodiments, V is selected from a 3-7 membered saturated ring, 3-7 membered unsaturated ring, 4-10 membered fused bicyclic ring, and 5-11 membered spiro bicyclic ring. V may be optionally substituted with one or more R12 groups, such as with 1, 2, 3, 4, or 5 R12 groups. In some embodiments, V is a 3-7 membered saturated ring, such as a 3-7 membered cycloalkyl or 3-7 membered aromatic or non-aromatic heterocycle. In some embodiments, V is a 3-7 membered unsaturated ring, such as a 6 membered aryl, 5-6 membered heteroaryl, or 3-7 membered cycloalkenyl.

In certain embodiments, V is a 4-10 membered fused bicyclic ring, such as a 8-10 membered fused bicyclic ring. In certain embodiments, the fused bicyclic ring includes one or more heteroatoms such as one or more atoms selected from N, O, and S. In certain embodiments, the fused bicyclic ring includes two heteroatoms such as two nitrogen atoms.

Each of the rings of the fused bicyclic ring may be saturated or unsaturated. In particular embodiments, both rings of the fused bicyclic ring are saturated. Non-limiting examples of V comprising a fused bicyclic ring include

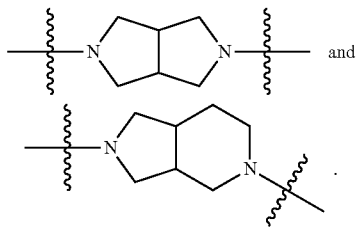

In some embodiments, V is a 5-11 membered spiro bicyclic ring, such as a 7-11 membered spiro bicyclic ring. In certain embodiments, the fused bicyclic ring includes one or more heteroatoms such as one or more atoms selected from N, O, and S. In particular embodiments, the fused bicyclic ring includes two heteroatoms such as two nitrogen atoms. Non-limiting examples of V comprising a spiro bicyclic ring include

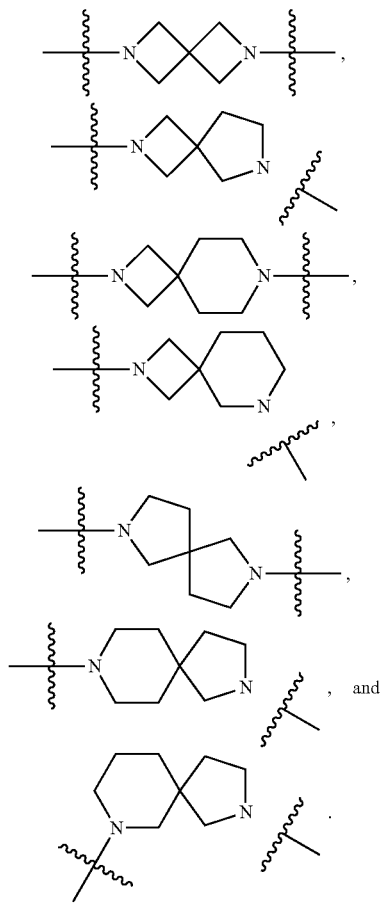

In some embodiments, R12 comprises or consists of: H, alkyl (e.g. methyl, ethyl, propyl, butyl, etc.), cycloalkyl, halogen, halogen substituted alkyl, primary alcohol (e.g. —OH, methanol, ethanol, etc.), a secondary alcohol, amide (e.g., CONH$_2$), methylcarboxamido (e.g., CH$_2$CONH$_2$, CH$_2$CONH—C$_{1-6}$), sulfonamide, alkyl substituted sulfonamide (e.g. —SO$_2$NHCH$_3$), —SO$_2$CH$_3$ group, —SO$_3$alkyl (ethyl, propyl, cyclopropyl), dialkylphosphine oxide (e.g., —PO(CH$_3$)$_2$), amino, amide, cyano group, ketone, hydrogen bond acceptor, etc. In some embodiments, multiple R$^{12}$ are present at multiple positions of the ring.

In some embodiments, the substituted indole ring is: cyano substituted (e.g., 1-carbonitrile, 2-carbonitrile, etc.), methyl-carbonitrile substituted (e.g., 4-methyl-carbonitrile, etc.), methylcyclopropane substituted (e.g., 1-methylcyclopropane), halo-substituted (e.g., 3-halo (e.g., 3-fluoro, 4-fluoro, 6-fluoro, etc.)), alkyl substituted (e.g., 1-alkyl (e.g., 1-methyl, 1-ethyl, 1-propyl, etc.)), alcohol-substituted (e.g., OH substituted (e.g., 6-OH), methanol substituted (e.g., 1-methanol), ethanol substituted (e.g., 1-ethanol), etc.), O-methyl substituted (e.g., 4-O-methyl, 6-O-methyl, etc.), alkoxy substituted (e.g. 6-O-methoxy, 6-O-ethoxy, etc), heterocyclic aromatic ring (or ring system) substituted (e.g., imidazole), amine substituted (e.g., NH$_2$, methylamine, ethylamine (e.g., 1-ethylamine, etc.), aminomethyl, etc.), dihydroxy substituted (e.g., 1,2-propanediol, etc.), amide substituted (e.g., 1-propanamide), acetamide substituted, 1-methyl 1,2,3-triazole substituted, 1-ethyl imidazole substituted, non-aromatic heterocycle substituted, carboxamido substituted (e.g., 1-carboxamido), sulfonyl substituted (e.g., 1-sulfonyl methyl (SO$_2$CH$_3$)), ether substituted (e.g., isopropanol methyl ether (CH$_2$CHOHCH$_2$CH$_3$)), keto-substituted (e.g., 1-keto), isopropanol-amine-isopropyl substituted (CH$_2$CHOHCH$_2$NHCH(CH$_3$)$_2$), 1-piperazine substituted, 1-piperidine substituted, or combinations thereof.

In some embodiments, compositions comprising one or more of compounds 1-264 of Table 1, or salt thereof are provided.

In some embodiments, a compound is capable of (a) binding covalently to menin and (b) inhibiting the interaction of menin and MLL. In some embodiments, covalent binders of menin display a functional group (e.g., at the R7 position, at the R9 position, at the R10 position, at the position R12, etc.) that covalently reacts with one or more residues on menin. In some embodiments, a functional group (e.g., at the R7 position, at the R9 position, at the R10 position, at the R12 position, etc.) covalently reacts with one or more cysteine residues on menin. In some embodiments, covalent binding of the compound to menin properly positions and/or orients the compound (e.g., Scaffold 1, Scaffold 2) to inhibit the menin/MLL interaction. In some embodiments, covalent binders of menin display a functional group (e.g., at the R9 position, at the R10 position, at the R12 position, etc.) comprising:

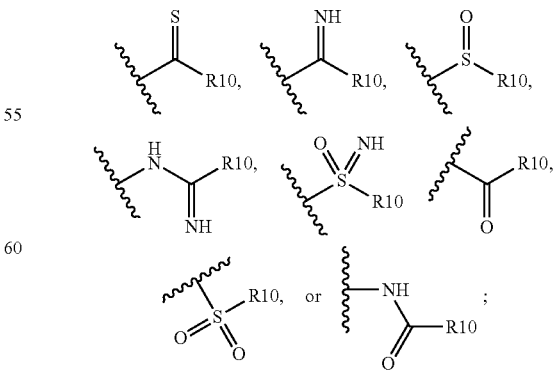

wherein R10 is selected from the functional groups: alkyl (e.g., methyl, ethyl, propyl, butyl, etc.), alkene (e.g., ethylene, methylethylene, ethylenemethyl, etc.), alkyne (e.g., acetylene, methylacetylene, acetylenemethyl, etc.), O-alkyl (e.g., O-methyl, O-ethyl, O-propyl), N-alkyl (e.g., NH-methyl, NH-ethyl, NH-propyl), S-alkyl (e.g., S-methyl, S-ethyl, S-propyl), alcohol (e.g., OH, CH$_2$OH, CH$_2$CH$_2$OH, etc.), thiol (e.g., SH, CH$_2$SH, CH$_2$CH$_2$SH, etc.), amine (e.g., NH$_2$, CH$_2$NH$_2$, CH$_2$CH$_2$NH$_2$, etc.), halogen (e.g., Br, Cl, F, I), alkyl halides (e.g., CH$_2$F, CHF$_2$, CF$_3$, CH$_2$CH$_2$F, CH$_2$CHF$_2$, CH$_2$CF$_3$, or the same substituents with Cl, Br, or I in place of F, etc.), substituted alkene (e.g. halogen-substituted alkene group, e.g. chloroalkene, fluoroalkene, etc., alkyl substituted alkene, amino substituted alkene, etc.), substituted alkyne (e.g. halogen substituted alkyne group, e.g. chloroalkyne, fluoroalkyne, etc., alkyl substituted alkyne, amino substituted alkyne, etc.), nitrile (e.g., CN, CH$_2$CN, CH$_2$CH$_2$CN, etc.), aromatic ring (e.g., C$_3$-C$_6$), heteroaryl (e.g., C$_3$-C$_6$), non aromatic heterocycle (e.g., C$_3$-C$_6$), carbocycle (e.g., C$_3$-C$_7$), CHCHCH$_2$N(CH$_3$)$_2$, CHCHCH$_2$NH(CH$_3$), CHCHCH$_2$NH$_2$, any suitable hydrocarbon (e.g., alkane, alkene, alkyne, and combinations thereof) capped by R11, R11a, R11b, and/or R11c (e.g., CH=CHCH$_2$R11, C≡CCH$_2$R11), and any suitable combinations thereof; wherein each of R11, R11a, R11b, and R11c, when present, is independently selected from H, alkyl group (e.g., straight-chain alkyl (e.g., methane, ethane, propane, butane, pentane, hexane, etc.), branched alkyl group (e.g., iso-propyl, 2-methyl-hexane, 3-methyl, 2-propyl-octane, etc.), cycloalkyl (e.g., cyclopropane, cyclobutane, cyclopentane, cyclohexane, cyclooctane, etc.), branched cyclic alkyl (e.g., methylcyclohexane, ethylcyclobutane, propylcyclohexane, etc.)), a substituted alkyl group (e.g., halogen-substituted alkyl group (e.g., trihaloethane (e.g., trifluoroethane), halomethane (e.g., fluoromethane), dihalomethane (e.g., difluoromethane), trihalomethane (e.g., trifluoromethane), etc.), hydroxyl, alkoxy group (e.g., ether, etc.), amine, alkylamine (e.g., primary amine (e.g., ethylamine, iso-butylamine, n-propylamine, sec-butylamine, iso-propylamine, iso-amylamine, methylamine, dimethylamine, n-amylamine, etc.), secondary amines (e.g., dimethylamine, methylethanolamine, diphenylamine, etc.), tertiary amine (e.g., trimethylamine, triphenylamine, etc.), thioalkyl, combinations thereof, etc.), a substituted cycloalkyl group (e.g., halogen-substituted cycloalkyl group, cycloalkoxy group, cycloalkylamine, etc.), a halogen (e.g., F, Cl, Br, I, and At), a ketone, an amide, an alkylamide, a cyano group, methyl carbonitrile (e.g. CH$_2$CN), —SO$_2$CH$_3$ group, sulfonyl group, a carbocyclic ring, an aromatic ring, a substituted aromatic ring (e.g., branched aromatic ring (e.g., ethylbenzene, methyl benzene, etc.), halobenzene (e.g., chlorobenzene, fluorobenzene, etc.)), a heterocyclic aromatic ring (e.g., comprising one or more nitrogen, oxygen and/or sulfur members which may be non-substituted or substituted with alkyl, aryl, halogen, hydrogen bond donor or acceptor), a substituted or non-substituted heterocyclic non-aromatic ring (e.g., comprising carbon and one or more nitrogen, oxygen and/or sulfur members), carbocyclic or heterocyclic aromatic ring comprising carbon atoms and one or more nitrogen, oxygen and/or sulfur members fused to another aromatic ring, a multi-ring system comprising a combination of elements selected from aromatic rings, cycloalkane, heterocyclic rings, alkyl chains, and suitable C-, N-, O-, S-, and/or halogen-containing substituents, a hydrogen bond donor or a hydrogen bond acceptor, and/or combinations thereof, wherein R11a and R11b may optionally join together to form an optionally substituted carbocycle. For example, suitable R9/R10 or R12 groups include, but are not limited by:

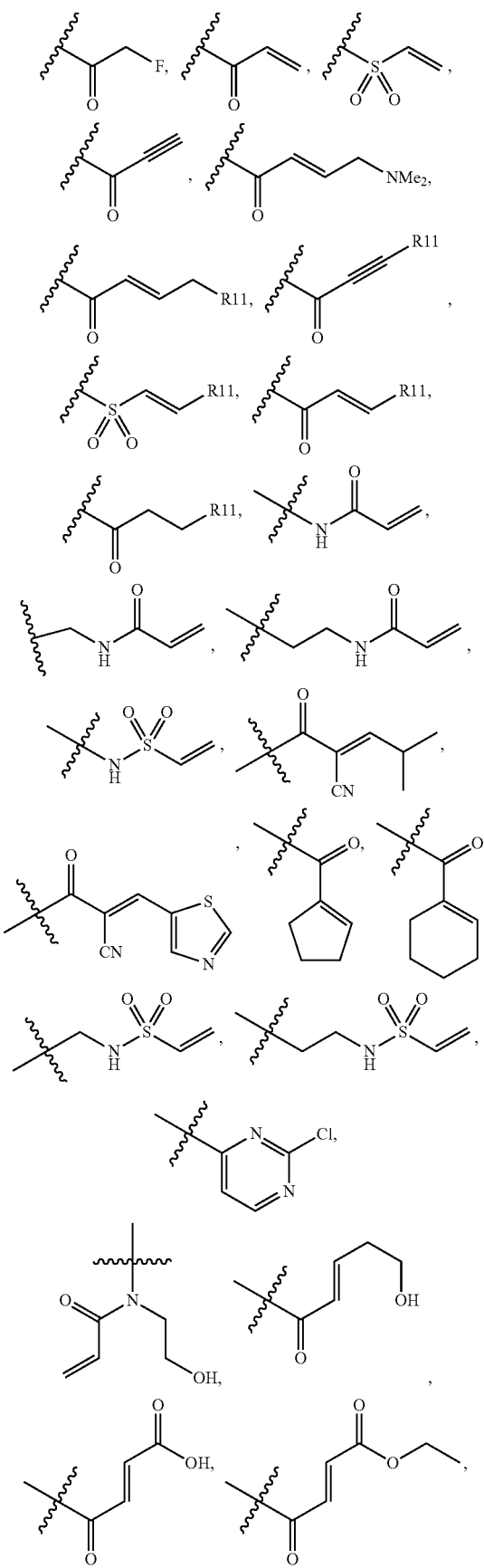

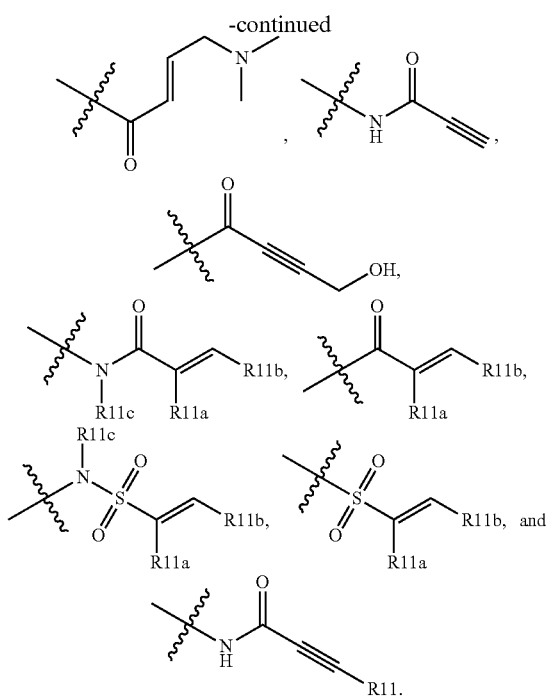

In some embodiments, R11 is H or $C_1$-$C_6$ alkyl. In certain embodiments, R11a is H, cyano or $C_1$-$C_6$ alkyl or R11a joins with R11b to form a carbocycle. In certain embodiments, R11b is H or $C_1$-$C_6$ alkyl or R11b joins with R11a to form a carbocycle. R11c may be H or $C_1$-$C_6$ alkyl.

In certain embodiments, compounds of the disclosure include one or more electrophilic groups such as one, two or three electrophilic groups. In particular embodiments, compounds of the disclosure include a single electrophilic group. In certain embodiments, the single electrophilic group is R9 or R12. In other embodiments, the compounds of the disclosure include two or more electrophilic groups, such as R9 and R12 are electrophilic groups.

In some embodiments, a compound is capable of inhibiting the interaction of menin and MLL without covalent binding to menin or MLL. For example, in some embodiments, a compound of:

(Scaffold 2)

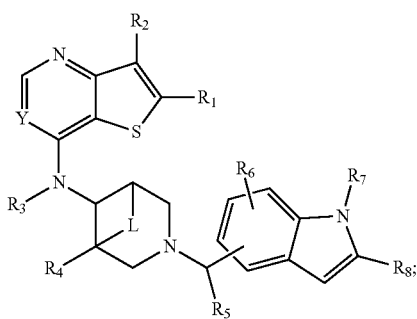

wherein R1, R2, R3, R4, R5, R6, R8 and R12 are defined as above, comprises an R7 selected from H, alkyl (e.g., methyl, ethyl, propyl, butyl, etc.), haloalkane, cycloalkyl (e.g., cyclopropane (e.g., methyl cyclopropane), cyclobutane, cyclopentane, cyclohexane, etc.), an alcohol (e.g., OH, methanol, ethanol, propanol, butanol, etc.), a substituted or non-substituted heteroaromatic ring (e.g., pyrazole, triazole (e.g., 1,2,4 triazole), isoxazole (e.g., dimethyl isoxazole), $(CH_2)n$-OR (wherein n=1-10 and R is an aromatic ring, heteroaromatic ring, cycloalkyl, non-aromatic heterocycle, substituted ring, etc.), $(CH_2)n$-R (wherein n=1-10 and R is an aromatic ring, heteroaromatic ring, cycloalkyl, non-aromatic heterocycle, substituted ring, etc.), $(CH_2)n$-O—$(CH_2)$m-R (wherein n=1-10, m=1-10, and R is an aromatic ring, heteroaromatic ring (e.g., 4-member ring, 5-member ring, 6-member ring), cycloalkyl, non-aromatic heterocycle, substituted ring, etc.), alkyl-heteroaromatic ring (e.g. $CH_2$-pyrazole, $CH_2$-triazole, $CH_2$—$CH_2$-triazole, etc), amide (e.g. acetamide, see, e.g., compound 189), amine (e.g., $NH_2$, NH-alkyl (e.g., NH-methyl, NH-ethyl, NH—$CH_2$-Ph, etc., NH-alcohol (e.g., NH—$CH_2$—$CH_2$—OH), etc.), substituted or non-substituted alcohol (e.g., methanol, ethanol, butanol, propanol, $CH_2$CHOH $CH_2$OH, etc.).

In other embodiments, a noncovalent inhibitor comprises a compound of Scaffold 1 or Scaffold 2:

(Scaffold 1)

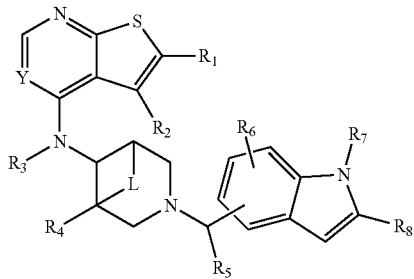

(Scaffold 2)

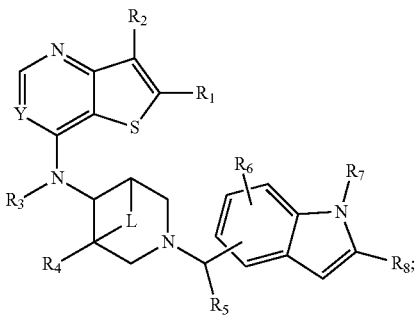

or a pharmaceutically acceptable salt thereof, wherein:
R1, R2, R3, R4, R5, R6, and R8 are defined as above; wherein R7 comprises:

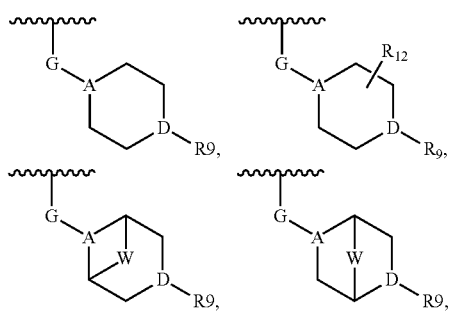

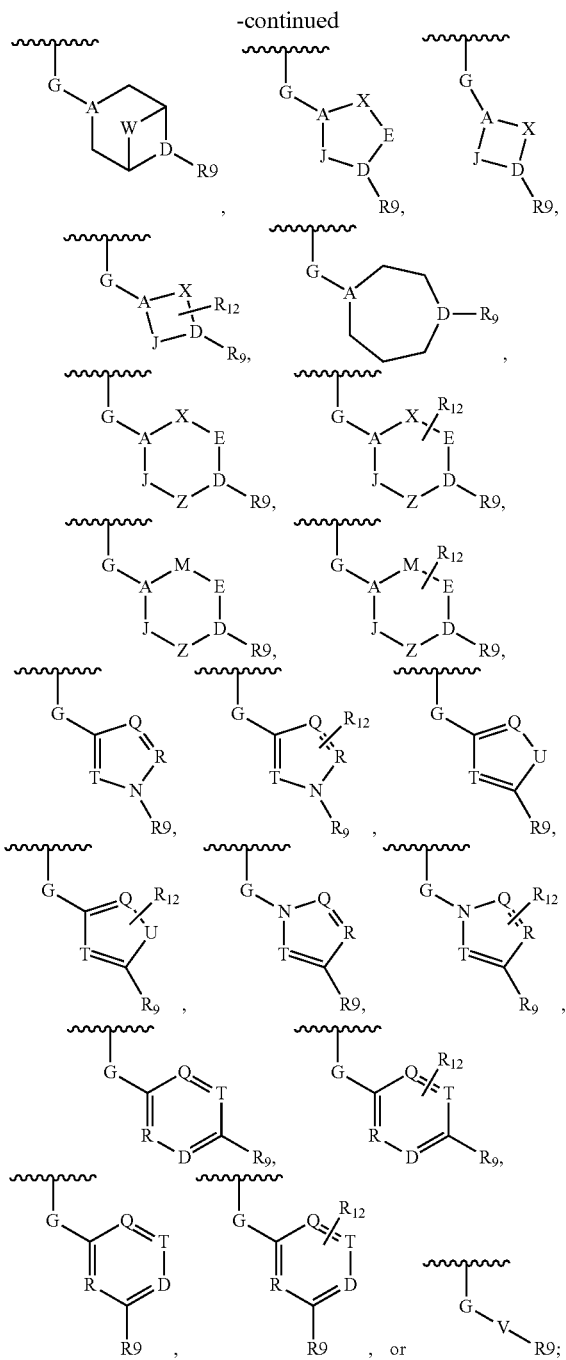

(e.g. —CH$_2$—CH(NHCH$_3$)—, etc.), carbocycle (cyclopropane, cyclobutane, cyclopentane, etc.), alkylcycloalkyl (e.g. methylcyclopropyl, methylcyclobuthyl, methylcyclopenthyl, etc.), hydoxycycloalkyl (e.g. hydroxycyclopropyl, dihydroxycyclopropyl, hydroxycyclobuthyl, dihydroxycyclobuthyl, hydroxycyclopenthyl, etc), alcoxycycloalkyl, hydroxalkylycycloalkyl (e.g. hydroxymethylcyclopropyl, hydroxymethylcyclobuthyl), disubstituted cycloalkyl (e.g. methyl-hydroxy-substituted cycloaklyl), aminocycloalkyl (e.g. aminocyclopropyl, diaminocyclopenthyl, aminocyclobuthyl, diaminocyclobuthyl, aminocyclopenthyl, etc.), alkylaminocycloalkyl (e.g. methylaminocyclopropyl, methylaminocyclobuthyl, etc.), substituted carbocycle, aromatic or non-aromatic heterocycle (aziridine, azetidine, pyrrole, etc) or combinations thereof;

wherein A and D independently comprise C or N;

wherein E, J, X and Z independently comprise C, N, S, or O;

wherein M, when present, independently comprises (—CH$_2$—)$_n$, with n=0-4 wherein Q, R, T when present, independently comprises C or N wherein U when present independently comprises O, N or S wherein W, when present comprises CH$_2$, CH$_2$CH$_2$, or CH$_2$CH$_2$CH$_2$, aminoalkylene (e.g. —NH—, —CH$_2$—NH—CH$_2$), oxalkylene (e.g. —O—, —CH$_2$—O—CH$_2$) groups;

wherein one or more of any H atoms on of R7 (e.g., H atoms on the R7 ring structure), may be independently replaced with a halogen (e.g., F, Cl, Br, I, etc.), alcohol (e.g., OH, methanol, ethanol, etc.), alkyl (C$_1$-C$_5$), alkoxy (e.g. methoxy, ethoxy, etc), amine (e.g. NH$_2$, methylamine, ethylamine, etc), ester (methyl carboxylate, ethyl carboxylate etc.) cyano group (e.g., CN, methyl carbonitrile, ethyl carbonitrile, etc.), an amide (e.g. CONH$_2$, acetamide, etc), —SO$_2$CH$_3$ group, sulfonamide (e.g. SO$_2$NH$_2$, SO$_2$NHCH$_3$, SO$_2$NHCH$_2$CH$_3$ etc.) —COOH, etc.;

wherein V, when present, comprises a 3-7 membered saturated ring, 3-7 membered unsaturated ring, 4-10 membered fused bicyclic ring, or 5-11 membered spiro bicyclic ring; wherein V may be optionally substituted with one or more R12 groups;

wherein R12, when present, comprises H, alkyl group (e.g., straight-chain alkyl (e.g., methane, ethane, propane, butane, pentane, hexane, etc.)), branched alkyl group (e.g., iso-propyl, 2-methyl-hexane, 3-methyl, 2-propyl-octane, etc.), cycloalkyl (e.g., cyclopropane, cyclobutane, cyclopentane, cyclohexane, cyclooctane, etc.), branched cyclic alkyl (e.g., methylcyclohexane, ethylcyclobutane, propylcyclohexane, etc.)), a substituted alkyl group (e.g., halogen-substituted alkyl group (e.g., trihaloethane (e.g., trifluoroethane), dihaloethane (e.g. difluroethane), haloethane (e.g. fluoroethane), halomethane (e.g., fluoromethane), dihalomethane (e.g., difluoromethane), trihalomethane (e.g., trifluoromethane), etc.), alkene (e.g., CH═CH$_2$, CH$_2$CH═CH$_2$, CH═CHCH$_3$, etc.), alkyne (e.g., C≡CH, C≡CCH$_3$, CH$_2$C≡CH, etc.), hydroxyl (e.g. —OH), hydroxyalkyl (e.g. —CH$_2$OH, etc), alkoxy group (e.g., ether, —CH$_2$—O-alky, CH$_2$—O-cycloalkyl (e.g., —CH$_2$—O-cyclopropyl, etc.), etc.), amine, alkylamine (e.g., primary amine (e.g., ethylamine, iso-butylamine, n-propylamine, sec-butylamine, iso-propylamine, iso-amylamine, methylamine, dimethylamine, n-amylamine, etc.), secondary amines (e.g., dimethylamine, methylethanolamine, diphenylamine, etc.), tertiary amine (e.g., trimethylamine, triphenylamine, etc.), thioalkyl, combinations thereof, etc.), a substituted cycloalkyl group (e.g., halogen-substituted wherein G, when present, comprises alkylene (e.g. methylene, —CH$_2$—, ethylene, —CH$_2$—CH$_2$—, propylene, —CH$_2$—CH$_2$—CH$_2$—, etc), branched alkylene (e.g. —CH(CH$_3$)—CH$_2$—, —CH$_2$—CH(CH$_3$)—, etc.), aminoalkylene (e.g. —NH—, —CH$_2$—NH—CH$_2$), oxalkylene (e.g. —O—, —CH$_2$—O—CH$_2$), haloalkylene groups; or heteroalkyl; hydroxyalkyl (e.g. —CH(OH)—, —CH(OH)—CH$_2$—, —CH(OH)—CH$_2$—, CH$_2$—CH(OH)—, —CH$_2$—CH(OH)—CH$_2$, —CH(OH)—CH$_2$—CH$_2$—, —CH$_2$—CH$_2$—CH(OH)—, etc.), alkylhydroxyalkyl (e.g. —CH$_2$—CH(CH$_2$OH), etc.), alkoxyalkyl (e.g. —CH$_2$—CH(OCH$_3$), etc.), aminoalkyl OR alkylamine (e.g. —CH(NH$_2$)—, —CH(NH$_2$)—CH$_2$—, —CH$_2$—CH(NH$_2$)—, etc.), alkylaminoalkyl (e.g. —CH$_2$—CH(NHCH$_2$), etc.)-, alkylaminoalkyl cycloalkyl group, cycloalkoxy group, cycloalkylamine, etc.), a halogen (e.g., F, Cl, Br, I, and At), a ketone, an amide, an alkylamide, a cyano group, methyl carbonitrile (e.g. $CH_2CN$), $—SO_2alkyl$ (e.g., $—SO_2CH_3$, $—SO_2ethyl$, $—SO_2propyl$, $—SO_2cyclopropyl$, etc.,), $—SO_2NH_2$ (e.g., $—SO_2NHalkyl$ (e.g., $—SO_2NHmethyl$, $—SO_2NHethyl$, $—SO_2NHpropyl$, $—SO_2NHcyclopropyl$, etc.), $SO_2Ndialkyl$ (e.g., $—SO_2N$-nm, wherein n and m are independently selected from methyl, ethyl, propyl, cyclopropyl, etc.), sulfonyl group, dialkylphosphine oxide (e.g., $—PO(CH_3)_2$), a carbocyclic ring, an aromatic ring, a substituted aromatic ring (e.g., branched aromatic ring (e.g., ethylbenzene, methyl benzene, etc.), halobenzene (e.g., chlorobenzene, fluorobenzene, etc.)), a heterocyclic aromatic ring (e.g., comprising one or more nitrogen, oxygen and/or sulfur members which may be non-substituted or substituted with alkyl, aryl, halogen, hydrogen bond donor or acceptor), a substituted or non-substituted heterocyclic non-aromatic ring (e.g., comprising carbon and one or more nitrogen, oxygen and/or sulfur members), carbocyclic or heterocyclic aromatic ring comprising carbon atoms and one or more nitrogen, oxygen and/or sulfur members fused to another aromatic ring, a multi-ring system comprising a combination of elements selected from aromatic rings, cycloalkane, heterocyclic rings, alkyl chains, and suitable C-, N-, O-, S-, and/or halogen-containing substituents, or a hydrogen bond donor or a hydrogen bond acceptor, and/or combinations thereof; and wherein R9 is selected from the functional groups: alkyl (e.g., methyl, ethyl, propyl, butyl, etc.), alkene (e.g., ethylene, methylethylene, ethylenemethyl, etc.), alkyne (e.g., acetylene, methylacetylene, acetylenemethyl, etc.), O-alkyl (e.g., O-methyl, O-ethyl, O-propyl), N-alkyl (e.g., NH-methyl, NH-ethyl, NH-propyl), S-alkyl (e.g., S-methyl, S-ethyl, S-propyl), alcohol (e.g., OH, $CH_2OH$, $CH_2CH_2OH$, etc.), thiol (e.g., SH, $CH_2SH$, $CH_2CH_2SH$, etc.), amine (e.g., $NH_2$, $CH_2NH_2$, $CH_2CH_2NH_2$, etc.), halogen (e.g., Br, Cl, F, I), alkyl halides (e.g., $CH_2F$, $CHF_2$, $CF_3$, $CH_2CH_2F$, $CH_2CHF_2$, $CH_2CF_3$, or the same substituents with Cl, Br, or I in place of F, etc.), nitrile (e.g., CN, $CH_2CN$, $CH_2CH_2CN$, etc.), aromatic ring (e.g., $C_3$-$C_6$), heteroaryl (e.g., $C_3$-$C_6$), non-aromatic heterocycle (e.g., $C_3$-$C_6$), carbocycle (e.g., $C_3$-$C_7$), and combinations thereof (e.g., $R^9=CHCHCH_2NCH_3$, $CCCF_3$, $CH2OCH2NH2$, CH2CHCHBr, or any other suitable combination of the aforementioned functional groups).

The disclosure further provides pharmaceutical compositions of a compound or salt of any one of Formulas (1) (2), (3), and Scaffold 1 and 2 and a pharmaceutically acceptable carrier or excipient.

The disclosure provides methods for the treatment of a disease, comprising administering a pharmaceutical composition of a compound or salt of any one of Formulas (1) (2), (3), (1A), (1B), (1C), (1D), (1E), (1F), (1G), (1H), (1I), and (1J), and Scaffold 1 and 2 to a subject suffering from said disease. The disease may be leukemia, hematologic malignancies, solid tumor cancer, glioma, or diabetes. In particular embodiments, the leukemia is AML, ALL, Mixed Lineage Leukemia or leukemias with Partial Tandem Duplications of MLL.

The disclosure provides methods for inhibiting the interaction of menin with MLL in a sample, comprising administering the compound or salt of any one of Formulas (1) (2), (3), (1A), (1B), (1C), (1D), (1E), (1F), (1G), (1H), (1I), and (1J), and Scaffold 1 and 2 to said sample comprising MLL and menin. MLL may be selected from one or more of MLL1, MLL2, a MLL fusion protein, and a MLL Partial Tandem Duplication. In certain embodiments, the disclosure provides a method of treating a disease mediated by chromosomal rearrangement on chromosome 11q23, comprising administering to a subject in need thereof a therapeutically effective amount of the pharmaceutical composition of a compound or salt of any one of Formulas Formulas (1) (2), (3), (1A), (1B), (1C), (1D), (1E), (1F), (1G), (1H), (1I), and (1J), and Scaffold 1 and 2. In certain embodiments, the disease is mediated by menin. In certain embodiments the compound or salt of any one of Formulas Formulas (1) (2), (3), (1A), (1B), (1C), (1D), (1E), (1F), (1G), (1H), (1I), and (1J), and Scaffold 1 and 2 covalently binds to menin and inhibits the interaction of menin and MLL.

In some embodiments, provided herein are methods of screening compounds effective in the treatment of diseases or conditions dependent on the interaction of menin with MLL1, MLL2, and/or MLL fusion proteins (e.g., leukemia (AML, ALL, etc.), solid cancers (e.g., glioma), etc.) comprising assaying one or more compounds for inhibition of the interaction between MLL (or MLL fusion protein) and menin. In some embodiments, the screening is performed in vitro. In some embodiments, the screening is performed in vivo. In some embodiments, the assaying comprises a fluorescence polarization assay. In some embodiments, the assaying comprises a time-resolved fluorescence resonance energy transfer assay. In some embodiments, the assaying comprises a nuclear magnetic resonance (NMR) methods. In some embodiments, the assaying comprises cellular assays and/or animal (e.g., mice) studies.

BRIEF DESCRIPTION OF THE DRAWINGS

FIG. 5 depicts cellular activity of menin-MLL inhibitors in MLL leukemia cell lines (MLL-AF9 BMC, MV4;11, KOPN-8 and MOLM13) and in control cell line (HM-2 and REH) demonstrating selectivity towards MLL fusion transformed cells. Growth inhibition ($GI_{50}$) is provided after 7 days of treatment with menin-MLL inhibitors measured in MTT cell viability assay. (ND is not determined).

FIG. 8 is an amino acid sequence of human menin, isoform 1 (SEQ ID NO: 1).

FIG. 9 is an amino acid sequence of human menin, isoform 2 (SEQ ID NO: 2).

FIG. 10 is an amino acid sequence of human menin, isoform 3 (SEQ ID NO: 3).

DEFINITIONS

Figure 1:
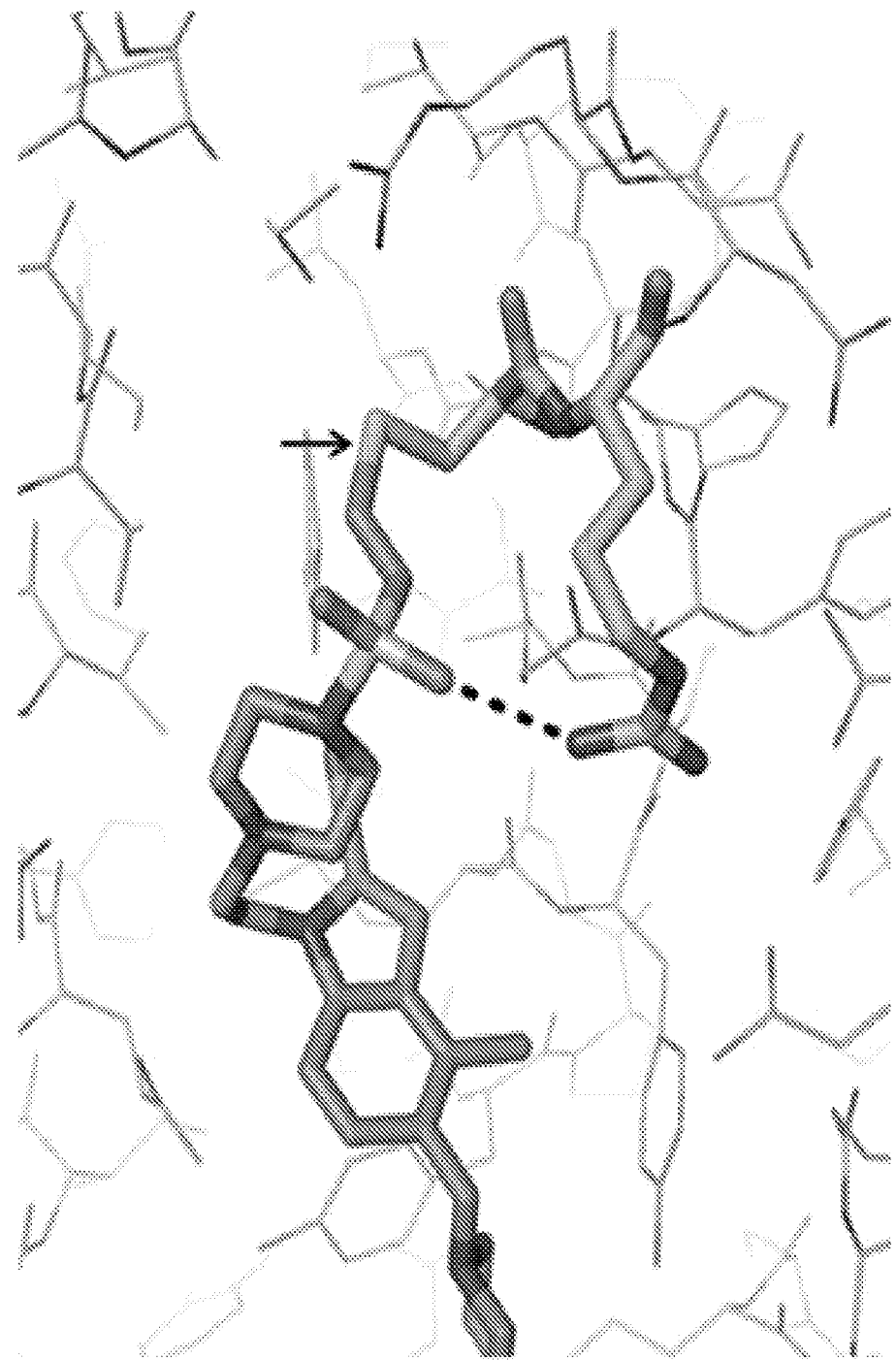
FIG. 1 depicts the crystal structure of menin in complex with Compound 3, demonstrating covalent binding of the compound to a Cys residue on menin (covalent bond indicated by arrow).
Figure 2:
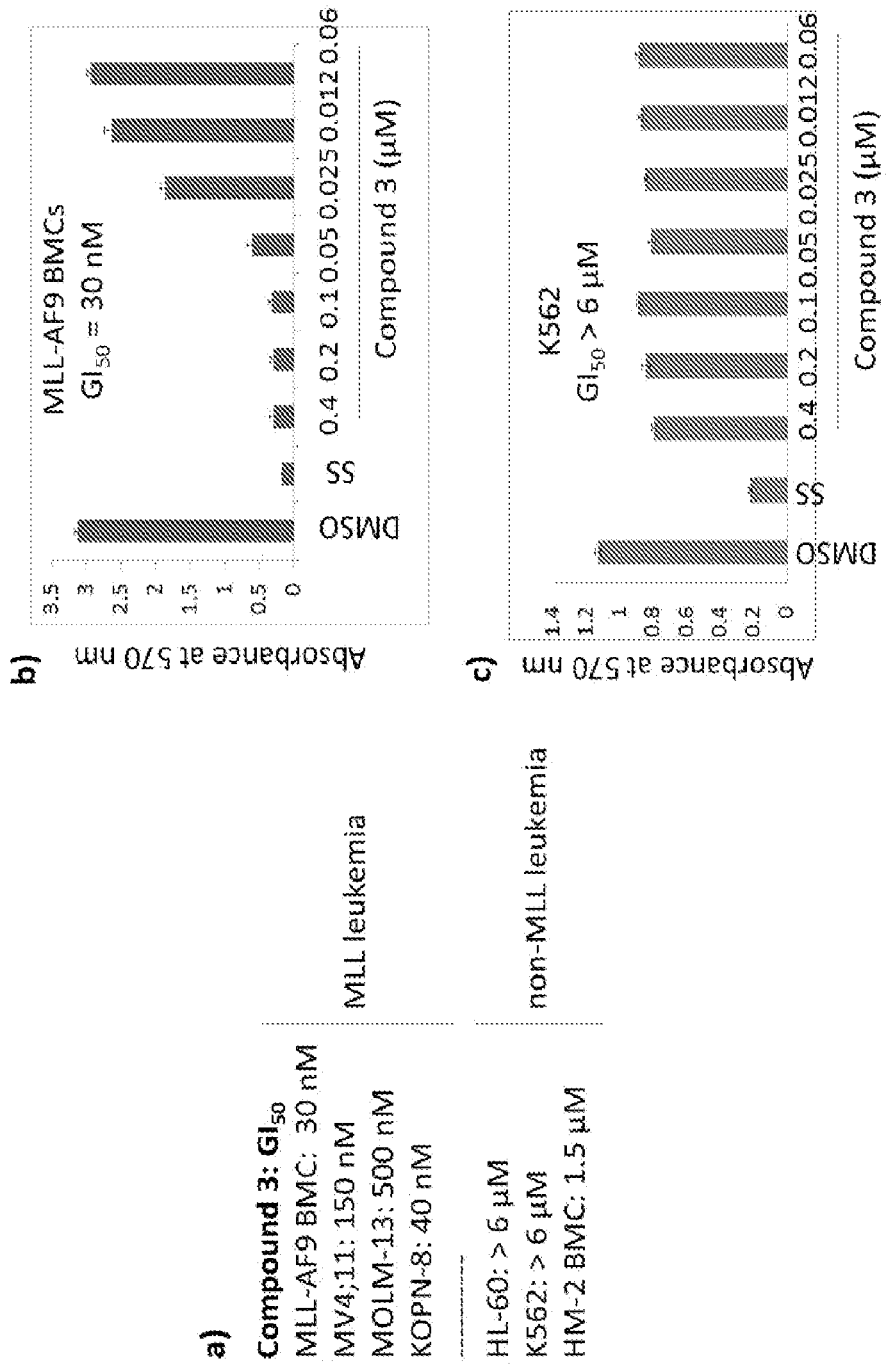
FIG. 2 depicts (a) a comparison of $GI_{50}$ (growth inhibition) values in MLL leukemia cells and control cell lines (non-MLL leukemia cells) measured for Compound 3 in the MTT cell viability assay; and (b) data from a MTT cell viability assay upon treatment of MLL-AF9 transformed murine bone marrow cells (BMC) and K562 control cell line (panel c) with Compound 3.
Figure 3:
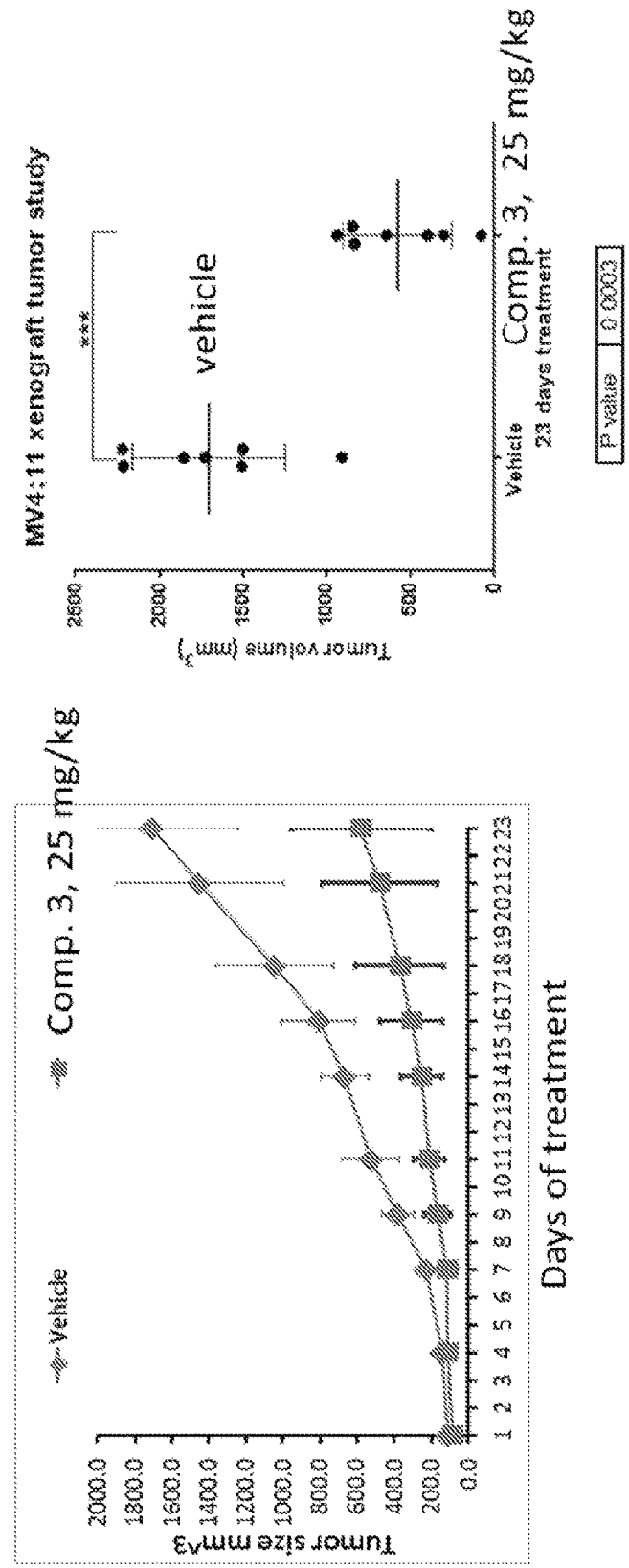
FIG. 3 depicts in vivo xenograft studies with MV4; 11 cells (harboring MLL-AF4 fusion protein) injected subcutaneously into CB17 SCID mice. Treatment with Compound 3 (once daily, i.p., 25 mg/kg) was initiated when tumors reached ~100 mm$^3$ volume and resulted in strong reduction of tumor volume (mean values and s.d. are shown).
Figure 4:
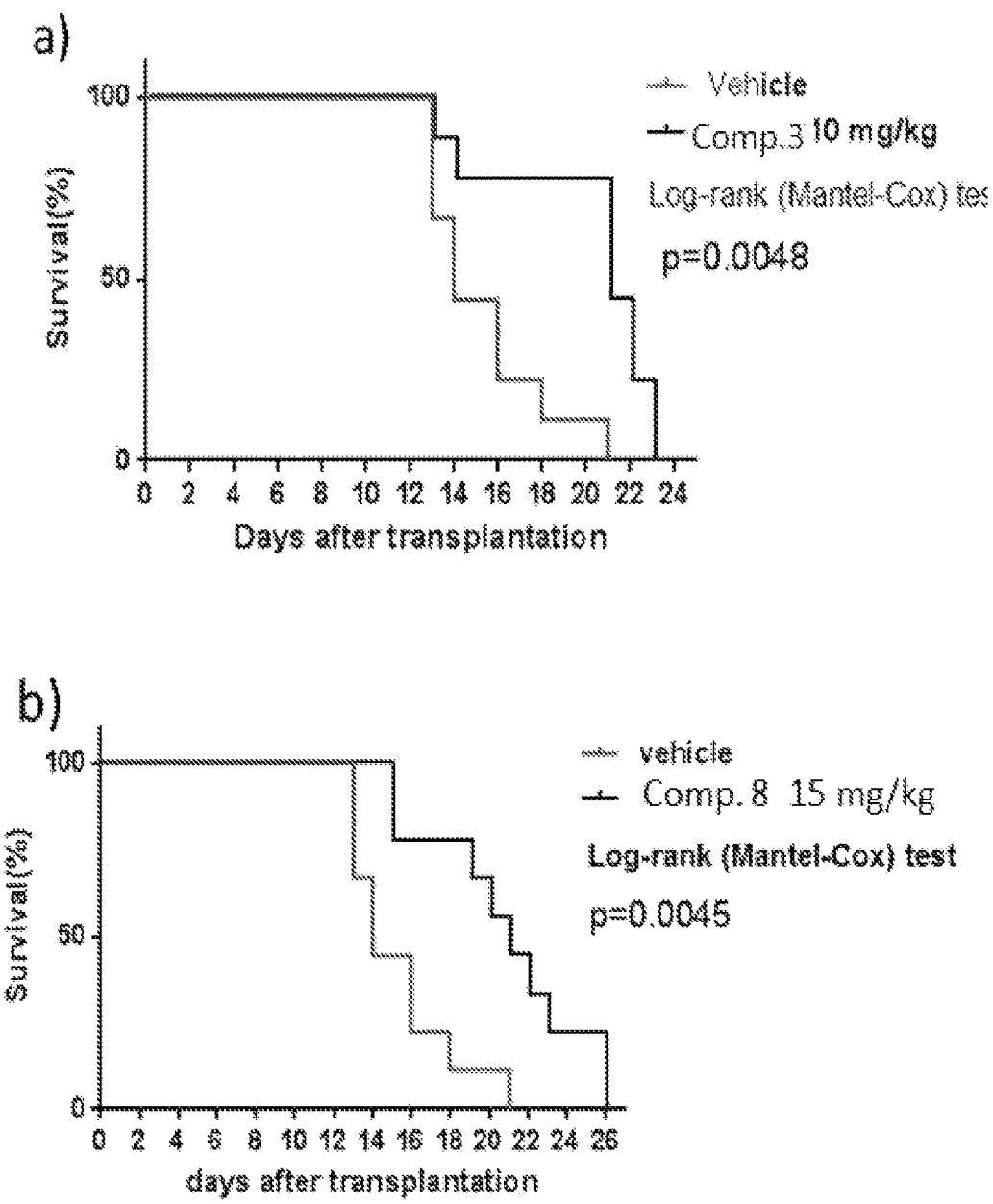
FIG. 4 depicts (a) the survival of MLL-AF9 mice administered compound 3 (10 mg/kg) in bone marrow transplantation model; and (b) the survival of MLL-AF9 mice administered compound 8 (15 mg/kg) in bone marrow transplantation model. Treatment (b.i.d., i.p.) was initiated 5 days after transplantation of mice with MLL-AF9 transformed cells and continued for 10 days.
Figure 6:
FIG. 6 depicts (a) growth inhibition, $GI_{50}$, induced by treatment (7 days) with the menin-MLL inhibitor (compound 101) in NP glioma cells; and (b) growth inhibition, GI$_{50}$, induced by treatment (7 days) with the menin-MLL inhibitor (compound 101) in NP_H3.3K27M (harboring the K27M mutation) glioma cells. Growth inhibition was measured in the MTT cell viability assay.
Figure 7:
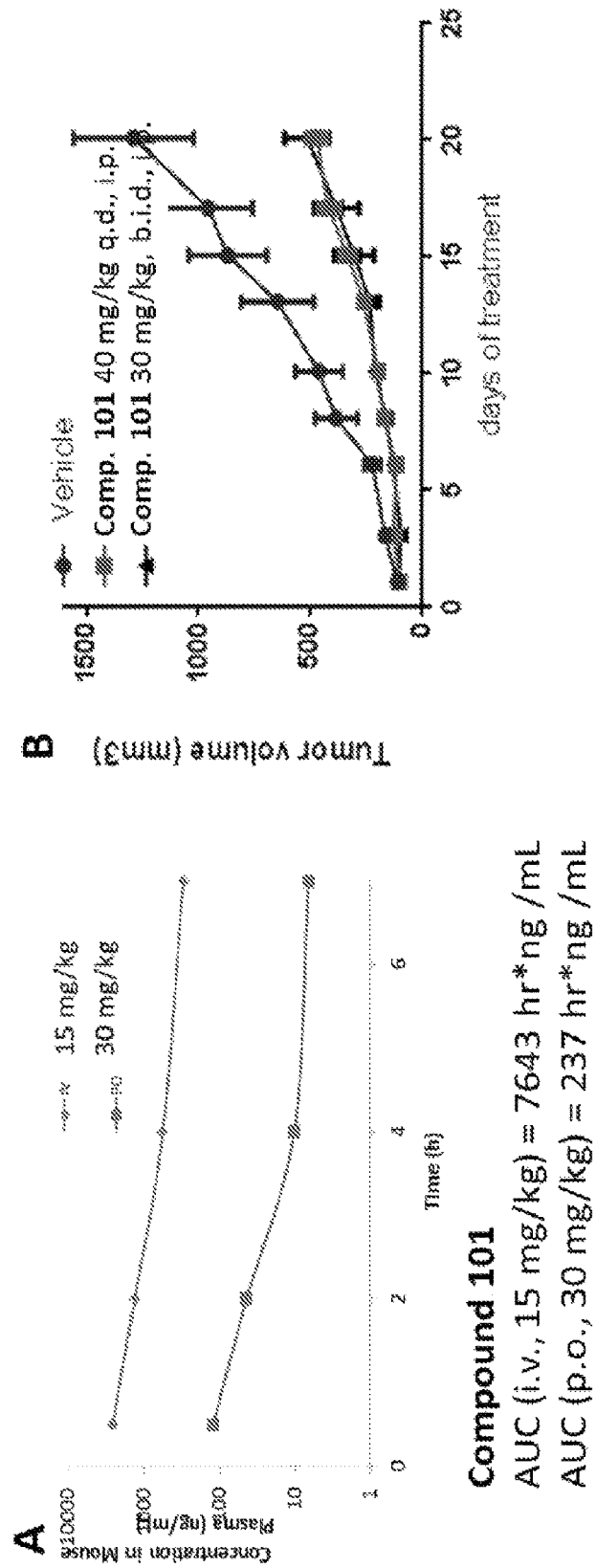
FIG. 7 depicts: A. the pharmacokinetic profile for compound 101 in C57BL/6 mice after i.v. (15 mg/kg) or oral (30 mg/kg) administration of the compound, and B. In vivo xenograft studies with MV4;11 cells (harboring MLL-AF4 fusion protein) injected subcutaneously into CB17 SCID mice. Treatment with Compound 101 (i.p., 40 mg/kg q.d. and 30 mg/kg b.i.d.) was initiated when tumors reached ~100 mm$^3$ volume (mean values and s.e.m are shown).

All chemical names of substituents should be interpreted in light of IUPAC and/or a modified format in which functional groups within a substituent are read in the order in which they branch from the scaffold or main structure. For example, in the modified nomenclature, methyl-sulfonyl-propanol refers to CH$_3$SO$_2$CH$_2$CH$_2$CH$_2$OH or:

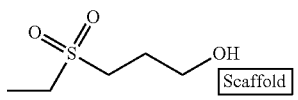

As another example, according to the modified nomenclature, a methyl-amine substituent is:

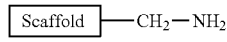

while an amino-methyl substituent is:

All chemical names of substituents should be interpreted in light of IUPAC and/or the modified nomenclature and with reference to the chemical structures depicted and/or described herein.

The term "system" refers a group of objects, compounds, methods, and/or devices that form a network for performing a desired objective.

As used herein a "sample" refers to anything capable of being subjected to the compositions and methods provided herein. The sample may be in vitro or in vivo. In some embodiments, samples are "mixture" samples, which samples from more than one subject or individual. In some embodiments, the methods provided herein comprise purifying or isolating the sample. In some embodiments, the sample is purified or unpurified protein. In some embodiments, a sample may be from a clinical or research setting. In some embodiments, a sample may comprise cells, fluids (e.g. blood, urine, cytoplasm, etc.), tissues, organs, lysed cells, whole organisms, etc. In some embodiments, a sample may be derived from a subject. In some embodiments, a sample may comprise one or more partial or whole subjects.

As used herein, the term "subject" refers to any animal including, but not limited to, humans, non-human primates, bovines, equines, felines, canines, pigs, rodents (e.g., mice), and the like. The terms "subject" and "patient" may be used interchangeably, wherein the term "patient" generally refers to a human subject seeking or receiving treatment or preventative measures from a clinician or health care provider.

As used herein, the terms "subject at risk for cancer" or "subject at risk for leukemia" refer to a subject with one or more risk factors for developing cancer and/or leukemia. Risk factors include, but are not limited to, gender, age, genetic predisposition, environmental exposure, and previous incidents of cancer, preexisting non-cancer diseases, and lifestyle.

As used herein, the terms "characterizing cancer in a subject" and "characterizing leukemia in a subject" refer to the identification of one or more properties of a cancer and/or leukemia sample in a subject, including but not limited to, the presence of benign, pre-cancerous or cancerous tissue or cells and the stage of the cancer (e.g., leukemia). Cancers (e.g., leukemia) may be characterized by identifying cancer cells with the compositions and methods of the present invention.

The terms "test agent" and "candidate agent" refer to any chemical entity, pharmaceutical, drug, peptide, antibody, etc. that is a candidate for use to treat or prevent a disease, illness, sickness, or disorder of bodily function (e.g., cancer). Test agents (e.g., test compounds) comprise both known and potential therapeutic compounds. A test agent (e.g., test compound) can be determined to be therapeutic by screening using the screening methods of the present invention.

As used herein, the term "effective amount" refers to the amount of a compound (e.g., a compound having a structure presented above or elsewhere described herein) sufficient to effect beneficial or desired results. An effective amount can be administered in one or more administrations, applications or dosages and is not limited to or intended to be limited to a particular formulation or administration route.

As used herein, the term "co-administration" refers to the administration of at least two agent(s) (e.g., a compound having a structure presented above or elsewhere described herein) or therapies to a subject. In some embodiments, the co-administration of two or more agents/therapies is concurrent. In other embodiments, a first agent/therapy is administered prior to a second agent/therapy. Those of skill in the art understand that the formulations and/or routes of administration of the various agents/therapies used may vary. The appropriate dosage for co-administration can be readily determined by one skilled in the art. In some embodiments, when agents/therapies are co-administered, the respective agents/therapies are administered at lower dosages than appropriate for their administration alone. Thus, co-administration is especially desirable in embodiments where the co-administration of the agents/therapies lowers the requisite dosage of a known potentially harmful (e.g., toxic) agent(s).

As used herein, the term "covalently reacts" refers to the interaction between two chemical moities, e.g., a nucleophile and an electrophile, that results in a covalent bond between said moieties.

As used herein, the term "pharmaceutical composition" refers to the combination of an active agent with a carrier, inert or active, making the composition especially suitable for diagnostic or therapeutic use in vivo, in vivo or ex vivo.

As used herein, the term "pharmaceutically acceptable carrier" refers to any of the standard pharmaceutical carriers, such as a phosphate buffered saline solution, water, emulsions (e.g., such as an oil/water or water/oil emulsions), and various types of wetting agents. The compositions also can include stabilizers and preservatives. For examples of carriers, stabilizers and adjuvants. (See e.g., Martin, Remington's Pharmaceutical Sciences, 15th Ed., Mack Publ. Co., Easton, Pa. [1975]).

As used herein, the term "pharmaceutically acceptable salt" refers to any pharmaceutically acceptable salt (e.g., acid or base) of a compound of the present invention which, upon administration to a subject, is capable of providing a compound of this invention or an active metabolite or residue thereof. As is known to those of skill in the art, "salts" of the compounds of the present invention may be derived from inorganic or organic acids and bases. Examples of acids include, but are not limited to, hydrochloric, hydrobromic, sulfuric, nitric, perchloric, fumaric, maleic, phosphoric, glycolic, lactic, salicylic, succinic, toluene-p-sulfonic, tartaric, acetic, citric, methanesulfonic, ethanesulfonic, formic, benzoic, malonic, naphthalene-2-sulfonic, benzenesulfonic acid, and the like. Other acids, such as oxalic, while not in themselves pharmaceutically acceptable, may be employed in the preparation of salts useful as intermediates in obtaining the compounds of the invention and their pharmaceutically acceptable acid addition salts.

Examples of bases include, but are not limited to, alkali metals (e.g., sodium) hydroxides, alkaline earth metals (e.g., magnesium), hydroxides, ammonia, and compounds of formula $NW_4^+$, wherein W is $C_{1-4}$ alkyl, and the like.

Examples of salts include, but are not limited to: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, flucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, palmoate, pectinate, persulfate, phenylpropionate, picrate, pivalate, propionate, succinate, tartrate, thiocyanate, tosylate, undecanoate, and the like. Other examples of salts include anions of the compounds of the present invention compounded with a suitable cation such as $Na^+$, $NH_4^+$, and $NW_4^+$ (wherein W is a $C_{1-4}$ alkyl group), and the like.

For therapeutic use, salts of the compounds of the present invention are contemplated as being pharmaceutically acceptable. However, salts of acids and bases that are non-pharmaceutically acceptable may also find use, for example, in the preparation or purification of a pharmaceutically acceptable compound.

As used herein, the term "instructions for administering said compound to a subject," and grammatical equivalents thereof, includes instructions for using the compositions contained in a kit for the treatment of conditions (e.g., providing dosing, route of administration, decision trees for treating physicians for correlating patient-specific characteristics with therapeutic courses of action).

As used herein, the term "alkyl" refers to a moiety consisting of carbon and hydrogen containing no double or triple bonds. An alkyl may be linear, branched, cyclic, or a combination thereof, and may contain from one to fifty carbon atoms, such as straight chain or branched $C^1$-$C^{20}$ alkane. Examples of alkyl groups include but are not limited to methyl, ethyl, propyl, isopropyl, cyclopropyl, butyl isomers (e.g. n-butyl, iso-butyl, tert-butyl, etc.) cyclobutyl isomers (e.g. cyclobutyl, methylcyclopropyl, etc.), pentyl isomers, cyclopentane isomers, hexyl isomers, cyclohexane isomers, and the like. Unless specified otherwise (e.g., substituted alkyl group, heteroalkyl, alkoxy group, haloalkyl, alkylamine, thioalkyl, etc.), an alkyl group contains carbon and hydrogen atoms only.

As used herein, "alkylene" or "alkylene chain" refers to a straight or branched divalent hydrocarbon chain linking the rest of the molecule to a radical group, consisting solely of carbon and hydrogen, containing no unsaturation, and preferably having from one to twelve carbon atoms, for example, methylene, ethylene, propylene, n-butylene, and the like. The alkylene chain is attached to the rest of the molecule through a single bond and to the radical group through a single bond. The points of attachment of the alkylene chain to the rest of the molecule and to the radical group may be through any two carbons within the chain. In certain embodiments, an alkylene comprises one to ten carbon atoms (i.e., $C_1$-$C_{10}$ alkylene). In certain embodiments, an alkylene comprises one to eight carbon atoms (i.e., $C_1$-$C_8$ alkylene). In other embodiments, an alkylene comprises one to five carbon atoms (i.e., $C_1$-$C_5$ alkylene). In other embodiments, an alkylene comprises one to four carbon atoms (i.e., $C_1$-$C_4$ alkylene). In other embodiments, an alkylene comprises one to three carbon atoms (i.e., $C_1$-$C_3$ alkylene). In other embodiments, an alkylene comprises one to two carbon atoms (i.e., $C_1$-$C_2$ alkylene). In other embodiments, an alkylene comprises one carbon atom (i.e., $C_1$ alkylene). Unless stated otherwise specifically in the specification, an alkylene chain is optionally substituted by one or more substituents such as those substituents described herein.

As used herein, the term "alkenyl" refers to a straight or branched hydrocarbon chain radical group consisting solely of carbon and hydrogen atoms, containing at least one carbon-carbon double bond, and preferably having from two to twelve carbon atoms (i.e., $C_2$-$C_{12}$ alkenyl). In certain embodiments, an alkenyl comprises two to eight carbon atoms (i.e., $C_2$-$C_8$ alkenyl). In certain embodiments, an alkenyl comprises two to six carbon atoms (i.e., $C_2$-$C_6$ alkenyl). In other embodiments, an alkenyl comprises two to four carbon atoms (i.e., $C_2$-$C_4$ alkenyl). The alkenyl is attached to the rest of the molecule by a single bond, for example, ethenyl (i.e., vinyl), prop-1-enyl (i.e., allyl), but-1-enyl, pent-1-enyl, penta-1,4-dienyl, and the like. Unless stated otherwise specifically in the specification, an alkenyl group is optionally substituted by one or more substituents such as those substituents described herein.

As used herein, "alkenylene" or "alkenylene chain" refers to a straight or branched divalent hydrocarbon chain linking the rest of the molecule to a radical group, consisting solely of carbon and hydrogen, containing at least one carbon-carbon double bond, and preferably having from two to twelve carbon atoms. The alkenylene chain is attached to the rest of the molecule through a single bond and to the radical group through a single bond. The points of attachment of the alkenylene chain to the rest of the molecule and to the radical group may be through any two carbons within the chain. In certain embodiments, an alkenylene comprises two to ten carbon atoms (i.e., $C_2$-$C_{10}$ alkenylene). In certain embodiments, an alkenylene comprises two to eight carbon atoms (i.e., $C_2$-$C_8$ alkenylene). In other embodiments, an alkenylene comprises two to five carbon atoms (i.e., $C_2$-$C_5$ alkenylene). In other embodiments, an alkenylene comprises two to four carbon atoms (i.e., $C_2$-$C_4$ alkenylene). In other embodiments, an alkenylene comprises two to three carbon atoms (i.e., $C_2$-$C_3$ alkenylene). In other embodiments, an alkenylene comprises two carbon atom (i.e., $C_2$ alkenylene). Unless stated otherwise specifically in the specification, an alkenylene chain is optionally substituted by one or more substituents such as those substituents described herein.

As used herein, the term "alkynyl" refers to a straight or branched hydrocarbon chain radical group consisting solely of carbon and hydrogen atoms, containing at least one carbon-carbon triple bond, and preferably having from two to twelve carbon atoms (i.e., $C_2$-$C_{12}$ alkynyl). In certain embodiments, an alkynyl comprises two to eight carbon atoms (i.e., $C_2$-$C_8$ alkynyl). In other embodiments, an alkynyl comprises two to six carbon atoms (i.e., $C_2$-$C_6$ alkynyl). In other embodiments, an alkynyl comprises two to four carbon atoms (i.e., $C_2$-$C_4$ alkynyl). The alkynyl is attached to the rest of the molecule by a single bond, for example, ethynyl, propynyl, butynyl, pentynyl, hexynyl, and the like. Unless stated otherwise specifically in the specification, an alkynyl group is optionally substituted by one or more substituents such as those substituents described herein.

As used herein "alkynylene" or "alkynylene chain" refers to a straight or branched divalent hydrocarbon chain linking the rest of the molecule to a radical group, consisting solely of carbon and hydrogen, containing at least one carbon-carbon triple bond, and preferably having from two to twelve carbon atoms. The alkynylene chain is attached to the rest of the molecule through a single bond and to the radical group through a single bond. The points of attachment of the alkynylene chain to the rest of the molecule and to the radical group may be through any two carbons within the chain. In certain embodiments, an alkynylene comprises two to ten carbon atoms (i.e., $C_2$-$C_{10}$ alkynylene). In certain embodiments, an alkynylene comprises two to eight carbon atoms (i.e., $C_2$-$C_8$ alkynylene). In other embodiments, an alkynylene comprises two to five carbon atoms (i.e., $C_2$-$C_5$ alkynylene). In other embodiments, an alkynylene comprises two to four carbon atoms (i.e., $C_2$-$C_4$ alkynylene). In other embodiments, an alkynylene comprises two to three carbon atoms (i.e., $C_2$-$C_3$ alkynylene). In other embodiments, an alkynylene comprises two carbon atom (i.e., $C_2$ alkynylene). Unless stated otherwise specifically in the specification, an alkynylene chain is optionally substituted by one or more substituents such as those substituents described herein.

As used herein, the term "amine" or "amino" includes primary, secondary, and tertiary amines wherein each non-hydrogen group on nitrogen may be selected from alkyl, aryl, and the like. Amines include but are not limited to —$NH_2$, —NH-phenyl, —NH—$CH_3$, —NH—$CH_2CH_3$, and —N($CH_3$)benzyl.

The term "amide" or "amido" includes C- and N-amide groups, i.e., —C(O)$NR_2$, and —NRC(O)R groups, respectively, where R can be H, alkyl, aryl, etc. Amide groups therefore include but are not limited to —C(O)$NH_2$, —NHC(O)H, —C(O)NH$CH_2CH_3$, —NHC(O)$CH_3$, —C(O)N($CH_2CH_3$)phenyl.

As used herein, the term "linear alkyl" refers to a chain of carbon and hydrogen atoms (e.g., ethane, propane, butane, pentane, hexane, etc.). A linear alkyl group may be referred to by the designation —$(CH_2)_q CH_3$, where q is 0-49. The designation "$C_{1-12}$ alkyl" or a similar designation, refers to alkyl having from 1 to 12 carbon atoms such as methyl, ethyl, propyl isomers (e.g. n-propyl, isopropyl, etc.), butyl isomers, cyclobutyl isomers (e.g. cyclobutyl, methylcyclopropyl, etc.), pentyl isomers, cyclopentyl isomers, hexyl isomers, cyclohexyl isomer, heptyl isomers, cycloheptyl isomers, octyl isomers, cyclooctyl isomers, nonyl isomers, cyclononyl isomers, decyl isomer, cyclodecyl isomers, etc. Similar designations refer to alkyl with a number of carbon atoms in a different range.

The term "$C_{x-y}$" when used in conjunction with a chemical moiety, such as alkyl, alkenyl, alkynyl, or carbocycle is meant to include groups that contain from x to y carbons in the chain or ring. For example, the term "$C_{x-y}$alkyl" refers to substituted or unsubstituted saturated hydrocarbon groups, including straight-chain alkyl and branched-chain alkyl groups that contain from x to y carbons in the chain, including haloalkyl groups such as trifluoromethyl and 2,2,2-trifluoroethyl, etc. The terms "$C_{x-y}$alkenyl" and "$C_{x-y}$alkynyl" refer to substituted or unsubstituted unsaturated aliphatic groups analogous in length and possible substitution to the alkyls described above, but that contain at least one double or triple bond respectively. The term "$C_{x-y}$ carbocycle" refers to a substituted or unsubstituted carbocycle, that contain from x to y ring carbons.

As used herein, the term "branched alkyl" refers to a chain of carbon and hydrogen atoms, without double or triple bonds, that contains a fork, branch, and/or split in the chain (e.g., 3,5-dimethyl-2-ethylhexane, 2-methyl-pentane, 1-methyl-cyclobutane, ortho-diethyl-cyclohexane, etc.). "Branching" refers to the divergence of a carbon chain, whereas "substitution" refers to the presence of non-carbon/non-hydrogen atoms in a moiety. Unless specified otherwise (e.g., substituted branched alkyl group, branched heteroalkyl, branched alkoxy group, branched haloalkyl, branched alkylamine, branched thioalkyl, etc.), a branched alkyl group contains carbon and hydrogen atoms only.

As used herein, the term "carbocycle" refers to a saturated, unsaturated or aromatic ring in which each atom of the ring is carbon. Carbocycle includes monocyclic, bicyclic and polycyclic rings, wherein bicyclic or polycyclic rings may include fused, or spiro rings. Carbocycle may include 3- to 10-membered monocyclic rings, 6- to 12-membered bicyclic rings, and 6- to 12-membered bridged rings. Each ring of a bicyclic or polycyclic carbocycle may be selected from saturated, unsaturated, and aromatic rings. In an exemplary embodiment, an aromatic carbocycle, e.g., phenyl, may be fused to a saturated or unsaturated ring, e.g., cyclohexane, cyclopentane, or cyclohexene. In some embodiments, the carbocycle is an aromatic carbocycle. In some embodiments, the carbocycle is a cycloalkyl. In some embodiments, the carbocycle is a cycloalkenyl. Exemplary carbocycles include cyclopentyl, cyclohexyl, cyclohexenyl, adamantyl, phenyl, indanyl, and naphthyl. Unless stated otherwise specifically in the specification, a carbocycle is optionally substituted by one or more substituents such as those substituents described herein.

As used herein, the term "cycloalkyl" refers to a completely saturated mono- or multi-cyclic hydrocarbon ring system. When composed of two or more rings, the rings may be joined together in a fused, bridged or spiro-connected fashion. Cycloalkyl groups of the present application may range from three to ten carbons ($C_3$ to $C_{10}$). A cycloalkyl group may be unsubstituted, substituted, branched, and/or unbranched. Typical cycloalkyl groups include, but are not limited to, cyclopropyl, cyclobutyl, cyclopentyl, cyclohexyl, and the like. If substituted, the substituent(s) may be an alkyl or selected from those indicated above with regard to substitution of an alkyl group unless otherwise indicated. Unless specified otherwise (e.g., substituted cycloalkyl group, heterocyclyl, cycloalkoxy group, halocycloalkyl, cycloalkylamine, thiocycloalkyl, etc.), an alkyl group contains carbon and hydrogen atoms only.

As used herein, the term "cycloalkenyl" refers to a stable unsaturated non-aromatic monocyclic, bicyclic or polycyclic hydrocarbon radical consisting solely of carbon and hydrogen atoms, which includes fused or bridged ring systems, preferably having from three to twelve carbon atoms and comprising at least one double bond. In certain embodiments, a cycloalkenyl comprises three to ten carbon atoms. In other embodiments, a cycloalkenyl comprises five to seven carbon atoms. The cycloalkenyl may be attached to the rest of the molecule by a single bond. Examples of monocyclic cycloalkenyls include, e.g., cyclopentenyl, cyclohexenyl, cycloheptenyl, and cyclooctenyl. Unless otherwise stated specifically in the specification, the term "cycloalkenyl" is meant to include cycloalkenyl radicals that are optionally substituted by one or more substituents such as those substituents described herein.

As used herein, the term "heteroalkyl" refers to an alkyl group, as defined herein, wherein one or more carbon atoms are independently replaced by one or more heteroatoms (e.g., oxygen, sulfur, nitrogen, phosphorus, silicon, or combinations thereof). The alkyl group containing the non-carbon substitution(s) may be a linear alkyl, branched alkyl, cycloalkyl (e.g., cycloheteroalkyl), or combinations thereof. Non-carbons may be at terminal locations (e.g., 2-hexanol) or integral to an alkyl group (e.g., diethyl ether). Unless stated otherwise specifically in the specification, the heteroalkyl group may be optionally substituted as described herein. Representative heteroalkyl groups include, but are not limited to —OCH$_2$OMe, —OCH$_2$CH$_2$OMe, or —OCH$_2$CH$_2$OCH$_2$CH$_2$NH$_2$.

As used herein, the term "heteroalkylene" refers to an alkyl radical as described above where one or more carbon atoms of the alkyl is replaced with a heteroatom, e.g., O, N or S. "Heteroalkylene" or "heteroalkylene chain" refers to a straight or branched divalent heteroalkyl chain linking the rest of the molecule to a radical group. Unless stated otherwise specifically in the specification, the heteroalkylene group may be optionally substituted as described herein. Representative heteroalkylene groups include, but are not limited to —OCH$_2$CH$_2$O—, —OCH$_2$CH$_2$OCH$_2$CH$_2$O—, or —OCH$_2$CH$_2$OCH$_2$CH$_2$OCH$_2$CH$_2$O—.

The term "substituted" refers to moieties having substituents replacing a hydrogen on one or more carbons or substitutable heteroatoms, e.g., NH, of the structure. It will be understood that "substitution" or "substituted with" includes the implicit proviso that such substitution is in accordance with permitted valence of the substituted atom and the substituent, and that the substitution results in a stable compound, i.e., a compound which does not spontaneously undergo transformation such as by rearrangement, cyclization, elimination, etc. In certain embodiments, substituted refers to moieties having substituents replacing two hydrogen atoms on the same carbon atom, such as substituting the two hydrogen atoms on a single carbon with an oxo, imino or thioxo group. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds. For purposes of this disclosure, the heteroatoms such as nitrogen may have hydrogen substituents and/or any permissible substituents of organic compounds described herein which satisfy the valences of the heteroatoms.

The term "optionally substituted", as used herein, means that the referenced group (e.g., alkyl, cycloalkyl, etc.) may or may not be substituted with one or more additional group(s). Non-limiting examples of substituents include, for example: halogen, hydroxy, oxo (=O), thioxo (=S), cyano (—CN), nitro (—NO$_2$), imino (=N—H), oximo (=N—OH), hydrazino (=N—NH$_2$), —R$^b$—OR$^a$, —R$^b$—OC(O)—R$^a$, —R$^b$—OC(O)—OR$^a$, —R$^b$—OC(O)—N(R$^a$)$_2$, —R$^b$—N(R$^a$)$_2$, —R$^b$—C(O)R$^a$, —R$^b$—C(O)OR$^a$, —R$^b$—C(O)N(R$^a$)$_2$, —R$^b$—O—R$^c$—C(O)N(R$^a$)$_2$, —R$^b$—N(R$^a$)C(O)OR$^a$, —R$^b$—N(R$^a$)C(O)R$^a$, —R$^b$—N(R$^a$)S(O)$_t$R$^a$ (where t is 1 or 2), —R$^b$—S(O)$_t$R$^a$ (where t is 1 or 2), —R$^b$—S(O)$_t$OR$^a$ (where t is 1 or 2), and —R$^b$—S(O)$_t$N(R$^a$)$_2$ (where t is 1 or 2); and alkyl, alkenyl, alkynyl, each of which may be optionally substituted by halogen, oxo (=O), thioxo (=S), cyano (—CN), nitro (—NO$_2$), imino (=N—H), oximo (=N—OH), hydrazine (=N—NH$_2$), —R$^b$—OR$^a$, —R$^b$—OC(O)—R$^a$, —R$^b$—OC(O)—OR$^a$, —R$^b$—OC(O)—N(R$^a$)$_2$, —R$^b$—N(R$^a$)$_2$, —R$^b$—C(O)R$^a$, —R$^b$—C(O)OR$^a$, —R$^b$—C(O)N(R$^a$)$_2$, —R$^b$—O—R$^c$—C(O)N(R$^a$)$_2$, —R$^b$—N(R$^a$)C(O)OR$^a$, —R$^b$—N(R$^a$)C(O)R$^a$, —R$^b$—N(R$^a$)S(O)$_t$R$^a$ (where t is 1 or 2), carbocycle and heterocycle; wherein each R$^a$ is independently selected from hydrogen, alkyl, alkenyl, alkynyl, carbocycle and heterocycle, wherein each R$^a$, valence permitting, may be optionally substituted with halogen, oxo (=O), thioxo (=S), cyano (—CN), nitro (—NO$_2$), imino (=N—H), oximo (=N—OH), hydrazine (=N—NH$_2$), —R$^b$—OR$^a$, —R$^b$—OC(O)—R$^a$, —R$^b$—OC(O)—OR$^a$, —R$^b$—OC(O)—N(R$^a$)$_2$, —R$^b$—N(R$^a$)$_2$, —R$^b$—C(O)R$^a$, —R$^b$—C(O)OR$^a$, —R$^b$—C(O)N(R$^a$)$_2$, —R$^b$—O—R$^c$—C(O)N(R$^a$)$_2$, —R$^b$—N(R$^a$)C(O)OR$^a$, —R$^b$—N(R$^a$)C(O)R a, —R$^b$—N(R$^a$)S(O)$_t$R$^a$ (where t is 1 or 2), —R$^b$—S(O)$_t$R$^a$ (where t is 1 or 2), —R$^b$—S(O)$_t$OR$^a$ (where t is 1 or 2) and —R$^b$—S(O)$_t$N(R$^a$)$_2$ (where t is 1 or 2); and wherein each R$^b$ is independently selected from a direct bond or a straight or branched alkylene, alkenylene, or alkynylene chain, and each R$^c$ is a straight or branched alkylene, alkenylene or alkynylene chain. Substituent groups may be selected from, but are not limited to: alkyl, alkenyl, alkynyl, cycloalkyl, aryl, heteroaryl, heterocycloalkyl, hydroxyl, alkoxy, mercaptyl, cyano, halo, carbonyl, thiocarbonyl, isocyanato, thiocyanato, isothiocyanato, nitro, perhaloalkyl, perfluoroalkyl, and amino, including mono- and di-substituted amino groups, and the protected derivatives thereof.

As used herein, the term "haloalkyl" or "haloalkane" refers to an alkyl radical, as defined above, that is substituted by one or more halogen radicals, for example, trifluoromethyl, dichloromethyl, bromomethyl, 2,2,2-trifluoroethyl, 1-fluoromethyl-2-fluoroethyl, and the like. In some embodiments, the alkyl part of the fluoroalkyl radical is optionally further substituted. Examples of halogen substituted alkanes ("haloalkanes") include halomethane (e.g., chloromethane, bromomethane, fluoromethane, iodomethane), di- and trihalomethane (e.g., trichloromethane, tribromomethane, trifluoromethane, triiodomethane), 1-haloethane, 2-haloethane, 1,2-dihaloethane, 1-halopropane, 2-halopropane, 3-halopropane, 1,2-dihalopropane, 1,3-dihalopropane, 2,3-dihalopropane, 1,2,3-trihalopropane, and any other suitable combinations of alkanes (or substituted alkanes) and halogens (e.g., Cl, Br, F, I, etc.). When an alkyl group is substituted with more than one halogen radicals, each halogen may be independently selected e.g., 1-chloro, 2-fluoroethane.

As used herein, the term "aromatic ring" refers to aromatic carbocycles and aromatic heterocycles. Exemplary aromatic rings include furan, benzofuran, isobenzofuran, pyrrole, indole, isoindole, thiophene, benzothiophene, benzo[c]thiophene, imidazole, benzimidazole, purine, pyrazole, indazole, oxazole, benzooxazole, isoxazole, benzisoxazole, thiazole, benzothiazole, benzene, napthalene, pyridine, quinolone, isoquinoline, pyrazine, quinoxaline, pyrimidine, quinazoline, pyridazine, cinnoline, phthalazine, triazine (e.g., 1,2,3-triazine; 1,2,4-triazine; 1,3,5 triazine), and thiadiazole.

As used herein, the terms "heteroaryl" or "heteroaromatic" refer to monocyclic, bicyclic, or polycyclic ring systems, wherein at least one ring in the system is aromatic and contains at least one heteroatom, for example, nitrogen, oxygen and sulfur. Each ring of the heteroaromatic ring systems may contain 3 to 7 ring atoms. Exemplary heteroaromatic monocyclic ring systems include 5- to 7-membered rings whose ring structures include one to four heteroatoms, for example, one or two heteroatoms. Heteroaryl groups include, for example, pyrrole, furan, thiophene, imidazole, oxazole, thiazole, pyrazole, pyridine, pyrazine, pyridazine, and pyrimidine, and the like.

Unless otherwise defined herein, suitable substituents on a heteroaryl group are generally selected from halogen; —R, —OR, —SR, —NO$_2$, —CN, —N(R)$_2$, —NRC(O)R, —NRC(S)R, —NRC(O)N(R)$_2$, —NRC(S)N(R)$_2$, —NRCO$_2$R, —NRNRC(O)R, —NRNRC(O)N(R)$_2$, —NRNRCO$_2$R, —C(O)C(O)R, —C(O)CH$_2$C(O)R, —CO$_2$R, —C(S)R, —C(O)N(R)$_2$, —C(S)N(R)$_2$, —OC(O)N(R)$_2$, —OC(O)R, —C(O)N(OR)R, —C(NOR)R, —S(O)$_2$R, —S(O)$_3$R, —SO$_2$N(R)$_2$, —S(O)R, —NRSO$_2$N(R)$_2$, —NRSO$_2$R, —N(OR)R, —C(=NH)—N(R)$_2$, —P(O)$_2$R, —PO(R)$_2$, —OPO(R)$_2$, —(CH$_2$)O$_2$NHC(O)R, phenyl (Ph) optionally substituted with R, —O(Ph) optionally substituted with R, —(CH$_2$)1-2(Ph), optionally substituted with R, or —CH=CH(Ph), optionally substituted with R, wherein each independent occurrence of R is selected from hydrogen, optionally substituted C$_1$-C$_6$ alkyl, optionally substituted C$_1$-C$_6$ alkoxy, an unsubstituted 5-6 membered heteroaryl, phenyl, —O(Ph), or —CH$_2$(Ph), or two independent occurrences of R, on the same substituent or different substituents, taken together with the atom(s) to which each R is bound, to form an optionally substituted 3-12 membered saturated, partially unsaturated, or fully unsaturated monocyclic or bicyclic ring having 0-4 heteroatoms independently selected from nitrogen, oxygen, or sulfur. Non-limiting examples of heteroaryl groups, as used herein, include benzofuranyl, benzofurazanyl, benzoxazolyl, benzopyranyl, benzthiazolyl, benzothienyl, benzazepinyl, benzimidazolyl, benzothiopyranyl, benzo[1,3]dioxole, benzo[b]furyl, benzo[b]thienyl, cinnolinyl, furazanyl, furyl, furopyridinyl, imidazolyl, indolyl, indolizinyl, indolin-2-one, indazolyl, isoindolyl, isoquinolinyl, isoxazolyl, isothiazolyl, 1,8-naphthyridinyl, oxazolyl, oxaindolyl, oxadiazolyl, pyrazolyl, pyrrolyl, phthalazinyl, pteridinyl, purinyl, pyridyl, pyridazinyl, pyrazinyl, pyrimidinyl, quinoxalinyl, quinolinyl, quinazolinyl, 4H-quinolizinyl, thiazolyl, thiadiazolyl, thienyl, triazinyl, triazolyl and tetrazolyl. Any substituents depicted in structures or examples herein, should be viewed as suitable substituents for use in embodiments of the present invention.

As used herein, the term "heterocycle" refers to a saturated, unsaturated or aromatic ring comprising one or more heteroatoms. Exemplary heteroatoms include N, O, Si, P, B, and S atoms. Heterocycles include monocyclic, bicyclic or polycyclic rings, wherein bicyclic or polycyclic rings may include fused, or spiro rings. For bicyclic and polycyclic rings, at least one ring of the bicyclic or polycyclic ring comprises one or more heteroatoms. Heterocycles may include 3- to 10-membered monocyclic rings, 6- to 12-membered bicyclic rings, and 6- to 12-membered bridged rings. Each ring of a bicyclic or polycyclic heterocycle may be selected from saturated, unsaturated, and aromatic rings, as valence permits. In an exemplary embodiment, a heterocycle, e.g., pyridyl, may be fused to a saturated or unsaturated ring, e.g., cyclohexane, cyclopentane, or cyclohexene. In some embodiments, heterocyclic is selected from heteroaryl, heterocycloalkyl and heterocycloalkenyl.

As used herein, the term "non-aromatic heterocycle" refers to a cycloalkyl or cycloalkenyl, as defined herein, wherein one or more of the ring carbons are replaced by a moiety selected from —O—, —N=, —NR—, —C(O)—, —S—, —S(O)— or —S(O)$_2$—, wherein R is hydrogen, C$_1$-C$_8$ alkyl or a nitrogen protecting group, with the proviso that the ring of said group does not contain two adjacent O or S atoms. Non-limiting examples of non-aromatic heterocycles, as used herein, include morpholino, pyrrolidinyl, pyrrolidinyl-2-one, piperazinyl, piperidinyl, piperidinylone, 1,4-dioxa-8-aza-spiro[4.5]dec-8-yl, 2H-pyrrolyl, 2-pyrrolinyl, 3-pyrrolinyl, 1,3-dioxolanyl, 2-imidazolinyl, imidazolidinyl, 2-pyrazolinyl, pyrazolidinyl, 1,4-dioxanyl, 1,4-dithianyl, thiomorpholinyl, azepanyl, hexahydro-1,4-diazepinyl, tetrahydrofuranyl, dihydrofuranyl, tetrahydrothienyl, tetrahydropyranyl, dihydropyranyl, tetrahydrothiopyranyl, thioxanyl, azetidinyl, oxetanyl, thietanyl, oxepanyl, thiepanyl, 1,2,3,6-tetrahydropyridinyl, 2H-pyranyl, 4H-pyranyl, dioxanyl, 1,3-dioxolanyl, dithianyl, dithiolanyl, dihydropyranyl, dihydrothienyl, dihydrofuranyl, imidazolinyl, imidazolidinyl, 3-azabicyclo[3.1.0]hexanyl, and 3-azabicyclo[4.1.0]heptanyl, 3,8-diazabicyclo[3.2.1]octanyl, and 2,5-diazabicyclo[2.2.1]heptanyl. In certain embodiments, a non-aromatic heterocyclic ring is aziridine, thiirane, oxirane, oxaziridine, dioxirane, azetidine, oxetan, thietane, diazetidine, dioxetane, dithietane, pyrrolidine, tetrahydrofuran, thiolane, imidazolidine, pyrazolidine, oxazolidine, isoxazolidine, thiazolidine, isothiazolidine, dioxolane, dithiolane, piperdine, oxane, thiane, piperazine, morpholine, thiomorpholine, dioxane, dithiane, trioxane, thithiane, azepane, oxepane, thiepane, homopiperazine, or azocane.

As used herein, the term "electrophile", "electrophilic group", or "electrophilic moiety" refers to any moiety capable of reacting with a nucleophile (e.g., a moiety having a lone pair of electrons, a negative charge, a partial negative charge and/or an excess of electrons, for example a —SH group). Electrophiles typically are electron poor or comprise atoms which are electron poor. In certain embodiments, an electrophile contains a positive charge or partial positive charge, has a resonance structure which contains a positive charge or partial positive charge, or is a moiety in which delocalization or polarization of electrons results in one or more atoms which contain a positive charge or partial positive charge. In some embodiments, the electrophile comprises conjugated double bonds, for example an α,β-unsaturated carbonyl or α,β-unsaturated thiocarbonyl compound. In some embodiments, the electrophile is capable of covalent and/or irreversible binding to cysteine sulfhydryl groups. In some embodiments, the electrophile is capable of forming an irreversible covalent bond with a menin protein, such as position 329 of a menin protein.

"MLL fusion protein" refers to a protein with a fragment (e.g., N-terminal fragment) of MLL fused with a partner protein. Non-limiting examples of a partner protein include 11q23, 11q23.3, 11q24, 1p13.1, 1p32 (EPS15), 21q22, 9p13.3, 9p22 (MLLT3/AF9), ABI1, ABI2, ACACA, ACTN4, AFF1/AF4, AFF3/LAF4, AFF4/AF5, AKAP13, AP2A2, ARHGEF12, ARHGEF17, BCL9L, BTBD18, BUD13, C2CD3, CASC5, CASP8AP2, CBL, CEP164, CEP170B, CREBBP, DCP1A, DCPS, EEFSEC/SELB, ELL, EPS15, FLNA, FNBP1, FOXO3, GAS7, GMPS, KIAA1524, LAMC3, LOC100131626, MAML2, ME2, MLLT1/ENL, MLLT10/AF10, MLLT11/AF1Q, MLLT3/AF9, MLLT4/AF6, MLLT6/AF17, MYH11, MYO1F, NA, NEBL, NRIP3, PDS5A, PICALM, PRPF 19, PTD, RUNDC3B, SEPT11, SEPT2, SEPT5, SEPT6, SEPT9, SMAP1, TET1, TNRC18, TOP3A, VAV1, and Xq26.3 (CT45A2). MLL fusion proteins may be created through the joining of a gene that codes for an MLL protein and a gene that codes for a partner protein creating a fusion gene. Translation of this fusion gene may result in a single or multiple polypeptides with functional properties derived from each of the original proteins.

DETAILED DESCRIPTION

The present disclosure provides compounds for modulating the interaction of menin with proteins such as MLL1, MLL2 and MLL-fusion oncoproteins. In certain embodiments, the disclosure provides compounds and methods for inhibiting the interaction of menin with its upstream or downstream signaling molecules including but not limited to MLL1, MLL2 and MLL-fusion oncoproteins. Compounds of the disclosure may be used in methods for the treatment of a wide variety of cancers and other diseases associated with one or more of MLL1, MLL2, MLL fusion proteins, and menin. In certain embodiments, a compound of the disclosure covalently binds menin and inhibits the interaction of menin with MLL. In certain embodiments, a compound of the disclosure interacts non-covalently with menin and inhibits the interaction of menin with MLL.

Compounds of the disclosure may be used in methods for treating a wide variety of diseases associated with MLL1, MLL2, MLL fusion proteins, and menin. In certain embodiments, a compound of the disclosure covalently binds menin and inhibits the interaction of menin with MLL. In certain embodiments, a compound of the disclosure interacts non-covalently with menin and inhibits the interaction of menin with MLL.

In certain aspects, compounds of the disclosure covalently bond with menin and inhibit the interaction of menin with MLL. Such bonding may lead to an increase in the affinity of the compound for menin, which is an advantageous property in many applications, including therapeutic and diagnostic uses. In certain embodiments, the compounds of the disclosure comprise electrophilic groups capable of reacting with a nucleophilic group present in a menin protein. Suitable electrophilic groups are described throughout the application, while suitable nucleophilic groups include, for example, cysteine moieties present in the binding domain of a menin protein. Without wishing to be bound by theory, a cysteine residue in the menin binding domain may react with the electrophilic group of a compound of the disclosure, leading to formation of a conjugate product. In certain embodiments, the compounds of the disclosure are capable of covalently bonding to the cysteine residue at position 329 of a menin isoform 2 or cysteine 334 in menin isoform 1. In certain embodiments, the disclosure provides a conjugate of a compound of the disclosure with a menin protein. For example, the disclosure provides a conjugate of a compound of the invention with menin, bound at the cysteine residue 329 of menin isoform 2 or cysteine 334 in menin isoform 1.

In certain embodiments, provided herein is a compound having a structure of Formula (1) or (2):

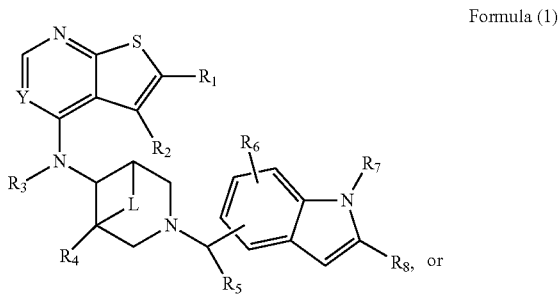

Formula (1)

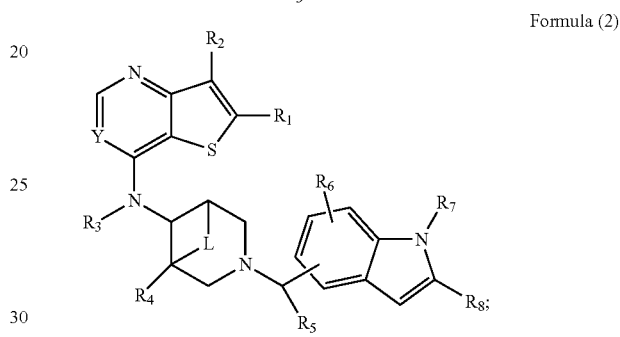

Formula (2)

or a salt thereof, wherein:

R1, R2, R4, R5, R6, and R8 are each independently selected from H, alkyl, substituted alkyl, hydroxy, alkoxy, amine, thioalkyl, halogen, ketone, amide, cyano, sulfonyl, dialkylphosphine oxide, a carbocyclic ring, an aromatic ring, a substituted aromatic ring, a heterocyclic aromatic ring, a substituted heterocyclic aromatic ring, a substituted or non-substituted heterocyclic non-aromatic ring, carbocyclic or heterocyclic aromatic ring fused to another aromatic ring, a hydrogen bond donor, a hydrogen bond acceptor, and combinations thereof; wherein R6 can be present at one or more of the positions of the benzyl and/or pyrrole portion of the indole ring that are not otherwise occupied by a substituent;

R3 is selected from H, alkyl, substituted alkyl, hydroxy, alkoxy, thioalkyl, ketone, amide, sulfonyl, a carbocyclic ring, an aromatic ring, a substituted aromatic ring, a heterocyclic aromatic ring, a substituted heterocyclic aromatic ring, a substituted or non-substituted heterocyclic non-aromatic ring, carbocyclic or heterocyclic aromatic ring fused to another aromatic ring, a hydrogen bond donor, a hydrogen bond acceptor, and combinations thereof;

Y is N or C(R$^a$), wherein R$^a$ is selected from hydrogen, alkyl, heteroalkyl, substituted aryl, substituted alkyl, alcohol, alkoxy, amino, cyano, sulfonyl, aldehyde, heterocycle, and aromatic ring;

L is present or absent, and if present it is selected from alkylene, oxalkylene and aminoalkylene; and R7 comprises a functional group that covalently reacts with one or more residues on menin.

In certain embodiments, the functional group covalently reacts with one or more cysteine residues on menin. In certain embodiments, the functional group covalently reacts with one or more residues on menin selected from cysteine 329, cysteine 241, and/or cysteine 230 on menin. In certain embodiments, the functional group covalently reacts with cysteine 329.

In certain embodiments, a compound of Formula (1) or (2) is capable of (a) binding covalently to menin and (b) inhibiting the interaction of menin and MLL.

In some embodiments, the $R_1$-$R_8$, L, and Y of the above scaffolds each independently include one or any combination of the following moieties: halogens, alkanes, alkenes, alkynes, cycloalkanes, aromatic rings, heteroaromatic rings, non-aromatic rings, haloalkanes, alcohols, ketones, aldehydes, carboxylates, carboxylic acids, ethers, amides, primary amines, secondary amines, tertiary amines, azides, cyanates, cyano, thiols, sulfides, sulfoxides, sulfones, sulfonamides, sulfinic acids, thiocyanate, and phosphates. In various embodiments, the above listed functional groups or combinations thereof are attached at the A, D, E, G, J, L, M, Y, Q, R, T, U, W, X, Z and/or R positions, e.g., R1-R11, in any suitable combinations.

In certain embodiments, a compound or salt described herein has a structure of Formula (1):

Formula (1)

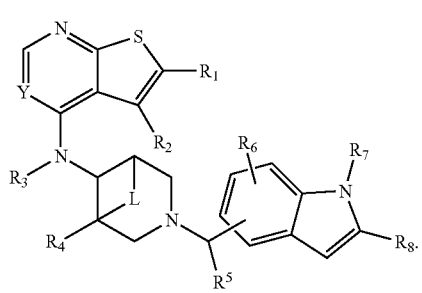

In certain embodiments, a compound of Formula (1) has a structure of Formula (1A):

Formula (1A)

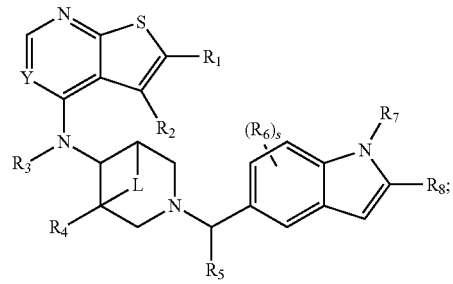

wherein s is selected from 0, 1, 2, 3, or 4.

In certain embodiments, a compound of Formula (1) has a structure of Formula (1B):

Formula (1B)

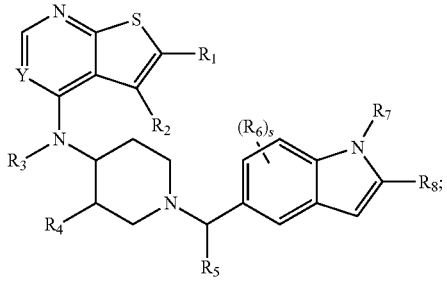

wherein s is selected from 0, 1, 2, 3, or 4.

In certain embodiments, a compound of Formula (1) has a structure of Formula (1C):

Formula (1C)

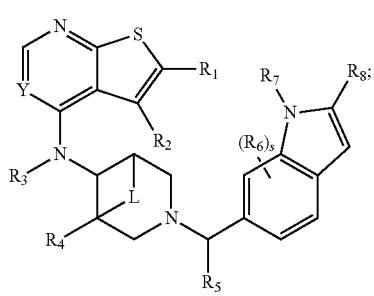

wherein s is selected from 0, 1, 2, 3, or 4.

In certain embodiments, a compound of Formula (1) has a structure of Formula (1D):

Formula (1D)

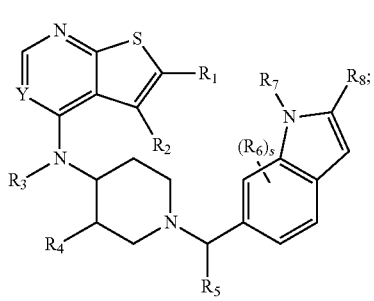

wherein s is selected from 0, 1, 2, 3, or 4.

In certain embodiments, a compound of Formula (1) has a structure of Formula (1E):

Formula (1E)

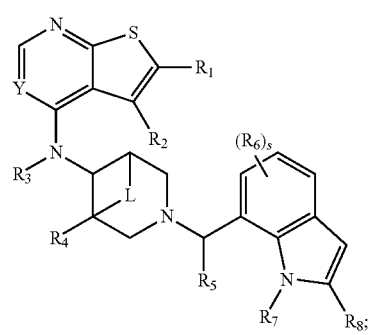

wherein s is selected from 0, 1, 2, 3, or 4.

In certain embodiments, a compound of Formula (1) has a structure of Formula (1F):

Formula (1F)

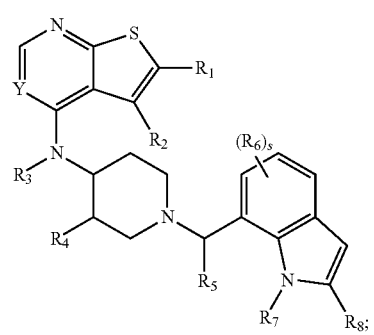

wherein s is selected from 0, 1, 2, 3, or 4.

In certain embodiments, a compound of Formula (1) has a structure of Formula (1G):

Formula (1G)

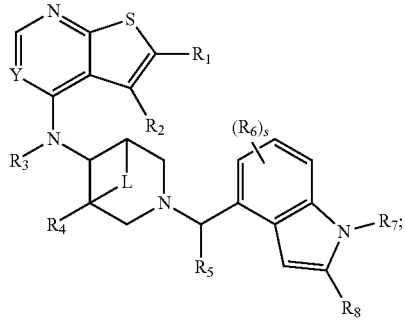

wherein s is selected from 0, 1, 2, 3, or 4.

In certain embodiments, a compound of Formula (1) has a structure of Formula (1H):

Formula (1H)

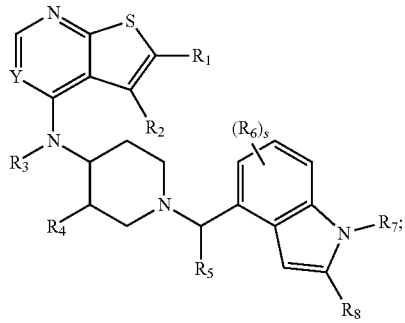

wherein s is selected from 0, 1, 2, 3, or 4.

In certain embodiments, a compound of Formula (1) has a structure of Formula (1I):

Formula (1I)

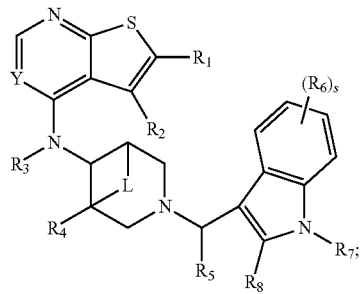

wherein s is selected from 0, 1, 2, 3, or 4.

In certain embodiments, a compound of Formula (1) has a structure of Formula (1J):

Formula (1J)

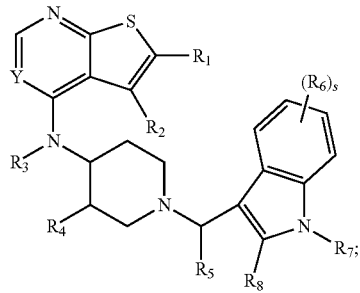

wherein s is selected from 0, 1, 2, 3, or 4.

In certain embodiments, for a compound of any one of Formulas (1), (2), (1A), (1B), (1C), (1D), (1E), (1F), (1G), (1H), (1I), and (1J), $R_1$ and $R_2$ are independently selected from hydrogen, halogen, hydroxy, alkoxy, cyano, nitro, amino, alkyl, substituted alkyl, alkenyl, substituted alkenyl, alkynyl, and substituted alkynyl. In certain embodiments, $R_1$ is selected from halogen, alkyl, substituted alkyl, alkenyl, substituted alkenyl, alkynyl, and substituted alkynyl, such as from halogen, haloalkyl, haloalkenyl, and haloalkynyl. In particular embodiments, $R_1$ is selected from —$CH_2CF_3$ and —$CH_2CHF_2$. In certain embodiments, for a compound of Formula (1A) or (1B), $R_1$ is selected from —$CH_2CF_3$ and —$CH_2CHF_2$.

In certain embodiments, for a compound of any one of Formulas (1), (2), (1A), (1B), (1C), (1D), (1E), (1F), (1G), (1H), (1I), and (1J), $R_2$ is selected from hydrogen, hydroxy, nitro, cyano, halogen, alkyl, and alkoxy. In particular embodiments, $R_2$ is hydrogen. In certain embodiments, for a compound of Formula (1A) or (1B), $R_1$ is selected from —$CH_2CF_3$ and —$CH_2CHF_2$ and $R_2$ is hydrogen.

In certain embodiments, for a compound of any one of Formulas (1), (2), (1A), (1B), (1C), (1D), (1E), (1F), (1G), (1H), (1I), and (1J), $R_3$ is selected from hydrogen, alkyl, and substituted alkyl. In particular embodiments, $R_3$ is hydrogen. In certain embodiments, for a compound of Formula (1A) or (1B), $R_1$ is selected from —$CH_2CF_3$ and —$CH_2CHF_2$, $R_2$ is hydrogen and $R_3$ is hydrogen.

In certain embodiments, for a compound of any one of Formulas (1), (2), (1A), (1B), (1C), (1D), (1E), (1F), (1G), (1H), (1I), and (1J), $R_4$ is selected from hydrogen, halogen, hydroxy, alkoxy, cyano, nitro, amino, alkyl, substituted alkyl, alkenyl, substituted alkenyl, alkynyl, and substituted alkynyl. In particular embodiments, $R_4$ is selected from hydrogen and halogen such as $R_4$ is hydrogen. In certain embodiments, for a compound of Formula (1A) or (1B), $R_1$ is selected from —$CH_2CF_3$ and —$CH_2CHF_2$, $R_2$ is hydrogen, $R_3$ is hydrogen and $R_4$ is hydrogen.

In certain embodiments, for a compound of any one of Formulas (1), (2), (1A), (1B), (1C), (1D), (1E), (1F), (1G), (1H), (1I), and (1J), $R_5$ is independently selected from hydrogen, halogen, hydroxy, alkoxy, cyano, nitro, amino, alkyl, substituted alkyl, alkenyl, substituted alkenyl, alkynyl, and substituted alkynyl. In particular embodiments, $R_5$ is hydrogen. In certain embodiments, for a compound of Formula (1A) or (1B), $R_1$ is selected from —$CH_2CF_3$ and —$CH_2CHF_2$, $R_2$ is hydrogen, $R_3$ is hydrogen, $R_4$ is hydrogen, and $R_5$ is hydrogen.

In certain embodiments, for a compound of any one of Formulas (1), (2), (1A), (1B), (1C), (1D), (1E), (1F), (1G), (1H), (1I), and (1J), $R_6$, at each occurrence, is independently selected from halogen, hydroxy, alkoxy, cyano, nitro, amino, alkyl, substituted alkyl, alkenyl, substituted alkenyl, alkynyl, and substituted alkynyl, for example, from halogen, hydroxy, alkoxy, and alkyl. In particular embodiments, $R_6$, at each occurrence, is selected from halogen, methyl, hydroxy and methoxy, for example, $R_6$, at each occurrence, is selected from methyl, hydroxy and methoxy. In certain embodiments, s is 0. In certain embodiments, s is 1. In certain embodiments, for a compound of Formula (1A) or (1B), $R_1$ is selected from —$CH_2CF_3$ and —$CH_2CHF_2$, $R_2$ is hydrogen, $R_3$ is hydrogen, $R_4$ is hydrogen, $R_5$ is hydrogen, $R_6$, at each occurrence, is selected from methyl, hydroxy and methoxy and s is 0 or 1.

In certain embodiments, for a compound of any one of Formulas (1), (2), (1A), (1B), (1C), (1D), (1E), (1F), (1G), (1H), (1I), and (1J), $R_8$ is selected from hydrogen, halogen, hydroxy, alkoxy, cyano, nitro, amino, alkyl, substituted alkyl, alkenyl, substituted alkenyl, alkynyl, and substituted alkynyl. In particular embodiments, $R_8$ is cyano. In certain embodiments, for a compound of Formula (1A) or (1B), $R_1$ is selected from —$CH_2CF_3$ and —$CH_2CHF_2$, $R_2$ is hydrogen, $R_3$ is hydrogen, $R_4$ is hydrogen, $R_5$ is hydrogen, $R_6$, at each occurrence, is selected from methyl, hydroxy and methoxy, s is 0 or 1, and $R_8$ is cyano.

In certain embodiments, for a compound of any one of Formulas (1), (2), (1A), (1B), (1C), (1D), (1E), (1F), (1G), (1H), (1I), and (1J), Y is N. In certain embodiments, for a compound of Formula (1A) or (1B), $R_1$ is selected from —$CH_2CF_3$ and —$CH_2CHF_2$, $R_2$ is hydrogen, $R_3$ is hydrogen, $R_4$ is hydrogen, $R_5$ is hydrogen, $R_6$, at each occurrence, is selected from methyl, hydroxy and methoxy, s is 0 or 1, $R_8$ is cyano and Y is N.

In certain embodiments, for a compound of any one of Formulas (1), (2), (1A), (1B), (1C), (1D), (1E), (1F), (1G), (1H), (1I), and (1J), Y is $C(R^a)$ and $R^a$ is selected from hydrogen, halogen, nitro, amino, cyano, alkyl, alcohol, heteroalkyl, and substituted alkyl, for example, $R^a$ is selected from hydrogen, halogen, alkyl, and substituted alkyl. In particular embodiments, $R^a$ is selected from hydrogen, substituted alkyl, e.g., —$CH_2OH$, and cyano. In certain emdbodiments, for a compound of Formula (1A) or (1B), $R_1$ is selected from —$CH_2CF_3$ and —$CH_2CHF_2$, $R_2$ is hydrogen, $R_3$ is hydrogen, $R_4$ is hydrogen, $R_5$ is hydrogen, $R_6$, at each occurrence, is selected from methyl, hydroxy and methoxy, s is 0 or 1, $R_8$ is cyano, Y is $C(R^a)$ and $R^a$ is selected from hydrogen, —$CH_2OH$ and cyano.

In certain embodiments, for a compound of any one of Formulas (1), (2), (1A), (1B), (1C), (1D), (1E), (1F), (1G), (1H), (1I), and (1J), $R^7$ comprises a functional group that covalently reacts with one or more cysteine residues on menin, for example, as one or more of cysteine 329, cysteine 241, and cysteine 230 on menin. In certain embodiments, a compound of any one of Formulas (1), (2), (1A), (1B), (1C), (1D), (1E), (1F), (1G), (1H), (1I), and (1J), $R^7$ comprises a functional group that is capable of (a) binding covalently to menin and (b) inhibiting the interaction of menin and MLL. In certain embodiments, $R^7$ comprises a functional group that covalently reacts with cysteine 329. In certain embodiments, for a compound of Formula (1A) or (1B), $R_1$ is selected from —$CH_2CF_3$ and —$CH_2CHF_2$, $R_2$ is hydrogen, $R_3$ is hydrogen, $R_4$ is hydrogen, $R_5$ is hydrogen, $R_6$, at each occurrence, is selected from methyl, hydroxy and methoxy, s is 0 or 1, $R_8$ is cyano, Y is $C(R^a)$, $R^a$ is selected from hydrogen, —$CH_2OH$ and cyano and $R^7$ comprises a functional group that covalently reacts with cysteine 329 or $R^7$ comprises a functional group that is capable of (a) binding covalently to menin and (b) inhibiting the interaction of menin and MLL.

In certain embodiments, for a compound of any one of Formulas (1), (2), (1A), (1B), (1C), (1D), (1E), (1F), (1G), (1H), (1I), and (1J), for example, for a compound of Formula (1B), $R_1$ is selected from halogen, alkyl, substituted alkyl, alkenyl, substituted alkenyl, alkynyl, and substituted alkynyl, for example, from halogen, haloalkyl, haloalkenyl, and haloalkynyl, such as $R_1$ is —$CH_2CF_3$ or —$CH_2CHF_2$; $R_2$ is selected from hydrogen, hydroxy, nitro, cyano, halogen, alkyl, and alkoxy, such as $R_2$ is hydrogen; and $R_8$ is selected from hydrogen, halogen, hydroxy, alkoxy, cyano, nitro, amino, alkyl, substituted alkyl, alkenyl, substituted alkenyl, alkynyl, and substituted alkynyl, for example, $R_8$ is cyano.

In certain embodiments, for a compound of any one of Formulas (1), (2), (1A), (1B), (1C), (1D), (1E), (1F), (1G), (1H), (1I), and (1J), for example, for a compound of Formula (1B), $R_1$ is selected from halogen, alkyl, substituted alkyl, alkenyl, substituted alkenyl, alkynyl, and substituted alkynyl, for example, from halogen, haloalkyl, haloalkenyl, and haloalkynyl, for example, $R_1$ is —$CH_2CF_3$ or —$CH_2CHF_2$; $R_3$ is selected from hydrogen, alkyl, and substituted alkyl, for example, $R_3$ is hydrogen; and $R_8$ is selected from hydrogen, halogen, hydroxy, alkoxy, cyano, nitro, amino, alkyl, substituted alkyl, alkenyl, substituted alkenyl, alkynyl, and substituted alkynyl, for example, $R_8$ is cyano.

In certain embodiments, for a compound of any one of Formulas (1), (2), (1A), (1B), (1C), (1D), (1E), (1F), (1G), (1H), (1I), and (1J), for example, for a compound of Formula (1B), $R_2$ is selected from hydrogen, hydroxy, nitro, cyano, halogen, alkyl, and alkoxy, for example, $R_2$ is hydrogen; $R_3$ is selected from hydrogen, alkyl, and substituted alkyl, for example, $R_3$ is hydrogen; and $R_5$ is independently selected from hydrogen, halogen, hydroxy, alkoxy, cyano, nitro, amino, alkyl, substituted alkyl, alkenyl, substituted alkenyl, alkynyl, and substituted alkynyl, for example, $R_5$ is hydrogen.

In certain embodiments, for a compound of any one of Formulas (1), (2), (1A), (1B), (1C), (1D), (1E), (1F), (1G), (1H), (1I), and (1J), for example, for a compound of Formula (1B), $R_1$ is selected from halogen, alkyl, substituted alkyl, alkenyl, substituted alkenyl, alkynyl, and substituted alkynyl, for example, from halogen, haloalkyl, haloalkenyl, and haloalkynyl, for example, $R_1$ is —$CH_2CF_3$ or —$CH_2CHF_2$; $R_3$ is selected from hydrogen, alkyl, and substituted alkyl, for example, $R_3$ is hydrogen; and $R_5$ is independently selected from hydrogen, halogen, hydroxy, alkoxy, cyano, nitro, amino, alkyl, substituted alkyl, alkenyl, substituted alkenyl, alkynyl, and substituted alkynyl, for example, $R_5$ is hydrogen.

In certain embodiments, for a compound of any one of Formulas (1), (2), (1A), (1B), (1C), (1D), (1E), (1F), (1G), (1H), (1I), and (1J), for example, for a compound of Formula (1B), $R_1$ is selected from halogen, alkyl, substituted alkyl, alkenyl, substituted alkenyl, alkynyl, and substituted alkynyl, for example, from halogen, haloalkyl, haloalkenyl, and haloalkynyl, for example, $R_1$ is —$CH_2CF_3$ or —$CH_2CHF_2$; $R_8$ is selected from hydrogen, halogen, hydroxy, alkoxy, cyano, nitro, amino, alkyl, substituted alkyl, alkenyl, substituted alkenyl, alkynyl, and substituted alkynyl, for example, $R_8$ is cyano; and $R^7$ comprises a functional group that covalently reacts with cysteine 329.

In certain embodiments, for a compound of any one of Formulas (1), (2), (1A), (1B), (1C), (1D), (1E), (1F), (1G), (1H), (1I), and (1J), the substituents on the substituted alkyl, substituted aromatic ring, substituted heterocyclic aromatic ring, and substituted heterocyclic non-aromatic ring described with respect to any of variables $R_1$, $R_2$, $R_3$, $R_4$, $R_5$, $R_6$, and $R_8$ are independently selected from one or more of: halogen, —$OR^{20}$, —$SR^{20}$, —$N(R^{20})_2$, —$N(R^{20})C(O)R^{20}$, —$C(O)R^{20}$, —$C(O)OR^{20}$, —$C(O)N(R^{20})_2$, —$OC(O)R^{20}$, —$S(O)_2R^{20}$, —$S(O)_2N(R^{20})_2$, —$N(R^{20})S(O)_2R^{20}$, —$NO_2$, =O, =S, =$N(R^{20})$, —$P(O)(OR^{20})_2$, —$P(O)(R^{20})_2$, —$OP(O)(OR^{20})_2$, and —CN; $C_{1-6}$ alkyl, $C_{2-6}$ alkenyl, and $C_{2-6}$ alkynyl, each of which is independently optionally substituted at each occurrence with one or more substituents selected from halogen, —$OR^{20}$, —$SR^{20}$, —$N(R^{20})_2$, —$N(R^{20})C(O)R^{20}$, —$C(O)R^{20}$, —$C(O)OR^{20}$, —$C(O)N(R^{20})_2$, —$OC(O)R^{20}$, —$S(O)_2R^{20}$, —$S(O)_2N(R^{20})_2$, —$N(R^{20})S(O)_2R^{20}$, —$NO_2$, =O, =S, =$N(R^{20})$, —$P(O)(OR^{20})_2$, —$P(O)(R^{20})_2$, —$OP(O)(OR^{20})_2$, —CN, $C_{3-10}$ carbocycle, and 3- to 10-membered heterocycle or two substituents on the same carbon atom of an $C_{1-6}$ alkyl, $C_{2-6}$ alkenyl, or $C_{2-6}$ alkynyl come together to form a $C_{3-10}$ carbocycle or 3- to 10-membered heterocycle; and $C_{3-10}$ carbocycle and 3- to 10-membered heterocycle; wherein any $C_{3-10}$ carbocycle and 3- to 10-membered heterocycle is independently optionally substituted with one or more substituents selected from halogen, —OR$^{20}$, —SR$^{20}$, —N(R$^{20}$)$_2$, —N(R$^{20}$)C(O)R$^{20}$, —C(O)R$^{20}$, —C(O)OR$^{20}$, —C(O)N(R$^{20}$)$_2$, —OC(O)R$^{20}$, —S(O)$_2$R$^{20}$, —S(O)$_2$N(R$^{20}$)$_2$, —N(R$^{20}$)S(O)$_2$R$^{20}$, —NO$_2$, =O, =S, =N(R$^{20}$), —P(O)(OR$^{20}$)$_2$, —P(O)(R$^{20}$)$_2$, —OP(O)(OR$^{20}$)$_2$, —CN, $C_{1-6}$ alkyl, $C_{2-6}$ alkenyl, and $C_{2-6}$ alkynyl. In certain embodiments, R$^{20}$ at each occurrence is independently selected from hydrogen; $C_{1-6}$ alkyl, $C_{2-6}$ alkenyl, and $C_{2-6}$ alkynyl, each of which is independently optionally substituted at each occurrence with one or more substituents selected from halogen, —OR$^{30}$, —SR$^{30}$, —N(R$^{30}$)$_2$, —N(R$^{30}$)C(O)R$^{30}$, —C(O)R$^{30}$, —C(O)OR$^{30}$, —C(O)N(R$^{30}$)$_2$, —OC(O)R$^{30}$, —S(O)$_2$R$^{30}$, —S(O)$_2$ N(R$^{30}$)$_2$, —N(R$^{30}$)S(O)$_2$R$^{30}$, —NO$_2$, —P(O)(OR$^{30}$)$_2$, —P(O)(R$^{30}$)$_2$, —OP(O)(OR$^{30}$)$_2$, and —CN; and 3- to 10-membered heterocycle and $C_{3-10}$ carbocycle. In certain embodiments, R$^{30}$ at each occurrence is independently selected from hydrogen, $C_{1-6}$ alkyl, $C_{2-6}$ alkenyl, and $C_{2-6}$ alkynyl.

In certain embodiments, for a compound of any one of Formulas (1), (2), (1A), (1B), (1C), (1D), (1E), (1F), (1G), (1H), (1I), and (1J), R7 is selected from:

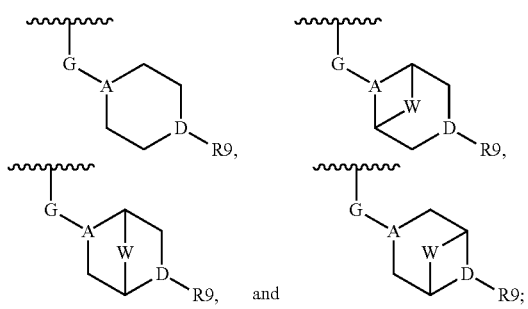

G is selected from alkylene and heteroalkylene;
A and D are independently selected from CH and N;
W is selected from alkylene, aminoalkylene, and oxalkylene;
wherein one or more of the H atoms on the ring structure of R7 is optionally replaced with a halogen, alcohol, alkyl, alkoxy, amine, cyano, an amide, —SO$_2$CH$_3$, or —COOH;
R9 is selected from:

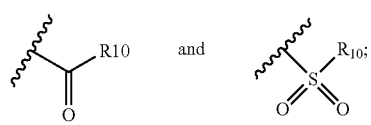

R10 is selected from optionally substituted alkane, optionally substituted alkene, and optionally substituted alkyne, wherein the substituents are independently selected from alkoxy, amine, a halogen, a ketone, an amide, cyano, sulfonyl, a carbocyclic ring, an aromatic ring, a substituted aromatic ring, a heterocyclic aromatic ring, a substituted heterocyclic aromatic ring, a substituted or non-substituted heterocyclic non-aromatic ring, carbocyclic or heterocyclic aromatic ring fused to another aromatic ring, a hydrogen bond donor, a hydrogen bond acceptor, and combinations thereof.

In certain embodiments, for a compound of Formula (1), (2), (1A), (1B), (1C), (1D), (1E), (1F), (1G), (1H), (1I), and (1J), R10 is selected from optionally substituted alkene and optionally substituted alkyne, for example, from optionally substituted C2 alkene and optionally substituted C2 alkyne.

In certain embodiments, for a compound of any one of Formulas (1), (2), (1A), (1B), (1C), (1D), (1E), (1F), (1G), (1H), (1I), and (1J), R7 is selected from:

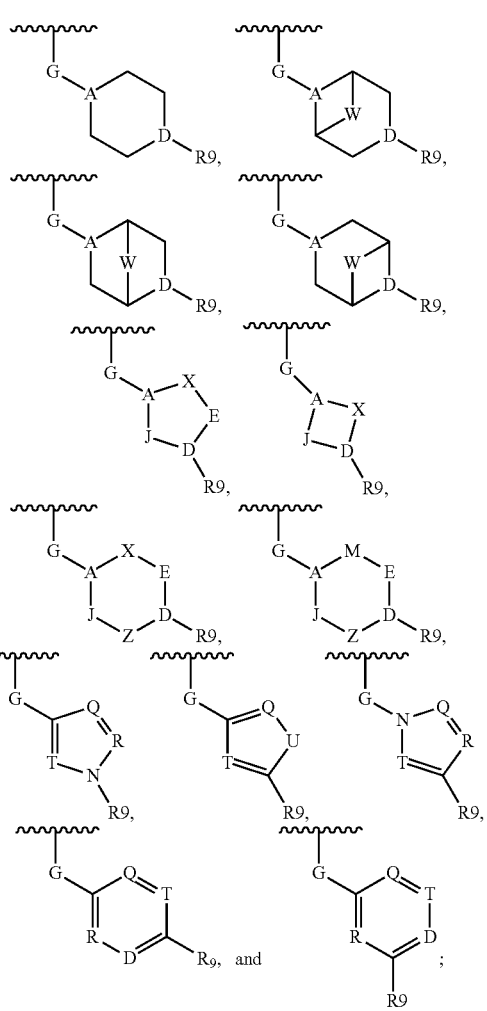

G is selected from alkylene, aminoalkylene, oxalkylene, or heteroalkylene;
A and D are independently selected from CH and N;
E, J, X, and Z are independently selected from CH$_2$, NH, S, and O;
M is (—CH$_2$—)$_n$, wherein n is selected from 0, 1, 2, 3, and 4;
Q, R, and T are independently selected from CH and N;
U is selected from O, NH, and S;
W is selected from alkylene, aminoalkylene, and oxalkylene;
wherein one or more of the H atoms on the ring structure of R7, when present, is optionally replaced with a halogen, alcohol, alkyl, alkoxy, amine, cyano, an amide, —SO$_2$CH$_3$, sulfonamide, or COOH;

R9, when present, is selected from:

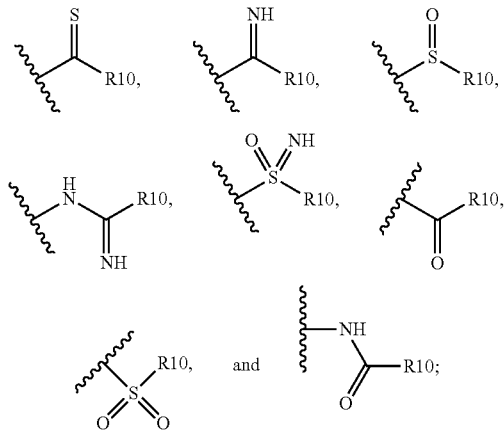

R10, when present, is selected from: alkene optionally substituted with R11, alkyne optionally substituted with R11, and any electrophilic group capable of covalent and/or irreversible binding to cysteine sulfhydryl groups;

R11 is selected from alkyl, a substituted alkyl, alkoxy, amine, thioalkyl, halogen, ketone, amide, alkylamide, cyano, sulfonyl, a carbocyclic ring, an aromatic ring, a substituted aromatic ring, a heterocyclic aromatic ring, a substituted heterocyclic aromatic ring, a substituted or non-substituted heterocyclic non-aromatic ring, carbocyclic or heterocyclic aromatic ring fused to another aromatic ring, a hydrogen bond donor, a hydrogen bond acceptor, and combinations thereof.

In certain embodiments, for a compound of any one of Formulas (1), (2), (1A), (1B), (1C), (1D), (1E), (1F), (1G), (1H), (1I), and (1J), R7 is selected from:

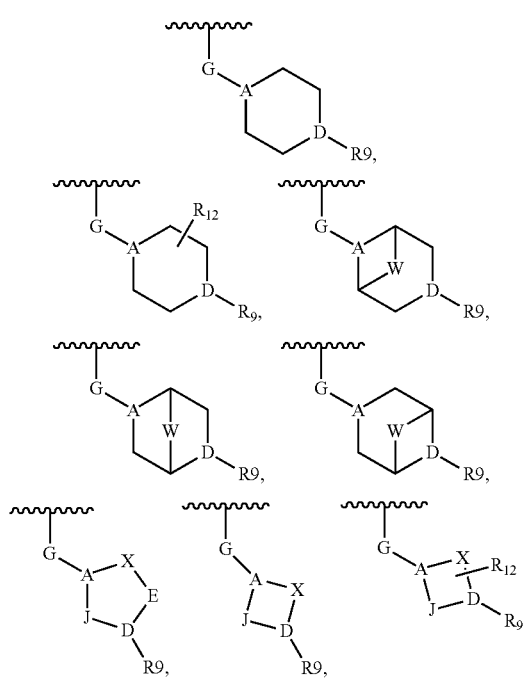

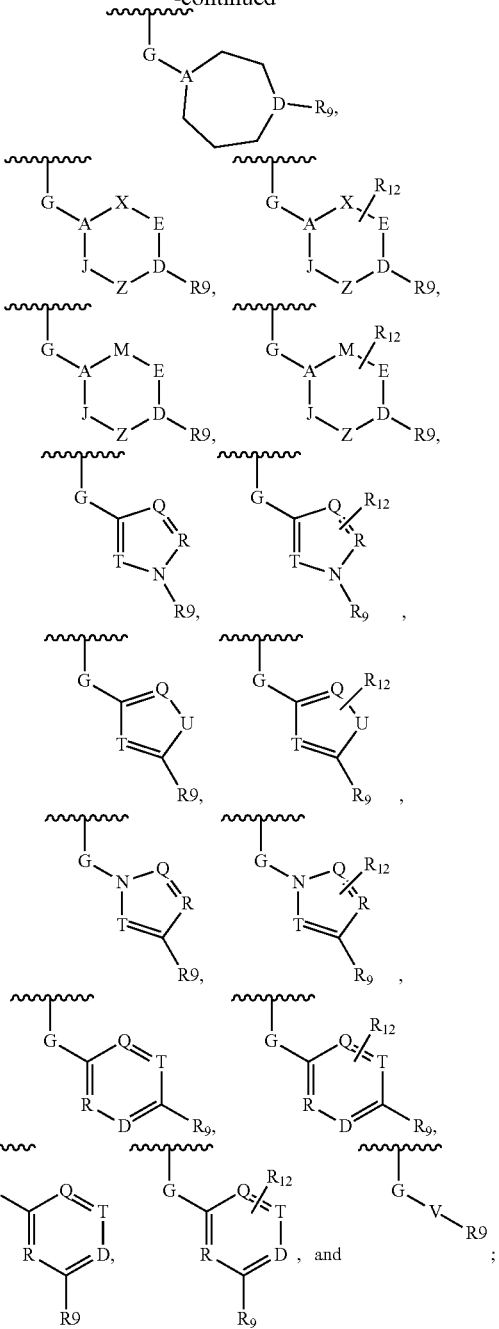

G is selected from alkylene, branched alkylene, aminoalkylene, oxalkylene, haloalkylene, heteroalkylene, hydroxyalkyl, alkylhydroxyalkyl, alkoxyalkyl, aminoalkyl or alkylamine, alkylaminoalkyl, carbocycle, alkylcycloalkyl, hydroxycycloalkyl, alkoxycycloalkyl, hydroxyalkylcycloalkyl, disubstituted cycloalkyl, aminocycloalkyl, alkylaminocycloalkyl, substituted carbocycle, heterocycle, and substituted heterocycle;

V is selected from a 3-7 membered saturated ring, 3-7 membered unsaturated ring, 4-10 membered fused bicyclic ring, and 5-11 membered spiro bicyclic ring; wherein V is optionally substituted with one or more R12 groups;

R12 at each occurrence is selected from alkyl, a substituted alkyl, alkene, alkyne, hydroxyl, alcohol, alkoxy, amine, alkylamine, a halogen, a ketone, an amide, an alkylamide, cyano, methyl carbonitrile, —SO$_2$alkyl, —SO$_2$NH$_2$, —SO$_2$NHalkyl, —SO$_2$Ndialkyl, sulfonyl, dialkylphosphine oxide, a carbocyclic ring, an aromatic ring, a substituted aromatic ring, a heterocyclic aromatic ring, a substituted heterocyclic aromatic ring, a substituted or non-substituted heterocyclic non-aromatic ring, carbocyclic or heterocyclic aromatic ring fused to another aromatic ring, a hydrogen bond donor, a hydrogen bond acceptor, and combinations thereof;

A and D are independently selected from CH and N;

E, J, X, and Z are independently selected from CH$_2$, NH, S, and O;

M is (—CH$_2$—)$_n$ and n is selected from 0, 1, 2, 3, and 4;

Q, R, T are independently selected from CH and N;

U is selected from O, NH, and S;

W is selected from alkylene, aminoalkylene, and oxalkylene;

wherein one or more H atoms of R7 is independently optionally replaced with a halogen, alcohol, alkyl (C1-C5), cycloalkyl (C1-C7), haloalkyl, alkene (C1-C5), alkyne (C1-C5), alkoxy, amine, ester, cyano, amide, —SO$_2$alkyl, sulfonamide, or COOH;

R9 is selected from:

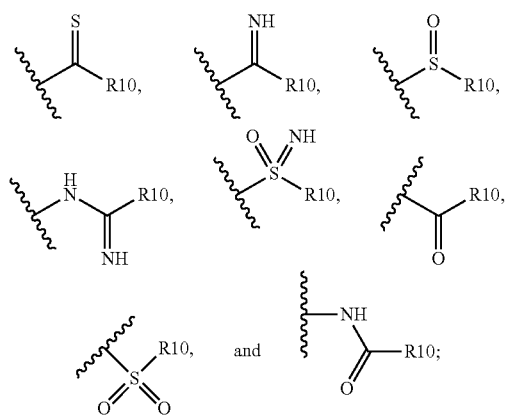

R10 is selected from alkene optionally substituted with R11 and alkyne optionally substituted with R11;

R11 is selected from H, alkyl, a substituted alkyl, alcohol, alkoxy, amine, halogen, ketone, amide, alkylamide, cyano, sulfonyl, a carbocyclic ring, an aromatic ring, a substituted aromatic ring, a heterocyclic aromatic ring, a substituted heterocyclic aromatic ring, a substituted or non-substituted heterocyclic non-aromatic ring, carbocyclic or heterocyclic aromatic ring fused to another aromatic ring, a hydrogen bond donor, a hydrogen bond acceptor, and combinations thereof.

In certain embodiments, for a compound of any one of Formulas (1), (2), (1A), (1B), (1C), (1D), (1E), (1F), (1G), (1H), (1I), and (1J), R$^9$ is selected from:

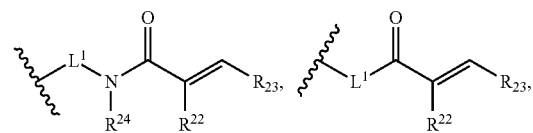

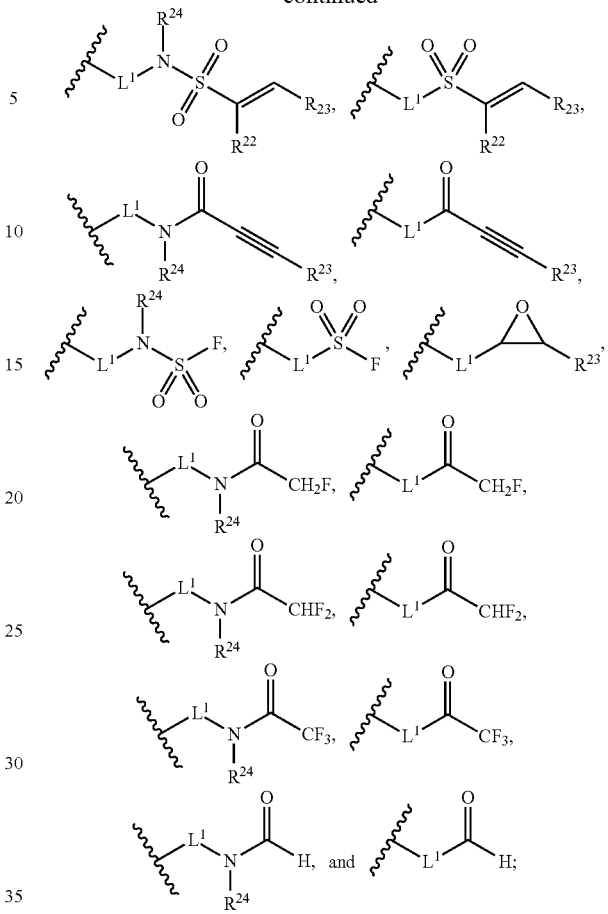

wherein:

L$^1$ is selected from a bond; and C$_{1-6}$ alkylene, C$_{1-6}$ heteroalkylene, C$_{2-6}$ alkenylene, and C$_{2-6}$ alkynylene, each of which may be optionally substituted with one or more R$^{32}$ groups;

R$^{22}$ and R$^{23}$ are selected from hydrogen, halogen, —OR$^{20}$, —SR$^{20}$, —N(R$^{20}$)$_2$, —N(R$^{20}$)C(O)R$^{20}$, —C(O)R$^{20}$, —C(O)OR$^{20}$, —C(O)N(R$^{20}$)$_2$, —OC(O)R$^{20}$, —S(O)$_2$R$^{20}$, —S(O)$_2$N(R$^{20}$)$_2$, —N(R$^{20}$)S(O)$_2$R$^{20}$, —NO$_2$, =O, =S, =N(R$^{20}$), —P(O)(OR$^{20}$)$_2$, —P(O)(R$^{20}$)$_2$, —OP(O)(OR$^{20}$)$_2$, and —CN; C$_{1-6}$ alkyl, C$_{2-6}$ alkenyl, and C$_{2-6}$ alkynyl, each of which is independently optionally substituted at each occurrence with one or more substituents selected from halogen, —OR$^{20}$, —SR$^{20}$, —N(R$^{20}$)$_2$, —N(R$^{20}$)C(O)R$^{20}$, —C(O)R$^{20}$, —C(O)OR$^{20}$, —C(O)N(R$^{20}$)$_2$, —OC(O)R$^{20}$, —S(O)$_2$R$^{20}$, —S(O)$_2$N(R$^{20}$)$_2$, —N(R$^{20}$)S(O)$_2$R$^{20}$, —NO$_2$, =O, =S, =N(R$^{20}$), —P(O)(OR$^{20}$)$_2$, —P(O)(R$^{20}$)$_2$, —OP(O)(OR$^{20}$)$_2$, —CN, C$_{3-10}$ carbocycle, and 3- to 10-membered heterocycle; and C$_{3-10}$ carbocycle and 3- to 10-membered heterocycle, wherein each C$_{3-10}$ carbocycle and 3- to 10-membered heterocycle of R$^{22}$ and R$^{23}$ is independently optionally substituted with one or more substituents selected from halogen, —OR$^{20}$, —SR$^{20}$, —N(R$^{20}$)$_2$, —N(R$^{20}$)C(O)R$^{20}$, —C(O)R$^{20}$, —C(O)OR$^{20}$, —C(O)N(R$^{20}$)$_2$, —OC(O)R$^{20}$, —S(O)$_2$R$^{20}$, —S(O)$_2$N(R$^{20}$)$_2$, —N(R$^{20}$)S(O)$_2$R$^{20}$, —NO$_2$, =O, =S, =N(R$^{20}$), —P(O)(OR$^{20}$)$_2$, —P(O)(R$^{20}$)$_2$, —OP(O)(OR$^{20}$)$_2$, —CN, C$_{1-6}$ alkyl, C$_{2-6}$ alkenyl, and C$_{2-6}$ alkynyl; or R$^{22}$ and R$^{23}$, together with the carbon atoms to which they are attached, form a carbocyclic ring;

$R^{24}$ is selected from hydrogen, $-C(O)R^{20}$, $-C(O)OR^{20}$, $-C(O)N(R^{20})_2$, $-OC(O)R^{20}$, $-S(O)_2R^{20}$, and $-S(O)_2N(R^{20})_2$; $C_{1-6}$ alkyl, $C_{2-6}$ alkenyl, and $C_{2-6}$ alkynyl, each of which is independently optionally substituted at each occurrence with one or more substituents selected from halogen, $-OR^{20}$, $-SR^{20}$, $-N(R^{20})_2$, $-N(R^{20})C(O)R^{20}$, $-C(O)R^{20}$, $-C(O)OR^{20}$, $-C(O)N(R^{20})_2$, $-OC(O)R^{20}$, $-S(O)_2R^{20}$, $-S(O)_2N(R^{20})_2$, $-N(R^{20})S(O)_2R^{20}$, $-NO_2$, $=O$, $=S$, $=N(R^{20})$, $-P(O)(OR^{20})_2$, $-P(O)(R^{20})_2$, $-OP(O)(OR^{20})_2$, $-CN$, $C_{3-10}$ carbocycle, and 3- to 10-membered heterocycle; and $C_{3-10}$ carbocycle and 3- to 10-membered heterocycle, wherein each $C_{3-10}$ carbocycle and 3- to 10-membered heterocycle of $R^{24}$ is independently optionally substituted with one or more substituents selected from halogen, $-OR^{20}$, $-SR^{20}$, $-N(R^{20})_2$, $-N(R^{20})C(O)R^{20}$, $-C(O)R^{20}$, $-C(O)OR^{20}$, $-C(O)N(R^{20})_2$, $-OC(O)R^{20}$, $-S(O)_2R^{20}$, $-S(O)_2N(R^{20})_2$, $-N(R^{20})S(O)_2R^{20}$, $-NO_2$, $=O$, $=S$, $=N(R^{20})$, $-P(O)(OR^{20})_2$, $-P(O)(R^{20})_2$, $-OP(O)(OR^{20})_2$, $-CN$, $C_{1-6}$ alkyl, $C_{2-6}$ alkenyl, and $C_{2-6}$ alkynyl;

$R^{32}$ at each occurrence is selected from halogen, $-OR^{20}$, $-SR^{20}$, $-N(R^{20})_2$, $-N(R^{20})C(O)R^{20}$, $-C(O)R^{20}$, $-C(O)OR^{20}$, $-C(O)N(R^{20})_2$, $-OC(O)R^{20}$, $-S(O)_2R^{20}$, $-S(O)_2N(R^{20})_2$, $-N(R^{20})S(O)_2R^{20}$, $-NO_2$, $=O$, $=S$, $=N(R^{20})$, $-P(O)(OR^{20})_2$, $-P(O)(R^{20})_2$, $-OP(O)(OR^{20})_2$, and $-CN$; $C_{1-6}$ alkyl, $C_{2-6}$ alkenyl, and $C_{2-6}$ alkynyl, each of which is independently optionally substituted at each occurrence with one or more substituents selected from halogen, $-OR^{20}$, $-SR^{20}$, $-N(R^{20})_2$, $-N(R^{20})C(O)R^{20}$, $-C(O)R^2$, $-C(O)OR^{20}$, $-C(O)N(R^{20})_2$, $-OC(O)R^{20}$, $-S(O)_2R^{20}$, $-S(O)_2N(R^{20})_2$, $-N(R^{20})S(O)_2R^{20}$, $-NO_2$, $=O$, $=S$, $=N(R^{20})$, $-P(O)(OR^{20})_2$, $-P(O)(R^{20})_2$, $-OP(O)(OR^{20})_2$, $-CN$, $C_{3-10}$ carbocycle, and 3- to 10-membered heterocycle; $C_{3-10}$ carbocycle and 3- to 10-membered heterocycle; or two $R^{32}$ on the same carbon atom can come together to form a $C_{3-10}$ carbocycle or 3- to 10-membered heterocycle, wherein each $C_{3-10}$ carbocycle and 3- to 10-membered heterocycle of $R^{32}$ is independently optionally substituted with one or more substituents selected from halogen, $-OR^{20}$, $-SR^{20}$, $-N(R^{20})_2$, $-N(R^{20})C(O)R^{20}$, $-C(O)R^{20}$, $-C(O)OR^{20}$, $-C(O)N(R^{20})_2$, $-OC(O)R^{20}$, $-S(O)_2R^{20}$, $-S(O)_2N(R^{20})_2$, $-N(R^{20})S(O)_2R^{20}$, $-NO_2$, $=O$, $=S$, $=N(R^{20})$, $-P(O)(OR^{20})_2$, $-P(O)(R^{20})_2$, $-OP(O)(OR^{20})_2$, $-CN$, $C_{1-6}$ alkyl, $C_{2-6}$ alkenyl, and $C_{2-6}$ alkynyl;

$R^{20}$ at each occurrence is independently selected from hydrogen; $C_{1-6}$ alkyl, $C_{2-6}$ alkenyl, and $C_{2-6}$ alkynyl, each of which is independently optionally substituted at each occurrence with one or more substituents selected from halogen, $-OR^{30}$, $-SR^{30}$, $-N(R^{30})_2$, $-N(R^{30})C(O)R^{30}$, $-C(O)R^{30}$, $-C(O)OR$, $-C(O)N(R^{30})_2$, $-OC(O)R^{30}$, $-S(O)_2R^{30}$, $-S(O)_2N(R^{30})_2$, $-N(R^{30})S(O)_2R^{30}$, $-NO_2$, $-P(O)(OR^{30})_2$, $-P(O)(R^{30})_2$, $-OP(O)(OR^{30})_2$, and $-CN$; and 3- to 10-membered heterocycle and $C_{3-10}$ carbocycle; and $R^{30}$ at each occurrence is independently selected from hydrogen, $C_{1-6}$ alkyl, $C_{2-6}$ alkenyl, and $C_{2-6}$ alkynyl.

In certain embodiments, for a compound of any one of Formulas (1), (2), (1A), (1B), (1C), (1D), (1E), (1F), (1G), (1H), (1I), and (1J), $R^9$ is selected from:

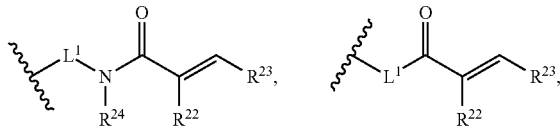

wherein $L^1$, $R^{22}$, $R^{23}$, and $R^{24}$ are as defined above.

In certain embodiments, for $R^9$ of a compound of any one of Formulas (1), (2), (1A), (1B), (1C), (1D), (1E), (1F), (1G), (1H), (1I), and (1J), $L^1$ is a bond.

In certain embodiments, for $R^9$ of a compound of any one of Formulas (1), (2), (1A), (1B), (1C), (1D), (1E), (1F), (1G), (1H), (1I), and (1J), $L^1$ is optionally substituted $C_{1-6}$ alkylene.

In certain embodiments, for $R^9$ of a compound of any one of Formulas (1), (2), (1A), (1B), (1C), (1D), (1E), (1F), (1G), (1H), (1I), and (1J), $L^1$ is substituted with one or more substituents selected from halogen, $-NO_2$, $=O$, $=S$, $-OR^{20}$, $-SR^{20}$, and $-N(R^{20})_2$.

In certain embodiments, for $R^9$ of a compound of any one of Formulas (1), (2), (1A), (1B), (1C), (1D), (1E), (1F), (1G), (1H), (1I), and (1J), $R^{23}$ is selected from hydrogen; and $C_{1-6}$ alkyl, $C_{2-6}$ alkenyl, and $C_{2-6}$ alkynyl, each of which is independently optionally substituted at each occurrence with one or more substituents selected from halogen, $-OR^{20}$, $-SR^{20}$, $-N(R^{20})_2$, $-N(R^{20})C(O)R^{20}$, $-C(O)R^{20}$, $-C(O)OR^{20}$, $-C(O)N(R^{20})_2$, $-OC(O)R^{20}$, $-S(O)_2R^{20}$, $-S(O)_2N(R^{20})_2$, $-N(R^{20})S(O)_2R^{20}$, $-NO_2$, $=O$, $=S$, $=N(R^{20})$, $-P(O)(OR^{20})_2$, $-P(O)(R^{20})_2$, $-OP(O)(OR^{20})_2$, $-CN$, $C_{3-10}$ carbocycle and 3- to 10-membered heterocycle; and $C_{3-10}$ carbocycle, and 3- to 10-membered heterocycle, wherein each $C_{3-10}$ carbocycle and 3- to 10-membered heterocycle is independently optionally substituted with one or more substituents selected from halogen, $-OR^{20}$, $-SR^{20}$, $-N(R^{20})_2$, $-N(R^{20})C(O)R^{20}$, $-C(O)R^{20}$, $-C(O)OR^{20}$, $-C(O)N(R^{20})_2$, $-OC(O)R^{20}$, $-S(O)_2R^{20}$, $-S(O)_2N(R^{20})_2$, $-N(R^{20})S(O)_2R^{20}$, $-NO_2$, $=O$, $=S$, $=N(R^{20})$, $-P(O)(OR^{20})_2$, $-P(O)(R^{20})_2$, $-OP(O)(OR^{20})_2$, $-CN$, $C_{1-6}$ alkyl, $C_{2-6}$ alkenyl, and $C_{2-6}$ alkynyl.

In certain embodiments, for $R^9$ of a compound of Formula (1), (2), (1A), (1B), (1C), (1D), (1E), (1F), (1G), (1H), (1I), and (1J), $R^{23}$ is selected from hydrogen; $C_{1-6}$ alkyl optionally substituted with one or more substituents selected from halogen, $-OR^{20}$, $-SR^{20}$, $-N(R^{20})_2$, $=O$, $=S$, $=N(R^{20})$, and $-CN$; and 3- to 10-membered heterocycle optionally substituted with one or more substituents selected from halogen, $-OR^{20}$, $-SR^{20}$, $-N(R^{20})_2$, $-N(R^{20})C(O)R^{20}$, $-C(O)R^{20}$, $-C(O)OR^{20}$, $-C(O)N(R^{20})_2$, $-OC(O)R^{20}$, $-S(O)_2R^{20}$, $-S(O)_2N(R^{20})_2$, $-N(R^{20})S(O)_2R^{20}$, $-NO_2$, $=O$, $=S$, $=N(R^{20})$, $-P(O)(OR^{20})_2$, $-P(O)(R^{20})_2$, $-OP(O)(OR^{20})_2$, $-CN$, $C_{1-6}$ alkyl, $C_{2-6}$ alkenyl, and $C_{2-6}$ alkynyl. In particular embodiments, $R^{23}$ is selected from hydrogen and $C_{1-6}$ alkyl optionally substituted with one or more substituents selected from halogen, $-OR^{20}$, $-SR^{20}$, $-N(R^{20})_2$, $=O$, $=S$, $=N(R^{20})$, and $-CN$.

In certain embodiments, for $R^9$ of a compound of Formula (1), (2), (1A), (1B), (1C), (1D), (1E), (1F), (1G), (1H), (1I), and (1J), $R^{22}$ is selected from hydrogen, and $-CN$; $C_{1-6}$ alkyl, $C_{2-6}$ alkenyl, and $C_{2-6}$ alkynyl, each of which is independently optionally substituted at each occurrence with one or more substituents selected from halogen, —OR[20], —SR[20], —N(R[20])$_2$, —N(R[20])C(O)R[20], —C(O)R[20], —C(O)OR[20], —C(O)N(R[20])$_2$, —OC(O)R[20], —S(O)$_2$R[20], —S(O)$_2$N(R[20])$_2$, —N(R[20])S(O)$_2$R[20], —NO$_2$, =O, =S, =N(R[20]), —P(O)(OR[20])$_2$, —P(O)(R[20])$_2$, —OP(O)(OR[20])$_2$, —CN, $C_{3-10}$ carbocycle and 3- to 10-membered heterocycle; and $C_{3-10}$ carbocycle and 3- to 10-membered heterocycle, wherein each $C_{3-10}$ carbocycle and 3- to 10-membered heterocycle is independently optionally substituted with one or more substituents selected from halogen, —OR[20], —SR[20], —N(R[20])$_2$, —N(R[20])C(O)R[20], —C(O)R[20], —C(O)OR[20], —C(O)N(R[20])$_2$, —OC(O)R[20], —S(O)$_2$R[20], —S(O)$_2$N(R[20])$_2$, —N(R[20])S(O)$_2$R[20], —NO$_2$, =O, =S, =N(R[20]), —P(O)(OR[20])$_2$, —P(O)(R[20])$_2$, —OP(O)(OR[20])$_2$, —CN, $C_{1-6}$ alkyl, $C_{2-6}$ alkenyl, and $C_{2-6}$ alkynyl. In particular embodiments, R[22] is selected from hydrogen; —CN; and $C_{1-6}$ alkyl optionally substituted with one or more substituents selected from halogen, —OR[20], —SR[20], and —N(R[20])$_2$.

In certain embodiments, for R[9] of a compound of any one of Formulas (1), (2), (1A), (1B), (1C), (1D), (1E), (1F), (1G), (1H), (1I), and (1J), R[22] and R[23], together with the carbon atoms to which they are attached, form a 5-, 6-, or 7-membered carbocyclic ring.

In certain embodiments, for R[9] of a compound of any one of Formulas (1), (2), (1A), (1B), (1C), (1D), (1E), (1F), (1G), (1H), (1I), and (1J), R[24] is selected from hydrogen and $C_{1-6}$ alkyl optionally substituted with one or more substituents selected from halogen, —OR[20], —SR[20], —N(R[20])$_2$, —NO$_2$, =O, and —CN.

In certain embodiments, for a compound or salt of any one of Formulas (1), (2), (1A), (1B), (1C), (1D), (1E), (1F), (1G), (1H), (1I), and (1J), R[9] is selected from:

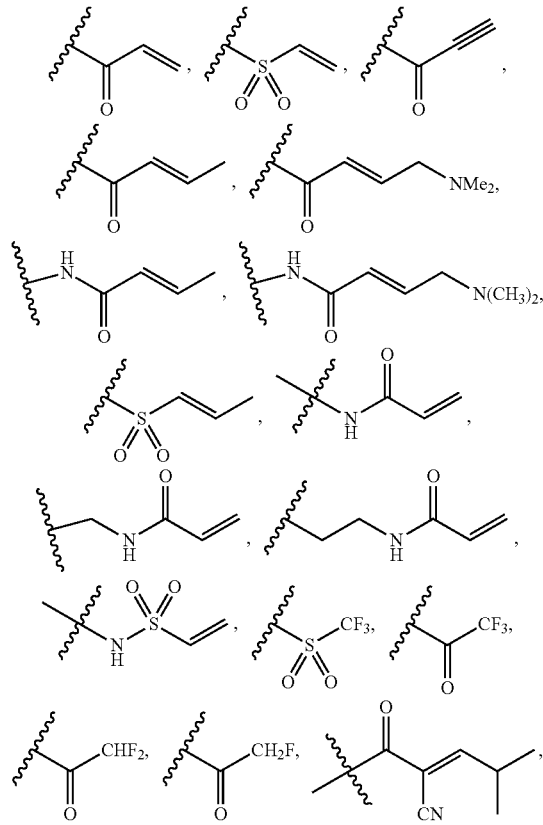

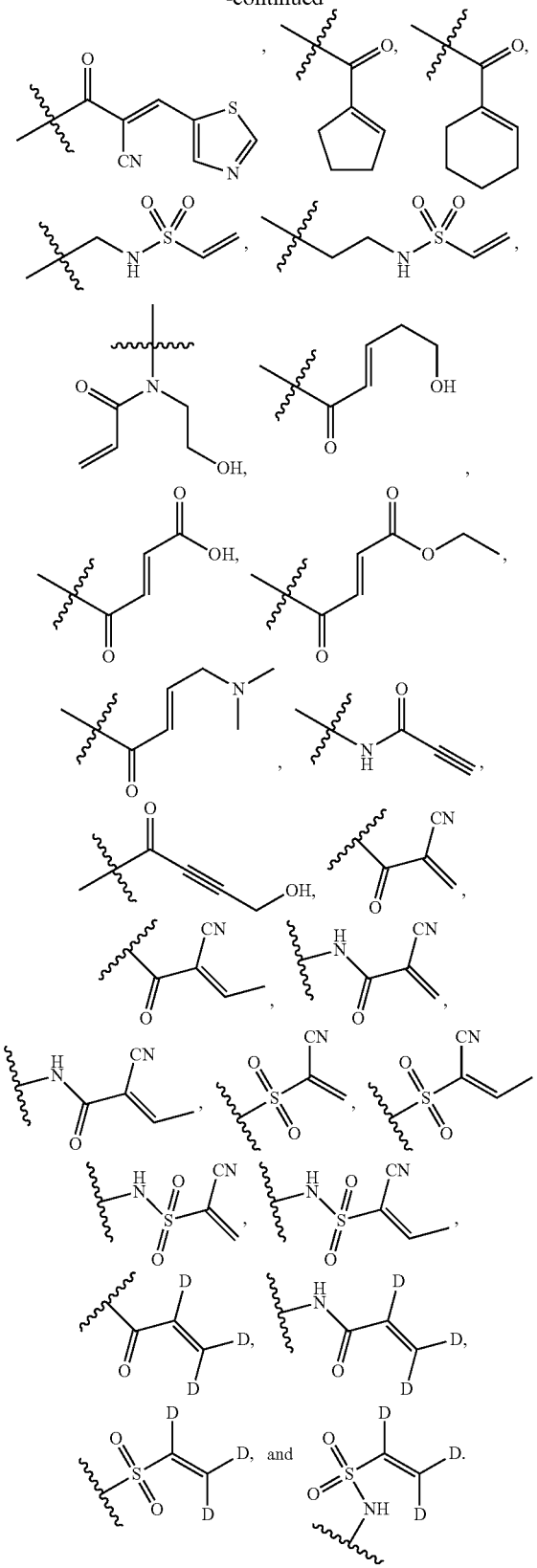

In certain embodiments, for a compound or salt of any of Formulas (1), (2), (1A), (1B), (1C), (1D), (1E), (1F), (1G), (1H), (1I), and (1J), R[9] is selected from:

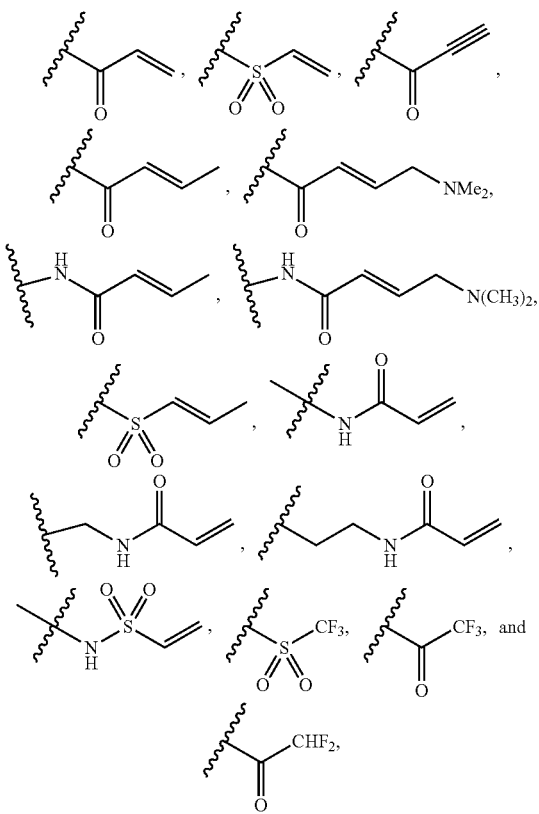

In certain embodiments, for a compound or salt of any of Formulas (1), (2), (1A), (1B), (1C), (1D), (1E), (1F), (1G), (1H), (1I), and (1J), $R^9$ is selected from:

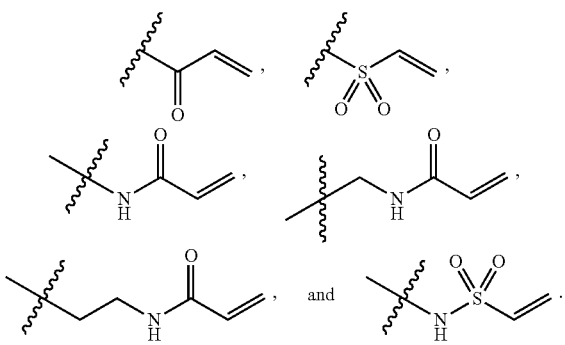

In certain embodiments, for a compound or salt of any one of Formulas (1), (2), (1A), (1B), (1C), (1D), (1E), (1F), (1G), (1H), (1I), and (1J), G is a bond.

In certain embodiments, for a compound or salt of any one of Formulas (1), (2), (1A), (1B), (1C), (1D), (1E), (1F), (1G), (1H), (1I), and (1J), G is alkylene optionally substituted with one or more $R^{32}$ groups, wherein:

$R^{32}$ at each occurrence is independently selected from halogen, —OR$^{20}$, —SR$^{20}$, —N(R$^{20}$)$_2$, —N(R$^{20}$)C(O)R$^{20}$, —C(O)R$^{20}$, —C(O)OR$^{20}$, —C(O)N(R$^{20}$)$_2$, —OC(O)R$^{20}$, —S(O)$_2$R$^{20}$, —S(O)$_2$N(R$^{20}$)$_2$, —N(R$^{20}$)S(O)$_2$R$^{20}$, —NO$_2$, =O, =S, =N(R$^{20}$), —P(O)(OR$^{20}$)$_2$, —P(O)(R$^{20}$)$_2$, —OP(O)(OR$^{20}$)$_2$, and —CN; C$_{1-6}$ alkyl, C$_{2-6}$ alkenyl, and C$_{2-6}$ alkynyl, each of which is independently optionally substituted at each occurrence with one or more substituents selected from halogen, —OR$^{20}$, —SR$^{20}$, —N(R$^{20}$)$_2$, —N(R$^{20}$)C(O)R$^{20}$, —C(O)R$^{20}$, —C(O)OR$^{20}$, —C(O)N(R$^{20}$)$_2$, —OC(O)R$^{20}$, —S(O)$_2$R$^{20}$, —S(O)$_2$N(R$^{20}$)$_2$, —N(R$^{20}$)S(O)$_2$R$^{20}$, —NO$_2$, =O, =S, =N(R$^{20}$), —P(O)(OR$^{20}$)$_2$, —P(O)(R$^{20}$)$_2$, —OP(O)(OR$^{20}$)$_2$, —CN, C$_{3-10}$ carbocycle, and 3- to 10-membered heterocycle; C$_{3-10}$ carbocycle and 3- to 10-membered heterocycle; or two $R^{32}$ on the same carbon atom can come together to form a C$_{3-10}$ carbocycle or 3- to 10-membered heterocycle, wherein each C$_{3-10}$ carbocycle and 3- to 10-membered heterocycle of $R^{32}$ is independently optionally substituted with one or more substituents selected from halogen, —OR$^{20}$, —SR$^{20}$, —N(R$^{20}$)$_2$, —N(R$^{20}$)C(O)R$^{20}$, —C(O)R$^{20}$, —C(O)OR$^{20}$, —C(O)N(R$^{20}$)$_2$, —OC(O)R$^{20}$, —S(O)$_2$R$^{20}$, —S(O)$_2$N(R$^{20}$)$_2$, —N(R$^{20}$)S(O)$_2$R$^{20}$, —NO$_2$, =O, =S, =N(R$^{20}$), —P(O)(OR$^{20}$)$_2$, —P(O)(R$^{20}$)$_2$, —OP(O)(OR$^{20}$)$_2$, —CN, C$_{1-6}$ alkyl, C$_{2-6}$ alkenyl, and C$_{2-6}$ alkynyl;

$R^{20}$ at each occurrence is independently selected from hydrogen; C$_{1-6}$ alkyl, C$_{2-6}$ alkenyl, and C$_{2-6}$ alkynyl, each of which is independently optionally substituted at each occurrence with one or more substituents selected from halogen, —OR$^{30}$, —SR$^{30}$, —N(R$^{30}$)$_2$, —N(R$^{30}$)C(O)R$^{30}$, —C(O)R$^{30}$, —C(O)OR, —C(O)N(R$^{30}$)$_2$, —OC(O)R$^{30}$, —S(O)$_2$R$^{30}$, —S(O)$_2$N(R$^{30}$)$_2$, —N(R$^{30}$)S(O)$_2$R$^{30}$, —NO$_2$, —P(O)(OR$^{30}$)$_2$, —P(O)(R$^{30}$)$_2$, —OP(O)(OR$^{30}$)$_2$, and —CN; and 3- to 10-membered heterocycle and C$_{3-10}$ carbocycle; and $R^{30}$ at each occurrence is independently selected from hydrogen, C$_{1-6}$ alkyl, C$_{2-6}$ alkenyl, and C$_{2-6}$ alkynyl.

In certain embodiments, for a compound or salt of any one of Formulas (1), (2), (1A), (1B), (1C), (1D), (1E), (1F), (1G), (1H), (1I), and (1J), G is selected from methylene, ethylene, propylene, and butylene, any one of which is optionally substituted with one or more $R^{32}$ groups, for example, from:

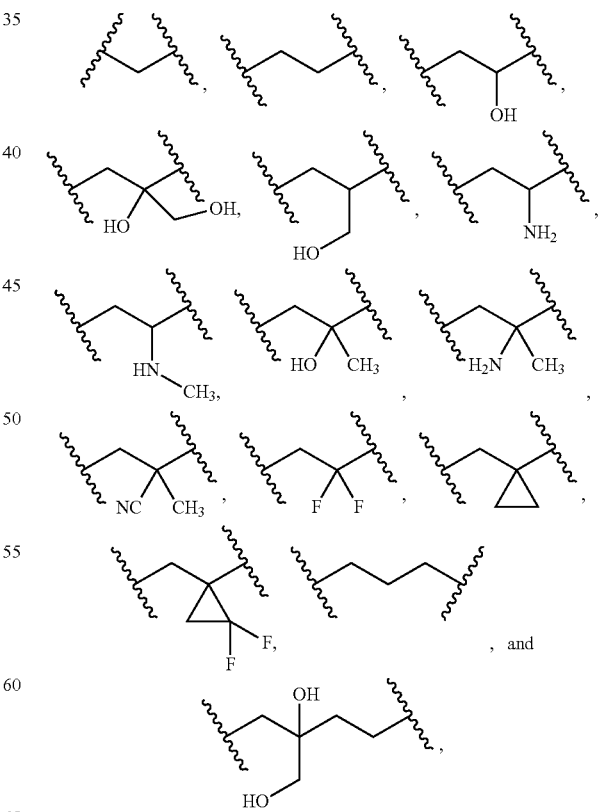

wherein any one of which is optionally substituted with one or more $R^{32}$ groups.

In certain embodiments, for a compound or salt of any one of Formulas (1), (2), (1A), (1B), (1C), (1D), (1E), (1F), (1G), (1H), (1I), and (1J), G is a heteroalkylene optionally substituted with one or more $R^{32}$ groups.

In certain embodiments, for a compound or salt of any one of Formulas (1), (2), (1A), (1B), (1C), (1D), (1E), (1F), (1G), (1H), (1I), and (1J), G is a heterocycle or carbocycle, any one of which is optionally substituted with one or more $R^{32}$ groups. In certain embodiments, G is a saturated carbocycle or saturated heterocycle, any one of which is optionally substituted with one or more $R^{32}$ groups. In particular embodiments, G is selected from:

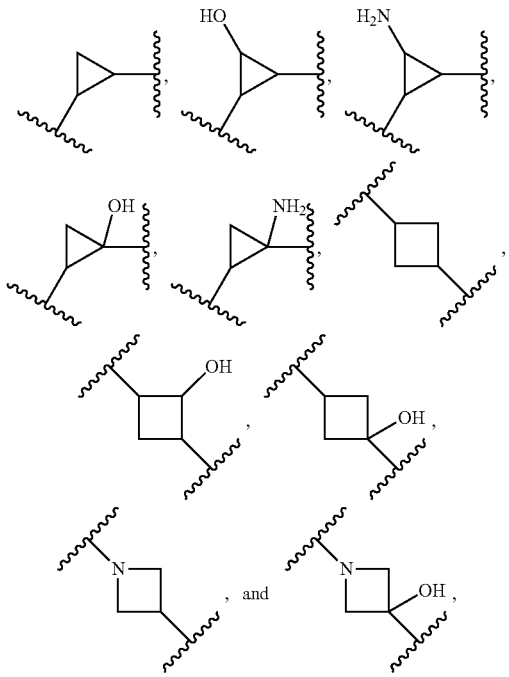

wherein any one of which is optionally substituted with one or more $R^{32}$ groups.

In certain embodiments, for a compound or salt of any one of Formulas (1), (2), (1A), (1B), (1C), (1D), (1E), (1F), (1G), (1H), (1I), and (1J), V is selected from a 3-8 membered saturated carbocyclic or heterocyclic ring optionally substituted with one or more $R^{32}$ groups. In certain embodiments, V is a 3-, 4-, 5-, 6- or 7-membered saturated carbocycle, any one of which is optionally substituted with one or more $R^{32}$ groups. In particular embodiments, V is selected from:

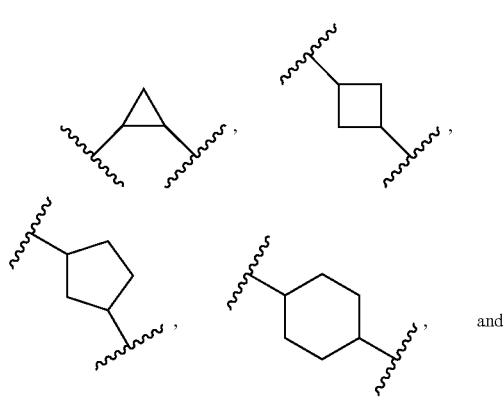

-continued

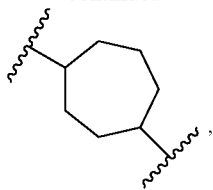

any one of which is optionally substituted with one or more $R^{32}$ groups. In certain embodiments, V is a 4-, 5-, 6-, 7- or 8-membered saturated heterocycle, any one of which is optionally substituted with one or more $R^{32}$ groups. In particular embodiments, V is selected from azetidine, oxetane, piperidine, oxane, piperazine, pyrrolidine, tetrahydrofuran, thiolane, imidazolidine, morpholine, thiomorpholine, azepane, and homopiperazine, any one of which is optionally substituted with one or more $R^{32}$ groups. In particular embodiments, V is selected from:

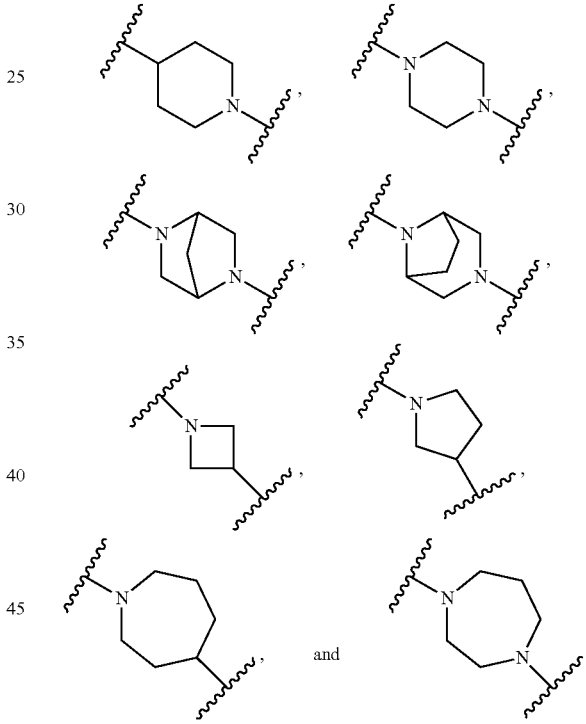

any one of which is optionally substituted with one or more $R^{32}$ groups.

In certain embodiments, for a compound or salt of any one of Formulas (1), (2), (1A), (1B), (1C), (1D), (1E), (1F), (1G), (1H), (1I), and (1J), V is a bicyclic heterocycle, optionally substituted with one or more $R^{32}$ groups. In particular embodiments, V is selected from

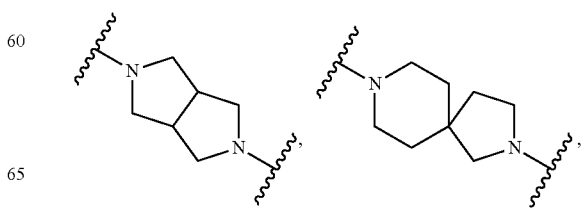

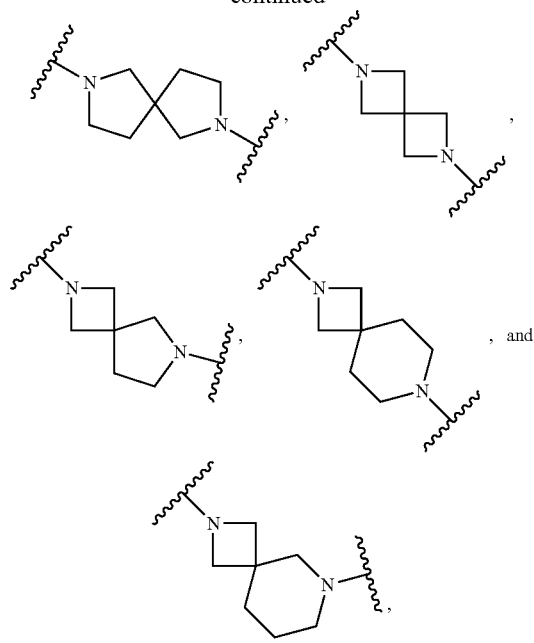

any one of which is optionally substituted with one or more $R^{32}$ groups.

In certain embodiments, for a compound or salt of any one of Formulas (1), (2), (1A), (1B), (1C), (1D), (1E), (1F), (1G), (1H), (1I), and (1J), V is selected from an unsaturated, aromatic, or heteroaromatic ring. In particular embodiments, V is selected from phenyl, pyridine, pyrazine, pyrimidine, pyridazine, naphthalene, anthracene, quinoline, isoquinoline, quinoxaline, acridine, quinazoline, cinnoline, phthalazine, furan, dihydrofuran, thiophene, dihydrothiophene, imidazole, imidazoline, oxazole, oxazoline, pyrrole, dihydropyrrole, thiazole, dihydrothiazole, pyrazole, dihydropyrazole, isoxazole, dihydroisoxazole, isothiazole, dihydroisothiazole, benzofuran, isobenzofuran, indole, isoindole, benzothiophene, benzimidazole, purine, indazole, benzoxazole, benzisoxazole, and benzothiazole, any one of which is optionally substituted with one or more $R^{32}$ groups. In particular embodiments, V is phenyl, optionally substituted with one or more $R^{32}$ groups. In some embodiments, V is a heteroaromatic ring optionally substituted with one or more $R^{32}$ groups. In particular embodiments, V is selected from pyridine, pyrazine, pyrimidine, pyridazine, naphthalene, anthracene, quinoline, isoquinoline, quinoxaline, acridine, quinazoline, cinnoline, phthalazine, furan, thiophene, imidazole, oxazole, pyrrole, thiazole, pyrazole, isoxazole, isothiazole, benzofuran, isobenzofuran, indole, isoindole, benzothiophene, benzimidazole, purine, indazole, benzoxazole, benzisoxazole, and benzothiazole, any one of which is optionally substituted with one or more $R^{32}$ groups, for example, V is selected from

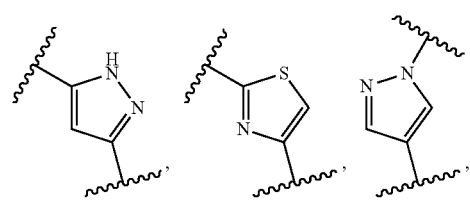

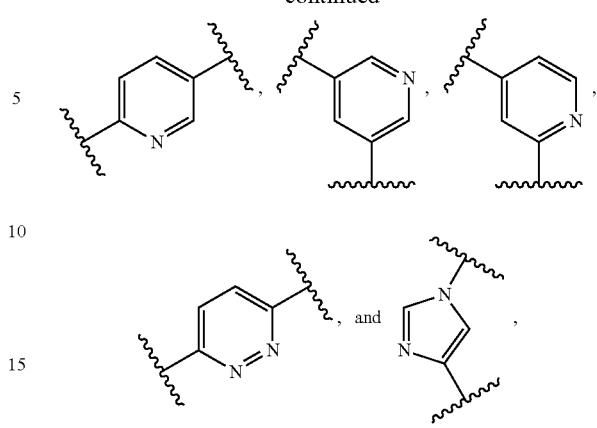

wherein any one of which is optionally substituted with one or more $R^{32}$ groups.

In certain embodiments, for a compound or salt of any one of Formulas (1), (2), (1A), (1B), (1C), (1D), (1E), (1F), (1G), (1H), (1I), and (1J), V is absent.

In certain emdbodiments, for a compound or salt of any one of Formulas (1), (2), (1A), (1B), (1C), (1D), (1E), (1F), (1G), (1H), (1I), and (1J), $R_1$ is selected from —$CH_2CF_3$ and —$CH_2CHF_2$, $R_2$ is hydrogen, $R_3$ is hydrogen, $R_4$ is hydrogen, $R_5$ is hydrogen, $R_6$, at each occurrence, is selected from methyl, hydroxy and methoxy, s is 0 or 1, $R_8$ is cyano, Y is $C(R^a)$; $R^a$ is selected from hydrogen, —$CH_2OH$ and cyano; $R^7$ is selected from

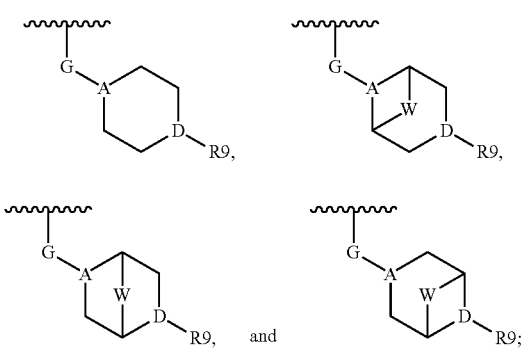

G is selected from alkylene; and $R_9$ is selected from:

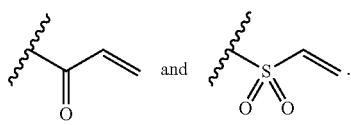

In certain embodiments, for a compound or salt of any one of Formulas (1), (2), (1A), (1B), (1C), (1D), (1E), (1F), (1G), (1H), (1I), and (1J), $R_1$ is selected from —$CH_2CF_3$ and —$CH_2CHF_2$, $R_2$ is hydrogen, $R_3$ is hydrogen, $R_4$ is hydrogen, $R_5$ is hydrogen, $R_6$, at each occurrence, is selected from methyl, hydroxy and methoxy, s is 0 or 1, $R_8$ is cyano, Y is $C(R^a)$; $R^a$ is selected from hydrogen, —$CH_2OH$ and cyano; $R^7$ is selected from:

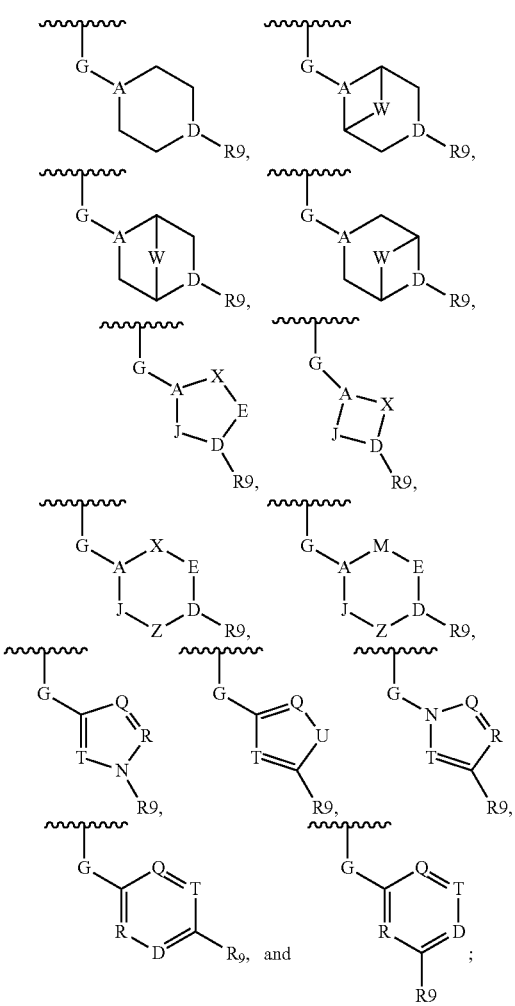

G is selected from alkylene, aminoalkylene, oxalkylene, or heteroalkylene; and R$_9$ is selected from:

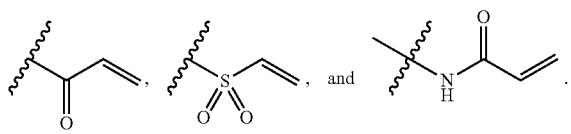

In certain embodiments, for a compound or salt of any one of Formulas (1), (2), (1A), (1B), (1C), (1D), (1E), (1F), (1G), (1H), (1I), and (1J), R$_1$ is selected from —CH$_2$CF$_3$ and —CH$_2$CHF$_2$, R$_2$ is hydrogen, R$_3$ is hydrogen, R$_4$ is hydrogen, R$_5$ is hydrogen, R$_6$, at each occurrence, is selected from methyl, hydroxy and methoxy, s is 0 or 1, R$_8$ is cyano, Y is C(R$^a$); R$^a$ is selected from hydrogen, —CH$_2$OH and cyano; R$^7$ is selected from:

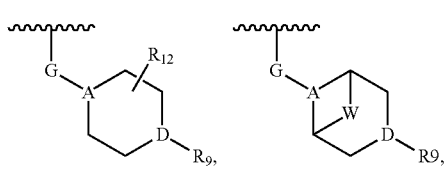

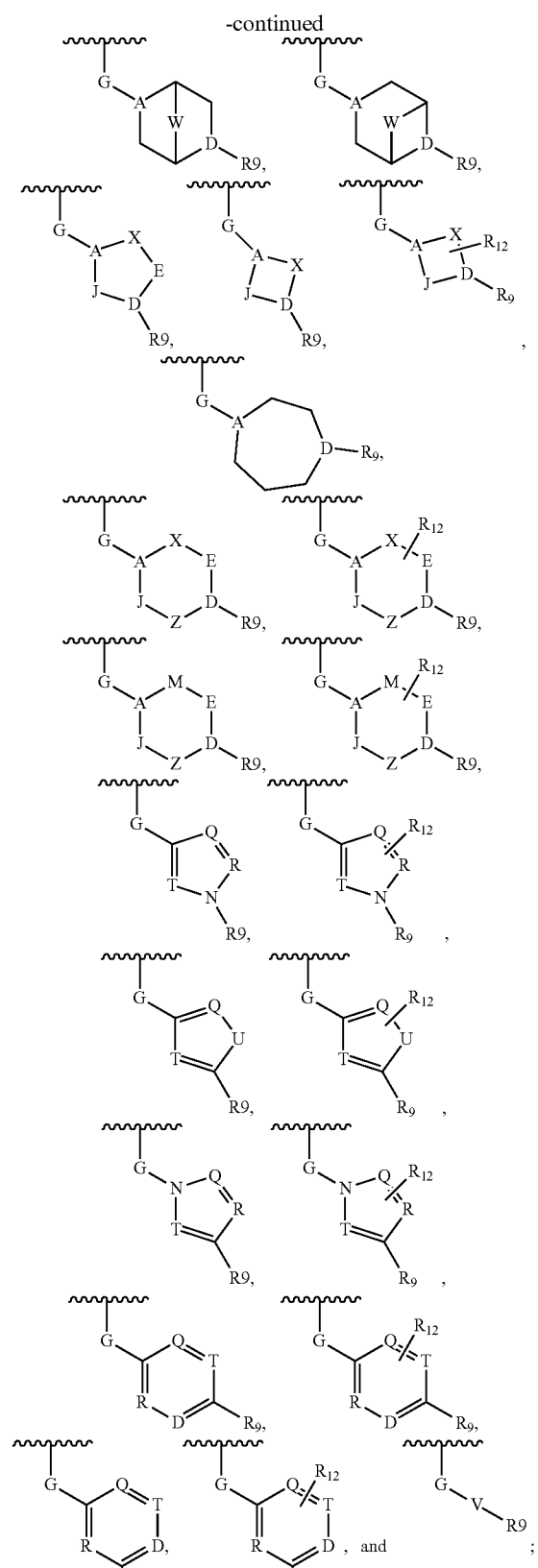

G is selected from alkylene, branched alkylene, aminoalkylene, oxalkylene, haloalkylene, heteroalkylene, hydroxyalkyl, alkylhydroxyalkyl, alkoxyalkyl, aminoalkyl or alkylamine, alkylaminoalkyl, carbocycle, alkylcycloalkyl, hydroxycycloalkyl, alkoxycycloalkyl, hydroxyalkylcycloalkyl, disubstituted cycloalkyl, aminocycloalkyl, alkylaminocycloalkyl, substituted carbocycle, heterocycle, and substituted heterocycle; V and $R_{12}$ are as described above; and $R_9$ is selected from:

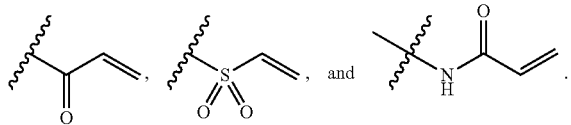

In certain embodiments, provided herein is a compound represented by the structure of Formula (3):

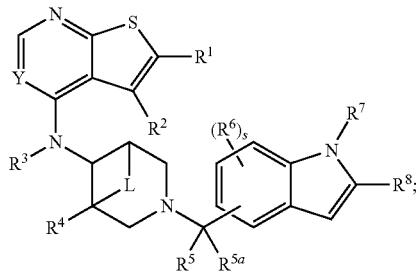

Formula (3)

or a salt thereof, wherein:

$R^1$, $R^2$, $R^4$, $R^5$, $R^{5a}$, $R^8$, and $R^a$ are independently selected from hydrogen, halogen, $-OR^{20}$, $-SR^{20}$, $-N(R^{20})_2$, $-N(R^{20})C(O)R^{20}$, $-C(O)R^{20}$, $-C(O)OR^{20}$, $-C(O)N(R^{20})_2$, $-OC(O)R^{20}$, $-S(O)_2R^{20}$, $-S(O)_2N(R^{20})_2$, $-N(R^{20})S(O)_2R^{20}$, $-NO_2$, $-P(O)(OR^{20})_2$, $-P(O)(R^{20})_2$, $-OP(O)(OR^{20})_2$, and $-CN$; $C_{1-6}$ alkyl, $C_{2-6}$ alkenyl, and $C_{2-6}$ alkynyl, each of which is independently optionally substituted at each occurrence with one or more substituents selected from halogen, $-OR^{20}$, $-SR^{20}$, $-N(R^{20})_2$, $-N(R^{20})C(O)R^{20}$, $-C(O)R^{20}$, $-C(O)OR^{20}$, $-C(O)N(R^{20})_2$, $-OC(O)R^{20}$, $-S(O)_2R^{20}$, $-S(O)_2N(R^{20})_2$, $-N(R^{20})S(O)_2R^{20}$, $-NO_2$, $=O$, $=S$, $=N(R^{20})$, $-P(O)(OR^{20})_2$, $-P(O)(R^{20})_2$, $-OP(O)(OR^{20})_2$, $-CN$, $C_{3-10}$ carbocycle, and 3- to 10-membered heterocycle, or two substituents on the same carbon atom of an $C_{1-6}$ alkyl, $C_{2-6}$ alkenyl, or $C_{2-6}$ alkynyl come together to form a $C_{3-10}$ carbocycle or 3- to 10-membered heterocycle; and $C_{3-10}$ carbocycle and 3- to 10-membered heterocycle; or $R^5$ and $R^{5a}$ together with the carbon atom to which they are attached, come together to form a $C_{3-10}$ carbocycle or a 3- to 10-membered heterocycle; wherein any $C_{3-10}$ carbocycle and 3- to 10-membered heterocycle of $R^1$, $R^2$, $R^4$, $R^5$, $R^{5a}$, $R^8$, and $R^a$ is independently optionally substituted with one or more substituents selected from halogen, $-OR^{20}$, $-SR^{20}$, $-N(R^{20})_2$, $-N(R^{20})C(O)R^{20}$, $-C(O)R^{20}$, $-C(O)OR^{20}$, $-C(O)N(R^{20})_2$, $-OC(O)R^{20}$, $-S(O)_2R^{20}$, $-S(O)_2N(R^{20})_2$, $-N(R^{20})S(O)_2R^{20}$, $-NO_2$, $=O$, $=S$, $=N(R^{20})$, $-P(O)(OR^{20})_2$, $-P(O)(R^{20})_2$, $-OP(O)(OR^{20})_2$, $-CN$, $C_{1-6}$ alkyl, $C_{2-6}$ alkenyl, and $C_{2-6}$ alkynyl;

$R^3$ is selected from selected from hydrogen, $-C(O)R^{20}$, $-C(O)OR^{20}$, $-C(O)N(R^{20})_2$, $-S(O)_2R^{20}$, and $-S(O)_2N(R^{20})_2$; $C_{1-6}$ alkyl, $C_{2-6}$ alkenyl, and $C_{2-6}$ alkynyl, each of which is independently optionally substituted at each occurrence with one or more substituents selected from halogen, $-OR^{20}$, $-SR^{20}$, $-N(R^{20})_2$, $-N(R^{20})C(O)R^{20}$, $-C(O)R^{20}$, $-C(O)OR^{20}$, $-C(O)N(R^{20})_2$, $-OC(O)R^{20}$, $-S(O)_2R^{20}$, $-S(O)_2N(R^{20})_2$, $-N(R^{20})S(O)_2R^{20}$, $-NO_2$, $=O$, $=S$, $=N(R^{20})$, $-P(O)(OR^{20})_2$, $-P(O)(R^{20})_2$, $-OP(O)(OR^{20})_2$, $-CN$, $C_{3-10}$ carbocycle, and 3- to 10-membered heterocycle, or two substituents on the same carbon atom of an $C_{1-6}$ alkyl, $C_{2-6}$ alkenyl, or $C_{2-6}$ alkynyl come together to form a $C_{3-10}$ carbocycle or 3- to 10-membered heterocycle; and $C_{3-10}$ carbocycle and 3- to 10-membered heterocycle; wherein any $C_{3-10}$ carbocycle and 3- to 10-membered heterocycle of $R^3$ is independently optionally substituted with one or more substituents selected from halogen, $-OR^{20}$, $-SR^{20}$, $-N(R^{20})_2$, $-N(R^{20})C(O)R^{20}$, $-C(O)R^{20}$, $-C(O)OR^{20}$, $-C(O)N(R^{20})_2$, $-OC(O)R^{20}$, $-S(O)_2R^{20}$, $-S(O)_2N(R^{20})_2$, $-N(R^{20})S(O)_2R^{20}$, $-NO_2$, $=O$, $=S$, $=N(R^{20})$, $-P(O)(OR^{20})_2$, $-P(O)(R^{20})_2$, $-OP(O)(OR^{20})_2$, $-CN$, $C_{1-6}$ alkyl, $C_{2-6}$ alkenyl, and $C_{2-6}$ alkynyl;

$R^6$ is independently selected at each occurrence from halogen, $-OR^{20}$, $-SR^{20}$, $-N(R^{20})_2$, $-N(R^{20})C(O)R^{20}$, $-C(O)R^{20}$, $-C(O)OR^{20}$, $-C(O)N(R^{20})_2$, $-OC(O)R^{20}$, $-S(O)_2R^{20}$, $-S(O)_2N(R^{20})_2$, $-N(R^{20})S(O)_2R^{20}$, $-NO_2$, $-P(O)(OR^{20})_2$, $-P(O)(R^{20})_2$, $-OP(O)(OR^{20})_2$, and $-CN$; $C_{1-6}$ alkyl, $C_{2-6}$ alkenyl, and $C_{2-6}$ alkynyl, each of which is independently optionally substituted at each occurrence with one or more substituents selected from halogen, $-OR^{20}$, $-SR^{20}$, $-N(R^{20})_2$, $-N(R^{20})C(O)R^{20}$, $-C(O)R^{20}$, $-C(O)OR^{20}$, $-C(O)N(R^{20})_2$, $-OC(O)R^{20}$, $-S(O)_2R^{20}$, $-S(O)_2N(R^{20})_2$, $-N(R^{20})S(O)_2R^{20}$, $-NO_2$, $=O$, $=S$, $=N(R^{20})$, $-P(O)(OR^{20})_2$, $-P(O)(R^{20})_2$, $-OP(O)(OR^{20})_2$, $-CN$, $C_{3-10}$ carbocycle, and 3- to 10-membered heterocycle, or two substituents on the same carbon atom of an $C_{1-6}$ alkyl, $C_{2-6}$ alkenyl, or $C_{2-6}$ alkynyl come together to form a $C_{3-10}$ carbocycle or 3- to 10-membered heterocycle; and $C_{3-10}$ carbocycle and 3- to 10-membered heterocycle; wherein any $C_{3-10}$ carbocycle and 3- to 10-membered heterocycle of $R^6$ is independently optionally substituted with one or more substituents selected from halogen, $-OR^{20}$, $-SR^{20}$, $-N(R^{20})_2$, $-N(R^{20})C(O)R^{20}$, $-C(O)R^{20}$, $-C(O)OR^{20}$, $-C(O)N(R^{20})_2$, $-OC(O)R^{20}$, $-S(O)_2R^{20}$, $-S(O)_2N(R^{20})_2$, $-N(R^{20})S(O)_2R^{20}$, $-NO_2$, $=O$, $=S$, $=N(R^{20})$, $-P(O)(OR^{20})_2$, $-P(O)(R^{20})_2$, $-OP(O)(OR^{20})_2$, $-CN$, $C_{1-6}$ alkyl, $C_{2-6}$ alkenyl, and $C_{2-6}$ alkynyl;

$R^{20}$ at each occurrence is independently selected from hydrogen; $C_{1-6}$ alkyl, $C_{2-6}$ alkenyl, and $C_{2-6}$ alkynyl, each of which is independently optionally substituted at each occurrence with one or more substituents selected from halogen, $-OR^{30}$, $-SR^{30}$, $-N(R^{30})_2$, $-N(R^{30})C(O)R^{30}$, $-C(O)R^{30}$, $-C(O)OR^{30}$, $-C(O)N(R^{30})_2$, $-OC(O)R^{30}$, $-S(O)_2R^{30}$, $-S(O)_2N(R^{30})_2$, $-N(R^{30})S(O)_2R^{30}$, $-NO_2$, $-P(O)(OR^{30})_2$, $-P(O)(R^{30})_2$, $-OP(O)(OR^{30})_2$, and $-CN$; and 3- to 10-membered heterocycle and $C_{3-10}$ carbocycle;

$R^{30}$ at each occurrence is independently selected from hydrogen, $C_{1-6}$ alkyl, $C_{2-6}$ alkenyl, and $C_{2-6}$ alkynyl;

Y is N or $C(R^a)$;

L is absent or selected from alkylene and heteroalkylene;

s is selected from 0, 1, 2, 3, and 4; and $R^7$ comprises a moiety that covalently reacts with one or more residues on menin.

In certain embodiments, a compound of Formula (3) has a structure of Formula (3A):

Formula (3A)

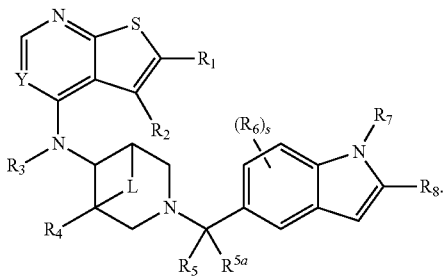

In certain embodiments, a compound of Formula (3) has a structure of Formula (3B):

Formula (3B)

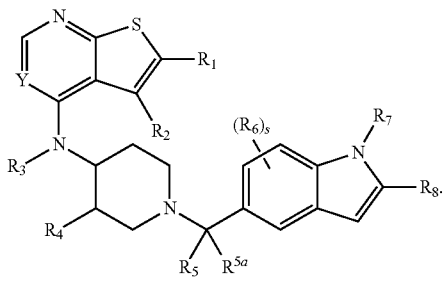

In certain embodiments, a compound of Formula (3) has a structure of Formula (3C):

Formula (3C)

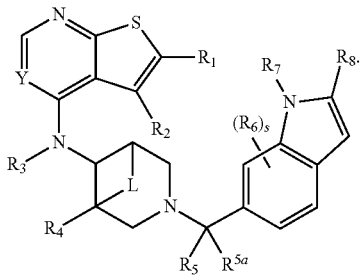

In certain embodiments, a compound of Formula (3) has a structure of Formula (3D):

Formula (3D)

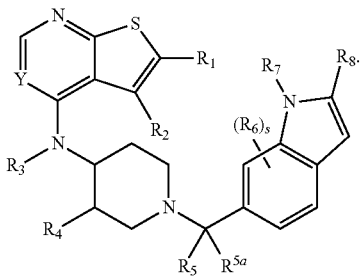

In certain embodiments, a compound of Formula (3) has a structure of Formula (3E):

Formula (3E)

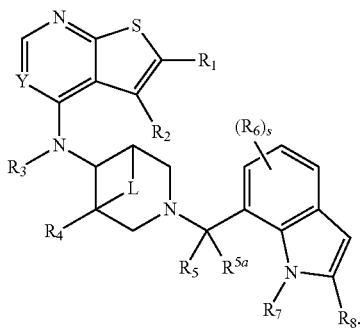

In certain embodiments, a compound of Formula (3) has a structure of Formula (3F):

Formula (3F)

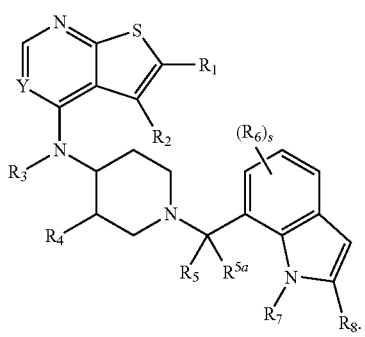

In certain embodiments, a compound of Formula (3) has a structure of Formula (3G):

Formula (3G)

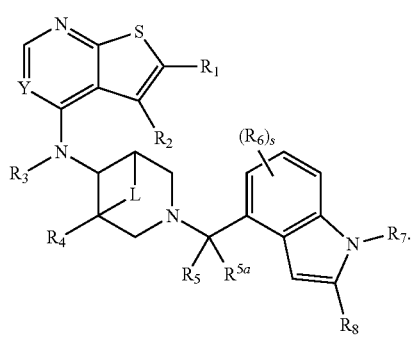

In certain embodiments, a compound of Formula (3) has a structure of Formula (3H):

Formula (3H)

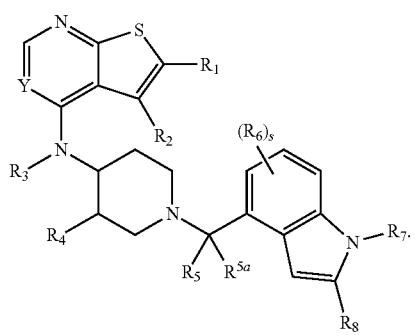

In certain embodiments, a compound of Formula (3) has a structure of Formula (3I):

Formula (3I)

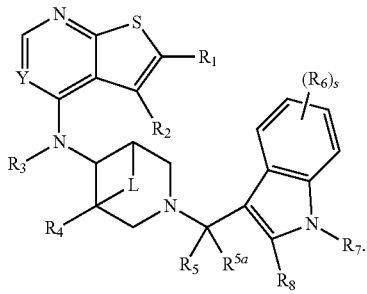

In certain embodiments, a compound of Formula (3) has a structure of Formula (3J):

Formula (3J)

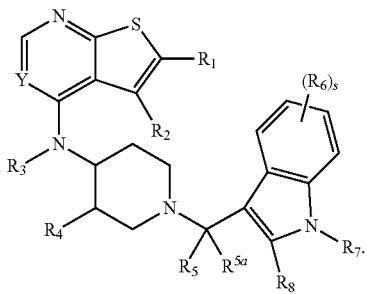

In certain embodiments, for a compound or salt of any one of Formulas (3), (3A), (3B), (3C), (3D), (3E), (3F), (3G), (3H), (3I), and (3J), $R^7$ comprises a moiety that covalently reacts with one or more residues on menin. In particular embodiments, $R^7$ comprises a moiety that covalently reacts with any one or more isoforms of menin, for example, isoform 1 (SEQ ID NO: 1), isoform 2 (SEQ ID NO: 2) or isoform 3 (SEQ ID NO: 3) of menin. In certain embodiments $R^7$ comprises a moiety that covalently reacts with menin, wherein the menin protein shares 60% or more, 70% or more, 75% or more, 80% or more, 85% or more, 90% or more, 95% or more, or even 99% sequence identity with isoform 1(SEQ ID NO: 1), isoform 2 (SEQ ID NO: 2) or isoform 3 (SEQ ID NO: 3).

In certain embodiments, for a compound or salt of any one of Formulas (3), (3A), (3B), (3C), (3D), (3E), (3F), (3G), (3H), (3I), and (3J), $R^7$ comprises an electrophilic group that is susceptible to nuclephilic attack from a residue on menin. Included in the present disclosure are all electrophilic moieties that are known by one of skill in the art to bind to nuclephilic residues, for example, any electrophilic moiety known to bind to cysteine residues. In certain embodiments, for a compound or salt of any one of Formulas (3), (3A), (3B), (3C), (3D), (3E), (3F), (3G), (3H), (3I), and (3J), $R^7$ comprises a moiety other than an electrophile wherein the moiety is capable of binding or covalently reacting with a residue on menin. In particular embodiments, for a compound or salt of any one of Formulas (3), (3A), (3B), (3C), (3D), (3E), (3F), (3G), (3H), (3I), and (3J), $R^7$ comprises a moiety that covalently reacts with one or more cysteine residues on menin, for example, one or more of cysteine 329, cysteine 241, and cysteine 230. In certain embodiments, $R^7$ comprises a moiety that covalently reacts with cysteine 329 in menin isoform 2 or cysteine 334 in menin isoform 1. In certain embodiments, a compound or salt of any one of Formulas (3), (3A), (3B), (3C), (3D), (3E), (3F), (3G), (3H), (3I), and (3J), is capable of (a) binding covalently to menin and (b) inhibiting the interaction of menin and MLL.

In certain embodiments, the disclosure provides a compound represented by the structure of Formula (4):

(4)

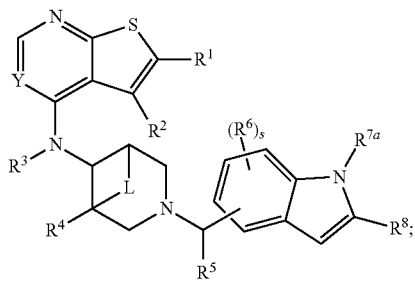

or a salt thereof, wherein:

$R^1$, $R^2$, $R^4$, $R^5$, $R^8$, and $R^a$ are independently selected from hydrogen, halogen, —$OR^{20}$, —$SR^{20}$, —$N(R^{20})_2$, —$N(R^{20})C(O)R^{20}$, —$C(O)R^{20}$, —$C(O)OR^{20}$, —$C(O)N(R^{20})_2$, —$OC(O)R^{20}$, —$S(O)_2R^{20}$, —$S(O)_2N(R^{20})_2$, —$N(R^{20})S(O)_2R^{20}$, —$NO_2$, —$P(O)(OR^{20})_2$, —$P(O)(R^{20})_2$, —$OP(O)(OR^{20})_2$, and —CN; $C_{1-6}$ alkyl, $C_{2-6}$ alkenyl, and $C_{2-6}$ alkynyl, each of which is independently optionally substituted at each occurrence with one or more substituents selected from halogen, —$OR^{20}$, —$SR^{20}$, —$N(R^{20})_2$, —$N(R^{20})C(O)R^{20}$, —$C(O)R^{20}$, —$C(O)OR^{20}$, —$C(O)N(R^{20})_2$, —$OC(O)R^{20}$, —$S(O)_2R^{20}$, —$S(O)_2N(R^{20})_2$, —$N(R^{20})S(O)_2R^{20}$, —$NO_2$, =O, =S, =$N(R^{20})$, —$P(O)(OR^{20})_2$, —$P(O)(R^{20})_2$, —$OP(O)(OR^{20})_2$, —CN, $C_{3-10}$ carbocycle, and 3- to 10-membered heterocycle, or two substituents on the same carbon atom of an $C_{1-6}$ alkyl, $C_{2-6}$ alkenyl, or $C_{2-6}$ alkynyl come together to form a $C_{3-10}$ carbocycle or 3- to 10-membered heterocycle; and $C_{3-10}$ carbocycle and 3- to 10-membered heterocycle; wherein any $C_{3-10}$ carbocycle and 3- to 10-membered heterocycle of $R^1$, $R^2$, $R^4$, $R^5$, $R^8$, and $R^a$ is independently optionally substituted with one or more substituents selected from halogen, —$OR^{20}$, —$SR^{20}$, —$N(R^{20})_2$, —$N(R^{20})C(O)R^{20}$, —$C(O)R^{20}$, —$C(O)OR^{20}$, —$C(O)N(R^{20})_2$, —$OC(O)R^{20}$, —$S(O)_2R^{20}$, —$S(O)_2N(R^{20})_2$, —$N(R^{20})S(O)_2R^{20}$, —$NO_2$, =O, =S, =$N(R^{20})$, —$P(O)(OR^{20})_2$, —$P(O)(R^{20})_2$, —$OP(O)(OR^{20})_2$, —CN, $C_{1-6}$ alkyl, $C_{2-6}$ alkenyl, and $C_{2-6}$ alkynyl;

$R^3$ is selected from selected from hydrogen, —$C(O)R^{20}$, —$C(O)OR^{20}$, —$C(O)N(R^{20})_2$, —$S(O)_2R^{20}$, and —$S(O)_2N(R^{20})_2$; $C_{1-6}$ alkyl, $C_{2-6}$ alkenyl, and $C_{2-6}$ alkynyl, each of which is independently optionally substituted at each occurrence with one or more substituents selected from halogen, —$OR^{20}$, —$SR^{20}$, —$N(R^{20})_2$, —$N(R^{20})C(O)R^{20}$, —$C(O)R^{20}$, —$C(O)OR^{20}$, —$C(O)N(R^{20})_2$, —$OC(O)R^{20}$, —$S(O)_2R^{20}$, —$S(O)_2N(R^{20})_2$, —$N(R^{20})S(O)_2R^{20}$, —$NO_2$, =O, =S, =$N(R^{20})$, —$P(O)(OR^{20})_2$, —$P(O)(R^{20})_2$, —$OP(O)(OR^{20})_2$, —CN, $C_{3-10}$ carbocycle, and 3- to 10-membered heterocycle, or two substituents on the same carbon atom of an $C_{1-6}$ alkyl, $C_{2-6}$ alkenyl, or $C_{2-6}$ alkynyl come together to form a $C_{3-10}$ carbocycle or 3- to 10-membered heterocycle; and $C_{3-10}$ carbocycle and 3- to 10-membered heterocycle; wherein any $C_{3-10}$ carbocycle and 3- to 10-membered heterocycle of $R^3$ is independently optionally substituted with one or more substituents selected from halogen, —$OR^{20}$, —$SR^{20}$, —$N(R^{20})_2$, —$N(R^{20})C(O)R^{20}$, —$C(O)R^{20}$, —$C(O)$ $OR^{20}$, $-C(O)N(R^{20})_2$, $-OC(O)R^{20}$, $-S(O)_2R^{20}$, $-S(O)_2N(R^{20})_2$, $-N(R^{20})S(O)_2R^{20}$, $-NO_2$, $=O$, $=S$, $=N(R^{20})$, $-P(O)(OR^{20})_2$, $-P(O)(R^{20})_2$, $-OP(O)(OR^{20})_2$, $-CN$, $C_{1-6}$ alkyl, $C_{2-6}$ alkenyl, and $C_{2-6}$ alkynyl;

$R^6$ is independently selected at each occurrence from halogen, $-OR^{20}$, $-SR^{20}$, $-N(R^{20})_2$, $-N(R^{20})C(O)R^{20}$, $-C(O)R^{20}$, $-C(O)OR^{20}$, $-C(O)N(R^{20})_2$, $-OC(O)R^{20}$, $-S(O)_2R^{20}$, $-S(O)_2N(R^{20})_2$, $-N(R^{20})S(O)_2R^{20}$, $-NO_2$, $-P(O)(OR^{20})_2$, $-P(O)(R^{20})_2$, $-OP(O)(OR^{20})_2$, and $-CN$; $C_{1-6}$ alkyl, $C_{2-6}$ alkenyl, and $C_{2-6}$ alkynyl, each of which is independently optionally substituted at each occurrence with one or more substituents selected from halogen, $-OR^{20}$, $-SR^{20}$, $-N(R^{20})_2$, $-N(R^{20})C(O)R^{20}$, $-C(O)R^{20}$, $-C(O)OR^{20}$, $-C(O)N(R^{20})_2$, $-OC(O)R^{20}$, $-S(O)_2R^{20}$, $-S(O)_2N(R^{20})_2$, $-N(R^{20})S(O)_2R^{20}$, $-NO_2$, $=O$, $=S$, $=N(R^{20})$, $-P(O)(OR^{20})_2$, $-P(O)(R^{20})_2$, $-OP(O)(OR^{20})_2$, $-CN$, $C_{3-10}$ carbocycle, and 3- to 10-membered heterocycle, or two substituents on the same carbon atom of an $C_{1-6}$ alkyl, $C_{2-6}$ alkenyl, or $C_{2-6}$ alkynyl come together to form a $C_{3-10}$ carbocycle or 3- to 10-membered heterocycle; and $C_{3-10}$ carbocycle and 3- to 10-membered heterocycle; wherein any $C_{3-10}$ carbocycle and 3- to 10-membered heterocycle of $R^6$ is independently optionally substituted with one or more substituents selected from halogen, $-OR^{20}$, $-SR^{20}$, $-N(R^{20})_2$, $-N(R^{20})C(O)R^{20}$, $-C(O)R^{20}$, $-C(O)OR^{20}$, $-C(O)N(R^{20})_2$, $-OC(O)R^{20}$, $-S(O)_2R^{20}$, $S(O)_2N(R^{20})_2$, $-N(R^{20})S(O)_2R^{20}$, $-NO_2$, $=O$, $=S$, $=N(R^{20})$, $-P(O)(OR^{20})_2$, $-P(O)(R^{20})_2$, $-OP(O)(OR^{20})_2$, $-CN$, $C_{1-6}$ alkyl, $C_{2-6}$ alkenyl, and $C_{2-6}$ alkynyl;

$R^{20}$ at each occurrence is independently selected from hydrogen; $C_{1-6}$ alkyl, $C_{2-6}$ alkenyl, and $C_{2-6}$ alkynyl, each of which is independently optionally substituted at each occurrence with one or more substituents selected from halogen, $-OR^{30}$, $-SR^{30}$, $-N(R^{30})_2$, $-N(R^{30})C(O)R^{30}$, $-C(O)R^{30}$, $-C(O)OR^{30}$, $-C(O)N(R^{30})_2$, $-OC(O)R^{30}$, $-S(O)_2R^{30}$, $-S(O)_2N(R^{30})_2$, $-N(R^{30})S(O)_2R^{30}$, $-NO_2$, $-P(O)(OR^{30})_2$, $-P(O)(R^{30})_2$, $-OP(O)(OR^{30})_2$, and $-CN$; and 3- to 10-membered heterocycle and $C_{3-10}$ carbocycle;

$R^{30}$ at each occurrence is independently selected from hydrogen, $C_{1-6}$ alkyl, $C_{2-6}$ alkenyl, and $C_{2-6}$ alkynyl;

Y is N or $C(R^a)$;

L is absent or selected from alkylene and heteroalkylene;

s is selected from 0, 1, 2, 3, and 4;

$R^{7a}$ is -G-V-$R^{9a}$;

G is selected from a bond, alkylene, heteroalkylene, $C_{3-12}$ carbocycle, 3- to 12-membered heterocycle, and combinations thereof, wherein G is optionally substituted with one or more $R^{32}$ groups;

V is absent or selected from a $C_{3-12}$ carbocycle, and 3- to 12-membered heterocycle; wherein V is optionally substituted with one or more $R^{32}$ groups;

$R^{9a}$ is selected from hydrogen and $R^{32}$; and $R^{32}$ at each occurrence is selected from halogen, $-OR^{20}$, $-SR^{20}$, $-N(R^{20})_2$, $-N(R^{20})C(O)R^{20}$, $-C(O)R^{20}$, $-C(O)OR^{20}$, $-C(O)N(R^{20})_2$, $-OC(O)R^{20}$, $-S(O)_2R^{20}$, $-S(O)_2N(R^{20})_2$, $-N(R^{20})S(O)_2R^{20}$, $-NO_2$, $=O$, $=S$, $=N(R^{20})$, $-P(O)(OR^{20})_2$, $-P(O)(R^{20})_2$, $-OP(O)(OR^{20})_2$, and $-CN$; $C_{1-6}$ alkyl, $C_{2-6}$ alkenyl, and $C_{2-6}$ alkynyl, each of which is independently optionally substituted at each occurrence with one or more substituents selected from halogen, $-OR^{20}$, $-SR^{20}$, $-N(R^{20})_2$, $-N(R^{20})C(O)R^{20}$, $-C(O)R^{20}$, $-C(O)OR^{20}$, $-C(O)N(R^{20})_2$, $-OC(O)R^{20}$, $-S(O)_2R^{20}$, $-S(O)_2N(R^{20})_2$, $-N(R^{20})S(O)_2R^{20}$, $-NO_2$, $=O$, $=S$, $=N(R^{20})$, $-P(O)(OR^{20})_2$, $-P(O)(R^{20})_2$, $-OP(O)(OR^{20})_2$, $-CN$, $C_{3-10}$ carbocycle, and 3- to 10-membered heterocycle; $C_{3-10}$ carbocycle and 3- to 10-membered heterocycle; or two $R^{32}$ on the same carbon atom can come together to form a $C_{3-10}$ carbocycle or 3- to 10-membered heterocycle, wherein each $C_{3-10}$ carbocycle and 3- to 10-membered heterocycle of $R^{32}$ is independently optionally substituted with one or more substituents selected from halogen, $-OR^{20}$, $-SR^{20}$, $-N(R^{20})_2$, $-N(R^{20})C(O)R^{20}$, $-C(O)R^{20}$, $-C(O)OR^{20}$, $-C(O)N(R^{20})_2$, $-OC(O)R^{20}$, $-S(O)_2R^{20}$, $-S(O)_2N(R^{20})_2$, $-N(R^{20})S(O)_2R^{20}$, $-NO_2$, $=O$, $=S$, $=N(R^{20})$, $-P(O)(OR^{20})_2$, $-P(O)(R^{20})_2$, $-OP(O)(OR^{20})_2$, $-CN$, $C_{1-6}$ alkyl, $C_{2-6}$ alkenyl, and $C_{2-6}$ alkynyl.

In certain embodiments, for a compound or salt of any one of Formulas (3), (3A), (3B), (3C), (3D), (3E), (3F), (3G), (3H), (3I), and (3J), $R^{5a}$ is hydrogen. In certain embodiments, for a compound or of any one of Formulas (3), (3A), (3B), (3C), (3D), (3E), (3F), (3G), (3H), (3I), and (3J), $R^5$ and $R^{5a}$ are not hydrogen.

In certain embodiments, for a compound or salt of any one of Formulas (3), (3A), (3B), (3C), (3D), (3E), (3F), (3G), (3H), (3I), and (3J), $R^5$ and $R^{5a}$ together with the carbon atom to which they are attached, come together to form a $C_{3-10}$ carbocycle or a 3- to 10-membered heterocycle; wherein the $C_{3-10}$ carbocycle or 3- to 10-membered heterocycle is optionally substituted with one or more substituents selected from halogen, $-OR^{20}$, $-SR^{20}$, $-N(R^{20})_2$, $-N(R^{20})C(O)R^{20}$, $-C(O)R^{20}$, $-C(O)OR^{20}$, $-C(O)N(R^{20})_2$, $-OC(O)R^{20}$, $-S(O)_2R^{20}$, $-S(O)_2N(R^{20})_2$, $-N(R^{20})S(O)_2R^{20}$, $-NO_2$, $=O$, $=S$, $=N(R^{20})$, $-P(O)(OR^{20})_2$, $-P(O)(R^{20})_2$, $-OP(O)(OR^{20})_2$, $-CN$, $C_{1-6}$ alkyl, $C_{2-6}$ alkenyl, and $C_{2-6}$ alkynyl.

In certain embodiments, for a compound or salt of any one of Formulas (3), (3A), (3B), (3C), (3D), (3E), (3F), (3G), (3H), (3I), (3J), and (4), $R^5$ is selected from hydrogen, halogen, $-OR^{20}$, $-SR^{20}$, $-N(R^{20})_2$, $-NO_2$, $-P(O)(OR^{20})_2$, $-P(O)(R^{20})_2$, $-OP(O)(OR^{20})_2$, and $-CN$; and $C_{1-6}$ alkyl, $C_{2-6}$ alkenyl, and $C_{2-6}$ alkynyl, each of which is optionally substituted with one or more substituents selected from halogen, $-OR^{20}$, $-SR^{20}$, $-N(R^{20})_2$, $-N(R^{20})C(O)R^{20}$, $-C(O)R^{20}$, $-C(O)OR^{20}$, $-C(O)N(R^{20})_2$, $-OC(O)R^{20}$, $-S(O)_2R^{20}$, $-S(O)_2N(R^{20})_2$, $-N(R^{20})S(O)_2R^{20}$, $-NO_2$, $=O$, $=S$, $=N(R^{20})$, $-P(O)(OR^{20})_2$, $-P(O)(R^{20})_2$, $-OP(O)(OR^{20})_2$, $-CN$, $C_{3-10}$ carbocycle, and 3- to 10-membered heterocycle, or two substituents on the same carbon atom of an $C_{1-6}$ alkyl, $C_{2-6}$ alkenyl, or $C_{2-6}$ alkynyl come together to form a $C_{3-10}$ carbocycle or 3- to 10-membered heterocycle. In certain embodiments, for a compound or salt of any one of Formulas (3), (3A), (3B), (3C), (3D), (3E), (3F), (3G), (3H), (3I), (3J), and (4), $R^5$ is hydrogen.

In certain embodiments, for a compound or salt of any one of Formulas (3), (3A), (3B), (3C), (3D), (3E), (3F), (3G), (3H), (3I), and (3J), $R^{5a}$ is selected from hydrogen, halogen, $-OR^{20}$, $-SR^{20}$, $-N(R^{20})_2$, $-NO_2$, $-P(O)(OR^{20})_2$, $-P(O)(R^{20})_2$, $-OP(O)(OR^{20})_2$, and $-CN$; and $C_{1-6}$ alkyl, $C_{2-6}$ alkenyl, and $C_{2-6}$ alkynyl, each of which is optionally substituted with one or more substituents selected from halogen, $-OR^{20}$, $-SR^{20}$, $-N(R^{20})_2$, $-N(R^{20})C(O)R^{20}$, $-C(O)R^{20}$, $-C(O)OR^{20}$, $-C(O)N(R^{20})_2$, $-OC(O)R^{20}$, $-S(O)_2R^{20}$, $-S(O)_2N(R^{20})_2$, $-N(R^{20})S(O)_2R^{20}$, $-NO_2$, $=O$, $=S$, $=N(R^{20})$, $-P(O)(OR^{20})_2$, $-P(O)(R^{20})_2$, $-OP(O)(OR^{20})_2$, $-CN$, $C_{3-10}$ carbocycle, and 3- to 10-membered heterocycle, or two substituents on the same carbon atom of an $C_{1-6}$ alkyl, $C_{2-6}$ alkenyl, or $C_{2-6}$ alkynyl come together to form a $C_{3-10}$ carbocycle or 3- to 10-membered heterocycle. In certain embodiments, for a compound or salt of any one of Formulas (3), (3A), (3B), (3C), (3D), (3E), (3F), (3G), (3H), (3I), and (3J), $R^{5a}$ is hydrogen. In certain embodiments, for a compound or salt of any one of Formulas (3), (3A), (3B), (3C), (3D), (3E), (3F), (3G), (3H), (3I), and (3J), $R^5$ and $R^{5a}$ are each hydrogen.

In certain embodiments, for a compound or salt of any one of Formulas (3), (3A), (3B), (3C), (3D), (3E), (3F), (3G), (3H), (3I), (3J), and (4), $R^1$ and $R^2$ are independently selected from hydrogen, halogen, $—OR^{20}$, $—SR^{20}$, $—N(R^{20})_2$, $—NO_2$, and $—CN$; and $C_{1-6}$ alkyl, $C_{2-6}$ alkenyl, and $C_{2-6}$ alkynyl, each of which is independently optionally substituted at each occurrence with one or more substituents selected from halogen, $—OR^{20}$, $—SR^{20}$, $—N(R^{20})_2$, $—N(R^{20})C(O)R^{20}$, $—C(O)R^{20}$, $—C(O)OR^{20}$, $—C(O)N(R^{20})_2$, $—OC(O)R^{20}$, $—S(O)_2R^{20}$, $—S(O)_2N(R^{20})_2$, $—N(R^{20})S(O)_2R^{20}$, $—NO_2$, $=O$, $=S$, $=N(R^{20})$, $—P(O)(OR^{20})_2$, $—P(O)(R^{20})_2$, $—OP(O)(OR^{20})_2$, $—CN$, $C_{3-10}$ carbocycle, and 3- to 10-membered heterocycle.

In certain embodiments, for a compound or salt of any one of Formulas (3), (3A), (3B), (3C), (3D), (3E), (3F), (3G), (3H), (3I), (3J), and (4), $R^1$ is selected from $C_{1-6}$ alkyl, $C_{2-6}$ alkenyl, and $C_{2-6}$ alkynyl, optionally substituted with one or more substituents selected from halogen, $—OR^{20}$, $—SR^{20}$, $—N(R^{20})_2$, $—N(R^{20})C(O)R^{20}$, $—C(O)R^{20}$, $—C(O)OR^{20}$, $—C(O)N(R^{20})_2$, $—OC(O)R^{20}$, $—S(O)_2R^{20}$, $—S(O)_2N(R^{20})_2$, $—N(R^{20})S(O)_2R^{20}$, $—NO_2$, $=O$, $=S$, $=N(R^{20})$, and $—CN$.

In certain embodiments, for a compound or salt of any one of Formulas (3), (3A), (3B), (3C), (3D), (3E), (3F), (3G), (3H), (3I), (3J), and (4), $R^1$ is selected from $C_{1-6}$ alkyl, $C_{2-6}$ alkenyl, and $C_{2-6}$ alkynyl, optionally substituted with one or more halogen atoms, for example, $R^1$ is selected from $—CH_2CF_3$ and $—CH_2CHF_2$. In certain embodiments, for a compound or salt of any one of Formulas (3), (3A), (3B), (3C), (3D), (3E), (3F), (3G), (3H), (3I), and (3J), $R^5$ and $R^{5a}$ are each hydrogen and $R^1$ is selected from $C_{1-6}$ alkyl, $C_{2-6}$ alkenyl, and $C_{2-6}$ alkynyl, optionally substituted with one or more halogen atoms, for example, $R^1$ is selected from $—CH_2CF_3$ and $—CH_2CHF_2$ In certain embodiments, for a compound or salt of any one of Formulas (3), (3A), (3B), (3C), (3D), (3E), (3F), (3G), (3H), (3I), (3J), and (4), $R^2$ is selected from hydrogen, halogen, $—OR^{20}$, $—SR^{20}$, $—N(R^{20})_2$, $—NO_2$, and $—CN$; and $C_{1-6}$ alkyl optionally substituted with one or more substituents selected from halogen, $—OR^{20}$, $—SR^{20}$, $—N(R^{20})_2$, $—N(R^{20})C(O)R^{20}$, $—C(O)R^{20}$, $—C(O)OR^{20}$, $—C(O)N(R^{20})_2$, $—OC(O)R^{20}$, $—S(O)_2R^{20}$, $—S(O)_2N(R^{20})_2$, $—N(R^{20})S(O)_2R^{20}$, $—NO_2$, $=O$, $=S$, $=N(R^{20})$, and $—CN$. In particular embodiments, $R^2$ is hydrogen. In certain embodiments, for a compound or salt of anyone of Formulas (3), (3A), (3B), (3C), (3D), (3E), (3F), (3G), (3H), (3I), and (3J), $R^5$ and $R^{5a}$ are each hydrogen; $R^1$ is selected from $C_{1-6}$ alkyl, $C_{2-6}$ alkenyl, and $C_{2-6}$ alkynyl, optionally substituted with one or more halogen atoms, for example, $R^1$ is selected from $—CH_2CF_3$ and $—CH_2CHF_2$; and $R^2$ is selected from hydrogen, halogen, $—OR^{20}$, $—SR^{20}$, $—N(R^{20})_2$, $—NO_2$, and $—CN$, for example, $R^2$ is hydrogen.

In certain embodiments, for a compound or salt of any one of Formulas (3), (3A), (3B), (3C), (3D), (3E), (3F), (3G), (3H), (3I), (3J), and (4), $R^3$ is selected from hydrogen, $—C(O)R^{20}$, $—C(O)OR^{20}$, and $—C(O)N(R^{20})_2$; and $C_{1-6}$ alkyl, $C_{2-6}$ alkenyl, and $C_{2-6}$ alkynyl, each of which is optionally substituted with one or more substituents selected from halogen, $—OR^{20}$, $—SR^{20}$, $—N(R^{20})_2$, $—N(R^{20})C(O)R^{20}$, $—C(O)R^{20}$, $—C(O)OR^{20}$, $—C(O)N(R^{20})_2$, $—OC(O)R^{20}$, $—S(O)_2R^{20}$, $—S(O)_2N(R^{20})_2$, $—N(R^{20})S(O)_2R^{20}$, $—NO_2$, $=O$, $=S$, $=N(R^{20})$, $—P(O)(OR^{20})_2$, $—P(O)(R^{20})_2$, $—OP(O)(OR^{20})_2$, $—CN$. In particular embodiments, $R^3$ is hydrogen. In certain embodiments, for a compound or salt of any one of Formulas (3), (3A), (3B), (3C), (3D), (3E), (3F), (3G), (3H), (3I), and (3J), $R^5$ and $R^{5a}$ are each hydrogen; $R^1$ is selected from $C_{1-6}$ alkyl, $C_{2-6}$ alkenyl, and $C_{2-6}$ alkynyl, optionally substituted with one or more halogen atoms, for example, $R^1$ is selected from $—CH_2CF_3$ and $—CH_2CHF_2$; $R^2$ is selected from hydrogen, halogen, $—OR^{20}$, $—SR^{20}$, $—N(R^{20})_2$, $—NO_2$, and $—CN$, for example, $R^2$ is hydrogen; and $R^3$ is selected from hydrogen, $C_{1-6}$ alkyl, $—C(O)R^{20}$, $—C(O)OR^{20}$, and $—C(O)N(R^{20})_2$, for example, $R^3$ is hydrogen.

In certain embodiments, for a compound or salt of any one of Formulas (3), (3A), (3B), (3C), (3D), (3E), (3F), (3G), (3H), (3I), (3J), and (4), $R^4$ is selected from hydrogen, halogen, $—OR^{20}$, $—SR^{20}$, $—N(R^{20})_2$, $—NO_2$, $—P(O)(OR^{20})_2$, $—P(O)(R^{20})_2$, $—OP(O)(OR^{20})_2$, and $—CN$; and $C_{1-6}$ alkyl, $C_{2-6}$ alkenyl, and $C_{2-6}$ alkynyl, optionally substituted with one or more substituents selected from halogen, $—OR^{20}$, $—SR^{20}$, $—N(R^{20})_2$, $—N(R^{20})C(O)R^{20}$, $—C(O)R^{20}$, $—C(O)OR^{20}$, $—C(O)N(R^{20})_2$, $—OC(O)R^{20}$, $—S(O)_2R^{20}$, $—S(O)_2N(R^{20})_2$, $—N(R^{20})S(O)_2R^{20}$, $—NO_2$, $=O$, $=S$, $=N(R^{20})$, $—P(O)(OR^{20})_2$, $—P(O)(R^{20})_2$, $—OP(O)(OR^{20})_2$, $—CN$, $C_{3-10}$ carbocycle, and 3- to 10-membered heterocycle. In particular embodiments, $R^4$ is selected from hydrogen and halogen. In certain embodiments, for a compound or salt of any one of Formulas (3), (3A), (3B), (3C), (3D), (3E), (3F), (3G), (3H), (3I), and (3J), $R^5$ and $R^{5a}$ are each hydrogen; $R^1$ is selected from $C_{1-6}$ alkyl, $C_{2-6}$ alkenyl, and $C_{2-6}$ alkynyl, optionally substituted with one or more halogen atoms, for example, $R^1$ is selected from $—CH_2CF_3$ and $—CH_2CHF_2$; $R^2$ is selected from hydrogen, halogen, $—OR^{20}$, $—SR^{20}$, $—N(R^{20})_2$, $—NO_2$, and $—CN$, for example, $R^2$ is hydrogen; $R^3$ is selected from hydrogen, $C_{1-6}$ alkyl, $—C(O)R^{20}$, $—C(O)OR^{20}$, and $—C(O)N(R^{20})_2$, for example, $R^3$ is hydrogen; and $R^4$ is selected from hydrogen, halogen, $—OR^{20}$, $—SR^{20}$, $—N(R^{20})_2$, $—CN$ and $C_{1-6}$ alkyl, for example, $R^4$ is hydrogen.

In certain embodiments, for a compound or salt of any one of Formulas (3), (3A), (3B), (3C), (3D), (3E), (3F), (3G), (3H), (3I), (3J), and (4), $R^6$, at each occurrence, is independently selected from hydrogen, halogen, $—OR^{20}$, $—SR^{20}$, $—N(R^{20})_2$, $—NO_2$, $—P(O)(OR^{20})_2$, $—P(O)(R^{20})_2$, $—OP(O)(OR^{20})_2$, and $—CN$; and $C_{1-6}$ alkyl, $C_{2-6}$ alkenyl, and $C_{2-6}$ alkynyl, optionally substituted with one or more substituents selected from halogen, $—OR^{20}$, $—SR^{20}$, $—N(R^{20})_2$, $—N(R^{20})C(O)R^{20}$, $—C(O)R^{20}$, $—C(O)OR^{20}$, $—C(O)N(R^{20})_2$, $—OC(O)R^{20}$, $—S(O)_2R^{20}$, $S(O)_2N(R^{20})_2$, $—N(R^{20})S(O)_2R^{20}$, $—NO_2$, $=O$, $=S$, $=N(R^{20})$, $—P(O)(OR^{20})_2$, $—P(O)(R^{20})_2$, $—OP(O)(OR^{20})_2$, $—CN$, $C_{3-10}$ carbocycle, and 3- to 10-membered heterocycle. In particular embodiments, $R^6$, at each occurrence, is independently selected from halogen, $—OR^{20}$, and $C_{1-6}$ alkyl optionally substituted with one or more substituents selected from halogen, $—OR^{20}$, $—SR^{20}$, $—N(R^{20})_2$, $—NO_2$, $=O$, $=S$, $=N(R^{20})$, and $—CN$. In certain embodiments, for a compound or salt of any one of Formulas (3), (3A), (3B), (3C), (3D), (3E), (3F), (3G), (3H), (3I), (3J), and (4), s is 0, 1, or 2, for example, s is 0 or 1. In certain embodiments, for a compound or salt of any one of Formulas (3), (3A), (3B), (3C), (3D), (3E), (3F), (3G), (3H), (3I), and (3J), $R^5$ and $R^{5a}$ are each hydrogen; $R^1$ is selected from $C_{1-6}$ alkyl, $C_{2-6}$ alkenyl, and $C_{2-6}$ alkynyl, optionally substituted with one or more halogen atoms, for example, $R^1$ is selected from $—CH_2CF_3$ and $—CH_2CHF_2$; $R^2$ is selected from hydrogen, halogen, $—OR^{20}$, $—SR^{20}$, $—N(R^{20})_2$, $—NO_2$, and $—CN$, for example, $R^2$ is hydrogen; $R^3$ is selected from hydrogen, $C_{1-6}$ alkyl, $—C(O)R^{20}$, $—C(O)OR^{20}$, and $—C(O)N(R^{20})_2$, for example, $R^3$ is hydrogen; $R^4$ is selected from hydrogen, halogen, $—OR^{20}$, $—SR^{20}$, $—N(R^{20})_2$, $—CN$ and $C_{1-6}$ alkyl, for example, $R^4$ is hydrogen; $R^6$, at each occurrence, is independently selected from halogen, —$OR^{20}$, and $C_{1-6}$ alkyl, for example, $R^6$, at each occurrence, is selected from halogen, —OH and —$OCH_3$; and s is selected from 0 and 1.

In certain embodiments, for a compound or salt of any one of Formulas (3), (3A), (3B), (3C), (3D), (3E), (3F), (3G), (3H), (3I), (3J), and (4), $R^8$ is selected from hydrogen, halogen, —$OR^{20}$, —$SR^{20}$, —$N(R^{20})_2$, —$NO_2$, and —CN; and $C_{1-6}$ alkyl, $C_{2-6}$ alkenyl, and $C_{2-6}$ alkynyl, optionally substituted with one or more substituents selected from halogen, —$OR^{20}$, —$SR^{20}$, —$N(R^{20})_2$, —$N(R^{20})C(O)R^{20}$, —$C(O)R^{20}$, —$C(O)OR^{20}$, —$C(O)N(R^{20})_2$, —$OC(O)R^{20}$, —$S(O)_2R^{20}$, —$S(O)_2N(R^{20})_2$, —$N(R^{20})S(O)_2R^{20}$, —$NO_2$, =O, =S, =$N(R^{20})$, and —CN. In particular embodiments, $R^8$ is —CN. In certain embodiments, for a compound or salt of any one of Formulas (3), (3A), (3B), (3C), (3D), (3E), (3F), (3G), (3H), (3I), and (3J), $R^5$ and $R^{5a}$ are each hydrogen; $R^1$ is selected from $C_{1-6}$ alkyl, $C_{2-6}$ alkenyl, and $C_{2-6}$ alkynyl, optionally substituted with one or more halogen atoms, for example, $R^1$ is selected from —$CH_2CF_3$ and —$CH_2CHF_2$; $R^2$ is selected from hydrogen, halogen, —$OR^{20}$, —$SR^{20}$, —$N(R^{20})_2$, —$NO_2$, and —CN, for example, $R^2$ is hydrogen; $R^3$ is selected from hydrogen, $C_{1-6}$ alkyl, —$C(O)R^{20}$, —$C(O)OR^{20}$, and —$C(O)N(R^{20})_2$, for example, $R^3$ is hydrogen; $R^4$ is selected from hydrogen, halogen, —$OR^{20}$, —$SR^{20}$, —$N(R^{20})_2$, —CN and $C_{1-6}$ alkyl, for example, $R^4$ is hydrogen; $R^6$, at each occurrence, is independently selected from halogen, —$OR^{20}$, and $C_{1-6}$ alkyl, for example, $R^6$, at each occurrence, is selected from halogen, —OH and —$OCH_3$; s is selected from 0 and 1; and $R^8$ is selected from hydrogen, halogen, —$OR^{20}$, —$SR^{20}$, —$N(R^{20})_2$, —$NO_2$, and —CN, for example, $R^8$ is —CN.

In certain embodiments, for a compound or salt of any one of Formulas (3), (3A), (3B), (3C), (3D), (3E), (3F), (3G), (3H), (3I), (3J), and (4), Y is N.

In certain embodiments, for a compound or salt of any one of Formulas (3), (3A), (3B), (3C), (3D), (3E), (3F), (3G), (3H), (3I), (3J), and (4), Y is C($R^a$) and $R^a$ is selected from hydrogen, halogen, —$OR^{20}$, —$SR^{20}$, —$N(R^{20})_2$, —$NO_2$, and —CN; and $C_{1-6}$ alkyl, $C_{2-6}$ alkenyl, and $C_{2-6}$ alkynyl, each of which is optionally substituted with one or more substituents selected from halogen, —$OR^{20}$, —$SR^{20}$, —$N(R^{20})_2$, —$N(R^{20})C(O)R^{20}$, —$C(O)R^{20}$, —$C(O)OR^{20}$, —$C(O)N(R^{20})_2$, —$OC(O)R^{20}$, —$S(O)_2R^{20}$, —$S(O)_2N(R^{20})_2$, —$N(R^{20})S(O)_2R^{20}$, —$NO_2$, =O, =S, =$N(R^{20})$, —$P(O)(OR^{20})_2$, —$P(O)(R^{20})_2$, —$OP(O)(OR^{20})_2$, —CN, $C_{3-10}$ carbocycle, and 3- to 10-membered heterocycle. In certain embodiments, Y is C($R^a$) and $R^a$ is selected from hydrogen, halogen, and $C_{1-6}$ alkyl optionally substituted with one or more substituents selected from halogen, —$OR^{20}$, —$SR^{20}$, —$N(R^{20})_2$, —$N(R^{20})C(O)R^{20}$, —$C(O)R^{20}$, —$C(O)OR^{20}$, —$C(O)N(R^{20})_2$, —$OC(O)R^{20}$, —$S(O)_2R^{20}$, —$S(O)_2N(R^{20})_2$, —$N(R^{20})S(O)_2R^{20}$, —$NO_2$, =O, =S, =$N(R^{20})$, —$P(O)(OR^{20})_2$, —$P(O)(R^{20})_2$, —$OP(O)(OR^{20})_2$, —CN, $C_{3-10}$ carbocycle, and 3- to 10-membered heterocycle. In particular embodiments, Y is C($R^a$) and $R^a$ is hydrogen. In certain embodiments, for a compound or salt of any one of Formulas (3), (3A), (3B), (3C), (3D), (3E), (3F), (3G), (3H), (3I), and (3J), $R^5$ and $R^{5a}$ are each hydrogen; $R^1$ is selected from $C_{1-6}$ alkyl, $C_{2-6}$ alkenyl, and $C_{2-6}$ alkynyl, optionally substituted with one or more halogen atoms, for example, $R^1$ is selected from —$CH_2CF_3$ and —$CH_2CHF_2$; $R^2$ is selected from hydrogen, halogen, —$OR^{20}$, —$SR^{20}$, —$N(R^{20})_2$, —$NO_2$, and —CN, for example, $R^2$ is hydrogen; $R^3$ is selected from hydrogen, $C_{1-6}$ alkyl, —$C(O)R^{20}$, —$C(O)OR^{20}$, and —$C(O)N(R^{20})_2$, for example, $R^3$ is hydrogen; $R^4$ is selected from hydrogen, halogen, —$OR^{20}$, —$SR^{20}$, —$N(R^{20})_2$, —CN and $C_{1-6}$ alkyl, for example, $R^4$ is hydrogen; $R^6$, at each occurrence, is independently selected from halogen, —$OR^{20}$, and $C_{1-6}$ alkyl, for example, $R^6$, at each occurrence, is selected from halogen, —OH and —$OCH_3$; s is selected from 0 and 1; $R^8$ is selected from hydrogen, halogen, —$OR^{20}$, —$SR^{20}$, —$N(R^{20})_2$, —$NO_2$, and —CN, for example, $R^8$ is —CN; Y is C($R^a$); and $R^a$ is selected from hydrogen, halogen, —$OR^{20}$, —$SR^{20}$, —$N(R^{20})_2$, —$NO_2$, —CN and $C_{1-6}$ alkyl, for example, $R^a$ is hydrogen.

In certain embodiments, for a compound or salt of any one of Formulas (3), (3A), (3B), (3C), (3D), (3E), (3F), (3G), (3H), (3I), (3J), and (4), $R^{20}$ at each occurrence is independently selected from hydrogen, $C_{1-6}$ alkyl, $C_{2-6}$ alkenyl, and $C_{2-6}$ alkynyl, 3- to 10-membered heterocycle and $C_{3-10}$ carbocycle.

In certain embodiments, for a compound or salt of any one of Formulas (3), (3A), (3B), (3C), (3D), (3E), (3F), (3G), (3H), (3I), (3J), and (4), $R^1$ is selected from $C_{1-6}$ alkyl, $C_{2-6}$ alkenyl, and $C_{2-6}$ alkynyl, optionally substituted with one or more halogen atoms, for example, $R^1$ is selected from —$CH_2CF_3$ and —$CH_2CHF_2$; $R^2$ is selected from hydrogen, halogen, —$OR^{20}$, —$SR^{20}$, —$N(R^{20})_2$, —$NO_2$, and —CN, for example, $R^2$ is hydrogen; and $R^8$ is selected from hydrogen, halogen, —$OR^{20}$, —$SR^{20}$, —$N(R^{20})_2$, —$NO_2$, and —CN, for example, $R^8$ is —CN.

In certain embodiments, for a compound or salt of any one of Formulas (3), (3A), (3B), (3C), (3D), (3E), (3F), (3G), (3H), (3I), (3J), and (4), $R^1$ is selected from $C_{1-6}$ alkyl, $C_{2-6}$ alkenyl, and $C_{2-6}$ alkynyl, optionally substituted with one or more halogen atoms, for example, $R^1$ is selected from —$CH_2CF_3$ and —$CH_2CHF_2$; $R^3$ is selected from hydrogen, $C_{1-6}$ alkyl, —$C(O)R^{20}$, —$C(O)OR^{20}$, and —$C(O)N(R^{20})_2$, for example, $R^3$ is hydrogen; and $R^8$ is selected from hydrogen, halogen, —$OR^{20}$, —$SR^{20}$, —$N(R^{20})_2$, —$NO_2$, and —CN, for example, $R^8$ is —CN.

In certain embodiments, for a compound or salt of any one of Formulas (3), (3A), (3B), (3C), (3D), (3E), (3F), (3G), (3H), (3I), and (3J), $R^5$ and $R^{5a}$ are independently selected from hydrogen, halogen, —$OR^{20}$, —$SR^{20}$, —$N(R^{20})_2$, —$NO_2$, —$P(O)(R^{20})_2$, —CN and $C_{1-6}$ alkyl, for example, $R^5$ and $R^{5a}$ are each hydrogen; $R^2$ is selected from hydrogen, halogen, —$OR^{20}$, —$SR^{20}$, —$N(R^{20})_2$, —$NO_2$, and —CN, for example, $R^2$ is hydrogen; and $R^3$ is selected from hydrogen, $C_{1-6}$ alkyl, —$C(O)R^{20}$, —$C(O)OR^{20}$, and —$C(O)N(R^{20})_2$, for example, $R^3$ is hydrogen.

In certain embodiments, for a compound or salt of any one of Formulas (3), (3A), (3B), (3C), (3D), (3E), (3F), (3G), (3H), (3I), and (3J), $R^5$ and $R^{5a}$ are independently selected from hydrogen, halogen, —$OR^{20}$, —$SR^{20}$, —$N(R^{20})_2$, —$NO_2$, —$P(O)(R^{20})_2$, —CN and $C_{1-6}$ alkyl, for example, $R^5$ and $R^{5a}$ are each hydrogen; $R^1$ is selected from $C_{1-6}$ alkyl, $C_{2-6}$ alkenyl, and $C_{2-6}$ alkynyl, optionally substituted with one or more halogen atoms, for example, $R^1$ is selected from —$CH_2CF_3$ and —$CH_2CHF_2$; and $R^3$ is selected from hydrogen, $C_{1-6}$ alkyl, —$C(O)R^{20}$, —$C(O)OR^{20}$, and —$C(O)N(R^{20})_2$, for example, $R^3$ is hydrogen.

from hydrogen, halogen, —OR$^{20}$, —SR$^{20}$, —N(R$^{20}$)$_2$, —NO$_2$, —CN and C$_{1-6}$ alkyl, for example, R$^a$ is hydrogen.

In certain embodiments, for a compound or salt of any one of Formulas (3), (3A), (3B), (3C), (3D), (3E), (3F), (3G), (3H), (3I), and (3J), R$^7$ is selected from:

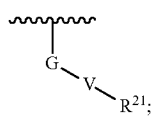

wherein:

G is selected from a bond, alkylene, heteroalkylene, C$_{3-12}$ carbocycle, 3- to 12-membered heterocycle, and combinations thereof, wherein G is optionally substituted with one or more R$^{32}$ groups;

V is absent or selected from a C$_{3-12}$ carbocycle, and 3- to 12-membered heterocycle; wherein V is optionally substituted with one or more R$^{32}$ groups;

R$^{32}$ at each occurrence is selected from halogen, —OR$^{20}$, —SR$^{20}$, —N(R$^{20}$)$_2$, —N(R$^{20}$)C(O)R$^{20}$, —C(O)R$^{20}$, —C(O)OR$^{20}$, —C(O)N(R$^{20}$)$_2$, —OC(O)R$^{20}$, —S(O)$_2$R$^{20}$, —S(O)$_2$N(R$^{20}$)$_2$, —N(R$^{20}$)S(O)$_2$R$^{20}$, —NO$_2$, =O, =S, =N(R$^{20}$), —P(O)(OR$^{20}$)$_2$, —P(O)(R$^{20}$)$_2$, —OP(O)(OR$^{20}$)$_2$, and —CN; C$_{1-6}$ alkyl, C$_{2-6}$ alkenyl, and C$_{2-6}$ alkynyl, each of which is independently optionally substituted at each occurrence with one or more substituents selected from halogen, —OR$^{20}$, —SR$^{20}$, —N(R$^{20}$)$_2$, —N(R$^{20}$)C(O)R$^{20}$, —C(O)R$^{20}$, —C(O)OR$^{20}$, —C(O)N(R$^{20}$)$_2$, —OC(O)R$^{20}$, —S(O)$_2$R$^{20}$, —S(O)$_2$N(R$^{20}$)$_2$, —N(R$^{20}$)S(O)$_2$R$^{20}$, —NO$_2$, =O, =S, =N(R$^{20}$), —P(O)(OR$^{20}$)$_2$, —P(O)(R$^{20}$)$_2$, —OP(O)(OR$^{20}$)$_2$, —CN, C$_{3-10}$ carbocycle, and 3- to 10-membered heterocycle; C$_{3-10}$ carbocycle and 3- to 10-membered heterocycle; or two R$^{32}$ on the same carbon atom can come together to form a C$_{3-10}$ carbocycle or 3- to 10-membered heterocycle, wherein each C$_{3-10}$ carbocycle and 3- to 10-membered heterocycle of R$^{32}$ is independently optionally substituted with one or more substituents selected from halogen, —OR$^{20}$, —SR$^{20}$, —N(R$^{20}$)$_2$, —N(R$^{20}$)C(O)R$^{20}$, —C(O)R$^{20}$, —C(O)OR$^{20}$, —C(O)N(R$^{20}$)$_2$, —OC(O)R$^{20}$, —S(O)$_2$R$^{20}$, —S(O)$_2$N(R$^{20}$)$_2$, —N(R$^{20}$)S(O)$_2$R$^{20}$, —NO$_2$, =O, =S, =N(R$^{20}$), —P(O)(OR$^{20}$)$_2$, —P(O)(R$^{20}$)$_2$, —OP(O)(OR$^{20}$)$_2$, —CN, C$_{1-6}$ alkyl, C$_{2-6}$ alkenyl, and C$_{2-6}$ alkynyl;

R$^{20}$ at each occurrence is independently selected from hydrogen; C$_{1-6}$ alkyl, C$_{2-6}$ alkenyl, and C$_{2-6}$ alkynyl, each of which is independently optionally substituted at each occurrence with one or more substituents selected from halogen, —OR$^{30}$, —SR$^{30}$, —N(R$^{30}$)$_2$, —N(R$^{30}$)C(O)R$^{30}$, —C(O)R$^{30}$, —C(O)OR$^{30}$, —C(O)N(R$^{30}$)$_2$, —OC(O)R$^{30}$, —S(O)$_2$R$^{30}$, —S(O)$_2$N(R$^{30}$)$_2$, —N(R$^{30}$)S(O)$_2$R$^{30}$, —NO$_2$, —P(O)(OR$^{30}$)$_2$, —P(O)(R$^{30}$)$_2$, —OP(O)(OR$^{30}$)$_2$, and —CN; and 3- to 10-membered heterocycle and C$_{3-10}$ carbocycle;

R$^{30}$ at each occurrence is independently selected from hydrogen, C$_{1-6}$ alkyl, C$_{2-6}$ alkenyl, and C$_{2-6}$ alkynyl; and R$^{21}$ is a moiety comprising an alpha, beta-unsaturated carbonyl; an alpha, beta-unsaturated sulfonyl; an epoxide; an aldehyde; sulfonyl fluoride; a halomethylcarbonyl, a dihalomethylcarbonyl, or a trihalomethylcarbonyl.

In certain embodiments, for a compound or salt of any one of Formulas (3), (3A), (3B), (3C), (3D), (3E), (3F), (3G), (3H), (3I), and (3J), R$^{21}$ is selected from:

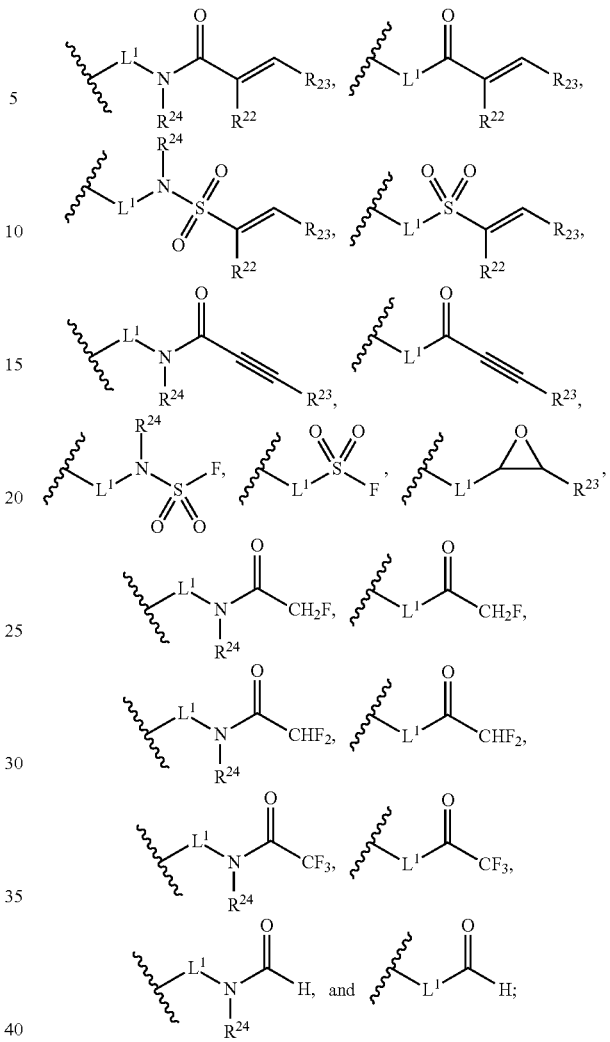

wherein:

L$^1$ is selected from a bond; and C$_{1-6}$ alkylene, C$_{1-6}$ heteroalkylene, C$_{2-6}$ alkenylene, and C$_{2-6}$ alkynylene, each of which may be optionally substituted with one or more R$^{32}$ groups;

R$^{22}$ and R$^{23}$ are selected from hydrogen, halogen, —OR$^{20}$, —SR$^{20}$, —N(R$^{20}$)$_2$, —N(R$^{20}$)C(O)R$^{20}$, —C(O)R$^{20}$, —C(O)OR$^{20}$, —C(O)N(R$^{20}$)$_2$, —OC(O)R$^{20}$, —S(O)$_2$R$^{20}$, —S(O)$_2$N(R$^{20}$)$_2$, —N(R$^{20}$)S(O)$_2$R$^{20}$, —NO$_2$, =O, =S, =N(R$^{20}$), —P(O)(OR$^{20}$)$_2$, —P(O)(R$^{20}$)$_2$, —OP(O)(OR$^{20}$)$_2$, and —CN; C$_{1-6}$ alkyl, C$_{2-6}$ alkenyl, and C$_{2-6}$ alkynyl, each of which is independently optionally substituted at each occurrence with one or more substituents selected from halogen, —OR$^{20}$, —SR$^{20}$, —N(R$^{20}$)$_2$, —N(R$^{20}$)C(O)R$^{20}$, —C(O)R$^{20}$, —C(O)OR$^{20}$, —C(O)N(R$^{20}$)$_2$, —OC(O)R$^{20}$, —S(O)$_2$R$^{20}$, —S(O)$_2$N(R$^{20}$)$_2$, —N(R$^{20}$)S(O)$_2$R$^{20}$, —NO$_2$, =O, =S, =N(R$^{20}$), —P(O)(OR$^{20}$)$_2$, —P(O)(R$^{20}$)$_2$, —OP(O)(OR$^{20}$)$_2$, —CN, C$_{3-10}$ carbocycle, and 3- to 10-membered heterocycle; and C$_{3-10}$ carbocycle and 3- to 10-membered heterocycle, wherein each C$_{3-10}$ carbocycle and 3- to 10-membered heterocycle of R$^{22}$ and R$^{23}$ is independently optionally substituted with one or more substituents selected from halogen, —OR$^{20}$, —SR$^{20}$, —N(R$^{20}$)$_2$, —N(R$^{20}$)C(O)R$^{20}$, —C(O)R$^{20}$, —C(O)OR$^{20}$, —C(O)N(R$^{20}$)$_2$, —OC(O)R$^{20}$, —S(O)$_2$R$^{20}$, —S(O)$_2$ N(R$^{20}$)$_2$, —N(R$^{20}$)S(O)$_2$R$^{20}$, —NO$_2$, =O, =S, =N(R$^{20}$), —P(O)(OR$^{20}$)$_2$, —P(O)(R$^{20}$)$_2$, —OP(O)(OR$^{20}$)$_2$, —CN, C$_{1-6}$ alkyl, C$_{2-6}$ alkenyl, and C$_{2-6}$ alkynyl; or R$^{22}$ and R$^{23}$, together with the carbon atoms to which they are attached, form a carbocyclic ring;

R$^{24}$ is selected from hydrogen, —C(O)R$^{20}$, —C(O)OR$^{20}$, —C(O)N(R$^{20}$)$_2$, —OC(O)R$^{20}$, —S(O)$_2$R$^{20}$, and —S(O)$_2$N(R$^{20}$)$_2$; C$_{1-6}$ alkyl, C$_{2-6}$ alkenyl, and C$_{2-6}$ alkynyl, each of which is independently optionally substituted at each occurrence with one or more substituents selected from halogen, —OR$^{20}$, —SR$^{20}$, —N(R$^{20}$)$_2$, —N(R$^{20}$)C(O)R$^{20}$, —C(O)R$^{20}$, —C(O)OR$^{20}$, —C(O)N(R$^{20}$)$_2$, —OC(O)R$^{20}$, —S(O)$_2$R$^{20}$, —S(O)$_2$N(R$^{20}$)$_2$, —N(R$^{20}$)S(O)$_2$R$^{20}$, —NO$_2$, =O, =S, =N(R$^{20}$), —P(O)(OR$^{20}$)$_2$, —P(O)(R$^{20}$)$_2$, —OP(O)(OR$^{20}$)$_2$, —CN, C$_{3-10}$ carbocycle, and 3- to 10-membered heterocycle; and C$_{3-10}$ carbocycle and 3- to 10-membered heterocycle, wherein each C$_{3-10}$ carbocycle and 3- to 10-membered heterocycle of R$^{24}$ is independently optionally substituted with one or more substituents selected from halogen, —OR$^{20}$, —SR$^{20}$, —N(R$^{20}$)$_2$, —N(R$^{20}$)C(O)R$^{20}$, —C(O)R$^{20}$, —C(O)OR$^{20}$, —C(O)N(R$^{20}$)$_2$, —OC(O)R$^{20}$, —S(O)$_2$R$^{20}$, —S(O)$_2$N(R$^{20}$)$_2$, —N(R$^{20}$)S(O)$_2$R$^{20}$, —NO$_2$, =O, =S, =N(R$^{20}$), —P(O)(OR$^{20}$)$_2$, —P(O)(R$^{20}$)$_2$, —OP(O)(OR$^{20}$)$_2$, —CN, C$_{1-6}$ alkyl, C$_{2-6}$ alkenyl, and C$_{2-6}$ alkynyl.

In certain embodiments, for a compound or salt of any one of Formulas (3), (3A), (3B), (3C), (3D), (3E), (3F), (3G), (3H), (3I), and (3J), R$^{21}$ is selected from:

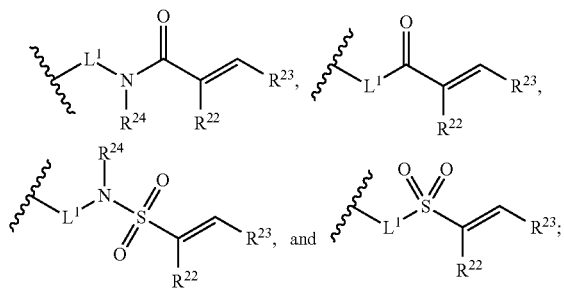

wherein L$^1$, R$^{22}$, R$^{23}$, and R$^{24}$ are as described above.

In certain embodiments, for a compound or salt of any one of Formulas (3), (3A), (3B), (3C), (3D), (3E), (3F), (3G), (3H), (3I), and (3J), R$^{21}$ is selected from a moiety comprising an alpha, beta-unsaturated carbonyl and an alpha, beta-unsaturated sulfonyl, wherein the alpha-position of the alpha, beta-unsaturated carbonyl or alpha, beta-unsaturated sulfonyl is substituted with an electron-withdrawing group. Exemplary electron withdrawing group include —CN, —CF$_3$, —C(O)alkyl, —SO$_3$H, etc. In certain embodiments, R$^{21}$ is selected from

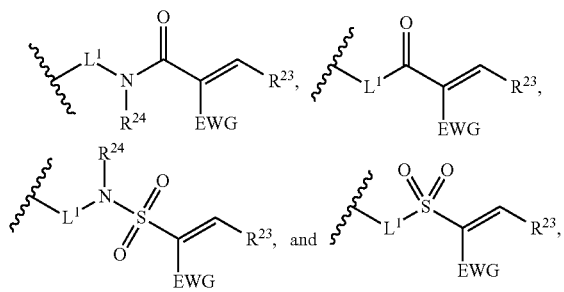

wherein EWG is an electron withdrawing group and L$^1$, R$^{23}$, and R$^{24}$ are as described above. In certain embodiments, R$^{21}$ is selected from:

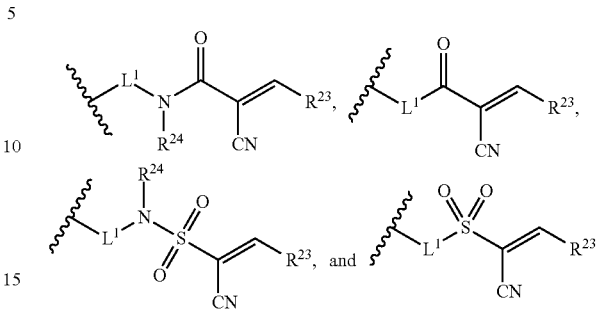

and L$^1$, R$^{23}$, and R$^{24}$ are as described above. In certain embodiments, for a compound or salt of any one of Formulas (3), (3A), (3B), (3C), (3D), (3E), (3F), (3G), (3H), (3I), and (3J), R$^{21}$ is selected from:

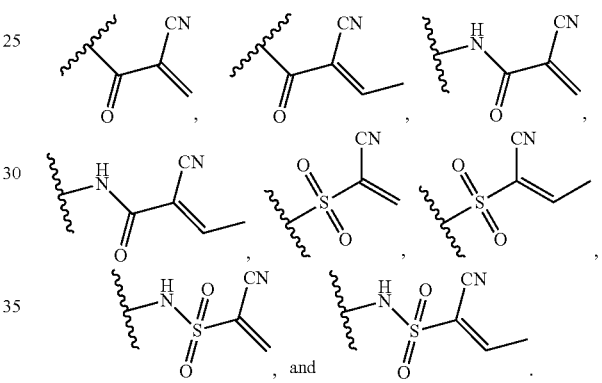

In certain embodiments, for a compound or salt of any one of Formulas (3), (3A), (3B), (3C), (3D), (3E), (3F), (3G), (3H), (3I), and (3J), L$^1$ is a bond.

In certain embodiments, for a compound or salt of any one of Formulas (3), (3A), (3B), (3C), (3D), (3E), (3F), (3G), (3H), (3I), and (3J), L$^1$ is optionally substituted C$_{1-6}$ alkylene.

In certain embodiments, for a compound or salt of any one of Formulas (3), (3A), (3B), (3C), (3D), (3E), (3F), (3G), (3H), (3I), and (3J), L$^1$ is selected from methylene, ethylene or propylene.

In certain embodiments, for a compound or salt of any one of Formulas (3), (3A), (3B), (3C), (3D), (3E), (3F), (3G), (3H), (3I), and (3J), L$^1$ is optionally substituted C$_{1-6}$ heteroalkylene.

In certain embodiments, for a compound or salt of any one of Formulas (3), (3A), (3B), (3C), (3D), (3E), (3F), (3G), (3H), (3I), and (3J), L$^1$ is substituted with one or more substituents selected from halogen, —NO$_2$, =O, =S, —OR$^{20}$, —SR$^{20}$, and —N(R$^{20}$)$_2$.

In certain embodiments, for a compound or salt of any one of Formulas (3), (3A), (3B), (3C), (3D), (3E), (3F), (3G), (3H), (3I), and (3J), R$^{23}$ is selected from hydrogen; and C$_{1-6}$ alkyl, C$_{2-6}$ alkenyl, and C$_{2-6}$ alkynyl, each of which is independently optionally substituted at each occurrence with one or more substituents selected from halogen, —OR$^{20}$, —SR$^{20}$, —N(R$^{20}$)$_2$, —N(R$^{20}$)C(O)R$^{20}$, —C(O)R$^{20}$, —C(O)OR$^{20}$, —C(O)N(R$^{20}$)$_2$, —OC(O)R$^{20}$, —S(O)$_2$R$^{20}$, —S(O)$_2$ N(R$^{20}$)$_2$, —N(R$^{20}$)S(O)$_2$R$^{20}$, —NO$_2$, =O, =S, =N(R$^{20}$), —P(O)(OR$^{20}$)$_2$, —P(O)(R$^{20}$)$_2$, —OP(O)(OR$^{20}$)$_2$, —CN, C$_{3-10}$ carbocycle and 3- to 10-membered heterocycle; and C$_{3-10}$ carbocycle, and 3- to 10-membered heterocycle, wherein each C$_{3-10}$ carbocycle and 3- to 10-membered heterocycle is independently optionally substituted with one or more substituents selected from halogen, —OR$^{20}$, —SR$^{20}$, —N(R$^{20}$)$_2$, —N(R$^{20}$)C(O)R$^{20}$, —C(O)R$^{20}$, —C(O)OR$^{20}$, —C(O)N(R$^{20}$)$_2$, —OC(O)R$^{20}$, —S(O)$_2$R$^{20}$, —S(O)$_2$N(R$^{20}$)$_2$, —N(R$^{20}$)S(O)$_2$R$^{20}$, —NO$_2$, =O, =S, =N(R$^{20}$), —P(O)(OR$^{20}$)$_2$, —P(O)(R$^{20}$)$_2$, —OP(O)(OR$^{20}$)$_2$, —CN, C$_{1-6}$ alkyl, C$_{2-6}$ alkenyl, and C$_{2-6}$ alkynyl. In certain embodiments, R$^{23}$ is selected from hydrogen; C$_{1-6}$ alkyl optionally substituted with one or more substituents selected from halogen, —OR$^{20}$, —SR$^{20}$, —N(R$^{20}$)$_2$, =O, =S, =N(R$^{20}$), and —CN; and 3- to 10-membered heterocycle optionally substituted with one or more substituents selected from halogen, —OR$^{20}$, —SR$^{20}$, —N(R$^{20}$)$_2$, —N(R$^{20}$)C(O)R$^{20}$, —C(O)R$^{20}$, —C(O)OR$^{20}$, —C(O)N(R$^{20}$)$_2$, —OC(O)R$^{20}$, —S(O)$_2$R$^{20}$, —S(O)$_2$N(R$^{20}$)$_2$, —N(R$^{20}$)S(O)$_2$R$^{20}$, —NO$_2$, =O, =S, =N(R$^{20}$), —P(O)(OR$^{20}$)$_2$, —P(O)(R$^{20}$)$_2$, —OP(O)(OR$^{20}$)$_2$, —CN, C$_{1-6}$ alkyl, C$_{2-6}$ alkenyl, and C$_{2-6}$ alkynyl. In particular embodiments, R$^{23}$ is selected from hydrogen; C$_{1-6}$ alkyl optionally substituted with one or more substituents selected from halogen, —OR$^{20}$, —SR$^{20}$, —N(R$^{20}$)$_2$, =O, =S, =N(R$^{20}$), and —CN.

In certain embodiments, for a compound or salt of any one of Formulas (3), (3A), (3B), (3C), (3D), (3E), (3F), (3G), (3H), (3I), and (3J), R$^{22}$ is selected from hydrogen, and —CN; C$_{1-6}$ alkyl, C$_{2-6}$ alkenyl, and C$_{2-6}$ alkynyl, each of which is independently optionally substituted at each occurrence with one or more substituents selected from halogen, —OR$^{20}$, —SR$^{20}$, —N(R$^{20}$)$_2$, —N(R$^{20}$)C(O)R$^{20}$, —C(O)R$^{20}$, —C(O)OR$^{20}$, —C(O)N(R$^{20}$)$_2$, —OC(O)R$^{20}$, —S(O)$_2$R$^{20}$, —S(O)$_2$N(R$^{20}$)$_2$, —N(R$^{20}$)S(O)$_2$R$^{20}$, —NO$_2$, =O, =S, =N(R$^{20}$), —P(O)(OR$^{20}$)$_2$, —P(O)(R$^{20}$)$_2$, —OP(O)(OR$^{20}$)$_2$, —CN, C$_{3-10}$ carbocycle and 3- to 10-membered heterocycle; and C$_{3-10}$ carbocycle and 3- to 10-membered heterocycle, wherein each C$_{3-10}$ carbocycle and 3- to 10-membered heterocycle is independently optionally substituted with one or more substituents selected from halogen, —OR$^{20}$, —SR$^{20}$, —N(R$^{20}$)$_2$, —N(R$^{20}$)C(O)R$^{20}$, —C(O)R$^{20}$, —C(O)OR$^{20}$, —C(O)N(R$^{20}$)$_2$, —OC(O)R$^{20}$, —S(O)$_2$R$^{20}$, —S(O)$_2$N(R$^{20}$)$_2$, —N(R$^{20}$)S(O)$_2$R$^{20}$, —NO$_2$, =O, =S, =N(R$^{20}$), —P(O)(OR$^{20}$)$_2$, —P(O)(R$^{20}$)$_2$, —OP(O)(OR$^{20}$)$_2$, —CN, C$_{1-6}$ alkyl, C$_{2-6}$ alkenyl, and C$_{2-6}$ alkynyl. In particular embodiments, R$^{22}$ is selected from hydrogen; —CN; and C$_{1-6}$ alkyl optionally substituted with one or more substituents selected from halogen, —OR$^{20}$, —SR$^{20}$, and —N(R$^{20}$)$_2$.

In certain embodiments, for a compound or salt of any one of Formulas (3), (3A), (3B), (3C), (3D), (3E), (3F), (3G), (3H), (3I), and (3J), R$^{22}$ and R$^{23}$, together with the carbon atoms to which they are attached, form a 5-, 6-, or 7-membered carbocyclic ring.

In certain embodiments, for a compound or salt of any one of Formulas (3), (3A), (3B), (3C), (3D), (3E), (3F), (3G), (3H), (3I), and (3J), R$^{24}$ is selected from hydrogen and C$_{1-6}$ alkyl optionally substituted with one or more substituents selected from —OR$^{20}$, —SR$^{20}$, —N(R$^{20}$)$_2$, —NO$_2$, =O, and —CN.

In certain embodiments, for a compound or salt of any one of Formulas (3), (3A), (3B), (3C), (3D), (3E), (3F), (3G), (3H), (3I), and (3J), R$^{21}$ is selected from:

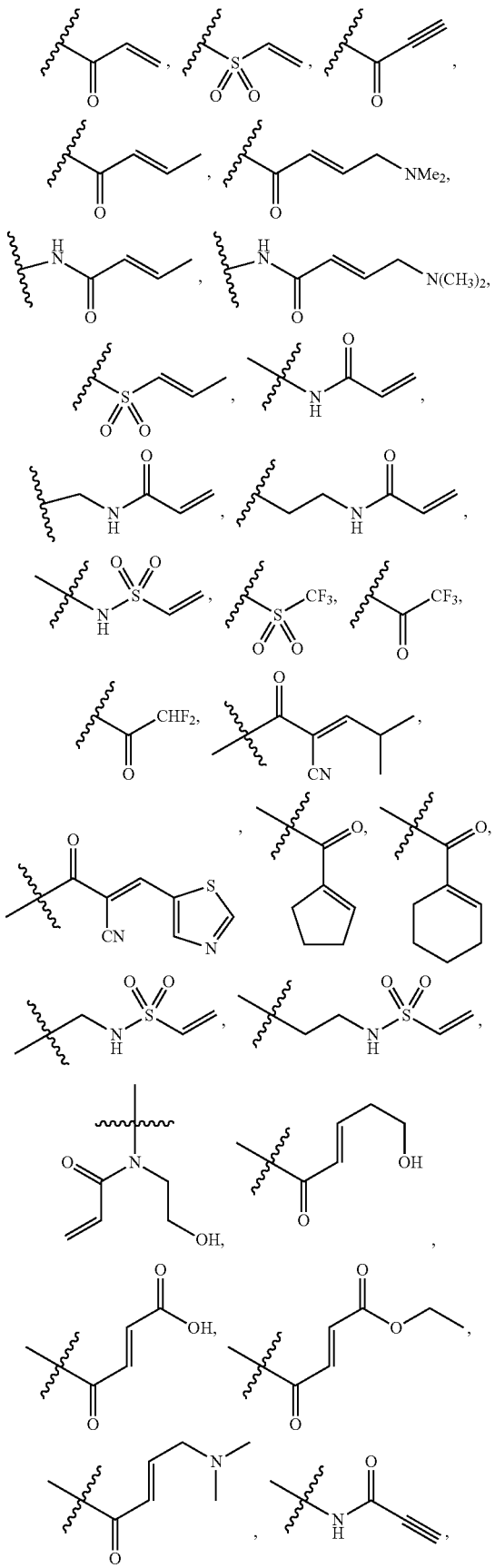

-continued

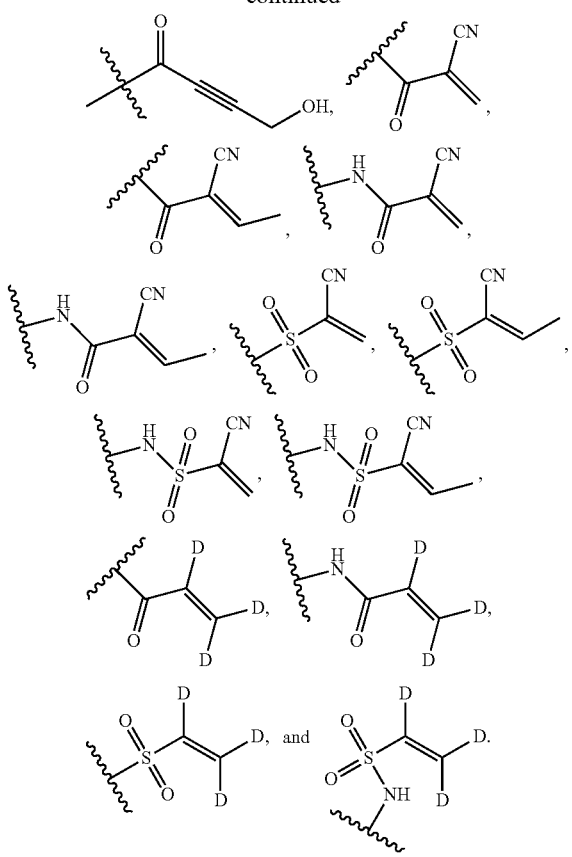

In certain embodiments, for a compound or salt of any one of Formulas (3), (3A), (3B), (3C), (3D), (3E), (3F), (3G), (3H), (3I), and (3J), R²¹ is selected from:

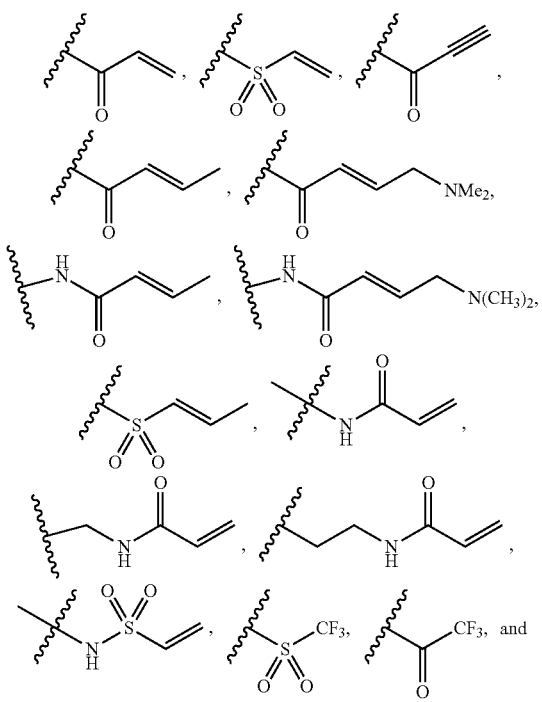

-continued

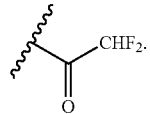

In certain embodiments, for a compound or salt of any one of Formulas (3), (3A), (3B), (3C), (3D), (3E), (3F), (3G), (3H), (3I), and (3J), $R^{21}$ is selected from:

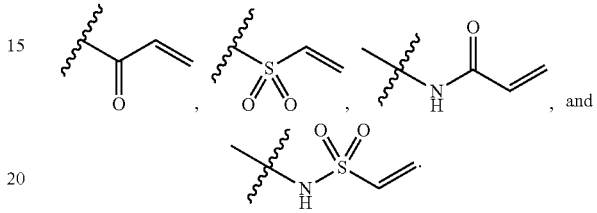

In certain embodiments, for a compound or salt of any one of Formulas (3), (3A), (3B), (3C), (3D), (3E), (3F), (3G), (3H), (3I), and (3J), $R^{21}$ is a moiety with 5 to 50 atoms, for example, $R^{21}$ is a moiety with 7 to 40 atoms. In some embodiments, $R^{21}$ is a moiety with 5-150, 5-100, 5-90, 5-80, 5-70, 5-60, 5-50, 5-40, 5-30, 5-150, 5-100, 5-90, 5-80, 5-70, 5-60, 5-50, 5-40, or 5-40 atoms.

In certain embodiments, for a compound or salt of any one of Formulas (3), (3A), (3B), (3C), (3D), (3E), (3F), (3G), (3H), (3I), (3J), and (4), V is selected from a 3-8 membered saturated carbocyclic or heterocyclic ring optionally substituted with one or more $R^{32}$ groups. In certain embodiments, V is a 3-, 4-, 5-, 6- or 7-membered saturated carbocycle, any one of which is optionally substituted with one or more $R^{32}$ groups. In particular embodiments, V is selected from:

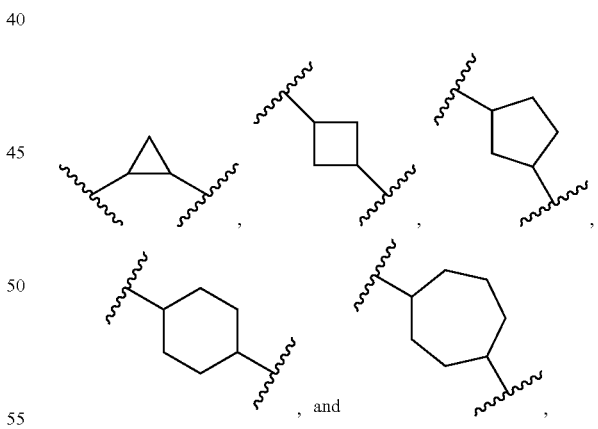

any one of which is optionally substituted with one or more $R^{32}$ groups. In certain embodiments, V is a 4-, 5-, 6-, 7- or 8-membered saturated heterocycle, any one of which is optionally substituted with one or more $R^{32}$ groups. In particular embodiments, V is selected from azetidine, oxetane, piperidine, oxane, piperazine, pyrrolidine, tetrahydrofuran, thiolane, imidazolidine, morpholine, thiomorpholine, azepane, and homopiperazine, any one of which is optionally substituted with one or more $R^{32}$ groups. In particular embodiments, V is selected from:

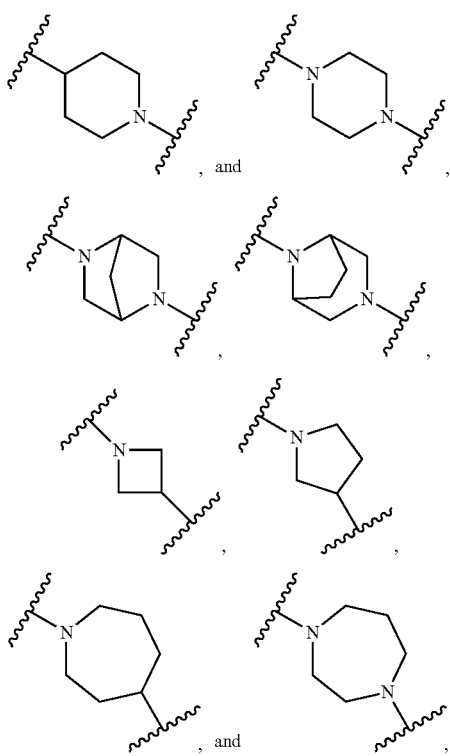

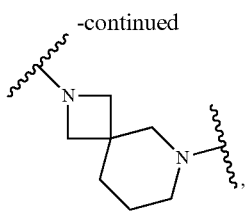

any one of which is optionally substituted with one or more $R^{32}$ groups.

In certain embodiments, for a compound or salt of any one of Formulas (3), (3A), (3B), (3C), (3D), (3E), (3F), (3G), (3H), (3I), (3J), and (4), V is a bicyclic heterocycle, optionally substituted with one or more $R^{32}$ groups. In particular embodiments, V is selected from

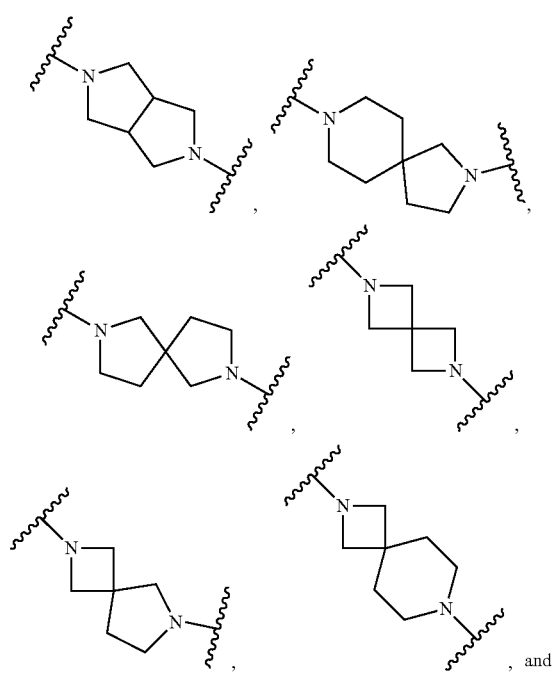

In certain embodiments, for a compound or salt of any one of Formulas (3), (3A), (3B), (3C), (3D), (3E), (3F), (3G), (3H), (3I), (3J), and (4), V is selected from an unsaturated, aromatic, or heteroaromatic ring. In particular embodiments, V is selected from phenyl, pyridine, pyrazine, pyrimidine, pyridazine, naphthalene, anthracene, quinoline, isoquinoline, quinoxaline, acridine, quinazoline, cinnoline, phthalazine, furan, dihydrofuran, thiophene, dihydrothiophene, imidazole, imidazoline, oxazole, oxazoline, pyrrole, dihydropyrrole, thiazole, dihydrothiazole, pyrazole, dihydropyrazole, isoxazole, dihydroisoxazole, isothiazole, dihydroisothiazole, benzofuran, isobenzofuran, indole, isoindole, benzothiophene, benzimidazole, purine, indazole, benzoxazole, benzisoxazole, and benzothiazole, any one of which is optionally substituted with one or more $R^{32}$ groups. In particular embodiments, V is phenyl, optionally substituted with one or more $R^{32}$ groups. In some embodiments, V is a heteroaromatic ring optionally substituted with one or more $R^{32}$ groups. In particular embodiments, V is selected from pyridine, pyrazine, pyrimidine, pyridazine, naphthalene, anthracene, quinoline, isoquinoline, quinoxaline, acridine, quinazoline, cinnoline, phthalazine, furan, thiophene, imidazole, oxazole, pyrrole, thiazole, pyrazole, isoxazole, isothiazole, benzofuran, isobenzofuran, indole, isoindole, benzothiophene, benzimidazole, purine, indazole, benzoxazole, benzisoxazole, and benzothiazole, any one of which is optionally substituted with one or more $R^{32}$ groups, for example, V is selected from

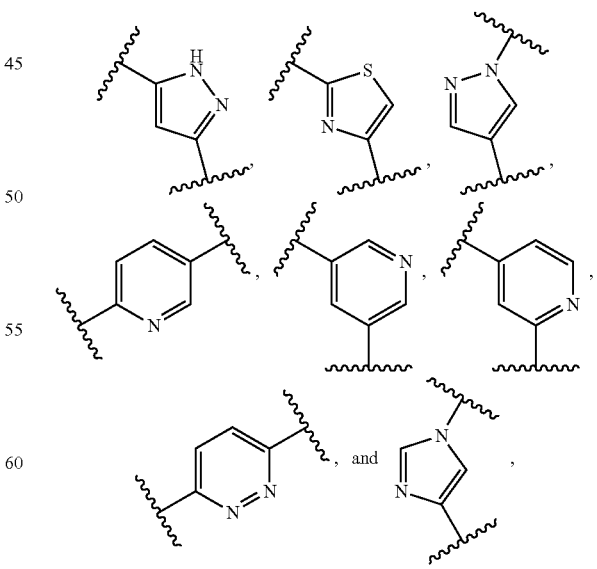

wherein any one of which is optionally substituted with one or more $R^{32}$ groups.

In certain embodiments, for a compound or salt of any one of Formulas (3), (3A), (3B), (3C), (3D), (3E), (3F), (3G), (3H), (3I), (3J), and (4), V is absent.

In certain embodiments, for a compound or salt of any one of Formulas (3), (3A), (3B), (3C), (3D), (3E), (3F), (3G), (3H), (3I), (3J), and (4), G is a bond.

In certain embodiments, for a compound or salt of any one of Formulas (3), (3A), (3B), (3C), (3D), (3E), (3F), (3G), (3H), (3I), (3J), and (4), G is alkylene optionally substituted with one or more $R^{32}$ groups. In particular embodiments, G is selected from methylene, ethylene, propylene, and butylene, any one of which is optionally substituted with one or more $R^{32}$ groups, for example, G is selected from:

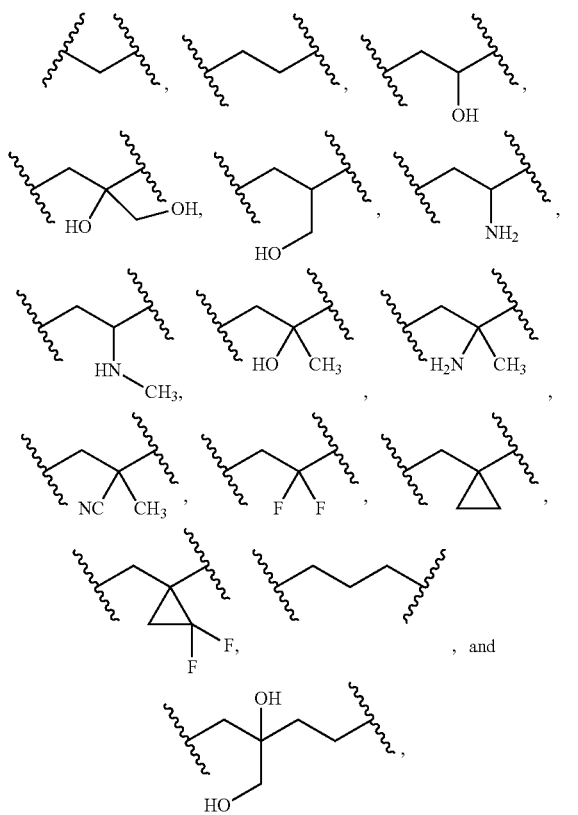

wherein any one of which is optionally substituted with one or more $R^{32}$ groups.

In certain embodiments, for a compound or salt of any one of Formulas (3), (3A), (3B), (3C), (3D), (3E), (3F), (3G), (3H), (3I), (3J), and (4), G is a heteroalkylene optionally substituted with one or more $R^{32}$ groups.

In certain embodiments, for a compound or salt of any one of Formulas (3), (3A), (3B), (3C), (3D), (3E), (3F), (3G), (3H), (3I), (3J), and (4), G is a $C_{3-10}$ carbocycle or 3- to 10-membered heterocycle, any one of which is optionally substituted with one or more $R^{32}$ groups.

In certain embodiments, for a compound or salt of any one of Formulas (3), (3A), (3B), (3C), (3D), (3E), (3F), (3G), (3H), (3I), (3J), and (4), G is a saturated $C_{3-10}$ carbocycle or saturated 3- to 10-membered heterocycle, any one of which is optionally substituted with one or more $R^{32}$ groups, for example, G is selected from:

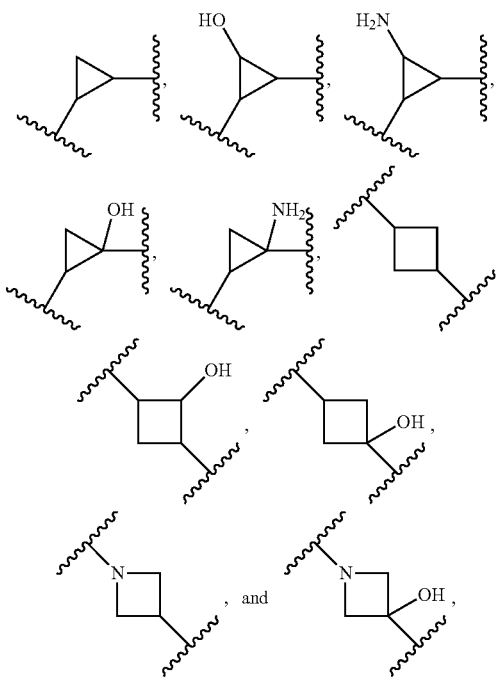

wherein any one of which is optionally substituted with one or more $R^{32}$ groups.

In certain embodiments, for a compound or salt of any one of Formulas (3), (3A), (3B), (3C), (3D), (3E), (3F), (3G), (3H), (3I), and (3J), R7 is selected from:

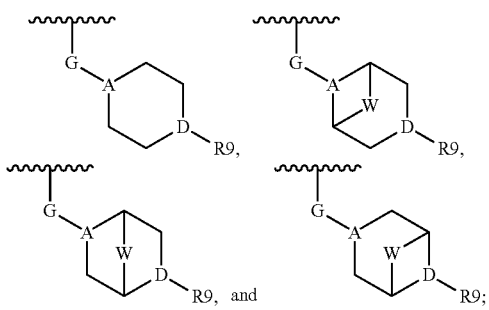

G is selected from alkylene and heteroalkylene;
A and D are independently selected from CH and N;
W is selected from alkylene, aminoalkylene, and oxalkylene;
wherein one or more of the H atoms on the ring structure of R7 is optionally replaced with a halogen, alcohol, alkyl, alkoxy, amine, cyano, an amide, —$SO_2CH_3$, or —COOH;
R9 is selected from:

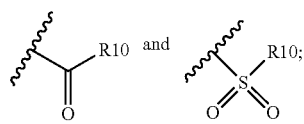

R10 is selected from optionally substituted alkane, optionally substituted alkene, and optionally substituted alkyne, wherein the substituents are independently selected from alkoxy, amine, a halogen, a ketone, an amide, cyano, sulfonyl, a carbocyclic ring, an aromatic ring, a substituted aromatic ring, a heterocyclic aromatic ring, a substituted heterocyclic aromatic ring, a substituted or non-substituted heterocyclic non-aromatic ring, carbocyclic or heterocyclic aromatic ring fused to another aromatic ring, a hydrogen bond donor, a hydrogen bond acceptor, and combinations thereof.

In certain embodiments, for a compound or salt of any one of Formulas (3), (3A), (3B), (3C), (3D), (3E), (3F), (3G), (3H), (3I), and (3J), R10 is selected from optionally substituted alkene and optionally substituted alkyne, for example, R1 is selected from optionally substituted C2 alkene and optionally substituted C2 alkyne.

In certain embodiments, for a compound or salt of any one of Formulas (3), (3A), (3B), (3C), (3D), (3E), (3F), (3G), (3H), (3I), and (3J), R7 is selected from:

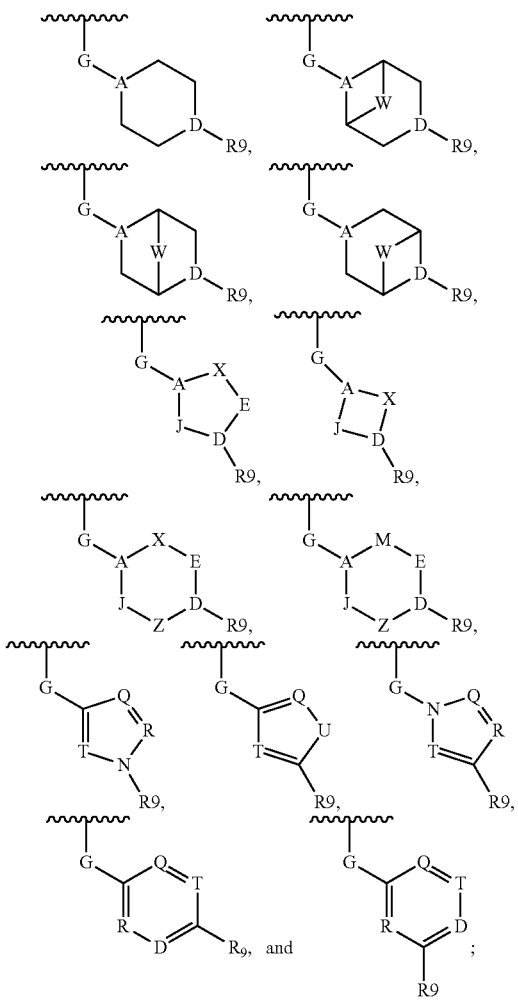

G is selected from alkylene, aminoalkylene, oxalkylene, or heteroalkylene;

A and D are independently selected from CH and N;

E, J, X, and Z are independently selected from $CH_2$, NH, S, and O;

M is $(-CH_2-)_n$, wherein n is selected from 0, 1, 2, 3, and 4;

Q, R, and T are independently selected from CH and N;

U is selected from O, NH, and S;

W is selected from alkylene, aminoalkylene, and oxalkylene;

wherein one or more of the H atoms on the ring structure of R7, when present, is optionally replaced with a halogen, alcohol, alkyl, alkoxy, amine, cyano, an amide, $-SO_2CH_3$, sulfonamide, or COOH;

R9, when present, is selected from:

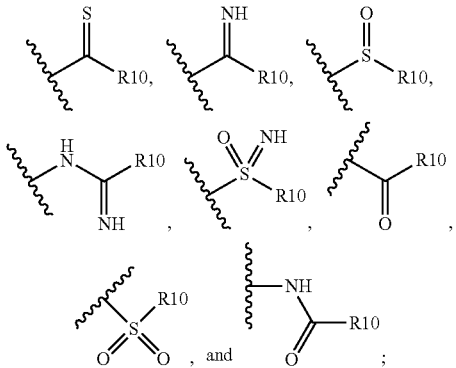

R10, when present, is selected from: alkene optionally substituted with R11, alkyne optionally substituted with R11, and any electrophilic group capable of covalent and/or irreversible binding to cysteine sulfhydryl groups;

R11 is selected from alkyl, a substituted alkyl, alkoxy, amine, thioalkyl, halogen, ketone, amide, alkylamide, cyano, sulfonyl, a carbocyclic ring, an aromatic ring, a substituted aromatic ring, a heterocyclic aromatic ring, a substituted heterocyclic aromatic ring, a substituted or non-substituted heterocyclic non-aromatic ring, carbocyclic or heterocyclic aromatic ring fused to another aromatic ring, a hydrogen bond donor, a hydrogen bond acceptor, and combinations thereof.

In certain embodiments, for a compound or salt of any one of Formulas (3), (3A), (3B), (3C), (3D), (3E), (3F), (3G), (3H), (3I), and (3J), R7 is selected from:

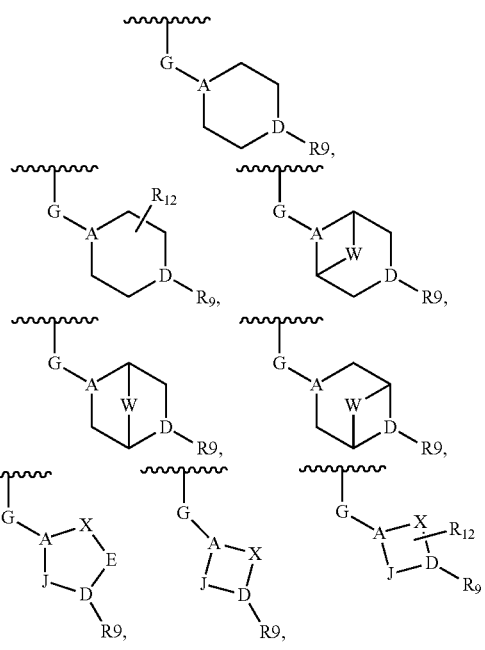

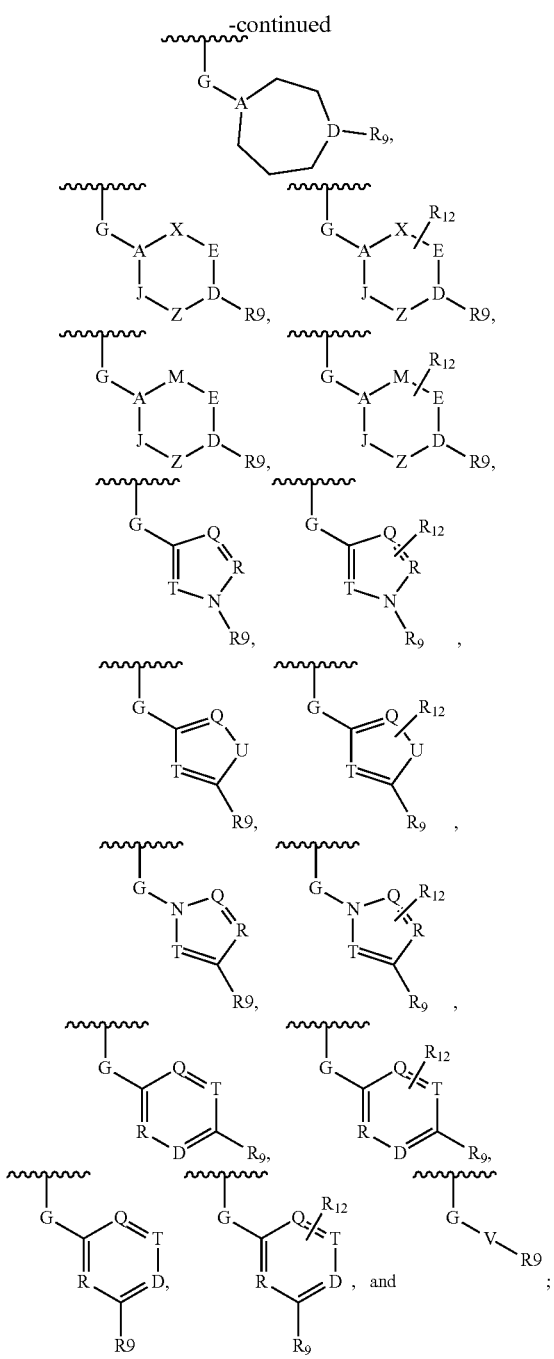

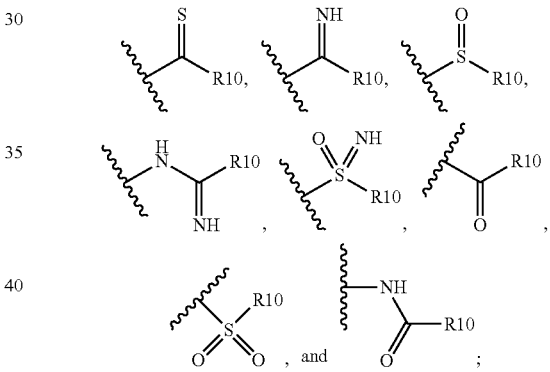

G is selected from alkylene, branched alkylene, aminoalkylene, oxalkylene, haloalkylene, heteroalkylene, hydroxyalkyl, alkylhydroxyalkyl, alkoxyalkyl, aminoalkyl or alkylamine, alkylaminoalkyl, carbocycle, alkylcycloalkyl, hydroxycycloalkyl, alkoxycycloalkyl, hydroxyalkylcycloalkyl, disubstituted cycloalkyl, aminocycloalkyl, alkylaminocycloalkyl, substituted carbocycle, heterocycle, and substituted heterocycle;

V is selected from a 3-7 membered saturated ring, 3-7 membered unsaturated ring, 4-10 membered fused bicyclic ring, and 5-11 membered spiro bicyclic ring; wherein V is optionally substituted with one or more R12 groups;

R12 at each occurrence is selected from alkyl, a substituted alkyl, alkene, alkyne, hydroxyl, alcohol, alkoxy, amine, alkylamine, a halogen, a ketone, an amide, an alkylamide, cyano, methyl carbonitrile, —SO$_2$alkyl, —SO$_2$NH$_2$, —SO$_2$NHalkyl, —SO$_2$Ndialkyl, sulfonyl, dialkylphosphine oxide, a carbocyclic ring, an aromatic ring, a substituted aromatic ring, a heterocyclic aromatic ring, a substituted heterocyclic aromatic ring, a substituted or non-substituted heterocyclic non-aromatic ring, carbocyclic or heterocyclic aromatic ring fused to another aromatic ring, a hydrogen bond donor, a hydrogen bond acceptor, and combinations thereof;

A and D are independently selected from CH and N;

E, J, X, and Z are independently selected from CH$_2$, NH, S, and O;

M is (—CH$_2$—)$_n$ and n is selected from 0, 1, 2, 3, and 4;

Q, R, T are independently selected from CH and N;

U is selected from O, NH, and S;

W is selected from alkylene, aminoalkylene, and oxalkylene;

wherein one or more H atoms of R7 is independently optionally replaced with a halogen, alcohol, alkyl (C1-C5), cycloalkyl (C1-C7), haloalkyl, alkene (C1-C5), alkyne (C1-C5), alkoxy, amine, ester, cyano, amide, —SO$_2$alkyl, sulfonamide, or COOH;

R9 is selected from:

R10 is selected from alkene optionally substituted with R11 and alkyne optionally substituted with R11;

R11 is selected from H, alkyl, a substituted alkyl, alcohol, alkoxy, amine, halogen, ketone, amide, alkylamide, cyano, sulfonyl, a carbocyclic ring, an aromatic ring, a substituted aromatic ring, a heterocyclic aromatic ring, a substituted heterocyclic aromatic ring, a substituted or non-substituted heterocyclic non-aromatic ring, carbocyclic or heterocyclic aromatic ring fused to another aromatic ring, a hydrogen bond donor, a hydrogen bond acceptor, and combinations thereof.

In certain embodiments, for a compound or salt of any one of Formulas (3), (3A), (3B), (3C), (3D), (3E), (3F), (3G), (3H), (3I), and (3J), R$^9$ is selected from:

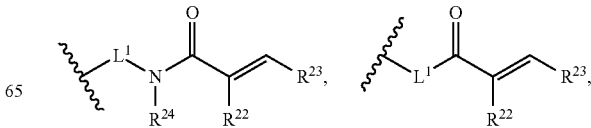

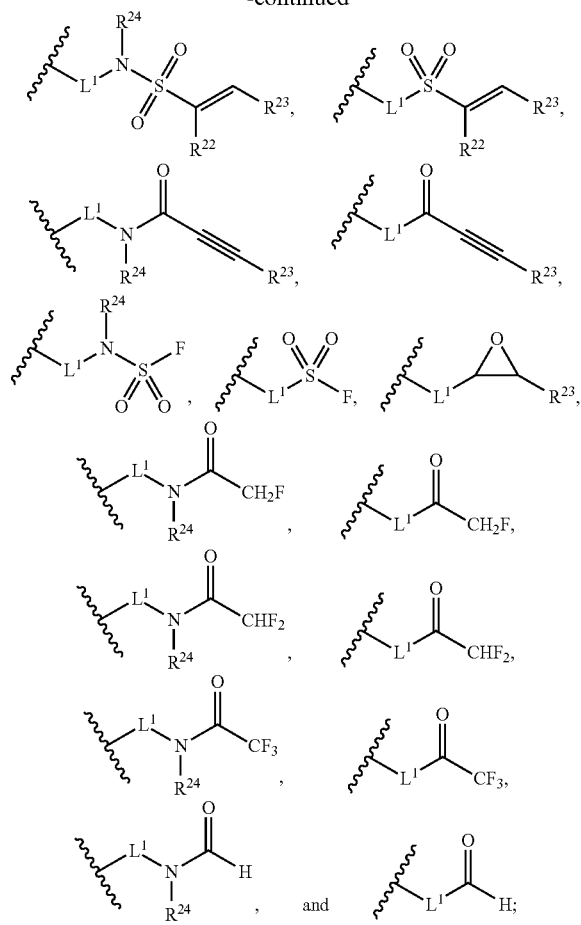

wherein:

L¹ is selected from a bond; and $C_{1-6}$ alkylene, $C_{1-6}$ heteroalkylene, $C_{2-6}$ alkenylene, and $C_{2-6}$ alkynylene, each of which may be optionally substituted with one or more $R^{32}$ groups;

$R^{22}$ and $R^{23}$ are selected from hydrogen, halogen, —OR$^{20}$, —SR$^{20}$, —N(R$^{20}$)$_2$, —N(R$^{20}$)C(O)R$^{20}$, —C(O)R$^{20}$, —C(O)OR$^{20}$, —C(O)N(R$^{20}$)$_2$, —OC(O)R$^{20}$, —S(O)$_2$R$^{20}$, —S(O)$_2$N(R$^{20}$)$_2$, —N(R$^{20}$)S(O)$_2$R$^{20}$, —NO$_2$, =O, =S, =N(R$^{20}$), —P(O)(OR$^{20}$)$_2$, —P(O)(R$^{20}$)$_2$, —OP(O)(OR$^{20}$)$_2$, and —CN; $C_{1-6}$ alkyl, $C_{2-6}$ alkenyl, and $C_{2-6}$ alkynyl, each of which is independently optionally substituted at each occurrence with one or more substituents selected from halogen, —OR$^{20}$, —SR$^{20}$, —N(R$^{20}$)$_2$, —N(R$^{20}$)C(O)R$^{20}$, —C(O)R$^{20}$, —C(O)OR$^{20}$, —C(O)N(R$^{20}$)$_2$, —OC(O)R$^{20}$, —S(O)$_2$R$^{20}$, —S(O)$_2$N(R$^{20}$)$_2$, —N(R$^{20}$)S(O)$_2$R$^{20}$, —NO$_2$, =O, =S, =N(R$^{20}$), —P(O)(OR$^{20}$)$_2$, —P(O)(R$^{20}$)$_2$, —OP(O)(OR$^{20}$)$_2$, —CN, $C_{3-10}$ carbocycle, and 3- to 10-membered heterocycle; and $C_{3-10}$ carbocycle and 3- to 10-membered heterocycle, wherein each $C_{3-10}$ carbocycle and 3- to 10-membered heterocycle of $R^{22}$ and $R^{23}$ is independently optionally substituted with one or more substituents selected from halogen, —OR$^{20}$, —SR$^{20}$, —N(R$^{20}$)$_2$, —N(R$^{20}$)C(O)R$^{20}$, —C(O)R$^{20}$, —C(O)OR$^{20}$, —C(O)N(R$^{20}$)$_2$, —OC(O)R$^{20}$, —S(O)$_2$R$^{20}$, —S(O)$_2$N(R$^{20}$)$_2$, —N(R$^{20}$)S(O)$_2$R$^{20}$, —NO$_2$, =O, =S, =N(R$^{20}$), —P(O)(OR$^{20}$)$_2$, —P(O)(R$^{20}$)$_2$, —OP(O)(OR$^{20}$)$_2$, —CN, $C_{1-6}$ alkyl, $C_{2-6}$ alkenyl, and $C_{2-6}$ alkynyl; or $R^{22}$ and $R^{23}$, together with the carbon atoms to which they are attached, form a carbocyclic ring;

$R^{24}$ is selected from hydrogen, —C(O)R$^{20}$, —C(O)OR$^{20}$, —C(O)N(R$^{20}$)$_2$, —OC(O)R$^{20}$, —S(O)$_2$R$^{20}$, and —S(O)$_2$N(R$^{20}$)$_2$; $C_{1-6}$ alkyl, $C_{2-6}$ alkenyl, and $C_{2-6}$ alkynyl, each of which is independently optionally substituted at each occurrence with one or more substituents selected from halogen, —OR$^{20}$, —SR$^{20}$, —N(R$^{20}$)$_2$, —N(R$^{20}$)C(O)R$^{20}$, —C(O)R$^{20}$, —C(O)OR$^{20}$, —C(O)N(R$^{20}$)$_2$, —OC(O)R$^{20}$, —S(O)$_2$R$^{20}$, —S(O)$_2$N(R$^{20}$)$_2$, —N(R$^{20}$)S(O)$_2$R$^{20}$, —NO$_2$, =O, =S, =N(R$^{20}$), —P(O)(OR$^{20}$)$_2$, —P(O)(R$^{20}$)$_2$, —OP(O)(OR$^{20}$)$_2$, —CN, $C_{3-10}$ carbocycle, and 3- to 10-membered heterocycle; and $C_{3-10}$ carbocycle and 3- to 10-membered heterocycle, wherein each $C_{3-10}$ carbocycle and 3- to 10-membered heterocycle of $R^{24}$ is independently optionally substituted with one or more substituents selected from halogen, —OR$^{20}$, —SR$^{20}$, —N(R$^{20}$)$_2$, —N(R$^{20}$)C(O)R$^{20}$, —C(O)R$^{20}$, —C(O)OR$^{20}$, —C(O)N(R$^{20}$)$_2$, —OC(O)R$^{20}$, —S(O)$_2$R$^{20}$, —S(O)$_2$N(R$^{20}$)$_2$, —N(R$^{20}$)S(O)$_2$R$^{20}$, —NO$_2$, =O, =S, =N(R$^{20}$), —P(O)(OR$^{20}$)$_2$, —P(O)(R$^{20}$)$_2$, —OP(O)(OR$^{20}$)$_2$, —CN, $C_{1-6}$ alkyl, $C_{2-6}$ alkenyl, and $C_{2-6}$ alkynyl;

$R^{32}$ at each occurrence is selected from halogen, —OR$^{20}$, —SR$^{20}$, —N(R$^{20}$)$_2$, —N(R$^{20}$)C(O)R$^{20}$, —C(O)R$^{20}$, —C(O)OR$^{20}$, —C(O)N(R$^{20}$)$_2$, —OC(O)R$^{20}$, —S(O)$_2$R$^{20}$, —S(O)$_2$N(R$^{20}$)$_2$, —N(R$^{20}$)S(O)$_2$R$^{20}$, —NO$_2$, =O, =S, =N(R$^{20}$), —P(O)(OR$^{20}$)$_2$, —P(O)(R$^{20}$)$_2$, —OP(O)(OR$^{20}$)$_2$, and —CN; $C_{1-6}$ alkyl, $C_{2-6}$ alkenyl, and $C_{2-6}$ alkynyl, each of which is independently optionally substituted at each occurrence with one or more substituents selected from halogen, —OR$^{20}$, —SR$^{20}$, —N(R$^{20}$)$_2$, —N(R$^{20}$)C(O)R$^{20}$, —C(O)R$^2$, —C(O)OR$^{20}$, —C(O)N(R$^{20}$)$_2$, —OC(O)R$^{20}$, —S(O)$_2$R$^{20}$, —S(O)$_2$N(R$^{20}$)$_2$, —N(R$^{20}$)S(O)$_2$R$^{20}$, —NO$_2$, =O, =S, =N(R$^{20}$), —P(O)(OR$^{20}$)$_2$, —P(O)(R$^{20}$)$_2$, —OP(O)(OR$^{20}$)$_2$, —CN, $C_{3-10}$ carbocycle, and 3- to 10-membered heterocycle; $C_{3-10}$ carbocycle and 3- to 10-membered heterocycle; or two $R^{32}$ on the same carbon atom can come together to form a $C_{3-10}$ carbocycle or 3- to 10-membered heterocycle, wherein each $C_{3-10}$ carbocycle and 3- to 10-membered heterocycle of $R^{32}$ is independently optionally substituted with one or more substituents selected from halogen, —OR$^{20}$, —SR$^{20}$, —N(R$^{20}$)$_2$, —N(R$^{20}$)C(O)R$^{20}$, —C(O)R$^{20}$, —C(O)OR$^{20}$, —C(O)N(R$^{20}$)$_2$, —OC(O)R$^{20}$, —S(O)$_2$R$^{20}$, —S(O)$_2$N(R$^{20}$)$_2$, —N(R$^{20}$)S(O)$_2$R$^{20}$, —NO$_2$, =O, =S, =N(R$^{20}$), —P(O)(OR$^{20}$)$_2$, —P(O)(R$^{20}$)$_2$, —OP(O)(OR$^{20}$)$_2$, —CN, $C_{1-6}$ alkyl, $C_{2-6}$ alkenyl, and $C_{2-6}$ alkynyl;

$R^{20}$ at each occurrence is independently selected from hydrogen; $C_{1-6}$ alkyl, $C_{2-6}$ alkenyl, and $C_{2-6}$ alkynyl, each of which is independently optionally substituted at each occurrence with one or more substituents selected from halogen, —OR$^{30}$, —SR$^{30}$, —N(R$^{30}$)$_2$, —N(R$^{30}$)C(O)R$^{30}$, —C(O)R$^{30}$, —C(O)OR, —C(O)N(R$^{30}$)$_2$, —OC(O)R$^{30}$, —S(O)$_2$R$^{30}$, —S(O)$_2$N(R$^{30}$)$_2$, —N(R$^{30}$)S(O)$_2$R$^{30}$, —NO$_2$, —P(O)(OR$^{30}$)$_2$, —P(O)(R$^{30}$)$_2$, —OP(O)(OR$^{30}$)$_2$, and —CN; and 3- to 10-membered heterocycle and $C_{3-10}$ carbocycle; and $R^{30}$ at each occurrence is independently selected from hydrogen, $C_{1-6}$ alkyl, $C_{2-6}$ alkenyl, and $C_{2-6}$ alkynyl.

In certain embodiments, for a compound or salt of any one of Formulas (3), (3A), (3B), (3C), (3D), (3E), (3F), (3G), (3H), (3I), and (3J), $R^9$ is selected from:

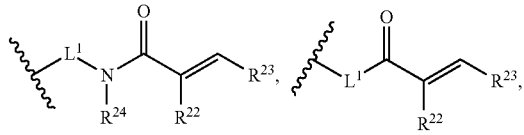

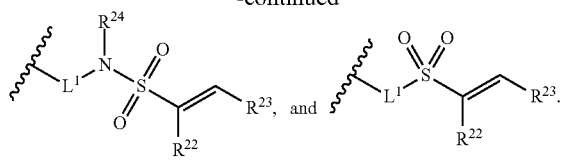

In certain embodiments, for a compound or salt of any one of Formulas (3), (3A), (3B), (3C), (3D), (3E), (3F), (3G), (3H), (3I), and (3J), $L^1$ is a bond.

In certain embodiments, for a compound or salt of any one of Formulas (3), (3A), (3B), (3C), (3D), (3E), (3F), (3G), (3H), (3I), and (3J), $L^1$ is optionally substituted $C_{1-6}$ alkylene.

In certain embodiments, for a compound or salt of any one of Formulas (3), (3A), (3B), (3C), (3D), (3E), (3F), (3G), (3H), (3I), and (3J), $L^1$ is substituted with one or more substituents selected from halogen, $-NO_2$, $=O$, $=S$, $-OR^{20}$, $-SR^{20}$, and $-N(R^{20})_2$.

In certain embodiments, for a compound or salt of any one of Formulas (3), (3A), (3B), (3C), (3D), (3E), (3F), (3G), (3H), (3I), and (3J), $R^{23}$ is selected from hydrogen; and $C_{1-6}$ alkyl, $C_{2-6}$ alkenyl, and $C_{2-6}$ alkynyl, each of which is independently optionally substituted at each occurrence with one or more substituents selected from halogen, $-OR^{20}$, $-SR^{20}$, $-N(R^{20})_2$, $-N(R^{20})C(O)R^{20}$, $-C(O)R^{20}$, $-C(O)OR^{20}$, $-C(O)N(R^{20})_2$, $-OC(O)R^{20}$, $-S(O)_2R^{20}$, $-S(O)_2N(R^{20})_2$, $-N(R^{20})S(O)_2R^{20}$, $-NO_2$, $=O$, $=S$, $=N(R^{20})$, $-P(O)(OR^{20})_2$, $-P(O)(R^{20})_2$, $-OP(O)(OR^{20})_2$, $-CN$, $C_{3-10}$ carbocycle and 3- to 10-membered heterocycle; and $C_{3-10}$ carbocycle, and 3- to 10-membered heterocycle, wherein each $C_{3-10}$ carbocycle and 3- to 10-membered heterocycle is independently optionally substituted with one or more substituents selected from halogen, $-OR^{20}$, $-SR^{20}$, $-N(R^{20})_2$, $-N(R^{20})C(O)R^{20}$, $-C(O)R^{20}$, $-C(O)OR^{20}$, $-C(O)N(R^{20})_2$, $-OC(O)R^{20}$, $-S(O)_2R^{20}$, $-S(O)_2N(R^{20})_2$, $-N(R^{20})S(O)_2R^{20}$, $-NO_2$, $=O$, $=S$, $=N(R^{20})$, $-P(O)(OR^{20})_2$, $-P(O)(R^{20})_2$, $-OP(O)(OR^{20})_2$, $-CN$, $C_{1-6}$ alkyl, $C_{2-6}$ alkenyl, and $C_{2-6}$ alkynyl.

In certain embodiments, for a compound or salt of any one of Formulas (3), (3A), (3B), (3C), (3D), (3E), (3F), (3G), (3H), (3I), and (3J), $R^{23}$ is selected from hydrogen; $C_{1-6}$ alkyl optionally substituted with one or more substituents selected from halogen, $-OR^{20}$, $-SR^{20}$, $-N(R^{20})_2$, $=O$, $=S$, $=N(R^{20})$, and $-CN$; and 3- to 10-membered heterocycle optionally substituted with one or more substituents selected from halogen, $-OR^{20}$, $-SR^{20}$, $-N(R^{20})_2$, $-N(R^{20})C(O)R^{20}$, $-C(O)R^{20}$, $-C(O)OR^{20}$, $-C(O)N(R^{20})_2$, $-OC(O)R^{20}$, $-S(O)_2R^{20}$, $-S(O)_2N(R^{20})_2$, $-N(R^{20})S(O)_2R^{20}$, $-NO_2$, $=O$, $=S$, $=N(R^{20})$, $-P(O)(OR^{20})_2$, $-P(O)(R^{20})_2$, $-OP(O)(OR^{20})_2$, $-CN$, $C_{1-6}$ alkyl, $C_{2-6}$ alkenyl, and $C_{2-6}$ alkynyl. In particular embodiments, $R^{23}$ is selected from hydrogen and $C_{1-6}$ alkyl optionally substituted with one or more substituents selected from halogen, $-OR^{20}$, $-SR^{20}$, $-N(R^{20})_2$, $=O$, $=S$, $=N(R^{20})$, and $-CN$.

In certain embodiments, for a compound or salt of any one of Formulas (3), (3A), (3B), (3C), (3D), (3E), (3F), (3G), (3H), (3I), and (3J), $R^{22}$ is selected from hydrogen, and $-CN$; $C_{1-6}$ alkyl, $C_{2-6}$ alkenyl, and $C_{2-6}$ alkynyl, each of which is independently optionally substituted at each occurrence with one or more substituents selected from halogen, $-OR^{20}$, $-SR^{20}$, $-N(R^{20})_2$, $-N(R^{20})C(O)R^{20}$, $-C(O)R^{20}$, $-C(O)OR^{20}$, $-C(O)N(R^{20})_2$, $-OC(O)R^{20}$, $-S(O)_2R^{20}$, $-S(O)_2N(R^{20})_2$, $-N(R^{20})S(O)_2R^{20}$, $-NO_2$, $=O$, $=S$, $=N(R^{20})$, $-P(O)(OR^{20})_2$, $-P(O)(R^{20})_2$, $-OP(O)(OR^{20})_2$, $-CN$, $C_{3-10}$ carbocycle and 3- to 10-membered heterocycle; and $C_{3-10}$ carbocycle and 3- to 10-membered heterocycle, wherein each $C_{3-10}$ carbocycle and 3- to 10-membered heterocycle is independently optionally substituted with one or more substituents selected from halogen, $-OR^{20}$, $-SR^{20}$, $-N(R^{20})_2$, $-N(R^{20})C(O)R^{20}$, $-C(O)R^{20}$, $-C(O)OR^{20}$, $-C(O)N(R^{20})_2$, $-OC(O)R^{20}$, $-S(O)_2R^{20}$, $-S(O)_2N(R^{20})_2$, $-N(R^{20})S(O)_2R^{20}$, $-NO_2$, $=O$, $=S$, $=N(R^{20})$, $-P(O)(OR^{20})_2$, $-P(O)(R^{20})_2$, $-OP(O)(OR^{20})_2$, $-CN$, $C_{1-6}$ alkyl, $C_{2-6}$ alkenyl, and $C_{2-6}$ alkynyl. In particular embodiments, $R^{22}$ is selected from hydrogen; $-CN$; and $C_{1-6}$ alkyl optionally substituted with one or more substituents selected from halogen, $-OR^{20}$, $-SR^{20}$, and $-N(R^{20})_2$.

In certain embodiments, for a compound or salt of any one of Formulas (3), (3A), (3B), (3C), (3D), (3E), (3F), (3G), (3H), (3I), and (3J), $R^{22}$ and $R^{23}$, together with the carbon atoms to which they are attached, form a 5-, 6-, or 7-membered carbocyclic ring.

In certain embodiments, for a compound or salt of any one of Formulas (3), (3A), (3B), (3C), (3D), (3E), (3F), (3G), (3H), (3I), and (3J), $R^{24}$ is selected from hydrogen and $C_{1-6}$ alkyl optionally substituted with one or more substituents selected from halogen, $-OR^{20}$, $-SR^{20}$, $-N(R^{20})_2$, $-NO_2$, $=O$, and $-CN$.

In certain embodiments, for a compound or salt of any one of Formulas (3), (3A), (3B), (3C), (3D), (3E), (3F), (3G), (3H), (3I), and (3J), $R^9$ is selected from:

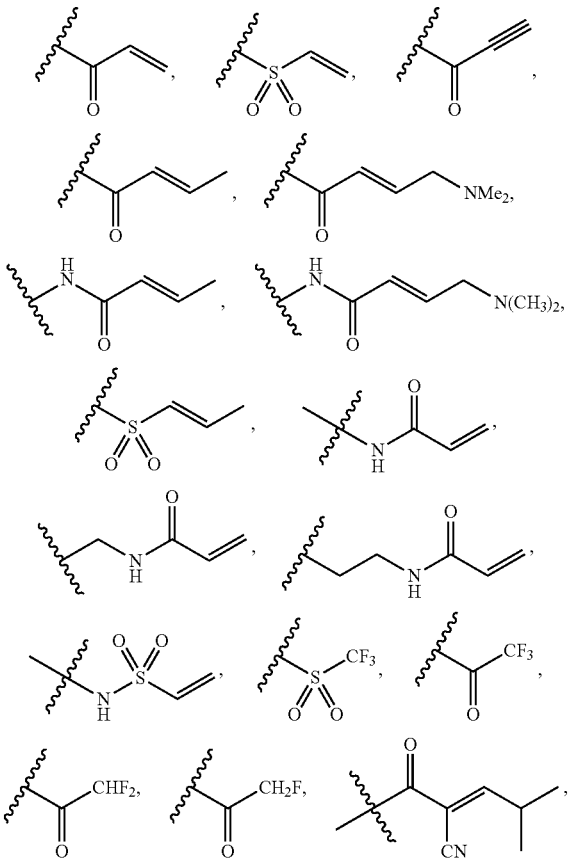

-continued

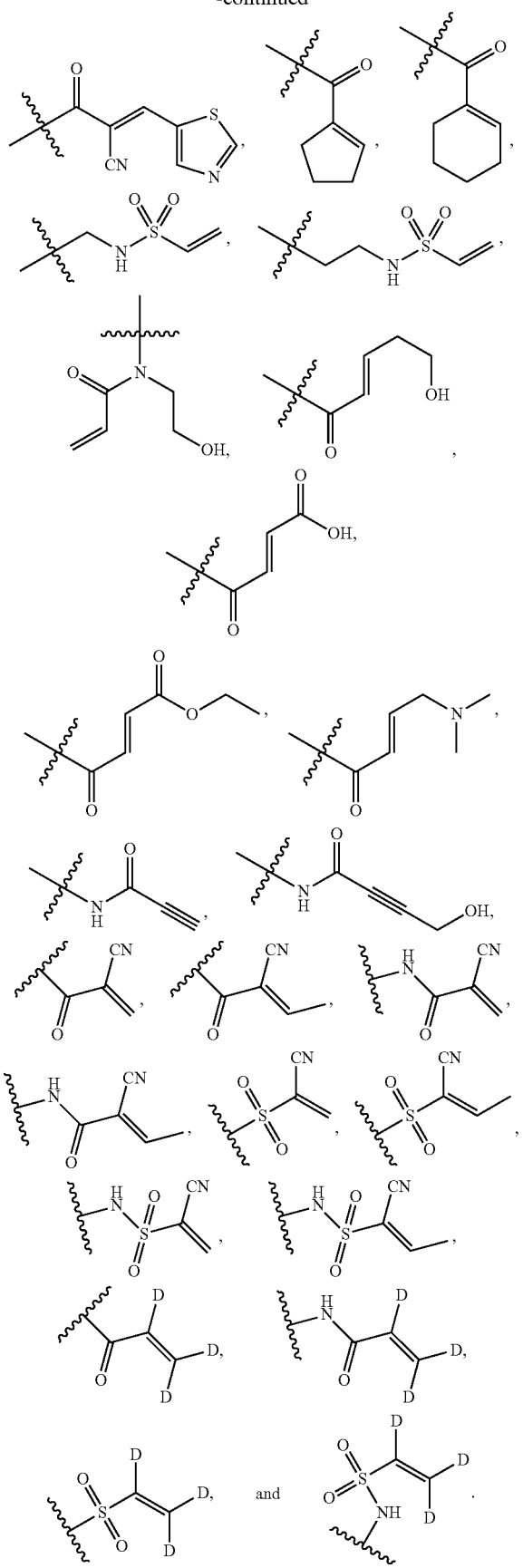

In certain embodiments, for a compound or salt of any one of Formulas (3), (3A), (3B), (3C), (3D), (3E), (3F), (3G), (3H), (3I), and (3J), $R^9$ is selected from:

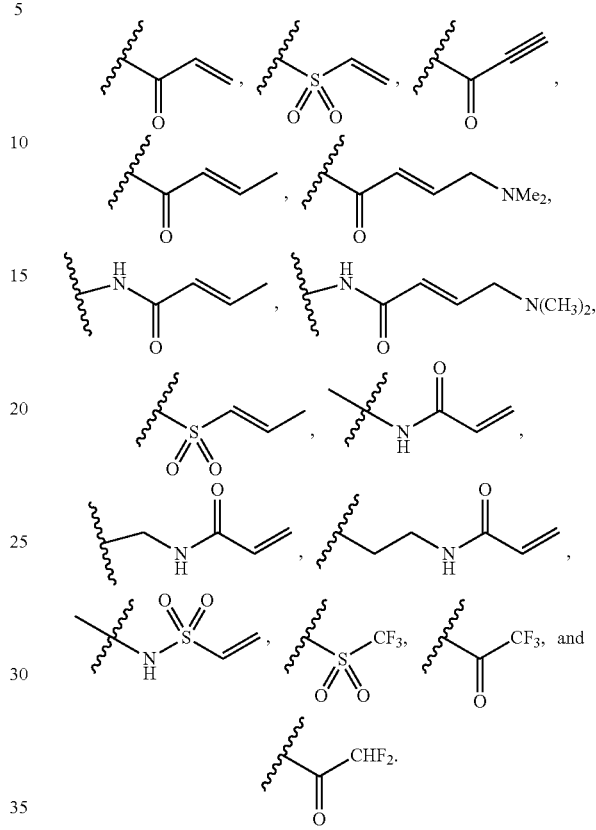

In certain embodiments, for a compound or salt of any one of Formulas (3), (3A), (3B), (3C), (3D), (3E), (3F), (3G), (3H), (3I), and (3J), $R^9$ is selected from:

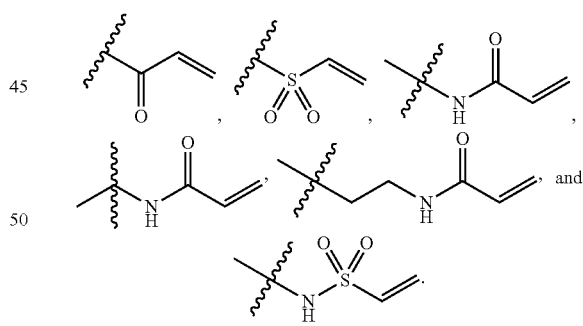

The compounds described herein may in some cases exist as diastereomers, enantiomers, or other stereoisomeric forms. The compounds presented herein include all diastereomeric, enantiomeric, and epimeric forms as well as the appropriate mixtures thereof. Separation of stereoisomers may be performed by chromatography or by the forming diastereomeric and separation by recrystallization, or chromatography, or any combination thereof. (Jean Jacques, Andre Collet, Samuel H. Wilen, "Enantiomers, Racemates and Resolutions", John Wiley And Sons, Inc., 1981, herein incorporated by reference for this disclosure). Stereoisomers may also be obtained by stereoselective synthesis.

In some situations, compounds may exist as tautomers. All tautomers are included within the formulas described herein.

Unless specified otherwise, divalent variables or groups described herein, such as variables V and G or any other divalent groups in any of the formulas described herein, e.g., Formulas (1), (2), (1A), (1B), (1C), (1D), (1E), (1F), (1G), (1H), (1I), (1J), (3), (3A), (3B), (3C), (3D), (3E), (3F), (3G), (3H), (3I), (3J), and (4) may be attached in the orientation in which they are depicted or they may be attached in the reverse orientation. For example, G may be depicted in the specification as

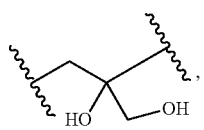 [SMILES: *CC(*)(O)CO]

wherein G may be oriented in the following structure:

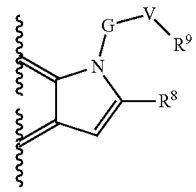

in the orientation depicted:

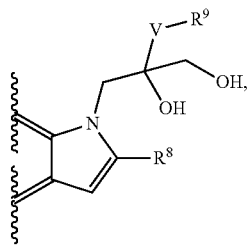

or in the reverse orientation:

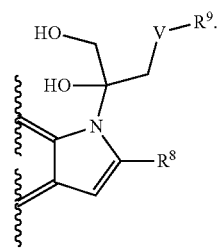

For another example, V may be depicted in the specification as

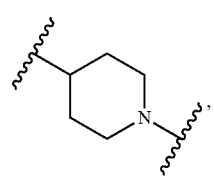 [SMILES: *C1CCN(*)CC1]

wherein V may be oriented in the following structure

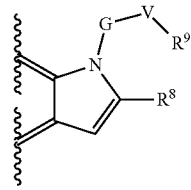

in the orientation depicted:

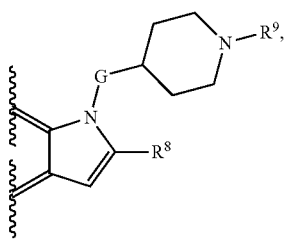

or in the reverse orientation:

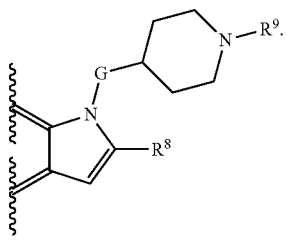

The methods and compositions described herein include the use of amorphous forms as well as crystalline forms (also known as polymorphs). The compounds described herein may be in the form of pharmaceutically acceptable salts. As well, active metabolites of these compounds having the same type of activity are included in the scope of the present disclosure. In addition, the compounds described herein can exist in unsolvated as well as solvated forms with pharmaceutically acceptable solvents such as water, ethanol, and the like. The solvated forms of the compounds presented herein are also considered to be disclosed herein.

In some embodiments, compounds or salts described herein may be prodrugs. A "prodrug" refers to an agent that is converted into the parent drug in vivo. Prodrugs are often useful because, in some situations, they may be easier to administer than the parent drug. They may, for instance, be bioavailable by oral administration whereas the parent is not. The prodrug may also have improved solubility in pharmaceutical compositions over the parent drug. An example, without limitation, of a prodrug would be a compound described herein, which is administered as an ester (the "prodrug") to facilitate transmittal across a cell membrane where water solubility is detrimental to mobility but which then is metabolically hydrolyzed to the carboxylic acid, the active entity, once inside the cell where water-solubility is beneficial. A further example of a prodrug might be a short peptide (polyaminoacid) bonded to an acid group where the peptide is metabolized to reveal the active moiety. In certain embodiments, upon in vivo administration, a prodrug is chemically converted to the biologically, pharmaceutically or therapeutically active form of the compound. In certain embodiments, a prodrug is enzymatically metabolized by one or more steps or processes to the biologically, pharmaceutically or therapeutically active form of the compound.

To produce a prodrug, a pharmaceutically active compound is modified such that the active compound will be regenerated upon in vivo administration. The prodrug can be designed to alter the metabolic stability or the transport characteristics of a drug, to mask side effects or toxicity, to improve the flavor of a drug or to alter other characteristics or properties of a drug. In some embodiments, by virtue of knowledge of pharmacodynamic processes and drug metabolism in vivo, once a pharmaceutically active compound is determined, prodrugs of the compound are designed. (see, for example, Nogrady (1985) *Medicinal Chemistry A Biochemical Approach*, Oxford University Press, New York, pages 388-392; Silverman (1992), The Organic Chemistry of Drug Design and Drug Action, Academic Press, Inc., San Diego, pages 352-401, Saulnier et al., (1994), *Bioorganic and Medicinal Chemistry Letters*, Vol. 4, p. 1985; Rooseboom et al., *Pharmacological Reviews*, 56:53-102, 2004; Miller et al., *J. Med. Chem. Vol.* 46, no. 24, 5097-5116, 2003; Aesop Cho, "Recent Advances in Oral Prodrug Discovery", *Annual Reports in Medicinal Chemistry*, Vol. 41, 395-407, 2006).

The compounds described herein may be labeled isotopically (e.g. with a radioisotope) or by other means, including, but not limited to, the use of chromophores or fluorescent moieties, bioluminescent labels, photoactivatable or chemiluminescent labels.

Compounds and salts described herein include isotopically-labeled compounds. In general, isotopically-labeled compounds are identical to those recited in the various formulae and structures presented herein, but for the fact that one or more atoms are replaced by an atom having an atomic mass or mass number different from the atomic mass or mass number most common in nature. Examples of isotopes that can be incorporated into the present compounds include isotopes of hydrogen, carbon, nitrogen, oxygen, fluorine and chlorine, for example, $^2$H, $^3$H, $^{13}$C, $^{15}$N, $^{18}$O, $^{17}$O, $^{35}$S, $^{18}$F, $^{36}$Cl, respectively. Certain isotopically-labeled compounds described herein, for example those into which radioactive isotopes such as $^3$H and $^{14}$C are incorporated, are useful in drug and/or substrate tissue distribution assays. Further, substitution with isotopes such as deuterium, i.e., $^2$H, can afford certain therapeutic advantages resulting from greater metabolic stability, such as, for example, increased in vivo half-life or reduced dosage requirements.

In additional or further embodiments, the compounds described herein are metabolized upon administration to an organism in need to produce a metabolite that is then used to produce a desired effect, including a desired therapeutic effect.

Compounds described herein may be formed as, and/or used as, pharmaceutically acceptable salts. The type of pharmaceutical acceptable salts, include, but are not limited to: (1) acid addition salts, formed by reacting the free base form of the compound with a pharmaceutically acceptable: inorganic acid, such as, for example, hydrochloric acid, hydrobromic acid, sulfuric acid, phosphoric acid, metaphosphoric acid, and the like; or with an organic acid, such as, for example, acetic acid, propionic acid, hexanoic acid, cyclopentanepropionic acid, glycolic acid, pyruvic acid, lactic acid, malonic acid, succinic acid, malic acid, maleic acid, fumaric acid, trifluoroacetic acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, toluenesulfonic acid, 2-naphthalenesulfonic acid, 4-methylbicyclo-[2.2.2]oct-2-ene-1-carboxylic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, butyric acid, phenylacetic acid, phenylbutyric acid, valproic acid, and the like; (2) salts formed when an acidic proton present in the parent compound is replaced by a metal ion, e.g., an alkali metal ion (e.g. lithium, sodium, potassium), an alkaline earth ion (e.g. magnesium, or calcium), or an aluminum ion. In some cases, compounds described herein may coordinate with an organic base, such as, but not limited to, ethanolamine, diethanolamine, triethanolamine, tromethamine, N-methylglucamine, dicyclohexylamine, tris(hydroxymethyl)methylamine. In other cases, compounds described herein may form salts with amino acids such as, but not limited to, arginine, lysine, and the like. Acceptable inorganic bases used to form salts with compounds that include an acidic proton, include, but are not limited to, aluminum hydroxide, calcium hydroxide, potassium hydroxide, sodium carbonate, sodium hydroxide, and the like.

It should be understood that a reference to a pharmaceutically acceptable salt includes the solvent addition forms or crystal forms thereof, particularly solvates or polymorphs. Solvates contain either stoichiometric or non-stoichiometric amounts of a solvent, and may be formed during the process of crystallization with pharmaceutically acceptable solvents such as water, ethanol, and the like. Hydrates are formed when the solvent is water, or alcoholates are formed when the solvent is alcohol. Solvates of compounds described herein can be conveniently prepared or formed during the processes described herein. In addition, the compounds provided herein can exist in unsolvated as well as solvated forms. In general, the solvated forms are considered equivalent to the unsolvated forms for the purposes of the compounds and methods provided herein.

In some embodiments, compounds described herein, such as compounds of any one of Formulas (1), (2), (1A), (1B), (1C), (1D), (1E), (1F), (1G), (1H), (1I), (1J), (3), (3A), (3B), (3C), (3D), (3E), (3F), (3G), (3H), (3I), (3J), and (4) are in various forms, including but not limited to, amorphous forms, milled forms and nano-particulate forms. In addition, compounds described herein include crystalline forms, also known as polymorphs. Polymorphs include the different crystal packing arrangements of the same elemental composition of a compound. Polymorphs usually have different X-ray diffraction patterns, melting points, density, hardness, crystal shape, optical properties, stability, and solubility. Various factors such as the recrystallization solvent, rate of crystallization, and storage temperature may cause a single crystal form to dominate.

The screening and characterization of the pharmaceutically acceptable salts, polymorphs and/or solvates may be accomplished using a variety of techniques including, but not limited to, thermal analysis, x-ray diffraction, spectroscopy, vapor sorption, and microscopy. Thermal analysis methods address thermo chemical degradation or thermo physical processes including, but not limited to, polymorphic transitions, and such methods are used to analyze the relationships between polymorphic forms, determine weight loss, to find the glass transition temperature, or for excipient compatibility studies. Such methods include, but are not limited to, Differential scanning calorimetry (DSC), Modulated Differential Scanning Calorimetry (MDCS), Thermogravimetric analysis (TGA), and Thermogravi-metric and Infrared analysis (TG/IR). X-ray diffraction methods include, but are not limited to, single crystal and powder diffractometers and synchrotron sources. The various spectroscopic techniques used include, but are not limited to, Raman, FTIR, UV-VIS, and NMR (liquid and solid state). The various microscopy techniques include, but are not limited to, polarized light microscopy, Scanning Electron Microscopy (SEM) with Energy Dispersive X-Ray Analysis (EDX), Environmental Scanning Electron Microscopy with EDX (in gas or water vapor atmosphere), IR microscopy, and Raman microscopy.

Throughout the specification, groups and substituents thereof can be chosen to provide stable moieties and compounds.

Pharmaceutical Compositions

In certain embodiments, compounds or salts of any one of Formulas (1), (2), (1A), (1B), (1C), (1D), (1E), (1F), (1G), (1H), (1I), (1J), (3), (3A), (3B), (3C), (3D), (3E), (3F), (3G), (3H), (3I), (3J), and (4) are combined with one or more additional agents to form pharmaceutical compositions. Pharmaceutical compositions may be formulated in a conventional manner using one or more physiologically acceptable carriers including excipients and auxiliaries which facilitate processing of the active compounds into preparations which can be used pharmaceutically. Proper formulation is dependent upon the route of administration chosen. Additional details about suitable excipients for pharmaceutical compositions described herein may be found, for example, in Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pa. 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins 1999), herein incorporated by reference for such disclosure.

A pharmaceutical composition, as used herein, refers to a mixture of a compound or salt of any one of Formulas (1), (2), (1A), (1B), (1C), (1D), (1E), (1F), (1G), (1H), (1I), (1J), (3), (3A), (3B), (3C), (3D), (3E), (3F), (3G), (3H), (3I), (3J), and (4) described herein, with other chemical components, such as carriers, stabilizers, diluents, dispersing agents, suspending agents, thickening agents, and/or excipients. The pharmaceutical composition facilitates administration of the compound to an organism. In practicing the methods of treatment or use provided herein, therapeutically effective amounts of compounds described herein are administered in a pharmaceutical composition to a mammal having a disease, disorder, or condition to be treated. In some embodiments, the mammal is a human. A therapeutically effective amount can vary widely depending on the severity of the disease, the age and relative health of the subject, the potency of the compound used and other factors. The compounds or salts of any one of Formulas (1), (2), (1A), (1B), (1C), (1D), (1E), (1F), (1G), (1H), (1I), (1J), (3), (3A), (3B), (3C), (3D), (3E), (3F), (3G), (3H), (3I), (3J), and (4) can be used singly or in combination with one or more therapeutic agents as components of mixtures (as in combination therapy).

The pharmaceutical formulations described herein can be administered to a subject by multiple administration routes, including but not limited to, oral, parenteral (e.g., intravenous, subcutaneous, intramuscular), intranasal, buccal, topical, rectal, or transdermal administration routes. Moreover, the pharmaceutical compositions described herein, which include a compound of any one of Formulas (1), (2), (1A), (1B), (1C), (1D), (1E), (1F), (1G), (1H), (1I), (1J), (3), (3A), (3B), (3C), (3D), (3E), (3F), (3G), (3H), (3I), (3J), and (4), can be formulated into any suitable dosage form, including but not limited to, aqueous oral dispersions, liquids, gels, syrups, elixirs, slurries, suspensions, aerosols, fast melt formulations, effervescent formulations, lyophilized formulations, tablets, powders, pills, dragees, and capsules.

One may administer the compounds and/or compositions in a local rather than systemic manner, for example, via injection of the compound directly into an organ or tissue, often in a depot preparation or sustained release formulation. Such long acting formulations may be administered by implantation (for example subcutaneously or intramuscularly) or by intramuscular injection. Furthermore, one may administer the drug in a targeted drug delivery system, for example, in a liposome coated with organ-specific antibody. The liposomes will be targeted to and taken up selectively by the organ. In addition, the drug may be provided in the form of a rapid release formulation, in the form of an extended release formulation, or in the form of an intermediate release formulation.

Pharmaceutical compositions including a compound described herein may be manufactured in a conventional manner, such as, by way of example only, by means of conventional mixing, dissolving, granulating, dragee-making, levigating, emulsifying, encapsulating, entrapping or compression processes.

The pharmaceutical compositions will include at least one compound of any one of Formulas (1), (2), (1A), (1B), (1C), (1D), (1E), (1F), (1G), (1H), (1I), (1J), (3), (3A), (3B), (3C), (3D), (3E), (3F), (3G), (3H), (3I), (3J), and (4), as an active ingredient in free-acid or free-base form, or in a pharmaceutically acceptable salt form.

In certain embodiments, compositions provided herein may also include one or more preservatives to inhibit microbial activity. Suitable preservatives include quaternary ammonium compounds such as benzalkonium chloride, cetyltrimethylammonium bromide and cetylpyridinium chloride.

Pharmaceutical preparations for oral use can be obtained by mixing one or more solid excipients with one or more of the compounds or salts of any one of Formulas (1), (2), (1A), (1B), (1C), (1D), (1E), (1F), (1G), (1H), (1I), (1J), (3), (3A), (3B), (3C), (3D), (3E), (3F), (3G), (3H), (3I), (3J), and (4), optionally grinding the resulting mixture, and processing the mixture of granules, after adding suitable auxiliaries, if desired, to obtain tablets, pills, or capsules. Suitable excipients include, for example, fillers such as sugars, including lactose, sucrose, mannitol, or sorbitol; cellulose preparations such as, for example, maize starch, wheat starch, rice starch, potato starch, gelatin, gum tragacanth, methylcellulose, microcrystalline cellulose, hydroxypropylmethylcellulose, sodium carboxymethylcellulose; or others such as: polyvinylpyrrolidone (PVP or povidone) or calcium phosphate. If desired, disintegrating agents may be added, such as the cross-linked croscarmellose sodium, polyvinylpyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations that can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added.

In some embodiments, the solid dosage forms disclosed herein may be in the form of a tablet, (including a suspension tablet, a fast-melt tablet, a bite-disintegration tablet, a rapid-disintegration tablet, an effervescent tablet, or a caplet), a pill, a powder (including a sterile packaged powder, a dispensable powder, or an effervescent powder), a capsule (including both soft or hard capsules, e.g., capsules made from animal-derived gelatin or plant-derived HPMC, or "sprinkle capsules"), solid dispersion, solid solution, bioerodible dosage form, multiparticulate dosage forms, pellets, granules, or an aerosol. In other embodiments, the pharmaceutical formulation is in the form of a powder. In still other embodiments, the pharmaceutical formulation is in the form of a tablet, including but not limited to, a fast-melt tablet. Additionally, pharmaceutical formulations of the compounds described herein may be administered as a single capsule or in multiple capsule dosage form. In some embodiments, the pharmaceutical formulation is administered in two, or three, or four, capsules or tablets.

In some embodiments, solid dosage forms, e.g., tablets, effervescent tablets, and capsules, are prepared by mixing particles of a compound or salt of any one of Formulas (1), (2), (1A), (1B), (1C), (1D), (1E), (1F), (1G), (1H), (1I), (1J), (3), (3A), (3B), (3C), (3D), (3E), (3F), (3G), (3H), (3I), (3J), and (4) described herein, with one or more pharmaceutical excipients to form a bulk blend composition. When referring to these bulk blend compositions as homogeneous, it is meant that the particles of the compound or salt of any one of Formulas (1), (2), (1A), (1B), (1C), (1D), (1E), (1F), (1G), (1H), (1I), (1J), (3), (3A), (3B), (3C), (3D), (3E), (3F), (3G), (3H), (3I), (3J), and (4) described herein, are dispersed evenly throughout the composition so that the composition may be subdivided into equally effective unit dosage forms, such as tablets, pills, and capsules. The individual unit dosages may also include film coatings, which disintegrate upon oral ingestion or upon contact with diluent. These formulations can be manufactured by conventional pharmacological techniques.

The pharmaceutical solid dosage forms described herein can include a compound of any one of Formulas (1), (2), (1A), (1B), (1C), (1D), (1E), (1F), (1G), (1H), (1I), (1J), (3), (3A), (3B), (3C), (3D), (3E), (3F), (3G), (3H), (3I), (3J), and (4) described herein, and one or more pharmaceutically acceptable additives such as a compatible carrier, binder, filling agent, suspending agent, flavoring agent, sweetening agent, disintegrating agent, dispersing agent, surfactant, lubricant, colorant, diluent, solubilizer, moistening agent, plasticizer, stabilizer, penetration enhancer, wetting agent, anti-foaming agent, antioxidant, preservative, or one or more combination thereof. In still other aspects, using standard coating procedures, such as those described in Remington's Pharmaceutical Sciences, 20th Edition (2000), a film coating is provided around the formulation of the compound described herein. In one embodiment, some or all of the particles of the compound described herein are coated. In another embodiment, some or all of the particles of the compound described herein are microencapsulated. In still another embodiment, the particles of the compound described herein are not microencapsulated and are uncoated.

Suitable carriers for use in the solid dosage forms described herein include, but are not limited to, acacia, gelatin, colloidal silicon dioxide, calcium glycerophosphate, calcium lactate, maltodextrin, glycerine, magnesium silicate, sodium caseinate, soy lecithin, sodium chloride, tricalcium phosphate, dipotassium phosphate, sodium stearoyl lactylate, carrageenan, monoglyceride, diglyceride, pregelatinized starch, hydroxypropylmethylcellulose, hydroxypropylmethylcellulose acetate stearate, sucrose, microcrystalline cellulose, lactose, mannitol and the like.

Suitable filling agents for use in the solid dosage forms described herein include, but are not limited to, lactose, calcium carbonate, calcium phosphate, dibasic calcium phosphate, calcium sulfate, microcrystalline cellulose, cellulose powder, dextrose, dextrates, dextran, starches, pregelatinized starch, hydroxypropylmethycellulose (HPMC), hydroxypropylmethycellulose phthalate, hydroxypropylmethylcellulose acetate stearate (HPMCAS), sucrose, xylitol, lactitol, mannitol, sorbitol, sodium chloride, polyethylene glycol, and the like.

In order to release the compound or salt of any one of Formulas (1), (2), (1A), (1B), (1C), (1D), (1E), (1F), (1G), (1H), (1I), (1J), (3), (3A), (3B), (3C), (3D), (3E), (3F), (3G), (3H), (3I), (3J), and (4) from a solid dosage form matrix as efficiently as possible, disintegrants are often used in the formulation, especially when the dosage forms are compressed with binder. Disintegrants help rupturing the dosage form matrix by swelling or capillary action when moisture is absorbed into the dosage form. Suitable disintegrants for use in the solid dosage forms described herein include, but are not limited to, natural starch such as corn starch or potato starch, a pregelatinized starch such as National 1551 or Amijel®, or sodium starch glycolate such as Promogel® or Explotab®, a cellulose such as a wood product, methylcrystalline cellulose, e.g., Avicel®, Avicel® PH101, Avicel® PH102, Avicel® PH105, Elcema® P100, Emcocel®, Vivacel®, Ming Tia®, and Solka-Floc®, methylcellulose, croscarmellose, or a cross-linked cellulose, such as cross-linked sodium carboxymethylcellulose (Ac-Di-Sol®), cross-linked carboxymethylcellulose, or cross-linked croscarmellose, a cross-linked starch such as sodium starch glycolate, a cross-linked polymer such as crospovidone, a cross-linked polyvinylpyrrolidone, alginate such as alginic acid or a salt of alginic acid such as sodium alginate, a clay such as Veegum® HV (magnesium aluminum silicate), a gum such as agar, guar, locust bean, Karaya, pectin, or tragacanth, sodium starch glycolate, bentonite, a natural sponge, a surfactant, a resin such as a cation-exchange resin, citrus pulp, sodium lauryl sulfate, sodium lauryl sulfate in combination starch, and the like.

Binders impart cohesiveness to solid oral dosage form formulations: for powder filled capsule formulation, they aid in plug formation that can be filled into soft or hard shell capsules and for tablet formulation, they ensure the tablet remaining intact after compression and help assure blend uniformity prior to a compression or fill step. Materials suitable for use as binders in the solid dosage forms described herein include, but are not limited to, carboxymethylcellulose, methylcellulose (e.g., Methocel®), hydroxypropylmethylcellulose (e.g. Hypromellose USP Pharmacoat-603, hydroxypropylmethylcellulose acetate stearate (Aqoate HS-LF and HS), hydroxyethylcellulose, hydroxypropylcellulose (e.g., Klucel®), ethylcellulose (e.g., Ethocel®), and microcrystalline cellulose (e.g., Avicel®), microcrystalline dextrose, amylose, magnesium aluminum silicate, polysaccharide acids, bentonites, gelatin, polyvinylpyrrolidone/vinyl acetate copolymer, crospovidone, povidone, starch, pregelatinized starch, tragacanth, dextrin, a sugar, such as sucrose (e.g., Dipac®), glucose, dextrose, molasses, mannitol, sorbitol, xylitol (e.g., Xylitab®), lactose, a natural or synthetic gum such as acacia, tragacanth, ghatti gum, mucilage of isapol husks, starch, polyvinylpyrrolidone (e.g., Povidone® CL, Kollidon® CL, Polyplasdone® XL-10, and Povidone® K-12), larch arabogalactan, Veegum®, polyethylene glycol, waxes, sodium alginate, and the like.

In general, binder levels of 20-70% are used in powder-filled gelatin capsule formulations. Binder usage level in tablet formulations varies whether direct compression, wet granulation, roller compaction, or usage of other excipients such as fillers which itself can act as moderate binder. In some embodiments, formulators determine the binder level for the formulations, but binder usage level of up to 70% in tablet formulations is common.

Suitable lubricants or glidants for use in the solid dosage forms described herein include, but are not limited to, stearic acid, calcium hydroxide, talc, corn starch, sodium stearyl fumerate, alkali-metal and alkaline earth metal salts, such as aluminum, calcium, magnesium, zinc, stearic acid, sodium stearates, magnesium stearate, zinc stearate, waxes, Stearowet®, boric acid, sodium benzoate, sodium acetate, sodium chloride, leucine, a polyethylene glycol or a methoxypolyethylene glycol such as Carbowax™, PEG 4000, PEG 5000, PEG 6000, propylene glycol, sodium oleate, glyceryl behenate, glyceryl palmitostearate, glyceryl benzoate, magnesium or sodium lauryl sulfate, and the like.

Suitable diluents for use in the solid dosage forms described herein include, but are not limited to, sugars (including lactose, sucrose, and dextrose), polysaccharides (including dextrates and maltodextrin), polyols (including mannitol, xylitol, and sorbitol), cyclodextrins and the like.

Suitable wetting agents for use in the solid dosage forms described herein include, for example, oleic acid, glyceryl monostearate, sorbitan monooleate, sorbitan monolaurate, triethanolamine oleate, polyoxyethylene sorbitan monooleate, polyoxyethylene sorbitan monolaurate, quaternary ammonium compounds (e.g., Polyquat 10®), sodium oleate, sodium lauryl sulfate, magnesium stearate, sodium docusate, triacetin, vitamin E TPGS and the like.

Suitable surfactants for use in the solid dosage forms described herein include, for example, sodium lauryl sulfate, sorbitan monooleate, polyoxyethylene sorbitan monooleate, polysorbates, polaxomers, bile salts, glyceryl monostearate, copolymers of ethylene oxide and propylene oxide, e.g., Pluronic® (BASF), and the like.

Suitable suspending agents for use in the solid dosage forms described here include, but are not limited to, polyvinylpyrrolidone, e.g., polyvinylpyrrolidone K12, polyvinylpyrrolidone K17, polyvinylpyrrolidone K25, or polyvinylpyrrolidone K30, polyethylene glycol, e.g., the polyethylene glycol can have a molecular weight of about 300 to about 6000, or about 3350 to about 4000, or about 5400 to about 7000, vinyl pyrrolidone/vinyl acetate copolymer (S630), sodium carboxymethylcellulose, methylcellulose, hydroxy-propylmethylcellulose, polysorbate-80, hydroxyethylcellulose, sodium alginate, gums, such as, e.g., gum tragacanth and gum acacia, guar gum, xanthans, including xanthan gum, sugars, cellulosics, such as, e.g., sodium carboxymethylcellulose, methylcellulose, sodium carboxymethylcellulose, hydroxypropylmethylcellulose, hydroxyethylcellulose, polysorbate-80, sodium alginate, polyethoxylated sorbitan monolaurate, polyethoxylated sorbitan monolaurate, povidone and the like.

Suitable antioxidants for use in the solid dosage forms described herein include, for example, e.g., butylated hydroxytoluene (BHT), sodium ascorbate, and tocopherol.

There is considerable overlap between additives used in the solid dosage forms described herein. Thus, the above-listed additives should be taken as merely exemplary, and not limiting, of the types of additives that can be included in solid dosage forms of the pharmaceutical compositions described herein.

In other embodiments, one or more layers of the pharmaceutical formulation are plasticized. Illustratively, a plasticizer is generally a high boiling point solid or liquid. Suitable plasticizers can be added from about 0.01% to about 50% by weight (w/w) of the coating composition. Plasticizers include, but are not limited to, diethyl phthalate, citrate esters, polyethylene glycol, glycerol, acetylated glycerides, triacetin, polypropylene glycol, polyethylene glycol, triethyl citrate, dibutyl sebacate, stearic acid, stearol, stearate, and castor oil.

Compressed tablets are solid dosage forms prepared by compacting the bulk blend of the formulations described above. In various embodiments, compressed tablets which are designed to dissolve in the mouth will include one or more flavoring agents. In other embodiments, the compressed tablets will include a film surrounding the final compressed tablet. In some embodiments, the film coating aids in patient compliance (e.g., Opadry® coatings or sugar coating). Film coatings including Opadry® typically range from about 1% to about 3% of the tablet weight. In other embodiments, the compressed tablets include one or more excipients.

A capsule may be prepared, for example, by placing the bulk blend of the formulation of the compound described above, inside of a capsule. In some embodiments, the formulations (non-aqueous suspensions and solutions) are placed in a soft gelatin capsule. In other embodiments, the formulations are placed in standard gelatin capsules or non-gelatin capsules such as capsules comprising HPMC. In other embodiments, the formulation is placed in a sprinkle capsule, wherein the capsule may be swallowed whole or the capsule may be opened and the contents sprinkled on food prior to eating. In some embodiments, the therapeutic dose is split into multiple (e.g., two, three, or four) capsules. In some embodiments, the entire dose of the formulation is delivered in a capsule form.

In various embodiments, the particles of the compound or salt of any one of Formulas (1), (2), (1A), (1B), (1C), (1D), (1E), (1F), (1G), (1H), (1I), (1J), (3), (3A), (3B), (3C), (3D), (3E), (3F), (3G), (3H), (3I), (3J), and (4), and one or more excipients are dry blended and compressed into a mass, such as a tablet, having a hardness sufficient to provide a pharmaceutical composition that substantially disintegrates within less than about 30 minutes, less than about 35 minutes, less than about 40 minutes, less than about 45 minutes, less than about 50 minutes, less than about 55 minutes, or less than about 60 minutes, after oral administration, thereby releasing the formulation into the gastrointestinal fluid.

In another aspect, dosage forms may include microencapsulated formulations. In some embodiments, one or more other compatible materials are present in the microencapsulation material. Exemplary materials include, but are not limited to, pH modifiers, erosion facilitators, anti-foaming agents, antioxidants, flavoring agents, and carrier materials such as binders, suspending agents, disintegration agents, filling agents, surfactants, solubilizers, stabilizers, lubricants, wetting agents, and diluents.

Materials useful for the microencapsulation described herein include materials compatible with compounds described herein, which sufficiently isolate the compound from other non-compatible excipients.

In still other embodiments, effervescent powders are also prepared in accordance with the present disclosure. Effervescent salts have been used to disperse medicines in water for oral administration. Effervescent salts are granules or coarse powders containing a medicinal agent in a dry mixture, usually composed of sodium bicarbonate, citric acid and/or tartaric acid. When such salts are added to water, the acids and the base react to liberate carbon dioxide gas, thereby causing "effervescence." Examples of effervescent salts include, e.g., the following ingredients: sodium bicarbonate or a mixture of sodium bicarbonate and sodium carbonate, citric acid and/or tartaric acid. Any acid-base combination that results in the liberation of carbon dioxide can be used in place of the combination of sodium bicarbonate and citric and tartaric acids, as long as the ingredients were suitable for pharmaceutical use and result in a pH of about 6.0 or higher.

In other embodiments, the formulations described herein, which include a compound or salt of any one of Formulas (1), (2), (1A), (1B), (1C), (1D), (1E), (1F), (1G), (1H), (1I), (1J), (3), (3A), (3B), (3C), (3D), (3E), (3F), (3G), (3H), (3I), (3J), and (4), are solid dispersions. Methods of producing such solid dispersions include, but are not limited to, for example, U.S. Pat. Nos. 4,343,789, 5,340,591, 5,456,923, 5,700,485, 5,723,269, and U.S. patent publication no. 2004/0013734. In still other embodiments, the formulations described herein are solid solutions. Solid solutions incorporate a substance together with the active agent and other excipients such that heating the mixture results in dissolution of the drug and the resulting composition is then cooled to provide a solid blend which can be further formulated or directly added to a capsule or compressed into a tablet. Methods of producing such solid solutions include, but are not limited to, for example, U.S. Pat. Nos. 4,151,273, 5,281,420, and 6,083,518.

In some embodiments, pharmaceutical formulations are provided that include particles of the compounds or salt of any one of Formulas (1), (2), (1A), (1B), (1C), (1D), (1E), (1F), (1G), (1H), (1I), (1J), (3), (3A), (3B), (3C), (3D), (3E), (3F), (3G), (3H), (3I), (3J), and (4), and at least one dispersing agent or suspending agent for oral administration to a subject. The formulations may be a powder and/or granules for suspension, and upon admixture with water, a substantially uniform suspension is obtained.

Liquid formulation dosage forms for oral administration can be aqueous suspensions selected from the group including, but not limited to, pharmaceutically acceptable aqueous oral dispersions, emulsions, solutions, elixirs, gels, and syrups. See, e.g., Singh et al., Encyclopedia of Pharmaceutical Technology, 2nd Ed., pp. 754-757 (2002).

The aqueous suspensions and dispersions described herein can remain in a homogenous state, as defined in The USP Pharmacists' Pharmacopeia (2005 edition, chapter 905), for at least 4 hours. The homogeneity should be determined by a sampling method consistent with regard to determining homogeneity of the entire composition. In one embodiment, an aqueous suspension can be re-suspended into a homogenous suspension by physical agitation lasting less than 1 minute. In another embodiment, an aqueous suspension can be re-suspended into a homogenous suspension by physical agitation lasting less than 45 seconds. In yet another embodiment, an aqueous suspension can be re-suspended into a homogenous suspension by physical agitation lasting less than 30 seconds. In still another embodiment, no agitation is necessary to maintain a homogeneous aqueous dispersion.

The pharmaceutical compositions described herein may include sweetening agents such as, but not limited to, acacia syrup, acesulfame K, alitame, anise, apple, aspartame, banana, Bavarian cream, berry, black currant, butterscotch, calcium citrate, camphor, caramel, cherry, cherry cream, chocolate, cinnamon, bubble gum, citrus, citrus punch, citrus cream, cotton candy, cocoa, cola, cool cherry, cool citrus, cyclamate, cylamate, dextrose, *eucalyptus*, eugenol, fructose, fruit punch, ginger, glycyrrhetinate, *glycyrrhiza* (licorice) syrup, grape, grapefruit, honey, isomalt, lemon, lime, lemon cream, monoammonium glyrrhizinate (MagnaSweet®), maltol, mannitol, maple, marshmallow, menthol, mint cream, mixed berry, neohesperidine DC, neotame, orange, pear, peach, peppermint, peppermint cream, Prosweet® Powder, raspberry, root beer, rum, saccharin, safrole, sorbitol, spearmint, spearmint cream, strawberry, strawberry cream, *stevia*, sucralose, sucrose, sodium saccharin, saccharin, aspartame, acesulfame potassium, mannitol, talin, sucralose, sorbitol, swiss cream, tagatose, tangerine, thaumatin, tutti fruitti, vanilla, walnut, watermelon, wild cherry, wintergreen, xylitol, or any combination of these flavoring ingredients, e.g., anise-menthol, cherry-anise, cinnamon-orange, cherry-cinnamon, chocolate-mint, honey-lemon, lemon-lime, lemon-mint, menthol-*eucalyptus*, orange-cream, vanilla-mint, and mixtures thereof.

In some embodiments, the pharmaceutical formulations described herein can be self-emulsifying drug delivery systems (SEDDS). Emulsions are dispersions of one immiscible phase in another, usually in the form of droplets. Generally, emulsions are created by vigorous mechanical dispersion. SEDDS, as opposed to emulsions or microemulsions, spontaneously form emulsions when added to an excess of water without any external mechanical dispersion or agitation. An advantage of SEDDS is that only gentle mixing is required to distribute the droplets throughout the solution. Additionally, water or the aqueous phase can be added just prior to administration, which ensures stability of an unstable or hydrophobic active ingredient. Thus, the SEDDS provides an effective delivery system for oral and parenteral delivery of hydrophobic active ingredients. SEDDS may provide improvements in the bioavailability of hydrophobic active ingredients. Methods of producing self-emulsifying dosage forms include, but are not limited to, for example, U.S. Pat. Nos. 5,858,401, 6,667,048, and 6,960,563.

There is overlap between the above-listed additives used in the aqueous dispersions or suspensions described herein, since a given additive is often classified differently by different practitioners in the field, or is commonly used for any of several different functions. Thus, the above-listed additives should be taken as merely exemplary, and not limiting, of the types of additives that can be included in formulations described herein.

Potential excipients for intranasal formulations include, for example, U.S. Pat. Nos. 4,476,116, 5,116,817 and 6,391,452. Formulations solutions in saline, employing benzyl alcohol or other suitable preservatives, fluorocarbons, and/or other solubilizing or dispersing agents. See, for example, Ansel, H. C. et al., Pharmaceutical Dosage Forms and Drug Delivery Systems, Sixth Ed. (1995). Preferably these compositions and formulations are prepared with suitable non-toxic pharmaceutically acceptable ingredients. The choice of suitable carriers is highly dependent upon the exact nature of the nasal dosage form desired, e.g., solutions, suspensions, ointments, or gels. Nasal dosage forms generally contain large amounts of water in addition to the active ingredient. Minor amounts of other ingredients such as pH adjusters, emulsifiers or dispersing agents, preservatives, surfactants, gelling agents, or buffering and other stabilizing and solubilizing agents may also be present. Preferably, the nasal dosage form should be isotonic with nasal secretions.

For administration by inhalation, the compounds described herein may be in a form as an aerosol, a mist or a powder. Pharmaceutical compositions described herein are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. Capsules and cartridges of, such as, by way of example only, gelatin for use in an inhaler or insufflator may be formulated containing a powder mix of the compound described herein and a suitable powder base such as lactose or starch.

Buccal formulations that include compounds described herein may be administered using a variety of formulations which include, but are not limited to, U.S. Pat. Nos. 4,229,447, 4,596,795, 4,755,386, and 5,739,136. In addition, the buccal dosage forms described herein can further include a bioerodible (hydrolysable) polymeric carrier that also serves to adhere the dosage form to the buccal mucosa. The buccal dosage form is fabricated so as to erode gradually over a predetermined time period, wherein the delivery of the compound is provided essentially throughout. Buccal drug delivery avoids the disadvantages encountered with oral drug administration, e.g., slow absorption, degradation of the active agent by fluids present in the gastrointestinal tract and/or first-pass inactivation in the liver. With regard to the bioerodible (hydrolysable) polymeric carrier, virtually any such carrier can be used, so long as the desired drug release profile is not compromised, and the carrier is compatible with the compounds described herein, and any other components that may be present in the buccal dosage unit. Generally, the polymeric carrier comprises hydrophilic (water-soluble and water-swellable) polymers that adhere to the wet surface of the buccal mucosa. Examples of polymeric carriers useful herein include acrylic acid polymers and co, e.g., those known as "carbomers" (Carbopol®, which may be obtained from B.F. Goodrich, is one such polymer). Other components may also be incorporated into the buccal dosage forms described herein include, but are not limited to, disintegrants, diluents, binders, lubricants, flavoring, colorants, preservatives, and the like. For buccal or sublingual administration, the compositions may take the form of tablets, lozenges, or gels formulated in a conventional manner.

Transdermal formulations described herein may be administered using a variety of devices including but not limited to, U.S. Pat. Nos. 3,598,122, 3,598,123, 3,710,795, 3,731,683, 3,742,951, 3,814,097, 3,921,636, 3,972,995, 3,993,072, 3,993,073, 3,996,934, 4,031,894, 4,060,084, 4,069,307, 4,077,407, 4,201,211, 4,230,105, 4,292,299, 4,292,303, 5,336,168, 5,665,378, 5,837,280, 5,869,090, 6,923,983, 6,929,801 and 6,946,144.

The transdermal dosage forms described herein may incorporate certain pharmaceutically acceptable excipients which are conventional in the art. In one embodiment, the transdermal formulations described herein include at least three components: (1) a formulation of a compound or salt of any one of Formulas (1), (2), (1A), (1B), (1C), (1D), (1E), (1F), (1G), (1H), (1I), (1J), (3), (3A), (3B), (3C), (3D), (3E), (3F), (3G), (3H), (3I), (3J), and (4); (2) a penetration enhancer; and (3) an aqueous adjuvant. In addition, transdermal formulations can include additional components such as, but not limited to, gelling agents, creams and ointment bases, and the like. In some embodiments, the transdermal formulation can further include a woven or non-woven backing material to enhance absorption and prevent the removal of the transdermal formulation from the skin. In other embodiments, the transdermal formulations described herein can maintain a saturated or supersaturated state to promote diffusion into the skin.

Formulations suitable for transdermal administration of compounds described herein may employ transdermal delivery devices and transdermal delivery patches and can be lipophilic emulsions or buffered, aqueous solutions, dissolved and/or dispersed in a polymer or an adhesive. Such patches may be constructed for continuous, pulsatile, or on demand delivery of pharmaceutical agents. Still further, transdermal delivery of the compounds described herein can be accomplished by means of iontophoretic patches and the like. Additionally, transdermal patches can provide controlled delivery of the compounds described herein. The rate of absorption can be slowed by using rate-controlling membranes or by trapping the compound within a polymer matrix or gel. Conversely, absorption enhancers can be used to increase absorption. An absorption enhancer or carrier can include absorbable pharmaceutically acceptable solvents to assist passage through the skin. For example, transdermal devices are in the form of a bandage comprising a backing member, a reservoir containing the compound optionally with carriers, optionally a rate controlling barrier to deliver the compound to the skin of the host at a controlled and predetermined rate over a prolonged period of time, and means to secure the device to the skin.

Formulations suitable for intramuscular, subcutaneous, or intravenous injection may include physiologically acceptable sterile aqueous or non-aqueous solutions, dispersions, suspensions or emulsions, and sterile powders for reconstitution into sterile injectable solutions or dispersions. Examples of suitable aqueous and non-aqueous carriers, diluents, solvents, or vehicles including water, ethanol, polyols (propyleneglycol, polyethylene-glycol, glycerol, cremophor and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions, and by the use of surfactants. Formulations suitable for subcutaneous injection may also contain additives such as preserving, wetting, emulsifying, and dispensing agents. Prevention of the growth of microorganisms can be ensured by various antibacterial and antifungal agents, such as parabens, chlorobutanol, phenol, sorbic acid, and the like. It may also be desirable to include isotonic agents, such as sugars, sodium chloride, and the like. Prolonged absorption of the injectable pharmaceutical form can be brought about by the use of agents delaying absorption, such as aluminum monostearate and gelatin.

For intravenous injections, compounds described herein may be formulated in aqueous solutions, preferably in physiologically compatible buffers such as Hank's solution, Ringer's solution, or physiological saline buffer. For transmucosal administration, penetrants appropriate to the barrier to be permeated are used in the formulation. Such penetrants are generally recognized in the field. For other parenteral injections, appropriate formulations may include aqueous or nonaqueous solutions, preferably with physiologically compatible buffers or excipients. Such excipients are generally recognized in the field.

Parenteral injections may involve bolus injection or continuous infusion. Formulations for injection may be presented in unit dosage form, e.g., in ampoules or in multi-dose containers, with an added preservative. The pharmaceutical composition described herein may be in a form suitable for parenteral injection as a sterile suspensions, solutions or emulsions in oily or aqueous vehicles, and may contain formulatory agents such as suspending, stabilizing and/or dispersing agents. Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions. Alternatively, the active ingredient may be in powder form for constitution with a suitable vehicle, e.g., sterile pyrogen-free water, before use.

In certain embodiments, delivery systems for pharmaceutical compounds may be employed, such as, for example, liposomes and emulsions. In certain embodiments, compositions provided herein also include an mucoadhesive polymer, selected from among, for example, carboxymethylcellulose, carbomer (acrylic acid polymer), poly (methylmethacrylate), polyacrylamide, polycarbophil, acrylic acid/butyl acrylate copolymer, sodium alginate and dextran.

In some embodiments, the compounds described herein may be administered topically and are formulated into a variety of topically administrable compositions, such as solutions, suspensions, lotions, gels, pastes, medicated sticks, balms, creams or ointments. Such pharmaceutical compounds can contain solubilizers, stabilizers, tonicity enhancing agents, buffers and preservatives.

The compounds described herein may also be formulated in rectal compositions such as enemas, rectal gels, rectal foams, rectal aerosols, suppositories, jelly suppositories, or retention enemas, containing conventional suppository bases such as cocoa butter or other glycerides, as well as synthetic polymers such as polyvinylpyrrolidone, PEG, and the like. In suppository forms of the compositions, a low-melting wax such as, but not limited to, a mixture of fatty acid glycerides, optionally in combination with cocoa butter is first melted.

Generally, an agent, such as a compound of any one of Formulas (1), (2), (1A), (1B), (1C), (1D), (1E), (1F), (1G), (1H), (1I), (1J), (3), (3A), (3B), (3C), (3D), (3E), (3F), (3G), (3H), (3I), (3J), and (4), is administered in an amount effective for amelioration of, or prevention of the development of symptoms of, the disease or disorder (i.e., a therapeutically effective amount). Thus, a therapeutically effective amount can be an amount that is capable of at least partially preventing or reversing a disease or disorder. The dose required to obtain an effective amount may vary depending on the agent, formulation, disease or disorder, and individual to whom the agent is administered.

Determination of effective amounts may also involve in vitro assays in which varying doses of agent are administered to cells in culture and the concentration of agent effective for ameliorating some or all symptoms is determined in order to calculate the concentration required in vivo. Effective amounts may also be based in in vivo animal studies.

An agent can be administered prior to, concurrently with and subsequent to the appearance of symptoms of a disease or disorder. In some embodiments, an agent is administered to a subject with a family history of the disease or disorder, or who has a phenotype that may indicate a predisposition to a disease or disorder, or who has a genotype which predisposes the subject to the disease or disorder.

In some embodiments, the compositions described herein are provided as pharmaceutical and/or therapeutic compositions. The pharmaceutical and/or therapeutic compositions of the present invention can be administered in a number of ways depending upon whether local or systemic treatment is desired and upon the area to be treated. Administration can be topical (including ophthalmic and to mucous membranes including vaginal and rectal delivery), pulmonary (e.g., by inhalation or insufflation of powders or aerosols, including by nebulizer; intratracheal, intranasal, epidermal and transdermal), oral or parenteral. Parenteral administration includes intravenous, intraarterial, subcutaneous, intraperitoneal or intramuscular injection or infusion; or intracranial, e.g., intrathecal or intraventricular, administration. Compositions and formulations for topical administration can include transdermal patches, ointments, lotions, creams, gels, drops, suppositories, sprays, liquids and powders. Conventional carriers; aqueous, powder, or oily bases; thickeners; and the like can be necessary or desirable. Compositions and formulations for oral administration include powders or granules, suspensions or solutions in water or non-aqueous media, capsules, sachets or tablets. Thickeners, flavoring agents, diluents, emulsifiers, dispersing aids or binders can be desirable. Compositions and formulations for parenteral, intrathecal or intraventricular administration can include sterile aqueous solutions that can also contain buffers, diluents and other suitable additives such as, but not limited to, penetration enhancers, carrier compounds and other pharmaceutically acceptable carriers or excipients. Pharmaceutical and/or therapeutic compositions of the present invention include, but are not limited to, solutions, emulsions, and liposome containing formulations. These compositions can be generated from a variety of components that include, but are not limited to, preformed liquids, self-emulsifying solids and self-emulsifying semisolids.

The pharmaceutical and/or therapeutic formulations, which can conveniently be presented in unit dosage form, can be prepared according to conventional techniques well known in the pharmaceutical/nutriceutical industries. Such techniques include the step of bringing into association the active ingredients with the pharmaceutical carrier(s) or excipient(s). In general the formulations are prepared by uniformly and intimately bringing into association the active ingredients with liquid carriers or finely divided solid carriers or both, and then, if necessary, shaping the product. The compositions of the present invention can be formulated into any of many possible dosage forms such as, but not limited to, tablets, capsules, liquid syrups, soft gels, suppositories, and enemas. The compositions of the present invention can also be formulated as suspensions in aqueous, non-aqueous, oil-based, or mixed media. Suspensions can further contain substances that increase the viscosity of the suspension including, for example, sodium carboxymethylcellulose, sorbitol and/or dextran. The suspension can also contain stabilizers. In one embodiment of the present invention the pharmaceutical compositions can be formulated and used as foams. Pharmaceutical foams include formulations such as, but not limited to, emulsions, microemulsions, creams, jellies and liposomes. While basically similar in nature these formulations vary in the components and the consistency of the final product.

The pharmaceutical composition described herein may be in unit dosage forms suitable for single administration of precise dosages. In unit dosage form, the formulation is divided into unit doses containing appropriate quantities of one or more compound. The unit dosage may be in the form of a package containing discrete quantities of the formulation. Non-limiting examples are packaged tablets or capsules, and powders in vials or ampoules. Aqueous suspension compositions can be packaged in single-dose non-reclosable containers. Alternatively, multiple-dose reclosable containers can be used, in which case it is typical to include a preservative in the composition. By way of example only, formulations for parenteral injection may be presented in unit dosage form, which include, but are not limited to ampoules, or in multi-dose containers, with an added preservative.

Dosing and administration regimes are tailored by the clinician, or others skilled in the pharmacological arts, based upon well-known pharmacological and therapeutic considerations including, but not limited to, the desired level of therapeutic effect, and the practical level of therapeutic effect obtainable. Generally, it is advisable to follow well-known pharmacological principles for administrating chemotherapeutic agents (e.g., it is generally advisable to not change dosages by more than 50% at time and no more than every 3-4 agent half-lives). For compositions that have relatively little or no dose-related toxicity considerations, and where maximum efficacy is desired, doses in excess of the average required dose are not uncommon. This approach to dosing is commonly referred to as the "maximal dose" strategy. In certain embodiments, the compounds are administered to a subject at a dose of about 0.01 mg/kg to about 200 mg/kg, more preferably at about 0.1 mg/kg to about 100 mg/kg, even more preferably at about 0.5 mg/kg to about 50 mg/kg. When the compounds described herein are co-administered with another agent (e.g., as sensitizing agents), the effective amount may be less than when the agent is used alone. Dosing may be once per day or multiple times per day for one or more consecutive days.

Methods of Treatment

The present disclosure provides compounds and methods for modulating the interaction of menin with its upstream or downstream signaling molecules including but not limited to MLL1, MLL2 and MLL-fusion oncoproteins. In certain embodiments, the disclosure provides compounds and methods for inhibiting the interaction of menin with one or more proteins such as MLL1, MLL2, a MLL fusion protein and a MLL Partial Tandem Duplication.

Inhibition of the interaction of menin and one or more MLL proteins may be assessed and demonstrated by a wide variety of ways known in the art. Non-limiting examples include a showing of any one of (a) a decrease in menin binding to one or more MLL proteins or MLL protein fragments; (b) a decrease in cell proliferation and/or cell viability; (c) an increase in cell differentiation; (d) a decrease in the levels of downstream targets of MLL1, MLL2, a MLL fusion protein, and/or a MLL Partial Tandem Duplication, e.g., Hoxa9 and Meis1; and (e) decrease in tumor volume and/or tumor volume growth rate. Kits and commercially available assays can be utilized for determining one or more of the above.

The disclosure provides compounds and methods for treating a subject suffering from a disease, comprising administering a compound or salt described herein, for example, a compound or salt of any of Formulas (1), (2), (1A), (1B), (1C), (1D), (1E), (1F), (1G), (1H), (1I), (1J), (3), (3A), (3B), (3C), (3D), (3E), (3F), (3G), (3H), (3I), (3J), and (4), to the subject. In certain embodiments, the disease is selected from a disease associated with menin, MLL, MLL1, MLL2, and/or MLL fusion proteins (e.g., cancer). In certain embodiments, the disease is mediated by menin. In certain embodiments, the disease is leukemia, hematologic malignancies, solid tumor cancer, glioma, or diabetes. In particular embodiments, the leukemia is Acute lymphoblastic leukemia (ALL), Acute myelogenous leukemia (AML), Mixed Lineage Leukemia or leukemias with Partial Tandem Duplications of MLL. In certain embodiments, the compound covalently binds to menin and inhibits the interaction of menin and MLL.

In some embodiments, the disclosure provides a method for treating cancer in a subject, comprising administering a compound or salt described herein, for example, a compound or salt of any of Formulas (1), (2), (1A), (1B), (1C), (1D), (1E), (1F), (1G), (1H), (1I), (1J), (3), (3A), (3B), (3C), (3D), (3E), (3F), (3G), (3H), (3I), (3J), and (4), to the subject. In some embodiments, the cancer is mediated by a MLL fusion protein. In certain embodiments, the cancer is leukemia, breast cancer, prostate cancer, pancreatic cancer, lung cancer, liver cancer, skin cancer, or a brain tumor. In certain embodiments, the cancer is leukemia.

In certain embodiments, the disclosure provides method of treating a disease in a subject, wherein the the method comprises determining if the subject has a MLL fusion protein and if the subject is determined to have a MLL fusion protein, then administering to the subject a therapeutically effective dose of a compound or salt described herein, for example, a compound or salt of any one of Formulas (1), (2), (1A), (1B), (1C), (1D), (1E), (1F), (1G), (1H), (1I), (1J), (3), (3A), (3B), (3C), (3D), (3E), (3F), (3G), (3H), (3I), (3J), and (4).

MLL fusion proteins have been identified in hematological malignancies, e.g., cancers that affect blood, bone marrow and/or lymph nodes. Accordingly, certain embodiments are directed to administration of a compound or salt described herein, for example, a compound or salt of any of any one of Formulas (1), (2), (1A), (1B), (1C), (1D), (1E), (1F), (1G), (1H), (1I), (1J), (3), (3A), (3B), (3C), (3D), (3E), (3F), (3G), (3H), (3I), (3J), and (4), to a subject with a hematological malignancy. Such malignancies include, but are not limited to, leukemias and lymphomas. For example, the presently disclosed compounds can be used for treatment of diseases such as ALL, AML, Chronic lymphocytic leukemia (CLL), small lymphocytic lymphoma (SLL), Chronic myelogenous leukemia (CML), Acute monocytic leukemia (AMoL), hairy cell leukemia, and/or other leukemias. In certain embodiments, the compounds or salts of the disclosure can be used for treatment of lymphomas such as all subtypes of Hodgkins lymphoma or non-Hodgkins lymphoma.

Determining whether a tumor or cancer comprises a MLL fusion protein can be undertaken by assessing the nucleotide sequence encoding the MLL fusion protein, by assessing the amino acid sequence of the MLL fusion protein, or by assessing the characteristics of a putative MLL fusion protein.

Methods for detecting a nucleotide sequence encoding a MLL fusion protein are known by those of skill in the art. These methods include, but are not limited to, polymerase chain reaction-restriction fragment length polymorphism (PCR-RFLP) assays, polymerase chain reaction-single strand conformation polymorphism (PCR-SSCP) assays, real-time PCR assays, PCR sequencing, mutant allele-specific PCR amplification (MASA) assays, direct sequencing, primer extension reactions, electrophoresis, oligonucleotide ligation assays, hybridization assays, TaqMan assays, SNP genotyping assays, high resolution melting assays and microarray analyses. In some embodiments, the MLL fusion protein is identified using a direct sequencing method of specific regions, e.g., exon 2 and/or exon 3, in the MLL or fusion partner gene, for example. This technique will identify all possible mutations in the region sequenced.

Methods for detecting a MLL fusion protein are known by those of skill in the art. These methods include, but are not limited to, detection of a MLL fusion protein using a binding agent, e.g., an antibody, specific for the fusion protein, protein electrophoresis and Western blotting, and direct peptide sequencing.

Methods for determining whether a tumor or cancer comprises a MLL fusion protein can use a variety of samples. In some embodiments, the sample is taken from a subject having a tumor or cancer. In some embodiments, the sample is taken from a subject having a cancer or tumor. In some embodiments, the sample is a fresh tumor/cancer sample. In some embodiments, the sample is a frozen tumor/cancer sample. In some embodiments, the sample is a formalin-fixed paraffin-embedded sample. In some embodiments, the sample is processed to a cell lysate. In some embodiments, the sample is processed to DNA or RNA.

In certain embodiments, the disclosure provides a method of inhibiting the interaction of menin with MLL in a sample, comprising administering the compound or salt described herein to said sample comprising MLL and menin. In certain embodiments, the MLL is selected from one or more of MLL1, MLL2, a MLL fusion protein, and a MLL Partial Tandem Duplication.

In certain embodiments, the method comprises treating a disease mediated by chromosomal rearrangement on chromosome 11q23, comprising administering to a subject in need thereof a therapeutically effective amount of a compound or salt described herein or a pharmaceutical composition thereof. In certain embodiments, the disease is mediated by menin.

The disclosure provides methods for treating a disease by administering a compound or salt of any one of Formulas (1), (2), (1A), (1B), (1C), (1D), (1E), (1F), (1G), (1H), (1I), (1J), (3), (3A), (3B), (3C), (3D), (3E), (3F), (3G), (3H), (3I), (3J), and (4), to a subject suffering from the disease, wherein the compound binds to menin and inhibits the interaction of menin with one or more proteins such as MLL1, MLL2, a MLL fusion protein, and/or a MLL Partial Tandem Duplication. In certain embodiments, the compound covalently binds to menin and inhibits the interaction of menin and MLL.

The disclosure also relates to a method of treating a hyperproliferative disorder in a mammal that comprises administering to the mammal a therapeutically effective amount of a compound or salt of any one of Formulas (1), (2), (1A), (1B), (1C), (1D), (1E), (1F), (1G), (1H), (1I), (1J), (3), (3A), (3B), (3C), (3D), (3E), (3F), (3G), (3H), (3I), (3J), and (4). In some embodiments, the method relates to the treatment of cancer such as acute myeloid leukemia, cancer in adolescents, adrenocortical carcinoma childhood, AIDS-related cancers, e.g., Lymphoma and Kaposi's Sarcoma, anal cancer, appendix cancer, astrocytomas, atypical teratoid, basal cell carcinoma, bile duct cancer, bladder cancer, bone cancer, brain stem glioma, brain tumor, breast cancer, bronchial tumors, burkitt lymphoma, carcinoid tumor, atypical teratoid, embryonal tumors, germ cell tumor, primary lymphoma, cervical cancer, childhood cancers, chordoma, cardiac tumors, chronic lymphocytic leukemia (CLL), chronic myelogenous leukemia (CML), chronic myleoproliferative disorders, colon cancer, colorectal cancer, craniopharyngioma, cutaneous T-cell lymphoma, extrahepatic ductal carcinoma in situ (DCIS), embryonal tumors, CNS cancer, endometrial cancer, ependymoma, esophageal cancer, esthesioneuroblastoma, ewing sarcoma, extracranial germ cell tumor, extragonadal germ cell tumor, eye cancer, fibrous histiocytoma of bone, gall bladder cancer, gastric cancer, gastrointestinal carcinoid tumor, gastrointestinal stromal tumors (GIST), germ cell tumor, gestational trophoblastic tumor, hairy cell leukemia, head and neck cancer, heart cancer, liver cancer, hodgkin lymphoma, hypopharyngeal cancer, intraocular melanoma, islet cell tumors, pancreatic neuroendocrine tumors, kidney cancer, laryngeal cancer, lip and oral cavity cancer, liver cancer, lobular carcinoma in situ (LCIS), lung cancer, lymphoma, metastatic squamous neck cancer with occult primary, midline tract carcinoma, mouth cancer multiple endocrine neoplasia syndromes, multiple myeloma/plasma cell neoplasm, mycosis fungoides, myelodysplastic syndromes, myelodysplastic/myeloproliferative neoplasms, multiple myeloma, merkel cell carcinoma, malignant mesothelioma, malignant fibrous histiocytoma of bone and osteosarcoma, nasal cavity and paranasal sinus cancer, nasopharyngeal cancer, neuroblastoma, non-hodgkin lymphoma, non-small cell lung cancer (NSCLC), oral cancer, lip and oral cavity cancer, oropharyngeal cancer, ovarian cancer, pancreatic cancer, papillomatosis, paraganglioma, paranasal sinus and nasal cavity cancer, parathyroid cancer, penile cancer, pharyngeal cancer, pleuropulmonary blastoma, primary central nervous system (CNS) lymphoma, prostate cancer, rectal cancer, transitional cell cancer, retinoblastoma, rhabdomyosarcoma, salivary gland cancer, skin cancer, stomach (gastric) cancer, small cell lung cancer, small intestine cancer, soft tissue sarcoma, T-Cell lymphoma, testicular cancer, throat cancer, thymoma and thymic carcinoma, thyroid cancer, transitional cell cancer of the renal pelvis and ureter, trophoblastic tumor, unusual cancers of childhood, urethral cancer, uterine sarcoma, vaginal cancer, vulvar cancer, or Viral-Induced cancer. In some embodiments, the method relates to the treatment of a non-cancerous hyperproliferative disorder such as benign hyperplasia of the skin, e.g., psoriasis, restenosis, or prostate, e.g., benign prostatic hypertrophy (BPH). In some cases, the method relates to the treatment of leukemia, hematologic malignancy, solid tumor cancer, prostate cancer, e.g., castration-resistant prostate cancer, breast cancer, Ewing's sarcoma, bone sarcoma, primary bone sarcoma, T-cell prolymphocyte leukemia, glioma, glioblastoma, liver cancer, e.g., hepatocellular carcinoma, or diabetes. In some cases, the leukemia comprises AML, ALL, Mixed Lineage Leukemia or leukemias with Partial Tandem Duplications of MLL.

In certain particular embodiments, the disclosure relates to methods for treatment of lung cancers, the methods comprise administering an effective amount of any of the above described compound or salt or pharmaceutical composition thereof to a subject in need thereof. In certain embodiments the lung cancer is a non-small cell lung carcinoma (NSCLC), for example adenocarcinoma, squamous-cell lung carcinoma or large-cell lung carcinoma. In other embodiments, the lung cancer is a small cell lung carcinoma. Other lung cancers treatable with the disclosed compounds include, but are not limited to, glandular tumors, carcinoid tumors and undifferentiated carcinomas.

Subjects that can be treated with compounds of the invention, or pharmaceutically acceptable salt, ester, prodrug, solvate, tautomer, stereoisomer, isotopologue, hydrate or derivative of the compounds, according to the methods of this invention include, for example, subjects that have been diagnosed as having acute myeloid leukemia, acute myeloid leukemia, cancer in adolescents, adrenocortical carcinoma childhood, AIDS-related cancers, e.g., Lymphoma and Kaposi's Sarcoma, anal cancer, appendix cancer, astrocytomas, atypical teratoid, basal cell carcinoma, bile duct cancer, bladder cancer, bone cancer, brain stem glioma, brain tumor, breast cancer, bronchial tumors, burkitt lymphoma, carcinoid tumor, atypical teratoid, embryonal tumors, germ cell tumor, primary lymphoma, cervical cancer, childhood cancers, chordoma, cardiac tumors, chronic lymphocytic leukemia (CLL), chronic myelogenous leukemia (CML), chronic myleoproliferative disorders, colon cancer, colorectal cancer, craniopharyngioma, cutaneous T-cell lymphoma, extrahepatic ductal carcinoma in situ (DCIS), embryonal tumors, CNS cancer, endometrial cancer, ependymoma, esophageal cancer, esthesioneuroblastoma, ewing sarcoma, extracranial germ cell tumor, extragonadal germ cell tumor, eye cancer, fibrous histiocytoma of bone, gall bladder cancer, gastric cancer, gastrointestinal carcinoid tumor, gastrointestinal stromal tumors (GIST), germ cell tumor, gestational trophoblastic tumor, hairy cell leukemia, head and neck cancer, heart cancer, liver cancer, hodgkin lymphoma, hypopharyngeal cancer, intraocular melanoma, islet cell tumors, pancreatic neuroendocrine tumors, kidney cancer, laryngeal cancer, lip and oral cavity cancer, liver cancer, lobular carcinoma in situ (LCIS), lung cancer, lymphoma, metastatic squamous neck cancer with occult primary, midline tract carcinoma, mouth cancer multiple endocrine neoplasia syndromes, multiple myeloma/plasma cell neoplasm, mycosis fungoides, myelodysplastic syndromes, myelodysplastic/myeloproliferative neoplasms, multiple myeloma, merkel cell carcinoma, malignant mesothelioma, malignant fibrous histiocytoma of bone and osteosarcoma, nasal cavity and paranasal sinus cancer, nasopharyngeal cancer, neuroblastoma, non-hodgkin lymphoma, non-small cell lung cancer (NSCLC), oral cancer, lip and oral cavity cancer, oropharyngeal cancer, ovarian cancer, pancreatic cancer, papillomatosis, paraganglioma, paranasal sinus and nasal cavity cancer, parathyroid cancer, penile cancer, pharyngeal cancer, pleuropulmonary blastoma, primary central nervous system (CNS) lymphoma, prostate cancer, rectal cancer, transitional cell cancer, retinoblastoma, rhabdomyosarcoma, salivary gland cancer, skin cancer, stomach (gastric) cancer, small cell lung cancer, small intestine cancer, soft tissue sarcoma, T-Cell lymphoma, testicular cancer, throat cancer, thymoma and thymic carcinoma, thyroid cancer, transitional cell cancer of the renal pelvis and ureter, trophoblastic tumor, unusual cancers of childhood, urethral cancer, uterine sarcoma, vaginal cancer, vulvar cancer, Viral-Induced cancer, leukemia, hematologic malignancy, solid tumor cancer, prostate cancer, castration-resistant prostate cancer, breast cancer, Ewing's sarcoma, bone sarcoma, primary bone sarcoma, T-cell prolymphocyte leukemia, glioma, glioblastoma, hepatocellular carcinoma, liver cancer, or diabetes. In some embodiments subjects that are treated with the compounds of the invention include subjects that have been diagnosed as having a non-cancerous hyperproliferative disorder such as benign hyperplasia of the skin, e.g., psoriasis, restenosis, or prostate, e.g., benign prostatic hypertrophy (BPH).

The invention further provides methods of modulating the interaction of menin and one or more proteins such as MLL1, MLL2, a MLL fusion protein, and/or a MLL Partial Tandem Duplication, by contacting the menin with an effective amount of a compound or salt of any one of Formulas (1), (2), (1A), (1B), (1C), (1D), (1E), (1F), (1G), (1H), (1I), (1J), (3), (3A), (3B), (3C), (3D), (3E), (3F), (3G), (3H), (3I), (3J), and (4). Modulation can be inhibiting or activating protein activity of menin, one or more of its binding partners, and/or one or more of the downstream targets of menin or one or more of its binding partners. In some embodiments, the invention provides methods of inhibiting the interaction of menin and one or more proteins such as MLL1, MLL2, a MLL fusion protein, and/or a MLL Partial Tandem Duplication, by contacting menin with an effective amount of a compound of any one of Formulas (1), (2), (1A), (1B), (1C), (1D), (1E), (1F), (1G), (1H), (1I), (1J), (3), (3A), (3B), (3C), (3D), (3E), (3F), (3G), (3H), (3I), (3J), and (4) or pharmaceutically acceptable salts thereof. In some embodiments, the invention provides methods of inhibiting the interaction of menin and one or more proteins such as MLL1, MLL2, a MLL fusion protein, and/or a MLL Partial Tandem Duplication, by contacting a cell, tissue, or organ that expresses menin, MLL1, MLL2, a MLL fusion protein, and/or a MLL Partial Tandem Duplication. In some embodiments, the invention provides methods of inhibiting protein activity in subject including but not limited to rodents and mammals, e.g., humans, by administering into the subject an effective amount of a compound or salt of any one of Formulas (1), (2), (1A), (1B), (1C), (1D), (1E), (1F), (1G), (1H), (1I), (1J), (3), (3A), (3B), (3C), (3D), (3E), (3F), (3G), (3H), (3I), (3J), and (4). In some embodiments, the percentage modulation exceeds 25%, 30%, 40%, 50%, 60%, 70%, 80%, or 90%. In some embodiments, the percentage of inhibiting exceeds 25%, 30%, 40%, 50%, 60%, 70%, 80%, or 90%.

In some embodiments, the disclosure provides methods of inhibiting the interaction of menin and one or more proteins such as MLL1, MLL2, a MLL fusion protein, and/or a MLL Partial Tandem Duplication, in a cell by contacting the cell with an amount of a compound of the invention sufficient to inhibit the interaction of menin and one or more of MLL1, MLL2, a MLL fusion protein, and a MLL Partial Tandem Duplication in the cell. In some embodiments, the invention provides methods of inhibiting the interaction of menin and one or more proteins such as MLL proteins in a tissue by contacting the tissue with an amount of a compound or salt of any one of Formulas (1), (2), (1A), (1B), (1C), (1D), (1E), (1F), (1G), (1H), (1I), (1J), (3), (3A), (3B), (3C), (3D), (3E), (3F), (3G), (3H), (3I), (3J), and (4), sufficient to inhibit the interaction of menin and one or more proteins such as MLL proteins in the tissue. In some embodiments, the invention provides methods of inhibiting the interaction of menin and one or more proteins such as MLL1, MLL2, a MLL fusion protein, and/or a MLL Partial Tandem Duplication in an organism by contacting the organism with an amount of a compound or salt of any one of Formulas (1), (2), (1A), (1B), (1C), (1D), (1E), (1F), (1G), (1H), (1I), (1J), (3), (3A), (3B), (3C), (3D), (3E), (3F), (3G), (3H), (3I), (3J), and (4), sufficient to inhibit the interaction of menin and one or more proteins such as MLL1, MLL2, a MLL fusion protein, and/or a MLL Partial Tandem Duplication in the organism. In some embodiments, the invention provides methods of inhibiting the interaction of menin and one or more proteins such as MLL1, MLL2, a MLL fusion protein, and/or a MLL Partial Tandem Duplication in an animal by contacting the animal with an amount of a compound or salt of the disclosure sufficient to inhibit the interaction of menin and one or more proteins such as MLL1, MLL2, a MLL fusion protein, and/or a MLL Partial Tandem Duplication in the animal. In some embodiments, the invention provides methods of inhibiting the interaction of menin and one or more proteins such as MLL1, MLL2, a MLL fusion protein, and/or a MLL Partial Tandem Duplication in a mammal by contacting the mammal with an amount of a compound of the invention sufficient to inhibit the interaction of menin and one or more proteins such as MLL1, MLL2, a MLL fusion protein, and/or a MLL Partial Tandem Duplication in the mammal. In some embodiments, the invention provides methods of inhibiting the interaction of menin and one or more proteins such as MLL1, MLL2, a MLL fusion protein, and/or a MLL Partial Tandem Duplication in a human by contacting the human with an amount of a compound of the invention sufficient to inhibit the interaction of menin and one or more proteins such as MLL Proteins in the human. The invention also provides methods of treating a disease mediated by menin interaction with one or more proteins such as MLL1, MLL2, a MLL fusion protein, and/or a MLL Partial Tandem Duplication by administering to a subject in need thereof a therapeutically effective amount of a compound or salt of any one of Formulas (1), (2), (1A), (1B), (1C), (1D), (1E), (1F), (1G), (1H), (1I), (1J), (3), (3A), (3B), (3C), (3D), (3E), (3F), (3G), (3H), (3I), (3J), and (4).

The compositions containing the compounds or salts thereof described herein can be administered for prophylactic and/or therapeutic treatments. In therapeutic applications, the compositions are administered to a patient already suffering from a disease, in an amount sufficient to cure or at least partially arrest the symptoms of the disease. Amounts effective for this use will depend on the severity and course of the disease, previous therapy, the patient's health status, weight, and response to the drugs, and the judgment of the treating physician.

In prophylactic applications, compositions containing the compounds or salts thereof described herein are administered to a patient susceptible to or otherwise at risk of a particular disease, disorder or condition. Such an amount is defined to be a "prophylactically effective amount or dose." In this use, the precise amounts also depend on the patient's state of health, weight, and the like. When used in a patient, effective amounts for this use will depend on the severity and course of the disease, disorder or condition, previous therapy, the patient's health status and response to the drugs, and the judgment of the treating physician.

In the case wherein the patient's condition does not improve, upon the doctor's discretion the administration of the compounds may be administered chronically, that is, for an extended period of time, including throughout the duration of the patient's life in order to ameliorate or otherwise control or limit the symptoms of the patient's disease.

In the case wherein the patient's status does improve, upon the doctor's discretion the administration of the compounds may be given continuously; alternatively, the dose of drug being administered may be temporarily reduced or temporarily suspended for a certain length of time (i.e., a "drug holiday"). The length of the drug holiday can vary between 2 days and 1 year, including by way of example only, 2 days, 3 days, 4 days, 5 days, 6 days, 7 days, 10 days, 12 days, 15 days, 20 days, 28 days, 35 days, 50 days, 70 days, 100 days, 120 days, 150 days, 180 days, 200 days, 250 days, 280 days, 300 days, 320 days, 350 days, or 365 days.

The dose reduction during a drug holiday may be from about 10% to about 100%, including, by way of example only, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100%.

Once improvement of the patient's conditions has occurred, a maintenance dose is administered if necessary. Subsequently, the dosage or the frequency of administration, or both, can be reduced, as a function of the symptoms, to a level at which the improved disease, disorder or condition is retained. Patients can, however, require intermittent treatment on a long-term basis upon any recurrence of symptoms.

The amount of a given agent that will correspond to such an amount will vary depending upon factors such as the particular compound, disease and its severity, the identity (e.g., weight) of the subject or host in need of treatment, but can nevertheless be determined in a manner recognized in the field according to the particular circumstances surrounding the case, including, e.g., the specific agent being administered, the route of administration, the condition being treated, and the subject or host being treated. In general, however, doses employed for adult human treatment will typically be in the range of about 0.02- about 5000 mg per day, in some embodiments, about 1-about 1500 mg per day. The desired dose may conveniently be presented in a single dose or as divided doses administered simultaneously (or over a short period of time) or at appropriate intervals, for example as two, three, four or more sub-doses per day.

Toxicity and therapeutic efficacy of such therapeutic regimens can be determined by standard pharmaceutical procedures in cell cultures or experimental animals, including, but not limited to, the determination of the $LD_{50}$ (the dose lethal to 50% of the population) and the $ED_{50}$ (the dose therapeutically effective in 50% of the population). The dose ratio between the toxic and therapeutic effects is the therapeutic index and it can be expressed as the ratio between $LD_{50}$ and $ED_{50}$. Compounds exhibiting high therapeutic indices are preferred. The data obtained from cell culture assays and animal studies can be used in formulating a range of dosage for use in human. The dosage of such compounds lies preferably within a range of circulating concentrations that include the $ED_{50}$ with minimal toxicity. The dosage may vary within this range depending upon the dosage form employed and the route of administration utilized.

Combination Therapies

The present invention also provides methods for combination therapies in which an agent known to modulate other pathways, or other components of the same pathway, or even overlapping sets of target enzymes are used in combination with a compound or salt of any one of Formulas (1), (2), (1A), (1B), (1C), (1D), (1E), (1F), (1G), (1H), (1I), (1J), (3), (3A), (3B), (3C), (3D), (3E), (3F), (3G), (3H), (3I), (3J), and (4). In one aspect, such therapy includes but is not limited to the combination of one or more compounds of the invention with chemotherapeutic agents, therapeutic antibodies, and radiation treatment, to provide a synergistic or additive therapeutic effect.

In general, the compositions described herein and, in embodiments where combinational therapy is employed, other agents do not have to be administered in the same pharmaceutical composition, and may, because of different physical and chemical characteristics, have to be administered by different routes. The determination of the mode of administration and the advisability of administration, where possible, in the same pharmaceutical composition, is well within the knowledge of the clinician. The initial administration can be made according to established protocols recognized in the field, and then, based upon the observed effects, the dosage, modes of administration and times of administration can be modified by the clinician.

In certain instances, it may be appropriate to administer at least one compound described herein in combination with another therapeutic agent. By way of example only, if one of the side effects experienced by a patient upon receiving one of the compounds herein, such as a compound or salt of any one of Formulas (1), (2), (1A), (1B), (1C), (1D), (1E), (1F), (1G), (1H), (1I), (1J), (3), (3A), (3B), (3C), (3D), (3E), (3F), (3G), (3H), (3I), (3J), and (4), is nausea, then it may be appropriate to administer an anti-nausea agent in combination with the initial therapeutic agent. Or, by way of example only, the therapeutic effectiveness of one of the compounds described herein may be enhanced by administration of an adjuvant (i.e., by itself the adjuvant may have minimal therapeutic benefit, but in combination with another therapeutic agent, the overall therapeutic benefit to the patient is enhanced). Or, by way of example only, the benefit experienced by a patient may be increased by administering one of the compounds described herein with another therapeutic agent (which also includes a therapeutic regimen) that also has therapeutic benefit. In any case, regardless of the disease, disorder or condition being treated, the overall benefit experienced by the patient may simply be additive of the two therapeutic agents or the patient may experience a synergistic benefit.

The particular choice of compounds used will depend upon the diagnosis of the attending physicians and their judgment of the condition of the patient and the appropriate treatment protocol. The compounds may be administered concurrently (e.g., simultaneously, essentially simultaneously or within the same treatment protocol) or sequentially, depending upon the nature of the disease, disorder, or condition, the condition of the patient, and the actual choice of compounds used. The determination of the order of administration, and the number of repetitions of administration of each therapeutic agent during a treatment protocol, is well within the knowledge of the physician after evaluation of the disease being treated and the condition of the patient.

Therapeutically-effective dosages can vary when the drugs are used in treatment combinations. Methods for experimentally determining therapeutically-effective dosages of drugs and other agents for use in combination treatment regimens are described in the literature. For example, the use of metronomic dosing, i.e., providing more frequent, lower doses in order to minimize toxic side effects, has been described extensively in the literature. Combination treatment further includes periodic treatments that start and stop at various times to assist with the clinical management of the patient.

For combination therapies described herein, dosages of the co-administered compounds will of course vary depending on the type of co-drug employed, on the specific drug employed, on the disease being treated and so forth. In addition, when co-administered with one or more biologically active agents, the compound provided herein may be administered either simultaneously with the biologically active agent(s), or sequentially. If administered sequentially, the attending physician will decide on the appropriate sequence of administering protein in combination with the biologically active agent(s).

In any case, the multiple therapeutic agents (one of which is a compound or salt of any one of Formulas (1), (2), (1A), (1B), (1C), (1D), (1E), (1F), (1G), (1H), (1I), (1J), (3), (3A), (3B), (3C), (3D), (3E), (3F), (3G), (3H), (3I), (3J), and (4) may be administered in any order or even simultaneously. If simultaneously, the multiple therapeutic agents may be provided in a single, unified form, or in multiple forms (by way of example only, either as a single pill or as two separate pills). One of the therapeutic agents may be given in multiple doses, or both may be given as multiple doses. If not simultaneous, the timing between the multiple doses may vary from more than zero weeks to less than four weeks. In addition, the combination methods, compositions and formulations are not to be limited to the use of only two agents; the use of multiple therapeutic combinations are also envisioned.

It is understood that the dosage regimen to treat, prevent, or ameliorate the condition(s) for which relief is sought, can be modified in accordance with a variety of factors. These factors include the disorder or condition from which the subject suffers, as well as the age, weight, sex, diet, and medical condition of the subject. Thus, the dosage regimen actually employed can vary widely and therefore can deviate from the dosage regimens set forth herein.

The pharmaceutical agents which make up the combination therapy disclosed herein may be a combined dosage form or in separate dosage forms intended for substantially simultaneous administration. The pharmaceutical agents that make up the combination therapy may also be administered sequentially, with either therapeutic compound being administered by a regimen calling for two-step administration. The two-step administration regimen may call for sequential administration of the active agents or spaced-apart administration of the separate active agents. The time period between the multiple administration steps may range from, a few minutes to several hours, depending upon the properties of each pharmaceutical agent, such as potency, solubility, bioavailability, plasma half-life and kinetic profile of the pharmaceutical agent. Circadian variation of the target molecule concentration may also determine the optimal dose interval.

In addition, the compounds described herein also may be used in combination with procedures that may provide additional or synergistic benefit to the patient. By way of example only, patients are expected to find therapeutic and/or prophylactic benefit in the methods described herein, wherein pharmaceutical composition of a compound disclosed herein and/or combinations with other therapeutics are combined with genetic testing to determine whether that individual is a carrier of a mutant gene that is known to be correlated with certain diseases or conditions.

The compounds described herein and combination therapies can be administered before, during or after the occurrence of a disease, and the timing of administering the composition containing a compound can vary. Thus, for example, the compounds can be used as a prophylactic and can be administered continuously to subjects with a propensity to develop conditions or diseases in order to prevent the occurrence of the disease. The compounds and compositions can be administered to a subject during or as soon as possible after the onset of the symptoms. The administration of the compounds can be initiated within the first 48 hours of the onset of the symptoms, preferably within the first 48 hours of the onset of the symptoms, more preferably within the first 6 hours of the onset of the symptoms, and most preferably within 3 hours of the onset of the symptoms. The initial administration can be via any route practical, such as, for example, an intravenous injection, a bolus injection, infusion over about 5 minutes to about 5 hours, a pill, a capsule, transdermal patch, buccal delivery, and the like, or combination thereof. A compound is preferably administered as soon as is practicable after the onset of a disease is detected or suspected, and for a length of time necessary for the treatment of the disease, such as, for example, from 1 day to about 3 months. The length of treatment can vary for each subject, and the length can be determined using the known criteria. For example, the compound or a formulation containing the compound can be administered for at least 2 weeks, preferably about 1 month to about 5 years.

Where desired, the compounds or pharmaceutical composition of the present invention can be used in combination with Notch inhibitors and/or c-Myb inhibitors. Where desired, the compounds or pharmaceutical composition of the present invention can be used in combination with MLL-WDR5 inhibitors and/or Dot1 1 inhibitors.

Many chemotherapeutics are presently known in the art and can be used in combination with the compounds of the invention. In some embodiments, the chemotherapeutic is selected from the group consisting of mitotic inhibitors, alkylating agents, anti-metabolites, intercalating antibiotics, growth factor inhibitors, cell cycle inhibitors, enzymes, topoisomerase inhibitors, biological response modifiers, anti-hormones, angiogenesis inhibitors, and anti-androgens.

Non-limiting examples are chemotherapeutic agents, cytotoxic agents, and non-peptide small molecules such as Gleevec® (Imatinib Mesylate), Velcade® (bortezomib), Casodex (bicalutamide), Iressa® (gefitinib), and Adriamycin as well as a host of chemotherapeutic agents. Non-limiting examples of chemotherapeutic agents include alkylating agents such as thiotepa and cyclosphosphamide (CYTOXAN™); alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamine; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, carminomycin, carzinophilin, Casodex™, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elfomithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK®; razoxane; sizofiran; spirogermanium; tenuazonic acid; triaziquone; 2,2',2"-trichlorotriethylamine; urethan; vindesine; dacarbazine; mannomustine; mitobronitol; mitolactol; pipobroman; gacytosine; arabinoside ("Ara-C"); cyclophosphamide; thiotepa; taxanes, e.g., paclitaxel (TAXOL™, Bristol-Myers Squibb Oncology, Princeton, N.J.) and docetaxel (TAXOTERE™, Rhone-Poulenc Rorer, Antony, France); retinoic acid; esperamicins; capecitabine; and pharmaceutically acceptable salts, acids or derivatives of any of the above. Also included as suitable chemotherapeutic cell conditioners are anti-hormonal agents that act to regulate or inhibit hormone action on tumors such as anti-estrogens including for example tamoxifen, (Nolvadex™), raloxifene, aromatase inhibiting 4(5)-imidazoles, 4-hydroxytamoxifen, trioxifene, keoxifene, LY 117018, onapristone, and toremifene (Fareston); and anti-androgens such as flutamide, nilutamide, bicalutamide, leuprolide, and goserelin; chlorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; xeloda; ibandronate; camptothecin-11 (CPT-11); topoisomerase inhibitor RFS 2000; difluoromethylornithine (DMFO). Where desired, the compounds or pharmaceutical composition of the present invention can be used in combination with commonly prescribed anti-cancer drugs such as Herceptin®, Avastin®, Erbitux®, Rituxan®, Taxol®, Arimidex®, Taxotere®, ABVD, AVICINE, Abagovomab, Acridine carboxamide, Adecatumumab, 17-N-Allylamino-17-demethoxygeldanamycin, Alpharadin, Alvocidib, 3-Aminopyridine-2-carboxaldehyde thiosemicarbazone, Amonafide, Anthracenedione, Anti-CD22 immunotoxins, Antineoplastic, Antitumorigenic herbs, Apaziquone, Atiprimod, Azathioprine, Belotecan, Bendamustine, BIBW 2992, Biricodar, Brostallicin, Bryostatin, Buthionine sulfoximine, CBV (chemotherapy), Calyculin, cell-cycle nonspecific antineoplastic agents, Dichloroacetic acid, Discodermolide, Elsamitrucin, Enocitabine, Epothilone, Eribulin, Everolimus, Exatecan, Exisulind, Ferruginol, Forodesine, Fosfestrol, ICE chemotherapy regimen, IT-101, Imexon, Imiquimod, Indolocarbazole, Irofulven, Laniquidar, Larotaxel, Lenalidomide, Lucanthone, Lurtotecan, Mafosfamide, Mitozolomide, Nafoxidine, Nedaplatin, Olaparib, Ortataxel, PAC-1, Pawpaw, Pixantrone, Proteasome inhibitor, Rebeccamycin, Resiquimod, Rubitecan, SN-38, Salinosporamide A, Sapacitabine, Stanford V, Swainsonine, Talaporfin, Tariquidar, Tegafur-uracil, Temodar, Tesetaxel, Triplatin tetranitrate, Tris(2-chloroethyl)amine, Troxacitabine, Uramustine, Vadimezan, Vinflunine, ZD6126 or Zosuquidar.

This invention further relates to a method for using the compound or salt of any of Formulas (1), (2), (1A), (1B), (1C), (1D), (1E), (1F), (1G), (1H), (1I), (1J), (3), (3A), (3B), (3C), (3D), (3E), (3F), (3G), (3H), (3I), (3J), and (4) or pharmaceutical compositions provided herein, in combination with radiation therapy for inhibiting abnormal cell growth or treating the hyperproliferative disorder in the mammal. Techniques for administering radiation therapy are known in the art, and these techniques can be used in the combination therapy described herein. The administration of the compound of the invention in this combination therapy can be determined as described herein.

Radiation therapy can be administered through one of several methods, or a combination of methods, including without limitation external-beam therapy, internal radiation therapy, implant radiation, stereotactic radiosurgery, systemic radiation therapy, radiotherapy and permanent or temporary interstitial brachytherapy. The term "brachytherapy," as used herein, refers to radiation therapy delivered by a spatially confined radioactive material inserted into the body at or near a tumor or other proliferative tissue disease site. The term is intended without limitation to include exposure to radioactive isotopes (e.g., At-211, I-131, I-125, Y-90, Re-186, Re-188, Sm-153, Bi-212, P-32, and radioactive isotopes of Lu). Suitable radiation sources for use as a cell conditioner of the present invention include both solids and liquids. By way of non-limiting example, the radiation source can be a radionuclide, such as I-125, I-131, Yb-169, Ir-192 as a solid source, I-125 as a solid source, or other radionuclides that emit photons, beta particles, gamma radiation, or other therapeutic rays. The radioactive material can also be a fluid made from any solution of radionuclide(s), e.g., a solution of I-125 or I-131, or a radioactive fluid can be produced using a slurry of a suitable fluid containing small particles of solid radionuclides, such as Au-198, Y-90. Moreover, the radionuclide(s) can be embodied in a gel or radioactive micro spheres.

The compounds or pharmaceutical compositions of the invention can be used in combination with an amount of one or more substances selected from anti-angiogenesis agents, signal transduction inhibitors, antiproliferative agents, glycolysis inhibitors, or autophagy inhibitors.

Anti-angiogenesis agents, such as MMP-2 (matrix-metalloproteinase 2) inhibitors, MMP-9 (matrix-metalloproteinase 9) inhibitors, and COX-11 (cyclooxygenase 11) inhibitors, can be used in conjunction with a compound of the invention and pharmaceutical compositions described herein. Anti-angiogenesis agents include, for example, rapamycin, temsirolimus (CCI-779), everolimus (RAD001), sorafenib, sunitinib, and bevacizumab. Examples of useful COX-II inhibitors include CELEBREX™ (alecoxib), valdecoxib, and rofecoxib. Examples of useful matrix metalloproteinase inhibitors are described in WO 96/33172 (published Oct. 24, 1996), WO 96/27583 (published Mar. 7, 1996), European Patent Application No. 97304971.1 (filed Jul. 8, 1997), European Patent Application No. 99308617.2 (filed Oct. 29, 1999), WO 98/07697 (published Feb. 26, 1998), WO 98/03516 (published Jan. 29, 1998), WO 98/34918 (published Aug. 13, 1998), WO 98/34915 (published Aug. 13, 1998), WO 98/33768 (published Aug. 6, 1998), WO 98/30566 (published Jul. 16, 1998), European Patent Publication 606,046 (published Jul. 13, 1994), European Patent Publication 931, 788 (published Jul. 28, 1999), WO 90/05719 (published May 31, 1990), WO 99/52910 (published Oct. 21, 1999), WO 99/52889 (published Oct. 21, 1999), WO 99/29667 (published Jun. 17, 1999), PCT International Application No. PCT/IB98/01113 (filed Jul. 21, 1998), European Patent Application No. 99302232.1 (filed Mar. 25, 1999), Great Britain Patent Application No. 9912961.1 (filed Jun. 3, 1999), U.S. Provisional Application No. 60/148,464 (filed Aug. 12, 1999), U.S. Pat. No. 5,863, 949 (issued Jan. 26, 1999), U.S. Pat. No. 5,861,510 (issued Jan. 19, 1999), and European Patent Publication 780,386 (published Jun. 25, 1997), all of which are incorporated herein in their entireties by reference. Preferred MMP-2 and MMP-9 inhibitors are those that have little or no activity inhibiting MMP-1. More preferred, are those that selectively inhibit MMP-2 and/or AMP-9 relative to the other matrix-metalloproteinases (e.g., MAP-1, MMP-3, MMP-4, MMP-5, MMP-6, MMP-7, MMP-8, MMP-10, MMP-11, MMP-12, and MMP-13). Some specific examples of MMP inhibitors useful in the invention are AG-3340, RO 32-3555, and RS 13-0830.

Autophagy inhibitors include, but are not limited to chloroquine, 3-methyladenine, hydroxychloroquine (Plaquenil™), bafilomycin A1, 5-amino-4-imidazole carboxamide riboside (AICAR), okadaic acid, autophagy-suppressive algal toxins which inhibit protein phosphatases of type 2A or type 1, analogues of cAMP, and drugs which elevate cAMP levels such as adenosine, LY204002, N6-mercaptopurine riboside, and vinblastine. In addition, antisense or siRNA that inhibits expression of proteins including but not limited to ATG5 (which are implicated in autophagy), may also be used.

In some embodiments, the compounds described herein are formulated or administered in conjunction with liquid or solid tissue barriers also known as lubricants. Examples of tissue barriers include, but are not limited to, polysaccharides, polyglycans, seprafilm, interceed and hyaluronic acid.

In some embodiments, medicaments which are administered in conjunction with the compounds described herein include any suitable drugs usefully delivered by inhalation for example, analgesics, e.g., codeine, dihydromorphine, ergotamine, fentanyl or morphine; anginal preparations, e.g., diltiazem; antiallergics, e.g., cromoglycate, ketotifen or nedocromil; anti-infectives, e.g., cephalosporins, penicillins, streptomycin, sulphonamides, tetracyclines or pentamidine; antihistamines, e.g., methapyrilene; anti-inflammatories, e.g., beclomethasone, flunisolide, budesonide, tipredane, triamcinolone acetonide or fluticasone; antitussives, e.g., noscapine; bronchodilators, e.g., ephedrine, adrenaline, fenoterol, formoterol, isoprenaline, metaproterenol, phenylephrine, phenylpropanolamine, pirbuterol, reproterol, rimiterol, salbutamol, salmeterol, terbutalin, isoetharine, tulobuterol, orciprenaline or (−)-4-amino-3,5-dichloro-α-[[[6-[2-(2-pyridinyl)ethoxy]hexyl]-amino]methyl]benzenemethanol; diuretics, e.g., amiloride; anticholinergics e.g., ipratropium, atropine or oxitropium; hormones, e.g., cortisone, hydrocortisone or prednisolone; xanthines e.g., aminophylline, choline theophyllinate, lysine theophyllinate or theophylline; and therapeutic proteins and peptides, e.g., insulin or glucagon. It will be clear to a person skilled in the art that, where appropriate, the medicaments are used in the form of salts (e.g., as alkali metal or amine salts or as acid addition salts) or as esters (e.g., lower alkyl esters) or as solvates (e.g., hydrates) to optimize the activity and/or stability of the medicament.

Other exemplary therapeutic agents useful for a combination therapy include but are not limited to agents as described above, radiation therapy, hormone antagonists, hormones and their releasing factors, thyroid and antithyroid drugs, estrogens and progestins, androgens, adrenocorticotropic hormone; adrenocortical steroids and their synthetic analogs; inhibitors of the synthesis and actions of adrenocortical hormones, insulin, oral hypoglycemic agents, and the pharmacology of the endocrine pancreas, agents affecting calcification and bone turnover: calcium, phosphate, parathyroid hormone, vitamin D, calcitonin, vitamins such as water-soluble vitamins, vitamin B complex, ascorbic acid, fat-soluble vitamins, vitamins A, K, and E, growth factors, cytokines, chemokines, muscarinic receptor agonists and antagonists; anticholinesterase agents; agents acting at the neuromuscular junction and/or autonomic ganglia; catecholamines, sympathomimetic drugs, and adrenergic receptor agonists or antagonists; and 5-hydroxytryptamine (5-HT, serotonin) receptor agonists and antagonists.

Therapeutic agents can also include agents for pain and inflammation such as histamine and histamine antagonists, bradykinin and bradykinin antagonists, 5-hydroxytryptamine (serotonin), lipid substances that are generated by biotransformation of the products of the selective hydrolysis of membrane phospholipids, eicosanoids, prostaglandins, thromboxanes, leukotrienes, aspirin, nonsteroidal anti-inflammatory agents, analgesic-antipyretic agents, agents that inhibit the synthesis of prostaglandins and thromboxanes, selective inhibitors of the inducible cyclooxygenase, selective inhibitors of the inducible cyclooxygenase-2, autacoids, paracrine hormones, somatostatin, gastrin, cytokines that mediate interactions involved in humoral and cellular immune responses, lipid-derived autacoids, eicosanoids, β-adrenergic agonists, ipratropium, glucocorticoids, methylxanthines, sodium channel blockers, opioid receptor agonists, calcium channel blockers, membrane stabilizers and leukotriene inhibitors.

Additional therapeutic agents contemplated herein include diuretics, vasopressin, agents affecting the renal conservation of water, rennin, angiotensin, agents useful in the treatment of myocardial ischemia, anti-hypertensive agents, angiotensin converting enzyme inhibitors, β-adrenergic receptor antagonists, agents for the treatment of hypercholesterolemia, and agents for the treatment of dyslipidemia.

Other therapeutic agents contemplated include drugs used for control of gastric acidity, agents for the treatment of peptic ulcers, agents for the treatment of gastroesophageal reflux disease, prokinetic agents, antiemetics, agents used in irritable bowel syndrome, agents used for diarrhea, agents used for constipation, agents used for inflammatory bowel disease, agents used for biliary disease, agents used for pancreatic disease. Therapeutic agents used to treat protozoan infections, drugs used to treat Malaria, Amebiasis, Giardiasis, Trichomoniasis, Trypanosomiasis, and/or Leishmaniasis, and/or drugs used in the chemotherapy of helminthiasis. Other therapeutic agents include antimicrobial agents, sulfonamides, trimethoprim-sulfamethoxazole quinolones, and agents for urinary tract infections, penicillins, cephalosporins, and other, β-lactam antibiotics, an agent comprising an aminoglycoside, protein synthesis inhibitors, drugs used in the chemotherapy of tuberculosis, *mycobacterium avium* complex disease, and leprosy, antifungal agents, antiviral agents including nonretroviral agents and antiretroviral agents.

Examples of therapeutic antibodies that can be combined with a compound of the invention include but are not limited to anti-receptor tyrosine kinase antibodies (cetuximab, panitumumab, trastuzumab), anti CD20 antibodies (rituximab, tositumomab), and other antibodies such as alemtuzumab, bevacizumab, and gemtuzumab.

Moreover, therapeutic agents used for immunomodulation, such as immunomodulators, immunosuppressive agents, tolerogens, and immunostimulants are contemplated by the methods herein. In addition, therapeutic agents acting on the blood and the blood-forming organs, hematopoietic agents, growth factors, minerals, and vitamins, anticoagulant, thrombolytic, and antiplatelet drugs.

For treating renal carcinoma, one may combine a compound of the present invention with sorafenib and/or avastin. For treating an endometrial disorder, one may combine a compound of the present invention with doxorubincin, taxotere (taxol), and/or cisplatin (carboplatin). For treating ovarian cancer, one may combine a compound of the present invention with cisplatin (carboplatin), taxotere, doxorubincin, topotecan, and/or tamoxifen. For treating breast cancer, one may combine a compound of the present invention with taxotere (taxol), gemcitabine (capecitabine), tamoxifen, letrozole, tarceva, lapatinib, PD0325901, avastin, herceptin, OSI-906, and/or OSI-930. For treating lung cancer, one may combine a compound of the present invention with taxotere (taxol), gemcitabine, cisplatin, pemetrexed, Tarceva, PD0325901, and/or avastin.

Further therapeutic agents that can be combined with a compound of the invention are found in Goodman and Gilman's "The Pharmacological Basis of Therapeutics" Tenth Edition edited by Hardman, Limbird and Gilman or the Physician's Desk Reference, both of which are incorporated herein by reference in their entirety.

The compounds described herein can be used in combination with the agents disclosed herein or other suitable agents, depending on the condition being treated. Hence, in some embodiments the one or more compounds of the invention will be co-administered with other agents as described above. When used in combination therapy, the compounds described herein are administered with the second agent simultaneously or separately. This administration in combination can include simultaneous administration of the two agents in the same dosage form, simultaneous administration in separate dosage forms, and separate administration. That is, a compound described herein and any of the agents described above can be formulated together in the same dosage form and administered simultaneously. Alternatively, a compound of the invention and any of the agents described above can be simultaneously administered, wherein both the agents are present in separate formulations. In another alternative, a compound of the present invention can be administered just followed by and any of the agents described above, or vice versa. In some embodiments of the separate administration protocol, a compound of the invention and any of the agents described above are administered a few minutes apart, or a few hours apart, or a few days apart.

In some embodiments, a compound described herein is co-administered with another therapeutic agent effective in treating leukemia and/or other cancers. In some embodiments, a compound described herein is co-administered with one or more therapeutic agents approved for the treatment of Acute Lymphoblastic Leukemia (ALL), for example: ABITREXATE (Methotrexate), ADRIAMYCIN PFS (Doxorubicin Hydrochloride), ADRIAMYCIN RDF (Doxorubicin Hydrochloride), ARRANON (Nelarabine), Asparaginase *Erwinia chrysanthemi*, CERUBIDINE (Daunorubicin Hydrochloride), CLAFEN (Cyclophosphamide), CLOFARABINE, CLOFAREX (Clofarabine), CLOLAR (Clofarabine), Cyclophosphamide, Cytarabine, CYTOSAR-U (Cytarabine), CYTOXAN (Cyclophosphamide), Dasatinib, Daunorubicin Hydrochloride, Doxorubicin Hydrochloride, Erwinaze (Asparaginase *Erwinia Chrysanthemi*), FOLEX (Methotrexate), FOLEX PFS (Methotrexate), GLEEVEC (Imatinib Mesylate), ICLUSIG (Ponatinib Hydrochloride), Imatinib Mesylate, MARQIBO (Vincristine Sulfate Liposome), Methotrexate, METHOTREXATE LPF (Methorexate), MEXATE (Methotrexate), MEXATE-AQ (Methotrexate), Nelarabine, NEOSAR (Cyclophosphamide), ONCASPAR (Pegaspargase), Pegaspargase, Ponatinib Hydrochloride, RUBIDOMYCIN (Daunorubicin Hydrochloride), SPRYCEL (Dasatinib), TARABINE PFS (Cytarabine), VINCASAR PFS (Vincristine Sulfate), Vincristine Sulfate, etc.

In some embodiments, a compound described herein is co-administered with one or more therapeutic agents approved for the treatment of Acute Myeloid Leukemia (AML), for example: ADRIAMYCIN PFS (Doxorubicin Hydrochloride), ADRIAMYCIN RDF (Doxorubicin Hydrochloride), Arsenic Trioxide, CERUBIDINE (Daunorubicin Hydrochloride), CLAFEN (Cyclophosphamide), Cyclophosphamide, Cytarabine, CYTOSAR-U (Cytarabine), CYTOXAN (Cyclophosphamide), Daunorubicin Hydrochloride, Doxorubicin Hydrochloride, NEOSAR (Cyclophosphamide), RUBIDOMYCIN (Daunorubicin Hydrochloride), TARABINE PFS (Cytarabine), TRISENOX (Arsenic Trioxide), VINCASAR PFS (Vincristine Sulfate), Vincristine Sulfate, etc.

In some embodiments, a compound described herein is co-administered with one or more therapeutic agents approved for the treatment of Chronic Lymphocytic Leukemia (CLL), for example: Alemtuzumab, AMBOCHLORIN (Chlorambucil), AMBOCLORIN (Chlorambucil), ARZERRA (Ofatumumab), Bendamustine Hydrochloride, CAMPATH (Alemtuzumab), CHLORAMBUCILCLAFEN (Cyclophosphamide), Cyclophosphamide, CYTOXAN (Cyclophosphamide), FLUDARA (Fludarabine Phosphate), Fludarabine Phosphate, LEUKERAN (Chlorambucil), LINFOLIZIN (Chlorambucil), NEOSAR (Cyclophosphamide), Ofatumumab, TREANDA (Bendamustine Hydrochloride), etc.

In some embodiments, a compound described herein is co-administered with one or more therapeutic agents approved for the treatment of Chronic Myelogenous Leukemia (CML), for example: BOSULIF (Bosutinib), Bosutinib, CLAFEN (Cyclophosphamide), Cyclophosphamide, Cytarabine, CYTOSAR-U (Cytarabine), CYTOXAN (Cyclophosphamide), Dasatinib, GLEEVEC (Imatinib Mesylate), ICLUSIG (Ponatinib Hydrochloride), Imatinib Mesylate, NEOSAR (Cyclophosphamide), Nilotinib, Omacetaxine Mepesuccinate, Ponatinib Hydrochloride, SPRYCEL (Dasatinib), SYNRIBO (Omacetaxine Mepesuccinate), TARABINE PFS (Cytarabine), TASIGNA (Nilotinib), etc.

In some embodiments, a compound described herein is co-administered with one or more therapeutic agents approved for the treatment of Meningeal Leukemia, for example: CYTARABINE, CYTOSAR-U (Cytarabine), TARABINE PFS (Cytarabine), etc.

In some embodiments, a compound described herein is co-administered with one or more alkylating agents (e.g., for the treatment of cancer) selected from, for example, nitrogen mustard N-oxide, cyclophosphamide, ifosfamide, thiotepa, ranimustine, nimustine, temozolomide, altretamine, apaziquone, brostallicin, bendamustine, carmustine, estramustine, fotemustine, glufosfamide, mafosfamide, bendamustin, mitolactol, cisplatin, carboplatin, eptaplatin, lobaplatin, nedaplatin, oxaliplatin, and satraplatin.

In some embodiments, a compound described herein is co-administered with one or more anti-metabolites (e.g., for the treatment of cancer) selected from, for example, methotrexate, 6-mercaptopurineriboside, mercaptopurine, 5-fluorouracil, tegafur, doxifluridine, carmofur, cytarabine, cytarabine ocfosfate, enocitabine, gemcitabine, fludarabin, 5-azacitidine, capecitabine, cladribine, clofarabine, decitabine, eflornithine, ethynylcytidine, cytosine arabinoside, hydroxyurea, melphalan, nelarabine, nolatrexed, ocfosf[iota]te, disodium premetrexed, pentostatin, pelitrexol, raltitrexed, triapine, trimetrexate, vidarabine, vincristine, and vinorelbine;

In some embodiments, a compound described herein is co-administered with one or more hormonal therapy agents (e.g., for the treatment of cancer) selected from, for example, exemestane, Lupron, anastrozole, doxercalciferol, fadrozole, formestane, abiraterone acetate, finasteride, epristeride, tamoxifen citrate, fulvestrant, Trelstar, toremifene, raloxifene, lasofoxifene, letrozole, sagopilone, ixabepilone, epothilone B, vinblastine, vinflunine, docetaxel, and paclitaxel;

In some embodiments, a compound described herein is co-administered with one or more cytotoxic topoisomerase inhibiting agents (e.g., for the treatment of cancer) selected from, for example, aclarubicin, doxorubicin, amonafide, belotecan, camptothecin, 10-hydroxycamptothecin, 9-aminocamptothecin, diflomotecan, irinotecan, topotecan, edotecarin, epimbicin, etoposide, exatecan, gimatecan, lurtotecan, mitoxantrone, pirambicin, pixantrone, rubitecan, sobuzoxane, tafluposide;

In some embodiments, a compound described herein is co-administered with one or more anti-angiogenic compounds (e.g., for the treatment of cancer) selected from, for example, acitretin, aflibercept, angiostatin, aplidine, asentar, axitinib, recentin, bevacizumab, brivanib alaninat, cilengtide, combretastatin, DAST, endostatin, fenretinide, halofuginone, pazopanib, ranibizumab, rebimastat, removab, revlimid, sorafenib, vatalanib, squalamine, sunitinib, telatinib, thalidomide, ukrain, and vitaxin.

In some embodiments, a compound described herein is co-administered with one or more antibodies (e.g., for the treatment of cancer) selected from, for example, trastuzumab, cetuximab, bevacizumab, rituximab, ticilimumab, ipilimumab, lumiliximab, catumaxomab, atacicept, oregovomab, and alemtuzumab.

In some embodiments, a compound described herein is co-administered with one or more VEGF inhibitors (e.g., for the treatment of cancer) selected from, for example, sorafenib, DAST, bevacizumab, sunitinib, recentin, axitinib, aflibercept, telatinib, brivanib alaninate, vatalanib, pazopanib, and ranibizumab.

In some embodiments, a compound described herein is co-administered with one or more EGFR inhibitors (e.g., for the treatment of cancer) selected from, for example, cetuximab, panitumumab, vectibix, gefitinib, erlotinib, and Zactima.

In some embodiments, a compound described herein is co-administered with one or more HER2 inhibitors (e.g., for the treatment of cancer) selected from, for example, lapatinib, tratuzumab, and pertuzumab; CDK inhibitor is selected from roscovitine and flavopiridol;

In some embodiments, a compound described herein is co-administered with one or more proteasome inhibitors (e.g., for the treatment of cancer) selected from, for example, bortezomib and carfilzomib.

In some embodiments, a compound described herein is co-administered with one or more serine/threonine kinase inhibitors (e.g., for the treatment of cancer), for example, MEK inhibitors and Raf inhibitors such as sorafenib.

In some embodiments, a compound described herein is co-administered with one or more tyrosine kinase inhibitors (e.g., for the treatment of cancer) selected from, for example, dasatinib, nilotibib, DAST, bosutinib, sorafenib, bevacizumab, sunitinib, AZD2171, axitinib, aflibercept, telatinib, imatinib mesylate, brivanib alaninate, pazopanib, ranibizumab, vatalanib, cetuximab, panitumumab, vectibix, gefitinib, erlotinib, lapatinib, tratuzumab and pertuzumab.

In some embodiments, a compound described herein is co-administered with one or more androgen receptor antagonists (e.g., for the treatment of cancer) selected from, for example, nandrolone decanoate, fluoxymesterone, Android, Prostaid, andromustine, bicalutamide, flutamide, apocyproterone, apoflutamide, chlormadinone acetate, Androcur, Tabi, cyproterone acetate, and nilutamide.

In some embodiments, a compound described herein is co-administered with one or more aromatase inhibitors (e.g., for the treatment of cancer) selected from, for example, anastrozole, letrozole, testolactone, exemestane, aminoglutethimide, and formestane.

In some embodiments, a compound described herein is co-administered with one or more other anti-cancer agents including, e.g., alitretinoin, ampligen, atrasentan bexarotene, borte-zomib, bosentan, calcitriol, exisulind, fotemustine, ibandronic acid, miltefosine, mitoxantrone, 1-asparaginase, procarbazine, dacarbazine, hydroxycarbamide, pegaspargase, pentostatin, tazaroten, velcade, gallium nitrate, canfosfamide, darinaparsin, and tretinoin. In a preferred embodiment, the compounds of the present disclosure may be used in combination with chemotherapy (e.g., cytotoxic agents), anti-hormones and/or targeted therapies such as other kinase inhibitors, mTOR inhibitors and angiogenesis inhibitors.

Kits

For use in the therapeutic applications described herein, kits and articles of manufacture are also provided. In some embodiments, such kits comprise a carrier, package, or container that is compartmentalized to receive one or more containers such as vials, tubes, and the like, each of the container(s) comprising one of the separate elements to be used in a method described herein. Suitable containers include, for example, bottles, vials, syringes, and test tubes. The containers are formed from a variety of materials such as glass or plastic.

The articles of manufacture provided herein contain packaging materials. Packaging materials for use in packaging pharmaceutical products include those found in, e.g., U.S. Pat. Nos. 5,323,907, 5,052,558 and 5,033,252. Examples of pharmaceutical packaging materials include, but are not limited to, blister packs, bottles, tubes, inhalers, pumps, bags, vials, containers, syringes, bottles, and any packaging material suitable for a selected formulation and intended mode of administration and treatment. For example, the container(s) includes a compound or salt of any of Formulas (1), (2), (1A), (1B), (1C), (1D), (1E), (1F), (1G), (1H), (1I), (1J), (3), (3A), (3B), (3C), (3D), (3E), (3F), (3G), (3H), (3I), (3J), and (4), optionally in a composition or in combination with another agent as disclosed herein. The container(s) optionally have a sterile access port (for example the container is an intravenous solution bag or a vial having a stopper pierceable by a hypodermic injection needle). Such kits optionally comprising a compound with an identifying description or label or instructions relating to its use in the methods described herein.

For example, a kit typically includes one or more additional containers, each with one or more of various materials (such as reagents, optionally in concentrated form, and/or devices) desirable from a commercial and user standpoint for use of a compound described herein. Non-limiting examples of such materials include, but not limited to, buffers, diluents, filters, needles, syringes; carrier, package, container, vial and/or tube labels listing contents and/or instructions for use, and package inserts with instructions for use. A set of instructions will also typically be included. A label is optionally on or associated with the container. For example, a label is on a container when letters, numbers or other characters forming the label are attached, molded or etched into the container itself, a label is associated with a container when it is present within a receptacle or carrier that also holds the container, e.g., as a package insert. In addition, a label is used to indicate that the contents are to be used for a specific therapeutic application. In addition, the label indicates directions for use of the contents, such as in the methods described herein. In certain embodiments, the pharmaceutical composition is presented in a pack or dispenser device which contains one or more unit dosage forms containing a compound provided herein. The pack, for example, contains metal or plastic foil, such as a blister pack. Or, the pack or dispenser device is accompanied by instructions for administration. Or, the pack or dispenser is accompanied with a notice associated with the container in form prescribed by a governmental agency regulating the manufacture, use, or sale of pharmaceuticals, which notice is reflective of approval by the agency of the form of the drug for human or veterinary administration. Such notice, for example, is the labeling approved by the U.S. Food and Drug Administration for prescription drugs, or the approved product insert. In some embodiments, compositions containing a compound provided herein formulated in a compatible pharmaceutical carrier are prepared, placed in an appropriate container, and labeled for treatment of an indicated condition.

The examples and preparations provided below further illustrate and exemplify the compounds of the present invention and methods of preparing such compounds. It is to be understood that the scope of the present invention is not limited in any way by the scope of the following examples and preparations.

EXAMPLES

Where indicated, the compounds of Table 1 were analyzed by LC-MS and TLC under the following conditions. The LC-MS conditions for procedure A are as follows: Phenomenex Kinetex 2.6 u C18 column dimensions 3.0 mm×50 mm; temperature—60° C.; solvent A—0.1% TFA in water; solvent B—0.1% TFA in MeCN; gradient program—5% to 100% B/6 min; and UV wavelength: 254 nm. The LC-MS conditions for procedure B (indicated by * in Table 1) are as follows: Shimadzu VP-ODS 150LX2.0 5 u column; temperature—40° C.; solvent A—0.1% HOOH in water; solvent B—acetonitrile; flow rate -0.2 mL/min; gradient program—80% A and 20% B/0.1 min., 10% A and 90% B/5.0 min., 0% A and 100% B/5.1 min., and 0% A and 100% B/8.0 min. The TLC conditions are as follows: pre-coated Silica Gel 60 $F_{254}$ plates; and DCM:MeOH:$NH_3H_2O$, 20:1: 0.1.

TABLE 1
Inhibitors of the menin-MLL interaction
| Compound Number | Structure | [MH]+ | LC-MS RT (min.) or TLC Rf |
|---|---|---|---|
| 1 | 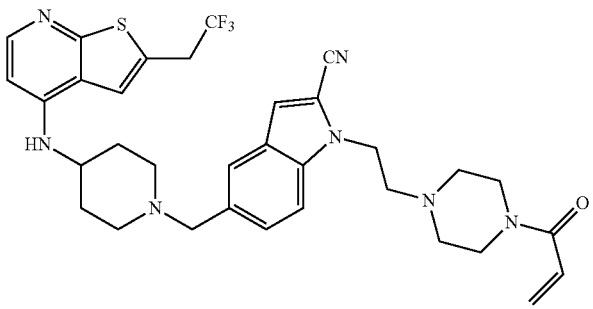 [SMILES: C=CC(=O)N1CCN(CCn2c(C#N)cc3cc(CN4CCC(Nc5ccnc6sc(CC(F)(F)F)cc56)CC4)ccc32)CC1] | 637.2684 | 0.25 |
| 2 | 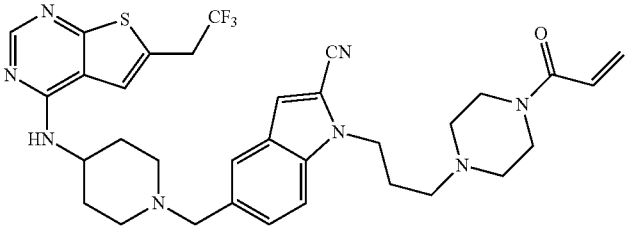 [SMILES: C=CC(=O)N1CCN(CCCn2c(C#N)cc3cc(CN4CCC(Nc5ncnc6sc(CC(F)(F)F)cc56)CC4)ccc32)CC1] | 651.2834 | 0.25 |
| 3 | 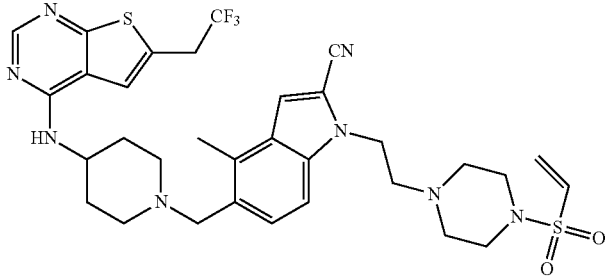 [SMILES: C=CS(=O)(=O)N1CCN(CCn2c(C#N)cc3c(C)c(CN4CCC(Nc5ncnc6sc(CC(F)(F)F)cc56)CC4)ccc32)CC1] | 687.2505 | 0.3 |
| 4 | 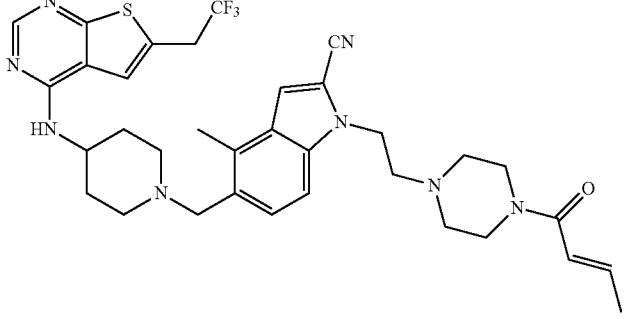 | 665.2993 | 0.25 |
| 5 | 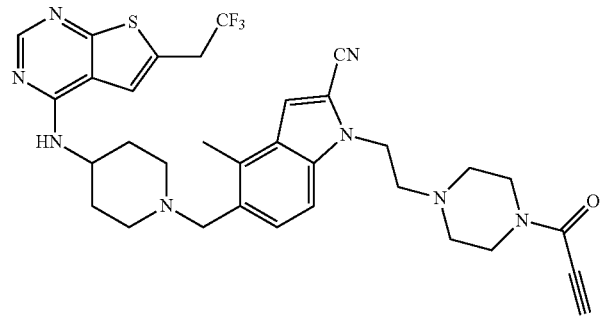 [SMILES: C#CC(=O)N1CCN(CCn2c(C#N)cc3c(C)c(CN4CCC(Nc5ncnc6sc(CC(F)(F)F)cc56)CC4)ccc32)CC1] | 649.2680 | 0.25 |

TABLE 1-continued
Inhibitors of the menin-MLL interaction
| Compound Number | Structure | [MH]+ | LC-MS RT (min.) or TLC Rf |
|---|---|---|---|
| 6 | 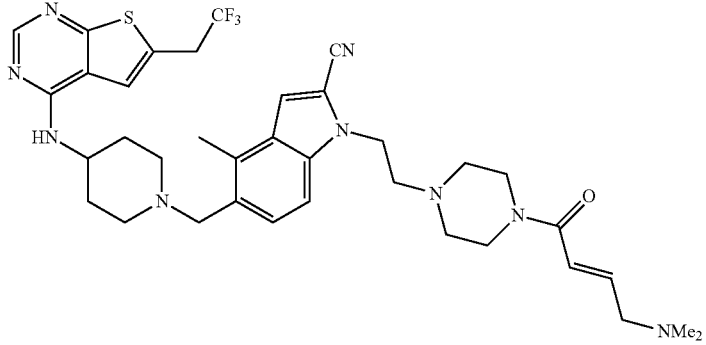 [SMILES: Cc1c(CN2CCC(Nc3ncnc4sc(CC(F)(F)F)cc34)CC2)ccc2c1cc(C#N)n2CCN1CCN(C(=O)/C=C/CN(C)C)CC1] | 708.3415 | 0.15 |
| 7 | 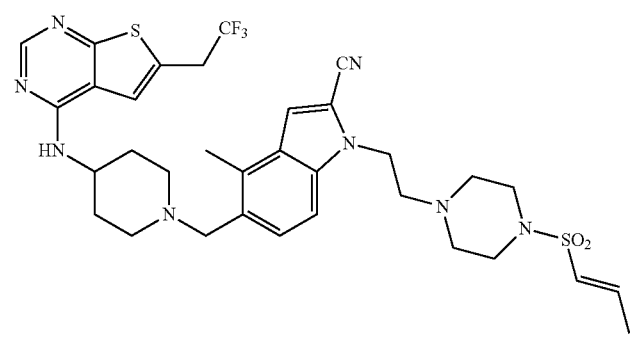 [SMILES: C/C=C/S(=O)(=O)N1CCN(CCn2c(C#N)cc3c(C)c(CN4CCC(Nc5ncnc6sc(CC(F)(F)F)cc56)CC4)ccc32)CC1] | 701.2661 | 0.3 |
| 8 | 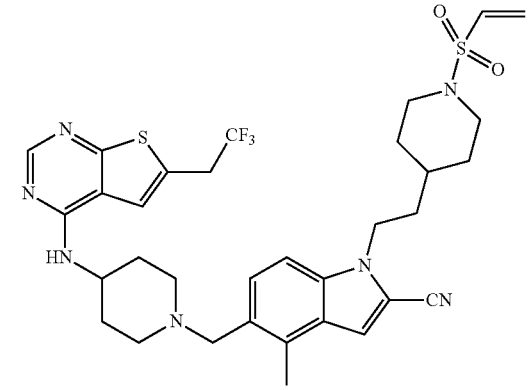 [SMILES: C=CS(=O)(=O)N1CCC(CCn2c(C#N)cc3c(C)c(CN4CCC(Nc5ncnc6sc(CC(F)(F)F)cc56)CC4)ccc32)CC1] | 686.2556 | 0.3 |
| 9 | 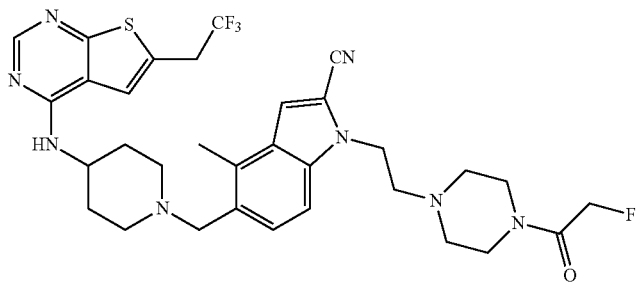 [SMILES: Cc1c(CN2CCC(Nc3ncnc4sc(CC(F)(F)F)cc34)CC2)ccc2c1cc(C#N)n2CCN1CCN(C(=O)CF)CC1] | 657.2745 | 0.25 |

TABLE 1-continued

Inhibitors of the menin-MLL interaction

| Compound Number | Structure | [MH]+ | LC-MS RT (min.) or TLC Rf |
|---|---|---|---|
| 10 | 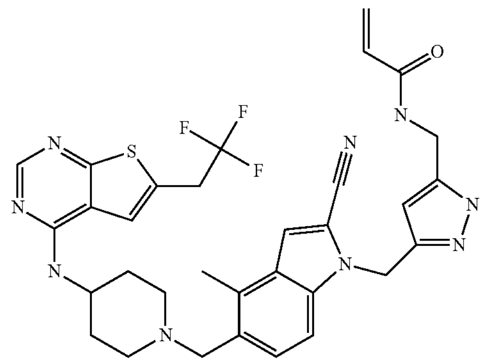 [SMILES: C=CC(=O)NCc1cc(Cn2c(C#N)cc3c(C)c(CN4CCC(Nc5ncnc6sc(CC(F)(F)F)cc56)CC4)ccc32)n[nH]1] | 648.5 | 1.83 min |
| 11 | 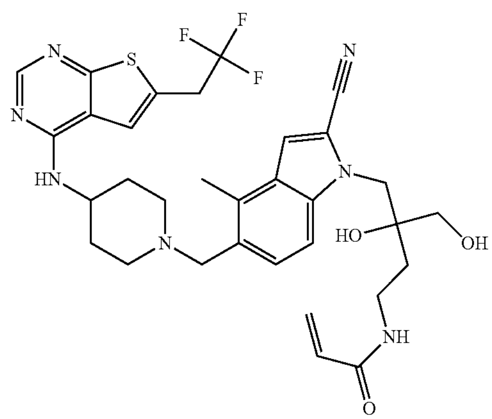 [SMILES: C=CC(=O)NCCC(O)(CO)Cn1c(C#N)cc2c(C)c(CN3CCC(Nc4ncnc5sc(CC(F)(F)F)cc45)CC3)ccc21] | 656.6 | 1.88 min |
| 12 | 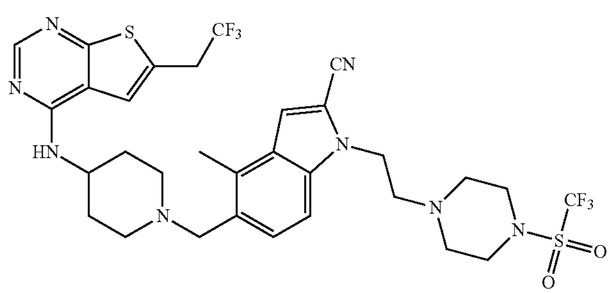 [SMILES: Cc1c(CN2CCC(Nc3ncnc4sc(CC(F)(F)F)cc34)CC2)ccc2c1cc(C#N)n2CCN1CCN(S(=O)(=O)C(F)(F)F)CC1] | 729.2222 | 0.3 |
| 13 | 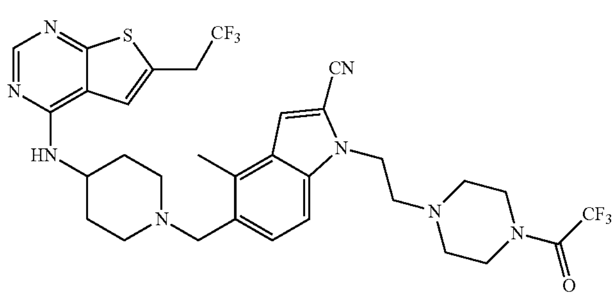 [SMILES: Cc1c(CN2CCC(Nc3ncnc4sc(CC(F)(F)F)cc34)CC2)ccc2c1cc(C#N)n2CCN1CCN(C(=O)C(F)(F)F)CC1] | 693.2551 | 0.25 |

TABLE 1-continued

Inhibitors of the menin-MLL interaction

| Compound Number | Structure | [MH]+ | LC-MS RT (min.) or TLC Rf |
|---|---|---|---|
| 14 | 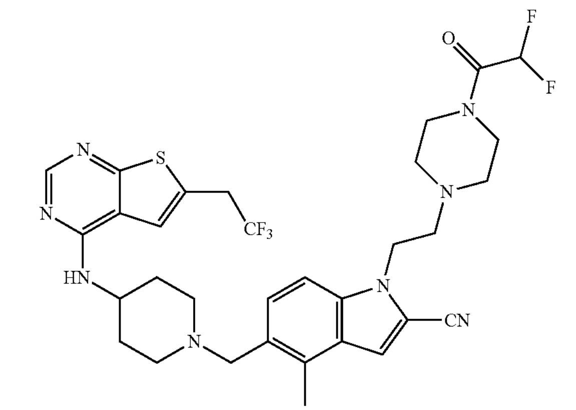 [SMILES: Cc1c(CN2CCC(Nc3ncnc4sc(CC(F)(F)F)cc34)CC2)ccc2c1cc(C#N)n2CCN1CCN(C(=O)C(F)F)CC1] | 675.2649 | 0.25 |
| 15 | 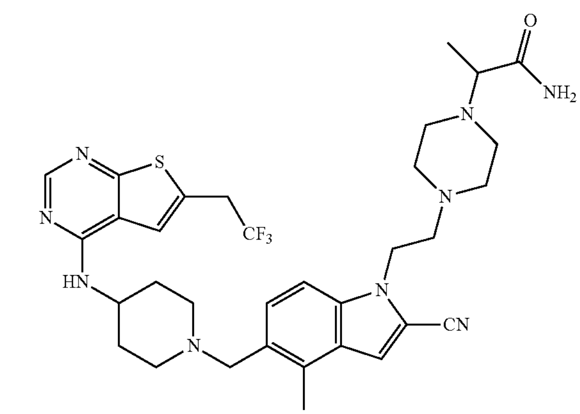 [SMILES: Cc1c(CN2CCC(Nc3ncnc4sc(CC(F)(F)F)cc34)CC2)ccc2c1cc(C#N)n2CCN1CCN(C(C)C(N)=O)CC1] | 668.3102 | 0.15 |
| 16 | 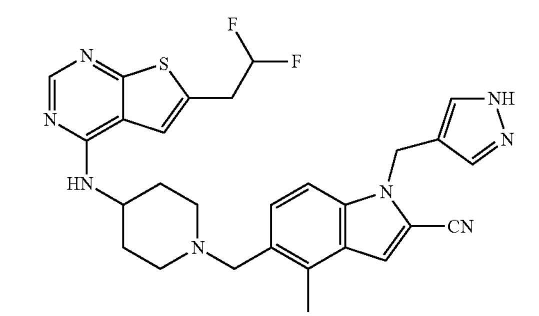 [SMILES: Cc1c(CN2CCC(Nc3ncnc4sc(CC(F)F)cc34)CC2)ccc2c1cc(C#N)n2Cc1cn[nH]c1] | 547.2198 | 0.3 |
| 17 | 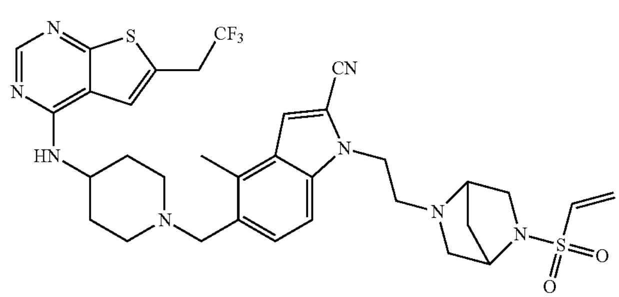 [SMILES: C=CS(=O)(=O)N1CC2CC1CN2CCn1c(C#N)cc2c(C)c(CN3CCC(Nc4ncnc5sc(CC(F)(F)F)cc45)CC3)ccc21] | 699.2508 | 0.3 |

TABLE 1-continued

Inhibitors of the menin-MLL interaction

| Compound Number | Structure | [MH]+ | LC-MS RT (min.) or TLC Rf |
|---|---|---|---|
| 18 | 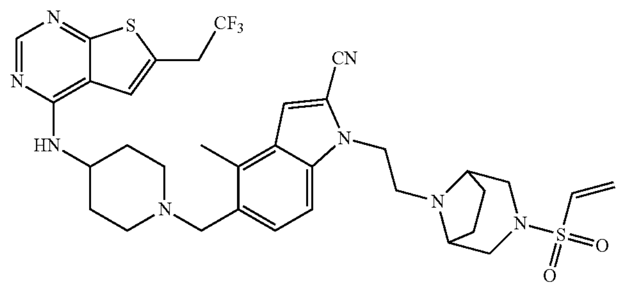 [SMILES: C=CS(=O)(=O)N1CC2CCC(C1)N2CCn1c(C#N)cc2c(C)c(CN3CCC(Nc4ncnc5sc(CC(F)(F)F)cc45)CC3)ccc21] | 713.2664 | 0.3 |
| 19 | 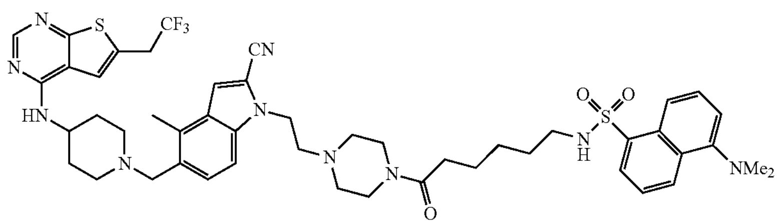 [SMILES: Cc1c(CN2CCC(Nc3ncnc4sc(CC(F)(F)F)cc34)CC2)ccc2c1cc(C#N)n2CCN1CCN(C(=O)CCCCCNS(=O)(=O)c2cccc3c(N(C)C)cccc23)CC1] | 943.4083 | 0.15 |
| 20 | 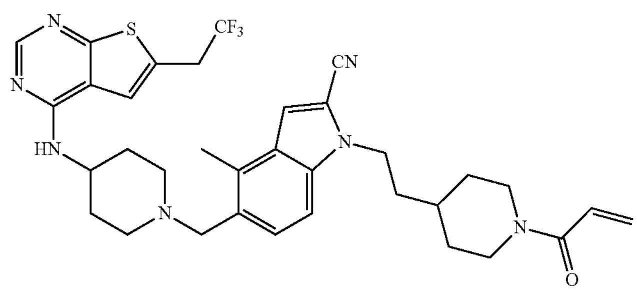 [SMILES: C=CC(=O)N1CCC(CCn2c(C#N)cc3c(C)c(CN4CCC(Nc5ncnc6sc(CC(F)(F)F)cc56)CC4)ccc32)CC1] | 650.2884 | 0.25 |
| 21 | 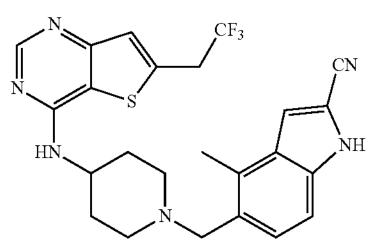 [SMILES: Cc1c(CN2CCC(Nc3ncnc4cc(CC(F)(F)F)sc34)CC2)ccc2[nH]c(C#N)cc12] | 485.1732 | 0.3 |
| 22 | 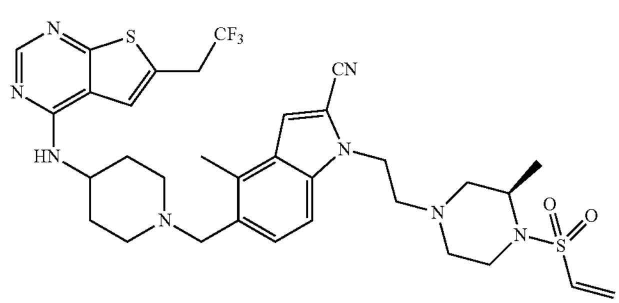 [SMILES: C=CS(=O)(=O)N1CCN(CCn2c(C#N)cc3c(C)c(CN4CCC(Nc5ncnc6sc(CC(F)(F)F)cc56)CC4)ccc32)C[C@H]1C] | 701.2669 | 0.25 |

TABLE 1-continued

Inhibitors of the menin-MLL interaction

| Compound Number | Structure | [MH]+ | LC-MS RT (min.) or TLC Rf |
|---|---|---|---|
| 23 | 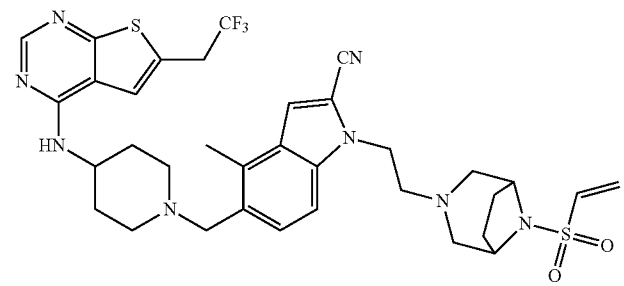 [SMILES: C=CS(=O)(=O)N1C2CCC1CN(CCn1c(C#N)cc3c(C)c(CN4CCC(Nc5ncnc6sc(CC(F)(F)F)cc56)CC4)ccc31)C2] | 713.2661 | 0.25 |
| 24 | 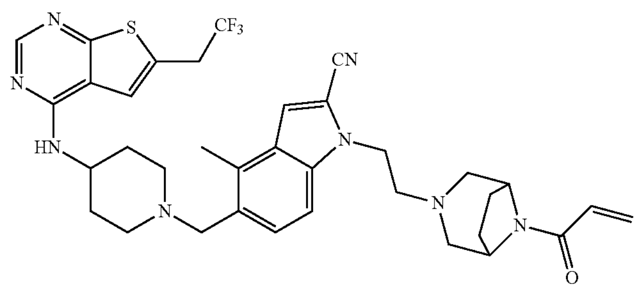 [SMILES: C=CC(=O)N1C2CCC1CN(CCn1c(C#N)cc3c(C)c(CN4CCC(Nc5ncnc6sc(CC(F)(F)F)cc56)CC4)ccc31)C2] | 677.2994 | 0.25 |
| 25 | 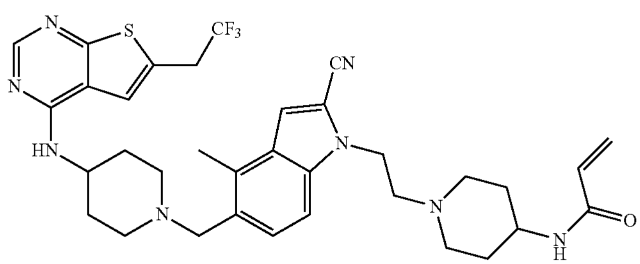 [SMILES: C=CC(=O)NC1CCN(CCn2c(C#N)cc3c(C)c(CN4CCC(Nc5ncnc6sc(CC(F)(F)F)cc56)CC4)ccc32)CC1] | 665.2997 | 0.25 |
| 26 | 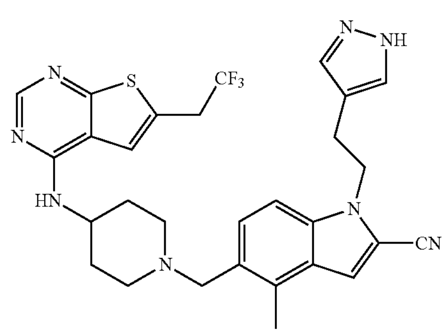 [SMILES: Cc1c(CN2CCC(Nc3ncnc4sc(CC(F)(F)F)cc34)CC2)ccc2c1cc(C#N)n2CCc1cn[nH]c1] | 579.2267 | 0.15 |

TABLE 1-continued

Inhibitors of the menin-MLL interaction

| Compound Number | Structure | [MH]+ | LC-MS RT (min.) or TLC Rf |
|---|---|---|---|
| 27 | 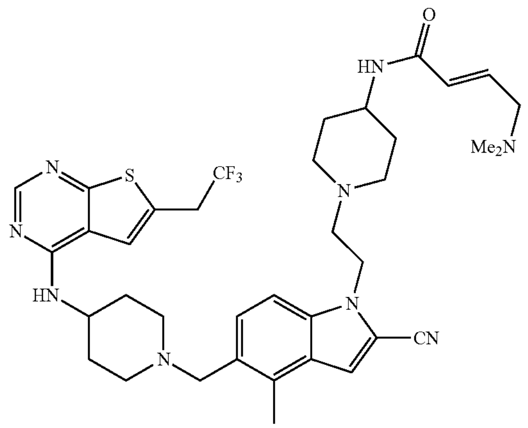 [SMILES: Cc1c(CN2CCC(Nc3ncnc4sc(CC(F)(F)F)cc34)CC2)ccc2c1cc(C#N)n2CCN1CCC(NC(=O)/C=C/CN(C)C)CC1] | 722.3578 | 0.15 |
| 28 | 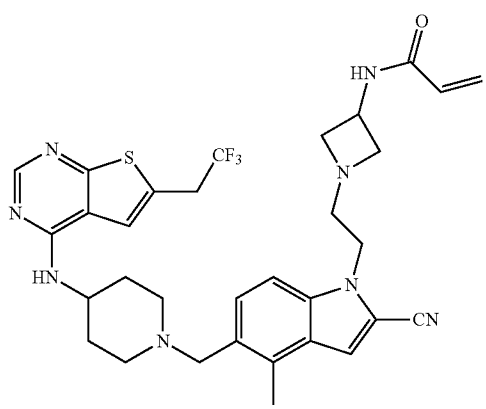 [SMILES: C=CC(=O)NC1CN(CCn2c(C#N)cc3c(C)c(CN4CCC(Nc5ncnc6sc(CC(F)(F)F)cc56)CC4)ccc32)C1] | 637.2679 | 0.25 |
| 29 | 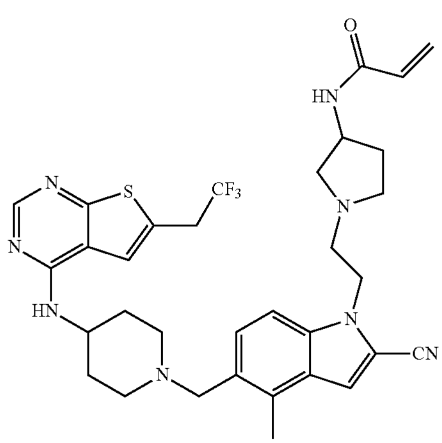 [SMILES: C=CC(=O)NC1CCN(CCn2c(C#N)cc3c(C)c(CN4CCC(Nc5ncnc6sc(CC(F)(F)F)cc56)CC4)ccc32)C1] | 651.2830 | 0.25 |

TABLE 1-continued
Inhibitors of the menin-MLL interaction
| Compound Number | Structure | [MH]+ | LC-MS RT (min.) or TLC Rf |
|---|---|---|---|
| 30 | 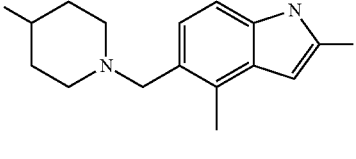 | 611.1987 | 0.1 |
| 31 | 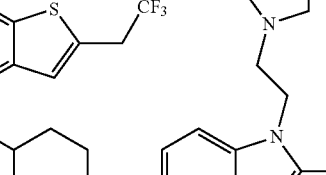 | 651.2841 | 0.25 |
| 32 | 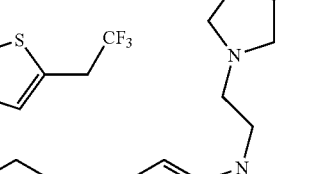 | 651.2838 | 0.25 |
| 33 | 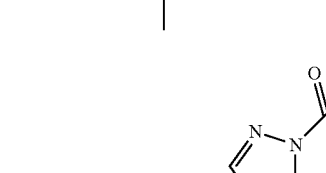 | | |

TABLE 1-continued

Inhibitors of the menin-MLL interaction

| Compound Number | Structure | [MH]+ | LC-MS RT (min.) or TLC Rf |
|---|---|---|---|
| 34 | 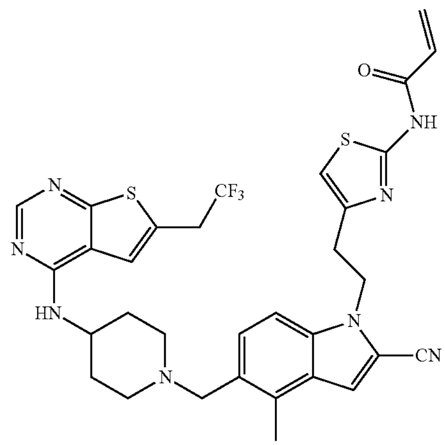 [SMILES: C=CC(=O)Nc1nc(CCn2c(C#N)cc3c(C)c(CN4CCC(Nc5ncnc6sc(CC(F)(F)F)cc56)CC4)ccc32)cs1] | 665.2081 | 0.2 |
| 35 | 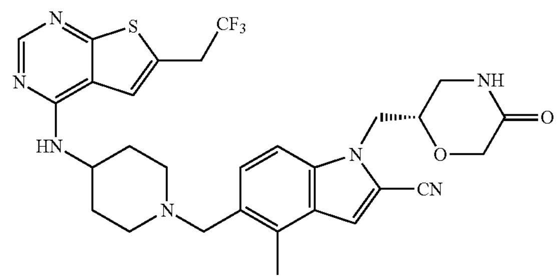 [SMILES: Cc1c(CN2CCC(Nc3ncnc4sc(CC(F)(F)F)cc34)CC2)ccc2c1cc(C#N)n2C[C@@H]1CNC(=O)CO1] | | |
| 36 | 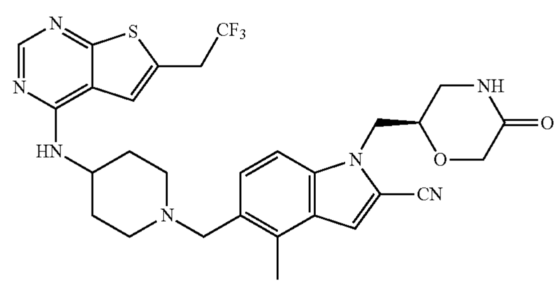 [SMILES: Cc1c(CN2CCC(Nc3ncnc4sc(CC(F)(F)F)cc34)CC2)ccc2c1cc(C#N)n2C[C@H]1CNC(=O)CO1] | | |
| 37 | 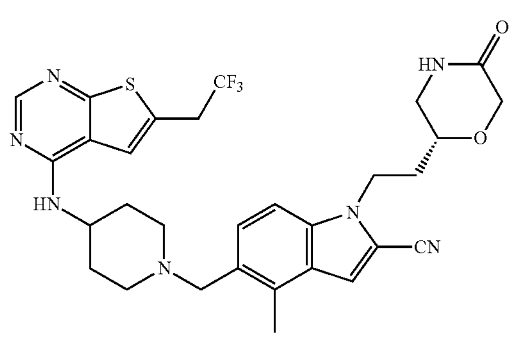 [SMILES: Cc1c(CN2CCC(Nc3ncnc4sc(CC(F)(F)F)cc34)CC2)ccc2c1cc(C#N)n2CC[C@@H]1CNC(=O)CO1] | | |

TABLE 1-continued

Inhibitors of the menin-MLL interaction

| Compound Number | Structure | [MH]+ | LC-MS RT (min.) or TLC Rf |
|---|---|---|---|
| 38 | 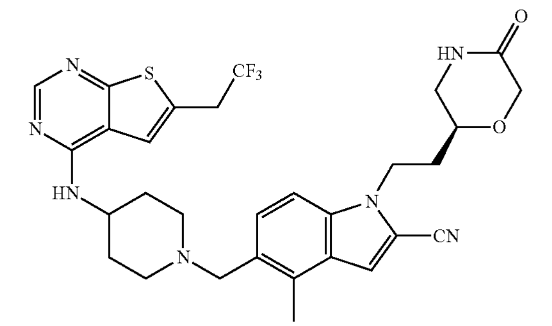 [SMILES: Cc1c(CN2CCC(Nc3ncnc4sc(CC(F)(F)F)cc34)CC2)ccc2c1cc(C#N)n2CC[C@H]1CNC(=O)CO1] | | |
| 39 | 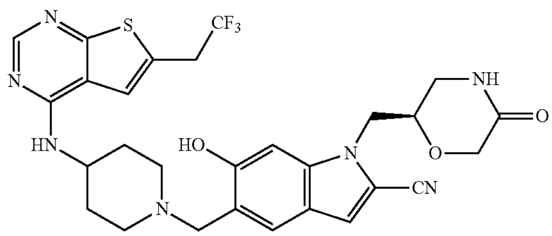 [SMILES: N#Cc1cc2cc(CN3CCC(Nc4ncnc5sc(CC(F)(F)F)cc45)CC3)c(O)cc2n1C[C@H]1CNC(=O)CO1] | | |
| 40 | 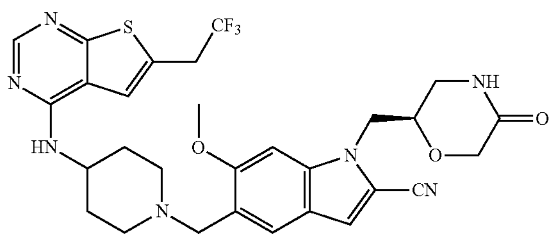 [SMILES: COc1cc2c(cc1CN1CCC(Nc3ncnc4sc(CC(F)(F)F)cc34)CC1)cc(C#N)n2C[C@H]1CNC(=O)CO1] | | |
| 41 | 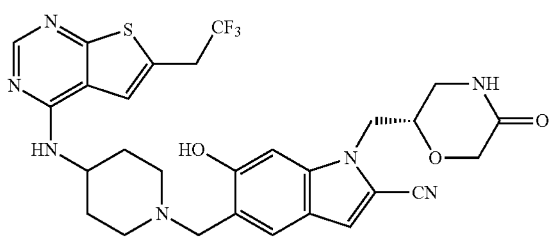 [SMILES: N#Cc1cc2cc(CN3CCC(Nc4ncnc5sc(CC(F)(F)F)cc45)CC3)c(O)cc2n1C[C@@H]1CNC(=O)CO1] | | |
| 42 | 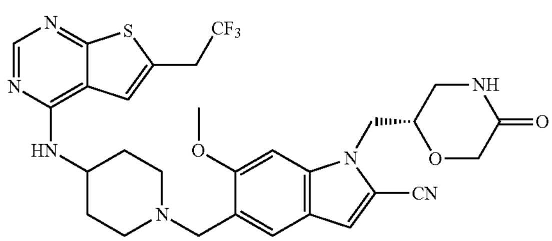 [SMILES: COc1cc2c(cc1CN1CCC(Nc3ncnc4sc(CC(F)(F)F)cc34)CC1)cc(C#N)n2C[C@@H]1CNC(=O)CO1] | | |
| 43 | 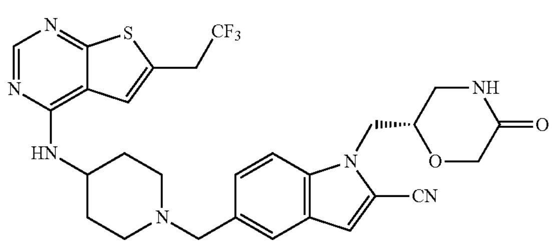 [SMILES: N#Cc1cc2cc(CN3CCC(Nc4ncnc5sc(CC(F)(F)F)cc45)CC3)ccc2n1C[C@@H]1CNC(=O)CO1] | | |

TABLE 1-continued

Inhibitors of the menin-MLL interaction

| Compound Number | Structure | [MH]+ | LC-MS RT (min.) or TLC Rf |
|---|---|---|---|
| 44 | 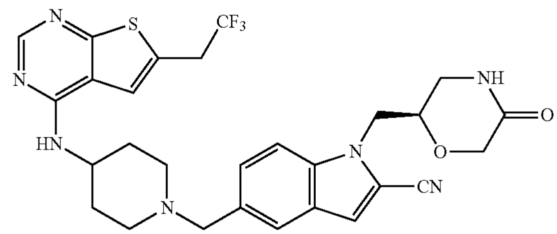 [SMILES: N#Cc1cc2cc(CN3CCC(Nc4ncnc5sc(CC(F)(F)F)cc45)CC3)ccc2n1C[C@H]1CNC(=O)CO1] | | |
| 45 | 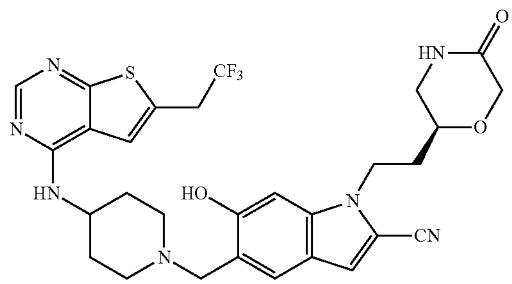 [SMILES: N#Cc1cc2cc(CN3CCC(Nc4ncnc5sc(CC(F)(F)F)cc45)CC3)c(O)cc2n1CC[C@H]1CNC(=O)CO1] | | |
| 46 | 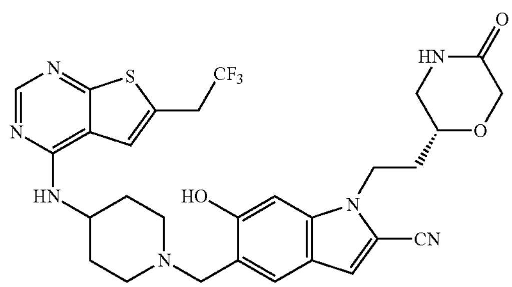 [SMILES: N#Cc1cc2cc(CN3CCC(Nc4ncnc5sc(CC(F)(F)F)cc45)CC3)c(O)cc2n1CC[C@@H]1CNC(=O)CO1] | | |
| 47 | 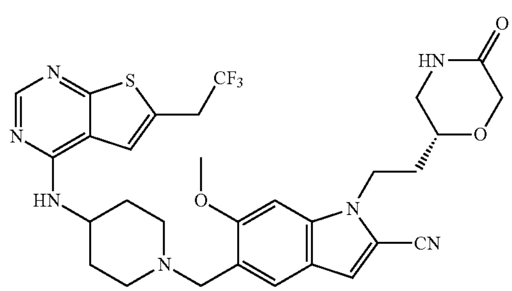 [SMILES: COc1cc2c(cc1CN1CCC(Nc3ncnc4sc(CC(F)(F)F)cc34)CC1)cc(C#N)n2CC[C@@H]1CNC(=O)CO1] | | |
| 48 | 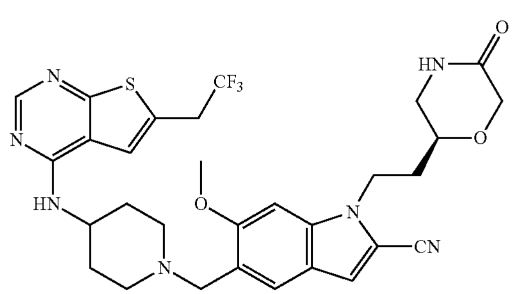 [SMILES: COc1cc2c(cc1CN1CCC(Nc3ncnc4sc(CC(F)(F)F)cc34)CC1)cc(C#N)n2CC[C@H]1CNC(=O)CO1] | | |

TABLE 1-continued

Inhibitors of the menin-MLL interaction

| Compound Number | Structure | [MH]+ | LC-MS RT (min.) or TLC Rf |
|---|---|---|---|
| 49 | 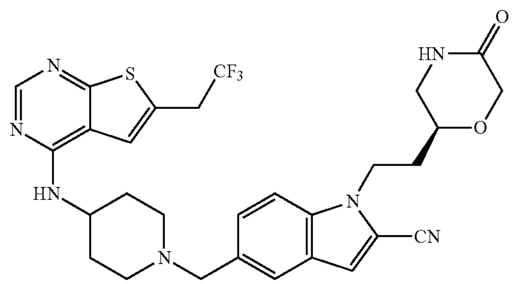 [SMILES: N#Cc1cc2cc(CN3CCC(Nc4ncnc5sc(CC(F)(F)F)cc45)CC3)ccc2n1CC[C@H]1CNC(=O)CO1] | | |
| 50 | 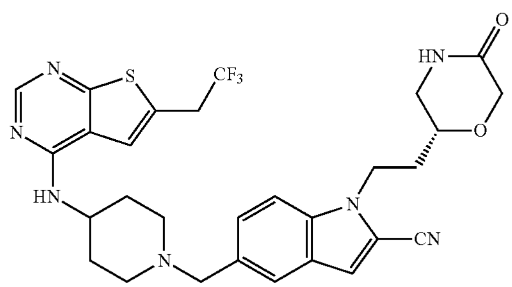 [SMILES: N#Cc1cc2cc(CN3CCC(Nc4ncnc5sc(CC(F)(F)F)cc45)CC3)ccc2n1CC[C@@H]1CNC(=O)CO1] | | |
| 51 | 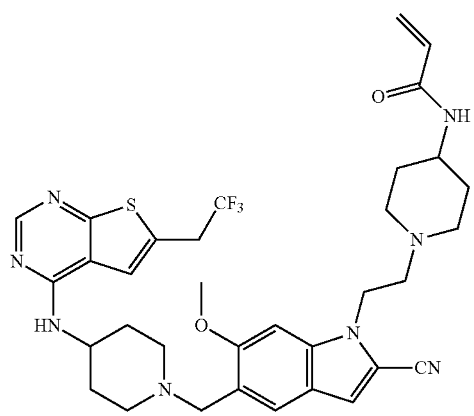 [SMILES: C=CC(=O)NC1CCN(CCn2c(C#N)cc3cc(CN4CCC(Nc5ncnc6sc(CC(F)(F)F)cc56)CC4)c(OC)cc32)CC1] | | |
| 52 | 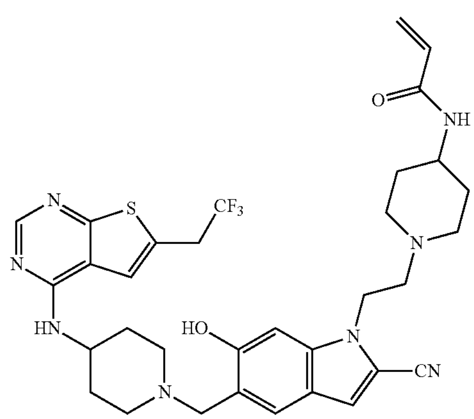 [SMILES: C=CC(=O)NC1CCN(CCn2c(C#N)cc3cc(CN4CCC(Nc5ncnc6sc(CC(F)(F)F)cc56)CC4)c(O)cc32)CC1] | | |

TABLE 1-continued

Inhibitors of the menin-MLL interaction

| Compound Number | Structure | [MH]+ | LC-MS RT (min.) or TLC Rf |
|---|---|---|---|
| 53 | 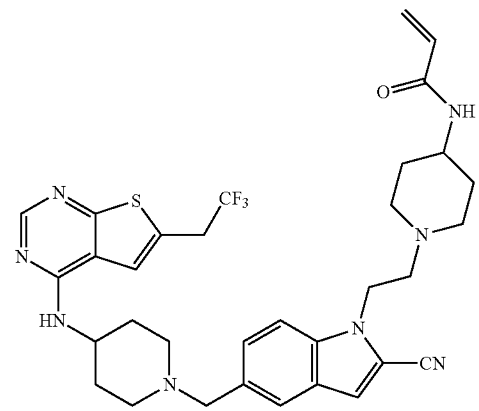 [SMILES: C=CC(=O)NC1CCN(CCn2c(C#N)cc3cc(CN4CCC(Nc5ncnc6sc(CC(F)(F)F)cc56)CC4)ccc32)CC1] | | |
| 54 | 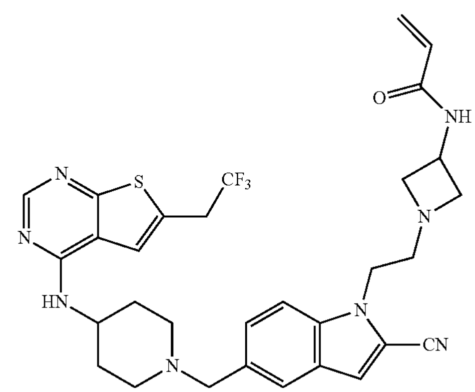 [SMILES: C=CC(=O)NC1CN(CCn2c(C#N)cc3cc(CN4CCC(Nc5ncnc6sc(CC(F)(F)F)cc56)CC4)ccc32)C1] | | |
| 55 | 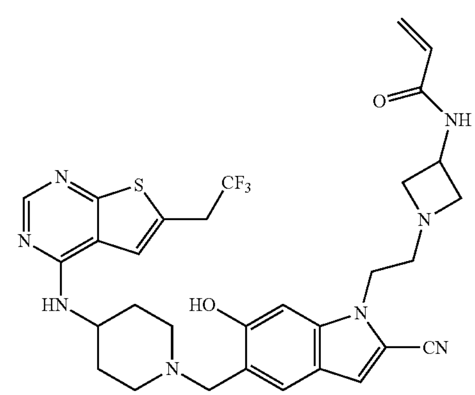 [SMILES: C=CC(=O)NC1CN(CCn2c(C#N)cc3cc(CN4CCC(Nc5ncnc6sc(CC(F)(F)F)cc56)CC4)c(O)cc32)C1] | | |

| Compound Number | Structure | [MH]+ | LC-MS RT (min.) or TLC Rf |
|---|---|---|---|
| 56 | 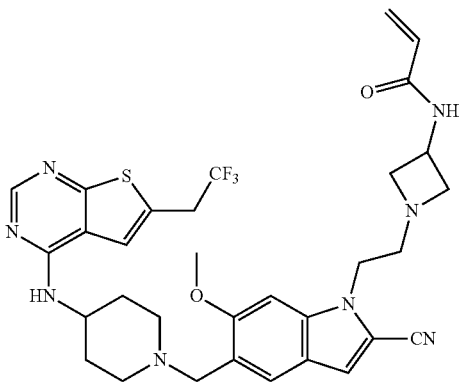 [SMILES: C=CC(=O)NC1CN(CCn2c(C#N)cc3cc(CN4CCC(Nc5ncnc6sc(CC(F)(F)F)cc56)CC4)c(OC)cc32)C1] | | |
| 57 | 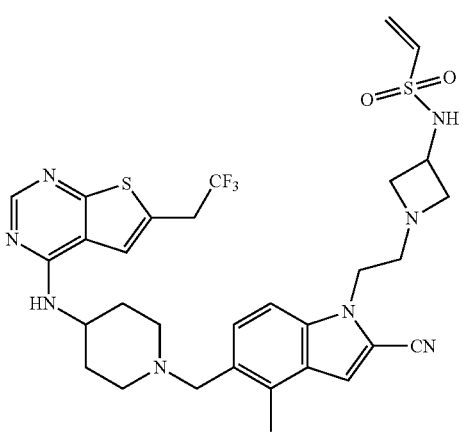 [SMILES: C=CS(=O)(=O)NC1CN(CCn2c(C#N)cc3c(C)c(CN4CCC(Nc5ncnc6sc(CC(F)(F)F)cc56)CC4)ccc32)C1] | | |
| 58 | 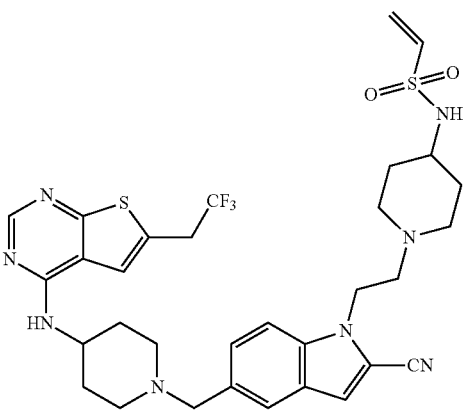 [SMILES: C=CS(=O)(=O)NC1CCN(CCn2c(C#N)cc3cc(CN4CCC(Nc5ncnc6sc(CC(F)(F)F)cc56)CC4)ccc32)CC1] | | |

TABLE 1-continued

Inhibitors of the menin-MLL interaction

| Compound Number | Structure | [MH]+ | LC-MS RT (min.) or TLC Rf |
|---|---|---|---|
| 59 | 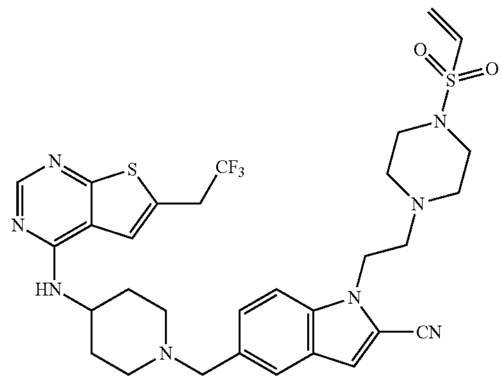 | | |
| 60 | 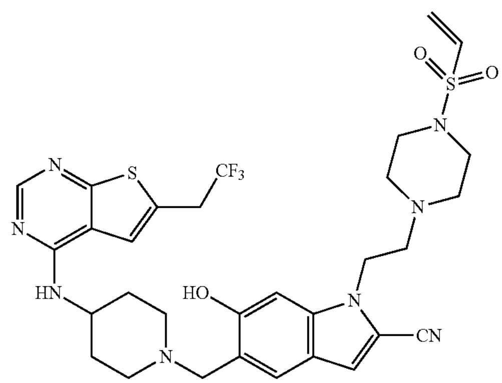 [SMILES: C=CS(=O)(=O)N1CCN(CCn2c(C#N)cc3cc(CN4CCC(Nc5ncnc6sc(CC(F)(F)F)cc56)CC4)c(O)cc32)CC1] | | |
| 61 | 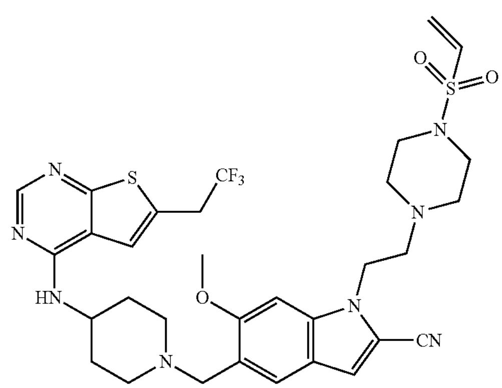 [SMILES: C=CS(=O)(=O)N1CCN(CCn2c(C#N)cc3cc(CN4CCC(Nc5ncnc6sc(CC(F)(F)F)cc56)CC4)c(OC)cc32)CC1] | | |
| 62 | 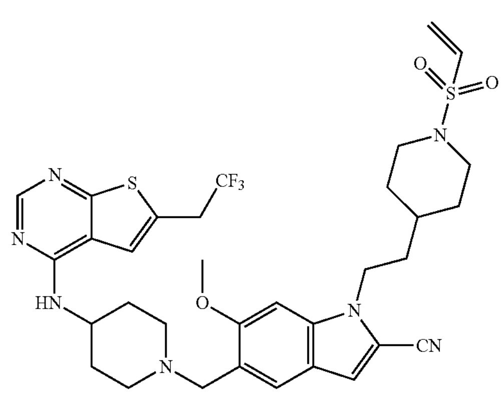 | | |

TABLE 1-continued

Inhibitors of the menin-MLL interaction

| Compound Number | Structure | [MH]+ | LC-MS RT (min.) or TLC Rf |
|---|---|---|---|
| 63 | 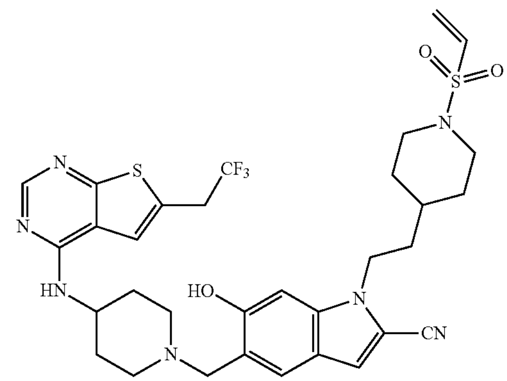 [SMILES: C=CS(=O)(=O)N1CCC(CCn2c(C#N)cc3cc(CN4CCC(Nc5ncnc6sc(CC(F)(F)F)cc56)CC4)c(O)cc32)CC1] | | |
| 64 | 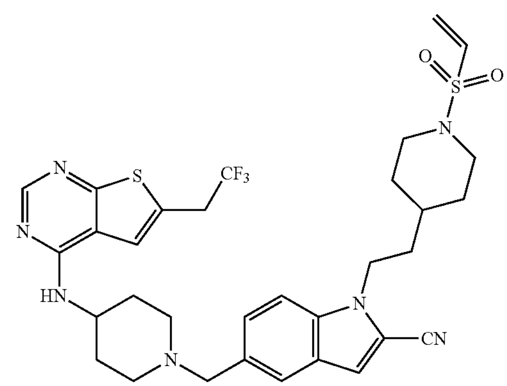 [SMILES: C=CS(=O)(=O)N1CCC(CCn2c(C#N)cc3cc(CN4CCC(Nc5ncnc6sc(CC(F)(F)F)cc56)CC4)ccc32)CC1] | | |
| 65 | 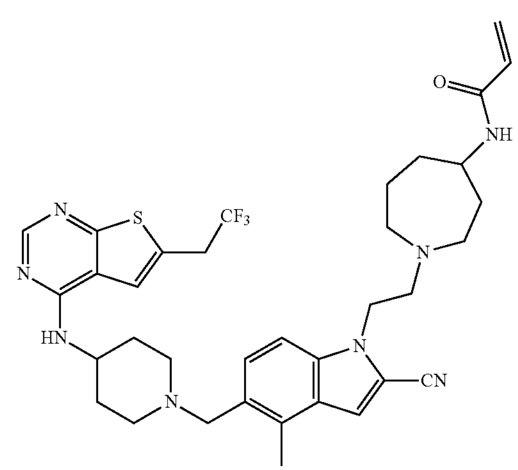 [SMILES: C=CC(=O)NC1CCCN(CCn2c(C#N)cc3c(C)c(CN4CCC(Nc5ncnc6sc(CC(F)(F)F)cc56)CC4)ccc32)CC1] | | |

TABLE 1-continued

Inhibitors of the menin-MLL interaction

| Compound Number | Structure | [MH]+ | LC-MS RT (min.) or TLC Rf |
|---|---|---|---|
| 66 | 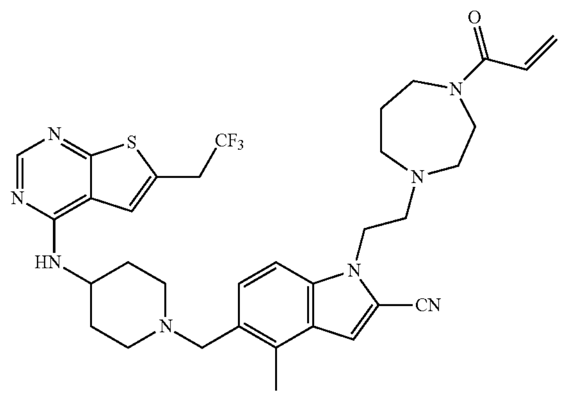 [SMILES: C=CC(=O)N1CCCN(CCn2c(C#N)cc3c(C)c(CN4CCC(Nc5ncnc6sc(CC(F)(F)F)cc56)CC4)ccc32)CC1] | | |
| 67 | 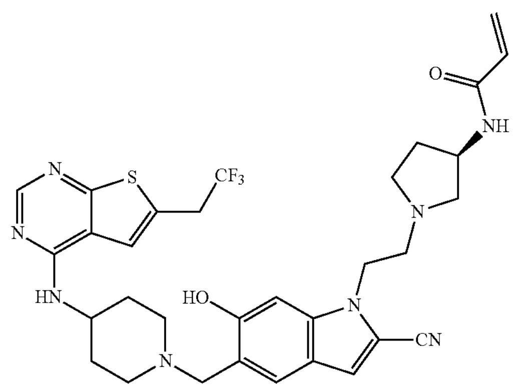 [SMILES: C=CC(=O)N[C@@H]1CCN(CCn2c(C#N)cc3cc(CN4CCC(Nc5ncnc6sc(CC(F)(F)F)cc56)CC4)c(O)cc32)C1] | | |
| 68 | 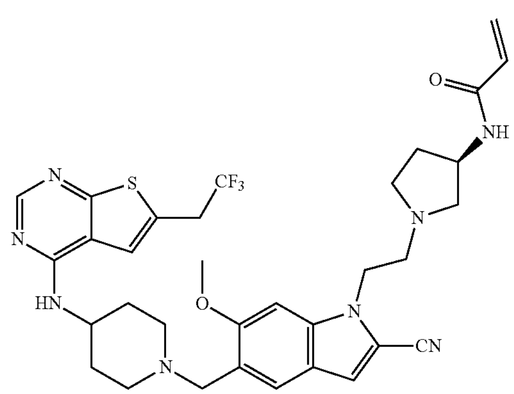 [SMILES: C=CC(=O)N[C@@H]1CCN(CCn2c(C#N)cc3cc(CN4CCC(Nc5ncnc6sc(CC(F)(F)F)cc56)CC4)c(OC)cc32)C1] | | |

TABLE 1-continued

Inhibitors of the menin-MLL interaction

| Compound Number | Structure | [MH]+ | LC-MS RT (min.) or TLC Rf |
|---|---|---|---|
| 69 | 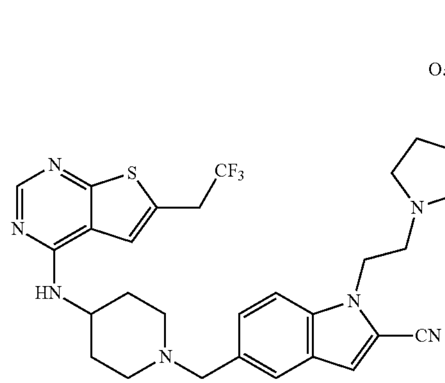 | | |
| 70 | 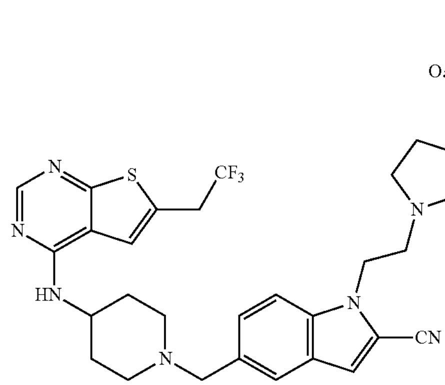 | | |
| 71 | 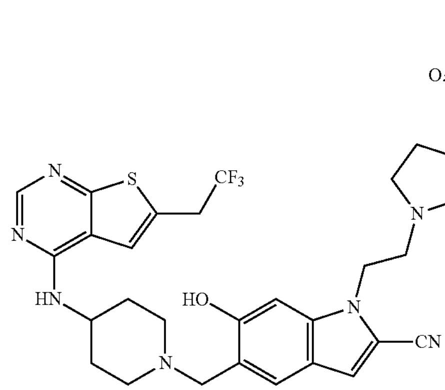 | | |
| 72 | 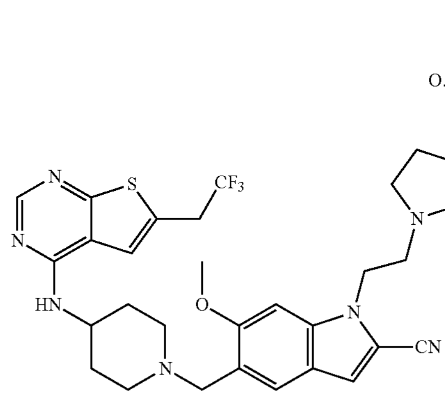 | | |

TABLE 1-continued

Inhibitors of the menin-MLL interaction

| Compound Number | Structure | [MH]+ | LC-MS RT (min.) or TLC Rf |
|---|---|---|---|
| 73 | 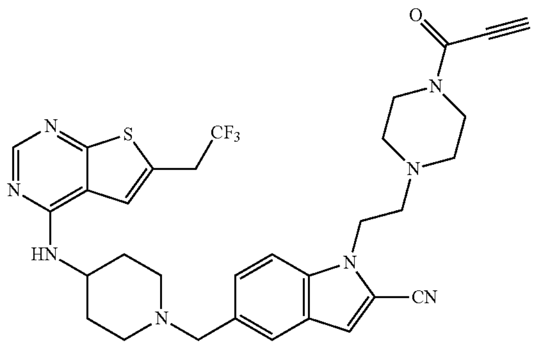 [SMILES: C#CC(=O)N1CCN(CCn2c(C#N)cc3cc(CN4CCC(Nc5ncnc6sc(CC(F)(F)F)cc56)CC4)ccc32)CC1] | | |
| 74 | 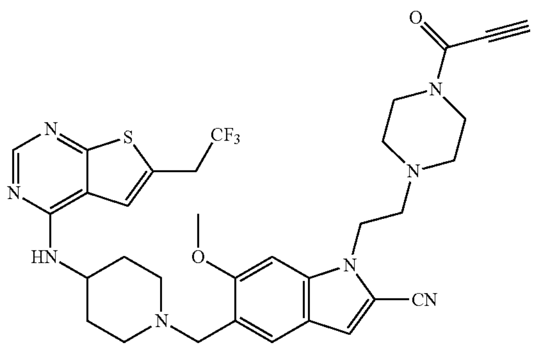 [SMILES: C#CC(=O)N1CCN(CCn2c(C#N)cc3cc(CN4CCC(Nc5ncnc6sc(CC(F)(F)F)cc56)CC4)c(OC)cc32)CC1] | | |
| 75 | 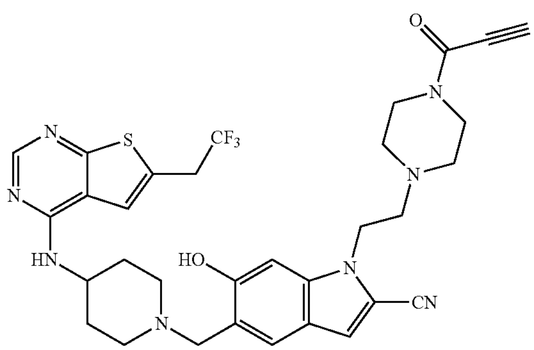 [SMILES: C#CC(=O)N1CCN(CCn2c(C#N)cc3cc(CN4CCC(Nc5ncnc6sc(CC(F)(F)F)cc56)CC4)c(O)cc32)CC1] | | |
| 76 | 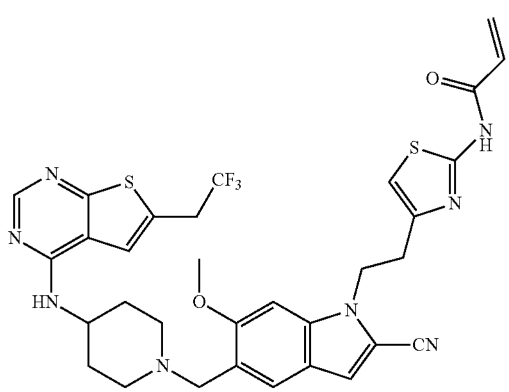 [SMILES: C=CC(=O)Nc1nc(CCn2c(C#N)cc3cc(CN4CCC(Nc5ncnc6sc(CC(F)(F)F)cc56)CC4)c(OC)cc32)cs1] | | |

TABLE 1-continued

Inhibitors of the menin-MLL interaction

| Compound Number | Structure | [MH]+ | LC-MS RT (min.) or TLC Rf |
|---|---|---|---|
| 77 | 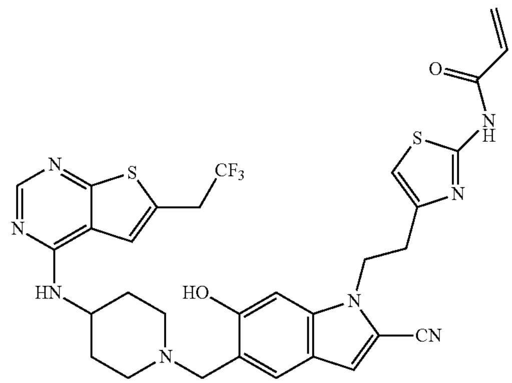 [SMILES: C=CC(=O)Nc1nc(CCn2c(C#N)cc3cc(CN4CCC(Nc5ncnc6sc(CC(F)(F)F)cc56)CC4)c(O)cc32)cs1] | | |
| 78 | 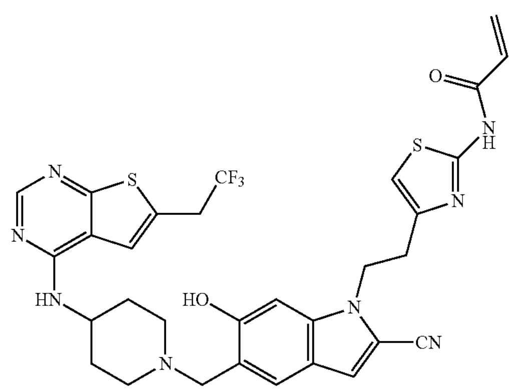 [SMILES: C=CC(=O)Nc1nc(CCn2c(C#N)cc3cc(CN4CCC(Nc5ncnc6sc(CC(F)(F)F)cc56)CC4)c(O)cc32)cs1] | | |
| 79 | 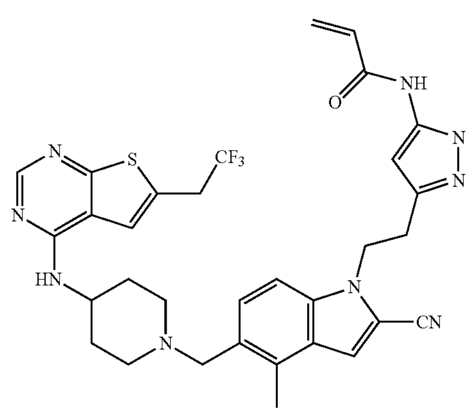 [SMILES: C=CC(=O)Nc1cc(CCn2c(C#N)cc3c(C)c(CN4CCC(Nc5ncnc6sc(CC(F)(F)F)cc56)CC4)ccc32)n[nH]1] | | |

TABLE 1-continued
Inhibitors of the menin-MLL interaction
| Compound Number | Structure | [MH]+ | LC-MS RT (min.) or TLC Rf |
|---|---|---|---|
| 80 | 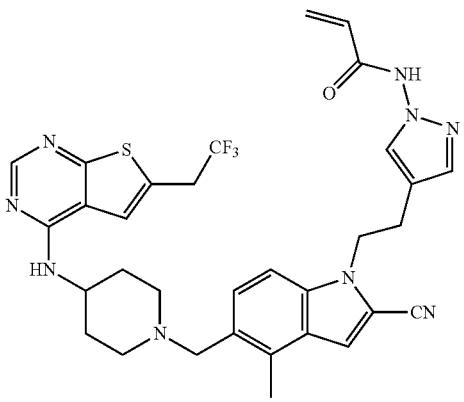 [SMILES: C=CC(=O)Nn1cc(CCn2c(C#N)cc3c(C)c(CN4CCC(Nc5ncnc6sc(CC(F)(F)F)cc56)CC4)ccc32)cn1] | | |
| 81 | 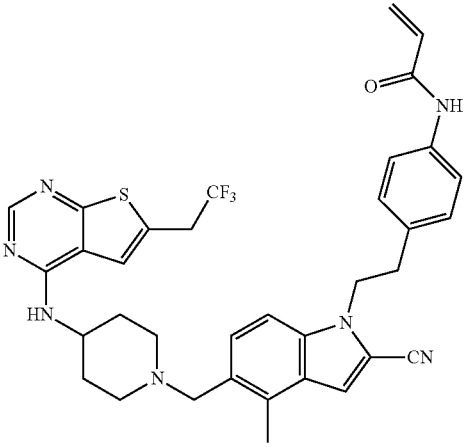 | | |
| 82 | 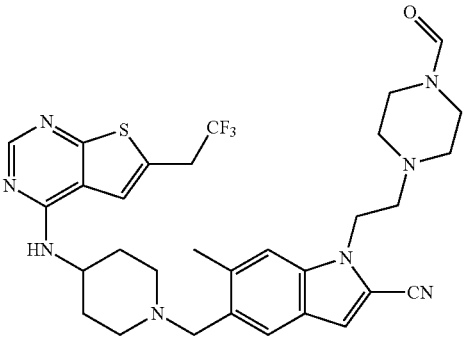 [SMILES: Cc1cc2c(cc1CN1CCC(Nc3ncnc4sc(CC(F)(F)F)cc34)CC1)cc(C#N)n2CCN1CCN(C=O)CC1] | | |
| 83 | 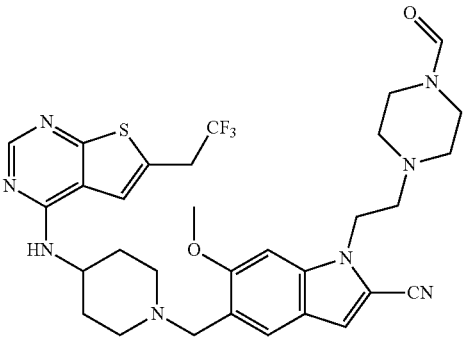 [SMILES: COc1cc2c(cc1CN1CCC(Nc3ncnc4sc(CC(F)(F)F)cc34)CC1)cc(C#N)n2CCN1CCN(C=O)CC1] | | |

TABLE 1-continued

Inhibitors of the menin-MLL interaction

| Compound Number | Structure | [MH]+ | LC-MS RT (min.) or TLC Rf |
|---|---|---|---|
| 84 | 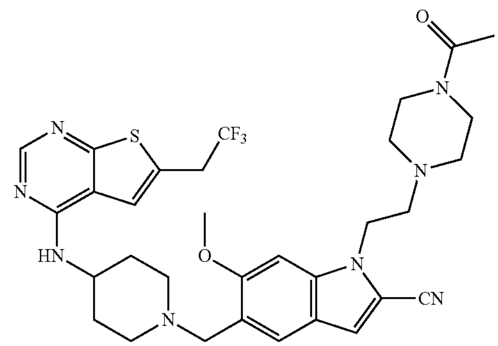 [SMILES: COc1cc2c(cc1CN1CCC(Nc3ncnc4sc(CC(F)(F)F)cc34)CC1)cc(C#N)n2CCN1CCN(C(C)=O)CC1] | | |
| 85 | 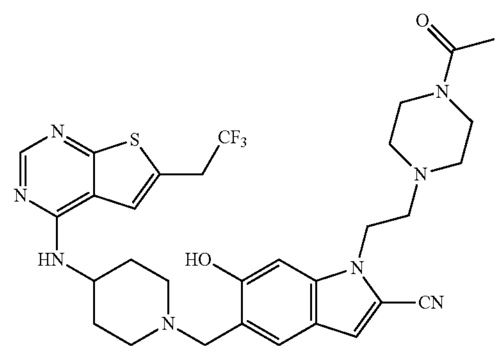 [SMILES: CC(=O)N1CCN(CCn2c(C#N)cc3cc(CN4CCC(Nc5ncnc6sc(CC(F)(F)F)cc56)CC4)c(O)cc32)CC1] | | |
| 86 | 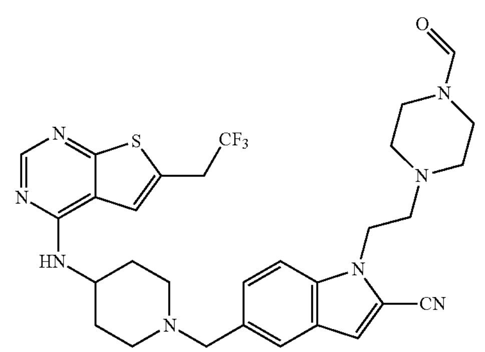 [SMILES: N#Cc1cc2cc(CN3CCC(Nc4ncnc5sc(CC(F)(F)F)cc45)CC3)ccc2n1CCN1CCN(C=O)CC1] | | |
| 87 | 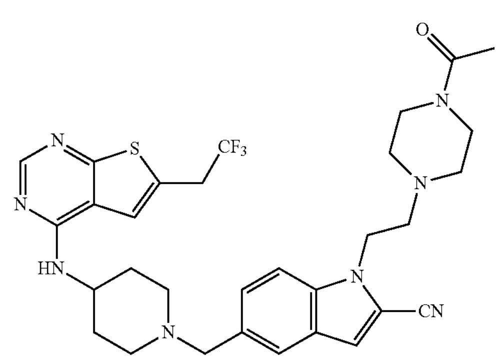 [SMILES: CC(=O)N1CCN(CCn2c(C#N)cc3cc(CN4CCC(Nc5ncnc6sc(CC(F)(F)F)cc56)CC4)ccc32)CC1] | | |

TABLE 1-continued

Inhibitors of the menin-MLL interaction

| Compound Number | Structure | [MH]+ | LC-MS RT (min.) or TLC Rf |
|---|---|---|---|
| 88 | 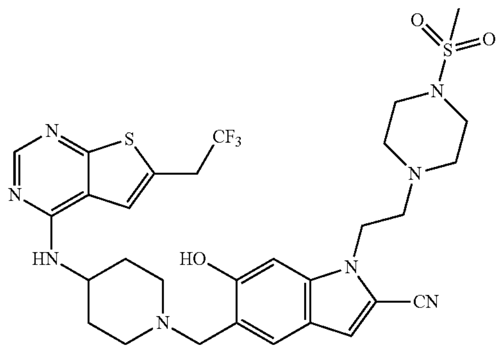 [SMILES: CS(=O)(=O)N1CCN(CCn2c(C#N)cc3cc(CN4CCC(Nc5ncnc6sc(CC(F)(F)F)cc56)CC4)c(O)cc32)CC1] | | |
| 89 | 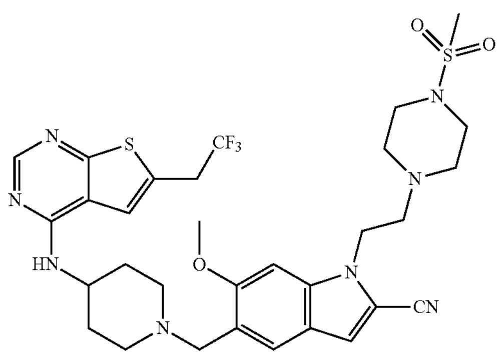 [SMILES: COc1cc2c(cc1CN1CCC(Nc3ncnc4sc(CC(F)(F)F)cc34)CC1)cc(C#N)n2CCN1CCN(S(C)(=O)=O)CC1] | | |
| 90 | 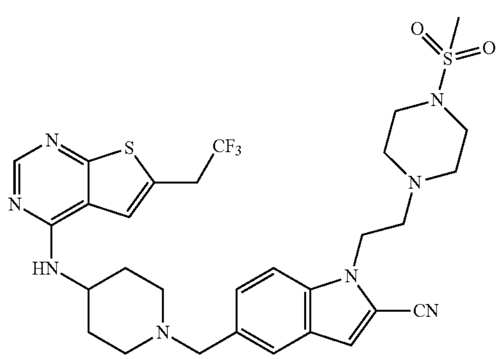 [SMILES: CS(=O)(=O)N1CCN(CCn2c(C#N)cc3cc(CN4CCC(Nc5ncnc6sc(CC(F)(F)F)cc56)CC4)ccc32)CC1] | | |
| 91 | 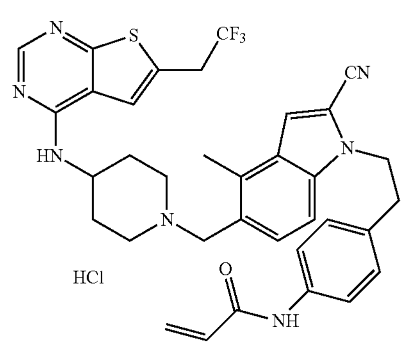 [SMILES: C=CC(=O)Nc1ccc(CCn2c(C#N)cc3c(C)c(CN4CCC(Nc5ncnc6sc(CC(F)(F)F)cc56)CC4)ccc32)cc1 ; Cl] | 658.2572 | 0.2 |

TABLE 1-continued

Inhibitors of the menin-MLL interaction

| Compound Number | Structure | [MH]+ | LC-MS RT (min.) or TLC Rf |
|---|---|---|---|
| 92 | 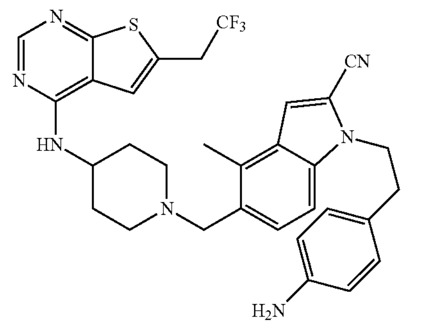 [SMILES: Cc1c(CN2CCC(Nc3ncnc4sc(CC(F)(F)F)cc34)CC2)ccc2c1cc(C#N)n2CCc1ccc(N)cc1] | 604.2467 | 0.25 |
| 93 | 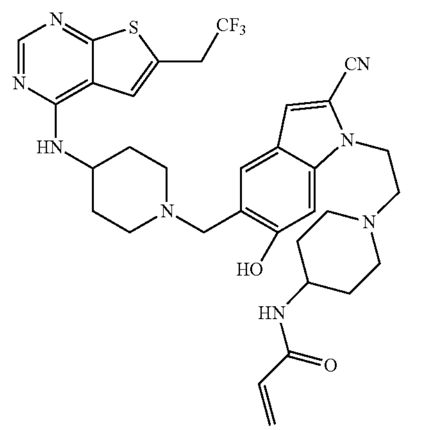 [SMILES: C=CC(=O)NC1CCN(CCn2c(C#N)cc3cc(CN4CCC(Nc5ncnc6sc(CC(F)(F)F)cc56)CC4)c(O)cc32)CC1] | 667.2765 | 0.2 |
| 94 | 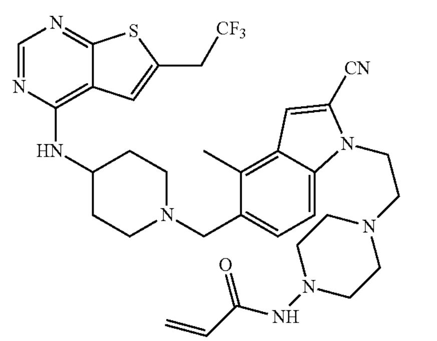 [SMILES: C=CC(=O)NN1CCN(CCn2c(C#N)cc3c(C)c(CN4CCC(Nc5ncnc6sc(CC(F)(F)F)cc56)CC4)ccc32)CC1] | 666.2945 | 0.15 |
| 95 | 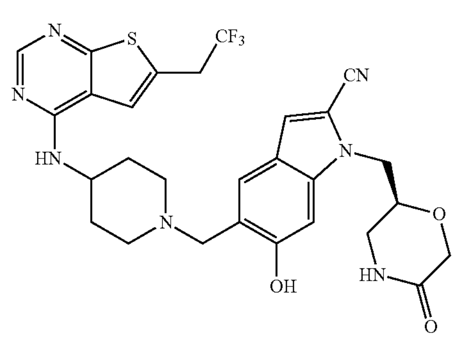 [SMILES: N#Cc1cc2cc(CN3CCC(Nc4ncnc5sc(CC(F)(F)F)cc45)CC3)c(O)cc2n1C[C@@H]1CNC(=O)CO1] | 600.1999 | 0.15 |

TABLE 1-continued

Inhibitors of the menin-MLL interaction

| Compound Number | Structure | [MH]+ | LC-MS RT (min.) or TLC Rf |
|---|---|---|---|
| 96 | 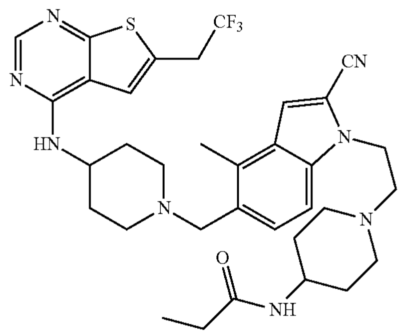 [SMILES: CCC(=O)NC1CCN(CCn2c(C#N)cc3c(C)c(CN4CCC(Nc5ncnc6sc(CC(F)(F)F)cc56)CC4)ccc32)CC1] | 667.3149 | 0.25 |
| 97 | 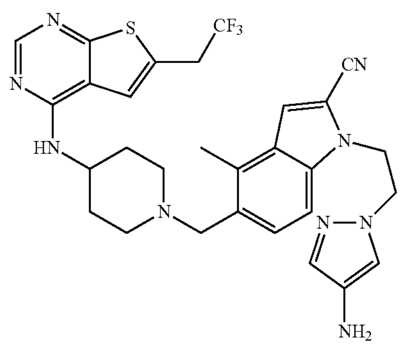 [SMILES: Cc1c(CN2CCC(Nc3ncnc4sc(CC(F)(F)F)cc34)CC2)ccc2c1cc(C#N)n2CCn1cc(N)cn1] | 594.2370 | 0.2 |
| 98 | 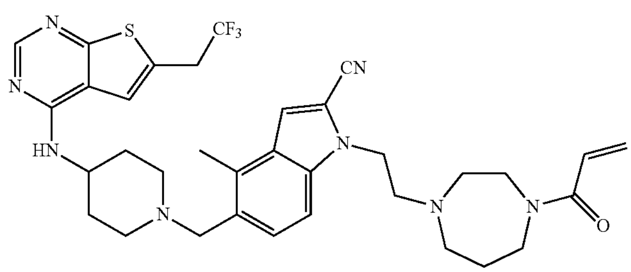 [SMILES: C=CC(=O)N1CCCN(CCn2c(C#N)cc3c(C)c(CN4CCC(Nc5ncnc6sc(CC(F)(F)F)cc56)CC4)ccc32)CC1] | 665.2992 | 0.25 |
| 99 | 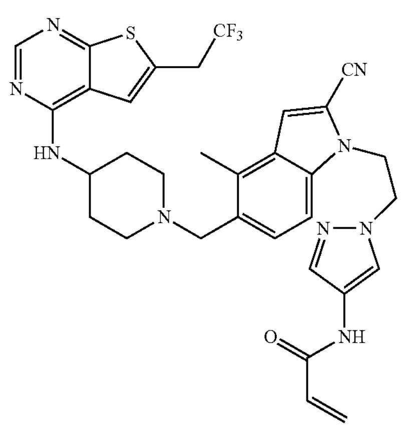 [SMILES: C=CC(=O)Nc1cnn(CCn2c(C#N)cc3c(C)c(CN4CCC(Nc5ncnc6sc(CC(F)(F)F)cc56)CC4)ccc32)c1] | 645.2475 | 0.25 |

TABLE 1-continued
Inhibitors of the menin-MLL interaction
| Compound Number | Structure | [MH]+ | LC-MS RT (min.) or TLC Rf |
|---|---|---|---|
| 100 | 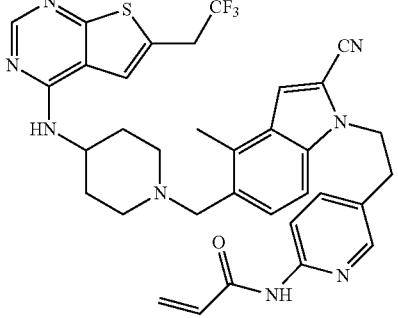 | 659.2523 | 0.25 |
| 101 | 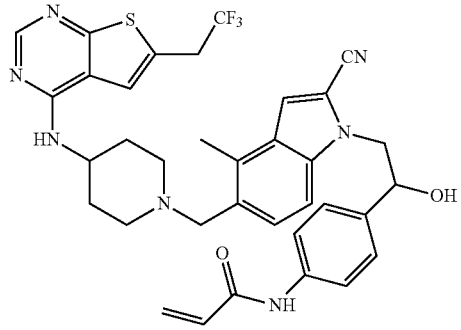 [SMILES: C=CC(=O)Nc1ccc(C(O)Cn2c(C#N)cc3c(C)c(CN4CCC(Nc5ncnc6sc(CC(F)(F)F)cc56)CC4)ccc32)cc1] | 674.2520 | 0.2 |
| 102 | 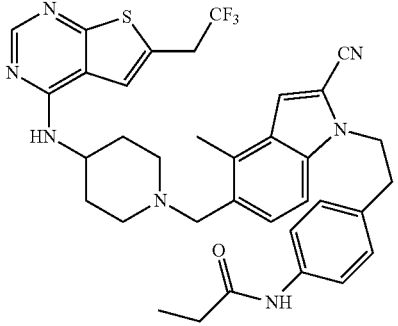 [SMILES: CCC(=O)Nc1ccc(CCn2c(C#N)cc3c(C)c(CN4CCC(Nc5ncnc6sc(CC(F)(F)F)cc56)CC4)ccc32)cc1] | 660.2727 | 0.25 |
| 103 | 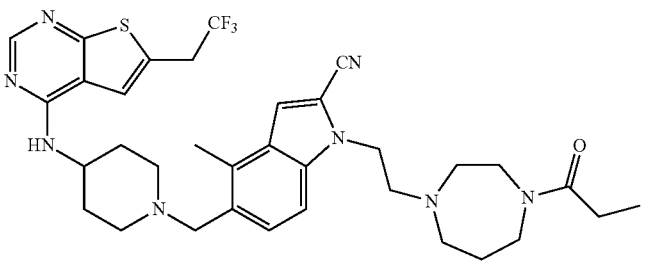 [SMILES: CCC(=O)N1CCCN(CCn2c(C#N)cc3c(C)c(CN4CCC(Nc5ncnc6sc(CC(F)(F)F)cc56)CC4)ccc32)CC1] | 667.3149 | 0.25 |

TABLE 1-continued

Inhibitors of the menin-MLL interaction

| Compound Number | Structure | [MH]+ | LC-MS RT (min.) or TLC Rf |
|---|---|---|---|
| 104 | 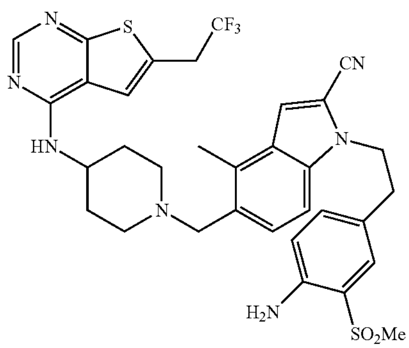 [SMILES: Cc1c(CN2CCC(Nc3ncnc4sc(CC(F)(F)F)cc34)CC2)ccc2c1cc(C#N)n2CCc1ccc(N)c(S(C)(=O)=O)c1] | 682.2240 | 0.25 |
| 105 | 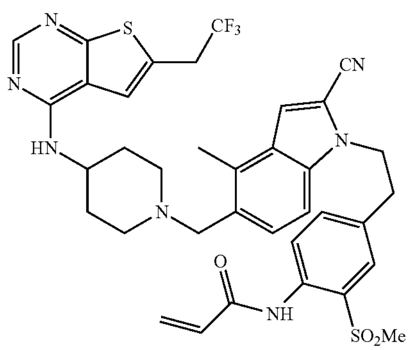 [SMILES: C=CC(=O)Nc1ccc(CCn2c(C#N)cc3c(C)c(CN4CCC(Nc5ncnc6sc(CC(F)(F)F)cc56)CC4)ccc32)cc1S(C)(=O)=O] | 736.2346 | 0.25 |
| 106 | 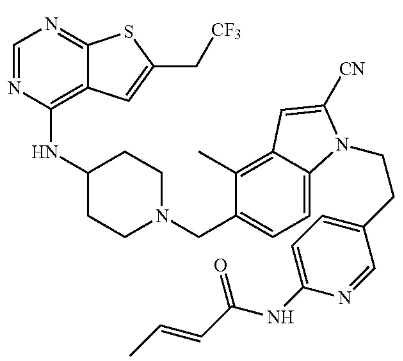 [SMILES: C/C=C/C(=O)Nc1ccc(CCn2c(C#N)cc3c(C)c(CN4CCC(Nc5ncnc6sc(CC(F)(F)F)cc56)CC4)ccc32)cn1] | 673.2679 | 0.3 |
| 107 | 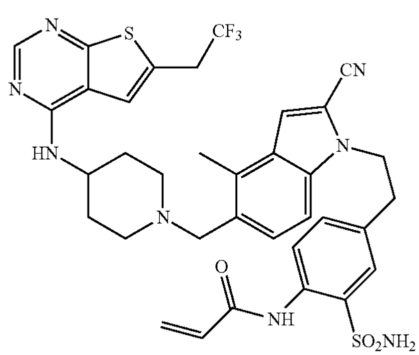 [SMILES: C=CC(=O)Nc1ccc(CCn2c(C#N)cc3c(C)c(CN4CCC(Nc5ncnc6sc(CC(F)(F)F)cc56)CC4)ccc32)cc1S(N)(=O)=O] | | |

TABLE 1-continued

Inhibitors of the menin-MLL interaction

| Compound Number | Structure | [MH]+ | LC-MS RT (min.) or TLC Rf |
|---|---|---|---|
| 108 | 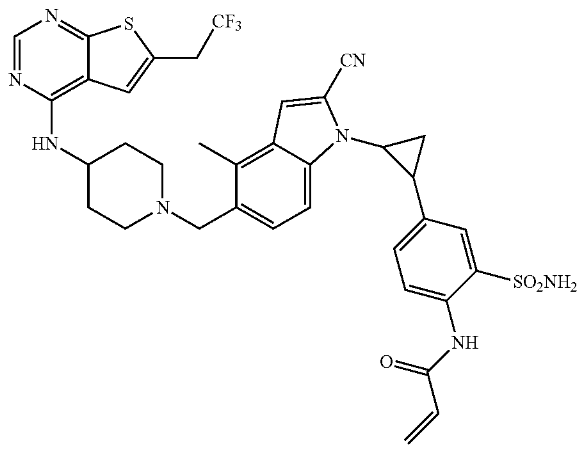 [SMILES: C=CC(=O)Nc1ccc(C2CC2n2c(C#N)cc3c(C)c(CN4CCC(Nc5ncnc6sc(CC(F)(F)F)cc56)CC4)ccc32)cc1S(N)(=O)=O] | | |
| 109 | 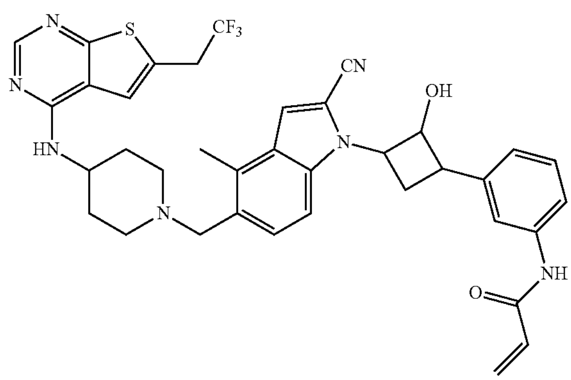 [SMILES: C=CC(=O)Nc1cccc(C2CC(n3c(C#N)cc4c(C)c(CN5CCC(Nc6ncnc7sc(CC(F)(F)F)cc67)CC5)ccc43)C2O)c1] | | |
| 110 | 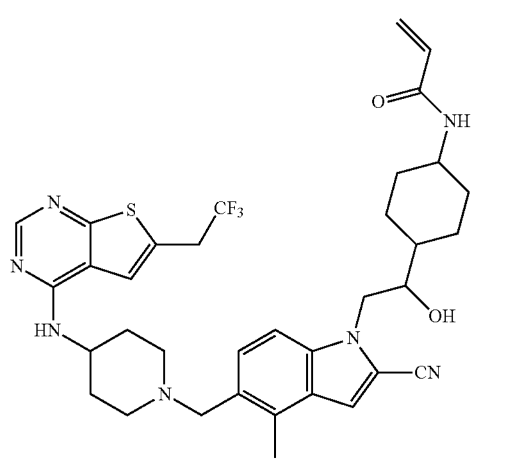 [SMILES: C=CC(=O)NC1CCC(C(O)Cn2c(C#N)cc3c(C)c(CN4CCC(Nc5ncnc6sc(CC(F)(F)F)cc56)CC4)ccc32)CC1] | | |

TABLE 1-continued
Inhibitors of the menin-MLL interaction
| Compound Number | Structure | [MH]+ | LC-MS RT (min.) or TLC Rf |
|---|---|---|---|
| 111 | 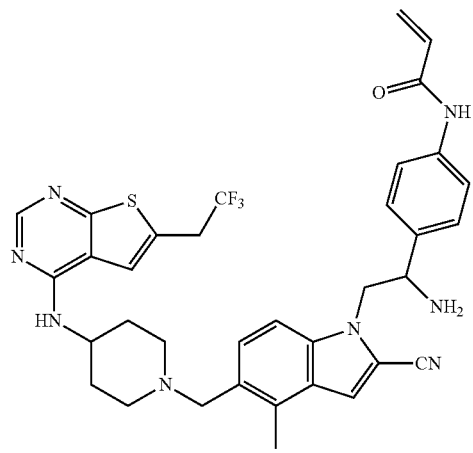 [SMILES: C=CC(=O)Nc1ccc(C(N)Cn2c(C#N)cc3c(C)c(CN4CCC(Nc5ncnc6sc(CC(F)(F)F)cc56)CC4)ccc32)cc1] | 673.2682 | 0.15 |
| 112 | 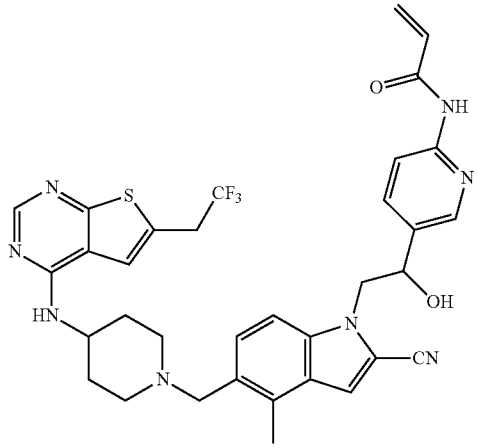 [SMILES: C=CC(=O)Nc1ccc(C(O)Cn2c(C#N)cc3c(C)c(CN4CCC(Nc5ncnc6sc(CC(F)(F)F)cc56)CC4)ccc32)cn1] | 675.2478 | 5.02 min |
| 113 | 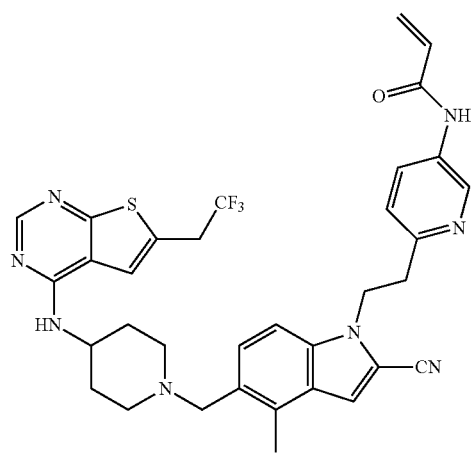 [SMILES: C=CC(=O)Nc1ccc(CCn2c(C#N)cc3c(C)c(CN4CCC(Nc5ncnc6sc(CC(F)(F)F)cc56)CC4)ccc32)nc1] | | |

TABLE 1-continued

Inhibitors of the menin-MLL interaction

| Compound Number | Structure | [MH]+ | LC-MS RT (min.) or TLC Rf |
|---|---|---|---|
| 114 | 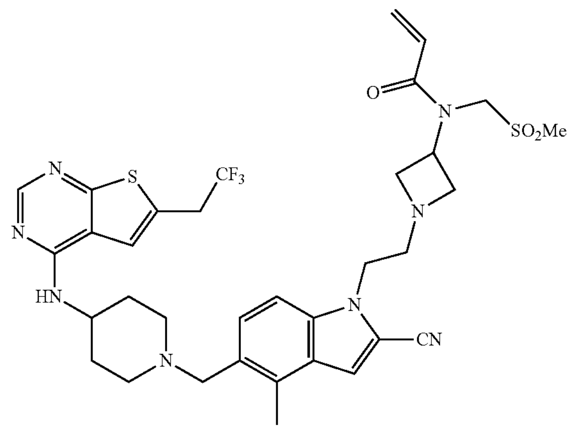 [SMILES: C=CC(=O)N(CS(C)(=O)=O)C1CN(CCn2c(C#N)cc3c(C)c(CN4CCC(Nc5ncnc6sc(CC(F)(F)F)cc56)CC4)ccc32)C1] | | |
| 115 | 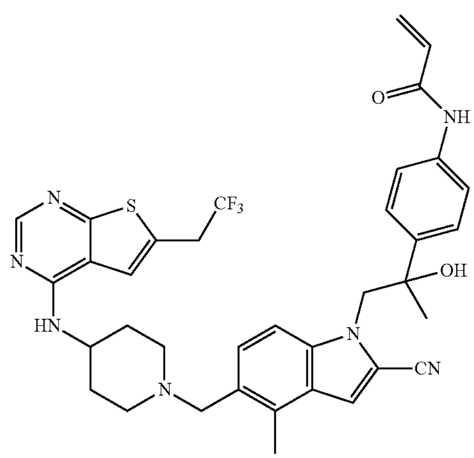 [SMILES: C=CC(=O)Nc1ccc(C(C)(O)Cn2c(C#N)cc3c(C)c(CN4CCC(Nc5ncnc6sc(CC(F)(F)F)cc56)CC4)ccc32)cc1] | 688.45 | 3.688* |
| 116 | 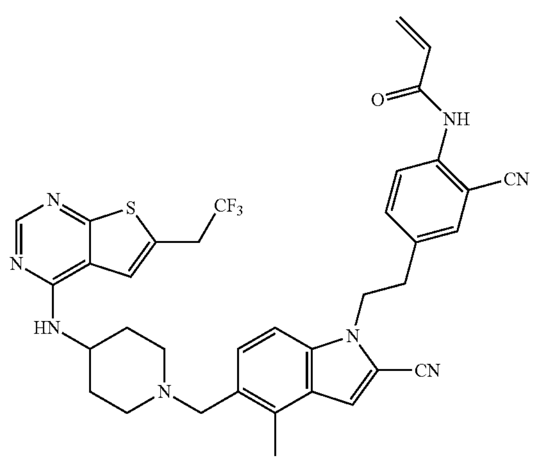 [SMILES: C=CC(=O)Nc1ccc(CCn2c(C#N)cc3c(C)c(CN4CCC(Nc5ncnc6sc(CC(F)(F)F)cc56)CC4)ccc32)cc1C#N] | | |

TABLE 1-continued

Inhibitors of the menin-MLL interaction

| Compound Number | Structure | [MH]+ | LC-MS RT (min.) or TLC Rf |
|---|---|---|---|
| 117 | 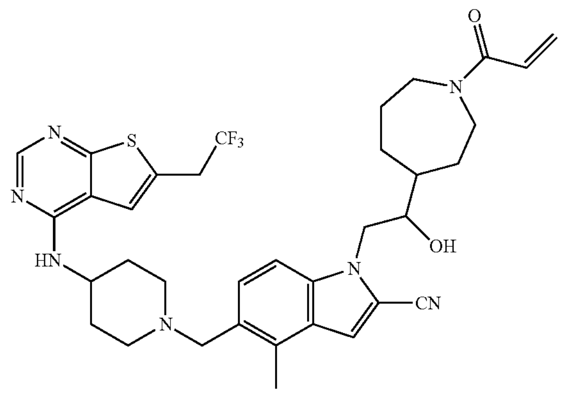 [SMILES: C=CC(=O)N1CCCC(C(O)Cn2c(C#N)cc3c(C)c(CN4CCC(Nc5ncnc6sc(CC(F)(F)F)cc56)CC4)ccc32)CC1] | | |
| 118 | 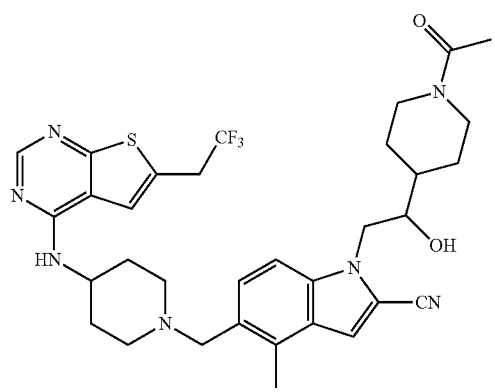 [SMILES: CC(=O)N1CCC(C(O)Cn2c(C#N)cc3c(C)c(CN4CCC(Nc5ncnc6sc(CC(F)(F)F)cc56)CC4)ccc32)CC1] | | |
| 119 | 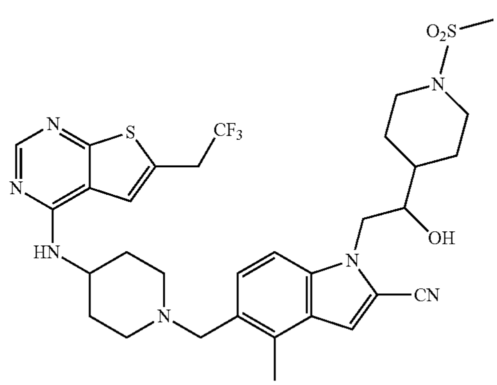 [SMILES: Cc1c(CN2CCC(Nc3ncnc4sc(CC(F)(F)F)cc34)CC2)ccc2c1cc(C#N)n2CC(O)C1CCN(S(C)(=O)=O)CC1] | | |

TABLE 1-continued

Inhibitors of the menin-MLL interaction

| Compound Number | Structure | [MH]+ | LC-MS RT (min.) or TLC Rf |
|---|---|---|---|
| 120 | 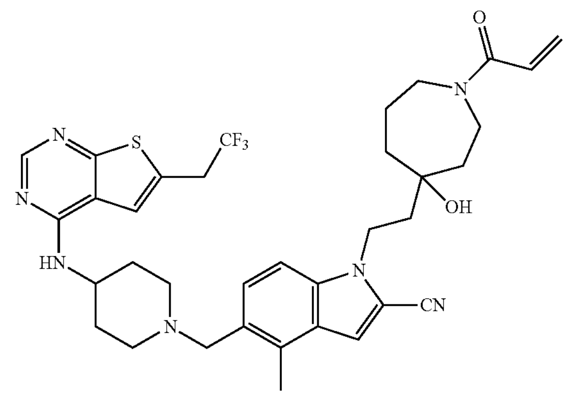 [SMILES: C=CC(=O)N1CCCC(O)(CCn2c(C#N)cc3c(C)c(CN4CCC(Nc5ncnc6sc(CC(F)(F)F)cc56)CC4)ccc32)CC1] | | |
| 121 | 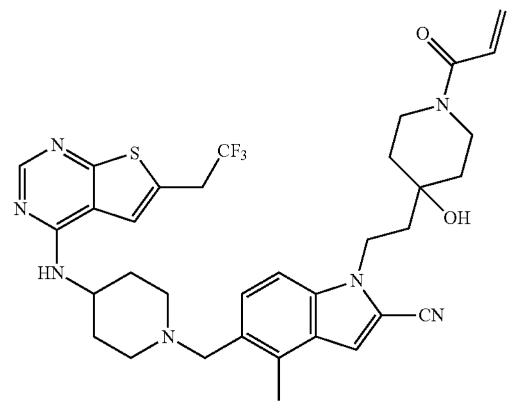 [SMILES: C=CC(=O)N1CCC(O)(CCn2c(C#N)cc3c(C)c(CN4CCC(Nc5ncnc6sc(CC(F)(F)F)cc56)CC4)ccc32)CC1] | | |
| 122 | 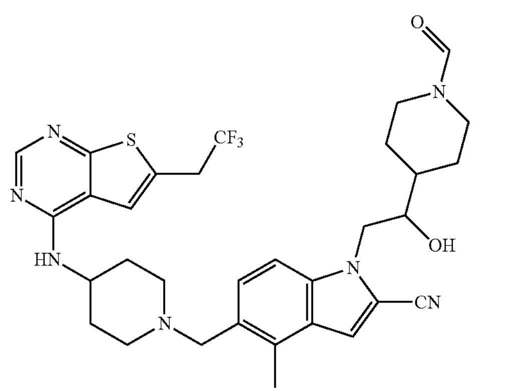 [SMILES: Cc1c(CN2CCC(Nc3ncnc4sc(CC(F)(F)F)cc34)CC2)ccc2c1cc(C#N)n2CC(O)C1CCN(C=O)CC1] | | |
| 123 | 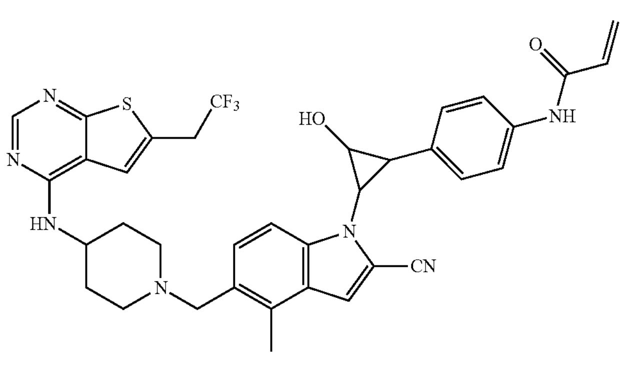 | | |

TABLE 1-continued
Inhibitors of the menin-MLL interaction
| Compound Number | Structure | [MH]+ | LC-MS RT (min.) or TLC Rf |
|---|---|---|---|
| 124 | 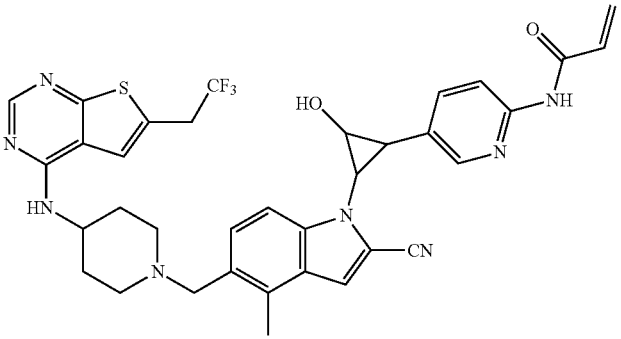 [SMILES: C=CC(=O)Nc1ccc(C2C(O)C2n2c(C#N)cc3c(C)c(CN4CCC(Nc5ncnc6sc(CC(F)(F)F)cc56)CC4)ccc32)cc1] | | |
| 125 | 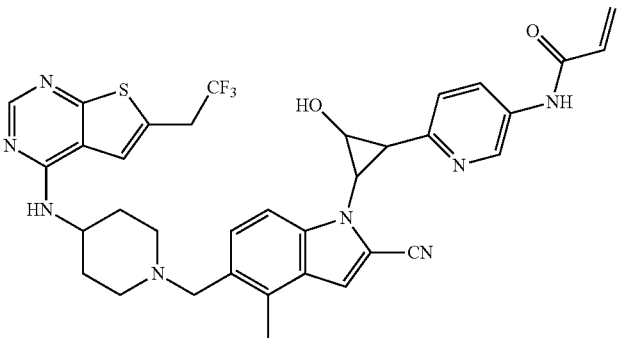 [SMILES: C=CC(=O)Nc1ccc(C2C(O)C2n2c(C#N)cc3c(C)c(CN4CCC(Nc5ncnc6sc(CC(F)(F)F)cc56)CC4)ccc32)nc1] | | |
| 126 | 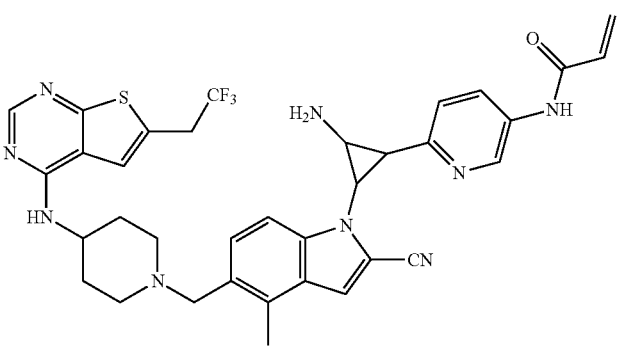 | | |
| 127 | 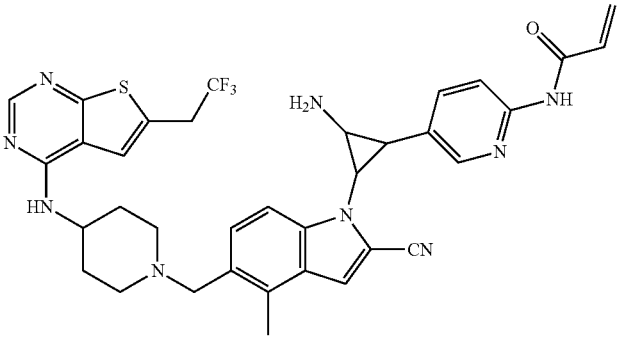 [SMILES: C=CC(=O)Nc1ccc(C2C(N)C2n2c(C#N)cc3c(C)c(CN4CCC(Nc5ncnc6sc(CC(F)(F)F)cc56)CC4)ccc32)cn1] | | |

TABLE 1-continued

Inhibitors of the menin-MLL interaction

| Compound Number | Structure | [MH]+ | LC-MS RT (min.) or TLC Rf |
|---|---|---|---|
| 128 | 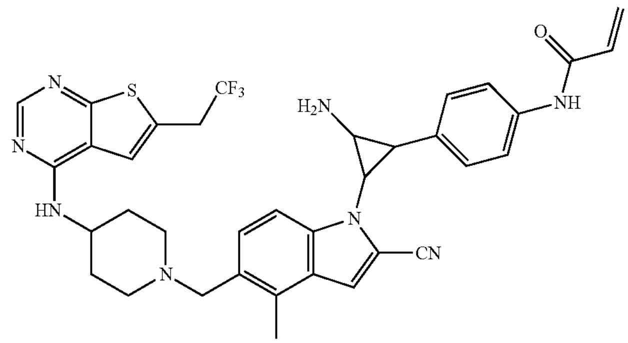 [SMILES: C=CC(=O)Nc1ccc(C2C(N)C2n2c(C#N)cc3c(C)c(CN4CCC(Nc5ncnc6sc(CC(F)(F)F)cc56)CC4)ccc32)cc1] | | |
| 129 | 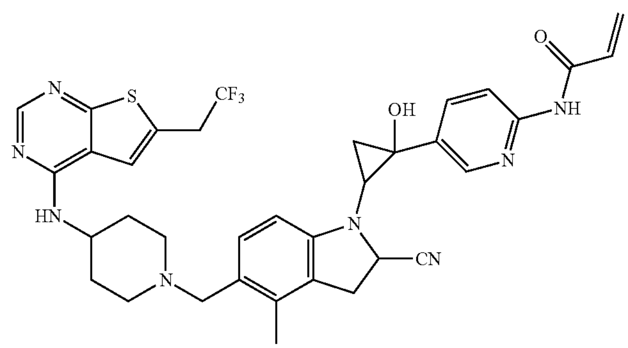 [SMILES: C=CC(=O)Nc1ccc(C2(O)CC2N2c3ccc(CN4CCC(Nc5ncnc6sc(CC(F)(F)F)cc56)CC4)c(C)c3CC2C#N)cn1] | | |
| 130 | 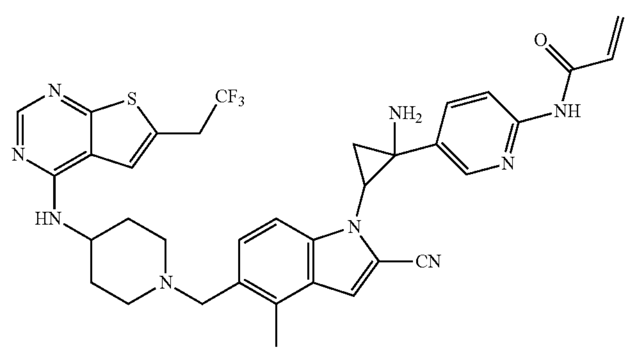 [SMILES: C=CC(=O)Nc1ccc(C2(N)CC2n2c(C#N)cc3c(C)c(CN4CCC(Nc5ncnc6sc(CC(F)(F)F)cc56)CC4)ccc32)cn1] | | |
| 131 | 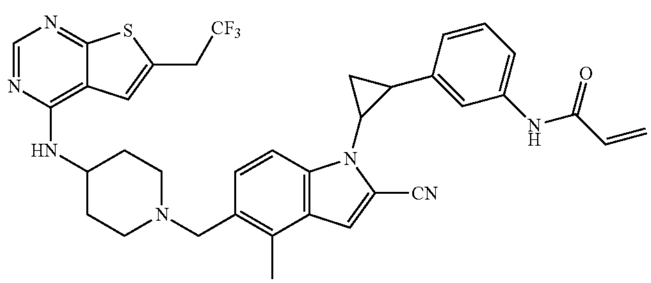 [SMILES: C=CC(=O)Nc1cccc(C2CC2n2c(C#N)cc3c(C)c(CN4CCC(Nc5ncnc6sc(CC(F)(F)F)cc56)CC4)ccc32)c1] | | |

TABLE 1-continued

Inhibitors of the menin-MLL interaction

| Compound Number | Structure | [MH]+ | LC-MS RT (min.) or TLC Rf |
|---|---|---|---|
| 132 | 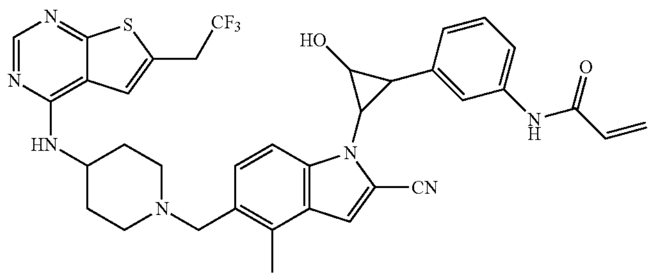 [SMILES: C=CC(=O)Nc1cccc(C2C(O)C2n2c(C#N)cc3c(C)c(CN4CCC(Nc5ncnc6sc(CC(F)(F)F)cc56)CC4)ccc32)c1] | | |
| 133 | 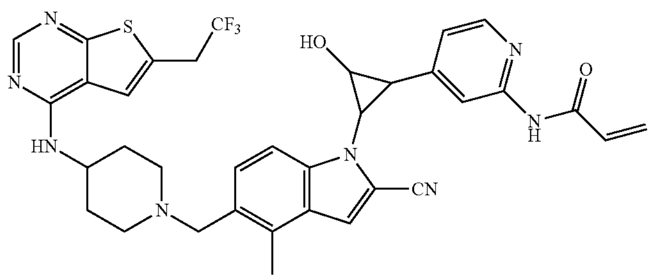 [SMILES: C=CC(=O)Nc1cc(C2C(O)C2n2c(C#N)cc3c(C)c(CN4CCC(Nc5ncnc6sc(CC(F)(F)F)cc56)CC4)ccc32)ccn1] | | |
| 134 | 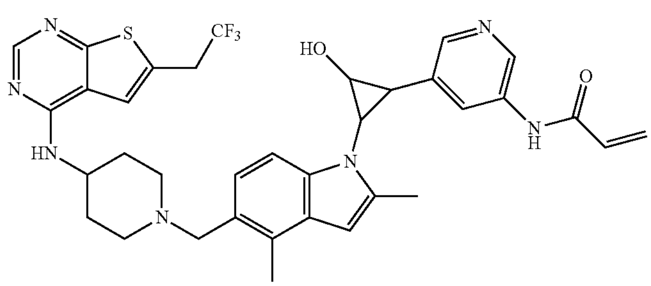 [SMILES: C=CC(=O)Nc1cncc(C2C(O)C2n2c(C)cc3c(C)c(CN4CCC(Nc5ncnc6sc(CC(F)(F)F)cc56)CC4)ccc32)c1] | | |
| 135 | 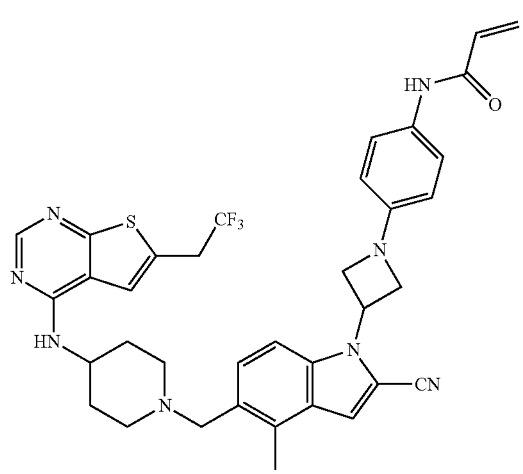 [SMILES: C=CC(=O)Nc1ccc(N2CC(n3c(C#N)cc4c(C)c(CN5CCC(Nc6ncnc7sc(CC(F)(F)F)cc67)CC5)ccc43)C2)cc1] | | |

TABLE 1-continued
Inhibitors of the menin-MLL interaction
| Compound Number | Structure | [MH]+ | LC-MS RT (min.) or TLC Rf |
|---|---|---|---|
| 136 | 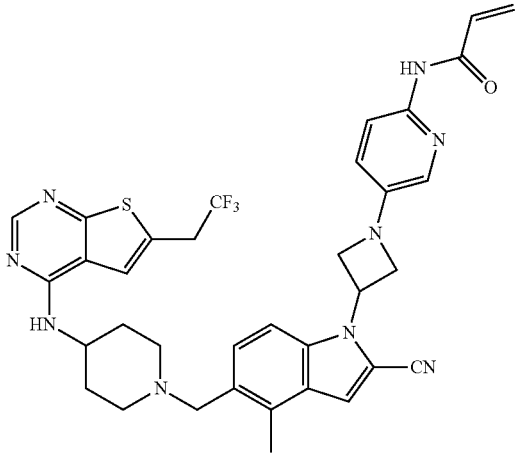 [SMILES: C=CC(=O)Nc1ccc(N2CC(n3c(C#N)cc4c(C)c(CN5CCC(Nc6ncnc7sc(CC(F)(F)F)cc67)CC5)ccc43)C2)cn1] | | |
| 137 | 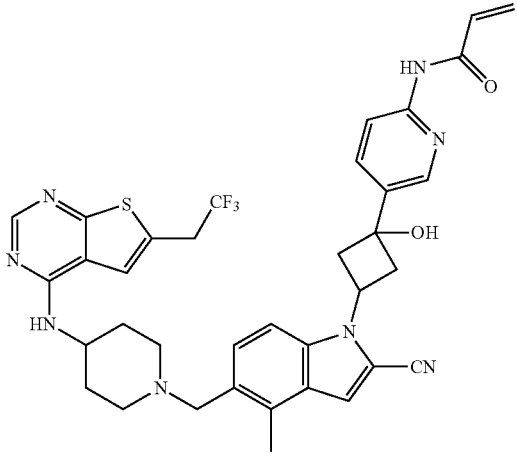 [SMILES: C=CC(=O)Nc1ccc(C2(O)CC(n3c(C#N)cc4c(C)c(CN5CCC(Nc6ncnc7sc(CC(F)(F)F)cc67)CC5)ccc43)C2)cn1] | | |
| 138 | 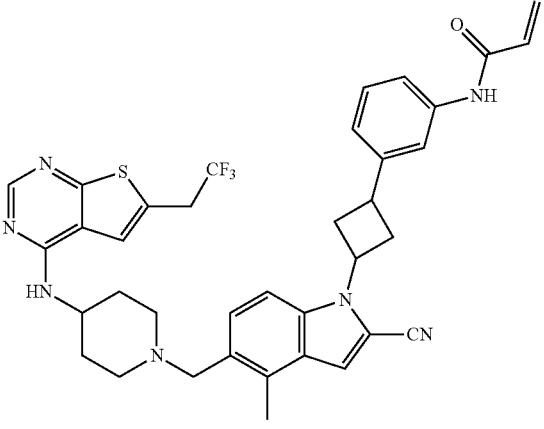 | | |

TABLE 1-continued

Inhibitors of the menin-MLL interaction

| Compound Number | Structure | [MH]+ | LC-MS RT (min.) or TLC Rf |
|---|---|---|---|
| 139 | 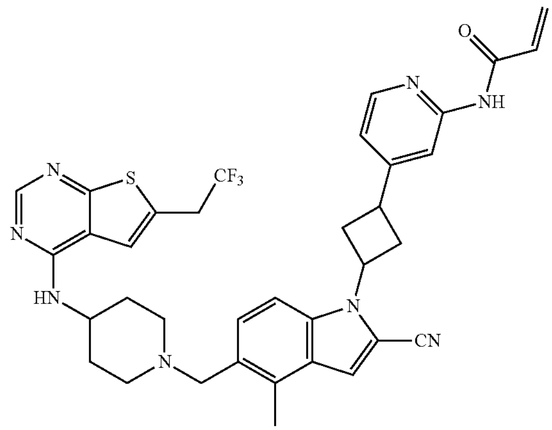 [SMILES: C=CC(=O)Nc1cc(C2CC(n3c(C#N)cc4c(C)c(CN5CCC(Nc6ncnc7sc(CC(F)(F)F)cc67)CC5)ccc43)C2)ccn1] | | |
| 140 | 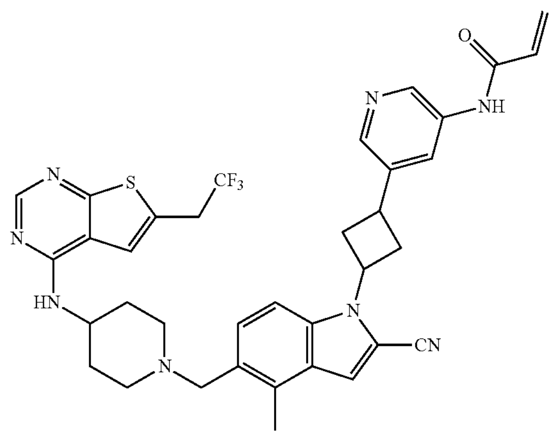 [SMILES: C=CC(=O)Nc1cncc(C2CC(n3c(C#N)cc4c(C)c(CN5CCC(Nc6ncnc7sc(CC(F)(F)F)cc67)CC5)ccc43)C2)c1] | | |
| 141 | 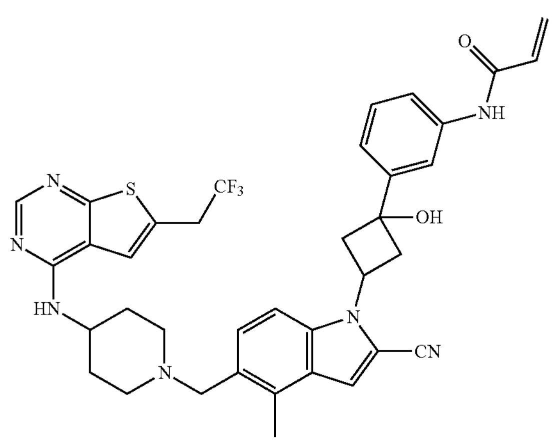 [SMILES: C=CC(=O)Nc1cccc(C2(O)CC(n3c(C#N)cc4c(C)c(CN5CCC(Nc6ncnc7sc(CC(F)(F)F)cc67)CC5)ccc43)C2)c1] | | |

TABLE 1-continued

Inhibitors of the menin-MLL interaction

| Compound Number | Structure | [MH]+ | LC-MS RT (min.) or TLC Rf |
|---|---|---|---|
| 142 | 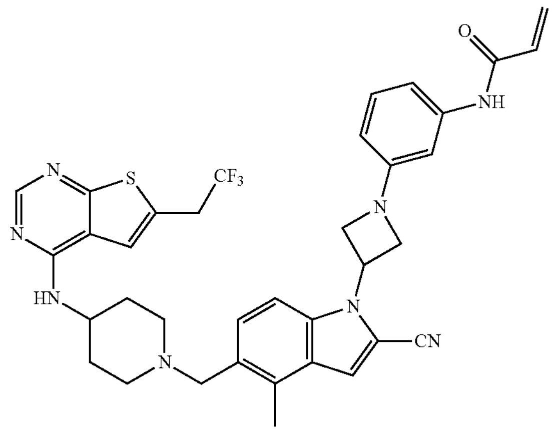 [SMILES: C=CC(=O)Nc1cccc(N2CC(n3c(C#N)cc4c(C)c(CN5CCC(Nc6ncnc7sc(CC(F)(F)F)cc67)CC5)ccc43)C2)c1] | | |
| 143 | 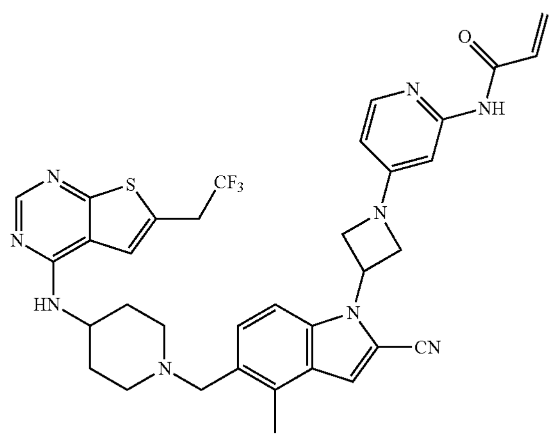 | | |
| 144 | 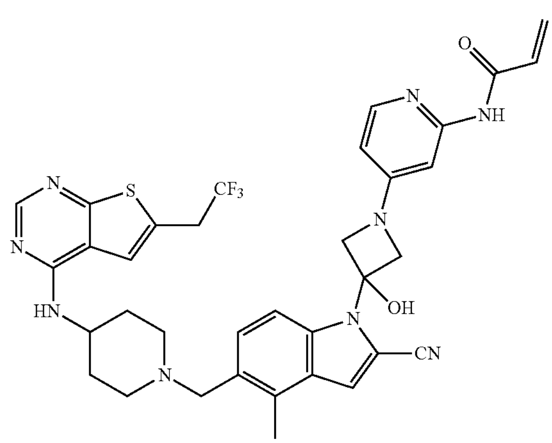 [SMILES: C=CC(=O)Nc1cc(N2CC(O)(n3c(C#N)cc4c(C)c(CN5CCC(Nc6ncnc7sc(CC(F)(F)F)cc67)CC5)ccc43)C2)ccn1] | | |

TABLE 1-continued

Inhibitors of the menin-MLL interaction

| Compound Number | Structure | [MH]+ | LC-MS RT (min.) or TLC Rf |
|---|---|---|---|
| 145 | 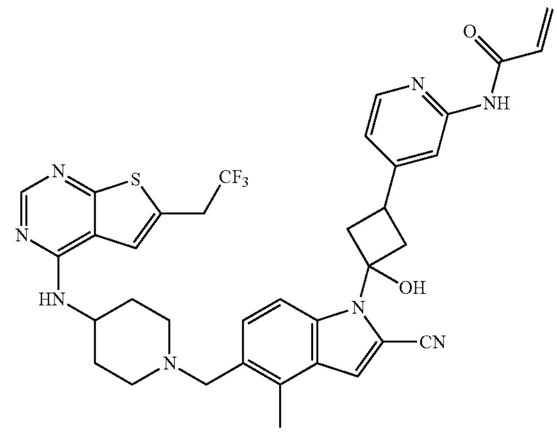 [SMILES: C=CC(=O)Nc1cc(C2CC(O)(n3c(C#N)cc4c(C)c(CN5CCC(Nc6ncnc7sc(CC(F)(F)F)cc67)CC5)ccc43)C2)ccn1] | | |
| 146 | 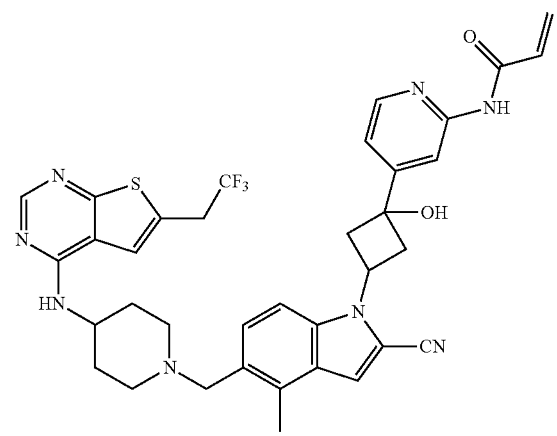 [SMILES: C=CC(=O)Nc1cc(C2(O)CC(n3c(C#N)cc4c(C)c(CN5CCC(Nc6ncnc7sc(CC(F)(F)F)cc67)CC5)ccc43)C2)ccn1] | | |
| 147 | 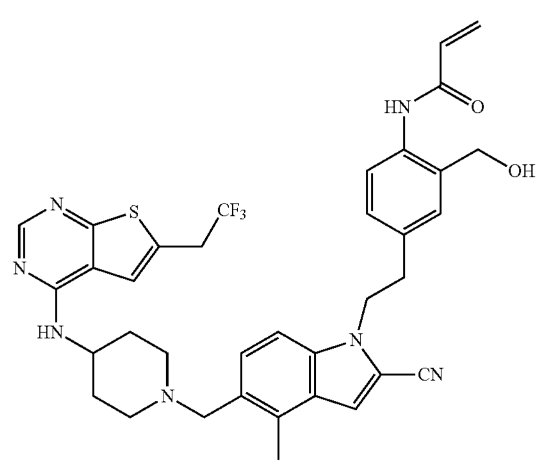 [SMILES: C=CC(=O)Nc1ccc(CCn2c(C#N)cc3c(C)c(CN4CCC(Nc5ncnc6sc(CC(F)(F)F)cc56)CC4)ccc32)cc1CO] | | |

TABLE 1-continued

Inhibitors of the menin-MLL interaction

| Compound Number | Structure | [MH]+ | LC-MS RT (min.) or TLC Rf |
|---|---|---|---|
| 148 | 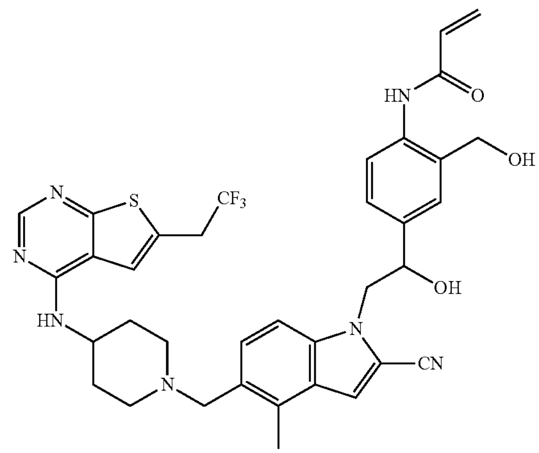 [SMILES: C=CC(=O)Nc1ccc(C(O)Cn2c(C#N)cc3c(C)c(CN4CCC(Nc5ncnc6sc(CC(F)(F)F)cc56)CC4)ccc32)cc1CO] | | |
| 149 | 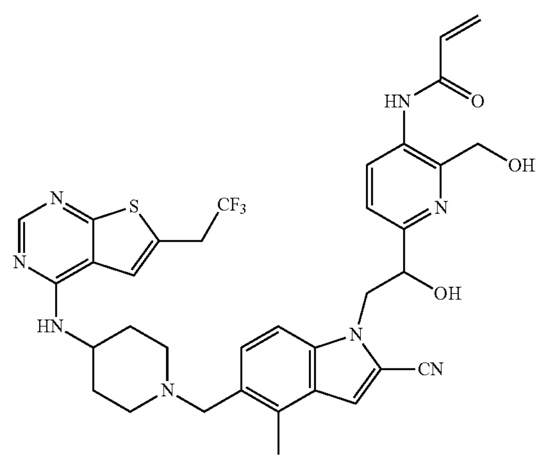 [SMILES: C=CC(=O)Nc1ccc(C(O)Cn2c(C#N)cc3c(C)c(CN4CCC(Nc5ncnc6sc(CC(F)(F)F)cc56)CC4)ccc32)nc1CO] | | |
| 150 | 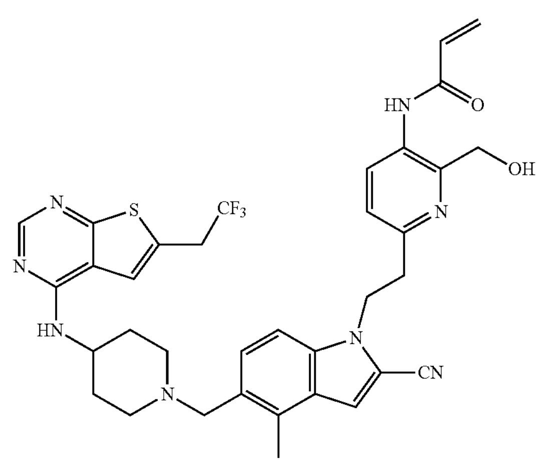 [SMILES: C=CC(=O)Nc1ccc(CCn2c(C#N)cc3c(C)c(CN4CCC(Nc5ncnc6sc(CC(F)(F)F)cc56)CC4)ccc32)nc1CO] | | |

TABLE 1-continued

Inhibitors of the menin-MLL interaction

| Compound Number | Structure | [MH]+ | LC-MS RT (min.) or TLC Rf |
|---|---|---|---|
| 151 | 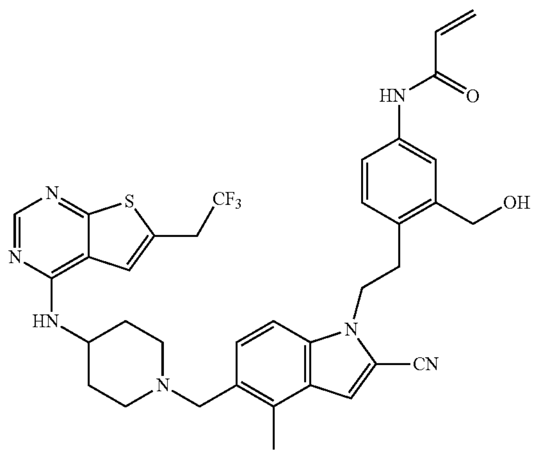 [SMILES: C=CC(=O)Nc1ccc(CCn2c(C#N)cc3c(C)c(CN4CCC(Nc5ncnc6sc(CC(F)(F)F)cc56)CC4)ccc32)c(CO)c1] | | |
| 152 | 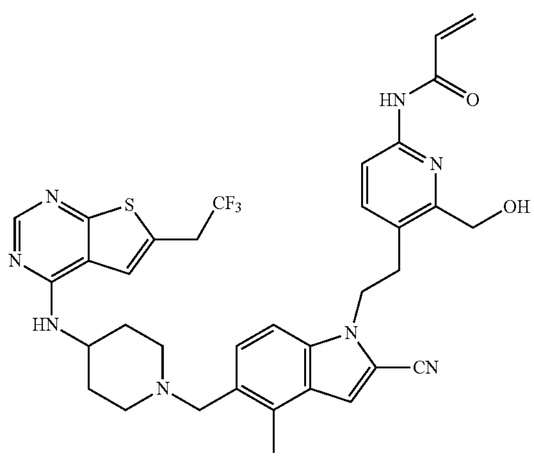 [SMILES: C=CC(=O)Nc1ccc(CCn2c(C#N)cc3c(C)c(CN4CCC(Nc5ncnc6sc(CC(F)(F)F)cc56)CC4)ccc32)c(CO)n1] | | |
| 153 | 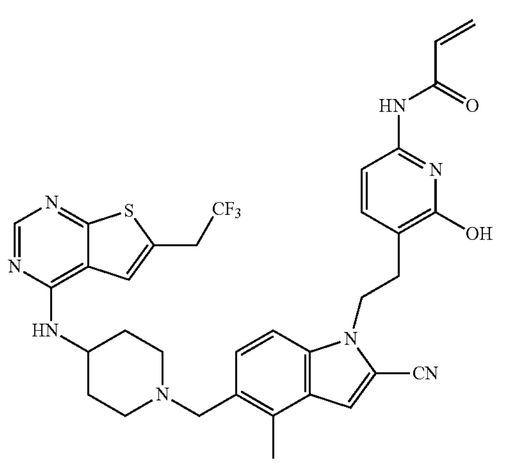 | | |

TABLE 1-continued

Inhibitors of the menin-MLL interaction

| Compound Number | Structure | [MH]+ | LC-MS RT (min.) or TLC Rf |
|---|---|---|---|
| 154 | 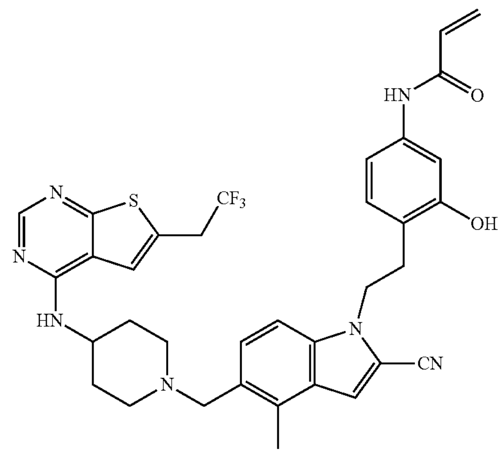 [SMILES: C=CC(=O)Nc1ccc(CCn2c(C#N)cc3c(C)c(CN4CCC(Nc5ncnc6sc(CC(F)(F)F)cc56)CC4)ccc32)c(O)c1] | | |
| 155 | 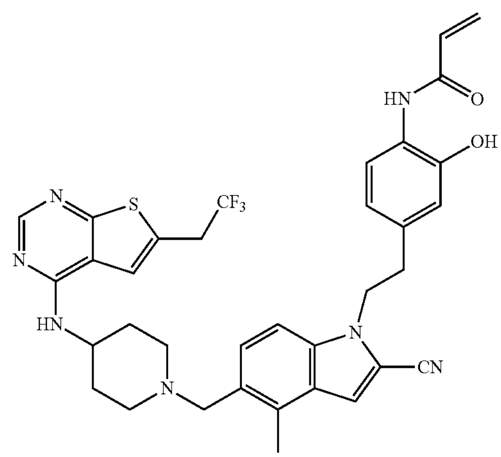 [SMILES: C=CC(=O)Nc1ccc(CCn2c(C#N)cc3c(C)c(CN4CCC(Nc5ncnc6sc(CC(F)(F)F)cc56)CC4)ccc32)cc1O] | | |
| 156 | 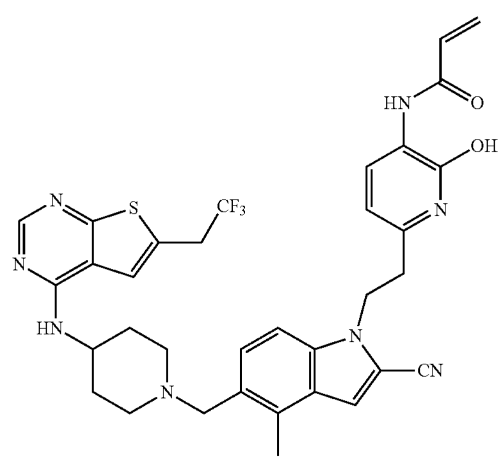 [SMILES: C=CC(=O)Nc1ccc(CCn2c(C#N)cc3c(C)c(CN4CCC(Nc5ncnc6sc(CC(F)(F)F)cc56)CC4)ccc32)nc1O] | | |

TABLE 1-continued

Inhibitors of the menin-MLL interaction

| Compound Number | Structure | [MH]+ | LC-MS RT (min.) or TLC Rf |
|---|---|---|---|
| 157 | 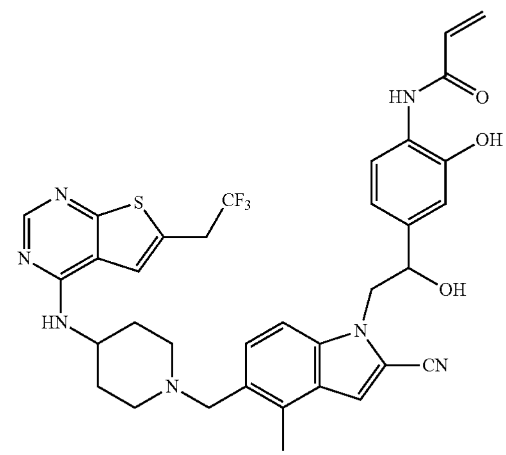 [SMILES: C=CC(=O)Nc1ccc(C(O)Cn2c(C#N)cc3c(C)c(CN4CCC(Nc5ncnc6sc(CC(F)(F)F)cc56)CC4)ccc32)cc1O] | | |
| 158 | 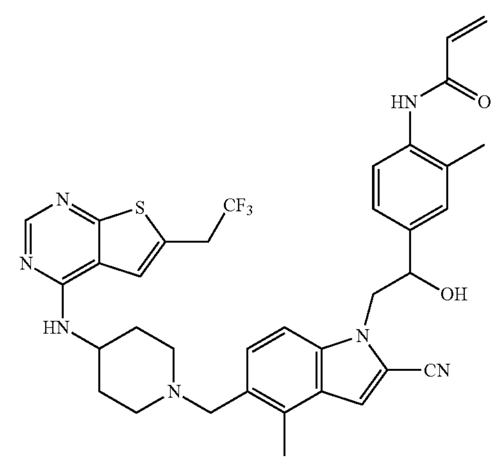 [SMILES: C=CC(=O)Nc1ccc(C(O)Cn2c(C#N)cc3c(C)c(CN4CCC(Nc5ncnc6sc(CC(F)(F)F)cc56)CC4)ccc32)cc1C] | | |
| 159 | 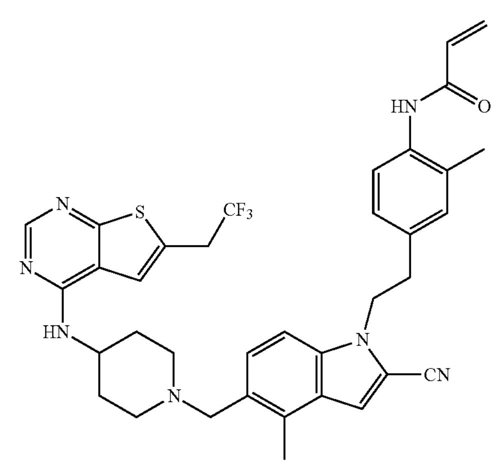 [SMILES: C=CC(=O)Nc1ccc(CCn2c(C#N)cc3c(C)c(CN4CCC(Nc5ncnc6sc(CC(F)(F)F)cc56)CC4)ccc32)cc1C] | | |

TABLE 1-continued

Inhibitors of the menin-MLL interaction

| Compound Number | Structure | [MH]+ | LC-MS RT (min.) or TLC Rf |
|---|---|---|---|
| 160 | 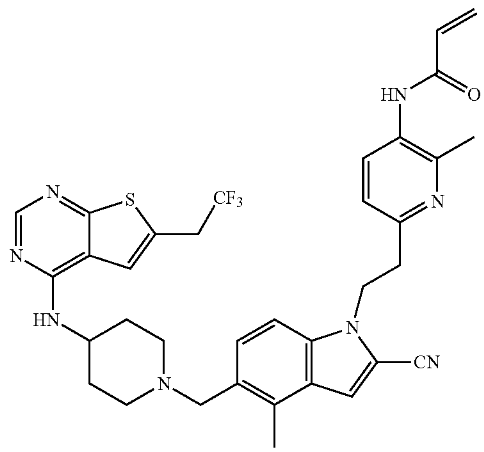 [SMILES: C=CC(=O)Nc1ccc(CCn2c(C#N)cc3c(C)c(CN4CCC(Nc5ncnc6sc(CC(F)(F)F)cc56)CC4)ccc32)nc1C] | | |
| 161 | 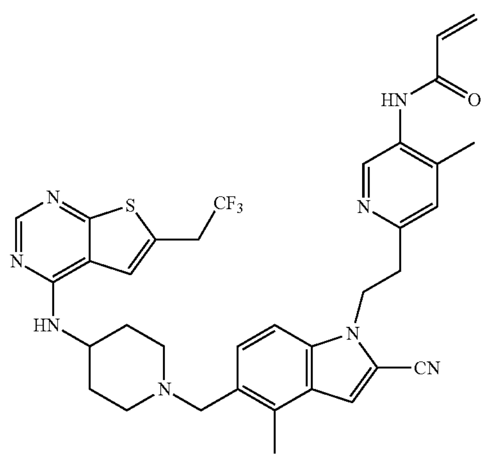 [SMILES: C=CC(=O)Nc1cnc(CCn2c(C#N)cc3c(C)c(CN4CCC(Nc5ncnc6sc(CC(F)(F)F)cc56)CC4)ccc32)cc1C] | | |
| 162 | 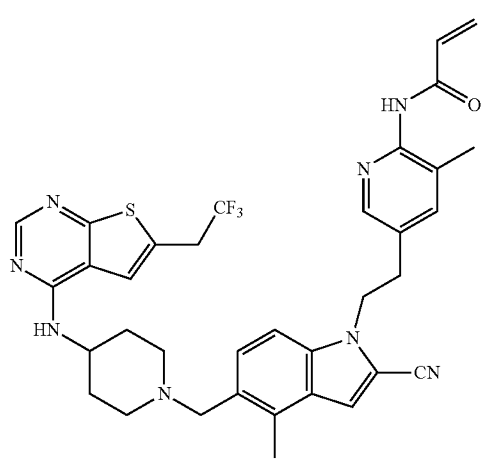 [SMILES: C=CC(=O)Nc1ncc(CCn2c(C#N)cc3c(C)c(CN4CCC(Nc5ncnc6sc(CC(F)(F)F)cc56)CC4)ccc32)cc1C] | | |

TABLE 1-continued

Inhibitors of the menin-MLL interaction

| Compound Number | Structure | [MH]+ | LC-MS RT (min.) or TLC Rf |
|---|---|---|---|
| 163 | 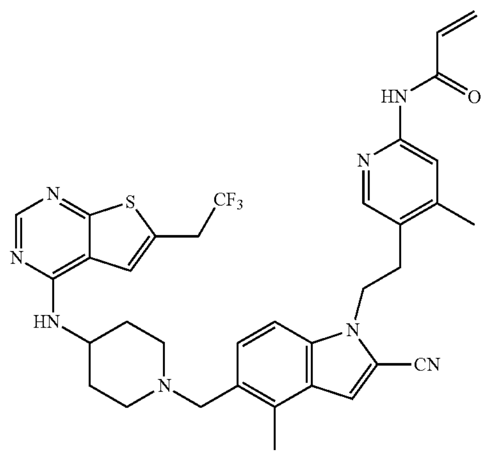 [SMILES: C=CC(=O)Nc1cc(C)c(CCn2c(C#N)cc3c(C)c(CN4CCC(Nc5ncnc6sc(CC(F)(F)F)cc56)CC4)ccc32)cn1] | | |
| 164 | 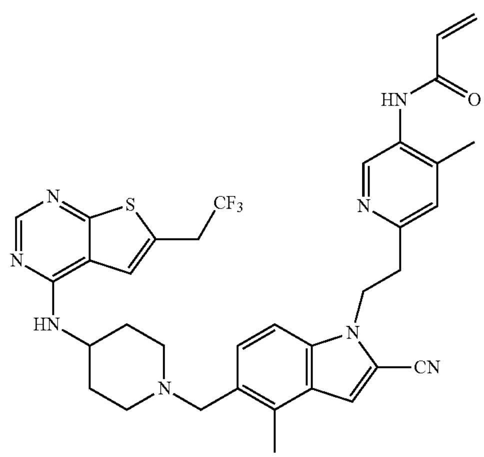 [SMILES: C=CC(=O)Nc1cnc(CCn2c(C#N)cc3c(C)c(CN4CCC(Nc5ncnc6sc(CC(F)(F)F)cc56)CC4)ccc32)cc1C] | | |
| 165 | 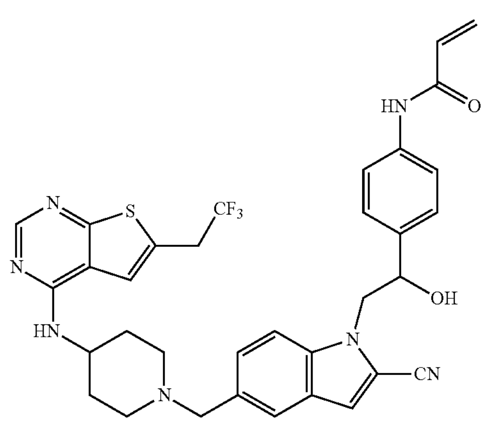 [SMILES: C=CC(=O)Nc1ccc(C(O)Cn2c(C#N)cc3cc(CN4CCC(Nc5ncnc6sc(CC(F)(F)F)cc56)CC4)ccc32)cc1] | | |

TABLE 1-continued

Inhibitors of the menin-MLL interaction

| Compound Number | Structure | [MH]+ | LC-MS RT (min.) or TLC Rf |
|---|---|---|---|
| 166 | 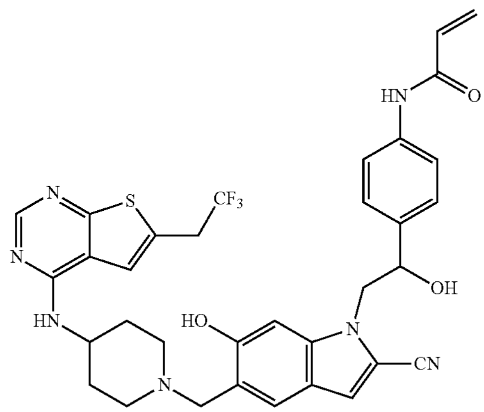 [SMILES: C=CC(=O)Nc1ccc(C(O)Cn2c(C#N)cc3cc(CN4CCC(Nc5ncnc6sc(CC(F)(F)F)cc56)CC4)c(O)cc32)cc1] | | |
| 167 | 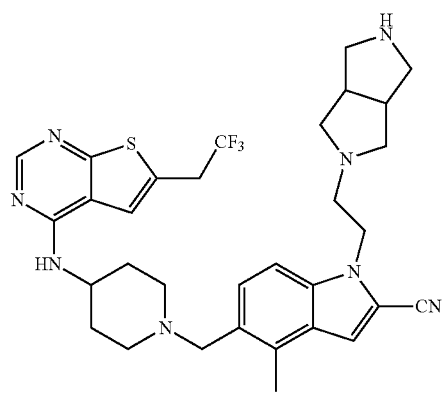 [SMILES: Cc1c(CN2CCC(Nc3ncnc4sc(CC(F)(F)F)cc34)CC2)ccc2c1cc(C#N)n2CCN1CC2CNCC2C1] | | |
| 168 | 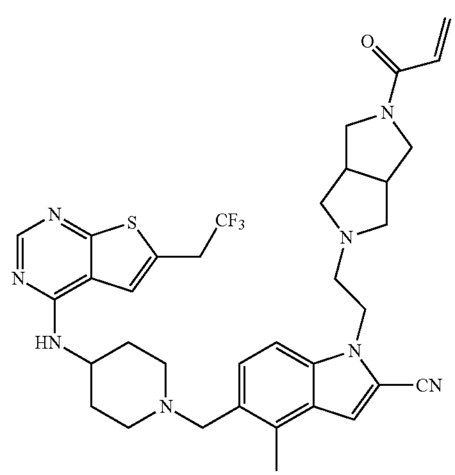 [SMILES: C=CC(=O)N1CC2CN(CCn3c(C#N)cc4c(C)c(CN5CCC(Nc6ncnc7sc(CC(F)(F)F)cc67)CC5)ccc43)CC2C1] | 677.45 | 1.45* |

TABLE 1-continued

Inhibitors of the menin-MLL interaction

| Compound Number | Structure | [MH]+ | LC-MS RT (min.) or TLC Rf |
|---|---|---|---|
| 169 | 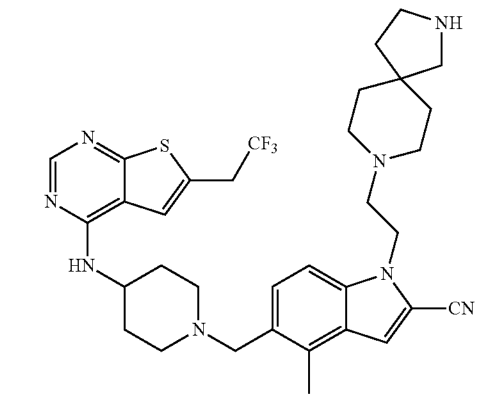 [SMILES: Cc1c(CN2CCC(Nc3ncnc4sc(CC(F)(F)F)cc34)CC2)ccc2c1cc(C#N)n2CCN1CCC2(CCNC2)CC1] | | |
| 170 | 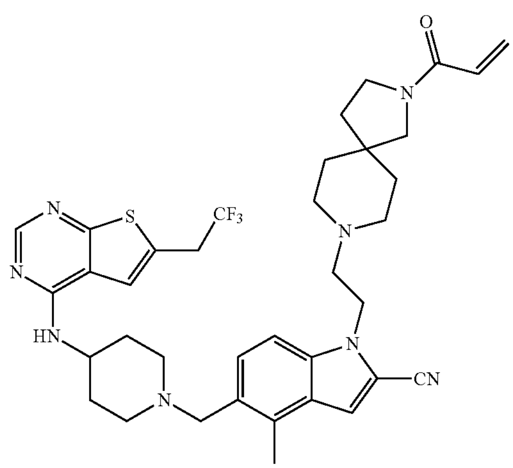 [SMILES: C=CC(=O)N1CCC2(CCN(CCn3c(C#N)cc4c(C)c(CN5CCC(Nc6ncnc7sc(CC(F)(F)F)cc67)CC5)ccc43)CC2)C1] | 705.5 | 2.262* |
| 171 | 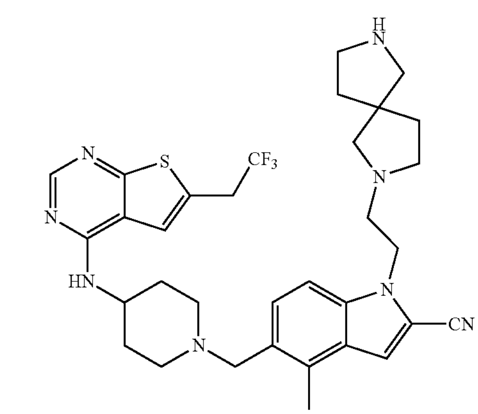 [SMILES: Cc1c(CN2CCC(Nc3ncnc4sc(CC(F)(F)F)cc34)CC2)ccc2c1cc(C#N)n2CCN1CCC2(CCNC2)C1] | | |

TABLE 1-continued

Inhibitors of the menin-MLL interaction

| Compound Number | Structure | [MH]+ | LC-MS RT (min.) or TLC Rf |
|---|---|---|---|
| 172 | 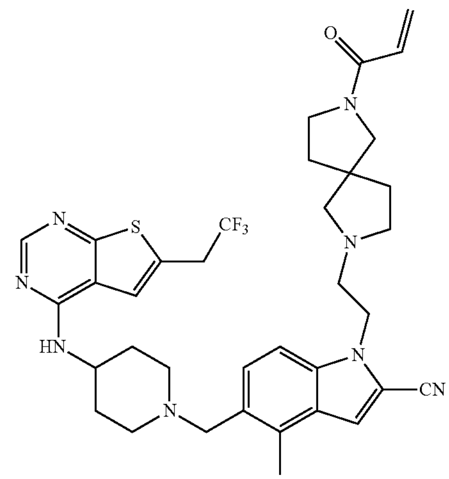 [SMILES: C=CC(=O)N1CCC2(CCN(CCn3c(C#N)cc4c(C)c(CN5CCC(Nc6ncnc7sc(CC(F)(F)F)cc67)CC5)ccc43)C2)C1] | 691.45 | 1.3* |
| 173 | 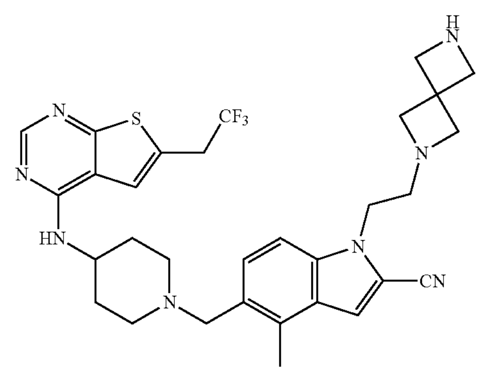 [SMILES: Cc1c(CN2CCC(Nc3ncnc4sc(CC(F)(F)F)cc34)CC2)ccc2c1cc(C#N)n2CCN1CC2(CNC2)C1] | | |
| 174 | 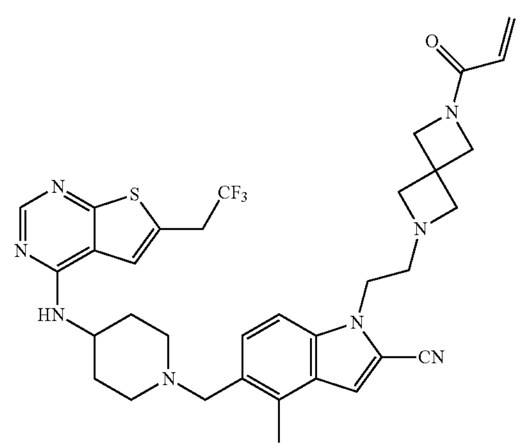 [SMILES: C=CC(=O)N1CC2(CN(CCn3c(C#N)cc4c(C)c(CN5CCC(Nc6ncnc7sc(CC(F)(F)F)cc67)CC5)ccc43)C2)C1] | 663.45 | 2.455* |

TABLE 1-continued

Inhibitors of the menin-MLL interaction

| Compound Number | Structure | [MH]+ | LC-MS RT (min.) or TLC Rf |
|---|---|---|---|
| 175 | 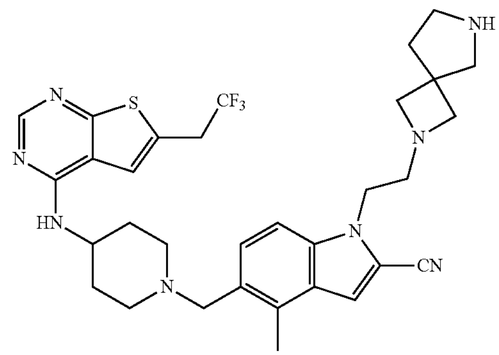 [SMILES: Cc1c(CN2CCC(Nc3ncnc4sc(CC(F)(F)F)cc34)CC2)ccc2c1cc(C#N)n2CCN1CC2(CCNC2)C1] | | |
| 176 | 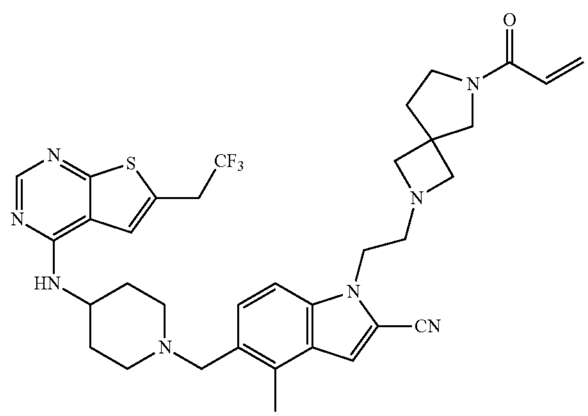 [SMILES: C=CC(=O)N1CCC2(CN(CCn3c(C#N)cc4c(C)c(CN5CCC(Nc6ncnc7sc(CC(F)(F)F)cc67)CC5)ccc43)C2)C1] | 677.5 | 2.519* |
| 177 | 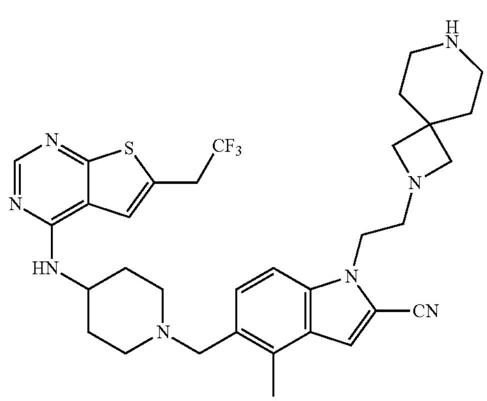 [SMILES: Cc1c(CN2CCC(Nc3ncnc4sc(CC(F)(F)F)cc34)CC2)ccc2c1cc(C#N)n2CCN1CC2(CCNCC2)C1] | | |

TABLE 1-continued

Inhibitors of the menin-MLL interaction

| Compound Number | Structure | [MH]+ | LC-MS RT (min.) or TLC Rf |
|---|---|---|---|
| 178 | 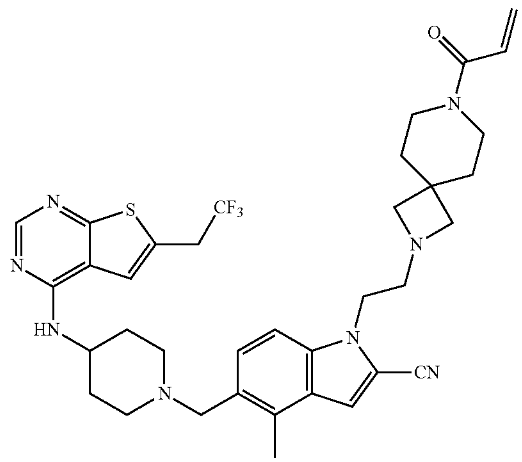 [SMILES: C=CC(=O)N1CCC2(CC1)CN(CCn1c(C#N)cc3c(C)c(CN4CCC(Nc5ncnc6sc(CC(F)(F)F)cc56)CC4)ccc31)C2] | 691.35 | 2.148* |
| 179 | 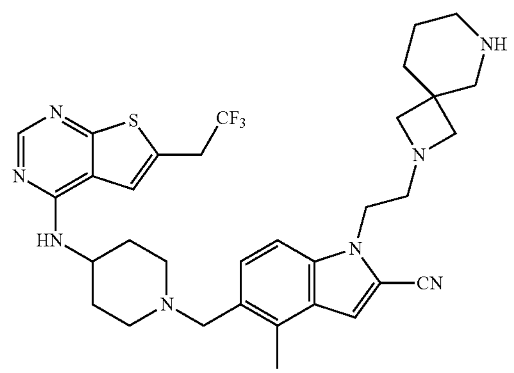 [SMILES: Cc1c(CN2CCC(Nc3ncnc4sc(CC(F)(F)F)cc34)CC2)ccc2c1cc(C#N)n2CCN1CC2(CCCNC2)C1] | | |
| 180 | 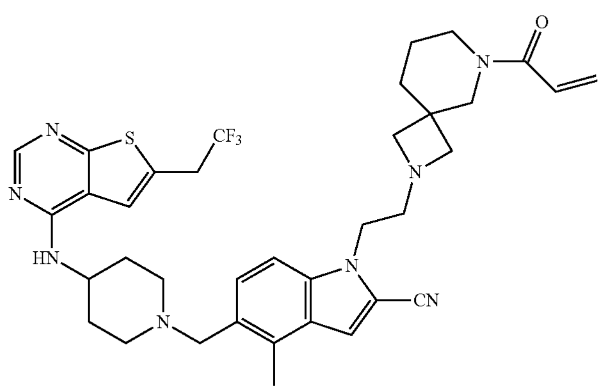 [SMILES: C=CC(=O)N1CCCC2(CN(CCn3c(C#N)cc4c(C)c(CN5CCC(Nc6ncnc7sc(CC(F)(F)F)cc67)CC5)ccc43)C2)C1] | | |
| 181 | 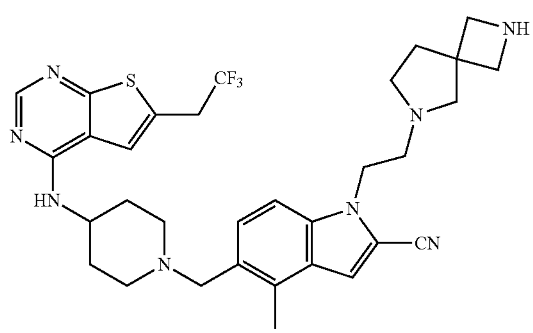 [SMILES: Cc1c(CN2CCC(Nc3ncnc4sc(CC(F)(F)F)cc34)CC2)ccc2c1cc(C#N)n2CCN1CCC2(CNC2)C1] | | |

TABLE 1-continued

Inhibitors of the menin-MLL interaction

| Compound Number | Structure | [MH]+ | LC-MS RT (min.) or TLC Rf |
|---|---|---|---|
| 182 | 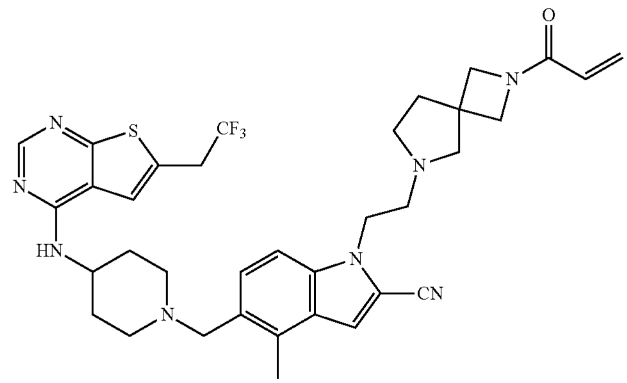 [SMILES: C=CC(=O)N1CC2(CCN(CCn3c(C#N)cc4c(C)c(CN5CCC(Nc6ncnc7sc(CC(F)(F)F)cc67)CC5)ccc43)C2)C1] | 677.35 | 2.351* |
| 183 | 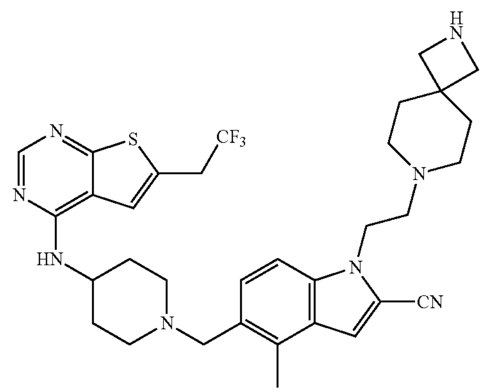 [SMILES: Cc1c(CN2CCC(Nc3ncnc4sc(CC(F)(F)F)cc34)CC2)ccc2c1cc(C#N)n2CCN1CCC2(CC1)CNC2] | | |
| 184 | 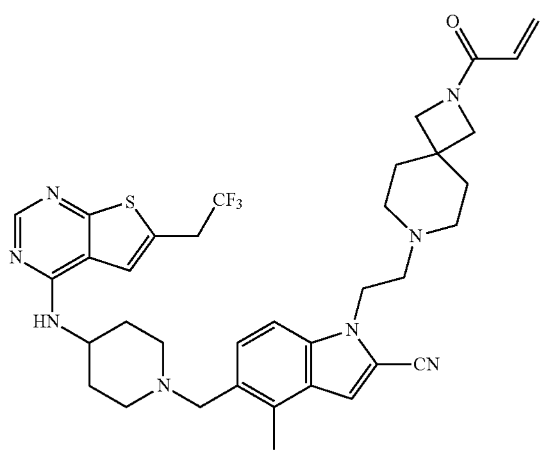 [SMILES: C=CC(=O)N1CC2(CCN(CCn3c(C#N)cc4c(C)c(CN5CCC(Nc6ncnc7sc(CC(F)(F)F)cc67)CC5)ccc43)CC2)C1] | 681.5 | 2.338* |
| 185 | 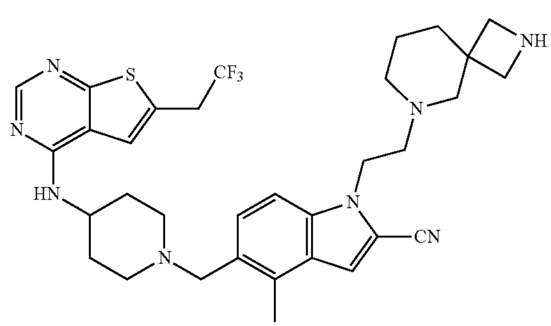 [SMILES: Cc1c(CN2CCC(Nc3ncnc4sc(CC(F)(F)F)cc34)CC2)ccc2c1cc(C#N)n2CCN1CCCC2(CNC2)C1] | | |

TABLE 1-continued

Inhibitors of the menin-MLL interaction

| Compound Number | Structure | [MH]+ | LC-MS RT (min.) or TLC Rf |
|---|---|---|---|
| 186 | 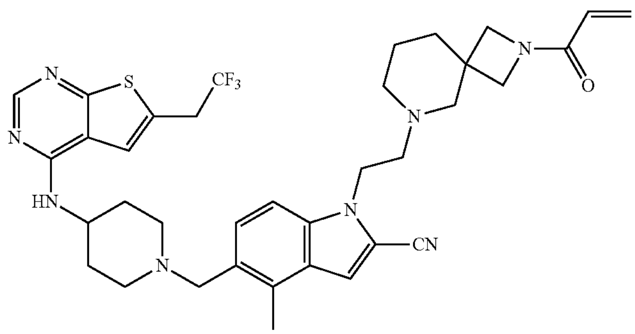 [SMILES: C=CC(=O)N1CC2(CCCN(CCn3c(C#N)cc4c(C)c(CN5CCC(Nc6ncnc7sc(CC(F)(F)F)cc67)CC5)ccc43)C2)C1] | | |
| 187 | 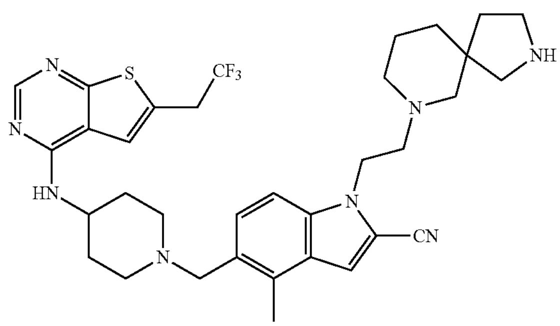 [SMILES: Cc1c(CN2CCC(Nc3ncnc4sc(CC(F)(F)F)cc34)CC2)ccc2c1cc(C#N)n2CCN1CCCC2(CCNC2)C1] | | |
| 188 | 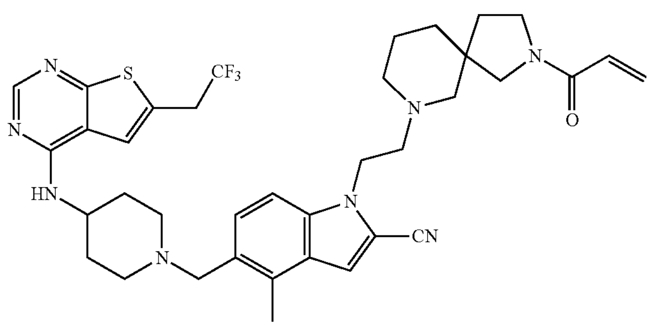 [SMILES: C=CC(=O)N1CCC2(CCCN(CCn3c(C#N)cc4c(C)c(CN5CCC(Nc6ncnc7sc(CC(F)(F)F)cc67)CC5)ccc43)C2)C1] | | |
| 189 | 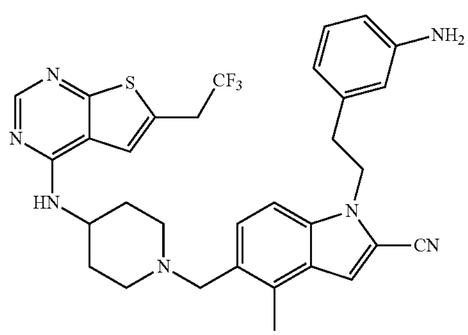 [SMILES: Cc1c(CN2CCC(Nc3ncnc4sc(CC(F)(F)F)cc34)CC2)ccc2c1cc(C#N)n2CCc1cccc(N)c1] | | |

TABLE 1-continued

Inhibitors of the menin-MLL interaction

| Compound Number | Structure | [MH]+ | LC-MS RT (min.) or TLC Rf |
|---|---|---|---|
| 190 | 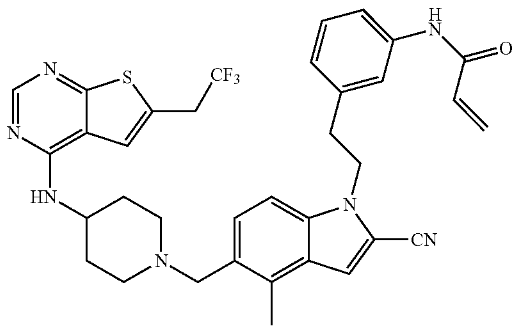 [SMILES: C=CC(=O)Nc1cccc(CCn2c(C#N)cc3c(C)c(CN4CCC(Nc5ncnc6sc(CC(F)(F)F)cc56)CC4)ccc32)c1] | 658 | 3.462* |
| 191 | 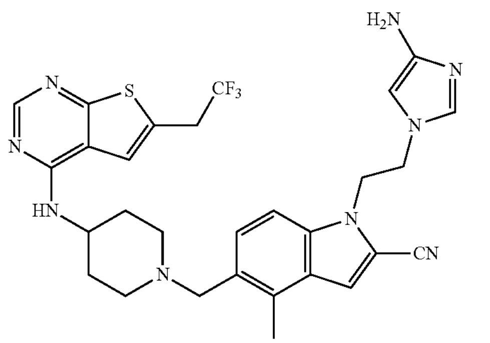 [SMILES: Cc1c(CN2CCC(Nc3ncnc4sc(CC(F)(F)F)cc34)CC2)ccc2c1cc(C#N)n2CCn1cnc(N)c1] | | |
| 192 | 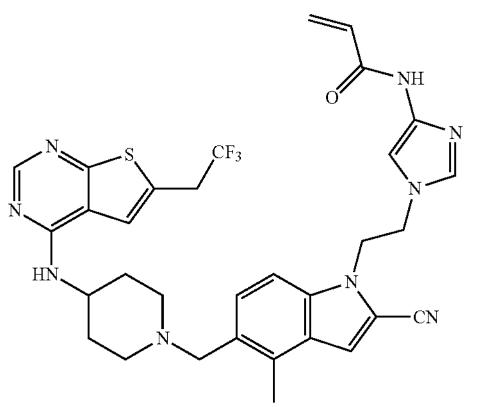 [SMILES: C=CC(=O)Nc1cn(CCn2c(C#N)cc3c(C)c(CN4CCC(Nc5ncnc6sc(CC(F)(F)F)cc56)CC4)ccc32)cn1] | 648.4 | 2.361* |
| 193 | 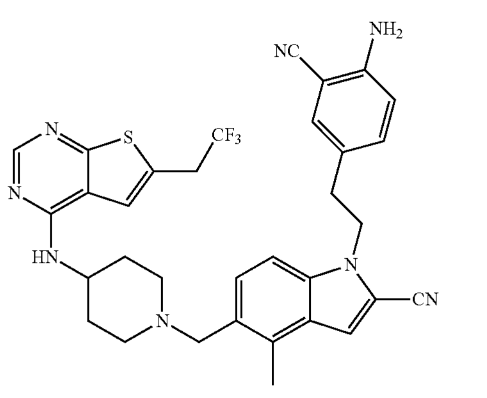 [SMILES: Cc1c(CN2CCC(Nc3ncnc4sc(CC(F)(F)F)cc34)CC2)ccc2c1cc(C#N)n2CCc1ccc(N)c(C#N)c1] | | |

TABLE 1-continued

Inhibitors of the menin-MLL interaction

| Compound Number | Structure | [MH]+ | LC-MS RT (min.) or TLC Rf |
|---|---|---|---|
| 194 | 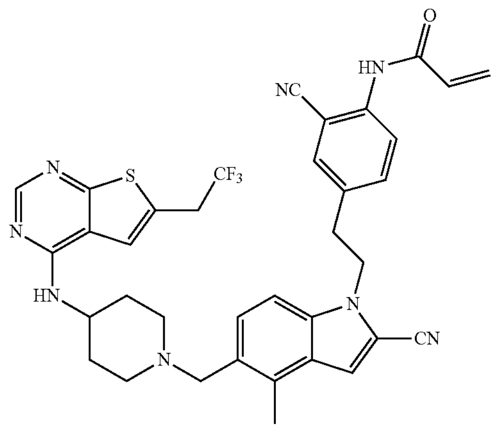 [SMILES: C=CC(=O)Nc1ccc(CCn2c(C#N)cc3c(C)c(CN4CCC(Nc5ncnc6sc(CC(F)(F)F)cc56)CC4)ccc32)cc1C#N] | 683.4 | 3.717* |
| 195 | 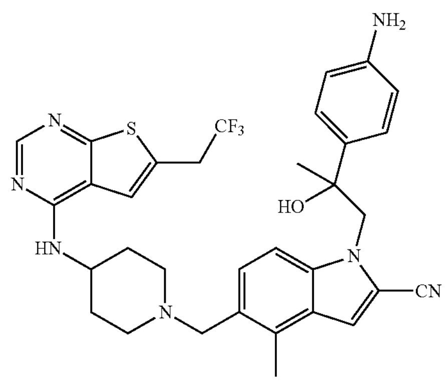 [SMILES: Cc1c(CN2CCC(Nc3ncnc4sc(CC(F)(F)F)cc34)CC2)ccc2c1cc(C#N)n2CC(C)(O)c1ccc(N)cc1] | | |
| 196 | 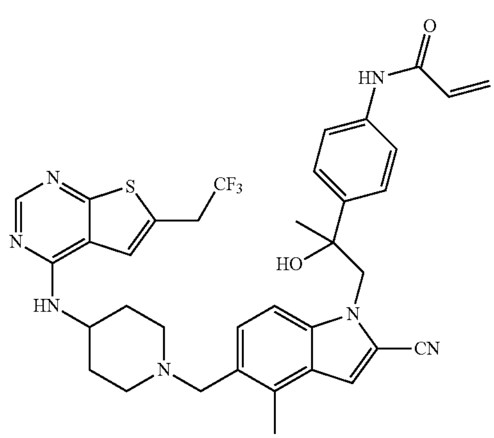 [SMILES: C=CC(=O)Nc1ccc(C(C)(O)Cn2c(C#N)cc3c(C)c(CN4CCC(Nc5ncnc6sc(CC(F)(F)F)cc56)CC4)ccc32)cc1] | | |

TABLE 1-continued
Inhibitors of the menin-MLL interaction
| Compound Number | Structure | [MH]+ | LC-MS RT (min.) or TLC Rf |
|---|---|---|---|
| 197 | 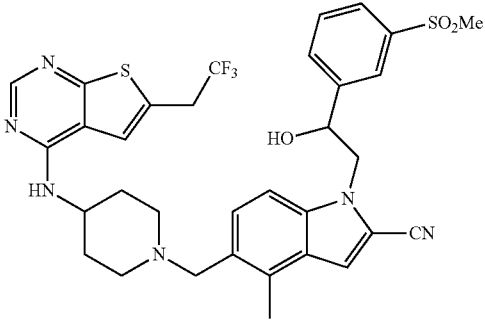 [SMILES: Cc1c(CN2CCC(Nc3ncnc4sc(CC(F)(F)F)cc34)CC2)ccc2c1cc(C#N)n2CC(O)c1cccc(S(C)(=O)=O)c1] | | |
| 198 | 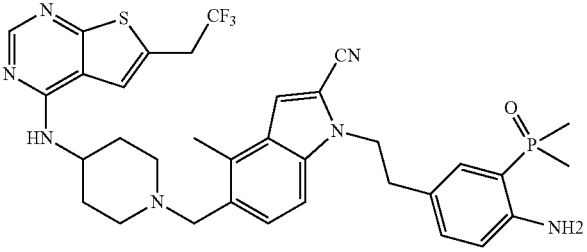 [SMILES: Cc1c(CN2CCC(Nc3ncnc4sc(CC(F)(F)F)cc34)CC2)ccc2c1cc(C#N)n2CCc1ccc(N)c(P(C)(C)=O)c1] | | |
| 199 | 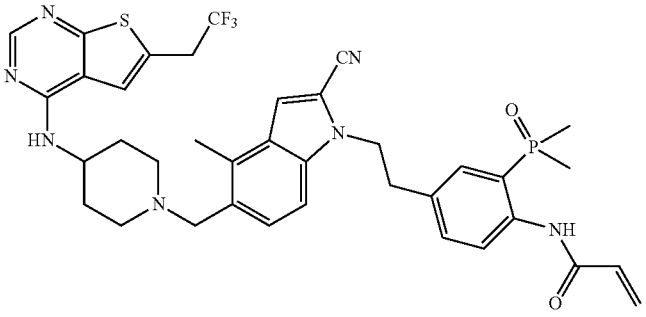 [SMILES: C=CC(=O)Nc1ccc(CCn2c(C#N)cc3c(C)c(CN4CCC(Nc5ncnc6sc(CC(F)(F)F)cc56)CC4)ccc32)cc1P(C)(C)=O] | 734.40 | 2.84* |
| 200 | 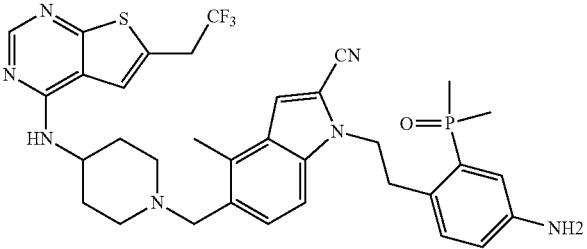 [SMILES: Cc1c(CN2CCC(Nc3ncnc4sc(CC(F)(F)F)cc34)CC2)ccc2c1cc(C#N)n2CCc1ccc(N)cc1P(C)(C)=O] | | |
| 201 | 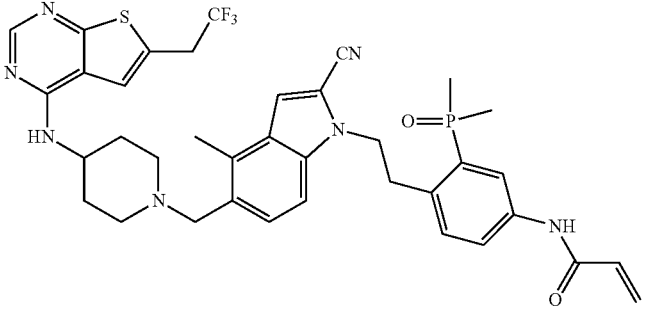 [SMILES: C=CC(=O)Nc1ccc(CCn2c(C#N)cc3c(C)c(CN4CCC(Nc5ncnc6sc(CC(F)(F)F)cc56)CC4)ccc32)c(P(C)(C)=O)c1] | | |

TABLE 1-continued

Inhibitors of the menin-MLL interaction

| Compound Number | Structure | [MH]+ | LC-MS RT (min.) or TLC Rf |
|---|---|---|---|
| 202 | 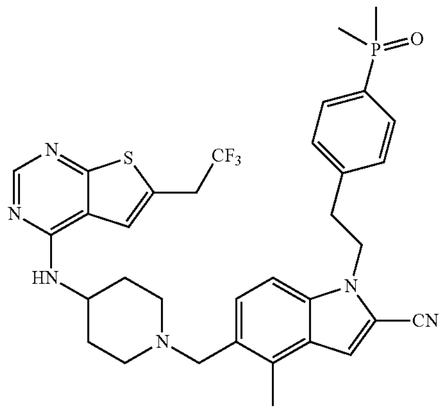 [SMILES: Cc1c(CN2CCC(Nc3ncnc4sc(CC(F)(F)F)cc34)CC2)ccc2c1cc(C#N)n2CCc1ccc(P(C)(C)=O)cc1] | | |
| 203 | 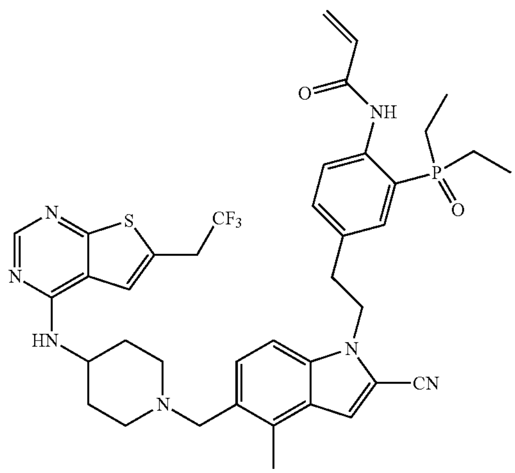 [SMILES: C=CC(=O)Nc1ccc(CCn2c(C#N)cc3c(C)c(CN4CCC(Nc5ncnc6sc(CC(F)(F)F)cc56)CC4)ccc32)cc1P(=O)(CC)CC] | 762.45 | 3.708* |
| 204 | 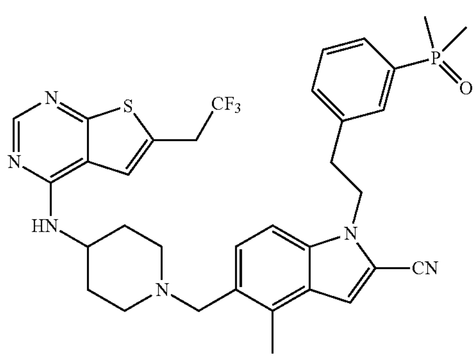 [SMILES: Cc1c(CN2CCC(Nc3ncnc4sc(CC(F)(F)F)cc34)CC2)ccc2c1cc(C#N)n2CCc1cccc(P(C)(C)=O)c1] | | |
| 205 | 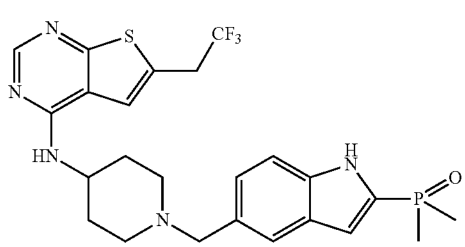 [SMILES: CP(C)(=O)c1cc2cc(CN3CCC(Nc4ncnc5sc(CC(F)(F)F)cc45)CC3)ccc2[nH]1] | | |

TABLE 1-continued

Inhibitors of the menin-MLL interaction

| Compound Number | Structure | [MH]+ | LC-MS RT (min.) or TLC Rf |
|---|---|---|---|
| 206 | 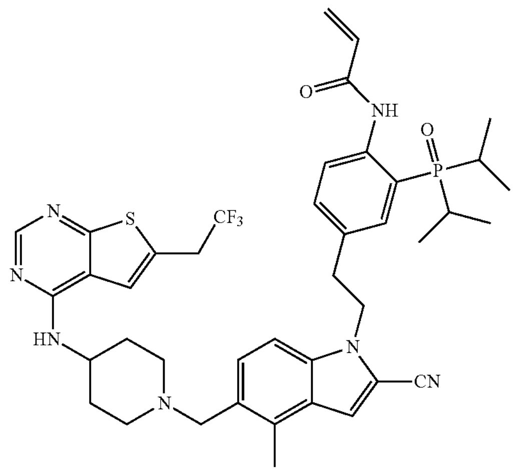 [SMILES: C=CC(=O)Nc1ccc(CCn2c(C#N)cc3c(C)c(CN4CCC(Nc5ncnc6sc(CC(F)(F)F)cc56)CC4)ccc32)cc1P(=O)(C(C)C)C(C)C] | 790.5 | 3.924* |
| 207 | 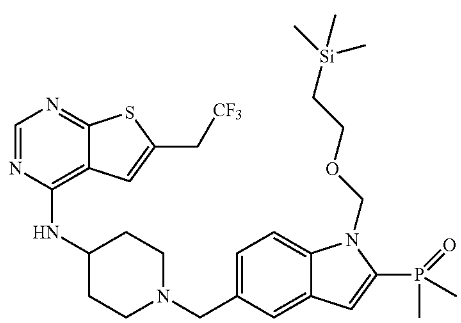 [SMILES: C[Si](C)(C)CCOCn1c(P(C)(C)=O)cc2cc(CN3CCC(Nc4ncnc5sc(CC(F)(F)F)cc45)CC3)ccc21] | | |
| 208 | 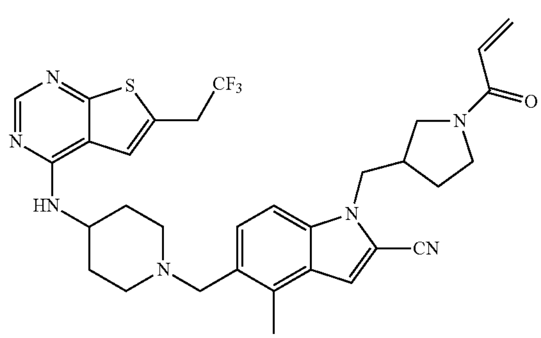 [SMILES: C=CC(=O)N1CCC(Cn2c(C#N)cc3c(C)c(CN4CCC(Nc5ncnc6sc(CC(F)(F)F)cc56)CC4)ccc32)C1] | 622.4 | 3.492* |

TABLE 1-continued

Inhibitors of the menin-MLL interaction

| Compound Number | Structure | [MH]+ | LC-MS RT (min.) or TLC Rf |
|---|---|---|---|
| 209 | 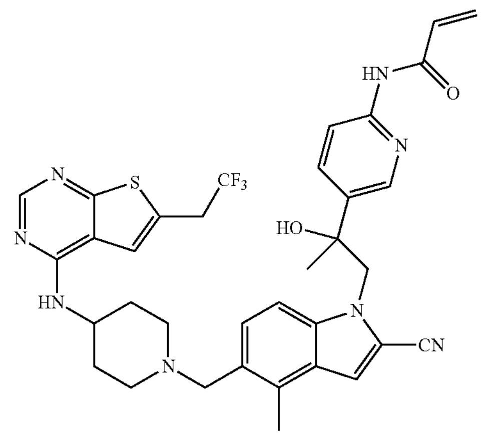 | 689.45 | 3.438* |
| 210 | 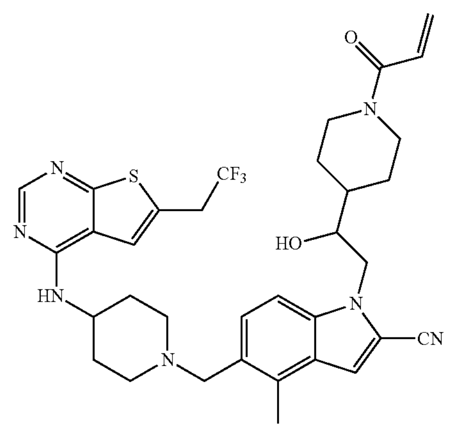 [SMILES: C=CC(=O)N1CCC(C(O)Cn2c(C#N)cc3c(C)c(CN4CCC(Nc5ncnc6sc(CC(F)(F)F)cc56)CC4)ccc32)CC1] | 666 | 3.307* |
| 211 | 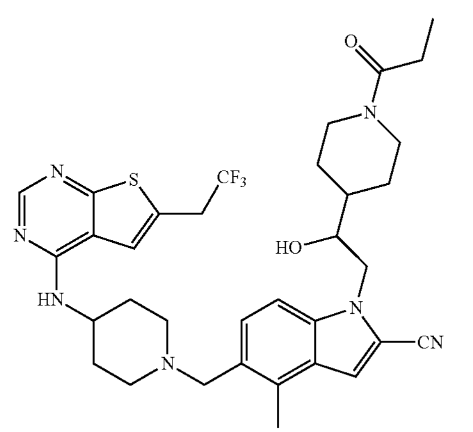 [SMILES: CCC(=O)N1CCC(C(O)Cn2c(C#N)cc3c(C)c(CN4CCC(Nc5ncnc6sc(CC(F)(F)F)cc56)CC4)ccc32)CC1] | | |

TABLE 1-continued

Inhibitors of the menin-MLL interaction

| Compound Number | Structure | [MH]+ | LC-MS RT (min.) or TLC Rf |
|---|---|---|---|
| 212 | 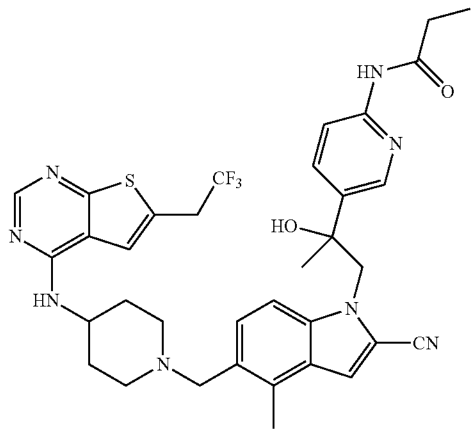 [SMILES: CCC(=O)Nc1ccc(C(C)(O)Cn2c(C#N)cc3c(C)c(CN4CCC(Nc5ncnc6sc(CC(F)(F)F)cc56)CC4)ccc32)cn1] | | |
| 213 | 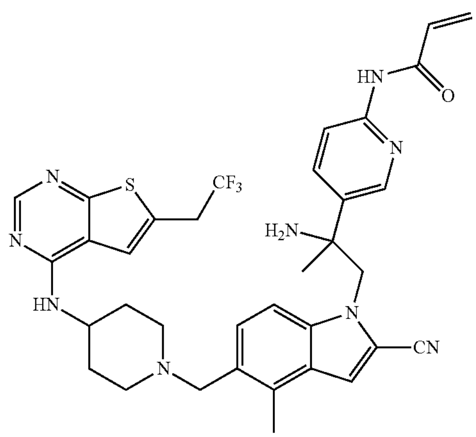 | | |
| 214 | 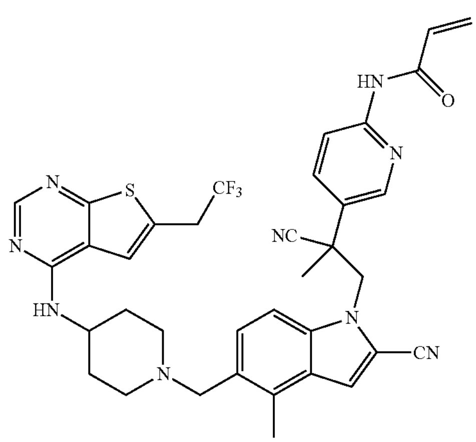 [SMILES: C=CC(=O)Nc1ccc(C(C)(C#N)Cn2c(C#N)cc3c(C)c(CN4CCC(Nc5ncnc6sc(CC(F)(F)F)cc56)CC4)ccc32)cn1] | | |

TABLE 1-continued

Inhibitors of the menin-MLL interaction

| Compound Number | Structure | [MH]+ | LC-MS RT (min.) or TLC Rf |
|---|---|---|---|
| 215 | 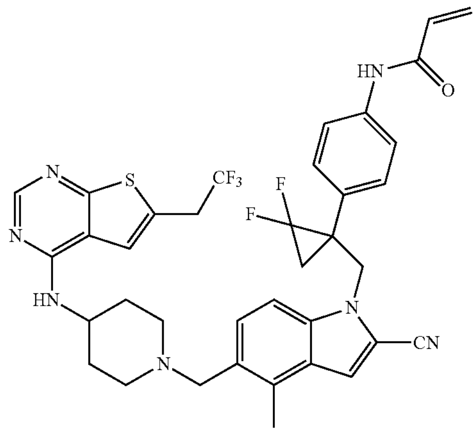 [SMILES: C=CC(=O)Nc1ccc(C2(Cn3c(C#N)cc4c(C)c(CN5CCC(Nc6ncnc7sc(CC(F)(F)F)cc67)CC5)ccc43)CC2(F)F)cc1] | | |
| 216 | 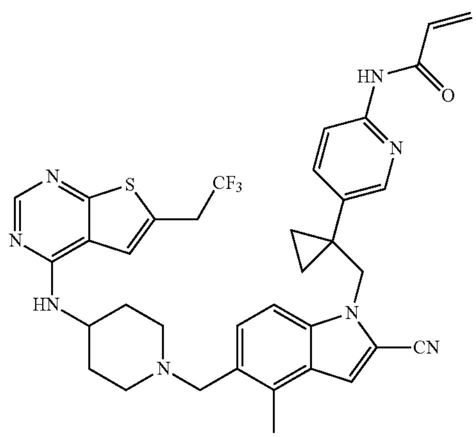 [SMILES: C=CC(=O)Nc1ccc(C2(Cn3c(C#N)cc4c(C)c(CN5CCC(Nc6ncnc7sc(CC(F)(F)F)cc67)CC5)ccc43)CC2)cn1] | 685.45 | 2.956* |
| 217 | 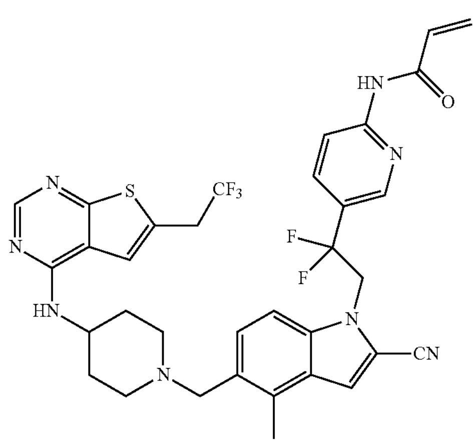 [SMILES: C=CC(=O)Nc1ccc(C(F)(F)Cn2c(C#N)cc3c(C)c(CN4CCC(Nc5ncnc6sc(CC(F)(F)F)cc56)CC4)ccc32)cn1] | | |

TABLE 1-continued
Inhibitors of the menin-MLL interaction
| Compound Number | Structure | [MH]+ | LC-MS RT (min.) or TLC Rf |
|---|---|---|---|
| 218 | 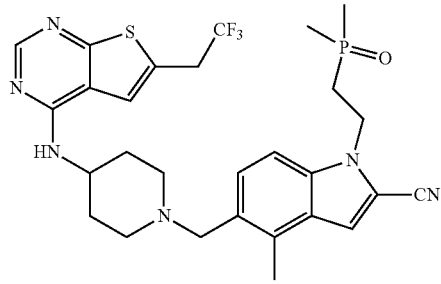 [SMILES: Cc1c(CN2CCC(Nc3ncnc4sc(CC(F)(F)F)cc34)CC2)ccc2c1cc(C#N)n2CCP(C)(C)=O] | | |
| 219 | 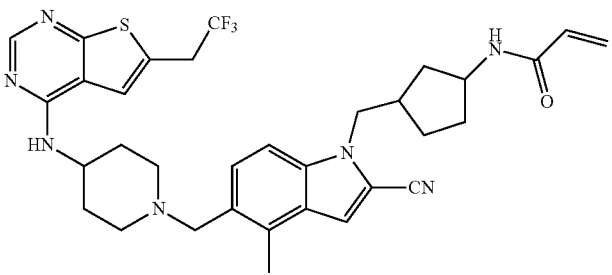 [SMILES: C=CC(=O)NC1CCC(Cn2c(C#N)cc3c(C)c(CN4CCC(Nc5ncnc6sc(CC(F)(F)F)cc56)CC4)ccc32)C1] | 636.35 | 3.263* |
| 220 | 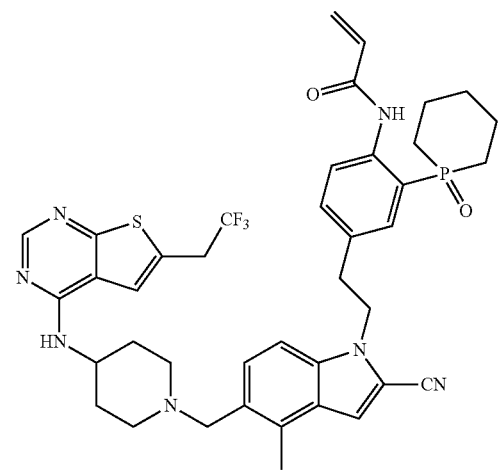 [SMILES: C=CC(=O)Nc1ccc(CCn2c(C#N)cc3c(C)c(CN4CCC(Nc5ncnc6sc(CC(F)(F)F)cc56)CC4)ccc32)cc1P1(=O)CCCCC1] | | |
| 221 | 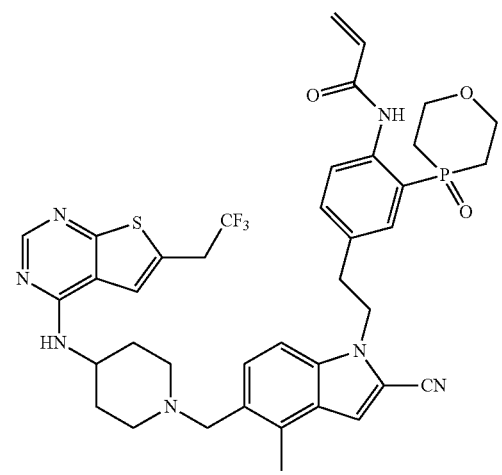 [SMILES: C=CC(=O)Nc1ccc(CCn2c(C#N)cc3c(C)c(CN4CCC(Nc5ncnc6sc(CC(F)(F)F)cc56)CC4)ccc32)cc1P1(=O)CCOCC1] | | |

TABLE 1-continued
Inhibitors of the menin-MLL interaction
| Compound Number | Structure | [MH]+ | LC-MS RT (min.) or TLC Rf |
|---|---|---|---|
| 222 | 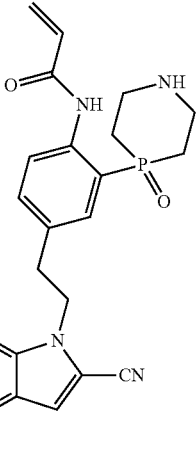 | | |
| 223 | 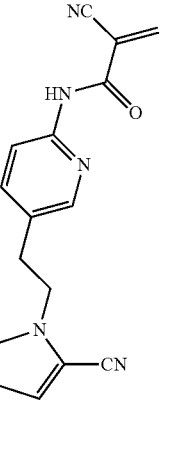 | | |
| 224 | 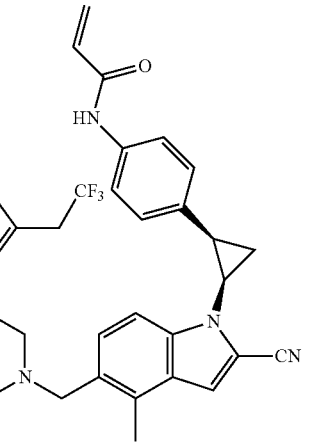 | | |

TABLE 1-continued

Inhibitors of the menin-MLL interaction

| Compound Number | Structure | [MH]+ | LC-MS RT (min.) or TLC Rf |
|---|---|---|---|
| 225 | 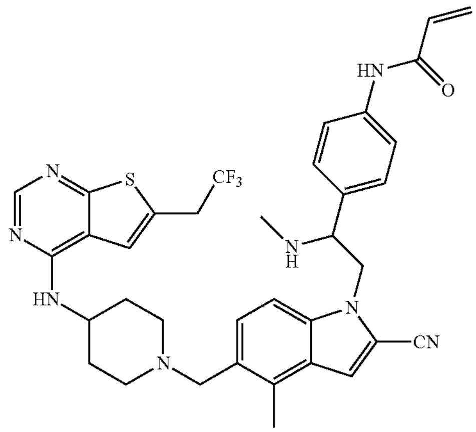 [SMILES: C=CC(=O)Nc1ccc(C(Cn2c(C#N)cc3c(C)c(CN4CCC(Nc5ncnc6sc(CC(F)(F)F)cc56)CC4)ccc32)NC)cc1] | | |
| 226 | 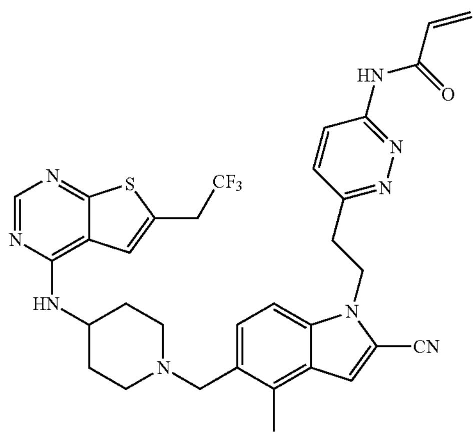 [SMILES: C=CC(=O)Nc1ccc(CCn2c(C#N)cc3c(C)c(CN4CCC(Nc5ncnc6sc(CC(F)(F)F)cc56)CC4)ccc32)nn1] | | |
| 227 | 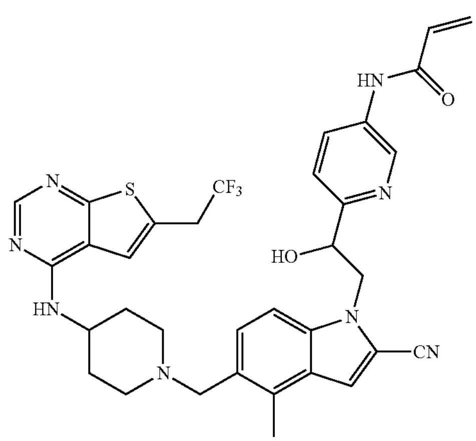 [SMILES: C=CC(=O)Nc1ccc(C(O)Cn2c(C#N)cc3c(C)c(CN4CCC(Nc5ncnc6sc(CC(F)(F)F)cc56)CC4)ccc32)nc1] | | |

TABLE 1-continued

Inhibitors of the menin-MLL interaction

| Compound Number | Structure | [MH]+ | LC-MS RT (min.) or TLC Rf |
|---|---|---|---|
| 228 | 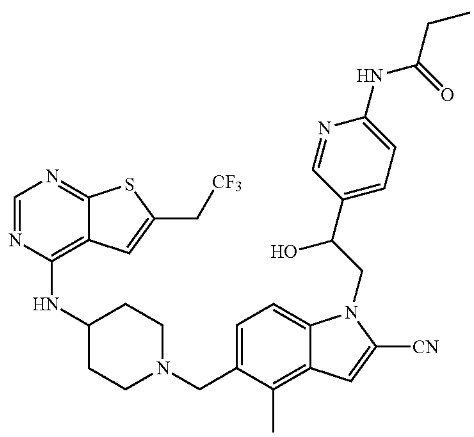 [SMILES: CCC(=O)Nc1ccc(C(O)Cn2c(C#N)cc3c(C)c(CN4CCC(Nc5ncnc6sc(CC(F)(F)F)cc56)CC4)ccc32)cn1] | | |
| 229 | 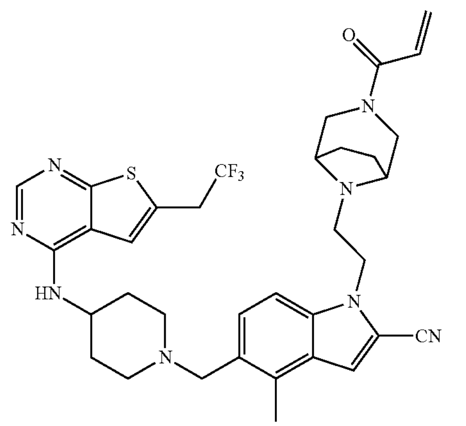 [SMILES: C=CC(=O)N1CC2CCC(C1)N2CCn1c(C#N)cc2c(C)c(CN3CCC(Nc4ncnc5sc(CC(F)(F)F)cc45)CC3)ccc21] | | |
| 230 | 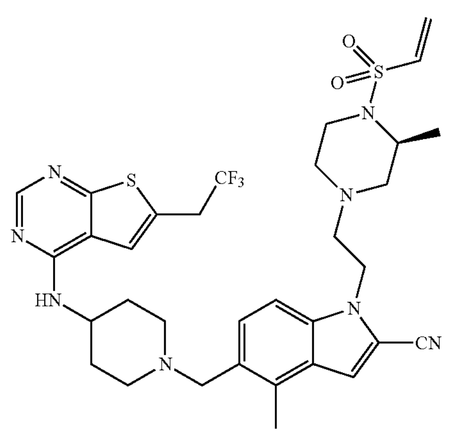 [SMILES: C=CS(=O)(=O)N1CCN(CCn2c(C#N)cc3c(C)c(CN4CCC(Nc5ncnc6sc(CC(F)(F)F)cc56)CC4)ccc32)C[C@@H]1C] | | |

TABLE 1-continued
Inhibitors of the menin-MLL interaction
| Compound Number | Structure | [MH]+ | LC-MS RT (min.) or TLC Rf |
|---|---|---|---|
| 231 | 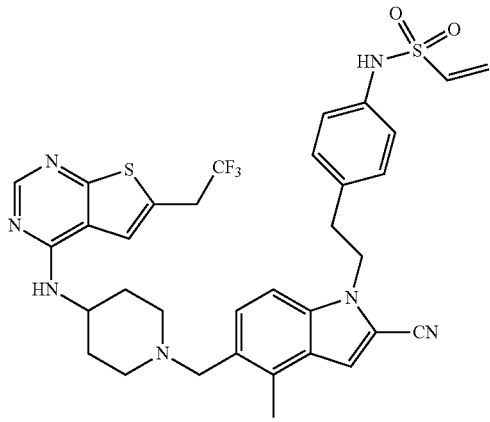 [SMILES: C=CS(=O)(=O)Nc1ccc(CCn2c(C#N)cc3c(C)c(CN4CCC(Nc5ncnc6sc(CC(F)(F)F)cc56)CC4)ccc32)cc1] | 694.2237 | 4.34 min |
| 232 | 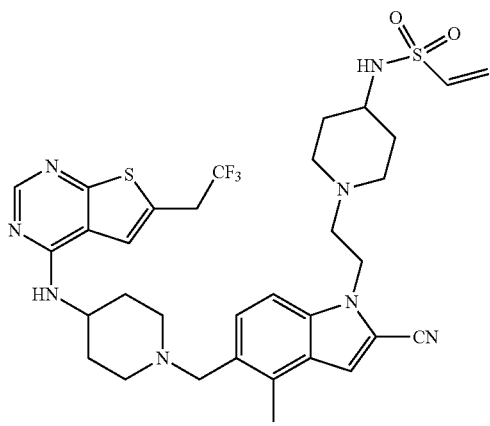 [SMILES: C=CS(=O)(=O)NC1CCN(CCn2c(C#N)cc3c(C)c(CN4CCC(Nc5ncnc6sc(CC(F)(F)F)cc56)CC4)ccc32)CC1] | 701.2658 | 4.56 min |
| 233 | 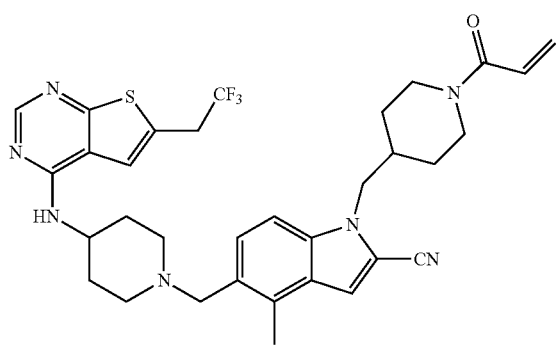 [SMILES: C=CC(=O)N1CCC(Cn2c(C#N)cc3c(C)c(CN4CCC(Nc5ncnc6sc(CC(F)(F)F)cc56)CC4)ccc32)CC1] | 636.4 | 3.58* |
| 234 | 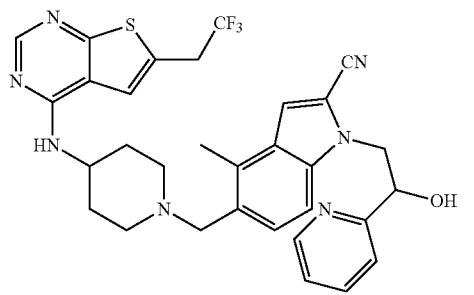 [SMILES: Cc1c(CN2CCC(Nc3ncnc4sc(CC(F)(F)F)cc34)CC2)ccc2c1cc(C#N)n2CC(O)c1ccccn1] | 606.2651 | 4.23 min |

TABLE 1-continued

Inhibitors of the menin-MLL interaction

| Compound Number | Structure | [MH]+ | LC-MS RT (min.) or TLC Rf |
|---|---|---|---|
| 235 | 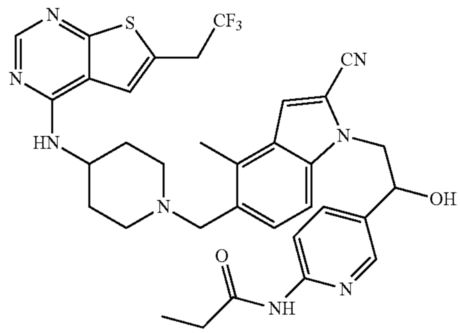 [SMILES: CCC(=O)Nc1ccc(C(O)Cn2c(C#N)cc3c(C)c(CN4CCC(Nc5ncnc6sc(CC(F)(F)F)cc56)CC4)ccc32)cn1] | 677.2634 | 4.82 min |
| 236 | 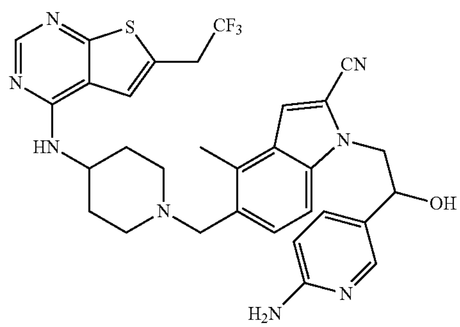 [SMILES: Cc1c(CN2CCC(Nc3ncnc4sc(CC(F)(F)F)cc34)CC2)ccc2c1cc(C#N)n2CC(O)c1ccc(N)nc1] | 621.2378 | 4.21 min |
| 237 | 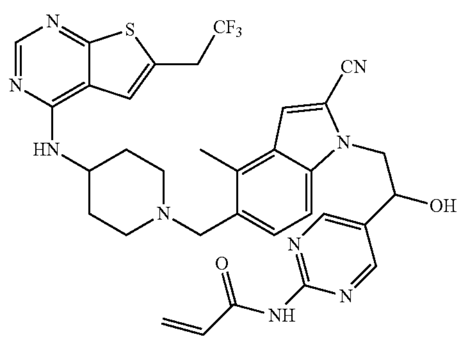 | | |
| 238 | 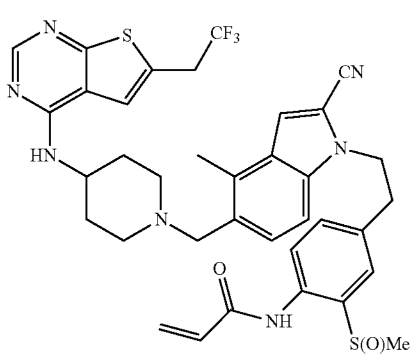 | | |

TABLE 1-continued

Inhibitors of the menin-MLL interaction

| Compound Number | Structure | [MH]+ | LC-MS RT (min.) or TLC Rf |
|---|---|---|---|
| 239 | 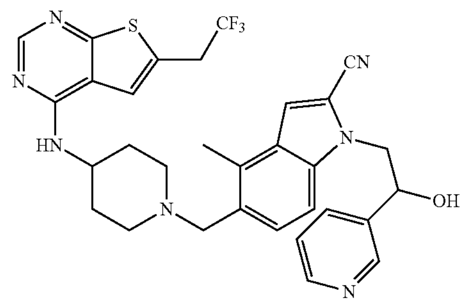 [SMILES: Cc1c(CN2CCC(Nc3ncnc4sc(CC(F)(F)F)cc34)CC2)ccc2c1cc(C#N)n2CC(O)c1cccnc1] | | |
| 240 | 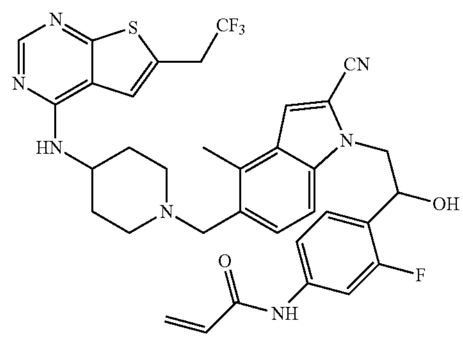 [SMILES: C=CC(=O)Nc1ccc(C(O)Cn2c(C#N)cc3c(C)c(CN4CCC(Nc5ncnc6sc(CC(F)(F)F)cc56)CC4)ccc32)c(F)c1] | | |
| 241 | 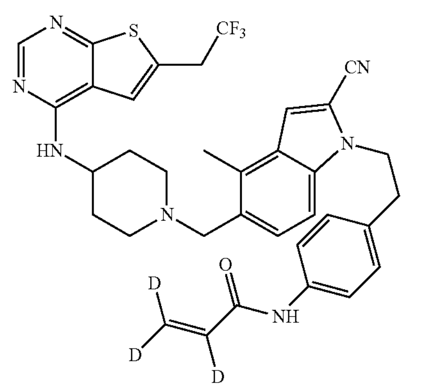 [SMILES: [2H]C([2H])=C([2H])C(=O)Nc1ccc(CCn2c(C#N)cc3c(C)c(CN4CCC(Nc5ncnc6sc(CC(F)(F)F)cc56)CC4)ccc32)cc1] | 661.2764 | 4.43 min |
| 242 | 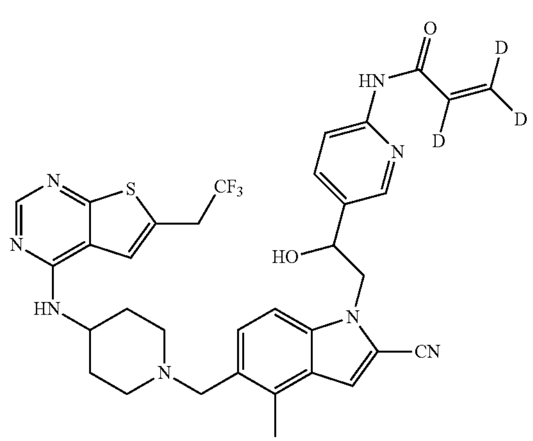 [SMILES: [2H]C([2H])=C([2H])C(=O)Nc1ccc(C(O)Cn2c(C#N)cc3c(C)c(CN4CCC(Nc5ncnc6sc(CC(F)(F)F)cc56)CC4)ccc32)cn1] | 678.2666 | 5.02 min |

TABLE 1-continued
Inhibitors of the menin-MLL interaction
| Compound Number | Structure | [MH]+ | LC-MS RT (min.) or TLC Rf |
|---|---|---|---|
| 243 | 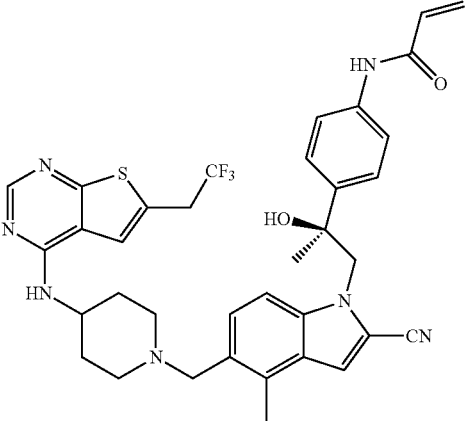 [SMILES: C=CC(=O)Nc1ccc([C@](C)(O)Cn2c(C#N)cc3c(C)c(CN4CCC(Nc5ncnc6sc(CC(F)(F)F)cc56)CC4)ccc32)cc1] | 688.5 | 2.784* |
| 244 | 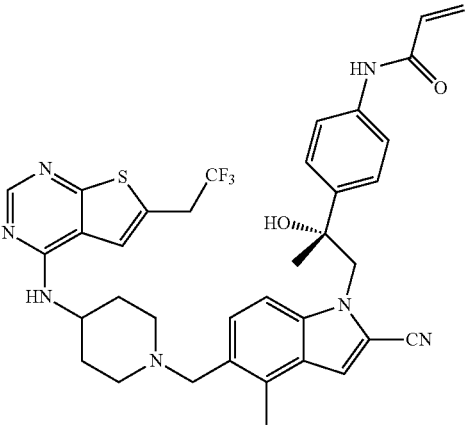 [SMILES: C=CC(=O)Nc1ccc([C@@](C)(O)Cn2c(C#N)cc3c(C)c(CN4CCC(Nc5ncnc6sc(CC(F)(F)F)cc56)CC4)ccc32)cc1] | 688.45 | 3.631* |
| 245 | 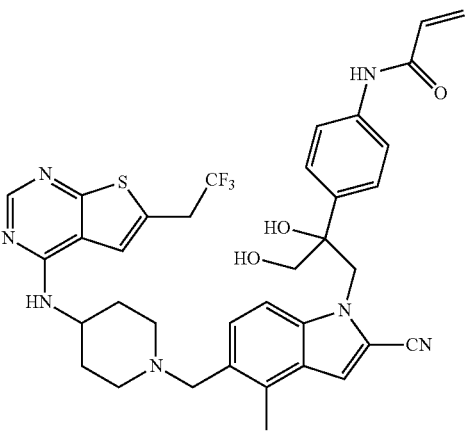 | | |

TABLE 1-continued

Inhibitors of the menin-MLL interaction

| Compound Number | Structure | [MH]+ | LC-MS RT (min.) or TLC Rf |
|---|---|---|---|
| 246 | 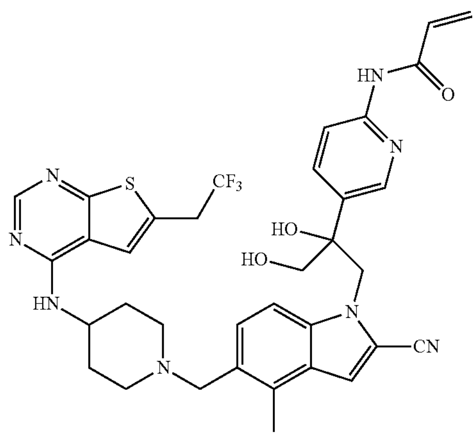 [SMILES: C=CC(=O)Nc1ccc(C(O)(CO)Cn2c(C#N)cc3c(C)c(CN4CCC(Nc5ncnc6sc(CC(F)(F)F)cc56)CC4)ccc32)cc1] | | |
| 247 | 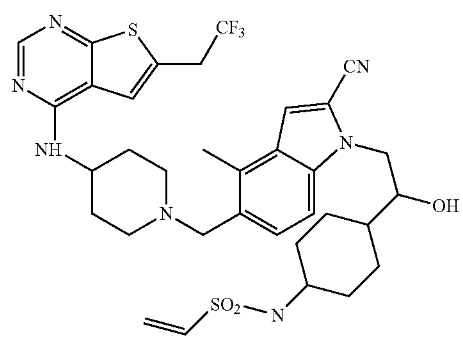 [SMILES: C=CS(=O)(=O)NC1CCC(C(O)Cn2c(C#N)cc3c(C)c(CN4CCC(Nc5ncnc6sc(CC(F)(F)F)cc56)CC4)ccc32)CC1] | | |
| 248 | 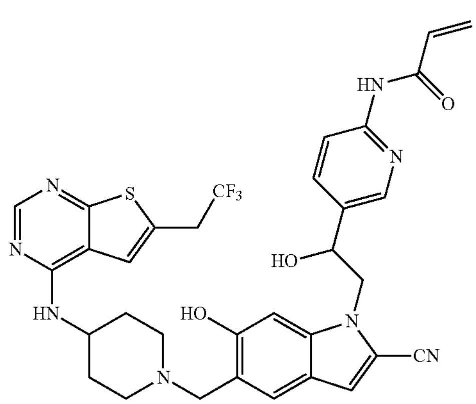 [SMILES: C=CC(=O)Nc1ccc(C(O)Cn2c(C#N)cc3cc(CN4CCC(Nc5ncnc6sc(CC(F)(F)F)cc56)CC4)c(O)cc32)cn1] | | |

TABLE 1-continued
Inhibitors of the menin-MLL interaction
| Compound Number | Structure | [MH]+ | LC-MS RT (min.) or TLC Rf |
|---|---|---|---|
| 249 | 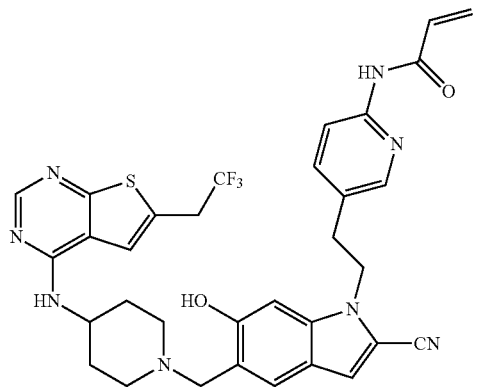 [SMILES: C=CC(=O)Nc1ccc(CCn2c(C#N)cc3cc(CN4CCC(Nc5ncnc6sc(CC(F)(F)F)cc56)CC4)c(O)cc32)cn1] | | |
| 250 | 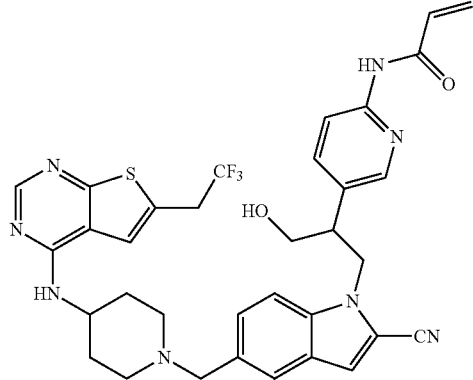 | | |
| 251 | 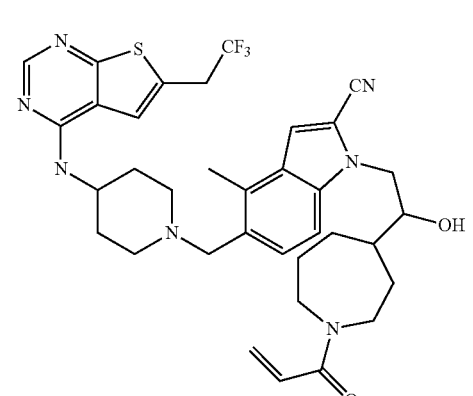 | | |
| 252 | 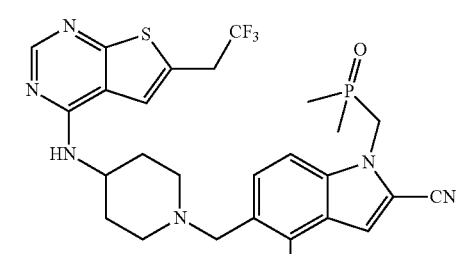 | | |

TABLE 1-continued
Inhibitors of the menin-MLL interaction
| Compound Number | Structure | [MH]+ | LC-MS RT (min.) or TLC Rf |
|---|---|---|---|
| 253 | 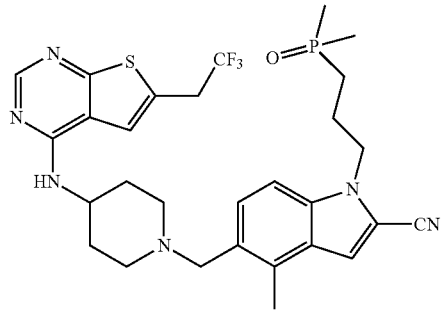 [SMILES: Cc1c(CN2CCC(Nc3ncnc4sc(CC(F)(F)F)cc34)CC2)ccc2c1cc(C#N)n2CCCP(C)(C)=O] | | |
| 254 | 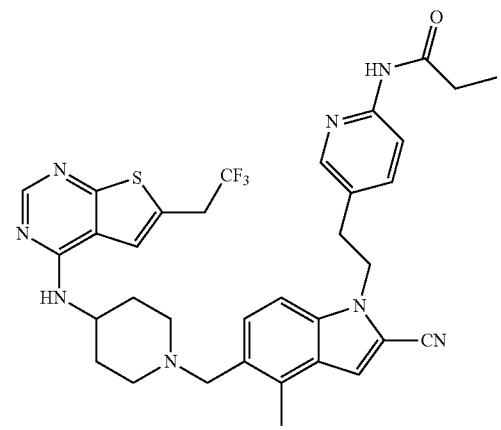 [SMILES: CCC(=O)Nc1ccc(CCn2c(C#N)cc3c(C)c(CN4CCC(Nc5ncnc6sc(CC(F)(F)F)cc56)CC4)ccc32)cn1] | | |
| 255 | 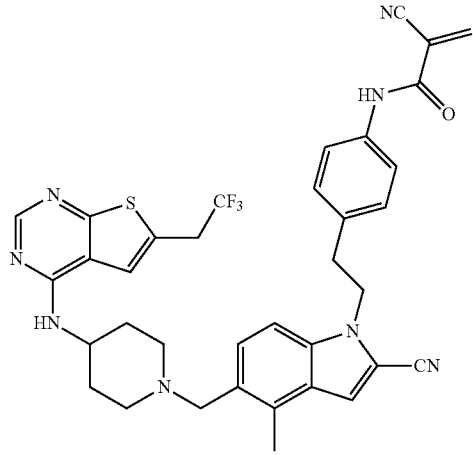 | | |

TABLE 1-continued

Inhibitors of the menin-MLL interaction

| Compound Number | Structure | [MH]+ | LC-MS RT (min.) or TLC Rf |
|---|---|---|---|
| 256 | 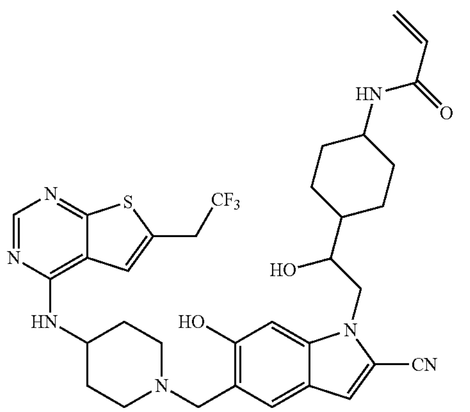 [SMILES: C=CC(=O)NC1CCC(C(O)Cn2c(C#N)cc3cc(CN4CCC(Nc5ncnc6sc(CC(F)(F)F)cc56)CC4)c(O)cc32)CC1] | | |
| 257 | 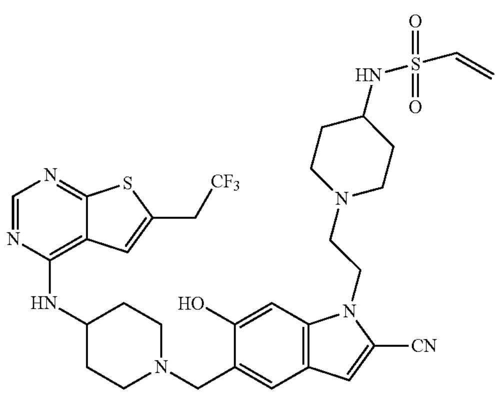 [SMILES: C=CS(=O)(=O)NC1CCN(CCn2c(C#N)cc3cc(CN4CCC(Nc5ncnc6sc(CC(F)(F)F)cc56)CC4)c(O)cc32)CC1] | | |
| 258 | 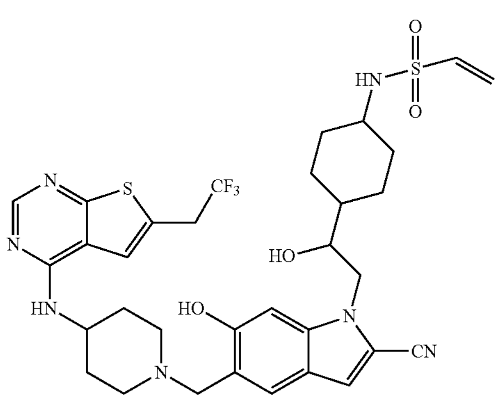 [SMILES: C=CS(=O)(=O)NC1CCC(C(O)Cn2c(C#N)cc3cc(CN4CCC(Nc5ncnc6sc(CC(F)(F)F)cc56)CC4)c(O)cc32)CC1] | | |

TABLE 1-continued
Inhibitors of the menin-MLL interaction
| Compound Number | Structure | [MH]+ | LC-MS RT (min.) or TLC Rf |
|---|---|---|---|
| 259 | 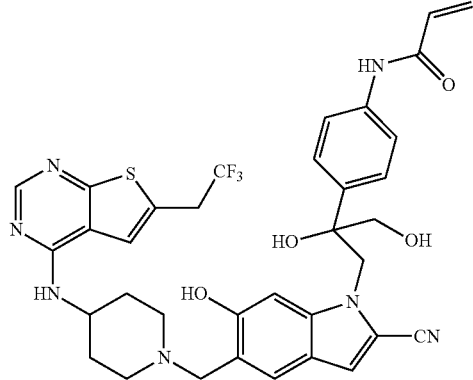 [SMILES: C=CC(=O)Nc1ccc(C(O)(CO)Cn2c(C#N)cc3cc(CN4CCC(Nc5ncnc6sc(CC(F)(F)F)cc56)CC4)c(O)cc32)cc1] | | |
| 260 | 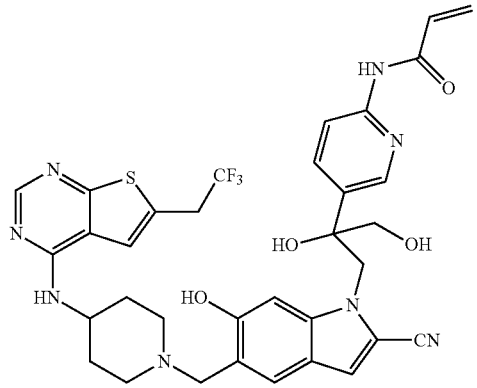 [SMILES: C=CC(=O)Nc1ccc(C(O)(CO)Cn2c(C#N)cc3cc(CN4CCC(Nc5ncnc6sc(CC(F)(F)F)cc56)CC4)c(O)cc32)cn1] | | |
| 261 | 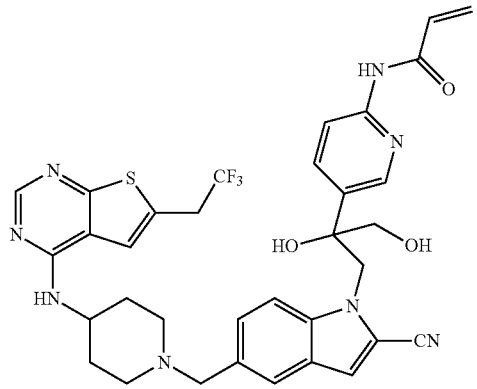 [SMILES: C=CC(=O)Nc1ccc(C(O)(CO)Cn2c(C#N)cc3cc(CN4CCC(Nc5ncnc6sc(CC(F)(F)F)cc56)CC4)ccc32)cn1] | | |

TABLE 1-continued

Inhibitors of the menin-MLL interaction

| Compound Number | Structure | [MH]+ | LC-MS RT (min.) or TLC Rf |
|---|---|---|---|
| 262 | 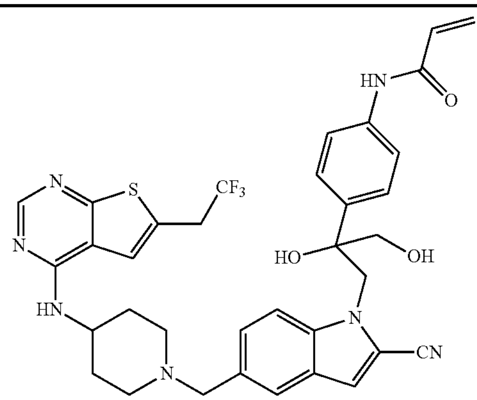 | | |
| 263 | 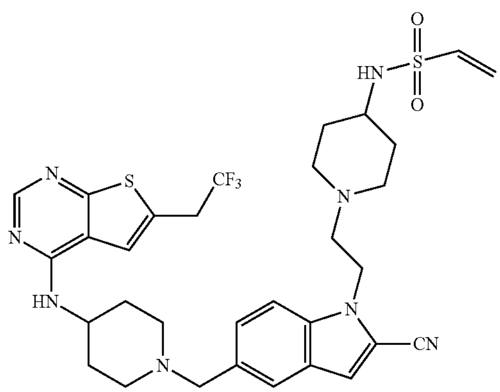 [SMILES: C=CS(=O)(=O)NC1CCN(CCn2c(C#N)cc3cc(CN4CCC(Nc5ncnc6sc(CC(F)(F)F)cc56)CC4)ccc32)CC1] | | |
| 264 | 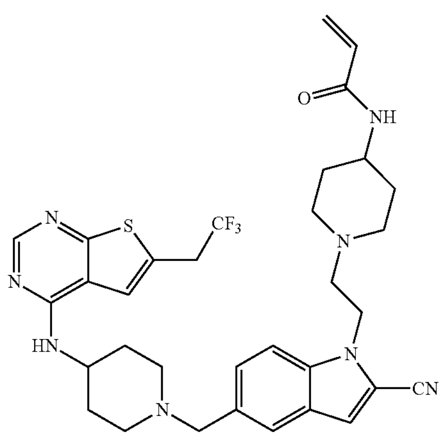 [SMILES: C=CC(=O)NC1CCN(CCn2c(C#N)cc3cc(CN4CCC(Nc5ncnc6sc(CC(F)(F)F)cc56)CC4)ccc32)CC1] | | |

TABLE 2

IC50 values for Table 1 inhibitors of menin

| ++++ (IC50 ≤30 nM) | +++ (30 nM < IC50 ≤ 100 nM) | ++ (100 < IC50 ≤ 1000 nM) | + (IC50 >1000 nM) |
|---|---|---|---|
| 167, 184, 199, 203, 102, 105, 112, 11, 3, 4, 6, 7, 8, 20, 229, 27, 29, 31, 81, 93, 66, 100, 101, 9, 18, | 169, 170, 171, 168, 172, 189, 182, 178, 115, 176, 174, 202, 204, 197, 103, 104, 106, 10, 20, 1, 2, 18, | 190, 192, 206, 17, 210, 211, 218, 193, 216, 254 | 205, 207 |

TABLE 2-continued

IC50 values for Table 1 inhibitors of menin

| ++++ (IC50 ≤30 nM) | +++ (30 nM < IC50 ≤ 100 nM) | ++ (100 < IC50 ≤ 1000 nM) | + (IC50 >1000 nM) |
|---|---|---|---|
| 230, 23, 32, 105, 112, 231, 232, 91 | 24, 25, 28, 34, 94, 5, 14, 106, 241, 208, 209, 233, 194, 219, 242, 243, 244, 212 | | |

TABLE 3

Reaction rate (k) for Table 1 inhibitors with menin

| ++++ ($k \geq 10^{-3}\ s^{-1}$) | +++ ($10^{-3}\ s^{-1} > k \geq 10^{-4}\ s^{-1}$) | ++ ($10^{-4}\ s^{-1} > k \geq 10^{-5}\ s^{-1}$) | + ($k < 10^{-5}\ s^{-1}$) |
|---|---|---|---|
| 199, 209, 3, 100, 101, 105, 112, 231, 241, 232, 242, 209, 194, 6, 8, 34, 5, 18, 23, 105, 244, 216 | 115, 81, 91, 99, 192, 203, 206, 18, 230, 243 | 25, 94, 66, 208, 210, 10, 28, 29, 93, 32, 168, 172, 182, 184, 176, 174 | 190, 233, 11, 20, 1, 2, 20, 17, 229, 24, 31, 178, 219 |

Example 1. Schemes for Preparing Compounds of the Disclosure

Compounds and salts described herein may be prepared according to the following general schemes.

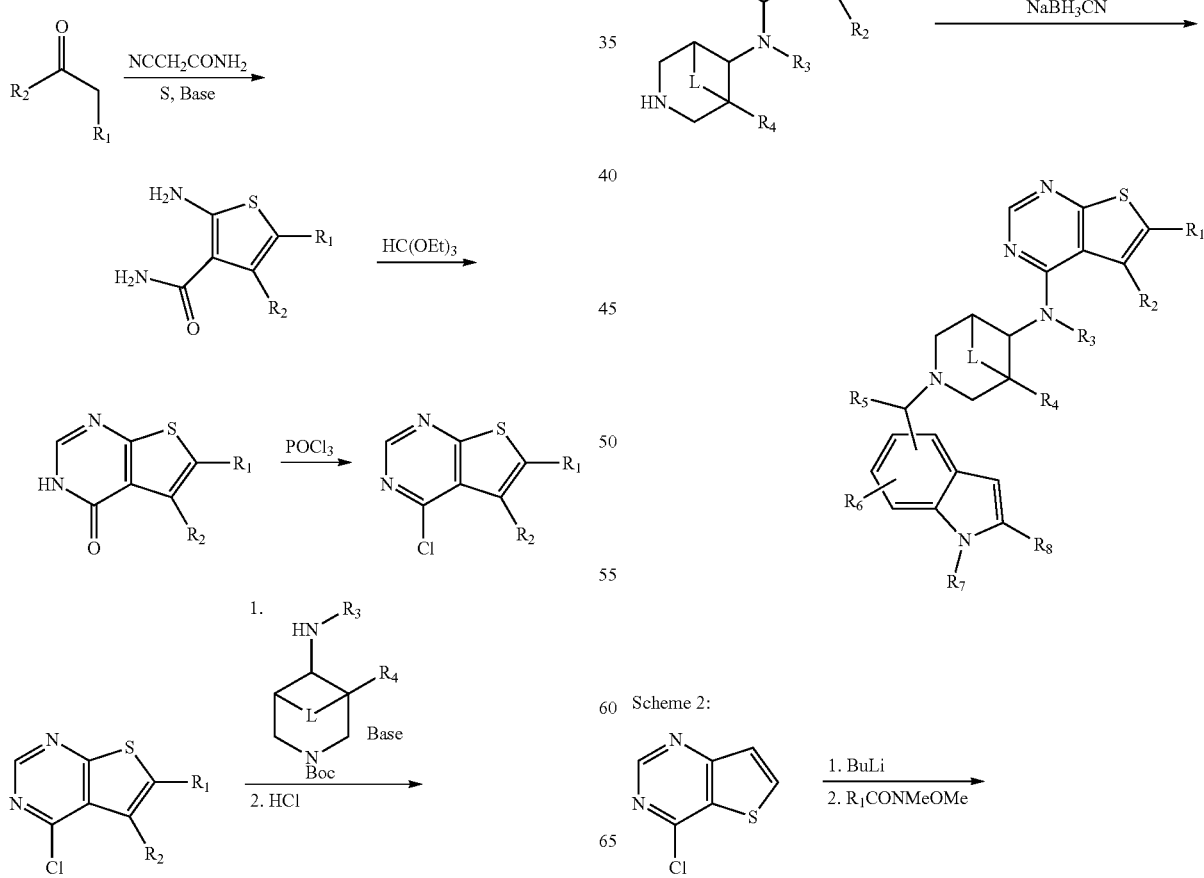

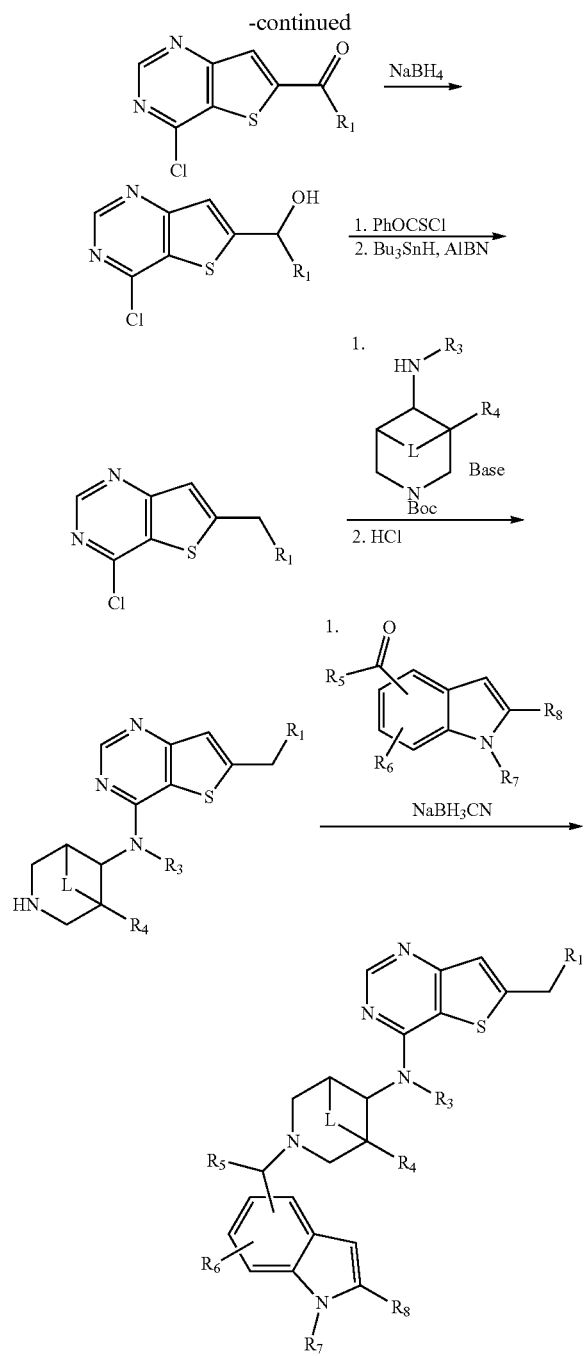

Example 2. Representative Procedure for Synthesis of Compounds 3, 8, and 20

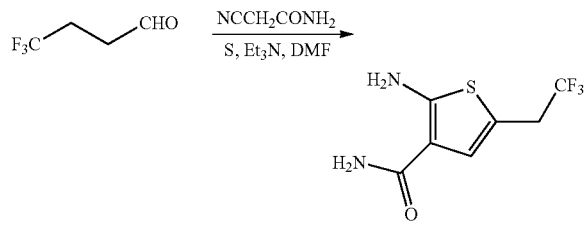

4,4,4-trifluorouteraldehyde (5 g, 39.6 mmol), cyanoacetamide (3.36 g, 39.6 mmol) and sulfur (1.28 g, 39.6 mmol) were stirred in N,N-dimethylformamide (DMF) (40 mL) in the presence of triethylamine (6.7 mL) for 24 h. Solvent was evaporated under reduced pressure and the residue was loaded on a silica gel column and eluted with pure ethyl acetate to afford 2-amino-5-(2,2,2-trifluoroethyl)thiophene-3-carboxamide (8.4 g). $^1$H NMR CDCl$_3$ (300 MHz): 7.97 (s, 1H), 6.76 (s, 1H), 3.59 (br, 2H), 3.35 (q, 2H, J 10.3 Hz), 2.98 (s, 1H), 2.88 (s, 1H). $^{13}$C NMR CDCl$_3$ (75 MHz): 168.6, 125.6, 124.3, 111.7, 107.3, 36.8, 34.7 (q, J 31.4 Hz).

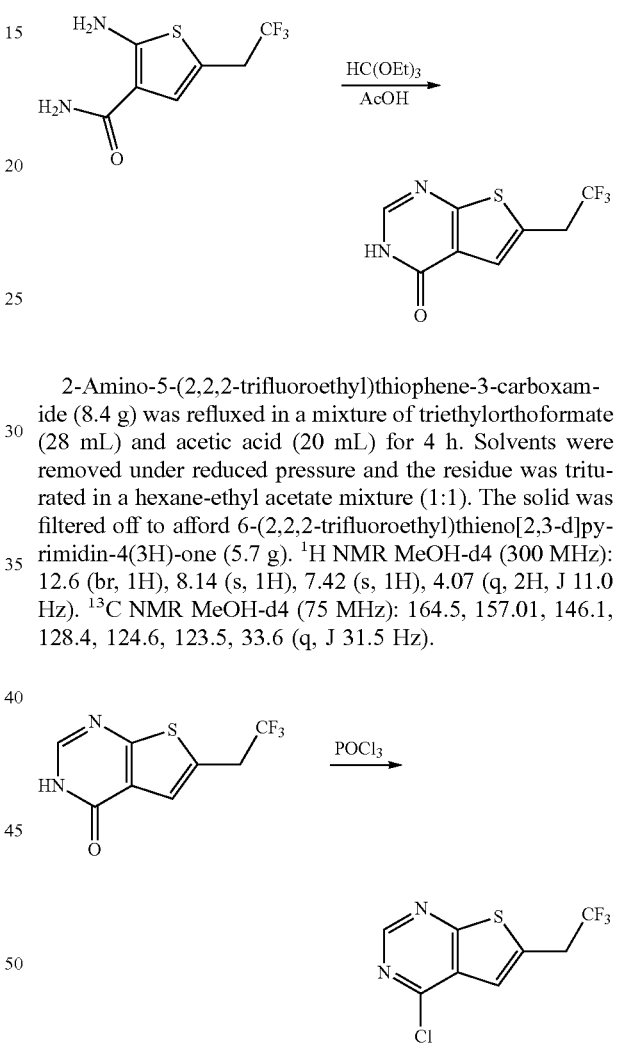

2-Amino-5-(2,2,2-trifluoroethyl)thiophene-3-carboxamide (8.4 g) was refluxed in a mixture of triethylorthoformate (28 mL) and acetic acid (20 mL) for 4 h. Solvents were removed under reduced pressure and the residue was triturated in a hexane-ethyl acetate mixture (1:1). The solid was filtered off to afford 6-(2,2,2-trifluoroethyl)thieno[2,3-d]pyrimidin-4(3H)-one (5.7 g). $^1$H NMR MeOH-d4 (300 MHz): 12.6 (br, 1H), 8.14 (s, 1H), 7.42 (s, 1H), 4.07 (q, 2H, J 11.0 Hz). $^{13}$C NMR MeOH-d4 (75 MHz): 164.5, 157.01, 146.1, 128.4, 124.6, 123.5, 33.6 (q, J 31.5 Hz).

6-(2,2,2-Trifluoroethyl)thieno[2,3-d]pyrimidin-4(3H)-one (5.7 g) was added to POCl$_3$ (16 mL) with one drop of DMF. The heterogeneous mixture was refluxed for 3 h, and the solvent was evaporated. The residue was quenched with ice and saturated ammonia solution and extracted with chloroform. Combined extracts were evaporated with silica gel and loaded on a short silica gel column. The column was eluted with hexane-ethyl acetate (5:1) to afford 4-chloro-6-(2,2,2-trifluoroethyl)thieno[2,3-d]pyrimidine (5.9 g). $^1$H NMR CDCl$_3$ (300 MHz): 8.86 (s, 1H), 7.39 (s, 1H), 3.76 (q, 2H, J 9.9 Hz). $^{13}$C NMR CDCl$_3$ (75 MHz): 169.0, 154.7, 153.2, 129.9, 125.3, 123.5, 121.3, 35.9 (q, J 33.0 Hz).

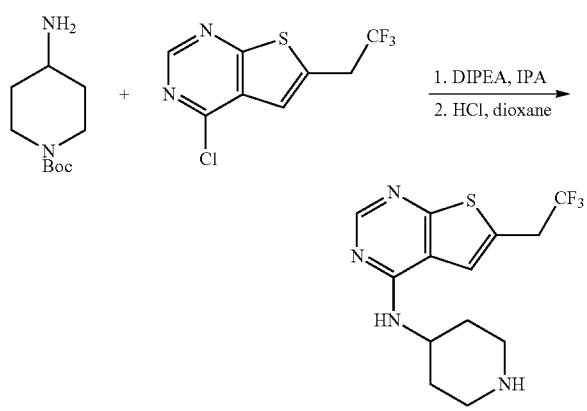

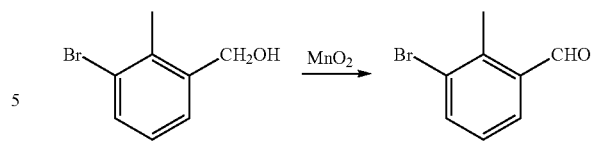

(3-Bromo-2-methylphenyl)methanol (24 g, 119 mmol) was dissolved in dichloromethane (240 mL) and manganese (IV) oxide (103 g, 1.2 mol) was added. After stirring overnight, TLC showed no starting material. Reaction mixture was evaporated with silica gel and loaded on a small silica gel column. The product was eluted with hexane:ethyl acetate (10:1) to afford the pure aldehyde 3-bromo-2-methylbenzaldehyde (18.6 g) after evaporation. $^1$H NMR (600 MHz, CDCl$_3$): 10.25 (s, 1H), 7.78 (m, 2H), 7.23 (t, 1H, J=7.7 Hz), 2.75 (s, 3H). $^{13}$C NMR (150 MHz, CDCl$_3$): 191.84, 137.72, 130.93, 130.20, 127.61, 127.37, 126.82, 18.13.

4-Chloro-6-(2,2,2-trifluoroethyl)thieno[2,3-d]pyrimidine (4.8 g, 19 mmol) was added to a stirred solution (95 mL) of N,N-diisopropylethylamine (7.4 g, 57 mmol) and 4-amino-N-Boc-piperidine (4.56 g, 22.8 mmol) and was heated at reflux overnight. In the morning, the reaction mixture was evaporated with silica gel and loaded on a column. The product was eluted with hexane-ethyl acetate (increasing from 1:1 to 1:5) yielding the boc-derivative (7.42 g). Boc-intermediate was dissolved in 4M HCl in dioxane (40 mL) and stirred for 2 h. Solvent was evaporated under reduced pressure and the residue was partitioned between ethyl acetate and saturated sodium carbonate solution. The organic layer was washed with brine, dried over MgSO$_4$ and evaporated to afford N-(piperidin-4-yl)-6-(2,2,2-trifluoroethyl)thieno[2,3-d]pyrimidin-4-amine (5.3 g), which was used in later steps without purification. $^1$H NMR (600 MHz, CDCl3): δ 8.47 (s, 1H), 7.13 (s, 1H), 5.32 (d, 1H, J=7.7 Hz), 4.32 (m, 1H), 3.64 (q, 2H, 10 Hz), 3.19 (m, 2H), 2.83 (m, 2H), 2.57 (br, 1H), 2.14 (m, 2H), 1.55 (m, 2H). $^{13}$C NMR (150 MHz, CDCl3): δC 166.85, 155.96, 154.33, 128.12, 126.62, 118.66, 116.48, 47.98, 45.32, 35.56 (q, J=31.5 Hz), 33.10. ESI MS [MH$^+$]: 317.2.

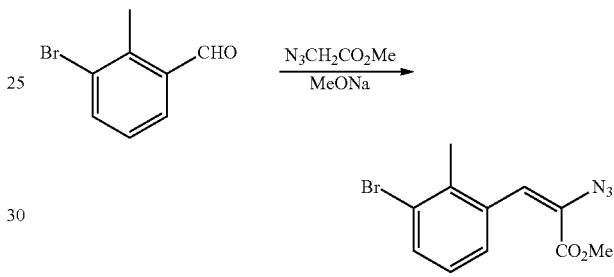

To the mixture of 3-bromo-2-methylbenzaldehyde (18.6 g, 93 mmol) and methyl azidoacetate (26.8 g, 233 mmol) in MeOH (130 mL) was added 5.4 M MeONa (43 mL) over 30 min at −10° C. After addition, the mixture was stirred for additional hour at the same temperature and then transferred to a cold room (4° C.) and stirred overnight. In the morning, the reaction mixture was poured into a mixture of ice and concentrated ammonium chloride solution (1 L), stirred for 10 minutes and filtered off. The solid was washed with plenty of ice cold water and then air dried for 1 hr at ambient temperature. Then the solid was dissolved in dichloromethane (DCM) (100 mL), dried over magnesium sulfate and passed through a short silica gel plug. Evaporation of solvent produced methyl (E)-2-azido-3-(3-bromo-2-methylphenyl)acrylate (21.1 g), that was used in the next step without further purification. $^1$H NMR (600 MHz, CDCl$_3$): 7.72 (d, 1H, J=7.7 Hz), 7.53 (d, 1H, J=7.7 Hz), 7.10 (s, 1H), 7.07 (t, 1H, J=7.7 Hz), 3.93 (s, 3H), 2.42 (s, 3H). $^{13}$C NMR (150 MHz, CDCl$_3$): 163.61, 136.65, 133.94, 133.09, 129.25, 128.76, 126.78, 125.81, 123.64, 53.10, 20.04.

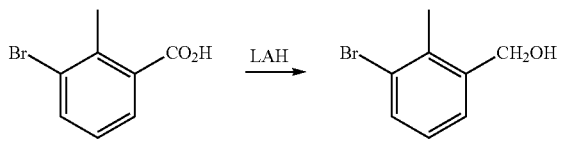

3-Bromo-2-methylbenzoic acid (30 g, 139 mmol) was dissolved in tetrahydrofuran (THF) (180 mL) and cooled to 0° C. Lithium aluminium hydride (9.5 g, 250 mmol) was added in small portions. After stirring for 3 h, no starting material was observed by TLC. The reaction mixture was carefully quenched with ethyl acetate (20 mL) and water (20 mL). Silica gel was added and the mixture was evaporated to dryness and loaded on a small silica gel column. The product was eluted with hexane:ethyl acetate (1:1) resulting in the pure alcohol (3-bromo-2-methylphenyl)methanol (24 g) after evaporation. $^1$H NMR (600 MHz, CDCl$_3$): 7.50 (d, 1H, J=8.1 Hz), 7.29 (d, 1H, J=8.1 Hz), 7.04 (t, 1H, J=8.1 Hz), 4.68 (s, 2H), 2.40 (s, 3H), 1.90 (br s, 1H). $^{13}$C NMR (150 MHz, CDCl$_3$): 140.60, 135.84, 132.03, 127.12, 126.70, 126.05.

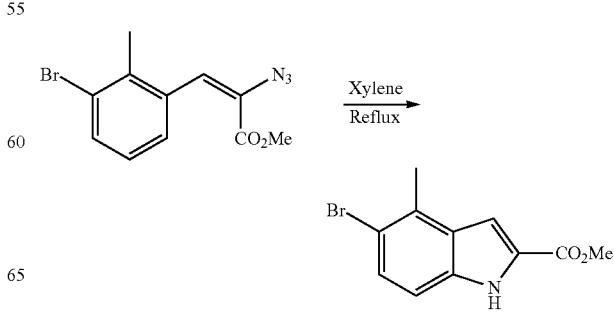

Methyl (E)-2-azido-3-(3-bromo-2-methylphenyl)acrylate (21.1 g, 71 mmol) was dissolved in xylene (700 mL). The mixture was refluxed for 10 minutes. Reaction mixture was cooled to room temperature (RT) and kept in a −20° C. freezer overnight. The precipitated product was filtered off and dried on a funnel to produce methyl 5-bromo-4-methyl-1H-indole-2-carboxylate (10.0 g). $^1$H NMR (600 MHz, CDCl$_3$): 8.98 (br s, 1H), 7.44 (d, 1H, J=8.4 Hz), 7.24 (s, 1H), 7.14 (d, 1H, J=8.4 Hz), 3.96 (s, 3H), 2.60 (s, 3H). $^{13}$C NMR (150 MHz, CDCl$_3$): 162.12, 135.38, 131.56, 129.52, 128.98, 127.36, 115.92, 110.82, 107.70, 52.15, 18.97.

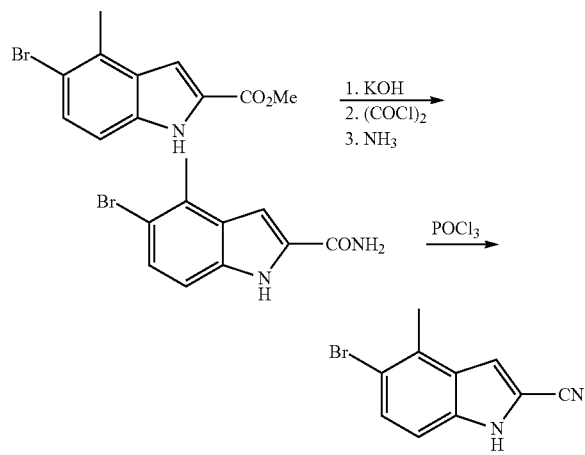

Methyl 5-bromo-4-methyl-1H-indole-2-carboxylate (10.0 g, 38 mmol) was refluxed in solution of KOH (10.6 g, 190 mmol) in methanol (130 mL) for 1 hr. The reaction mixture was then concentrated and acidified with 12 M HCl in water. The precipitated product was filtered off. After drying, the 5-bromo-4-methyl-1H-indole-2-carboxylic acid was added to a solution of oxalyl chloride (6.5 mL, 76 mmol) in dichloromethane (200 mL) with DMF (0.6 mL). After stirring for 1 hr, the reaction mixture was cooled in an ice-water bath and concentrated ammonia in water (40 mL) was added dropwise. The heterogeneous mixture was stirred for another 3 h and filtered off to obtain the carboxamide. A mixture of 5-bromo-4-methyl-1H-indole-2-carboxamide, phosphorus oxychloride (36 mL, 380 mmol) and chloroform (120 mL) was refluxed for 5 h. Then reaction mixture was evaporated to dryness and quenched with ice and concentrated ammonia (about 40 mL). The formed precipitate was filtered off, washed with plenty of water and dissolved in THF (100 mL). The solution was evaporated with silica gel and loaded on a medium silica gel column. The product was eluted in hexane:ethyl acetate (2:1) affording the pure carbonitrile (7.4 g) after evaporation. $^1$H NMR (600 MHz, Me$_2$CO-d$_6$): 11.42 (br s, 1H), 7.49 (d, 1H, J=8.8 Hz), 7.42 (s, 1H), 7.32 (d, 1H, J=8.4 Hz), 2.59 (s, 3H). $^{13}$C NMR (150 MHz, Me$_2$CO-d$_6$): 137.48, 131.99, 130.95, 129.33, 117.21, 114.93, 113.71, 112.95, 108.51, 19.59.

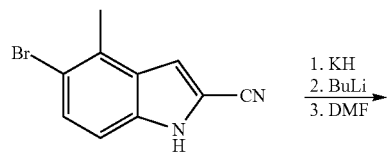

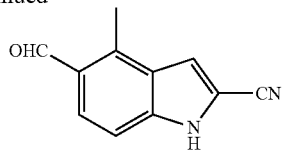

5-Bromo-4-methyl-1H-indole-2-carbonitrile (2.35 g, 10 mmol) was dissolved in THF (100 mL). The flask was flushed with argon and potassium hydride (3.2 g) was added (30% suspension in oil, 24 mmol). After stirring for 5 minutes, the reaction mixture was cooled to −90° C. (internal temperature, ethanol/N$_2$(liq.)) and tert-butyl lithium (11.8 mL, 20 mmol) was slowly added to maintain the temperature in the range between −95° C. and −90° C. After stirring for 1 h, DMF (3.8 ml, 50 mmol) was added dropwise and the reaction mixture was allowed to warm to −70° C. and kept for 30 minutes at that temperature. The reaction mixture was quenched with acetic acid (2.9 mL, 50 mmol) and warmed to room temperature. After the addition of brine (100 mL), the organic phase was separated, evaporated with silica gel and loaded on a medium silica gel column. Elution started with pure hexane and then product was washed out with hexane:THF (1:1). After evaporation of the product-containing fractions, the pure aldehyde (1.11 g) was obtained. $^1$H NMR (600 MHz, CD$_3$CN): 10.39 (s, 1H), 7.82 (d, 1H, J=8.4 Hz), 7.51 (s, 1H), 7.43 (d, 1H, J=8.4 Hz), 2.86 (s, 3H). $^{13}$C NMR (150 MHz, CD$_3$CN): 191.15, 138.90, 137.17, 127.26, 126.94, 126.55, 113.70, 113.11, 109.97, 107.19, 13.39.

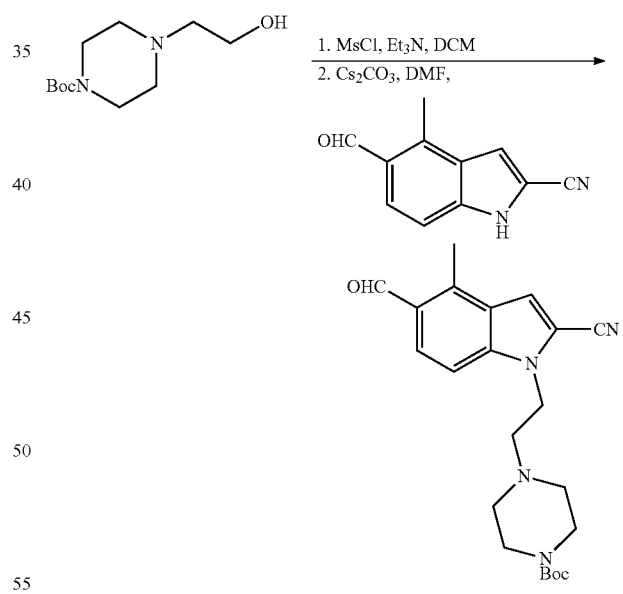

Tert-butyl 4-(2-hydroxyethyl)piperazine-1-carboxylate (1 g, 4.3 mmol) and triethyl amine (0.89 mL, 6.5 mmol) were dissolved in DCM (14 mL). MsCl (0.4 mL, 5.2 mmol) was added slowly and the reaction was stirred for 2 h. The reaction mixture was washed with brine, dried over anhydrous sodium sulfate and evaporated. The intermediate was dissolved in DMF (4 mL) and 5-formyl-4-methyl-1H-indole-2-carbonitrile (368 mg, 2 mmol) and cesium carbonate (2 g, 6 mmol) was added. After stirring for 18 h, TLC showed consumption of aldehyde. The reaction mixture was diluted with water (50 mL) and extracted with DCM (2×50 mL). The organic phase was evaporated with silica gel and loaded on a silica gel column. The product was eluted with hexane-ethyl acetate (1:1) to afford tert-butyl 4-(2-(2-cyano-5-formyl-4-methyl-1H-indol-1-yl)ethyl)piperazine-1-carboxylate (240 mg). HR MS (ESI): $C_{22}H_{28}N_4O_3+H^+$ calculated 397.2234; found 397.2239.

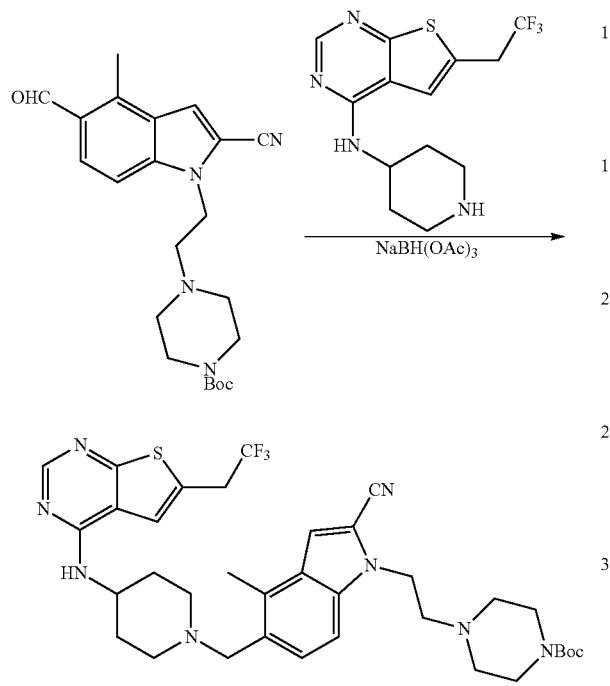

Tert-butyl 4-(2-(2-cyano-5-formyl-4-methyl-1H-indol-1-yl)ethyl)piperazine-1-carboxylate (120 mg, 0.3 mmol), N-(piperidin-4-yl)-6-(2,2,2-trifluoroethyl)thieno[2,3-d]pyrimidin-4-amine hydrochloride (126 mg, 0.36 mmol), and triethylamine (0.06 mL, 0.45 mmol) were mixed in dry dichloromethane (3 mL). Sodium triacetoxyborohydride (97 mg, 0.45 mmol) was added to the mixture in one portion. After stirring overnight, TLC showed absence of starting aldehyde and the reaction mixture was transferred to a separatory funnel and washed with 1M NaOH (20 mL). The organic phase was evaporated with silica gel and loaded on a silica gel column. The product was eluted starting from DCM:MeOH:NH$_3$*H$_2$O 40:1:0.1 and decreasing to 20:1:0.1. Evaporation of solvent gave tert-butyl 4-(2-(2-cyano-4-methyl-5-((4-((6-(2,2,2-trifluoroethyl)thieno[2,3-d]pyrimidin-4-yl)amino)piperidin-1-yl)methyl)-1H-indol-1-yl)ethyl)piperazine-1-carboxylate (180 mg). HR MS (ESI): $C_{35}H_{43}F_3N_8O_2S+H^+$ calculated 697.3255; found 697.3259.

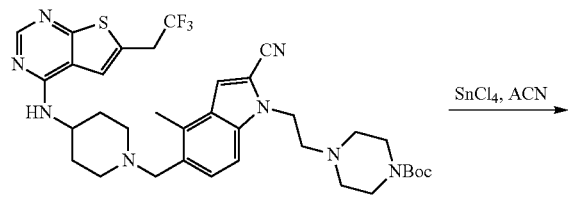

Tert-butyl 4-(2-(2-cyano-4-methyl-5-((4-((6-(2,2,2-trifluoroethyl)thieno[2,3-d]pyrimidin-4-yl)amino)piperidin-1-yl)methyl)-1H-indol-1-yl)ethyl)piperazine-1-carboxylate (180 mg, 0.26 mmol) was dissolved in acetonitrile (ACN) (2.6 mL) and SnCl$_4$ (0.3 mL, 2.6 mmol) was added. The homogenous reaction mixture was stirred for 1 h and then volatiles were removed in vacuo. The residue was quenched with ammonia and extracted with ethyl acetate. Combined organic fractions were dried over MgSO$_4$ and concentrated. The residue was purified using preparative TLC to afford 4-methyl-1-(2-(piperazin-1-yl)ethyl)-5-((4-((6-(2,2,2-trifluoroethyl)thieno[2,3-d]pyrimidin-4-yl)amino)piperidin-1-yl)methyl)-1H-indole-2-carbonitrile (88 mg). $^1$H NMR (600 MHz, CDCl$_3$): 8.46 (s, 1H), 7.35 (d, 1H, J=8.4 Hz), 7.17 (s, 1H), 7.15 (d, 1H, J=8.4 Hz), 7.10 (s, 1H), 5.20 (d, 1H, J=7.7 Hz), 4.32 (m, 2H), 4.22 (m, 1H), 3.63 (q, 2H, J=10.5 Hz), 3.60 (s, 2H), 2.91, (m, 6H), 2.69 (m, 2H), 2.54 (s, 3H), 2.50 (m, 4H), 2.26 (t, 2H, J=10.6 Hz), 2.09 (d, 2H, J=10.3 Hz), 1.58 (d, 2H, J=9.9 Hz). $^{13}$C NMR (150 MHz, CDCl$_3$): 166.79, 156.09, 154.36, 136.37, 131.18, 128.97, 128.65, 127.33, 125.61, 118.62, 116.43, 114.03, 111.64, 109.76, 107.23, 60.14, 57.80, 57.80, 53.86, 52.36, 51.34, 48.05, 45.48, 43.34, 35.53 (q, J=32 Hz), 32.39, 15.06. HR MS (ESI): $C_{30}H_{35}F_3N_8S+H^+$ calculated 597.2730; found 597.2727.

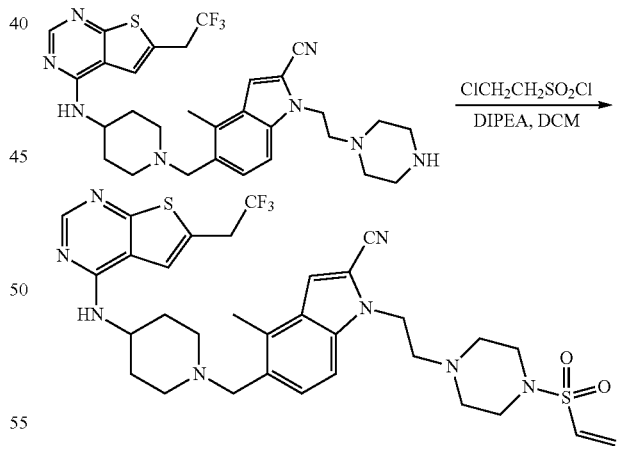

To a mixture of 4-methyl-1-(2-(piperazin-1-yl)ethyl)-5-((4-((6-(2,2,2-trifluoroethyl)thieno[2,3-d]pyrimidin-4-yl)amino)piperidin-1-yl)methyl)-1H-indole-2-carbonitrile (520 mg, 0.87 mmol) and N,N-diisopropylethylamine (DIPEA) (0.23 mL, 1.3 mmol) in DCM (17 mL) was added 2-chloroethanesulfonyl chloride (0.1 mL, 0.96 mmol) with external cooling of ice water. After stirring for 15 minutes, the reaction mixture was loaded directly on a column and eluted with DCM-MeOH (10:1) and then purified again in a column using Hexane-Ethyl Acetate-Methanol (1:1:0.2).

Evaporating the product-containing fractions resulted in 4-methyl-1-(2-(4-vinylsulfonylpiperazin-1-yl)ethyl)-5-((4-((6-(2,2,2-trifluoroethyl)thieno[2,3-d]pyrimidin-4-yl)amino)piperidin-1-yl)methyl)-1H-indole-2-carbonitrile (Compound 3) (308 mg). Compound 3 was converted to its hydrochloride salt by dissolving it in methanol (4 mL), adding 1M HCl in water (0.55 mL) and evaporating. $^1$H NMR (600 MHz, CD$_3$OD): 8.35 (s, 1H), 7.59 (m, 3H), 7.43 (s, 1H), 6.61 (dd, J=16.5, 10.3 Hz, 1H), 6.14 (m, 2H), 4.54 (m, 2H), 4.46 (s, 2H), 3.86 (q, 2H, J=10.5 Hz), 3.63 (m, 2H), 3.50 (m, 1H), 3.34 (m, 2H), 3.10 (m, 4H), 2.79 (m, 2H), 2.69 (s, 3H), 2.56 (m, 4H), 2.35 (m, 2H), 1.99 (m, 2H). $^{13}$C NMR (150 MHz, CD$_3$OD): 167.02, 157.69, 154.84, 138.70, 135.10 133.74, 130.56, 129.96, 129.77, 126.60 (q, J=289.5 Hz), 121.74, 121.01, 118.18, 114.62, 113.18, 112.65, 100.44, 58.59, 58.05, 53.85, 52.94, 47.11, 46.72, 44.46, 35.63 (q, J=32 Hz), 30.92, 30.01, 15.80. HR MS (ESI): $C_{32}H_{37}F_3N_8O_2S_2+H^+$ calculated 687.2506; found 687.2505.

Following the same general procedures for preparing Compound 3, Compound 8 was synthesized starting with the tert-butyl 4-(2-hydroxyethyl)piperidine-1-carboxylate. $^1$H NMR (600 MHz, CD$_3$OD): 8.36 (s, 1H), 7.59 (m, 3H), 7.47 (s, 1H), 6.60 (dd, J=16.5, 9.9 Hz, 1H), 6.12 (m, 2H), 4.54 (m, 2H), 4.42 (s, 2H), 3.86 (q, 2H, J=10.5 Hz), 3.64 (m, 2H), 3.45 (m, 1H), 3.33 (m, 2H), 3.10 (m, 4H), 2.69 (s, 3H), 2.61 (m, 2H), 2.35 (m, 2H), 1.84 (m, 3H), 1.44 (m, 1H), 1.32 (m, 3H). $^{13}$C NMR (150 MHz, CD$_3$OD): 166.69, 157.70, 154.70, 138.80, 135.23, 134.19, 130.71, 129.09, 128.74, 126.53 (q, J=289.5 Hz), 121.74, 120.99, 118.21, 114.26, 113.64, 111.43, 110.41, 58.91, 52.95, 46.94, 44.29, 37.47, 35.54 (q, J=32 Hz), 34.18, 32.71, 30.77, 30.00, 27.33, 15.79. HR MS (ESI); $C_{33}H_{38}F_3N_7O_2S_2+H^+$ calculated 686.2553; found 687.2556.

Following the same general procedures for preparing Compound 3, Compound 20 was synthesized starting with 4-methyl-1-(2-(piperidin-1-yl)ethyl)-5-((4-((6-(2,2,2-trifluoroethyl)thieno[2,3-d]pyrimidin-4-yl)amino)piperidin-1-yl)methyl)-1H-indole-2-carbonitrile. $^1$H NMR (600 MHz, CD$_3$OD): 8.36 (s, 1H), 7.63 (m, 1H), 7.55 (m, 2H) 7.48 (s, 1H), 6.60 (dd, J=16.9, 10.6 Hz, 1H), 6.18 (dd, J=16.7, 1.7 Hz, 1H), 5.74 (dd, J=10.6, 1.7 Hz, 1H), 4.57 (m, 3H), 4.44 (m, 1H), 4.42 (s, 2H), 4.12 (m, 1H), 3.88 (q, 2H, J=10.5 Hz), 3.64 (m, 2H), 3.33 (m, 2H), 3.12 (m, 1H), 2.72 (s, 3H), 2.66 (m, 1H), 2.34 (m, 2H), 2.05 (m, 2H), 1.84 (m, 4H), 1.65 (m, 1H), 1.23 (m, 2H). $^{13}$C NMR (150 MHz, CD$_3$OD): 167.45, 167.07, 157.72, 154.87, 138.79, 135.18, 130.77, 129.66, 129.23, 128.71, 128.28, 126.53 (q, J=289.5 Hz), 121.87, 121.15, 118.20, 114.32, 113.65, 111.35, 110.40, 58.82, 52.93, 47.20, 44.29, 43.37, 37.61, 35.68 (q, J=32 Hz), 34.81, 33.83, 32.88, 29.99, 15.85. HR MS (ESI): $C_{34}H_{38}F_3N_7OS+H^+$ calculated 650.2884; found 650.2881.

Example 3. Representative Procedure for Synthesis of Compounds 17, 18, 22-25, 27-29, 31 and 32

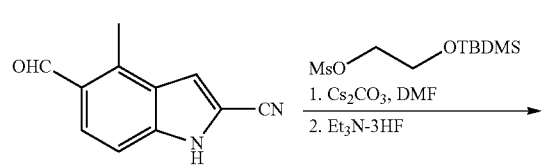

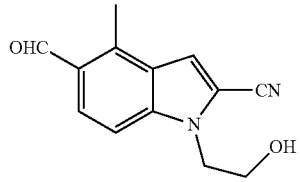

Monosilylated ethylene glycol (704 mg, 4 mmol) and triethylamine (0.89 mL, 6 mmol) were dissolved in DCM (10 mL). Ms$_2$O (835 mg, 4.8 mmol) was added slowly and the reaction was stirred for 2 h. The reaction mixture was washed with brine, dried over anhydrous sodium sulfate and evaporated. The reaction intermediate was dissolved in DMF (5.3 mL) and 5-formyl-4-methyl-1H-indole-2-carbonitrile (490.6 mg, 2.67 mmol) and cesium carbonate (2.6 g, 8 mmol) were added. After stirring for 4 h at 50° C., TLC showed consumption of the aldehyde. The reaction mixture was diluted with water (50 mL) and extracted with diethyl ether (2×50 mL). The organic phase was evaporated and dissolved in acetonitrile (4 mL). Et$_3$N-3HF (0.7 mL) was added and mixture was stirred for 1 h at 50° C. Reaction mixture was concentrated and purified using column chromatography eluting with hexane-ethyl acetate (1:1) to afford pure 5-formyl-1-(2-hydroxyethyl)-4-methyl-1H-indole-2-carbonitrile (369 mg). $^1$H NMR (600 MHz, CD$_3$OD): 10.38 (s, 1H), 7.84 (d, 1H, J=8.4 Hz), 7.53 (s, 1H), 7.47 (d, 1H, J=8.4 Hz), 4.40 (m, 2H), 3.85 (m, 2H), 3.07 (m, 1H), 2.86 (s, 3H).

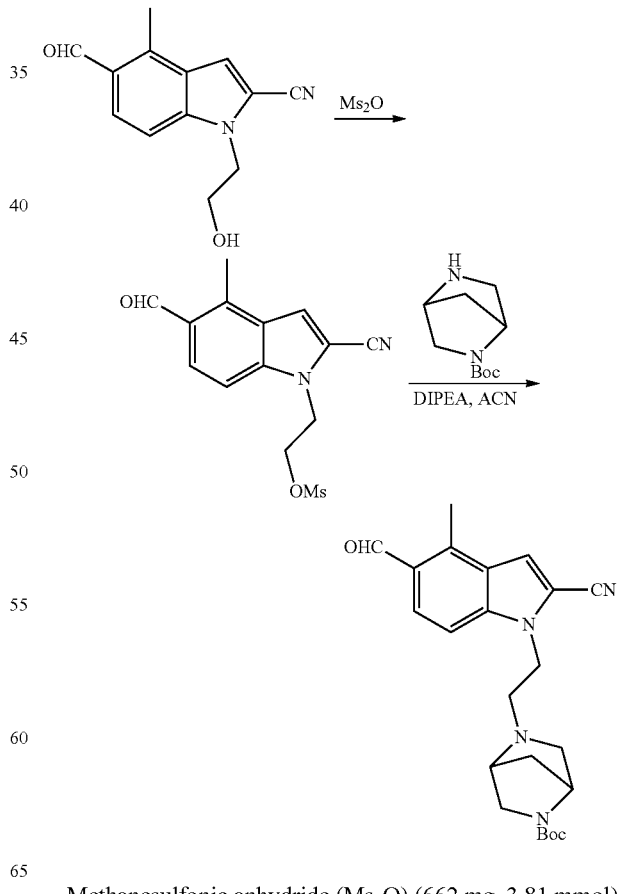

Methanesulfonic anhydride (Ms$_2$O) (662 mg, 3.81 mmol) was slowly added to a solution of 5-formyl-1-(2-hydroxyethyl)-4-methyl-1H-indole-2-carbonitrile (290 mg, 1.27 mmol) and DIPEA (1.1 mL) in THF (6.3 mL). After stirring for 10 minutes, the mixture was diluted with saturated bicarbonate solution and stirred for 20 minutes, and the product was filtered off and thoroughly dried. $^1$H NMR (600 MHz, CD$_3$CN): 10.39 (s, 1H), 7.88 (d, 1H, J=8.4 Hz), 7.59 (s, 1H), 7.49 (d, 1H, J=8.4 Hz), 4.66 (m, 2H), 4.53 (m, 2H), 2.86 (m, 6H). The mesylated derivative (130 mg, 0.42 mmol) was dissolved in DMF (2 mL) and tert-butyl 2,5-diazabicyclo[2.2.1]heptane-2-carboxylate (166 mg, 0.84 mmol) and potassium carbonate (86 mg, 0.63 mmol) were added. The mixture was heated at 85° C. for 1 h, cooled down, diluted with water, and extracted with DCM. The crude mixture was purified on silica gel column to produce tert-butyl 5-(2-(2-cyano-5-formyl-4-methyl-1H-indol-1-yl)ethyl)-2,5-diazabicyclo[2.2.1]heptane-2-carboxylate (10 mg). HR MS (ESI): C$_{23}$H$_{28}$N$_4$O$_3$+H$^+$ calculated 409.2234; found 409.2232.

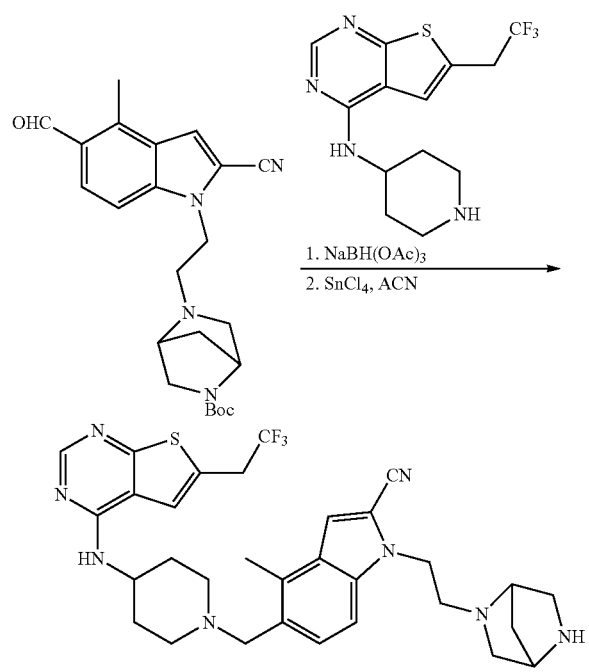

Tert-butyl 5-(2-(2-cyano-5-formyl-4-methyl-1H-indol-1-yl)ethyl)-2,5-diazabicyclo[2.2.1]heptane-2-carboxylate (10 mg, 0.025 mmol), N-(piperidin-4-yl)-6-(2,2,2-trifluoroethyl)thieno[2,3-d]pyrimidin-4-amine hydrochloride (126 mg, 0.038 mmol), and triethylamine (0.01 mL, 0.045 mmol) were mixed in dry dichloromethane (0.3 mL). Sodium triacetoxyborohydride (10 mg, 0.045 mmol) was added to it in one portion. After stirring overnight, TLC showed absence of starting aldehyde in reaction mixture. Reaction mixture was purified using preparative thin-layer chromatography (pTLC) eluting with DCM:MeOH:NH$_3$*H$_2$O (20:1:0.1). After washing the product from silica gel with methanol, it was dissolved in acetonitrile (0.5 mL) and tin chloride (0.03 mL, 0.26 mmol). After stirring for 15 minutes, volatiles were removed in vacuo. The residue was quenched with ammonia and extracted with ethyl acetate. Combined organic fractions were dried over MgSO$_4$ and concentrated. The residue was purified using preparative TLC to afford 1-(2-(2,5-diazabicyclo[2.2.1]heptan-2-yl)ethyl)-4-methyl-5-((4-((6-(2,2,2-trifluoroethyl)thieno[2,3-d]pyrimidin-4-yl)amino)piperidin-1-yl)methyl)-1H-indole-2-carbonitrile (10 mg).

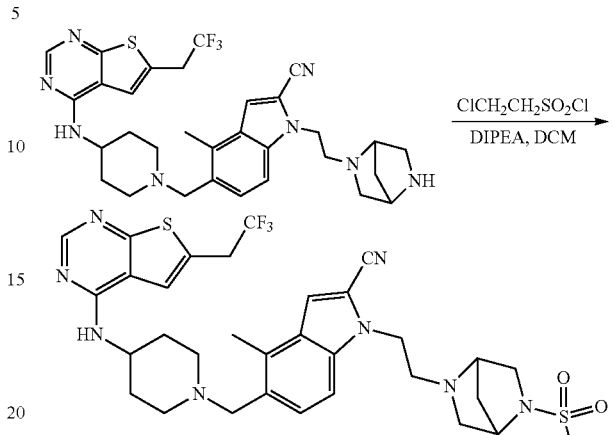

To a mixture of 1-(2-(2,5-diazabicyclo[2.2.1]heptan-2-yl)ethyl)-4-methyl-5-((4-((6-(2,2,2-trifluoroethyl)thieno[2,3-d]pyrimidin-4-yl)amino)piperidin-1-yl)methyl)-1H-indole-2-carbonitrile (10 mg, 0.016 mmol) and DIPEA (0.011 mL, 0.066 mmol) in DCM (0.32 mL) was added 2-chloroethanesulfonyl chloride (0.002 mL, 0.02 mmol) with external cooling of ice water. After stirring for 15 minutes, the reaction mixture was purified using pTLC and eluted with DCM-MeOH (15:1). The product was washed off from silica gel with methanol affording after evaporation 4-methyl-5-((4-((6-(2,2,2-trifluoroethyl)thieno[2,3-d]pyrimidin-4-yl)amino)piperidin-1-yl)methyl)-1-(2-(5-(vinylsulfonyl)-2,5-diazabicyclo[2.2.1]heptan-2-yl)ethyl)-1H-indole-2-carbonitrile (Compound 17) (0.7 mg). HR MS (ESI): C$_{33}$H$_{37}$F$_3$N$_8$O$_2$S$_2$+H$^+$ calculated 699.2506; found 699.2508.

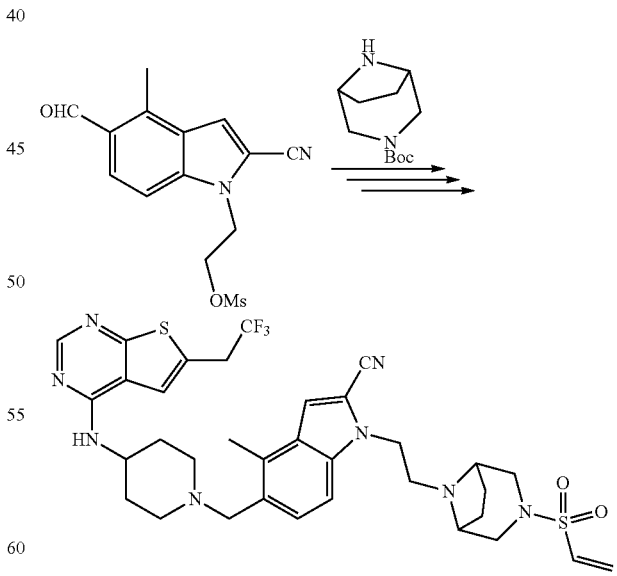

Following the same general procedures for preparing Compound 17, Compound 18 was synthesized starting with tert-butyl 3,8-diazabicyclo[3.2.1]octane-3-carboxylate. Compound 18 was converted to its hydrochloride salt by dissolving it in methanol (0.1 mL), adding 1 equivalent of 1M HCl in water and evaporating. ¹H NMR (600 MHz, CD₃OD): 8.35 (s, 1H), 7.53 (m, 3H), 7.44 (s, 1H), 6.57 (m, 1H), 6.08 (m, 1H), 5.96 (m, 1H), 4.43 (m, 5H), 3.86 (m, 2H), 3.58 (m, 2H), 3.35 (m, 2H), 3.16 (m, 2H), 3.06 (m, 2H), 2.82 (m, 2H), 2.69 (s, 3H), 2.32 (m, 2H), 1.88 (m, 4H), 1.71 (m, 2H). ¹³C NMR (150 MHz, CD₃OD, not all signals reported because of low conc.): 167.10, 157.76, 154.89, 138.74, 133.84, 130.37, 128.94, 128.82, 114.81, 113.06, 61.33, 54.03, 52.54, 46.60, 26.25, 15.73. HR MS (ESI): M+H calculated 713.2662; found 713.2664.

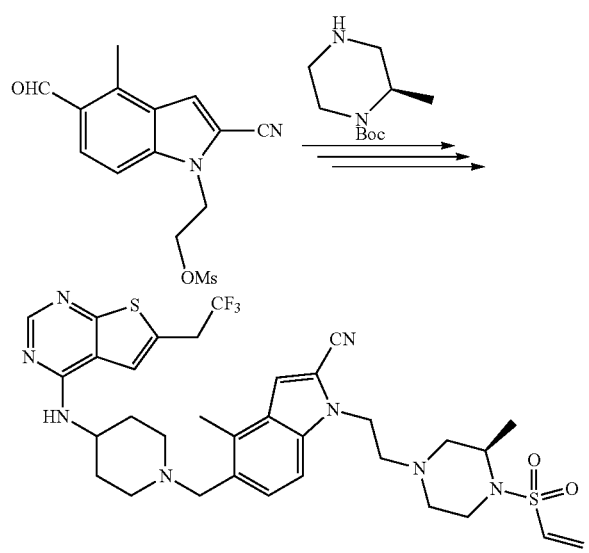

Following the same general procedures for preparing Compound 17, Compound 22 was synthesized starting with tert-butyl (R)-2-methylpiperazine-1-carboxylate. Compound 22 was converted to its hydrochloride salt by dissolving it in methanol (0.1 mL), adding 1 equivalent of 1M HCl in water and evaporating. ¹H NMR (600 MHz, CD₃OD): 8.37 (s, 1H), 7.59 (m, 3H), 7.47 (s, 1H), 6.63 (m, 1H), 6.13 (m, 1H), 5.98 (m, 1H), 4.55 (m, 2H), 4.48 (m, 3H), 3.88 (m, 2H), 3.63 (m, 2H), 3.41 (m, 1H), 3.25 (m, 1H), 2.94 (m, 1H), 2.77 (m, 1H), 2.72 (s, 3H), 2.38 (m, 4H), 2.15 (m, 1H), 2.04 (m, 2H), 1.09 (m, 3H). ¹³C NMR (150 MHz, CD₃OD): 167.09, 157.74, 154.89, 138.90, 137.71, 134.99, 130.47, 129.97, 128.76, 126.64 (q, J=289.5 Hz), 121.83, 121.20, 118.21, 114.70, 113.19, 112.48, 110.57, 60.33, 58.54, 53.84, 50.79, 44.63, 41.41, 35.66 (q, J=32 Hz), 16.34, 15.79. HR MS (ESI): C₃₃H₃₉F₃N₈O₂S₂+H⁺ calculated 701.2662; found 701.2669.

Following the same general procedures for preparing Compound 17, Compound 23 was synthesized starting with tert-butyl 3,8-diazabicyclo[3.2.1]octane-8-carboxylate. Compound 23 was converted to its hydrochloride salt by dissolving it in methanol (0.1 mL), adding 1 equivalent of 1M HCl in water and evaporating. ¹H NMR (600 MHz, CD₃OD): 8.38 (s, 1H), 7.59 (m, 3H), 7.50 (s, 1H), 6.65 (m, 1H), 6.19 (m, 1H), 5.96 (m, 1H), 4.56 (m, 2H), 4.47 (m, 3H), 3.97 (m, 2H), 3.89 (m, 2H), 3.64 (m, 2H), 2.88 (m, 2H), 2.73 (s, 3H), 2.64 (m, 2H), 2.40 (m, 4H), 2.02 (m, 2H), 1.72 (m, 4H), 1.32 (m, 2H). ¹³C NMR (150 MHz, CD₃OD): 167.10, 157.74, 154.89, 139.01, 137.36, 135.10, 130.53, 130.01, 128.75, 127.72, 126.64 (q, J=289.5 Hz), 121.79, 121.16, 118.21, 114.66, 113.42, 112.07, 110.6860.92, 58.54, 57.14, 44.75, 35.66 (q, J=32 Hz), 28.91, 15.80. HR MS (ESI): M+H⁺ calculated 713.2662; found 713.2661.

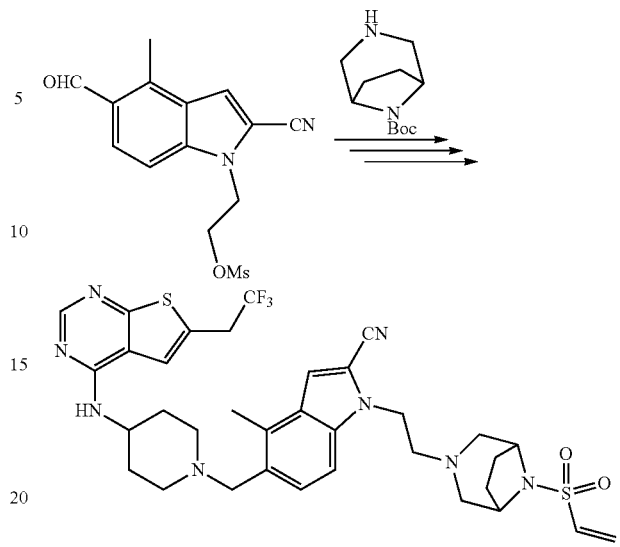

Following the same general procedures for preparing Compound 17, Compound 24 was synthesized starting with tert-butyl 3,8-diazabicyclo[3.2.1]octane-8-carboxylate. Compound 24 was converted to its hydrochloride salt by dissolving it in methanol (0.1 mL), adding 1 equivalent of 1M HCl in water and evaporating. ¹H NMR (600 MHz, CD₃OD): 8.38 (s, 1H), 7.62 (m, 3H), 7.52 (s, 1H), 6.65 (m, 1H), 6.28 (m, 1H), 5.76 (m, 1H), 4.58 (m, 5H), 3.88 (m, 2H), 3.66 (m, 2H), 2.88 (m, 2H), 2.73 (s, 3H), 2.64 (m, 2H), 2.38 (m, 4H), 2.02 (m, 2H), 1.83 (m, 2H), 1.71 (m, 2H), 1.31 (m, 2H). ¹³C NMR (150 MHz, CD₃OD): 166.71, 164.31, 157.69, 154.71, 139.05, 135.19, 130.63, 130.12, 129.07, 128.77, 126.63 (q, J=289.5 Hz), 121.79, 121.07, 118.19, 114.62, 113.53, 112.07, 110.72, 60.88, 59.35, 58.86, 57.20, 56.71, 53.87, 52.93, 47.14, 35.65 (q, J=32 Hz), 30.80, 29.98, 29.00, 27.27, 15.82. HR MS (ESI): M+H⁺ calculated 677.2992; found 677.2994.

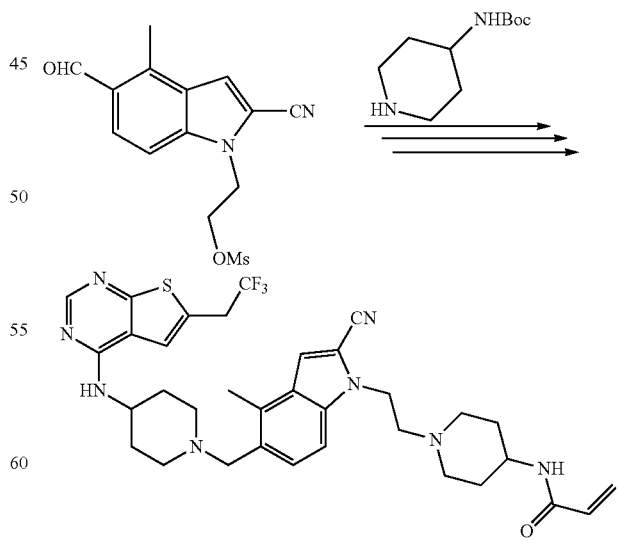

Following the same general procedures for preparing Compound 17, Compound 25 was synthesized starting with tert-butyl piperidin-4-ylcarbamate. Compound 25 was converted to its hydrochloride salt by dissolving it in methanol (0.1 mL), adding 1 equivalent of 1M HCl in water and evaporating. ¹H NMR (600 MHz, CD₃OD): 8.34 (s, 1H), 7.57 (m, 3H), 7.43, (s, 1H), 6.21 (m, 2H), 5.61 (m, 1H), 4.46 (m, 5H), 3.86 (q, 2H, J=10.5 Hz), 3.72 (m, 1H), 3.57 (m, 2H), 3.25 (m, 2H), 2.89 (m, 2H), 2.79 (m, 2H), 2.69 (s, 3H), 2.28 (m, 4H), 2.01 (m, 2H), 1.84 (m, 2H), 1.54 (m, 2H). ¹³C NMR (150 MHz, CD₃OD): 167.43, 167.06, 157.74, 154.88, 138.72, 134.83, 132.10, 130.57, 129.92, 128.77, 126.70, 126.63 (q, J=289.5 Hz), 121.85, 118.20, 114.42, 113.26, 112.24, 110.32, 58.91, 58.17, 53.85, 52.75, 47.77, 44.46, 35.66 (q, J=32 Hz), 32.50, 30.72, 15.77. HR MS (ESI): M+H⁺ calculated 665.2992; found 665.2997.

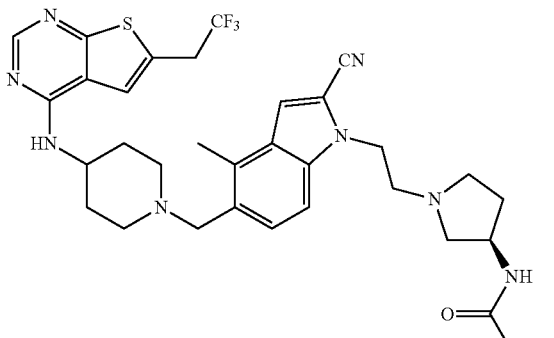

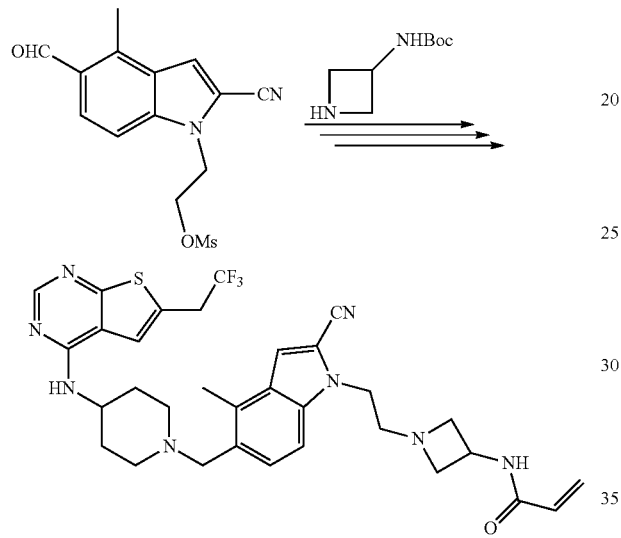

Following the same general procedures for preparing Compound 17, Compound 28 was synthesized starting with tert-butyl azetidin-3-ylcarbamate. Compound 28 was converted to its hydrochloride salt by dissolving it in methanol (0.1 mL), adding 1 equivalent of 1M HCl in water and evaporating. ¹H NMR (600 MHz, CD₃OD): 8.35 (s, 1H), 7.58 (m, 3H), 7.49, (s, 1H), 6.20 (m, 2H), 5.66 (m, 1H), 4.46 (m, 6H), 3.86 (q, 2H, J=10.5 Hz), 3.76 (m, 2H), 3.60 (m, 2H), 3.21 (m, 2H), 3.12 (m, 2H), 2.89 (m, 2H), 2.69 (s, 3H), 2.31 (m, 2H), 2.01 (m, 2H). ¹³C NMR (150 MHz, CD₃OD): 167.67, 167.09, 157.74, 154.89, 139.01, 135.09, 131.54, 130.83, 129.97, 128.76, 127.46, 126.65 (q, J=289.5 Hz), 21.85, 118.21, 114.27, 113.99, 111.76, 110.36, 62.42, 58.80, 55.87, 44.64, 43.84, 41.58, 35.66 (q, J=32 Hz), 18.74, 17.31, 15.78, 14.59, 13.21. M+H⁺ calculated 637.2679; found 635.2683.

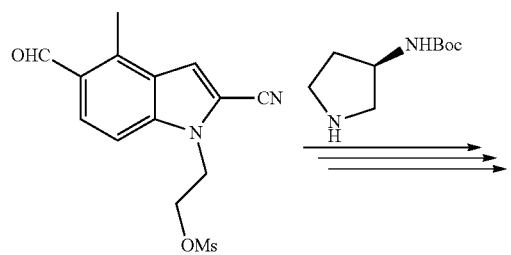

Following the same general procedures for preparing Compound 17, Compound 32 was synthesized starting with tert-butyl (R)-pyrrolidin-3-ylcarbamate. Compound 32 was converted to its hydrochloride salt by dissolving it in methanol (0.1 mL), adding 1 equivalent of 1M HCl in water and evaporating. ¹H NMR (600 MHz, CD₃OD): 8.35 (s, 1H), 7.56 (m, 3H), 7.47, (s, 1H), 6.21 (m, 2H), 5.64 (m, 1H), 4.51 (m, 4H), 4.34 (m, 1H), 3.86 (q, 2H, J=10.5 Hz), 3.86 (m, 2H), 3.59 (m, 2H), 3.01 (m, 2H), 2.93 (m, 2H), 2.69 (s, 3H), 2.31 (m, 2H), 2.01 (m, 2H), 1.74 (m, 1H). ¹³C NMR (150 MHz, CD₃OD): 167.75, 167.09, 157.74, 154.88, 138.87, 135.04, 131.87, 130.72, 129.96, 128.77, 126.92, 126.64 (q, J=289.5 Hz), 121.81, 118.21, 114.42, 113.74, 111.95, 110.35, 61.20, 55.87, 54.36, 45.29, 35.66 (q, J=32 Hz), 32.10, 30.50, 15.77. HR MS M+H⁺ calculated 651.2836; found 651.2838.

Example 4. Representative Procedure for the Synthesis of Compounds 30 and 34

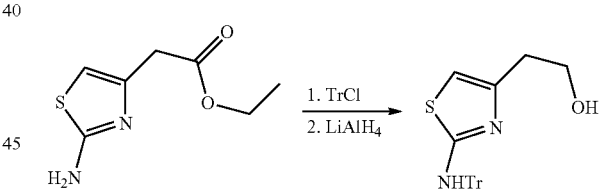

Ethyl 2-(2-aminothiazol-4-yl)acetate (0.93 g, 5 mmol) and trityl chloride (0.167 g, 0.6 mmol) were dissolved in DCM (8 mL). Triethyl amine (0.9 mL, 0.7 mmol) was added and mixture was stirred for 30 minutes. Then the reaction mixture was washed with water, washed with brine, dried over sodium sulfate and concentrated. The residue was dissolved in THF (50 mL) and a solution of 4 M lithium aluminum hydride (LAH) in ether (1.25 mL) was added slowly. After 30 minutes, the reaction was carefully quenched with ethyl acetate (10 mL) and then with water (4 mL). After stirring for 5 minutes, the mixture was evaporated with silica gel. Product was eluted with hexane-ethyl acetate mixture (1:1) resulting in 2-(2-(tritylamino)thiazol-4-yl)ethan-1-ol (1.5 g) after concentration. ¹H NMR (600 MHz, CDCl₃): 7.30 (m, 15H), 6.51 (s, 1H), 5.97 (s, 1H), 3.73 (m, 2H), 3.47 (br s, 1H), 2.65 (m, 2H). ¹³C NMR (150 MHz, CDCl₃): 167.88, 149.46, 143.77, 129.17, 128.10, 127.37, 103.25, 72.21, 61.87, 33.52.

315

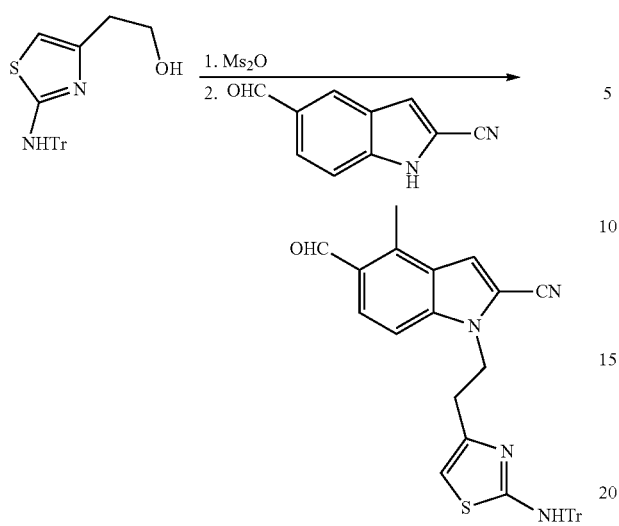

2-(2-(Tritylamino)thiazol-4-yl)ethan-1-ol (640 mg, 1.65 mmol) and triethyl amine (0.7 mL) were dissolved in DCM (8.3 mL). Ms$_2$O (574 mg, 3.3 mmol) was added in small portions with cooling of reaction mixture in an ice water bath. After 5 minutes of stirring, the mixture was quenched with saturated sodium bicarbonate solution, washed with brine, dried over sodium sulfate and concentrated. The mesylate intermediate was dissolved in DMF (0.5 mL) and 5-formyl-4-methyl-1H-indole-2-carbonitrile (50 mg, 0.27 mmol) and cesium carbonate (265 mg, 0.81 mmol) were added. After stirring for 3 h at 60° C., TLC showed consumption of aldehyde. The reaction mixture was diluted with water (20 mL) and extracted with DCM (2×25 mL). The organic phase was evaporated with silica gel and loaded on a silica gel column. The product was eluted with hexane-ethyl acetate (1:1) to afford 5-formyl-4-methyl-1-(2-(2-tritylthiazol-4-yl)ethyl)-1H-indole-2-carbonitrile (50 mg). $^1$H NMR (600 MHz, CDCl$_3$): 10.42 (s, 1H), 7.78 (m, 1H), 7.38 (m, 1H), 7.20 (s, 1H), 6.57 (s, 1H), 4.48 (m, 2H), 3.06 (m, 2H), 2.89 (s, 3H), 1.62 (s, 9H).

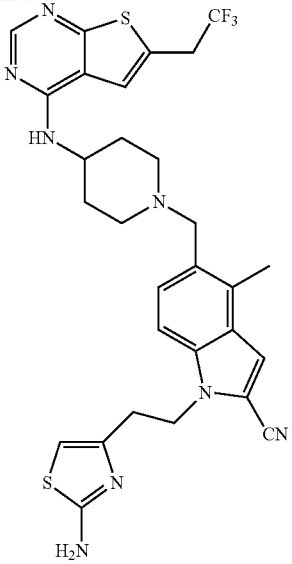

316

-continued 5-formyl-4-methyl-1-(2-(2-tritylthiazol-4-yl)ethyl)-1H-indole-2-carbonitrile (50 mg, 0.09 mmol), N-(piperidin-4-yl)-6-(2,2,2-trifluoroethyl)thieno[2,3-d]pyrimidin-4-amine hydrochloride (57 mg, 0.15 mmol), and triethylamine (0.0125 mL, 0.36 mmol) were mixed in dry dichloromethane (1 mL). Sodium triacetoxyborohydride (42 mg, 0.2 mmol) was added to the mixture in one portion. After stirring overnight, TLC showed absence of starting aldehyde in reaction mixture. The reaction mixture was transferred to a separatory funnel and washed with 1M NaOH (10 mL). The organic phase was evaporated with silica gel and loaded on a silica gel column. The product was eluted with DCM:MeOH:NH$_3$*H$_2$O (starting from 40:1:0.1 and decreasing to 20:1:0.1). Evaporation of solvent gave the trityl protected intermediate (25 mg) that was dissolved in chloroform (1 mL) and trifluoroacetic acid (0.5 mL). After 5 minutes, the reaction mixture was quenched with saturated sodium carbonate solution and extracted with ethyl dichloromethane. The organic phase was evaporated and purified using pTLC to obtain 1-(2-(2-aminothiazol-4-yl)ethyl)-4-methyl-5-((4-(((6-(2,2,2-trifluoroethyl)thieno[2,3-d]pyrimidin-4-yl)amino)piperidin-1-yl)methyl)-1H-indole-2-carbonitrile (Compound 30) (10 mg). $^1$H NMR (600 MHz, CDCl$_3$): 8.46 (s, 1H), 7.31 (d, 1H, J=8.4 Hz), 7.16 (s, 1H), 7.13 (d, 1H, J=8.4 Hz), 7.07 (s, 1H), 5.92 (s, 1H), 5.19 (br s, 2H), 512, (br s, 1H), 4.53 (m, 2H), 4.22 (m, 1H), 3.60 (m, 4H), 3.00 (m, 2H), 2.89 (m, 2H), 2.53 (s, 3H), 2.25 (m, 2H), 2.13 (m, 2H), 2.08 (m, 2H), 1.58 (m, 2H). $^{13}$C NMR (150 MHz, CDCl$_3$): 168.04, 166.76, 156.07, 154.34, 148.10, 136.50, 130.98, 128.96, 128.47, 128.09, 127.16, 126.64 (q, J=289.5 Hz), 118.48, 166.43, 113.72, 111.92, 108.97, 107.92, 107.38, 104.99, 104.94, 52.31, 50.77, 48.09, 45.00, 35.54 (q, J=32 Hz), 32.39, 32.32, 15.06. HR MS (ESI): M+H$^+$ calculated 611.1981; found 611.1987.

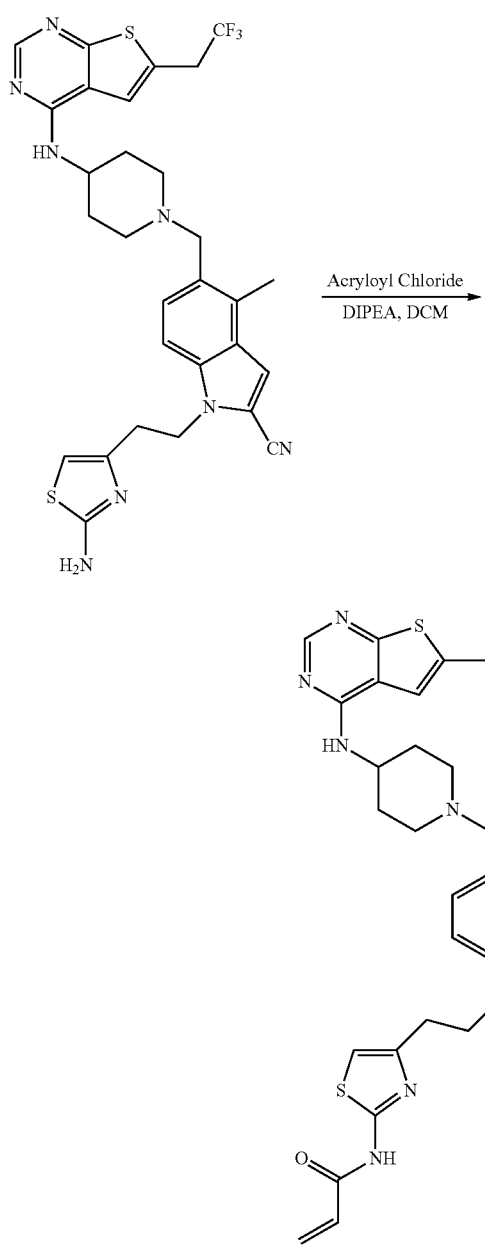

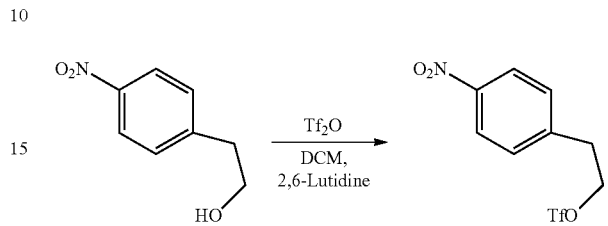

To a mixture of 1-(2-(2-aminothiazol-4-yl)ethyl)-4-methyl-5-((4-((6-(2,2,2-trifluoroethyl)thieno[2,3-d]pyrimidin-4-yl)amino)piperidin-1-yl)methyl)-1H-indole-2-carbonitrile (11.5 mg, 0.018 mmol) and DIPEA (0.0063 mL, 0.036 mmol) in DCM (0.2 mL) was added acryloyl chloride (0.00153 mL, 0.18 mmol) with external cooling of ice water. After stirring for 15 minutes, the reaction mixture was purified using pTLC and developed with DCM-MeOH (10:1) to isolate N-(4-(2-(2-cyano-4-methyl-5-((4-((6-(2,2,2-trifluoroethyl)thieno[2,3-d]pyrimidin-4-yl)amino)piperidin-1-yl)methyl)-1H-indol-1-yl)ethyl)thiazol-2-yl)acrylamide (Compound 34) (3 mg). $^1$H NMR (600 MHz, CD$_3$CN): 10.07 (br s, 1H), 8.33 (s, 1H), 7.35 (s, 1H), 7.29, (d, 1H, J=8.4 Hz), 7.26 (s, 1H), 7.19 (d, 1H, J=8.4 Hz), 6.44 (m, 3H), 6.19 (br d, 1H), 5.86 (m, 1H), 4.56 (m, 2H), 4.14 (m, 1H), 3.81 (q, 2H, J=10.5 Hz), 3.60 (s, 1H), 3.13 (m, 2H), 2.88 (m, 2H), 2.52 (s, 3H), 1.98 (m, 2H), 1.59 (m, 2H). $^{13}$C NMR (150 MHz, CD$_3$CN): 168.04, 164.40, 159.15, 157.80, 155.70, 149.28, 138.12, 132.38, 130.76, 130.47, 130.31, 128.99, 128.53, 126.92 (q, J=289.5 Hz), 121.94 117.90, 114.95, 113.24, 111.64, 110.49, 109.23, 61.05, 53.68, 49.57, 46.48, 36.01 (q, J=32 Hz), 33.16, 32.96, 30.49, 15.68. HR MS (ESI): M+H$^+$ calculated 65.2087; found 665.2081.

Example 5. Representative Procedure for the Synthesis of Compound 81

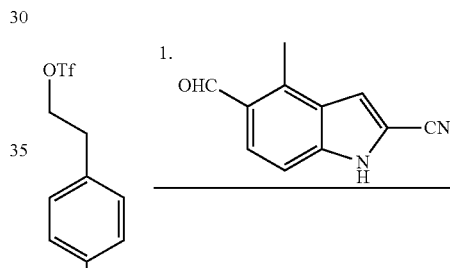

Trifluoromethanesulfonic anhydride (Tf$_2$O) (2.6 mL, 15 mmol) was added to a solution of 4-nitrophenyl-2-ethanol (1.67 g, 10 mmol) and 2,6-lutidine (2.1 mL, 18 mmol) in DCM (50 mL) at −50° C. The reaction mixture allowed to warm to room temperature and then washed with NaHCO$_3$, followed by 4% citric acid solution, and finally with brine. The reaction mixture was dried over Na$_2$SO$_4$. After concentration, the 4-nitrophenethyl trifluoromethanesulfonate (quantitative yield) was used immediately in the next step.

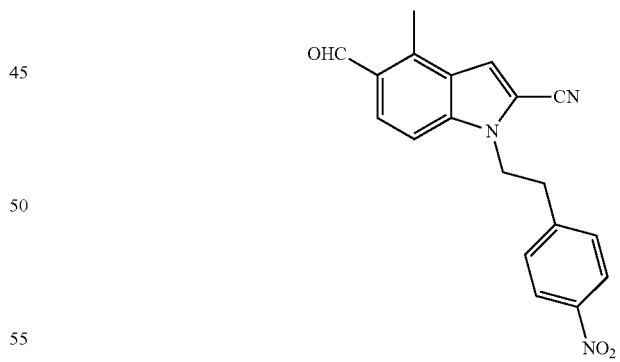

NaH (120 mg, 3 mmol) was added to a solution of 5-formyl-4-methyl-1H-indole-2-carbonitrile (368 mg, 2 mmol) in THF (4 mL) at room temperature and then cooled to −78° C. 4-Nitrophenethyl trifluoromethanesulfonate was dissolved in THF (4 mL) and transferred via syringe to the precooled flask containing the sodium salt of 5-formyl-4-methyl-1H-indole-2-carbonitrile. After stirring for 30 min, the reaction mixture was allowed to warm to room temperature and quenched with 7 M NH$_3$ in MeOH (2 mL). The reaction mixture was evaporated with silica gel and eluted starting with hexane:THF (4:1), then with hexane:THF (1:1), and finally with pure THF. 5-Formyl-4-methyl-1-(4-nitrophenethyl)-1H-indole-2-carbonitrile (1.4 g) (MW=333) was isolated. $^1$H NMR (600 MHz, CDCl$_3$): 10.42 (s, 1H), 8.10 (d, J=8.44 Hz, 2H), 7.87 (d, J=8.44 Hz, 1H), 7.33 (s, 1H), 7.18 (m, 3H), 4.58 (t, J=7.2 Hz, 2H), 3.28 (t, J=7.2 Hz, 2H), 2.9 (s, 3H). $^{13}$C NMR (150 MHz, CDCl$_3$): 191.1, 147.3, 144.2, 139.0, 138.1, 129.8, 127.9, 127.3, 124.1, 113.6, 112.5, 110.8, 108.1, 46.6, 36.1, 14.6.

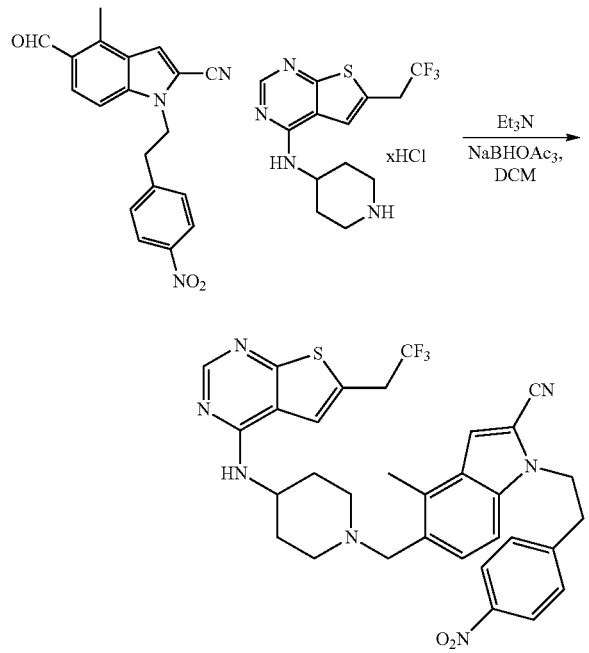

Following a similar general procedure as in Example 2 for preparing Compound 3, 4-methyl-1-(4-nitrophenethyl)-5-((4-(6-(2,2,2-trifluoroethyl)thieno[2,3-d]pyrimidin-4-ylamino)piperidin-1-yl)methyl)-1H-indole-2-carbonitrile was synthesized from 5-Formyl-4-methyl-1-(4-nitrophenethyl)-1H-indole-2-carbonitrile (666 mg, 2 mmol) and N-(piperidin-4-yl)-6-(2,2,2-trifluoroethyl)thieno[2,3-d]pyrimidin-4-amine hydrochloride (934 mg). The product was purified by column chromatography on silica gel and eluted with DCM:MeOH:NH$_3$—H$_2$O (15:1:0.1). Evaporation of solvent gave 4-methyl-1-(4-nitrophenethyl)-5-((4-(6-(2,2,2-trifluoroethyl)thieno[2,3-d]pyrimidin-4-ylamino)piperidin-1-yl)methyl)-1H-indole-2-carbonitrile (1070 mg).

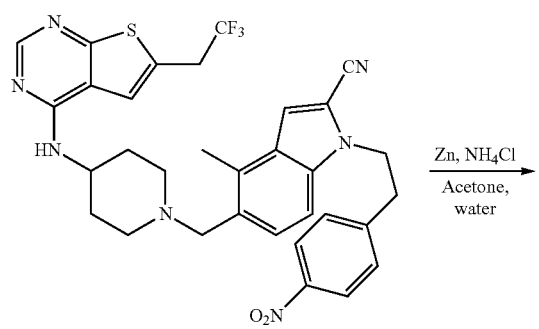

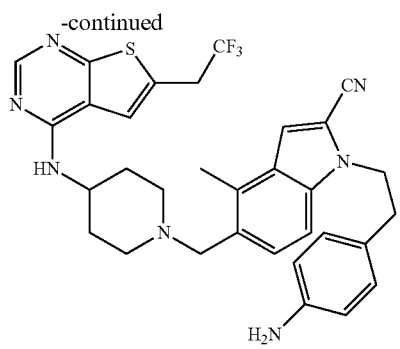

A mixture of 4-methyl-1-(4-nitrophenethyl)-5-((4-(6-(2,2,2-trifluoroethyl)thieno[2,3-d]pyrimidin-4-ylamino)piperidin-1-yl)methyl)-1H-indole-2-carbonitrile (1.2 g, 1.7 mmol), ammonium chloride (3.6 g, 68 mmol), and Zn powder (2.2 g, 34 mmol) were stirred in acetone-water (6:1 v/v) (40 mL). After stirring for 2 h, the mixture was concentrated, diluted with 1 M NaOH and EtOAc, and filtered through celite. The organic fraction was evaporated with silica gel, loaded on a column, and eluted with DCM:MeOH:NH$_3$—H$_2$O (starting with 20:10:0.1 and decreasing to 10:1:0.1). 1-(4-Aminophenethyl)-4-methyl-5-((4-(6-(2,2,2-trifluoroethyl)thieno[2,3-d]pyrimidin-4-ylamino)piperidin-1-yl)methyl)-1H-indole-2-carbonitrile (910 mg) was isolated. $^1$H NMR (600 MHz, CDCl$_3$): 8.47 (s, 1H), 7.32 (d, J=8.44 Hz), 7.15 (s, 1H), 7.10 (d, J=8.44 Hz), 7.06 (s, 1H), 6.87 (d, J=8.07 Hz, 2H), 6.59 (d, J=8.07 Hz, 2H), 5.11 (br d), 4.39 (t, J=7.5 Hz, 2H), 4.23 (m, 1H), 3.63 (m, 4H), 2.98 (t, J=7.5 Hz, 2H), 2.92 (m, 2H), 2.54 (s, 3H), 2.27 (m, 2H), 2.09 (m, 2H), 1.60 (m, 2H). $^{13}$C NMR (150 MHz, CDCl$_3$): 166.8, 156.1, 154.3, 145.3, 136.3, 131.1, 129.7, 129.0, 127.3, 127.2, 124.7 (q, J=277 Hz), 118.5, 116.4, 115.4, 113.7, 111.6, 109.1, 107.3, 60.1, 52.2, 50.8, 48.0, 47.6, 35.8, 35.6 (q, J=32 Hz), 32.3, 15.1.

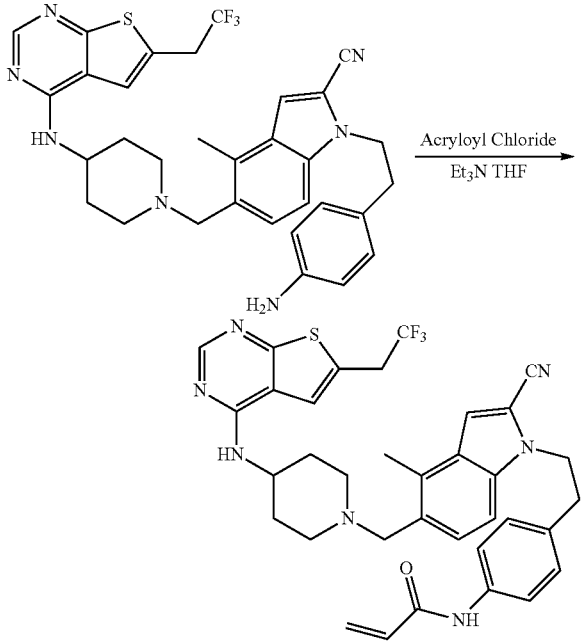

Acryloyl chloride (0.135 mL, 1.7 mmol) was added dropwise to a solution of 1-(4-aminophenethyl)-4-methyl- 5-((4-(6-(2,2,2-trifluoroethyl)thieno[2,3-d]pyrimidin-4-ylamino)piperidin-1-yl)methyl)-1H-indole-2-carbonitrile (917 mg, 1.5 mmol) and Et$_3$N (0.46 mL, 3.3 mmol) in THF (30 mL) at −78° C. The reaction mixture was slowly warmed to room temperature, evaporated with silica gel at room temperature, loaded on a column, and eluted with DCM:MeOH:NH$_3$—H$_2$O (starting with 15:1:0.1 and decreasing to 10:1:0.1) to isolate N-(4-(2-(2-cyano-4-methyl-5-((4-(6-(2,2,2-trifluoroethyl)thieno[2,3-d]pyrimidin-4-ylamino)piperidin-1-yl)methyl)-1H-indol-1-yl)ethyl)phenyl)acrylamide with a minor impurity of the starting material. N-(4-(2-(2-Cyano-4-methyl-5-((4-(6-(2,2,2-trifluoroethyl)thieno[2,3-d]pyrimidin-4-ylamino)piperidin-1-yl)methyl)-1H-indol-1-yl)ethyl)phenyl)acrylamide was recrystallized from MeOH to afford pure product (510 mg). $^1$H NMR (600 MHz, CD$_3$OD): 8.33 (s, 1H), 7.57 (s, 1H), 7.41 (m, 3H), 7.35 (s, 1H), 7.26 (d, J=8.44 Hz, 1H), 6.89 (d, J=8.07 Hz, 2H), 6.35 (m, 1H), 6.24 (d, J=16.87 Hz, 1H), 5.62 (d, J=10.27 Hz, 1H), 4.54 (t, J=7.5 Hz, 2H), 4.35 (m, 3H), 3.85 (q, J=10.5 Hz, 2H), 3.46 (m, 2H), 3.13 (m, 2H), 3.09 (m, 2H), 2.26 (m, 2H), 1.98 (m, 2H). $^{13}$C NMR (150 MHz, CD$_3$OD): 167.1, 166.0, 157.8, 155.0, 147.5, 139.0, 138.7, 135.1, 134.5, 132.6, 130.7, 130.6, 128.6, 127.8, 126.7 (q, J=277 Hz), 122.0, 121.4, 118.2, 116.9, 114.3, 113.5, 113.3, 111.3, 110.4, 59.1, 52.8, 37.0, 36.8, 35.7 (q, J=32 Hz), 30.2, 15.8. HRMS (ESI): M+H$^+$ calculated 658.2570; found 658.2572.

Example 6. Representative Procedure for the Synthesis of Compound 100

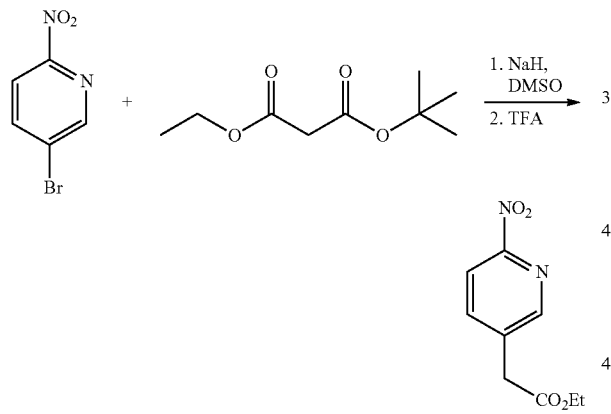

NaH (800 mg, 20 mmol) was added in small portions to a solution of tert-butyl ethyl malonate (3.8 mL, 20 mmol) in DMSO (10 mL). After 5 minutes, 5-bromo-2-nitropyridine (2.03 g, 10 mmol) was added, and the reaction mixture was sealed and heated at 80° C. for 5 h. Then the reaction mixture was diluted with saturated ammonium chloride solution and extracted with diethyl ether. Organic fractions were evaporated, purified by column chromatography, eluted with Hexane:EtOAc (4:1), and dissolved in trifluoroacetic acid (TFA) (30 mL). The reaction mixture was concentrated to dryness, dissolved in EtOAc and washed with saturated NaHCO$_3$. Organic fractions were evaporated with silica gel and purified by silica gel column chromatography, eluting with Hexane:EtOAc (2:1) to afford ethyl 2-(6-nitropyridin-3-yl)acetate (1.3 g). $^1$H NMR (600 MHz, CDCl$_3$): 8.25 (s, 1H), 8.25 (d, J=8.4 Hz, 1H), 8.00 (m, 1H), 4.21 (q, J=7.3 Hz, 2H), 3.79 (s, 2H), 1.28 (t, J=7.3 Hz, 3H). $^{13}$C NMR (150 MHz, CDCl$_3$): 169.3, 155.9, 149.5, 140.7, 136.4, 117.8, 61.8, 38.0, 14.1.

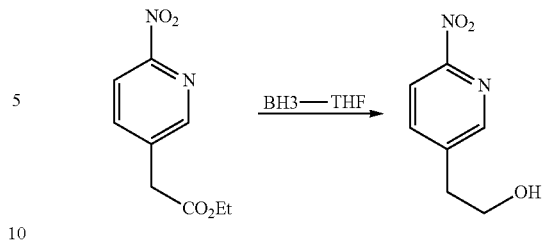

Ethyl 2-(6-nitropyridin-3-yl)acetate (1.4 g, 6.2 mmol) was dissolved in 1 M BH$_3$-THF complex in THF (19 mL). The mixture was heated at 60° C. for 0.5 h. Then the reaction mixture was concentrated to dryness, carefully quenched with 1 M NaOH and extracted with EtOAc. Organic fractions were evaporated with silica gel and purified by silica gel column chromatography, eluting with Hexane:EtOAc:MeOH (1:1:0.1) to afford 2-(6-nitropyridin-3-yl)ethanol (850 mg).

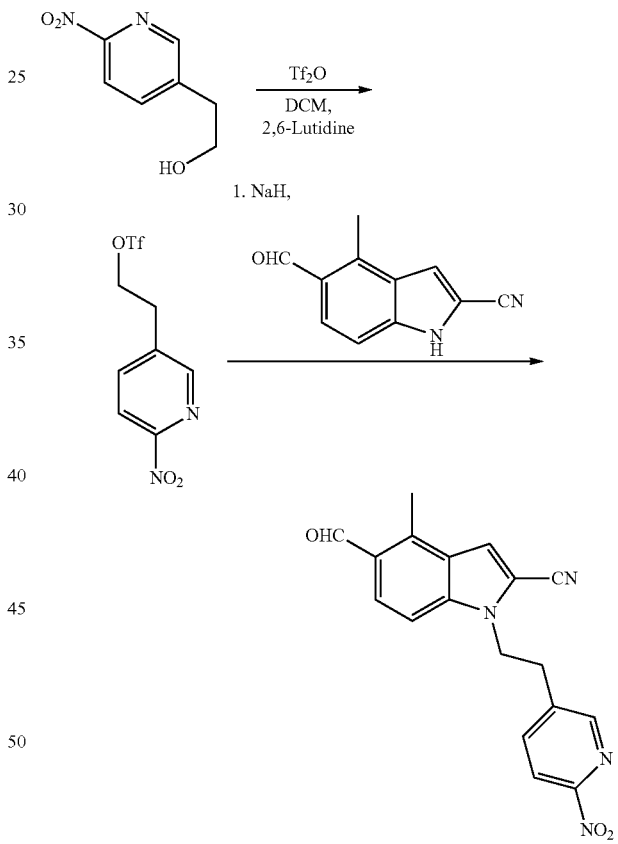

Following the same general procedure for synthesizing 4-nitrophenethyl trifluoromethanesulfonate in Example 5, 2-(6-nitropyridin-3-yl)ethyl trifluoromethanesulfonate was synthesized from 2-(6-nitropyridin-3-yl)ethanol (840 mg, 5 mmol). Following the same general procedure for synthesizing 5-Formyl-4-methyl-1-(4-nitrophenethyl)-1H-indole-2-carbonitrile in Example 5, 5-formyl-4-methyl-1-(2-(6-nitropyridin-3-yl)ethyl)-1H-indole-2-carbonitrile was synthesized from 5-formyl-4-methyl-1H-indole-2-carbonitrile (460 mg, 2.5 mmol) and 2-(6-nitropyridin-3-yl)ethyl trifluoromethanesulfonate. After reaction was complete, the reaction mixture was quenched with AcOH (2 mL) and carefully concentrated to dryness. The residue was suspended in water (50 mL), sonicated and filtered to afford crude 5-formyl-4-methyl-1-(2-(6-nitropyridin-3-yl)ethyl)-1H-indole-2-carbonitrile, used as is in the next step. $^1$H NMR (600 MHz, Me$_2$CO): 10.41, (s, 1H), 8.32 (s, 1H), 8.17 (d, J=8.07 Hz, 1H), 7.98 (m, 1H), 7.83 (d, J=8.80 Hz, 1H), 7.64 (s, 1H), 7.57 (d, J=8.80 Hz, 1H), 4.82 (t, J=6.97 Hz, 2H), 3.49 (t, J=6.97 Hz, 2H), 2.90 (s, 3H). $^{13}$C NMR (150 MHz, Me$_2$CO): 150.2, 141.8, 141.4, 140.3, 138.5, 128.8, 128.2, 128.1, 126.2, 118.7, 114.7, 113.4, 111.8, 110.0, 47.1, 33.7, 14.6.

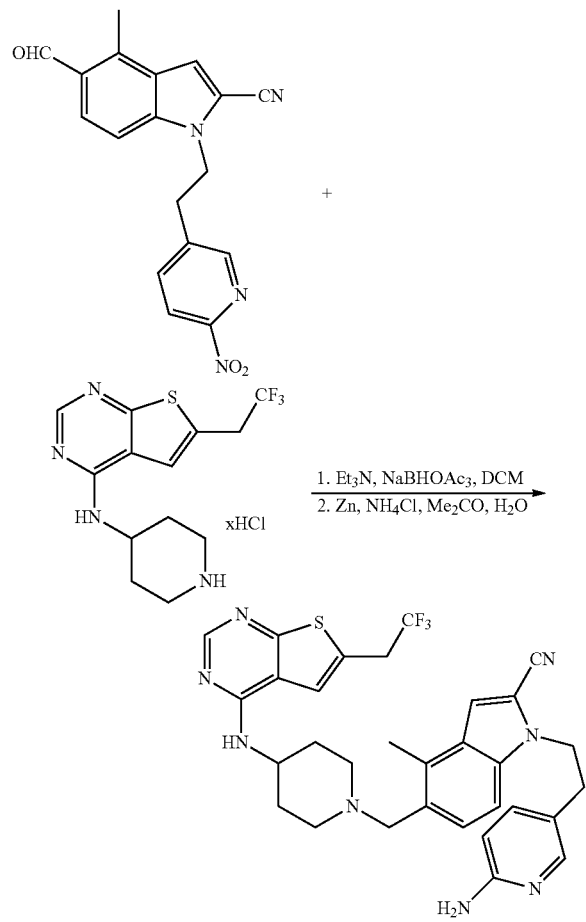

Following the same general procedure as described in Example 2 for the preparation of Compound 3, 1-(2-(6-aminopyridin-3-yl)ethyl)-4-methyl-5-((4-(6-(2,2,2-trifluoroethyl)thieno[2,3-d]pyrimidin-4-ylamino)piperidin-1-yl)methyl)-1H-indole-2-carbonitrile was synthesized from 5-formyl-4-methyl-1-(2-(6-nitropyridin-3-yl)ethyl)-1H-indole-2-carbonitrile and N-(piperidin-4-yl)-6-(2,2,2-trifluoroethyl)thieno[2,3-d]pyrimidin-4-amine hydrochloride. 1-(2-(6-Aminopyridin-3-yl)ethyl)-4-methyl-5-((4-(6-(2,2,2-trifluoroethyl)thieno[2,3-d]pyrimidin-4-ylamino)piperidin-1-yl)methyl)-1H-indole-2-carbonitrile (1080 mg) was isolated. $^1$H NMR (600 MHz, CDCl$_3$): 8.47 (s, 1H), 7.63 (s, 1H), 7.34 (d, J=8.44 Hz, 1H), 7.15 (m, 2H), 7.08 (d, J=8.80 Hz, 1H), 7.05 (s, 1H), 6.42 (d, J=8.44 Hz, 1H), 5.00 (br d), 4.40 (t, J=7.34 Hz, 2H), 4.27 (s, 2H), 4.22 (m, 1H), 3.63 (m 4H), 2.98 (t, J=7.34 Hz, 2H), 2.88 (m, 2H), 2.54 (s, 3H), 2.25 (m, 2H), 2.09 (m, 2H), 1.56 (m, 2H). $^{13}$C NMR (150 MHz, CDCl$_3$): 166.8, 157.5, 156.0, 154.4, 147.9, 138.4, 136.2, 131.2, 129.0, 128.7, 127.3, 126.7 (q, J=277 Hz), 122.5, 118.3, 116.4, 113.6, 111.8, 109.0, 108.6, 107.1, 60.2, 52.3, 48.1, 47.0, 35.5 (q, J=32 Hz), 32.8, 32.5, 15.0.

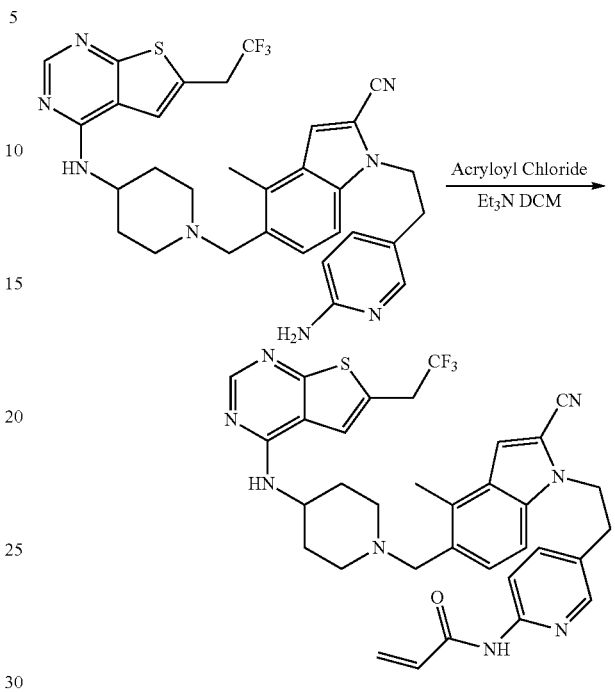

Acryloyl chloride was added dropwise to a solution of 1-(2-(6-aminopyridin-3-yl)ethyl)-4-methyl-5-((4-(6-(2,2,2-trifluoroethyl)thieno[2,3-d]pyrimidin-4-ylamino)piperidin-1-yl)methyl)-1H-indole-2-carbonitrile (1.03 g) and Et$_3$N in THF at −78° C. The reaction mixture was slowly warmed to room temperature, evaporated with silica gel at room temperature, loaded on a column, eluted with DCM:MeOH: NH$_3$—H$_2$O (starting with 15:1:0.1 and decreasing to 10:1: 0.1), and recrystallized from MeOH to afford N-(5-(2-(2-cyano-4-methyl-5-((4-(6-(2,2,2-trifluoroethyl)thieno[2,3-d]pyrimidin-4-ylamino)piperidin-1-yl)methyl)-1H-indol-1-yl) ethyl)pyridin-2-yl)acrylamide (470 mg). $^1$H NMR (600 MHz, CD$_3$OD for HCl salt): 8.35 (s, 1H), 7.93 (d, J=8.44 Hz, 1H), 7.83 (s, 1H), 7.54 (s, 1H), 7.40 (m, 2H), 7.30 (m, 2H), 6.41 (m, 1H), 6.30 (m, 1H), 5.67 (m, 1H), 4.62 (m, 3H), 4.39 (m, 2H), 3.86 (q, J=10.5 Hz, 2H), 3.45 (m, 2H), 3.17 (m, 2H), 2.64 (s, 3H), 2.26 (m, 2H), 2.15 (m, 2H), 1.91 (m, 2H). $^{13}$C NMR (150 MHz, CD$_3$OD): 167.2, 166.2, 157.9, 155.0, 152.1, 149.4, 140.1, 139.0, 135.0, 132.3, 131.0, 130.6, 130.1, 128.8, 128.6, 126.8 (q, J=277 Hz), 121.9, 118.3, 115.5, 114.1, 113.8, 111.5, 110.6, 47.8, 35.7 (q, J=32 Hz), 34.0, 15.8. HRMS (ESI): M+H$^+$ calculated 659.2523; found 659.2523.

Example 7. Representative Procedure for Synthesis of Compound 199

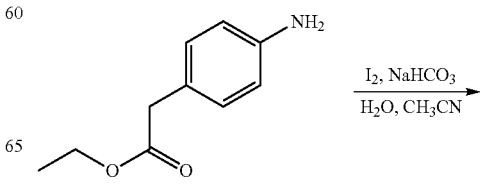

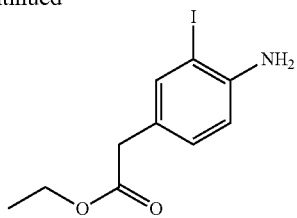

Ethyl 2-(4-aminophenyl)acetate (5.3 g, 29.6 mmol) was dissolved in 20 mL of acetonitrile, followed by the addition of NaHCO$_3$ (5 g, 59.2 mmol) and 50 mL of water. The reaction mixture was cooled to 0° C., iodine (7.8 g, 29.6 mmol) was added slowly. The black reaction mixture was stirred at room temperature overnight. TLC showed the reaction was completed and water was added. The reaction mixture was extracted with ethyl acetate. The organic layer was washed with saturated sodium thiosulfate solution and brine, dried over anhydrous Na$_2$SO$_4$, filtered, concentrated and purified by silica gel column chromatography (eluted with petroleum) to give ethyl 2-(4-amino-3-iodophenyl)acetate as a solid (5.3 g, yield: 58%), 305.9(M+H)$^+$.

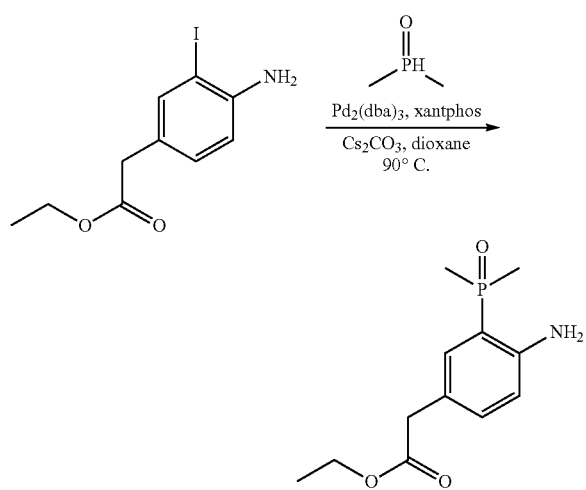

To a mixture of ethyl 2-(4-amino-3-iodophenyl)acetate (3.05 g, 10 mmol) in 30 mL of dioxane was added dimethylphosphine oxide (860 mg, 11 mmol), Pd$_2$(dba)$_3$ (460 mg, 0.50 mmol), xantphos (580 mg, 1 mmol), Cs$_2$CO$_3$ (6.5 g, 20 mmol). The resulting mixture was stirred at 90° C. overnight. LCMS showed the reaction was completed. The reaction mixture was filtered and the filtrate was concentrated to dryness. The residue was purified by silica gel column chromatography (eluted 5% methanol in dichloromethane) to give ethyl 2-(4-amino-3-(dimethylphosphoryl)phenyl)acetate as a solid (1.8 g, yield: 70%). 256(M+H)$^+$.

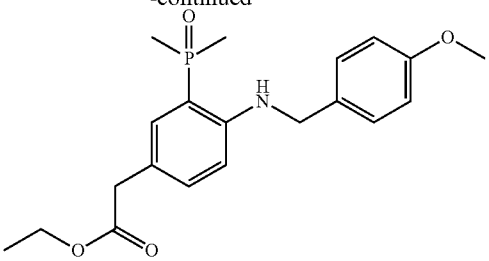

To a mixture of 2-(4-amino-3-(dimethylphosphoryl)phenyl)acetate (1.8 g, 7.0 mmol), 4-methoxybenzaldehyde (1.44 g, 10.5 mmol) in dichloromethane was added NaBH(OAc)$_3$ at room temperature. Then the reaction was stirred at room temperature overnight. TLC test indicated that reaction was complete. Water was added, and the reaction mixture was extracted with dichloromethane. The organic layer was washed with brine, dried over anhydrous Na$_2$SO$_4$, filtered, concentrated and purified by silica gel column chromatography (eluted 5% methanol in dichloromethane) to give ethyl 2-(4-(4-methoxybenzylamino)-3-(dimethylphosphoryl)phenyl)acetate (2.05 g, yield: 77%). 376(M+H)$^+$.

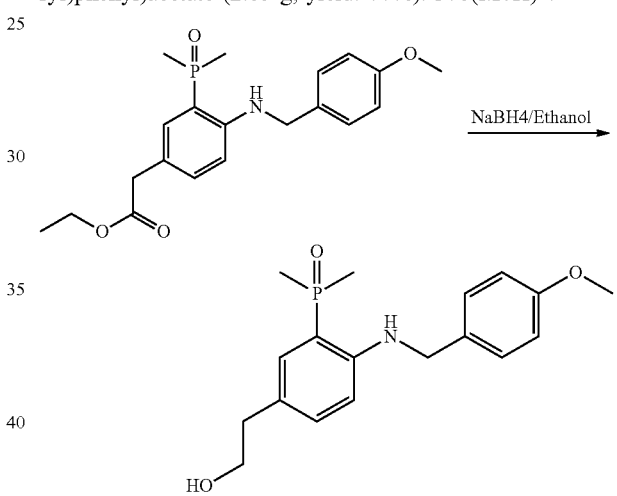

To a solution of 2-(4-(4-methoxybenzylamino)-3-(dimethylphosphoryl)phenyl)acetate (1.9 g, 5.0 mmol) in 20 mL of ethanol was added NaBH$_4$ (960 mg, 25 mmol) at 0° C. The mixture was stirred at room temperature overnight. LCMS showed that the reaction was complete. Water was added and the reaction mixture was extracted with ethyl acetate, dried over anhydrous Na$_2$SO$_4$, filtered, and concentrated to dryness. The residue was purified by silica gel column chromatography (eluted 5% methanol in dichloromethane) to give 2-(4-(4-methoxybenzylamino)-3-(dimethylphosphoryl)phenyl)ethanol as a solid (1.21 g, yield: 72%). 334(M+H)$^+$.

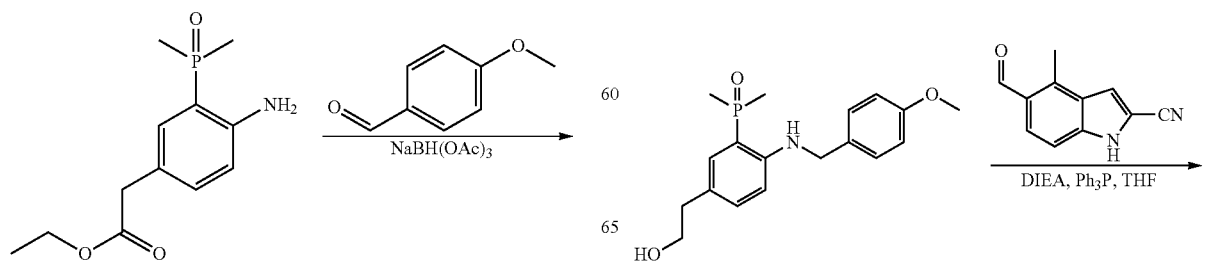

327

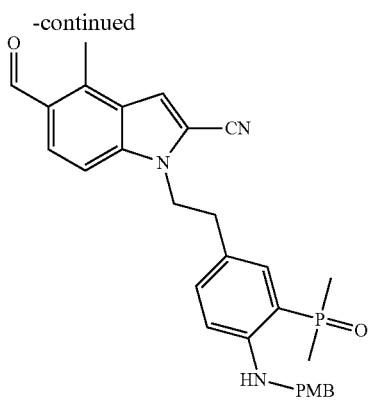

To a mixture of 5-formyl-4-methyl-1H-indole-2-carbonitrile (728 mg, 3.95 mmol), 2-(4-(4-methoxybenzylamino)-3-(dimethylphosphoryl)phenyl)ethanol (878 mg, 2.63 mmol) in 40 mL of anhydrous THF was added diisopropyl azodicarboxylateDiisopropyl azodicarboxylate (1.06 g, 5.3 mmol) under argon. The reaction mixture was stirred room temperature overnight. LCMS showed that the reaction was complete. Water was added, the reaction mixture was extracted with ethyl acetate. Organic layer was washed with brine, dried over Na$_2$SO$_4$, filtered, and concentrated to dryness. The residue was purified by silica gel column (eluted with 2% of methanol in dichloromethane) to give 1-(4-(4-methoxybenzylamino)-3-(dimethylphosphoryl)phenethyl)-5-formyl-4-methyl-1H-indole-2-carbonitrile as a solid (450 mg, yield: 34%). 500(M+H)$^+$.

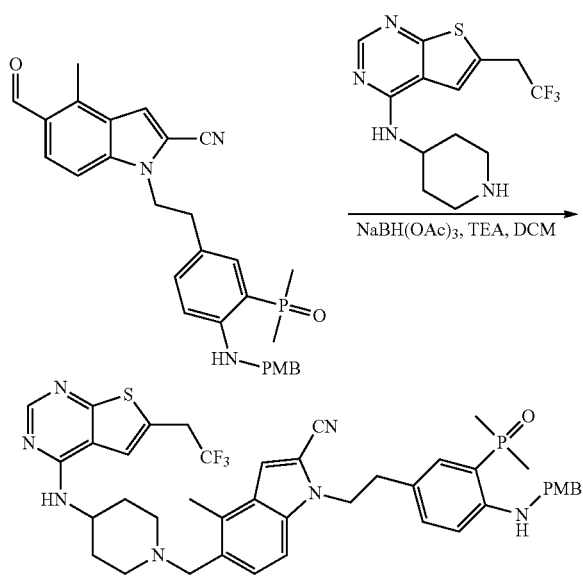

328

To a mixture of 1-(4-(4-methoxybenzylamino)-3-(dimethylphosphoryl)phenethyl)-5-formyl-4-methyl-1H-indole-2-carbonitrile (450 mg, 0.9 mmol) and N-(piperidin-4-yl)-6-(2,2,2-trifluoroethyl)thieno[2,3-d]pyrimidin-4-amine (313 mg, 1.0 mmol) in dichloromethane was added TEA (273 mg, 2.7 mmol), followed by NaBH(OAc)$_3$ (573 mg, 2.7 mmol). The reaction mixture was stirred at room temperature overnight. LCMS showed that the reaction was complete. Water was added, and the reaction mixture was extracted with dichloromethane, washed with brine, dried over Na$_2$SO$_4$, filtered, and concentrated to dryness. The residue was purified by flash column (eluted with 10% of methanol in dichloromethane) to give 1-(4-(4-methoxybenzylamino)-3-(dimethylphosphoryl)phenethyl)-4-methyl-5-((4-(6-(2,2,2-trifluoroethyl)thieno[2,3-d]pyrimidin-4-ylamino)piperidin-1-yl)methyl)-1H-indole-2-carbonitrile as a solid (180 mg, 25%). 800(M+H)$^+$.

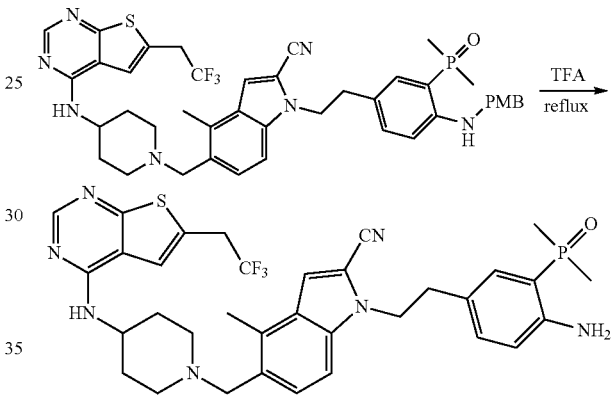

A mixture of 1-(4-(4-methoxybenzylamino)-3-(dimethylphosphoryl)phenethyl)-4-methyl-5-((4-(6-(2,2,2-trifluoroethyl)thieno[2,3-d]pyrimidin-4-ylamino)piperidin-1-yl)methyl)-1H-indole-2-carbonitrile (100 mg, 0.125 mmol) in 10 mL of trifluoroacetic acid was stirred at reflux overnight. The reaction mixture was then concentrated to dryness. 7 N NH$_3$ in methanol was added to neutralize the residue acid and the reaction mixture was concentrated again. The residue was purified by silica gel column (eluted with 10% of methanol in dichloromethane) to give 1-(4-amino-3-(dimethylphosphoryl)phenethyl)-4-methyl-5-((4-(6-(2,2,2-trifluoroethyl)thieno[2,3-d]pyrimidin-4-ylamino)piperidin-1-yl)methyl)-1H-indole-2-carbonitrile as a solid (48 mg, yield: 56%). 680(M+H)$^+$.

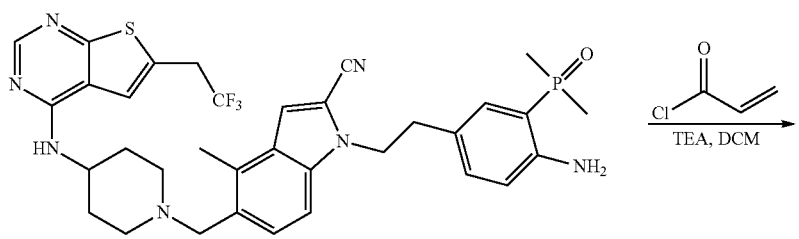

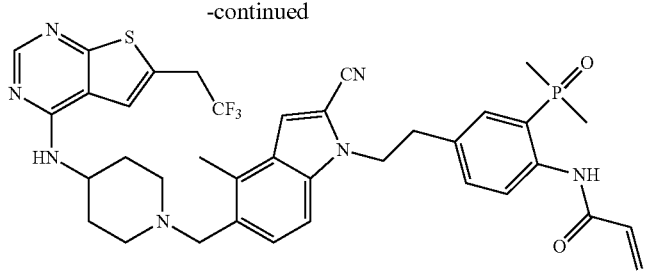

To a solution of 1-(4-amino-3-(dimethylphosphoryl)phenethyl)-4-methyl-5-((4-(6-(2,2,2-trifluoroethyl)thieno[2,3-d]pyrimidin-4-ylamino)piperidin-1-yl)methyl)-1H-indole-2-carbonitrile (48 mg, 0.07 mmol) in 10 mL of dichloromethane was added TEA (14 mg, 0.14 mmol) at −78° C., followed by acryloyl chloride (7 mg, 0.08 mmol), then the reaction was stirred at −78° C. for 30 min. A TLC test indicated that the reaction was complete. Dichloromethane was added, the reaction mixture was washed with saturated sodium hydrogen carbonate, brine. The organic solution was dried over $Na_2SO_4$, filtered, and concentrated to dryness. The residue was purified by silica gel column (eluted with 10% of methanol in dichloromethane) to give Compound 199 as a solid (46 mg, yield: 88%). 734(M+H)$^+$. $^1$HNMR (400 MHz, CDCl$_3$): 11.46 (s, 1H), 8.54 (dd, J=4.0, 8.8 Hz, 1H), 8.38 (s, 1H), 7.26 (d, J=8.4 Hz, 1H), 7.03-7.08 (m, 3H), 6.84 (d, J=8.4 Hz, 1H), 6.46 (d, J=10 Hz, 1H), 6.29 (dd, J=2.4, 17.2 Hz, 1H), 6.09-6.16 (m, 1H), 5.20 (dd, J=1.1, 10 Hz, 1H), 5.23 (s, 1H), 4.41 (t, J=6.4 Hz, 2H), 3.52-3.60 (m, 4H), 3.04 (t, J=6.4 Hz, 2H), 2.87 (br, 2H), 2.44 (s, 3H), 2.26 (t, J=10.8 Hz, 2H), 2.03 (d, J=10.4 Hz, 2H), 1.52 (s, 3H), 1.50 (s, 3H).

Example 8. Representative Procedure for Synthesis of Compound 196

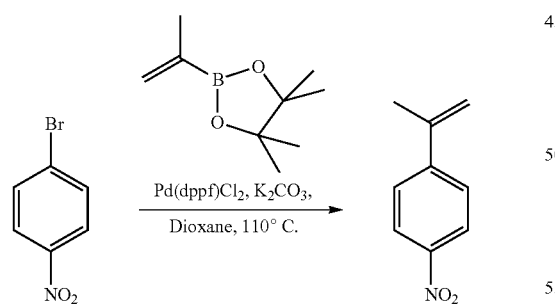

A mixture of 1-bromo-4-nitrobenzene (2 g, 9.9 mmol), 4,4,5,5-tetramethyl-2-(prop-1-en-2-yl)-1,3,2-dioxaborolane (3.3 g, 19.8 mmol), $K_2CO_3$ (4.14 g, 29.7 mmol) and Pd(dppf)Cl$_2$ (365 mg, 0.5 mmol) in dioxane (20 mL) was stirred at 110° C. under $N_2$ overnight. TLC test showed that the reaction was completed. The solid was removed by filtration and the solvent was evaporated under vacuum. The resulting residue was purified by silica gel column chromatography (eluted with petroleum) to give 1-nitro-4-(prop-1-en-2-yl)benzene as a yellow solid (1.6 g, yield: 99%).

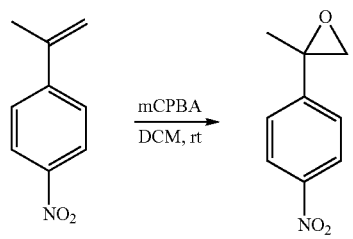

To a mixture of 1-nitro-4-(prop-1-en-2-yl)benzene (1.4 g, 8.6 mmol) in 20 mL of dichloromethane was added mCPBA (2.22 g, 12.9 mmol) at 0° C. and the reaction mixture was stirred overnight. TLC showed that the reaction was completed. Saturated NaHCO$_3$ aqueous was added to the reaction mixture, the organic layer was separated and washed with brine, dried over anhydrous Na$_2$SO$_4$. Solid was filtered off and the filtrate was concentrated. The residue was purified by silica gel column chromatography (eluted with petroleum) to give 2-methyl-2-(4-nitrophenyl)oxirane as a solid (1.1 g, yield: 71%).

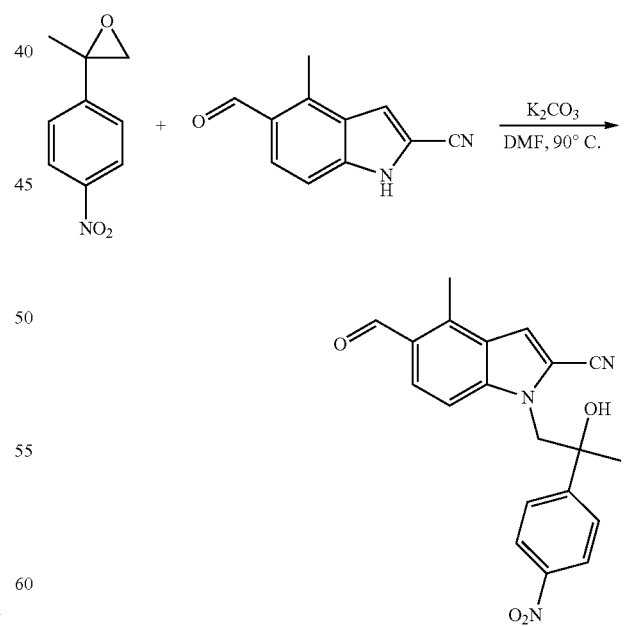

A mixture of 2-methyl-2-(4-nitrophenyl)oxirane (1.1 g, 6.1 mmol), 5-formyl-4-methyl-1H-indole-2-carbonitrile (1.13 g, 6.1 mmol) and $K_2CO_3$ (1.7 g, 12.2 mmol) in 15 mL of DMF was stirred at 90° C. for 5-6 hours. The solid was removed by filtration. Water and ethyl acetate were added to the filtrate, the organic layer was collected, washed with brine, dried over anhydrous Na₂SO₄. The dried organic solution was filtered and concentrated. The resulting residue was purified by silica gel column chromatography (eluted with 50% ethyl acetate in petroleum) to give 5-formyl-1-(2-hydroxy-2-(4-nitrophenyl)propyl)-4-methyl-1H-indole-2-carbonitrile as a solid (2.0 g, yield: 89%).

ESI-MS m/z: 363.05 (M+H).

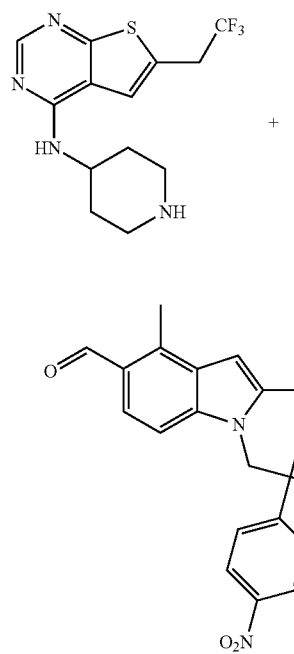

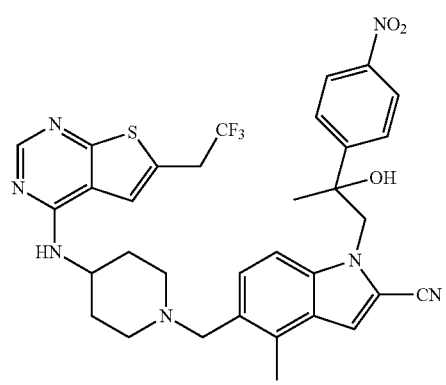

A mixture of 5-formyl-1-(2-hydroxy-2-(4-nitrophenyl) propyl)-4-methyl-1H-indole-2-carbonitrile (320 mg, 0.88 mmol), 6-(2,2,2-trifluoroethyl)-N-(piperidin-4-yl) thieno-[2,3-d]pyrimidin-4-amine (411 mg, 1.05 mmol) and TEA (534 mg, 5.29 mmol) in 15 mL of DCM was stirred at room temperature for 1 hours, then NaBH(OAc)₃ (1.12 g, 5.29 mmol) was added to the reaction under ice bath, the mixture reaction was stirred at room temperature overnight. The solvent was evaporated under vacuum and the residue was purified by silica gel column chromatography (eluted with 5% MeOH in dichloromethane) to give 5-((4-(6-(2,2,2-trifluoroethyl)thieno[2,3-d]pyrimidin-4-ylamino)piperidin-1-yl)methyl)-1-(2-hydroxy-2-(4-nitrophenyl)propyl)-4-methyl-1H-indole-2-carbonitrile as a solid (150 mg, yield: 26%).

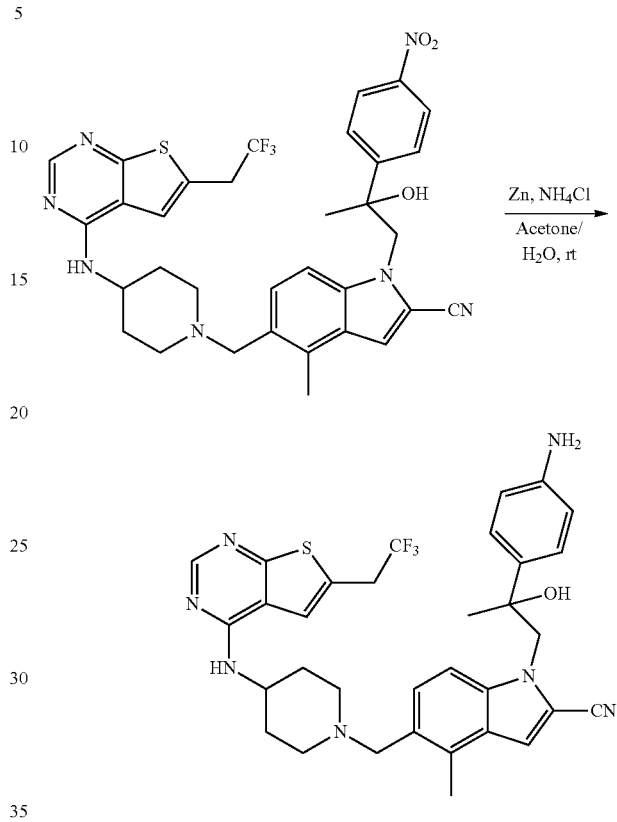

To a mixture of 5-((4-(6-(2,2,2-trifluoroethyl)thieno[2,3-d]pyrimidin-4-ylamino)piperidin-1-yl)methyl)-1-(2-hydroxy-2-(4-nitrophenyl)propyl)-4-methyl-1H-indole-2-carbonitrile (1.0 g, 1.51 mmol), NH₄Cl (3.23 mg, 60.3 mmol) and H₂O (5.9 g, 332 mmol) in 15 mL of acetone was add Zn dust (2.0 g, 30.2 mmol) and the mixture was stirred at room temperature for 2 hours. Then the solid was removed by filtration, the solvent was removed and the residue was purified by silica gel column chromatography (eluted with 6% MeOH in dichloromethane) to give 5-((4-(6-(2,2,2-trifluoroethyl)thieno[2,3-d]pyrimidin-4-ylamino)piperidin-1-yl)methyl)-1-(2-(4-aminophenyl)-2-hydroxypropyl)-4-methyl-1H-indole-2-carbonitrile as a solid (330 mg, yield: 35%).

ESI-MS m/z: 634.35 (M+H).

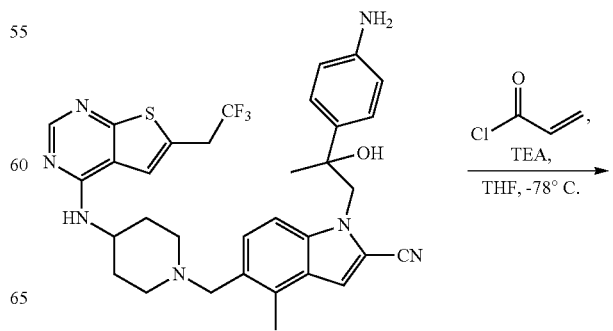

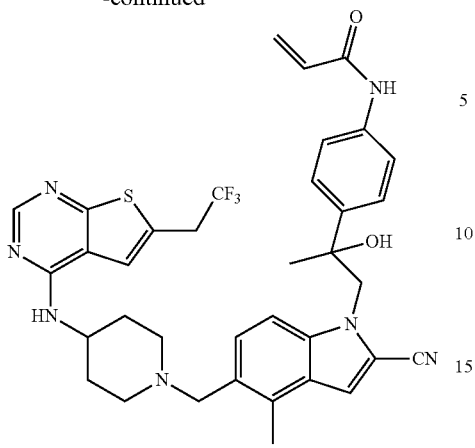

To a mixture of 5-((4-(6-(2,2,2-trifluoroethyl)thieno[2,3-d]pyrimidin-4-ylamino)piperidin-1-yl)methyl)-1-(2-(4-aminophenyl)-2-hydroxypropyl)-4-methyl-1H-indole-2-carbonitrile (100 mg, 0.16 mmol) and TEA (32 mg, 0.32 mmol) in 10 mL of THF was add slowly acryloyl chloride (16 mg, 0.17 mmol) in dry THF at −78° C. under N$_2$. The mixture was stirred at room temperature for 2 hours before NH$_3$/MeOH was added. Solvent was removed and the residue was purified by silica gel column chromatography (eluted with 5% MeOH in dichloromethane) to give Compound 196 as a solid (48 mg, yield: 44%). $^1$HNMR (400 MHz, DMSO) δ: 10.13 (s, 1H), 8.33 (s, 1H), 7.80 (s, 1H), 7.65 (s, 1H), 7.60 (d, J=8.4 Hz, 1H), 7.47 (s, 1H), 7.40 (d, J=8.4 Hz, 1H), 7.32 (br, 1H), 7.19 (br, 1H), 6.38-6.45 (m, 1H), 6.25-6.20 (m, 1H), 5.70 (dd, J=2.0, 10 Hz, 1H), 5.45 (s, 1H), 4.38-4.41 (m, 1H), 4.28-4.29 (m, 1H), 4.02-4.11 (m, 3H), 3.60 (m, 1H), 3.50-3.52 (br, 2H), 2.82 (br, 2H), 2.05-2.08 (m, 3H), 1.91 (br, 2H), 1.76 (m, 1H), 1.55-1.52 (br, 2H), 1.47 (s, 3H). ESI-MS m/z: 688.40 (M+H).

Example 9. Representative Procedure for Synthesis of Compound 174

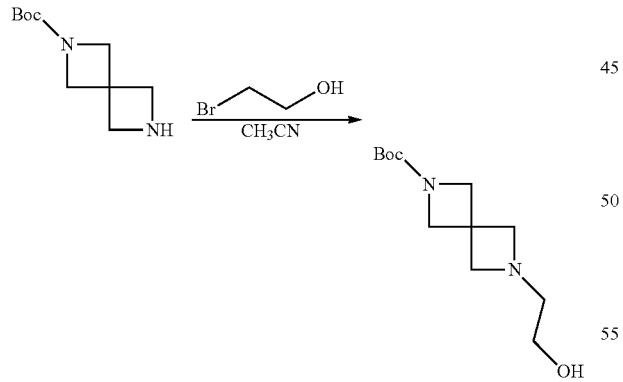

A mixture of tert-butyl 2,6-diazaspiro[3.3]heptane-2-carboxylate (200 mg, 1.01 mmol), 2-bromoethanol (251 mg, 2.02 mmol), and K$_2$CO$_3$ (558 mg, 4.04 mmol) in 30 mL of CH$_3$CN was stirred at 90° C. under N$_2$ overnight. TLC test showed that the reaction was completed. Solid was removed by filtration and solvent was removed under vacuum. The resulting residue was purified by silica gel column chromatography (eluted with 2.5% MeOH in dichloromethane) to give tert-butyl 6-(2-hydroxyethyl)-2,6-diazaspiro[3.3]heptane-2-carboxylate as a yellow oil (193 mg, yield: 80%).

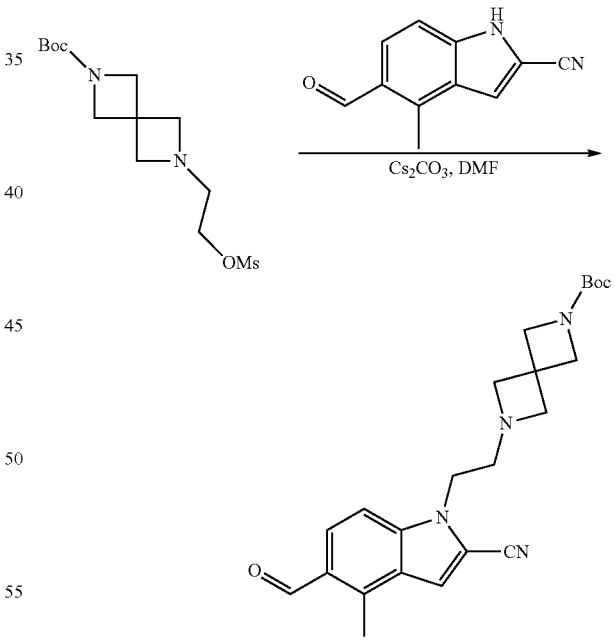

To a mixture of tert-butyl 6-(2-hydroxyethyl)-2,6-diazaspiro[3.3]heptane-2-carboxylate (193 mg, 0.8 mmol) and Et$_3$N (161 mg, 1.60 mmol) in 20 mL of dichloromethane was added MsCl (136 mg, 1.20 mmol) at 0° C. The reaction mixture was stirred for 1 h. TLC test showed that the reaction was completed. Saturated NaHCO$_3$ aqueous was added to the reaction mixture. Organic layer was separated, washed with brine, dried over anhydrous Na$_2$SO$_4$ and filtered. Solvent was removed and the resulting residue was purified by silica gel column chromatography (eluted with petroleum) to give tert-butyl 6-(2-((methylsulfonyl)oxy)ethyl)-2,6-diazaspiro[3.3]heptane-2-carboxylate as an oil (193 mg, yield: 75%).

A mixture of tert-butyl 6-(2-((methylsulfonyl)oxy)ethyl)-2,6-diazaspiro[3.3]heptane-2-carboxylate (193 mg, 0.6 mmol), 5-formyl-4-methyl-1H-indole-2-carbonitrile (92 mg, 0.5 mmol) and Cs$_2$CO$_3$ (328 mg, 1.0 mmol) in 10 mL of DMF was stirred at 60° C. for 4 hours. The solid was removed by filtered and water and ethyl acetate were added to the filtrate, the organic layer was collected, washed with brine, dried over anhydrous Na2SO4, filtered, concentrated and purified by silica gel column chromatography (eluted 20% ethyl acetate in petroleum) to give tert-butyl 6-(2-(2- cyano-5-formyl-4-methyl-1H-indol-1-yl)ethyl)-2,6-diazaspiro[3.3]heptane-2-carboxylate as an oil (99 mg, yield: 40%). ESI-MS m/z: 408.51 (M+H).

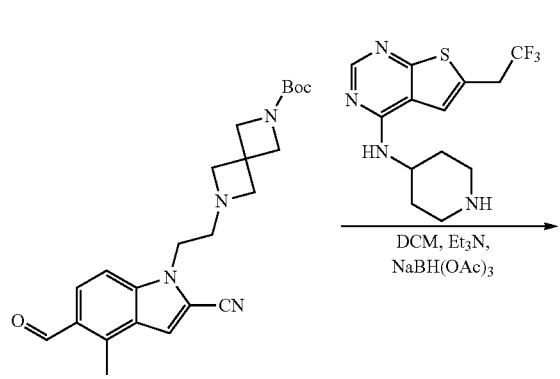

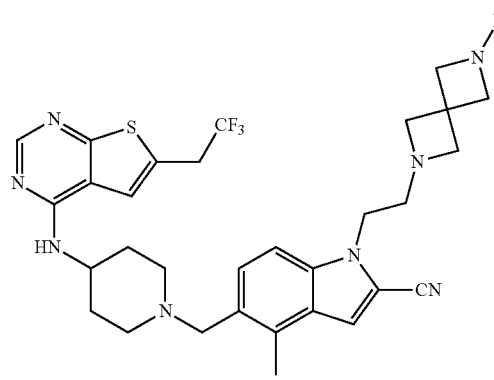

A mixture of tert-butyl 6-(2-(2-cyano-5-formyl-4-methyl-1H-indol-1-yl)ethyl)-2,6-diazaspiro[3.3]heptane-2-carboxylate (99 mg, 0.243 mmol), N-(piperidin-4-yl)-6-(2,2,2-trifluoroethyl)thieno[2,3-d]pyrimidin-4-amine (115 mg, 0.364 mmol) and Et3N (147 mg, 1.456 mmol) in 20 mL of DCM was stirred at room temperature for 1 hour, then NaBH(OAc)$_3$ (309 mg, 1.456 mmol) was added to the reaction under ice bath. The reaction mixture was stirred at room temperature overnight. Solvent was removed under vacuum and the residue was purified by silica gel column chromatography (eluted with 2.5% MeOH in dichloromethane) to give tert-butyl 6-(2-(2-cyano-4-methyl-5-((4-((6-(2,2,2-trifluoroethyl)thieno[2,3-d]pyrimidin-4-yl)amino)piperidin-1-yl)methyl)-1H-indol-1-yl)ethyl)-2,6-diazaspiro[3.3]heptane-2-carboxylate as an oil (18 mg, yield: 10%). ESI-MS m/z: 708.84 (M+H).

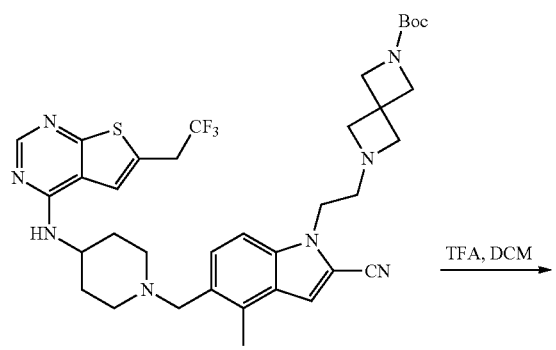

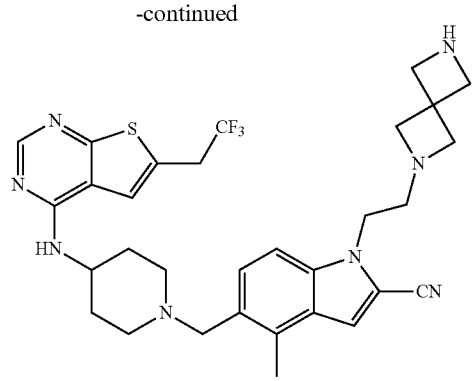

To a solution of tert-butyl 6-(2-(2-cyano-4-methyl-5-((4-((6-(2,2,2-trifluoroethyl)thieno[2,3-d]pyrimidin-4-yl)amino)piperidin-1-yl)methyl)-1H-indol-1-yl)ethyl)-2,6-diazaspiro[3.3]heptane-2-carboxylate (18 mg, 0.025 mmol) in 15 mL of DCM was added 5 mL of TFA. The reaction was stirred at room temperature for 2 hours. Then the reaction mixture was concentrated to dryness before 10 mL of 7 N NH$_3$ in MeOH solution was added. Solvent was removed and the resulting residue was purified by silica gel column chromatography (eluted with 10% MeOH in dichloromethane) to give 1-(2-(2,6-diazaspiro[3.3]heptan-2-yl)ethyl)-4-methyl-5-((4-((6-(2,2,2-trifluoroethyl)thieno[2,3-d]pyrimidin-4-yl)amino)piperidin-1-yl)methyl)-1H-indole-2-carbonitrile as an oil (11 mg, yield: 71%). ESI-MS m/z: 608.71 (M+H).

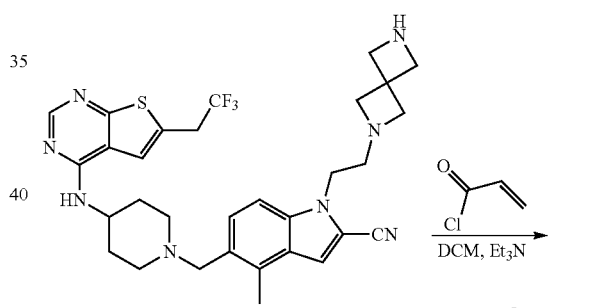

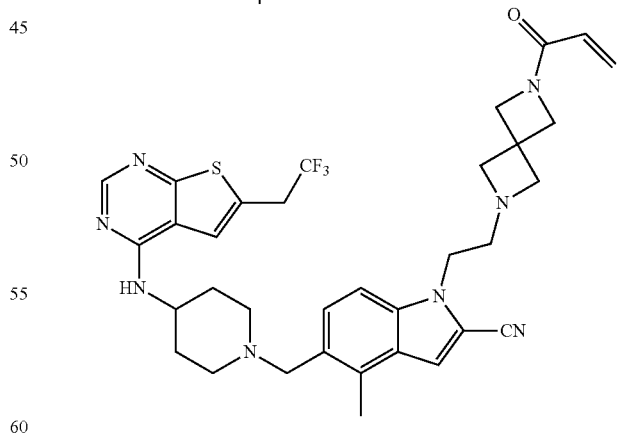

To a mixture of 1-(2-(2,6-diazaspiro[3.3]heptan-2-yl)ethyl)-4-methyl-5-((4-((6-(2,2,2-trifluoroethyl)thieno[2,3-d]pyrimidin-4-yl)amino)piperidin-1-yl)methyl)-1H-indole-2-carbonitrile (11 mg, 0.018 mmol) and Et3N (4 mg, 0.036 mmol) in 10 mL of DCM was slowly added acryloyl chloride (1.6 mg, 0.17 mmol) in dry THF at −78° C. under N$_2$. The reaction mixture was stirred at room temperature for 2 hours, then NH$_3$/MeOH was added. Solvent was removed and the resulting residue was purified by silica gel column chromatography (eluted with 10% MeOH in dichloromethane) to give Compound 174 as a solid (3 mg, yield: 25%). $^1$HNMR (400 MHz, DMSO) δ: 8.33 (s, 1H), 7.55~7.40 (m, 4H), 6.32~6.17 (m, 2H), 5.72~5.69 (m, 1H), 4.34~4.29 (m, 5H), 4.06~4.02 (m, 4H), 3.90~3.82 (m, 2H), 3.39~3.32 (m, 4H), 3.27~3.22 (m, 2H), 2.91~2.88 (m, 2H), 2.73~2.67 (m, 2H), 2.63 (s, 3H), 2.16~2.13 (m, 2H), 1.84~1.82 (m, 2H); ESI-MS m/z: 663.35 (M+H).

Example 9. Representative Procedure for Synthesis of Compound 210

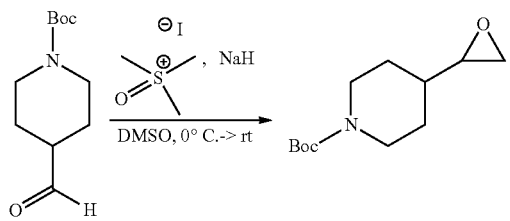

To a suspension of trimethylsulfoxonium iodide (1.2 g, 5.6 mmol) in DMSO at 0° C. was added NaH (250 mg, 6.1 mmol). The reaction mixture was allowed to warm to room temperature and stirred for 1 h. Then tert-butyl 4-formylpiperidine-1-carboxylate (1.0 g, 4.7 mmol) was added. The reaction was stirred at room temperature under N$_2$ overnight. TLC test showed that the reaction was completed. The reaction mixture was partitioned between ethyl acetate and H$_2$O. The organic layer was washed by brine, dried over Na$_2$SO$_4$. Solvent was removed under vacuum and the resulting residue was used without further purification as yellow oil (1.0 g, yield: 99%).

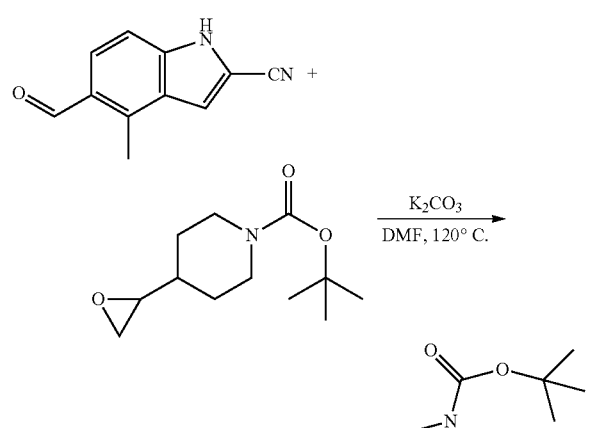

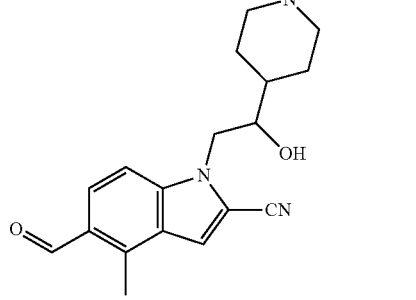

A mixture of tert-butyl 4-(oxiran-2-yl)piperidine-1-carboxylate (3.0 g, 13.2 mmol), 5-formyl-4-methyl-1H-indole-2-carbonitrile (1.2 g, 6.5 mmol) and K$_2$CO$_3$ (2.7 g, 19.5 mmol) in 30 mL of DMF was stirred at 120° C. for 10 hours. The reaction mixture was cooled to room temperature before solid was removed by filtration. The reaction mixture was partitioned between ethyl acetate and H$_2$O. The organic layer was washed by brine, dried over Na$_2$SO$_4$. Solvent was removed under vacuum to get the residue, which was purified by silica gel column chromatography (PE: ethyl acetate=10:1~5:1) to give tert-butyl 4-(2-(2-cyano-5-formyl-4-methyl-1H-indol-1-yl)-1-hydroxyethyl)piperidine-1-carboxylate as a yellow solid (800 mg, yield: 30%). ESI-MS m/z: 434.15 (M+Na), 312.15 (M−100+H).

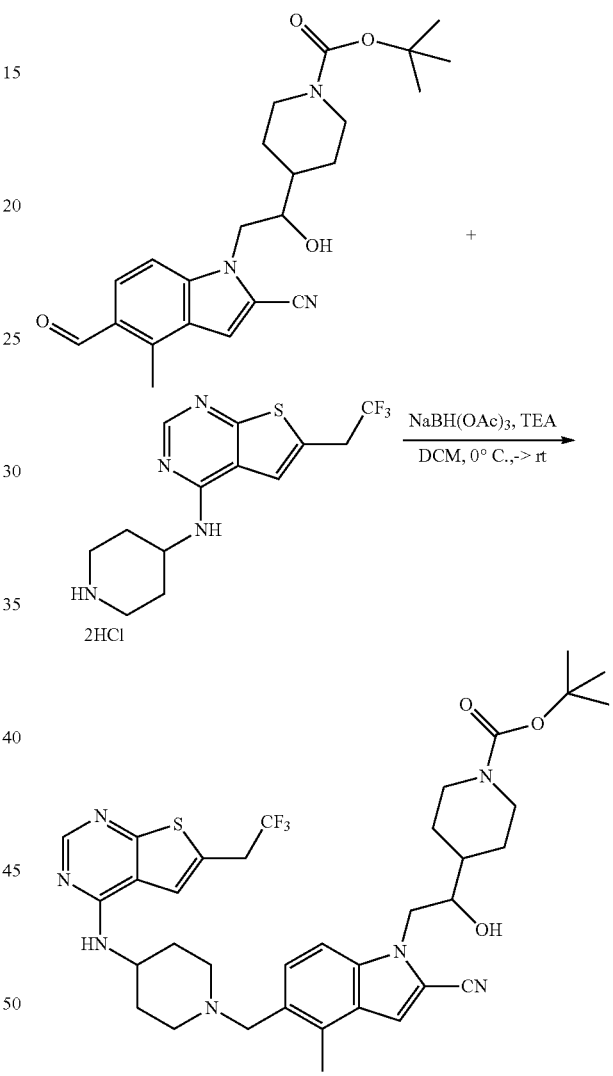

A mixture of tert-butyl 4-(2-(2-cyano-5-formyl-4-methyl-1H-indol-1-yl)-1-hydroxyethyl)piperidine-1-carboxylate (500 mg, 1.2 mmol), 6-(2,2,2-trifluoroethyl)-N-(piperidin-4-yl)thieno-[2,3-d]pyrimidin-4-amine (455 mg, 1.4 mmol) and triethylamine (727 mg, 7.2 mmol) in DCM (30 mL) was stirred at room temperature for 1 hour. NaBH(OAc)$_3$ (1.5 g, 7.2 mmol) was added with ice bath cooling. The reaction mixture was stirred at room temperature overnight before partitioned between DCM and NaHCO$_3$ (sat.). Organic layer was washed by brine, dried over Na$_2$SO$_4$. Solvent was removed under vacuum to get the residue, which was purified by silica gel column chromatography (DCM: MeOH=50:1~30:1) to give tert-butyl 4-(2-(2-cyano-4-methyl-5-((4-((6-(2,2,2-trifluoroethyl)thieno[2,3-d]pyrimidin-4-yl)amino)piperidin-1-yl)methyl)-1H-indol-1-yl)-1-hydroxyethyl)piperidine-1-carboxylate as a yellow solid (500 mg, yield: 60%). ESI-MS m/z: 712.55 (M+H).

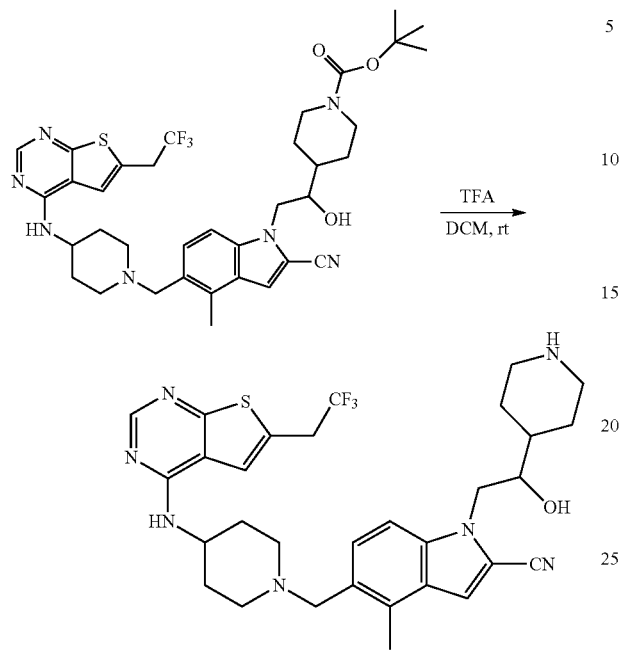

To a solution of tert-butyl 4-(2-(2-cyano-4-methyl-5-((4-((6-(2,2,2-trifluoroethyl)thieno[2,3-d]pyrimidin-4-yl)amino)piperidin-1-yl)methyl)-1H-indol-1-yl)-1-hydroxyethyl)piperidine-1-carboxylate (150 mg, 0.21 mmol) in 3 mL of DCM was added 2 mL of TFA. The reaction mixture was stirred for 4 hours. Solvent was removed under vacuum to get the residue, which was diluted with DCM and washed with NaHCO₃ (sat.). The organic layer was washed by brine, dried over Na₂SO₄. Then solvent was removed under vacuum to get the residue, which was used without further purification as a yellow foam (100 mg, yield: 99%).

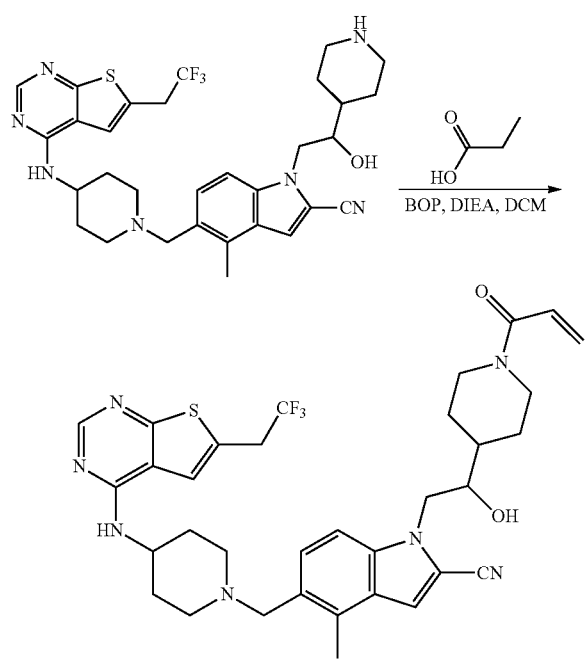

A mixture of acrylic acid (8.6 mg, 0.12 mmol), BOP (66 mg, 0.15 mmol) and DIEA (65 mg, 0.5 mmol) in DCM (10 mL) was stirred at room temperature for 2 hours, before 1-(2-hydroxy-2-(piperidin-4-yl)ethyl)-4-methyl-5-((4-((6-(2,2,2-trifluoroethyl)thieno[2,3-d]pyrimidin-4-yl)amino)piperidin-1-yl)methyl)-1H-indole-2-carbonitrile (70 mg, 0.1 mmol) was added under ice bath cooling. The reaction mixture was stirred at room temperature overnight. The reaction mixture was partitioned between DCM and NaHCO₃ (sat.), and the organic layer was washed by brine, dried over Na₂SO₄. Solvent was removed under vacuum to get the residue, which was purified by Prep-TLC (DCM:MeOH=15:1) to give Compound 210 as a white solid (10 mg, yield: 20%). ¹HNMR (400 MHz, DMSO) δ: 10.40 (br, 1H), 8.96 (br, 1H), 8.35 (m, 1H), 8.11-8.12 (m, 1H), 7.71 (s, 1H), 7.60 (s, 1H), 7.52 (s, 1H), 6.80-6.87 (m, 1H), 6.09 (dd, J=2.4, 16.8 Hz, 1H), 5.66 (dd, J=2.4, 10.8 Hz, 1H), 5.05 (d, J=5.2 Hz, 1H), 4.04-4.49 (m, 8H), 3.57~3.63 (m, 3H), 3.12~3.30 (m, 4H), 2.64 (s, 3H), 1.86-2.13 (m, 7H), 1.30-1.36 (m, 2H). ESI-MS m/z: 666.15 (M+H).

Example 10. Representative Procedure for Synthesis of Compound 216

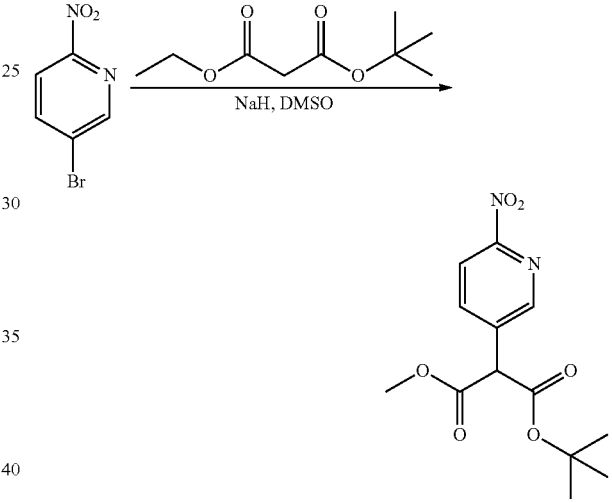

To a solution of tert-butyl ethyl malonate (37.64 g, 200 mmol) in DMSO (100 mL) was added NaH (8 g, 200 mmol) at 0° C. The reaction was stirred at room temperature for 0.5 hour before 5-bromo-2-nitropyridine (20.3 g, 100 mmol) was added. The reaction was stirred at 80° C. for 5 h. 100 mL of saturated NH₃Cl aqueous solution was added and 1000 mL of ethyl acetate was added. The organic solution was washed with H₂O, brine and dried over Na₂SO₄. Solvent was evaporated to give 1-(tert-butyl) 3-ethyl 2-(6-nitropyridin-3-yl)malonate as a solid (23 mg, yield: 74%). ESI-MS m/z: 310.33 (M+H).

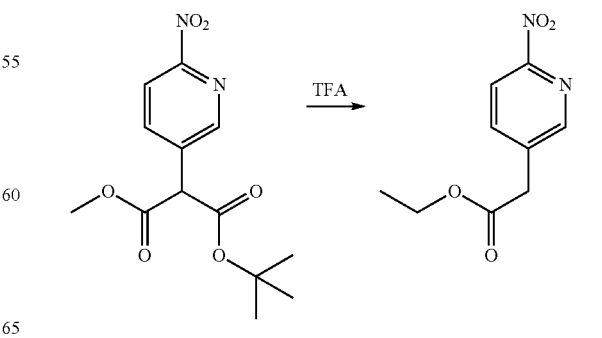

A solution of 1-(tert-butyl) 3-ethyl 2-(6-nitropyridin-3-yl) malonate (23 g, 74.2 mmol) in 40 mL of TFA was stirred at room temperature for 1 hour. Then the reaction was concentrated and 500 mL of ethyl acetate was added. Then, the solution was washed with NaHCO$_3$ and H$_2$O and brine and died over Na$_2$SO$_4$. The solution was filtered and concentrated. The residue was purified by silica gel column chromatography (eluted 20% ethyl acetate in PE) to give ethyl 2-(6-nitropyridin-3-yl)acetate as a solid (14.9 g, yield: 95%). ESI-MS m/z: 210.19 (M+H).

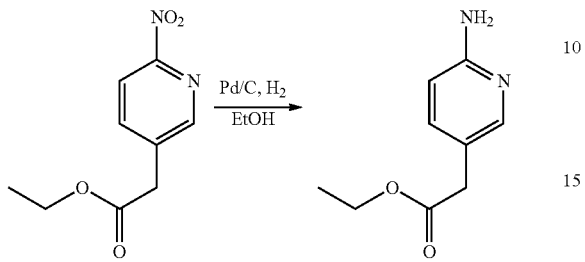

To a solution of ethyl 2-(6-nitropyridin-3-yl)acetate (14.9 g, 70.9 mmol) in 50 mL of EtOH was added catalytical amount of Pd/C. The reaction mixture was stirred at room temperature for 4 hours under H$_2$. TLC showed the reaction was completed. Then the reaction was filtered and concentrated to give ethyl 2-(6-aminopyridin-3-yl)acetate as a solid (12.5 g, yield: 98%).
ESI-MS m/z: 180.23 (M+H).

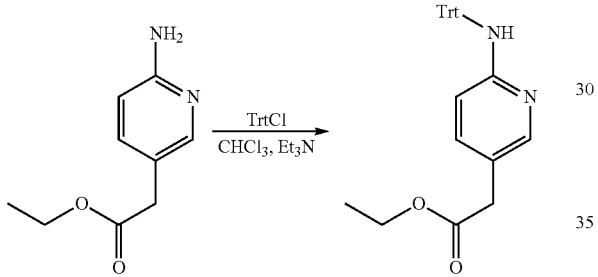

To a mixture of ethyl 2-(6-aminopyridin-3-yl)acetate (12.5 g, 69.4 mmol) in 50 mL of CHCl$_3$ were added Et$_3$N (19.07 g, 189 mmol) and TrtCl (24.1 g, 86.7 mmol) at room temperature. The reaction mixture was stirred at the same temperature overnight. TLC test showed that the reaction was completed. Then the reaction mixture was concentrated and the resulting residue was purified by silica gel column chromatography (eluted 20% ethyl acetate in PE) to give ethyl 2-(6-(tritylamino)pyridin-3-yl)acetate as a solid (25.6 g, yield: 87%).
ESI-MS m/z: 422.57 (M+H).

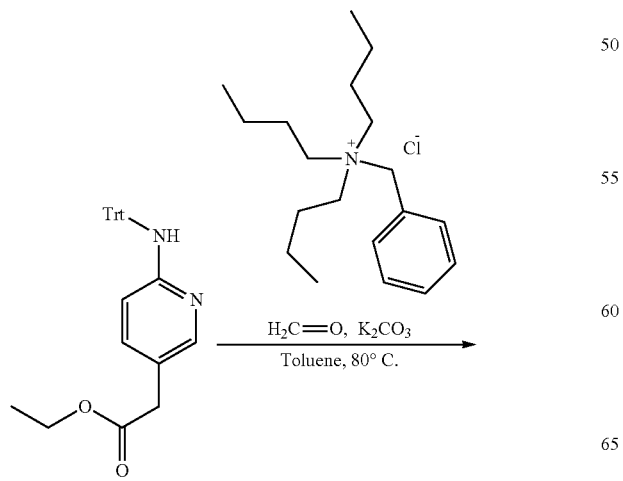

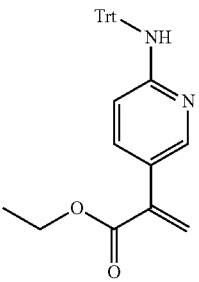

A mixture of ethyl 2-(6-(tritylamino)pyridin-3-yl)acetate (6 g, 14.2 mmol), K$_2$CO$_3$ (3.92 g, 28.4 mmol), Benzyltriethylammonium chloride (0.324 g, 1.42 mmol) in 30 mL of toluene was degassed and then paraformaldehyde (2.56 g, 85.3 mol) was added in portions to the mixture. The reaction mixture was heated with stirring at 80° C. overnight. The resulting mixture was cooled to room temperature and solvent was removed. The residue was dissolved in ice-water (100 mL), and extracted with ethyl acetate (50 mL×2). The combined organic layer was washed with brine (50 mL), dried over sodium sulphate and concentrated in vacuo. The residue was purified by flash column (eluted with 20% ethyl acetate in PE) to afford 2.3 g of ethyl 2-(6-(tritylamino)pyridin-3-yl)acrylate as a white solid (yield: 37%). ESI-MS m/z: 434.48 (M+H).

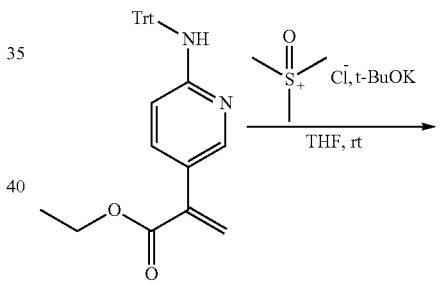

To a solution of trimethyl sulfoxide chloride (221 mg, 1.728 mmol) in THF (20 mL) was added potassium tert-butylate (194 mg, 1.728 mmol) at 0° C. The reaction was stirred at room temperature for 1 hour. Then a solution of ethyl 2-(6-(tritylamino)pyridin-3-yl)acrylate in 5 mL of THF was added. The reaction mixture was stirred at room temperature for 0.5 hour. The reaction was concentrated and the residue was purified by silica gel column chromatography (eluted 20% ethyl acetate in PE) to give ethyl 1-(6-(tritylamino)pyridin-3-yl)cyclopropane-1-carboxylate as a solid (493 mg, yield: 95%). ESI-MS m/z: 448.58 (M+H).

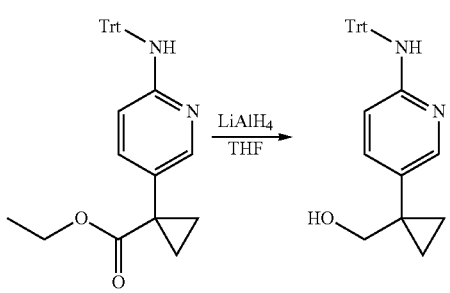

To a solution of ethyl 1-(6-(tritylamino)pyridin-3-yl)cyclopropane-1-carboxylate (493 mg, 1.1 mmol) in 20 mL of THF was added LiAlH₄ (125 mg, 3.3 mmol) at 0° C. The reaction was stirred at the same temperature for 1 hour before 0.12 ml of H₂O, 0.12 mL of 15% NaOH, 0.36 mL H₂O were added sequentially. The mixture was stirred at room temperature for 1 hour. The mixture was filtered and the organic solution was concentrated. The resulting residue was purified by silica gel column chromatography (eluted with 50% ethyl acetate in PE) to give (1-(6-(tritylamino)pyridin-3-yl)cyclopropyl)methanol as a solid (411 mg, yield: 92%). ESI-MS m/z: 406.52 (M+H).

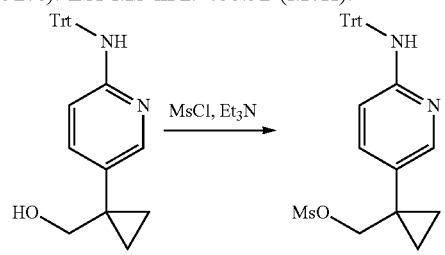

To a solution of (1-(6-(tritylamino)pyridin-3-yl)cyclopropyl)methanol (411 mg, 1.01 mmol) and Et₃N (351 mg, 3.47 mmol) in 20 mL of DCM was added MsCl (297 mg, 2.605 mmol) at 0° C. The reaction was stirred at room temperature for 1 hour. TLC test showed that the reaction was completed. The reaction mixture was washed with H₂O and brine, dried over sodium sulphate, and concentrated in vacuo to afford 332 m g of (1-(6-(tritylamino)pyridin-3-yl)cyclopropyl) methyl methanesulfonate as a white solid (yield: 68%). ESI-MS m/z: 484.63 (M+H).

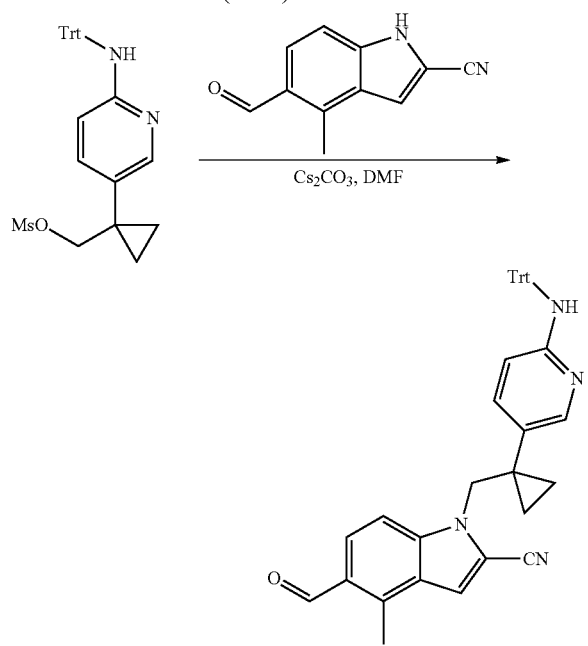

A mixture of (1-(6-(tritylamino)pyridin-3-yl)cyclopropyl) methyl methanesulfonate (332 mg, 0.686 mmol), Cs₂CO₃ (279 mg, 0.857 mmol), 5-formyl-4-methyl-1H-indole-2-carbonitrile (63 mg, 0.343 mmol) in 30 mL of DMF was stirred at 60° C. for 3 hours. 200 mL of ethyl acetate was added into the resulting mixture after cooling to room temperature. The combined organic layer was washed with H₂O and brine, dried over sodium sulphate, and concentrated. The residue was purified by flash column (eluted with 30% ethyl acetate in PE) to afford 103 mg of 5-formyl-4-methyl-1-((1-(6-(tritylamino)pyridin-3-yl)cyclopropyl)methyl)-1H-indole-2-carbonitrile as a white solid (yield: 26%). ESI-MS m/z: 572.71 (M+H).

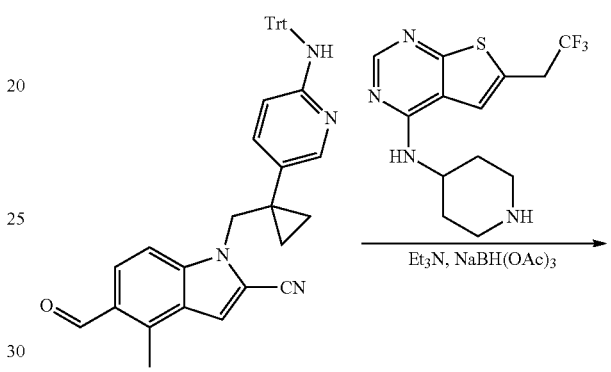

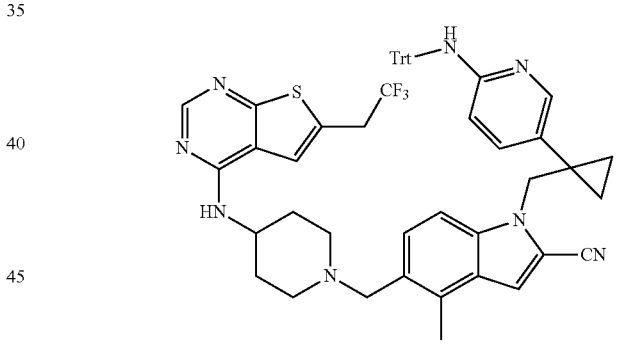

A mixture of 5-formyl-4-methyl-1-((1-(6-(tritylamino)pyridin-3-yl)cyclopropyl)methyl)-1H-indole-2-carbonitrile (103 mg, 0.18 mmol), N-(piperidin-4-yl)-6-(2,2,2-trifluoroethyl)thieno[2,3-d]pyrimidin-4-amine (85 mg, 0.27 mmol) and Et₃N (109 mg, 1.08 mmol) in 20 mL of DCM was stirred at room temperature for 1 hour before NaBH(OAc)₃ (229 mg, 1.08 mmol) was added under ice bath cooling. The mixture reaction was then stirred at room temperature overnight. Solvent was removed under vacuum and the residue was purified by silica gel column chromatography (eluted with 2.5% MeOH in dichloromethane) to give 4-methyl-5-((4-((6-(2,2,2-trifluoroethyl)thieno[2,3-d]pyrimidin-4-yl)amino)piperidin-1-yl)methyl)-1-((1-(6-(tritylamino)pyridin-3-yl)cyclopropyl)methyl)-1H-indole-2-carbonitrile as an oil (81 mg, yield: 52%). ESI-MS m/z: 873.04 (M+H).

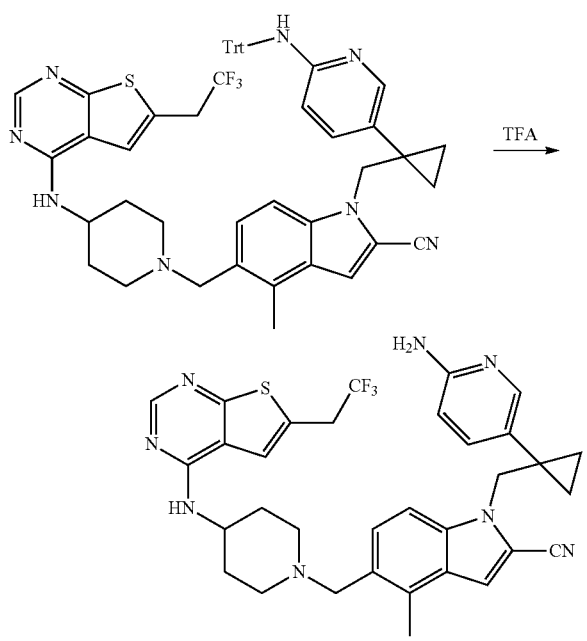

A solution of 4-methyl-5-((4-((6-(2,2,2-trifluoroethyl)thieno[2,3-d]pyrimidin-4-yl)amino)piperidin-1-yl)methyl)-1-((1-(6-(tritylamino)pyridin-3-yl)cyclopropyl)methyl)-1H-indole-2-carbonitrile (81 mg, 0.093 mmol) in TFA (15 mL) was stirred at room temperature for 2 hours. TFA was removed and 10 mL of 7N NH₃ in MeOH was added. The resulting mixture was concentrated and residue was purified by silica gel column chromatography (eluted with 10% MeOH in dichloromethane) to give 1-((1-(6-aminopyridin-3-yl)cyclopropyl)methyl)-4-methyl-5-((4-((6-(2,2,2-trifluoroethyl)thieno[2,3-d]pyrimidin-4-yl)amino)piperidin-1-yl)methyl)-1H-indole-2-carbonitrile as an oil (57 mg, yield: 99%). ESI-MS m/z: 630.75 (M+H).

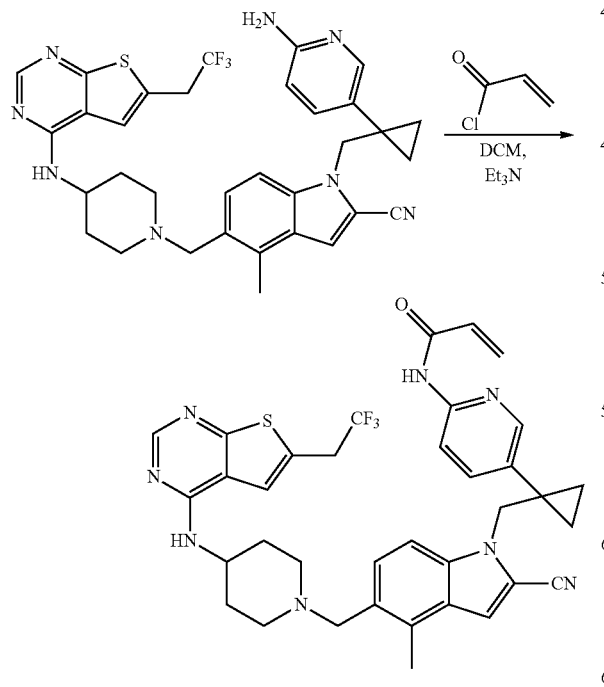

To a mixture of 1-((1-(6-aminopyridin-3-yl)cyclopropyl)methyl)-4-methyl-5-((4-((6-(2,2,2-trifluoroethyl)thieno[2,3-d]pyrimidin-4-yl)amino)piperidin-1-yl)methyl)-1H-indole-2-carbonitrile (57 mg, 0.09 mmol) and Et₃N (4 mg, 0.181 mmol) in 10 mL of DCM was add slowly acryloyl chloride (8 mg, 0.09 mmol) at −78° C. under N₂. The reaction mixture was stirred at room temperature for 2 hours before NH₃·MeOH was added. Solvent was removed and the residue was purified by silica gel column chromatography (eluted with 10% MeOH in dichloromethane) to give Compound 216 as a solid (12 mg, yield: 21%). ¹H NMR (400 MHz, DMSO) δ: 10.78 (s, 1H), 8.50 (s, 1H), 8.34 (s, 1H), 8.17 (d, J=9.2 Hz, 1H), 7.98~7.91 (m, 2H), 7.72~7.70 (m, 2H), 7.47 (br, 1H), 6.62~6.55 (m, 1H), 6.29 (dd, J=1.6, 17.2 Hz, 1H), 5.77 (dd, J=2.0, 10.4 Hz, 1H), 4.28~4.31 (m, 2H), 4.00~4.10 (m, 3H), 3.17~3.23 (m, 5H), 2.59 (s, 3H), 2.02~2.07 (m, 4H), 1.92 (m, 2H), 1.18~1.23 (m, 3H), 0.81~0.85 (m, 1H). ESI-MS m/z: 685.78 (M+H).

Example 11. Characterization of Compounds 110 and 112

Compound 110:

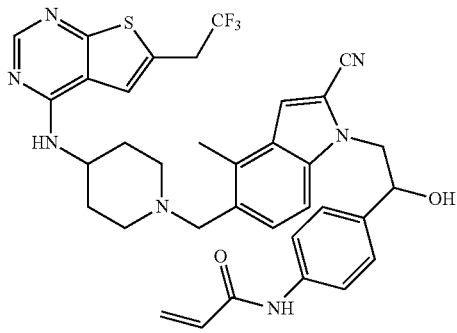 [SMILES: C=CC(=O)Nc1ccc(C(O)Cn2c(C#N)cc3c(C)c(CN4CCC(Nc5ncnc6sc(CC(F)(F)F)cc56)CC4)ccc32)cc1]

¹H NMR (600 MHz, CD₃OD): 8.38 (s, 1H), 7.54 (m, 2H), 7.42 (m, 2H), 7.36 (s, 1H), 7.21 (m, 2H), 6.38 (m, 1H), 6.30 (m, 1H), 5.66 (m, 1H), 5.05 (s, 1H), 4.5 (m, 4H), 3.88 (m, 2H), 3.59 (m, 2H), 2.67 (s, 3H), 2.35 (m, 2H), 1.95 (m, 2H). ¹³C NMR (150 MHz, CD₃OD): 166.0, 157.7, 139.6, 139.5, 138.9, 134.6, 132.4, 130.3, 130.1, 128.5, 127.9, 127.8, 126.5 (q, J=277 Hz), 121.7, 121.1, 120.7, 118.2, 114.3, 113.5, 112.4, 111.1, 73.5, 59.0, 53.9, 52.9, 47.2, 35.7 (q, J=32 Hz), 30.8, 30.0, 15.7. HRMS (ESI): M+H⁺ calculated 674.2520; found 674.2522.

Compound 112:

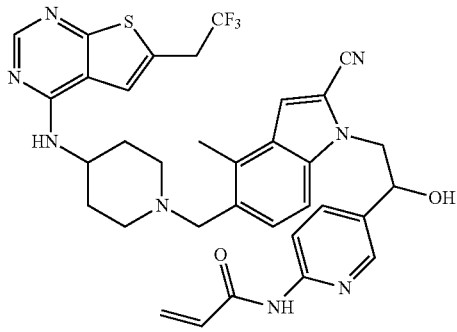 [SMILES: C=CC(=O)Nc1ccc(C(O)Cn2c(C#N)cc3c(C)c(CN4CCC(Nc5ncnc6sc(CC(F)(F)F)cc56)CC4)ccc32)cn1]

¹H NMR (600 MHz, CD$_3$OD): 8.30 (s, 1H), 8.06 (m, 2H), 7.60 (m, 1H), 7.52 (s, 1H), 7.29 (m, 2H), 7.19 (d, J=8.80 Hz. 1H), 6.45 (m, 1H), 6.34 (d, J=17.24 Hz, 1H), 5.69 (d, J=11.7 Hz), 5.10 (t, J=5.10 Hz, 2H), 4.55 (m, 1H), 4.45 (m, 1H), 4.15 (m, 1H), 3.84 (q, J=10.5 Hz, 2H), 3.64 (s, 2H), 2.97 (m, 2H), 2.55 (s, 3H), 2.25 (m, 2H), 2.01 (m, 2H), 1.66 (m, 2H). ¹³C NMR (150 MHz, CD$_3$OD): 166.7, 166.1, 157.8, 155.0, 152.8, 147.2, 138.6, 137.4, 134.8, 132.2, 130.30, 129.5, 128.7, 128.5, 126.7 (q, J=277 Hz), 121.9, 118.1, 115.3, 114.7, 113.1, 111.0, 109.4, 71.4, 60.8, 53.8, 53.4, 35.6, (q, J=32 Hz), 32.4, 30.7, 15.3. HRMS (ESI): M+$^H$ calculated 674.2472; found 675.2478.

Example 12. Biological Assays

Fluorescence Polarization Assay.

This example illustrates an assay effective in monitoring the binding of MLL to menin. Fluorescence polarization (FP) competition experiments are performed to determine the effectiveness with which a compound inhibits the menin-MLL interaction, reported as an IC$_{50}$ value. A fluorescein-labeled 12-amino acid peptide containing the high affinity menin binding motif found in MLL is produced according to Yokoyama et al. (*Cell*, 2005, 123(2): 207-218), herein incorporated by reference in its entirety. Binding of the labeled peptide (1.7 kDa) to the much larger menin (~67 kDa) is accompanied by a significant change in the rotational correlation time of the fluorophore, resulting in a substantial increase in the fluorescence polarization and fluorescence anisotropy (excitation at 500 nm, emission at 525 nm). The effectiveness with which a compound inhibits the menin-MLL interaction is measured in an FP competition experiment, wherein a decrease in fluorescence anisotropy correlates with inhibition of the interaction and is used as a read-out for IC$_{50}$ determination.

Homogenous Time-Resolve Fluorescence (HTRF) Assay.

A homogeneous time-resolve fluorescence (HTRF) assay may be utilized as a secondary assay to confirm the results of the FP assay. In some embodiments, the HTRF assay is the primary assay and the FP assay is used as a secondary assay to confirm results. HTRF is based on the non-radiative energy transfer of the long-lived emission from the Europium cryptate (Eu$^{3+}$-cryptate) donor to the allophycocyanin (XL665) acceptor, combined with time-resolved detection. An Eu$^{3+}$-cryptate donor is conjugated with mouse anti-6His monoclonal antibody (which binds His-tagged menin) and XL665-acceptor is conjugate to streptavidin (which binds biotinylated MLL peptide). When these two fluorophores are brought together by the interaction of menin with the MLL peptide, energy transfer to the acceptor results in an increase in fluorescence emission at 665 nm and increased HTRF ratio (emission intensity at 665 nm/emission intensity at 620 nm). Inhibition of the menin-MLL interaction separates the donor from the acceptor, resulting in a decrease in emission at 665 nm and decreased HTRF ratio.

Menin Engagement Assay.

Sample Preparation: 2.5 µL of 100 M compound is added to 47.5 µL of 526 nM menin in PBS (5 µM compound 500 nM menin in 5% DMSO final concentration). Reaction is incubated at room temperature for variable lengths of time and quenched with 2.5 µL of 4% formic acid (FA, 0.2% final concentration). Method: A Thermo Finnigan Surveyor Autosampler, PDA Plus UV detector and MS Pump along with an LTQ linear ion trap mass spectrometer were used to collect sample data under XCalibur software control. A 5 µL sample in "no waste" mode was injected onto a Phenomenex Jupiter 5 u 300A C5 (guard column) 2×4.00 mm at 45° C. Mobile phase composition: Buffer A (95:5 water:acetonitrile, 0.1% FA) and Buffer B (acetonitrile, 0.1% FA). Gradient elution was used with an initial mobile phase of 85:15 (Buffer A:B) and a flow rate of 250 µL/min. Upon injection, 85:15 A:B was held for 1.3 min, Buffer B was increased to 90% over 3.2 min, held for 1 min, and then returned to initial conditions in 0.1 min and held for 2.4 min. The total run time is 8 min. A post-column divert valve employed to direct void volume salts to waste was used for the first 2 min of the sample method. Blank injection of Buffer A is used in between each of the sample injections. A needle wash of 1:1 acetonitrile:water with 0.1% FA was used. The electrospray ionization (ESI) source used a 300° C. capillary temperature, 40 units sheath gas flow, 20 units aux gas flow, 3 units sweep gas flow, 3.5 kV spray voltage, 120 V tube lens. Data Collection: Data collection was performed in the positive ion full scan mode 550-1500 Da, 10 microscans, 200 ms max ion time. Data analysis: Protein mass spectra were acquired as XCalibur datafiles. The best scans were added together using XCalibur Qual Browser. The spectra were displayed using "View/Spectrum List with a Display option to display all peaks. The Edit/Copy cell menu was used to copy the mass spectrum into the PC clipboard. The spectrum in the PC clipboard was pasted into Excel. The first two columns (m/z and Intensity were kept and the third column (Relative) was deleted. The remaining two columns were then saved as a tab delimited file (m/z and intensity) as filename.txt from Excel. The Masslynx Databridge program was then used to convert the filename.txt tab delimited file to Masslynx format. In some cases, an external calibration using a (similarly converted) myoglobin spectrum was applied in Masslynx to correct the m/z values of the menin protein m/z data. MaxEnt1 software from the MassLynx software suite was used for deconvolution of the mass spectrum to yield the average MW of the protein(s). The percentage of covalent adduct formation was determined from the deconvoluted spectrum and used to calculate the reaction rate (k) of the covalent reaction.

Cellproliferation Assay.

The ability of a compound of the present invention to inhibit the growth of cells, such as human leukemia, VCaP, LNCaP, 22RV1, DU145, LNCaP-AR, MV4;11, KOPN-8, ML-2, MOLM-13, bone marrow cells (BMCs), MLL-AF9, MLL-ENL, E2A-HLF, HL-60 and NB4 cells, is tested using a cell viability assay, such as the Promega CellTiter-Glo® Luminescent Cell Viability Assay (Promega Technical Bulletin, 2015, "CellTiter-Glo® Luminescent Cell Viability Assay": 1-15, herein incorporated by reference in its entirety). Cells are plated at relevant concentrations, for example about 1×10$^5$-2×10$^5$ cells per well in a 96-well plate. A compound of the present invention is added at a concentration up to about 2 M with eight, 2-fold serial dilutions for each compound. Cells are incubated at 37° C. for a period of time, for example, 72 hours, then cells in the control wells are counted. Media is changed to restore viable cell numbers to the original concentration, and compounds are re-supplied. Proliferation is measured about 72 hours later using Promega CellTiter-Glo® reagents, as per kit instructions.

RT-PCR Analysis of MLL Fusion Protein Downstream Targets.

The effect of a compound of the present invention on expression of one or more MLL fusion protein downstream targets is assessed by RT-PCR. Cells, such as VCaP, LNCaP, 22RV1, DU145, LNCaP-AR, MV4;11, KOPN-8, ML-2, MOLM-13, bone marrow cells (BMCs), MLL-AF9, MLL-ENL, E2A-HLF, HL-60 and NB4 cells, are treated with an effective concentration of a compound for about 7 days or less, then total RNA is extracted from cells using an RNeasy mini kit (QIAGEN). Total RNA is reverse transcribed using a High Capacity cDNA Reverse Transcription Kit (Applied Biosystems), and relative quantification of relevant gene transcripts (e.g., Hoxa9 and Meis1) is determined by real-time PCR. Effective inhibition of the menin-MLL interaction is expected to result in the downregulation of downstream targets of MLL, including Hoxa9 and Meis1.

Pharmacokinatic Studies in Mice.

The pharmacokinetics of menin-MLL inhibitors are determined in female C57BL/6 mice following intravenous (iv) dosing at 15 mg/kg and oral dosing (po) at 30 mg/kg. Compounds are dissolved in the vehicle containing 25% (v/v) DMSO, 25% (v/v) PEG-400 and 50% (v/v) PBS. Serial blood samples (50 µL) are collected over 24 h, centrifuged at 15,000 rpm for 10 min and saved for analysis. Plasma concentrations of the compounds are determined by the LC-MS/MS method developed and validated for this study. The LC-MS/MS method consists of an Agilent 1200 HPLC system and chromatographic separation of tested compound is achieved using an Agilent Zorbax Extend-C18 column (5 cm×2.1 mm, 3.5 m; Waters). An AB Sciex QTrap 3200 mass spectrometer equipped with an electrospray ionization source (ABI-Sciex, Toronto, Canada) in the positive-ion multiple reaction monitoring (MRM) mode is used for detection. All pharmacokinetic parameters are calculated by noncompartmental methods using WinNonlin® version 3.2 (Pharsight Corporation, Mountain View, Calif., USA).

Efficacy Study in Mouse Xenograft Tumor Model.

Immunodeficient mice, such as 8-10 week-old female nude (nu/nu) mice, are used for in vivo efficacy studies in accordance with the guidelines approved by IACUC. Leukemia cells, such as human MV4-11 leukemia cells available from ATCC, are implanted subcutaneously via needle into female nude mice ($5 \times 10^6$ cells/mouse). When the tumor reaches a size of approximately 100 mm$^3$ in mice, the tumor-bearing mice are randomly assigned to a vehicle control or compound treatment group (8 animals per group). Animals are treated with a compound of the present invention by oral gavage or intraperitoneal injection in an appropriate amount and frequency as can be determined by the skilled artisan without undue experimentation. Subcutaneous tumor volume in nude mice and mice body weight are measured twice weekly. Tumor volumes are calculated by measuring two perpendicular diameters with calipers (V=(length×width$^2$)/2). Percentage tumor growth inhibition (% TGI=1−[change of tumor volume in treatment group/change of tumor volume in control group]*100) is used to evaluate anti-tumor efficacy. Statistical significance is evaluated using a one-tailed, two sample t test. P<0.05 is considered statistically significant.

Efficacy Study in Prostate Tumor Xenograft Model.

Immunodeficient mice, such as 4-6 week-old male CB17 severe combined immunodeficiency (SCID) mice, are used for in vivo efficacy studies in accordance with the guidelines approved by IACUC. Parental prostate cancer cells, such as VCaP or LNCaP-AR cells, are implanted subcutaneously into male CB. 17.SCID mice ($3-4\times10^6$ cells in 50% Matrigel). When the tumor reaches a palpable size of approximately 80 mm$^3$, the tumor-bearing mice are randomly assigned to a vehicle control or compound treatment group (6 or more animals per group). Animals are treated with a compound of the present invention by intraperitoneal injection in an appropriate amount and frequency as can be determined by the skilled artisan without undue experimentation. In one example, mice are treated with 40 mg/kg of a compound of the present invention daily by i.p. injection for two weeks, then 5 days per week thereafter. Subcutaneous tumor volume and mice body weight are measured twice weekly. Tumor volumes are calculated by measuring two perpendicular diameters with calipers (V=(length×width$^2$)/2).

Efficacy Study in Castration-Resistant Prostate Tumor Xenograft Model (VCaP).

Immunodeficient mice, such as 4-6 week-old male CB17 severe combined immunodeficiency (SCID) mice, are used for in vivo efficacy studies in accordance with the guidelines approved by IACUC. Parental prostate cancer cells, such as VCaP cells, are implanted subcutaneously into male CB. 17.SCID mice ($3-4\times10^6$ cells in 50% Matrigel). When the tumor reaches a size of approximately 200-300 mm$^3$, the tumor-bearing mice are physically castrated and tumors observed for regression and regrowth to approximately 150 mm$^3$. The tumor-bearing mice are randomly assigned to a vehicle control or compound treatment group (6 or more animals per group). Animals are treated with a compound of the present invention by intraperitoneal injection in an appropriate amount and frequency as can be determined by the skilled artisan without undue experimentation. In one example, mice are treated with 40 mg/kg of a compound of the present invention daily by i.p. injection. Subcutaneous tumor volume and mice body weight are measured twice weekly. Tumor volumes are calculated by measuring two perpendicular diameters with calipers (V=(length×width$^2$)/2).

Efficacy Study in Castration-Resistant Prostate Tumor Xenograft Model (LNCaP-AR).

Immunodeficient mice, such as 4-6 week-old male CB17 severe combined immunodeficiency (SCID) mice, are used for in vivo efficacy studies in accordance with the guidelines approved by IACUC. CB. 17.SCID mice are surgically castrated and allowed to recover for 2-3 weeks before implanting parental prostate cancer cells, such as LNCaP-AR cells, subcutaneously into ($3-4\times10^6$ cells in 50% Matrigel). When the tumor reaches a size of approximately 80-100 mm$^3$, the tumor-bearing mice are randomly assigned to a vehicle control or compound treatment group (6 or more animals per group). Animals are treated with a compound of the present invention by intraperitoneal injection in an appropriate amount and frequency as can be determined by the skilled artisan without undue experimentation. In one example, mice are treated with 60 mg/kg of a compound of the present invention daily by i.p. injection for 27 days. Subcutaneous tumor volume and mice body weight are measured twice weekly. Tumor volumes are calculated by measuring two perpendicular diameters with calipers (V=(length×width$^2$)/2).

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A compound represented by the structure of Formula (4):

Formula (1)

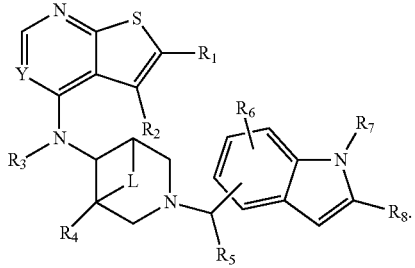

or a salt thereof, wherein:

$R^1$, $R^2$, $R^4$, $R^5$, $R^8$, and $R^a$ are independently selected from hydrogen, halogen, —$OR^{20}$, —$SR^{20}$, —$N(R^{20})_2$, —$N(R^{20})C(O)R^{20}$, —$C(O)R^{20}$, —$C(O)OR^{20}$, —$C(O)N(R^{20})_2$, —$OC(O)R^{20}$, —$S(O)_2R^{20}$, —$S(O)_2N(R^{20})_2$, —$N(R^{20})S(O)_2R^{20}$, —$NO_2$, —$P(O)(OR^{20})_2$, —$P(O)(R^{20})_2$, —$OP(O)(OR^{20})_2$, —CN, $C_{1-6}$ alkyl, $C_{2-6}$ alkenyl, and $C_{2-6}$ alkynyl, each of which is independently optionally substituted at each occurrence with one or more substituents selected from halogen, —$OR^{20}$, —$SR^{20}$, —$N(R^{20})_2$, —$N(R^{20})C(O)R^{20}$, —$C(O)R^{20}$, —$C(O)OR^{20}$, —$C(O)N(R^{20})_2$, —$OC(O)R^{20}$, —$S(O)_2R^{20}$, —$S(O)_2N(R^{20})_2$, —$N(R^{20})S(O)_2R^{20}$, —$NO_2$, =O, =S, =$N(R^{20})$, —$P(O)(OR^{20})_2$, —$P(O)(R^{20})_2$, —$OP(O)(OR^{20})_2$, —CN, $C_{3-10}$ carbocycle, and 3- to 10-membered heterocycle, or two substituents on the same carbon atom of an $C_{1-6}$ alkyl, $C_{2-6}$ alkenyl, or $C_{2-6}$ alkynyl come together to form a $C_{3-10}$ carbocycle or 3- to 10-membered heterocycle; and $C_{3-10}$ carbocycle and 3- to 10-membered heterocycle; wherein any $C_3$-10 carbocycle and 3- to 10-membered heterocycle of $R^1$, $R^2$, $R^4$, $R^5$, $R^8$, and $R^a$ is independently optionally substituted with one or more substituents selected from halogen, —$OR^{20}$, —$SR^{20}$, —$N(R^{20})_2$, —$N(R^{20})C(O)R^{20}$, —$C(O)R^{20}$, —$C(O)OR^{20}$, —$C(O)N(R^{20})_2$, —$OC(O)R^{20}$, —$S(O)_2R^{20}$, —$S(O)_2N(R^{20})_2$, —$N(R^{20})S(O)_2R^{20}$, —$NO_2$, =O, =S, =$N(R^{20})$, —$P(O)(OR^{20})_2$, —$P(O)(R^{20})_2$, —$OP(O)(OR^{20})_2$, —CN, $C_{1-6}$ alkyl, $C_{2-6}$ alkenyl, and $C_{2-6}$ alkynyl;

$R^3$ is selected from selected from hydrogen, —C(O)R$^{20}$, —C(O)OR$^{20}$, —C(O)N(R$^{20}$)$_2$, —S(O)$_2$R$^{20}$, —S(O)$_2$N(R$^{20}$)$_2$, C$_{1-6}$ alkyl, C$_{2-6}$ alkenyl, and C$_{2-6}$ alkynyl, each of which is independently optionally substituted at each occurrence with one or more substituents selected from halogen, —OR$^{20}$, —SR$^{20}$, —N(R$^{20}$)$_2$, —N(R$^{20}$)C(O)R$^{20}$, —C(O)R$^{20}$, —C(O)OR$^{20}$, —C(O)N(R$^{20}$)$_2$, —OC(O)R$^{20}$, —S(O)$_2$R$^{20}$, —S(O)$_2$N(R$^{20}$)$_2$, —N(R$^{20}$)S(O)$_2$R$^{20}$, —NO2, =O, =S, =N(R$^{20}$), —P(O)(OR$^{20}$)$_2$, —P(O)(R$^{20}$)$_2$, —OP(O)(OR$^{20}$)$_2$, —CN, C$_{3-10}$ carbocycle, and 3- to 10-membered heterocycle, or two substituents on the same carbon atom of an C$_{1-6}$ alkyl, C$_{2-6}$ alkenyl, or C$_{2-6}$ alkynyl come together to form a C$_{3-10}$ carbocycle or 3- to 10-membered heterocycle; and C$_{3-10}$ carbocycle and 3- to 10-membered heterocycle; wherein any C$_{3-10}$ carbocycle and 3- to 10-membered heterocycle of R$^3$ is independently optionally substituted with one or more substituents selected from halogen, —OR$^{20}$, —SR$^{20}$, —N(R$^{20}$)$_2$, —N(R$^{20}$)C(O)R$^{20}$, —C(O)R$^{20}$, —C(O)OR$^{20}$, —C(O)N(R$^{20}$)$_2$, —OC(O)R$^{20}$, —S(O)$_2$R$^{20}$, —S(O)$_2$N(R$^{20}$)$_2$, —N(R$^{20}$)S(O)$_2$R$^{20}$, —NO$_2$, =O, =S, =N(R$^{20}$), —P(O)(OR$^{20}$)$_2$, —P(O)(R$^{20}$)$_2$, —OP(O)(OR$^{20}$)$_2$, —CN, C$_{1-6}$ alkyl, C$_{2-6}$ alkenyl, and C$_{2-6}$ alkynyl;

$R^6$ is independently selected at each occurrence from halogen, —OR$^{20}$, —SR$^{20}$, —N(R$^{20}$)$_2$, —N(R$^{20}$)C(O)R$^{20}$, —C(O)R$^{20}$, —C(O)OR$^{20}$, —C(O)N(R$^{20}$)$_2$, —OC(O)R$^{20}$, —S(O)$_2$R$^{20}$, —S(O)$_2$N(R$^{20}$)$_2$, —N(R$^{20}$)S(O)$_2$R$^{20}$, —NO$_2$, —P(O)(OR$^{20}$)$_2$, —P(O)(R$^{20}$)$_2$, —OP(O)(OR$^{20}$)$_2$, —CN, C$_{1-6}$ alkyl, C$_{2-6}$ alkenyl, and C$_{2-6}$ alkynyl, each of which is independently optionally substituted at each occurrence with one or more substituents selected from halogen, —OR$^{20}$, —SR$^{20}$, —N(R$^{20}$)$_2$, —N(R$^{20}$)C(O)R$^{20}$, —C(O)R$^{20}$, —C(O)OR$^{20}$, —C(O)N(R$^{20}$)$_2$, —OC(O)R$^{20}$, —S(O)$_2$R$^{20}$, —S(O)$_2$N(R$^{20}$)$_2$, —N(R$^{20}$)S(O)$_2$R$^{20}$, —NO$_2$, =O, =S, =N(R$^{20}$), —P(O)(OR$^{20}$)$_2$, —P(O)(R$^{20}$)$_2$, —OP(O)(OR$^{20}$)$_2$, —CN, C$_{3-10}$ carbocycle, and 3- to 10-membered heterocycle, or two substituents on the same carbon atom of an C$_{1-6}$ alkyl, C$_{2-6}$ alkenyl, or C$_{2-6}$ alkynyl come together to form a C$_{3-10}$ carbocycle or 3- to 10-membered heterocycle; and C$_3$-10o carbocycle and 3- to 10-membered heterocycle; wherein any C$_{3-10}$ carbocycle and 3- to 10-membered heterocycle of R$^6$ is independently optionally substituted with one or more substituents selected from halogen, —OR$^{20}$, —SR$^{20}$, —N(R$^{20}$)$_2$, —N(R$^{20}$)C(O)R$^{20}$, —C(O)R$^{20}$, —C(O)OR$^{20}$, —C(O)N(R$^{20}$)$_2$, —OC(O)R$^{20}$, —S(O)$_2$R$^{20}$, —S(O)$_2$N(R$^{20}$)$_{22}$, —N(R$^{20}$)S(O)$_2$R$^{20}$, —NO$_2$, =O, =S, =N(R$^{20}$), —P(O)(OR$^{20}$)$_2$, —P(O)(R$^{20}$)$_2$, —OP(O)(OR$^{20}$)$_2$, —CN, C$_{1-6}$ alkyl, C$_{2-6}$ alkenyl, and C$_{2-6}$ alkynyl;

$R^{20}$ at each occurrence is independently selected from hydrogen; C$_{1-6}$ alkyl, C$_{2-6}$ alkenyl, and C$_{2-6}$ alkynyl, each of which is independently optionally substituted at each occurrence with one or more substituents selected from halogen, —OR$^{30}$, —SR$^{30}$, —N(R$^{30}$)$_2$, —N(R$^{30}$)C(O)R$^{30}$, —C(O)R$^{30}$, —C(O)OR$^{30}$, —C(O)N(R$^{30}$)$_2$, —OC(O)R$^{30}$, —S(O)$_2$R$^{30}$, —S(O)$_2$N(R$^{30}$)$_2$, —N(R$^{30}$)S(O)$_2$R$^{30}$, —NO$_2$, —P(O)(OR$^{30}$)$_2$, —P(O)(R$^{30}$)$_2$, —OP(O)(OR$^{30}$)$_2$, and —CN; and 3- to 10-membered heterocycle and C$_{3-10}$ carbocycle;

$R^{30}$ at each occurrence is independently selected from hydrogen, C$_{1-6}$ alkyl, C$_{2-6}$ alkenyl, and C$_{2-6}$ alkynyl;

Y is N or C(R$^a$);

L is absent or selected from alkylene and heteroalkylene;

s is selected from 0, 1, 2, 3, and 4;

$R^{7a}$ is -G-V-R$^{9a}$:

G is selected from alkylene, heteroalkylene, C$_{3-12}$ carbocycle, 3- to 12-membered heterocycle, and combinations thereof, wherein G is optionally substituted with one or more R$^{32}$ groups;

V is selected from a C$_{3-12}$ carbocycle, and 3- to 12-membered heterocycle;

wherein V is optionally substituted with one or more R$^{32}$ groups;

$R^{9a}$ is selected from halogen, —SR$^{20}$, —N(R$^{20}$)$_2$, —N(R$^{20}$)C(O)R$^{20}$, —C(O)OR$^{20}$, —OC(O)R$^{20}$, —N(R$^{20}$)S(O)$_2$R$^{20}$, —NO$_2$, =S, =N(R$^{20}$), —P(O)(OR$^{20}$)$_2$, —P(O)(R$^{20}$)$_2$, —OP(O)(OR$^{20}$)$_2$, —CN, C$_{2-6}$ alkenyl, and C$_{2-6}$ alkynyl, each of which is independently optionally substituted at each occurrence with one or more substituents selected from halogen, —OR$^{20}$, —SR$^{20}$, —N(R$^{20}$)$_2$, —N(R$^{20}$)C(O)R$^{20}$, —C(O)R$^{20}$, —C(O)OR$^{20}$, —C(O)N(R$^{20}$)$_2$, —OC(O)R$^{20}$, —S(O)$_2$R$^{20}$, —S(O)$_2$N(R$^{20}$)$_2$, —N(R$^{20}$)S(O)$_2$R$^{20}$, —NO$_2$, =O, =S, =N(R$^{20}$), —P(O)(OR$^{20}$)$_2$, —P(O)(R$^{20}$)$_2$, —OP(O)(OR$^{20}$)$_2$, —CN, C$_{3-10}$ carbocycle, and 3- to 10-membered heterocycle; C$_{3-10}$ carbocycle and 3- to 10-membered heterocycle; or two R$^{32}$ on the same carbon atom can come together to form a C$_{3-10}$ carbocycle or 3- to 10-membered heterocycle, wherein each C$_{3-10}$ carbocycle and 3- to 10-membered heterocycle of R$^{32}$ is independently optionally substituted with one or more substituents selected from halogen, —OR$^{20}$, —SR$^{20}$, —N(R$^{20}$)$_2$, —N(R$^{20}$)C(O)R$^{20}$, —C(O)R$^{20}$, —C(O)OR$^{20}$, —C(O)N(R$^{20}$)$_2$, —OC(O)R$^{20}$, —S(O)$_2$R$^{20}$, —S(O)$_2$N(R$^{20}$)$_2$, —N(R$^{20}$)S(O)$_2$R$^{20}$, —NO$_2$, =O, =S, =N(R$^{20}$), —P(O)(OR$^{20}$)$_2$, —P(O)(R$^{20}$)$_2$, —OP(O)(OR$^{20}$)$_2$, —CN, C$_{1-6}$ alkyl, C$_{2-6}$ alkenyl, and C$_{2-6}$ alkynyl; and $R^{32}$ at each occurrence is selected from halogen, —OR$^{20}$, —SR$^{20}$, —N(R$^{20}$)$_2$, —N(R$^{20}$)C(O)R$^{20}$, —C(O)R$^{20}$, —C(O)OR$^{20}$, —C(O)N(R$^{20}$)$_2$, —OC(O)R$^{20}$, —S(O)$_2$R$^{20}$, —S(O)$_2$N(R$^{20}$)$_2$, —N(R$^{20}$)S(O)$_2$R$^{20}$, —NO$_2$, =O, =S, =N(R$^{20}$), —P(O)(OR$^{20}$)$_2$, —P(O)(R$^{20}$)$_2$, —OP(O)(OR$^{20}$)$_2$, —CN, C$_{1-6}$ alkyl, C$_{2-6}$ alkenyl, and C$_{2-6}$ alkynyl, each of which is independently optionally substituted at each occurrence with one or more substituents selected from halogen, —OR$^{20}$, —SR$^{20}$, —N(R$^{20}$)$_2$, —N(R$^{20}$)C(O)R$^{20}$, —C(O)R$^{20}$, —C(O)OR$^{20}$, —C(O)N(R$^{20}$)$_2$, —OC(O)R$^{20}$, —S(O)$_2$R$^{20}$, —S(O)$_2$N(R$^{20}$)$_2$, —N(R$^{20}$)S(O)$_2$R$^{20}$, —NO$_2$, =O, =S, =N(R$^{20}$), —P(O)(OR$^{20}$)$_2$, —P(O)(R$^{20}$)$_2$, —OP(O)(OR$^{20}$)$_2$, —CN, C$_{3-10}$ carbocycle, and 3- to 10-membered heterocycle; C$_{3-10}$ carbocycle and 3- to 10-membered heterocycle; or two R$^{32}$ on the same carbon atom can come together to form a C$_{3-10}$ carbocycle or 3- to 10-membered heterocycle, wherein each C$_{3-10}$ carbocycle and 3- to 10-membered heterocycle of R$^{32}$ is independently optionally substituted with one or more substituents selected from halogen, —OR$^{20}$, —SR$^{20}$, —N(R$^{20}$)$_2$, —N(R$^{20}$)C(O)R$^{20}$, —C(O)R$^{20}$, —C(O)OR$^{20}$, —C(O)N(R$^{20}$)$_2$, —OC(O)R$^{20}$, —S(O)$_2$R$^{20}$, —S(O)$_2$N(R$^{20}$)$_2$, —N(R$^{20}$)S(O)$_2$R$^{20}$, —NO$_2$, =O, =S, =N(R$^{20}$), —P(O)(OR$^{20}$)$_2$, —P(O)(R$^{20}$)$_2$, —OP(O)(OR$^{20}$)$_2$, —CN, C$_{1-6}$ alkyl, C$_{2-6}$ alkenyl, and C$_{2-6}$ alkynyl.

2. The compound or salt of claim 1, wherein R$^1$ and R$^2$ are independently selected from hydrogen, halogen, —OH, —CN, —NO$_2$, —NH$_2$, C$_{1-6}$ alkyl, C$_{1-6}$ alkoxy, C$_{1-6}$ haloalkyl, C$_{2-6}$ alkenyl, C$_{2-6}$ haloalkenyl, C$_{2-6}$ alkynyl, and C$_{2-6}$ haloalkynyl.

3. The compound or salt of claim 2, wherein $R^1$ is selected from halogen, $C_{1-6}$ haloalkyl, $C_{2-6}$ haloalkenyl, and $C_{2-6}$ haloalkynyl.

4. The compound or salt of claim 3, wherein $R^1$ is selected from —$CH_2CF_3$ and —$CH_2CHF_2$.

5. The compound or salt of claim 2, wherein $R^2$ is selected from hydrogen, halogen, —OH, —CN, —$NO_2$, —$NH_2$, $C_{1-6}$ alkyl, and $C_{1-6}$ alkoxy.

6. The compound or salt of claim 5, wherein $R^2$ is hydrogen.

7. The compound or salt of claim 1, wherein $R^3$, $R^4$, and $R^5$ are each hydrogen.

8. The compound or salt of claim 1, wherein $R^6$, at each occurrence, is independently selected from halogen, —OH, $C_{1-6}$ alkyl, and $C_{1-6}$ alkoxy.

9. The compound or salt of claim 1, wherein $R^8$ is selected from hydrogen, halogen, —OH, —CN, —$NO_2$, —$NH_2$, $C_{1-6}$ alkyl, $C_{1-6}$ alkoxy, $C_{1-6}$ haloalkyl, $C_{2-6}$ alkenyl, $C_{2-6}$ haloalkenyl, $C_{2-6}$ alkynyl, and $C_{2-6}$ haloalkynyl.

10. The compound or salt of claim 9, wherein $R^8$ is —CN.

11. The compound or salt of claim 1, wherein Y is N.

12. The compound or salt of claim 1, wherein L is absent.

13. The compound or salt of claim 1, wherein G is alkylene optionally substituted with one or more $R^{32}$ groups.

14. The compound or salt of claim 13, wherein G is selected from:

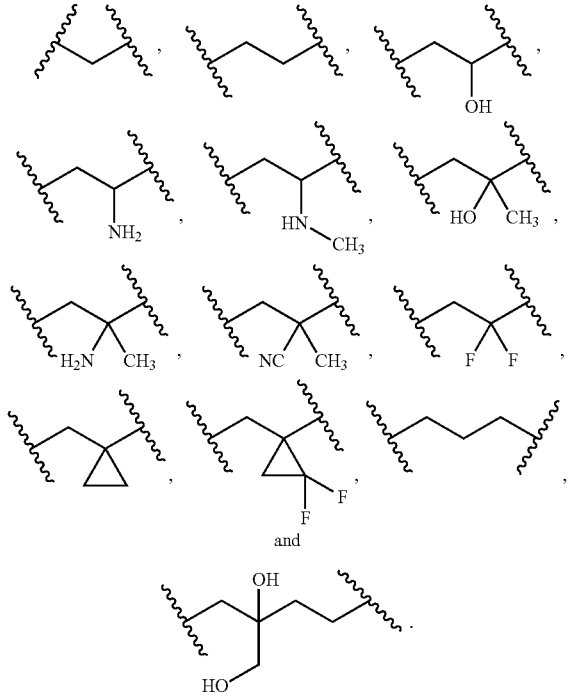

15. The compound or salt of claim 1, wherein V is selected from azetidine, oxetane, piperidine, oxane, piperazine, pyrrolidine, tetrahydrofuran, thiolane, imidazolidine, morpholine, thiomorpholine, azepane, and homopiperazine, any one of which is optionally substituted with one or more $R^{32}$ groups.

16. The compound or salt of claim 1, wherein V is selected from phenyl, pyridine, pyrazine, pyrimidine, pyridazine, naphthalene, anthracene, quinoline, isoquinoline, quinoxaline, acridine, quinazoline, cinnoline, phthalazine, furan, dihydrofuran, thiophene, dihydrothiophene, imidazole, imidazoline, oxazole, oxazoline, pyrrole, dihydropyrrole, thiazole, dihydrothiazole, pyrazole, dihydropyrazole, isoxazole, dihydroisoxazole, isothiazole, dihydroisothiazole, benzofuran, isobenzofuran, indole, isoindole, benzothiophene, benzimidazole, purine, indazole, benzoxazole, benzisoxazole, and benzothiazole, any one of which is optionally substituted with one or more $R^{32}$ groups.

17. The compound or salt of claim 1, wherein $R^{9a}$ is

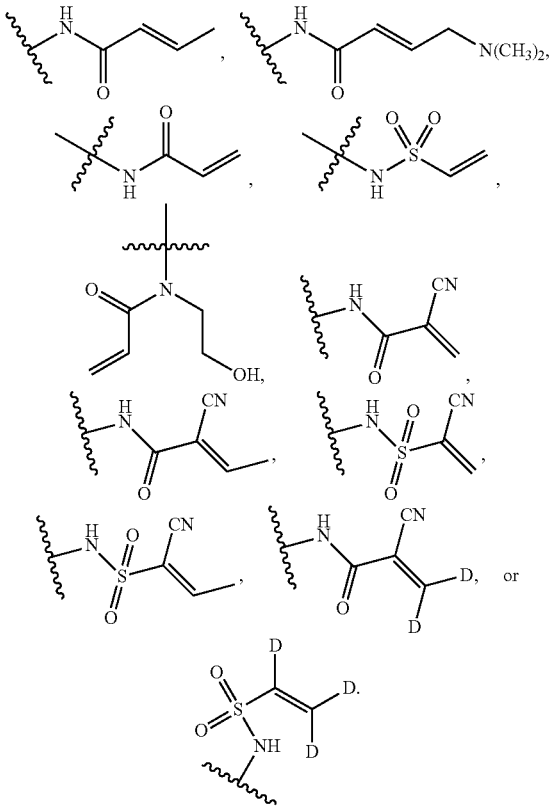

18. A compound selected from:

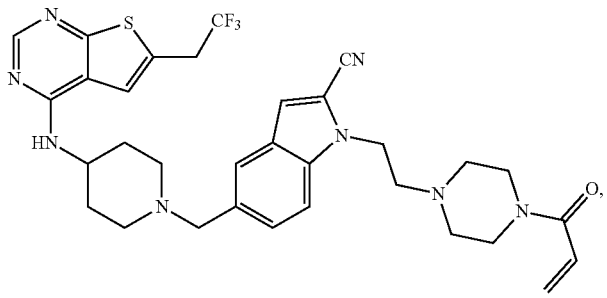

-continued
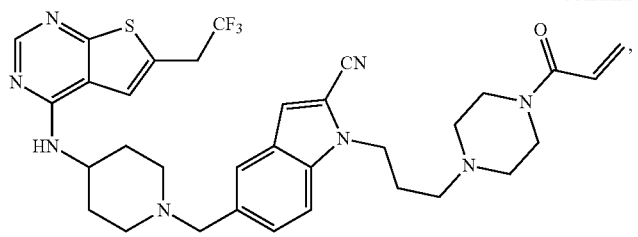
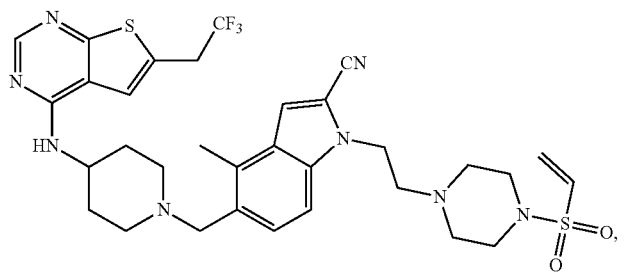
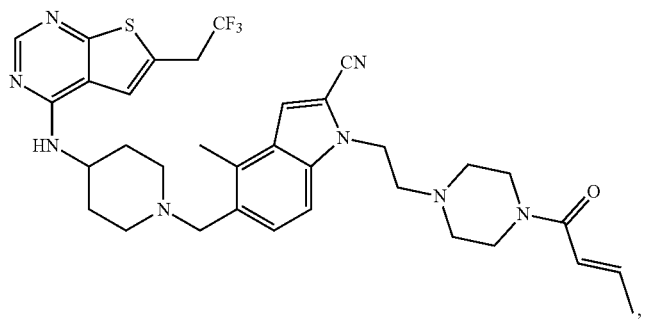
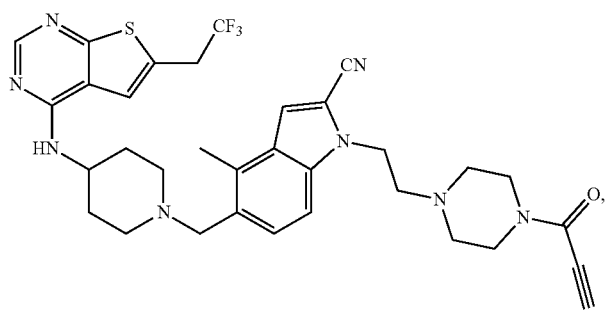
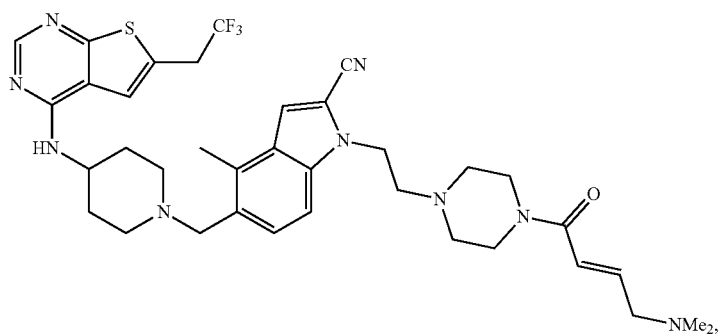

-continued
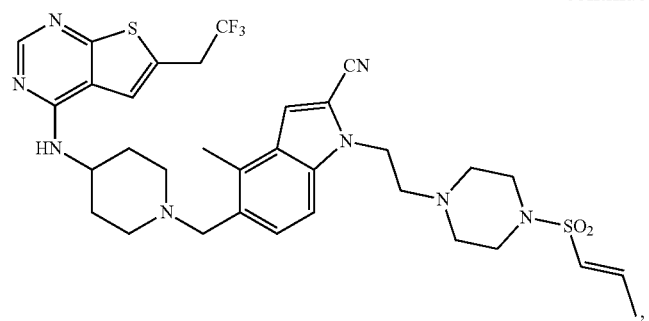
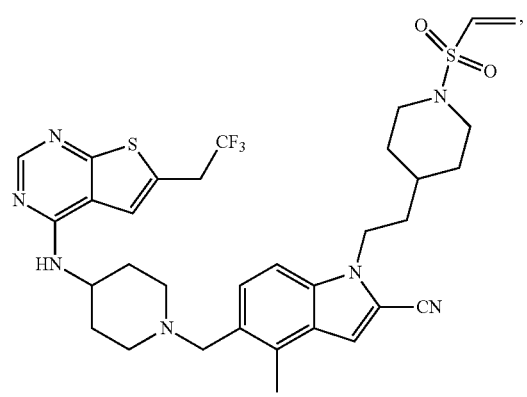
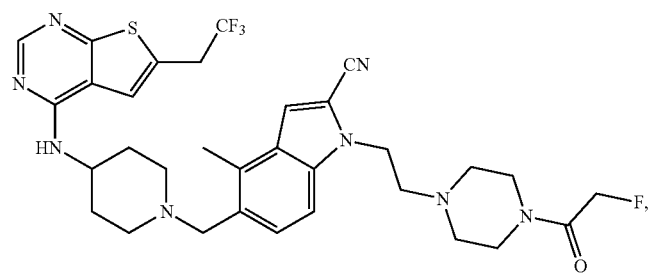
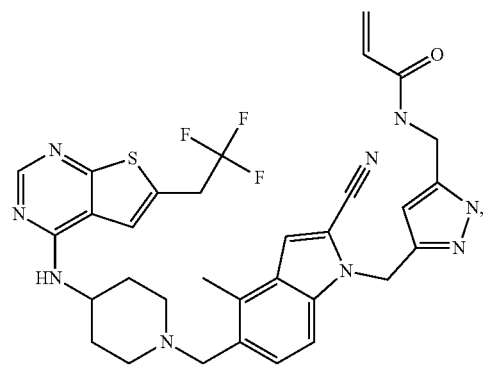

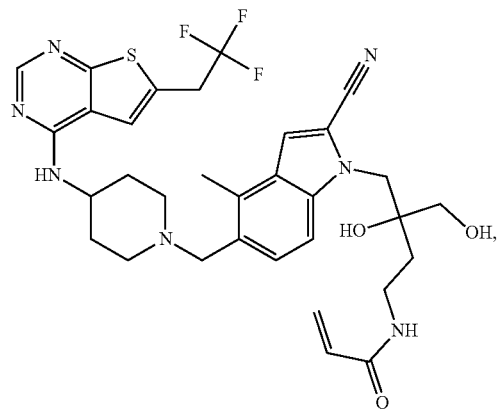
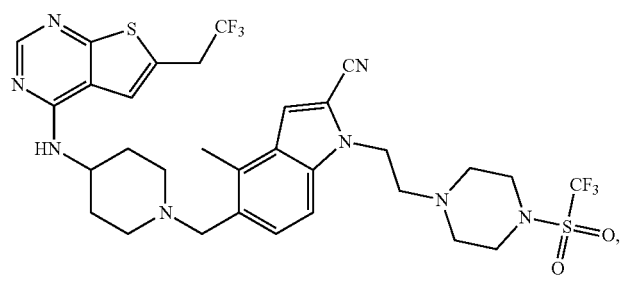
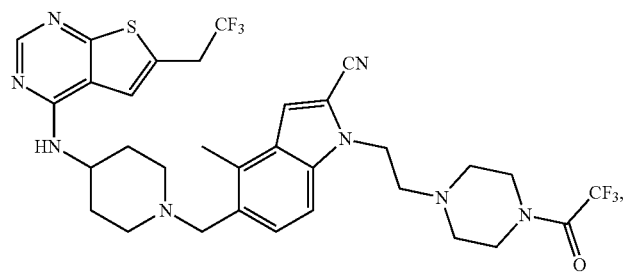
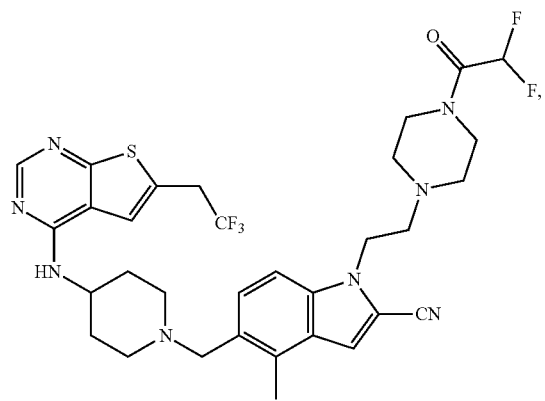

-continued
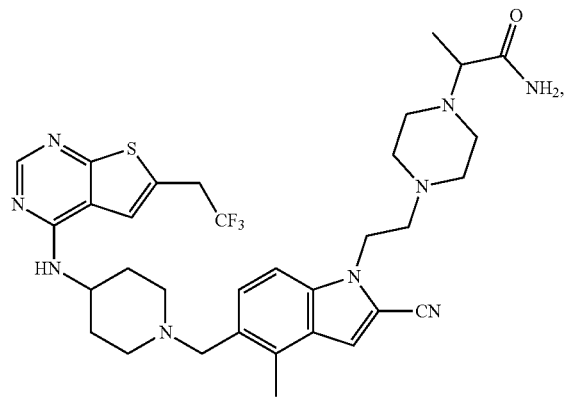
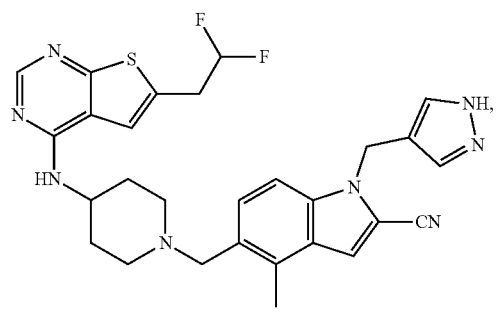
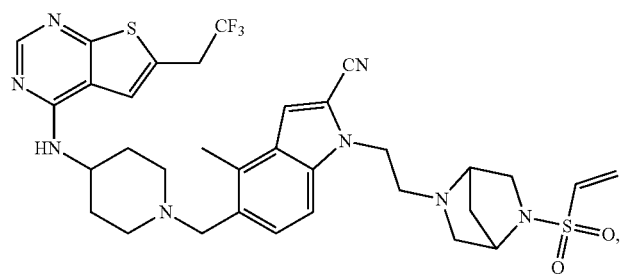
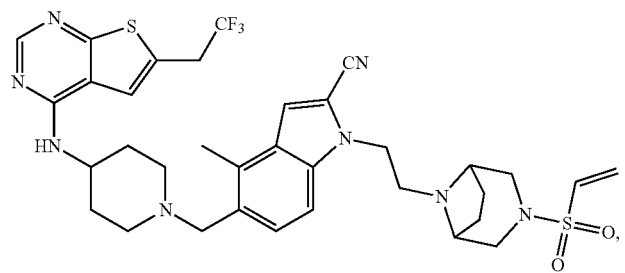
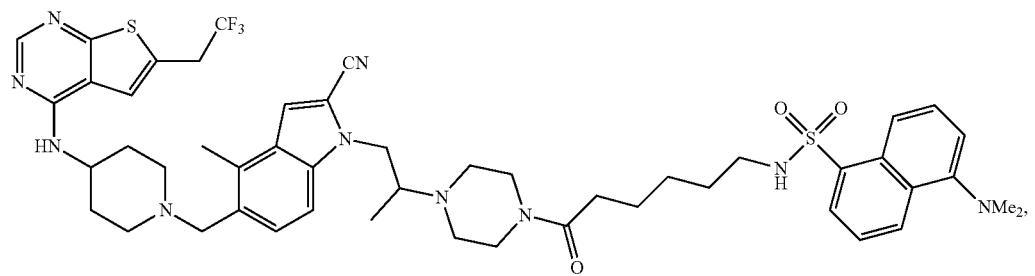

373
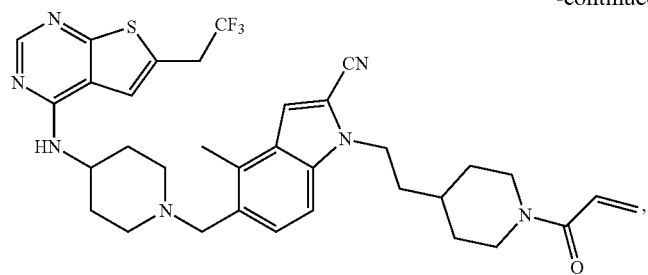
374
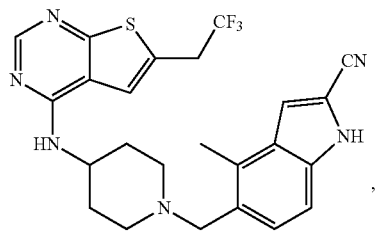
-continued
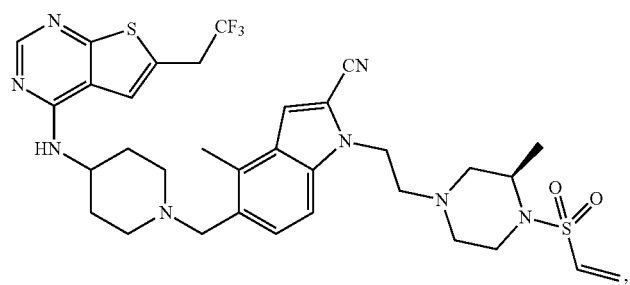
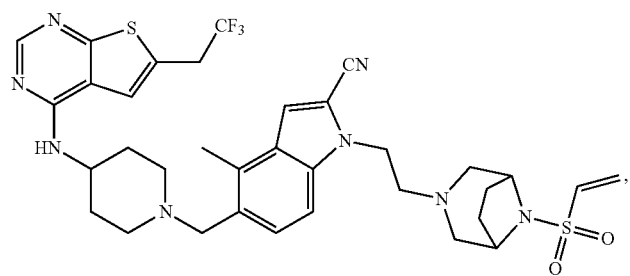
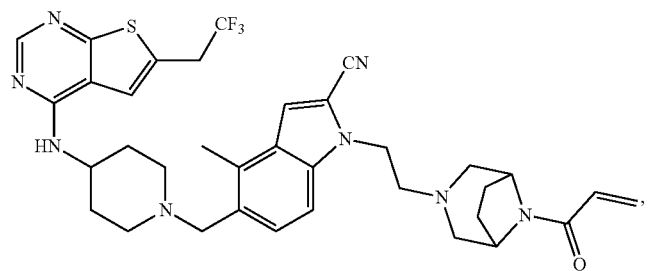
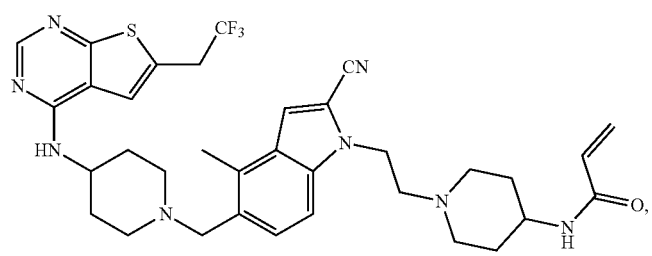

375
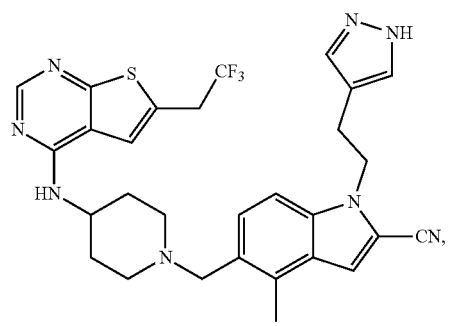
376
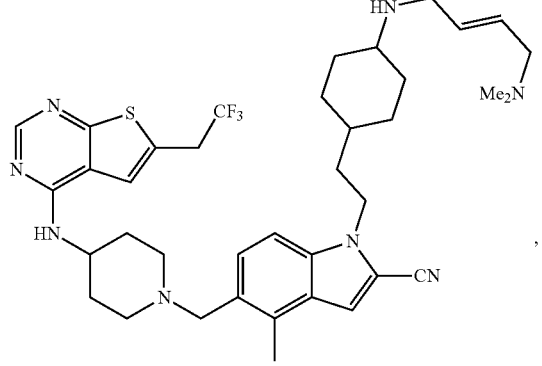
-continued
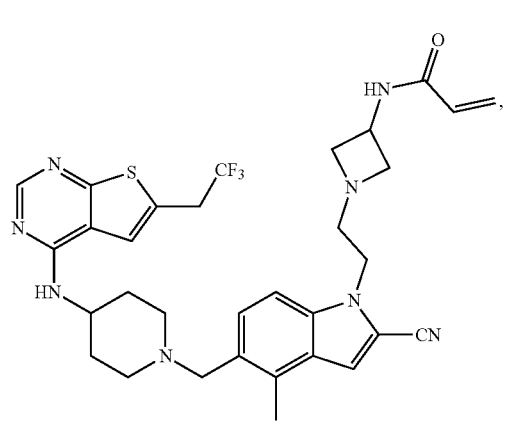
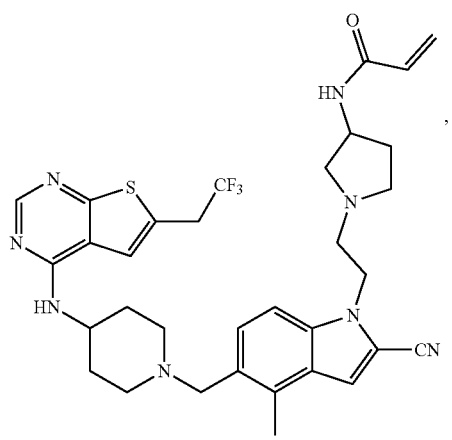
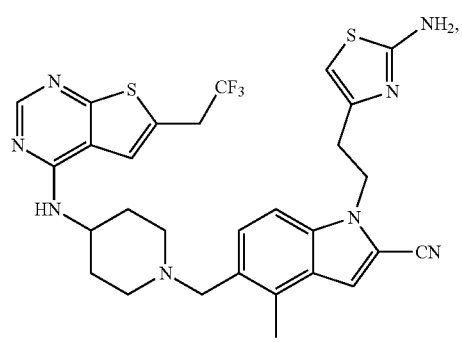
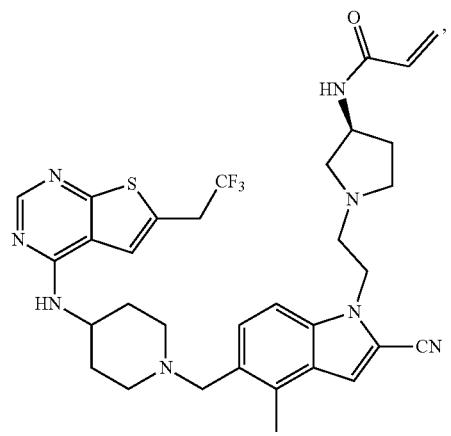
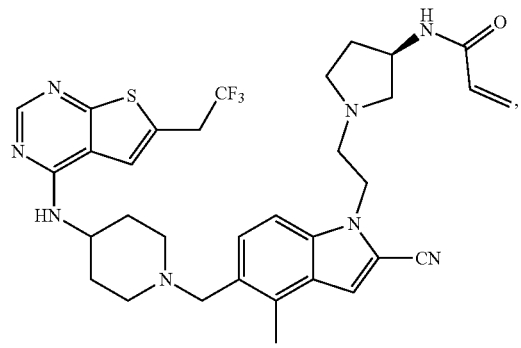

-continued
377
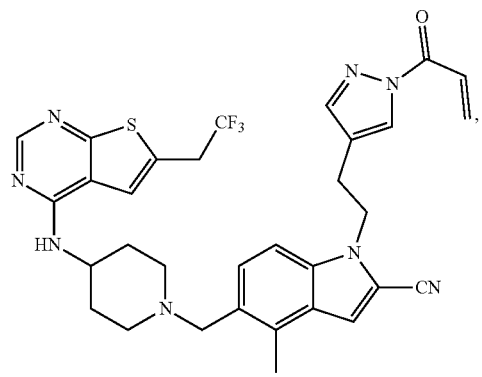
378
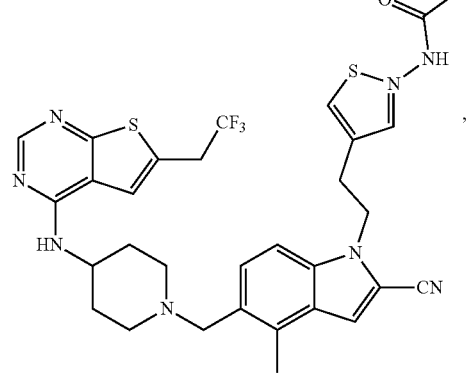
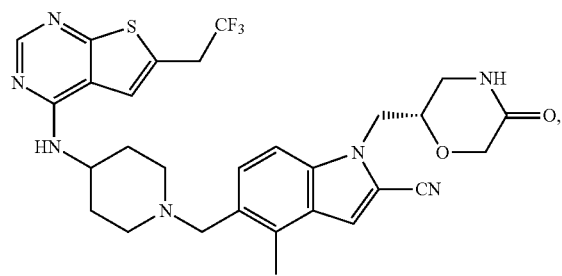
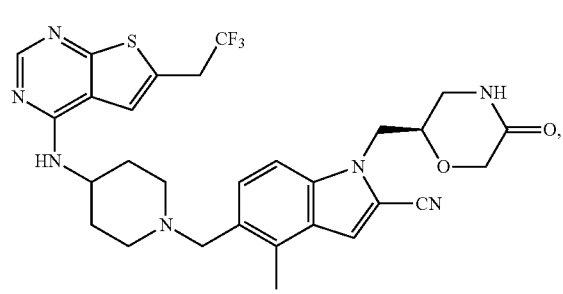
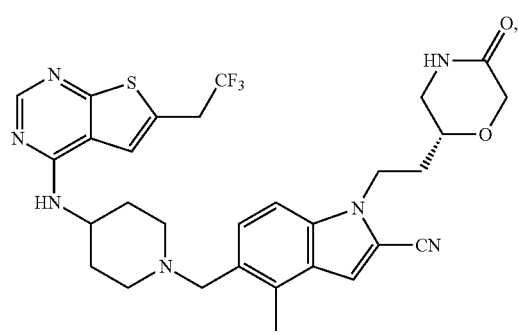
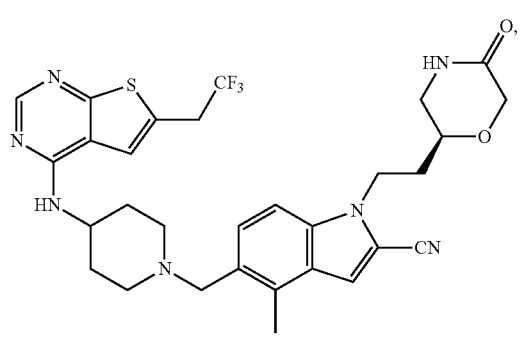
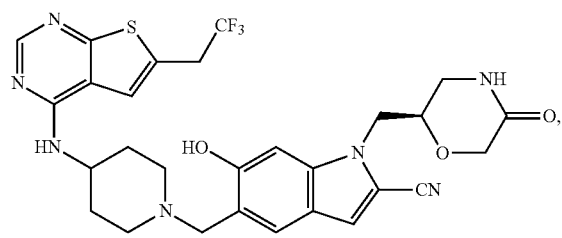
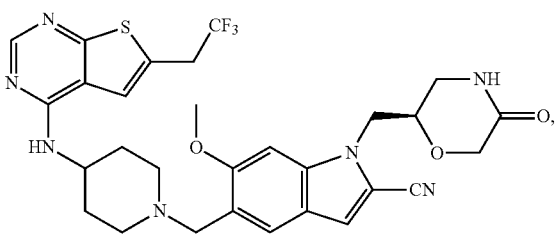
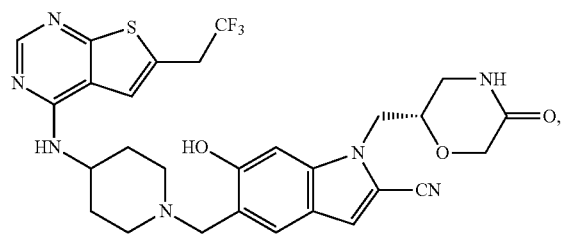
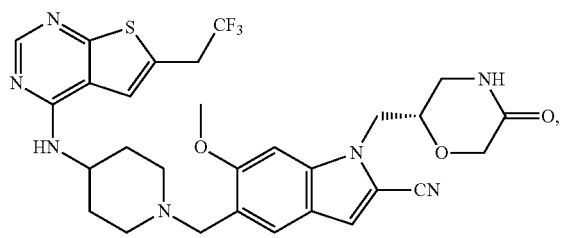

379 380
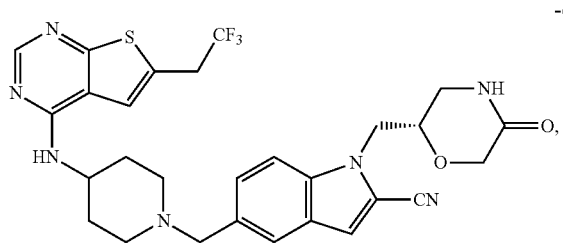 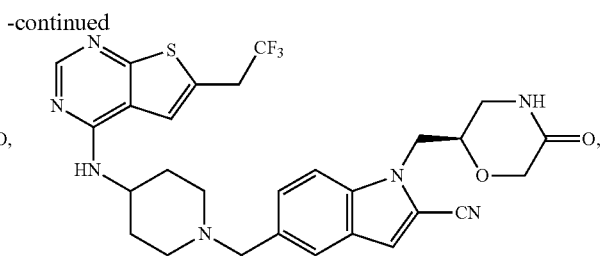
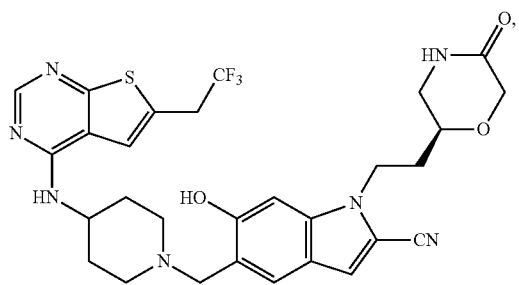 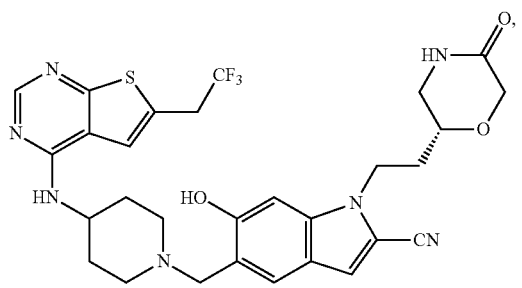
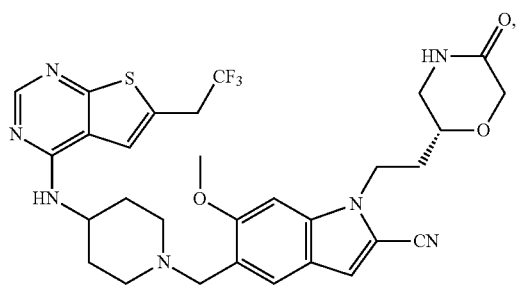 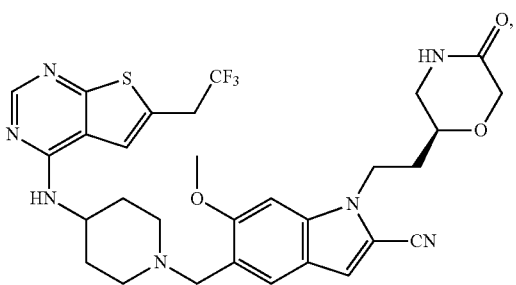
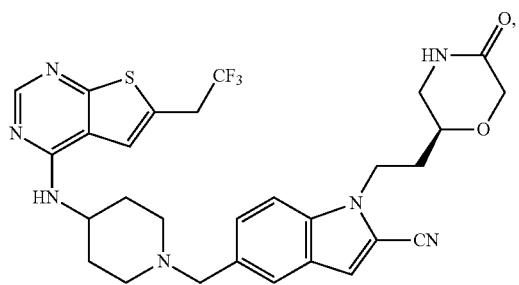 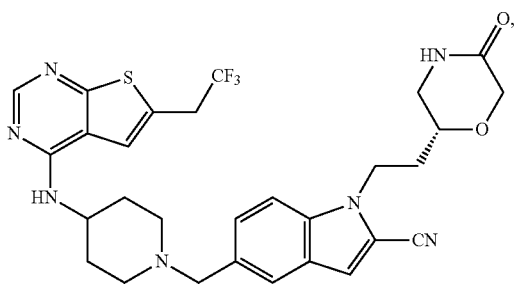
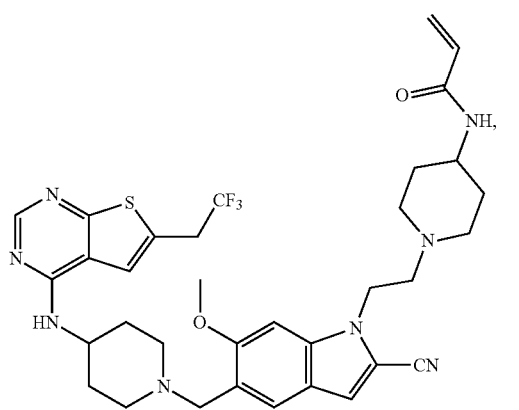 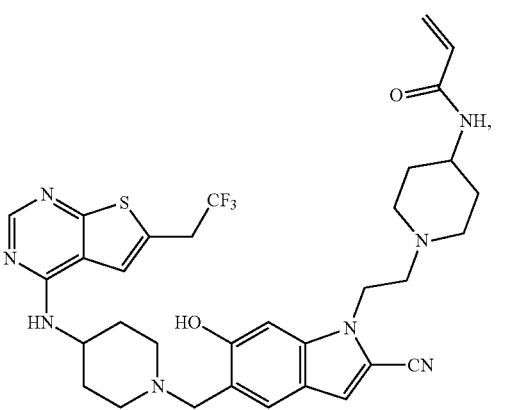

-continued
| 381 | 382 |
|---|---|
| 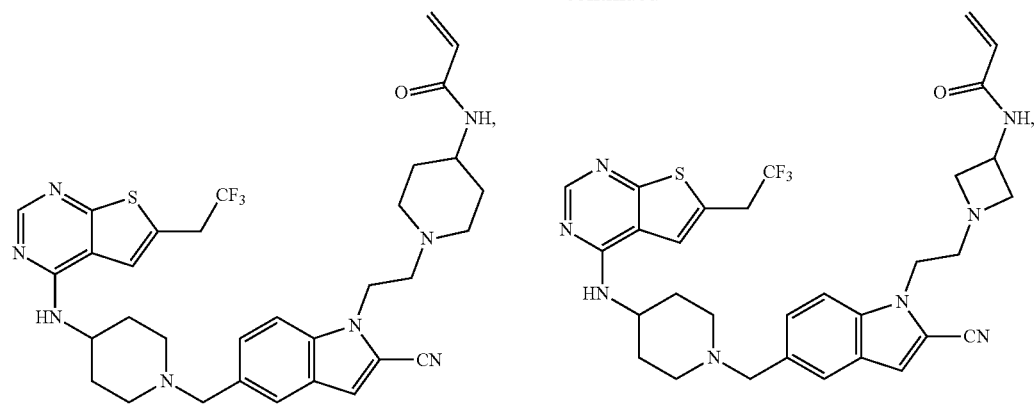 | |
| 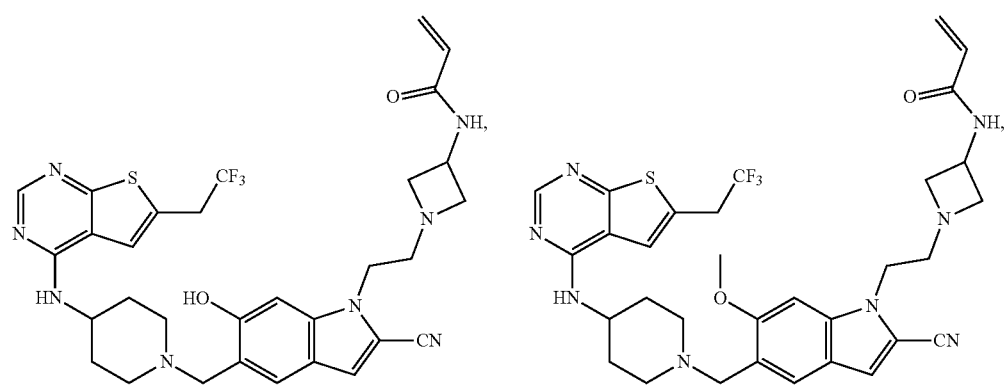 | |
| 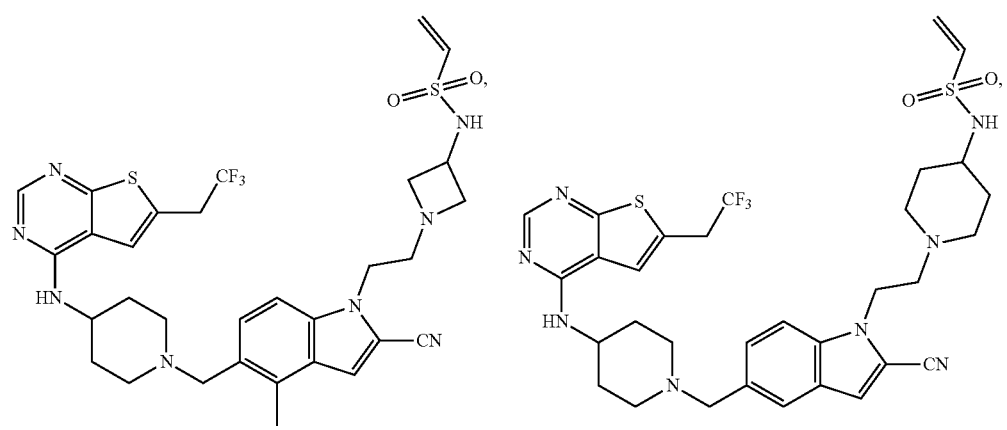 | |
| 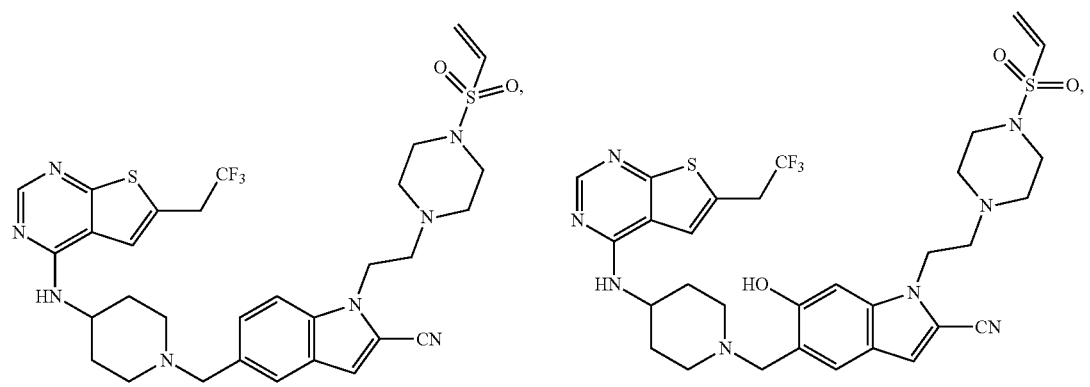 | |

383 384
-continued
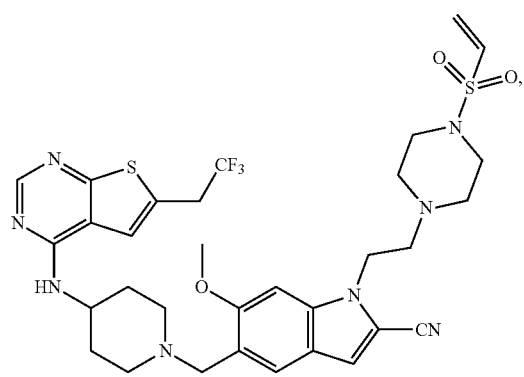
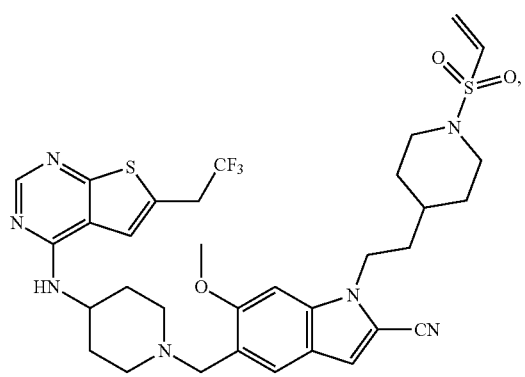
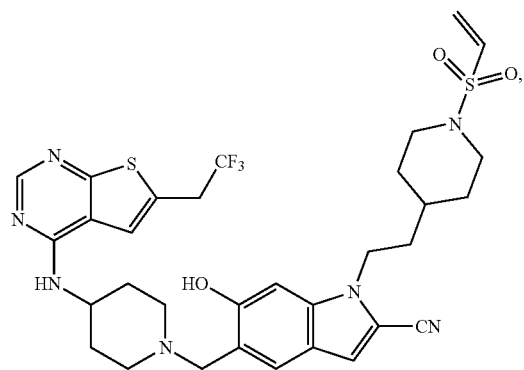
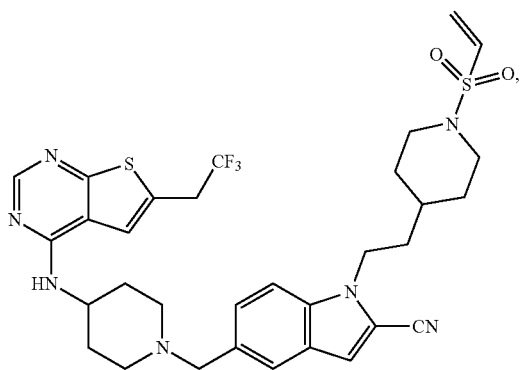
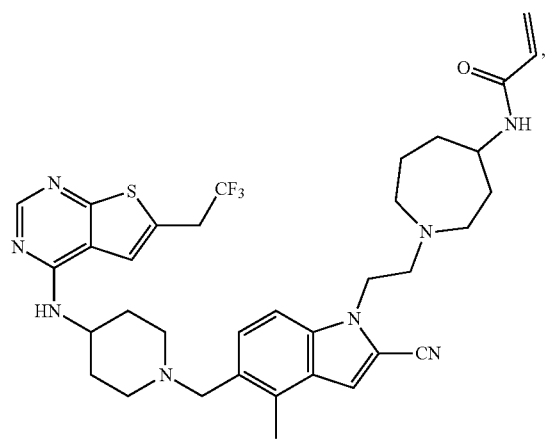
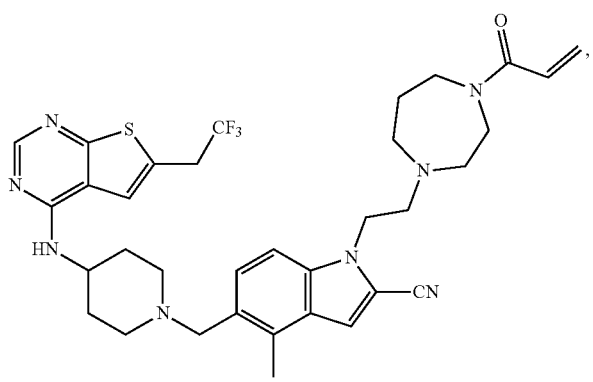
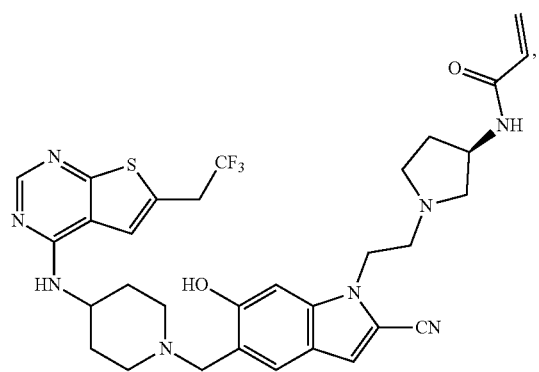
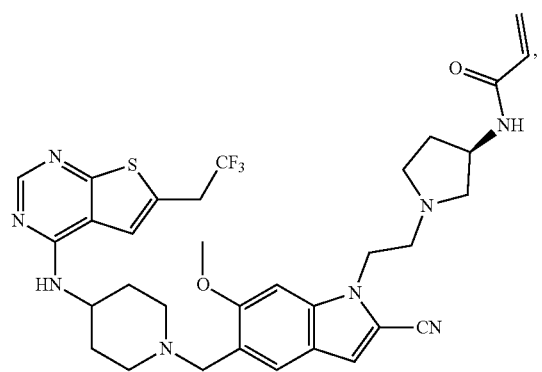

-continued
| 385 | 386 |
|---|---|
| 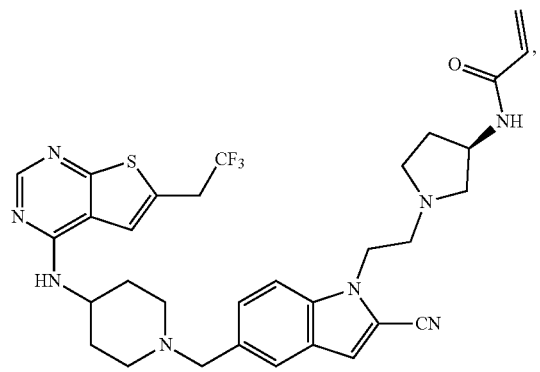 | 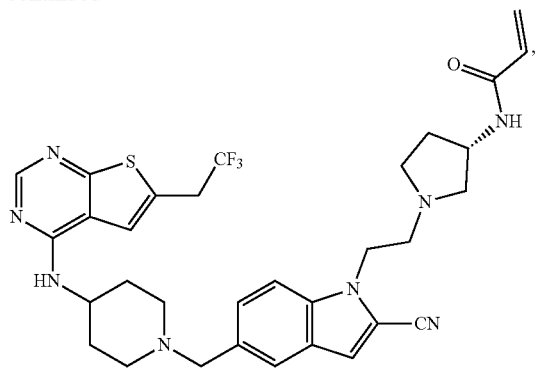 |
| 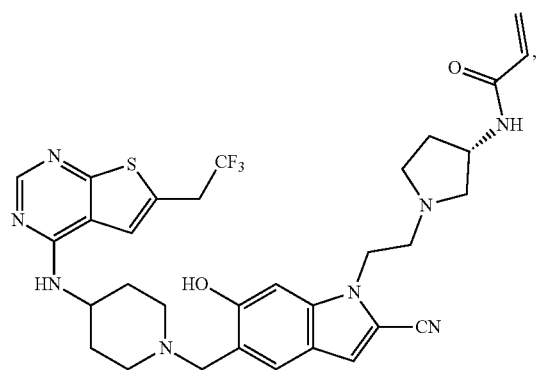 | 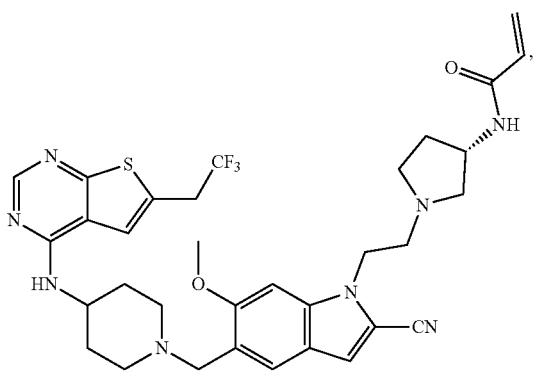 |
| 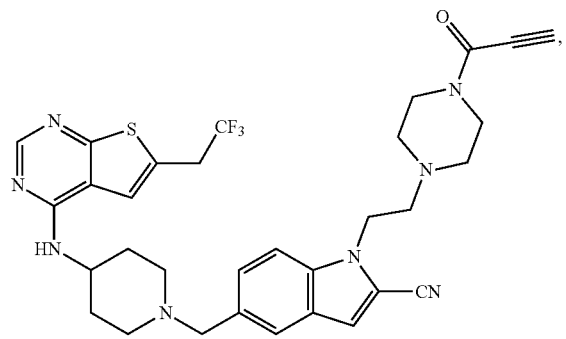 | 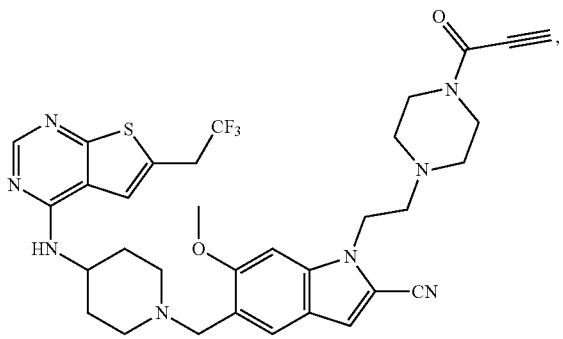 |
| 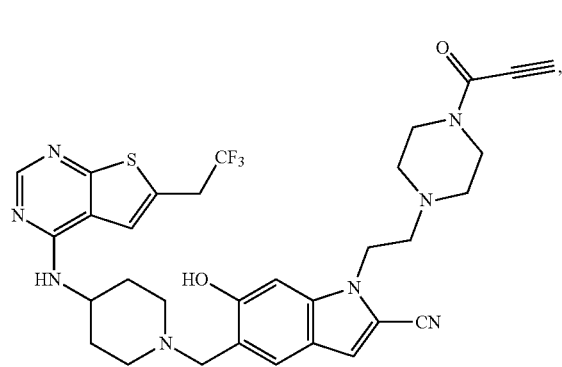 | 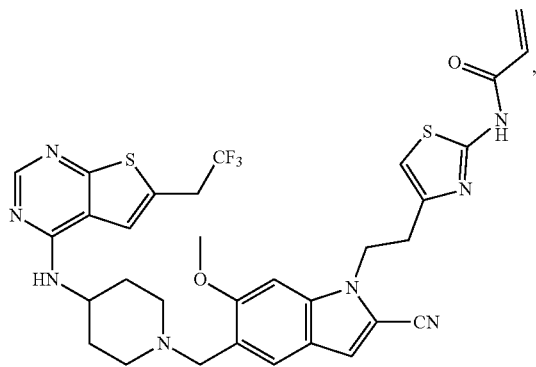 |

-continued
387
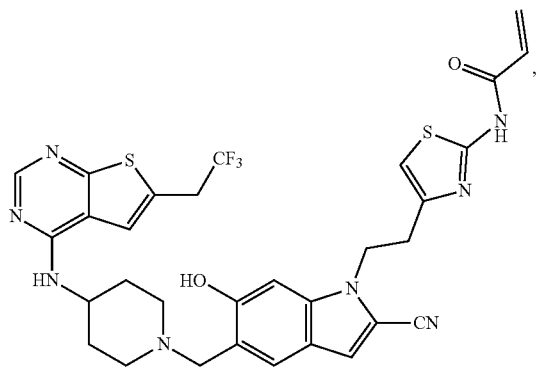
388
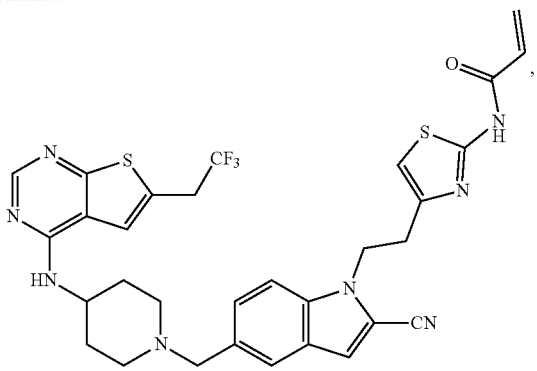
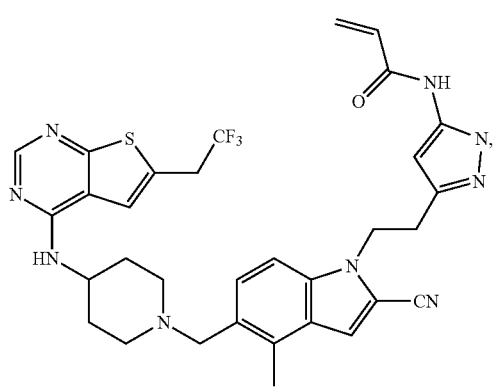
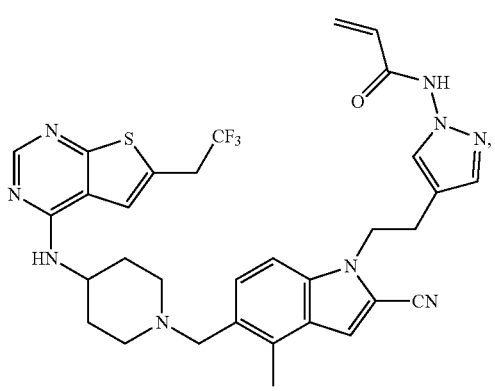
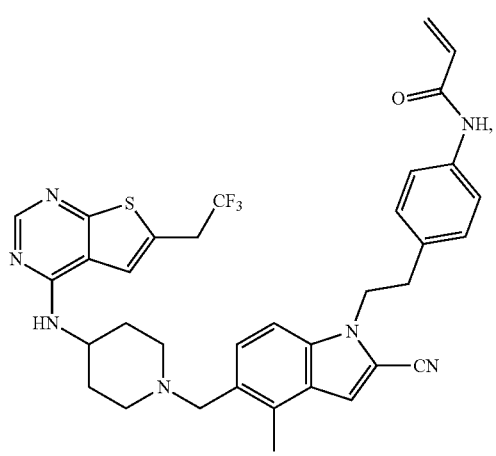
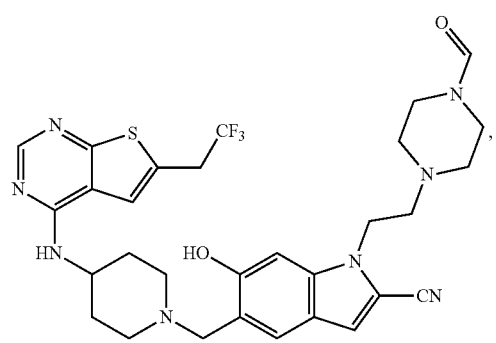
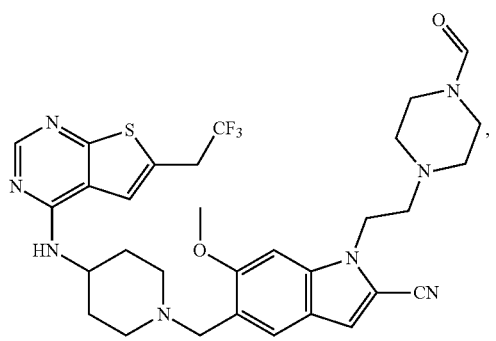
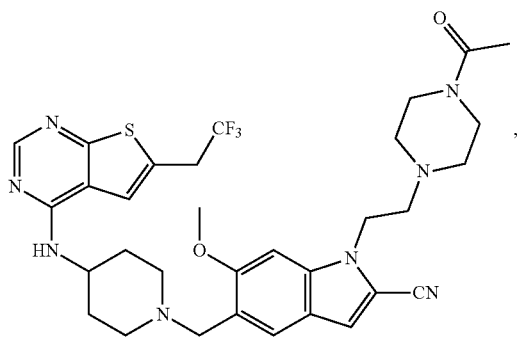

-continued
389
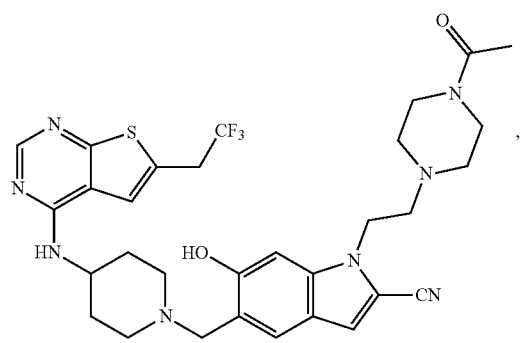
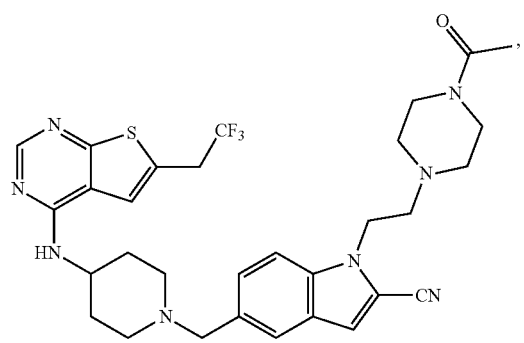
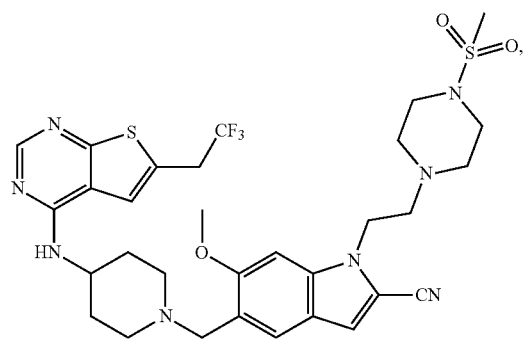
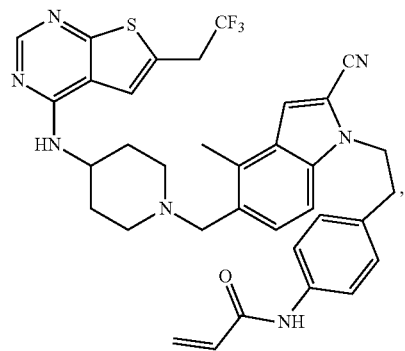
390
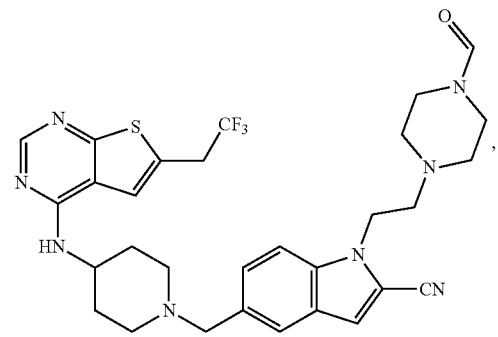
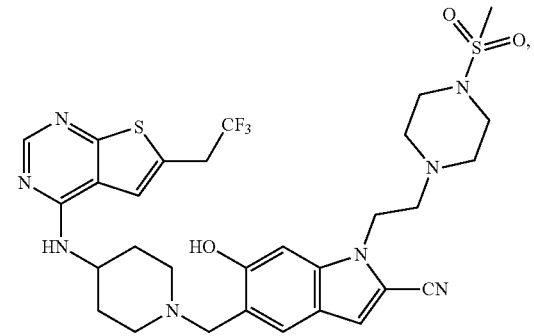
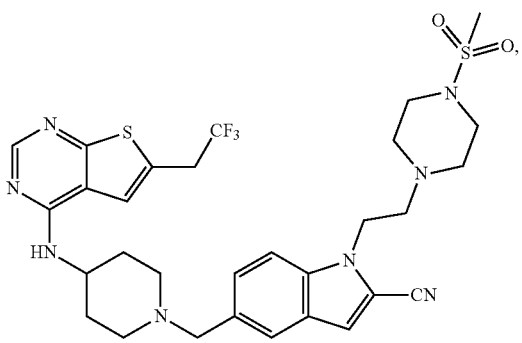
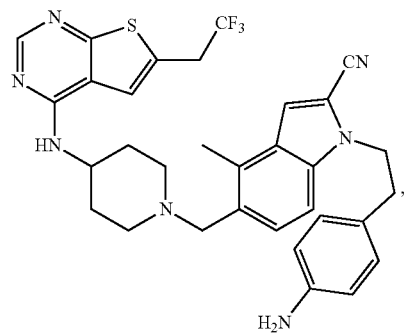

-continued
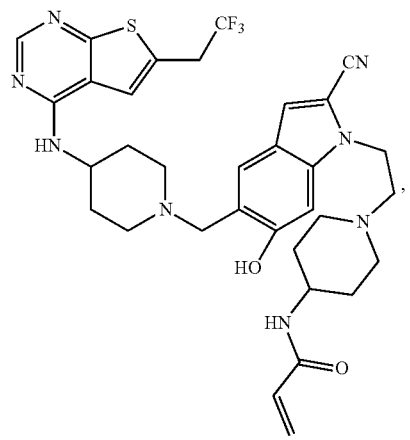
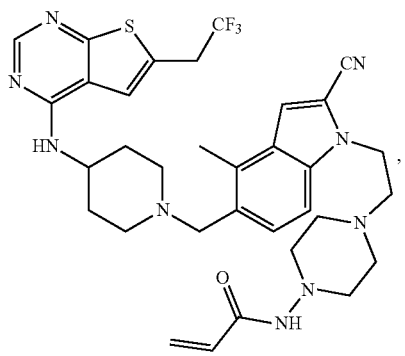
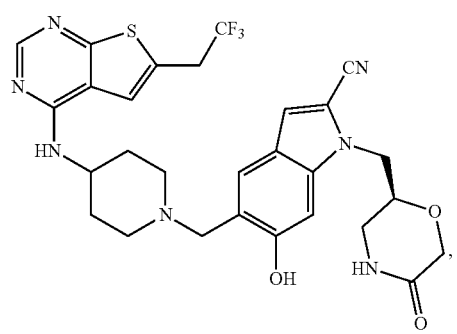
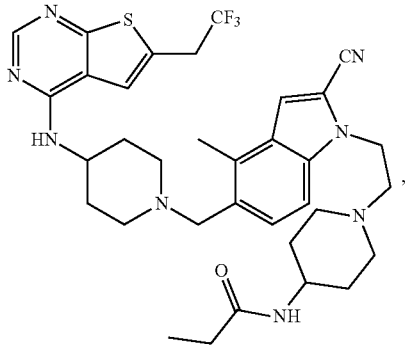
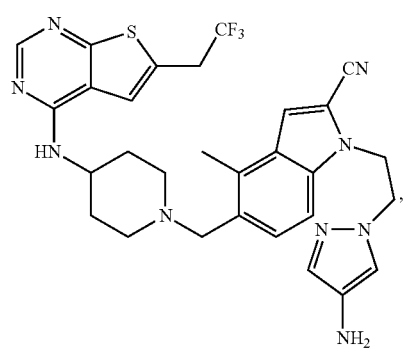
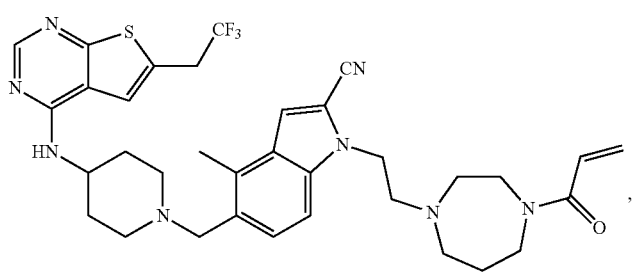
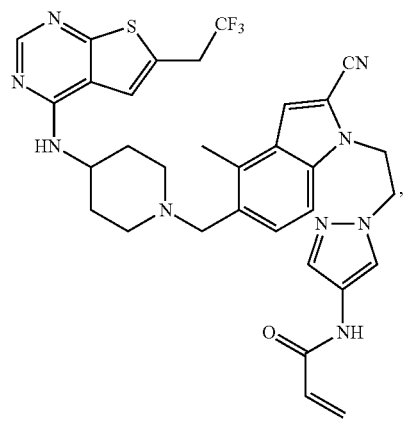
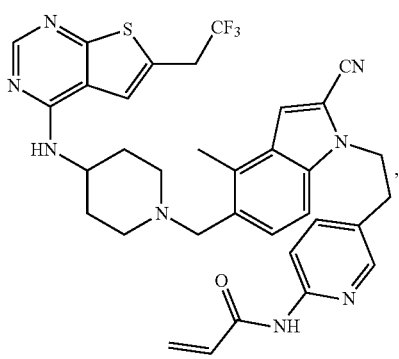

-continued
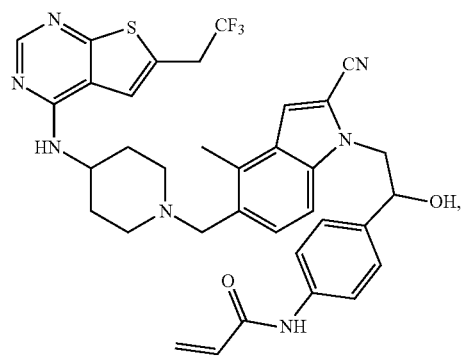
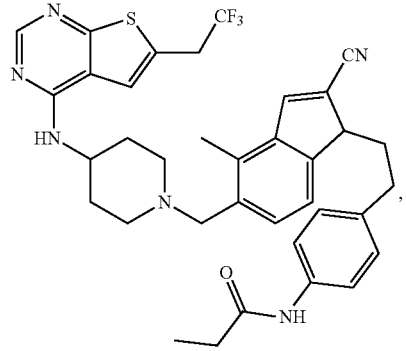
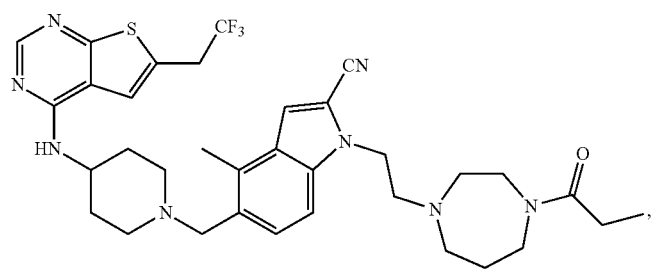
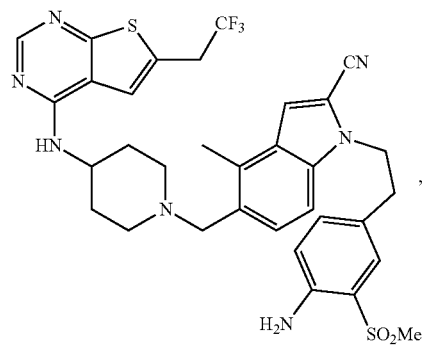
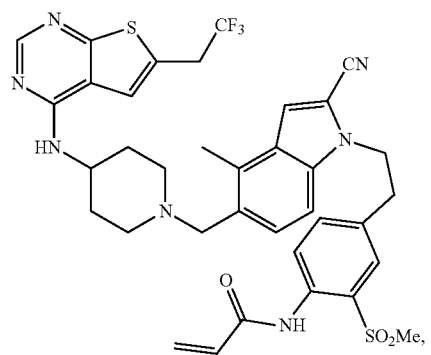
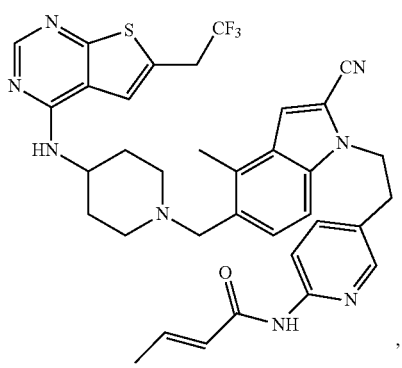
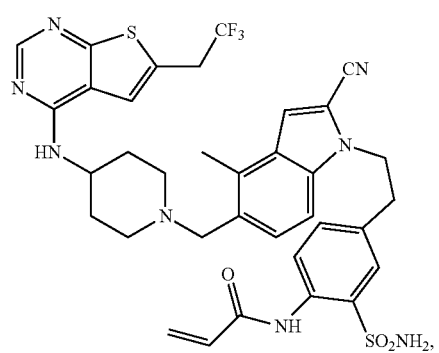
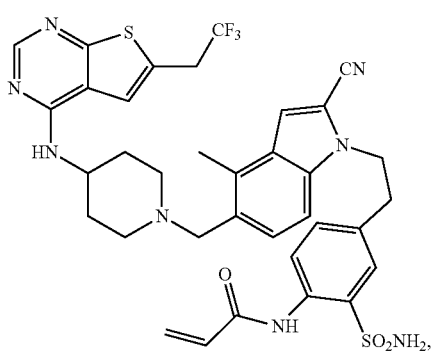

395
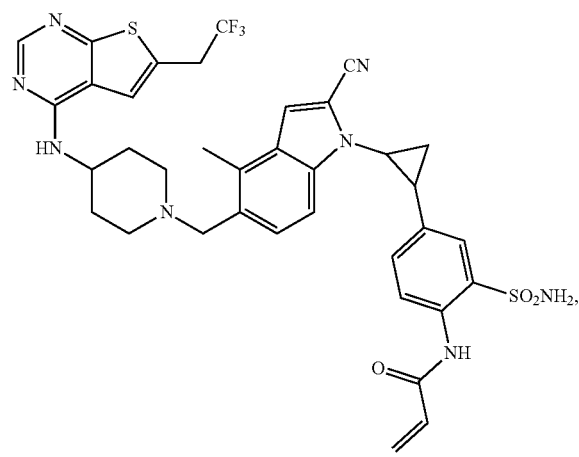
396
-continued
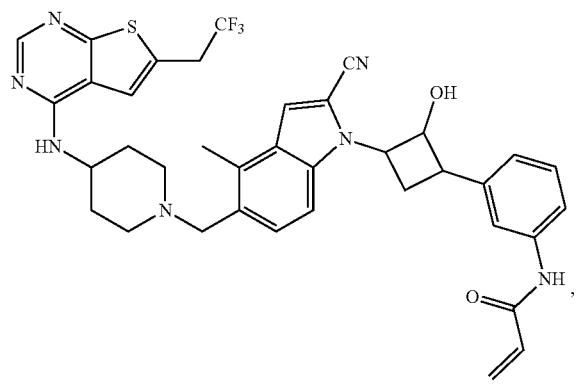
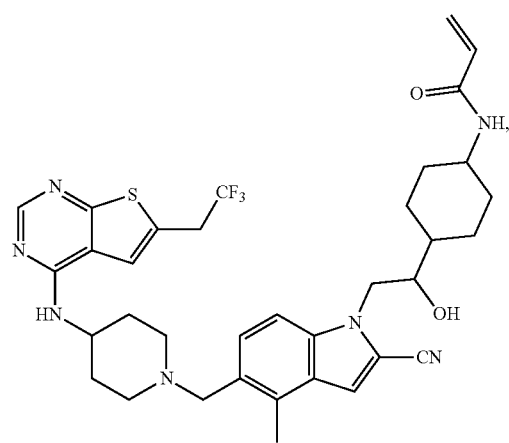
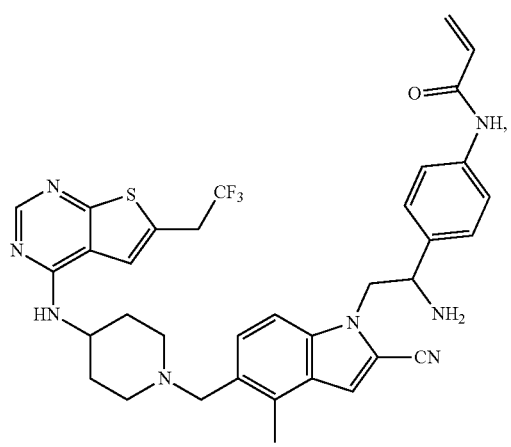
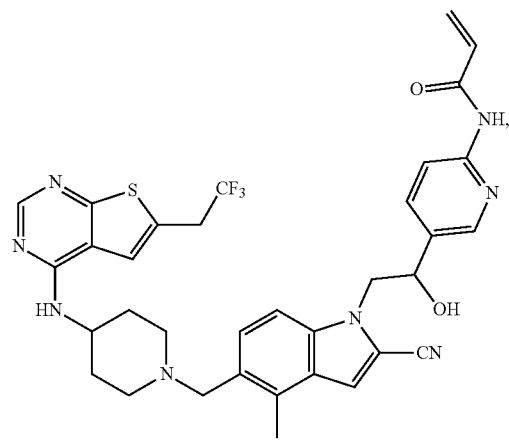
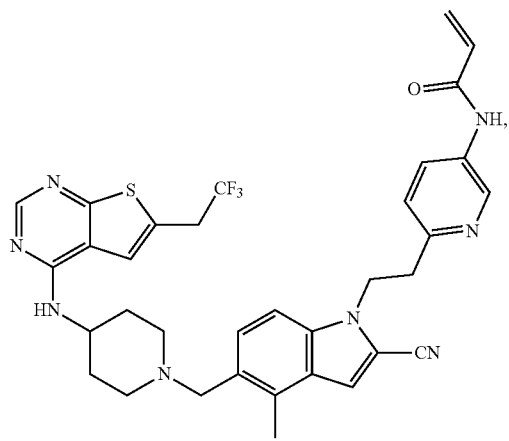

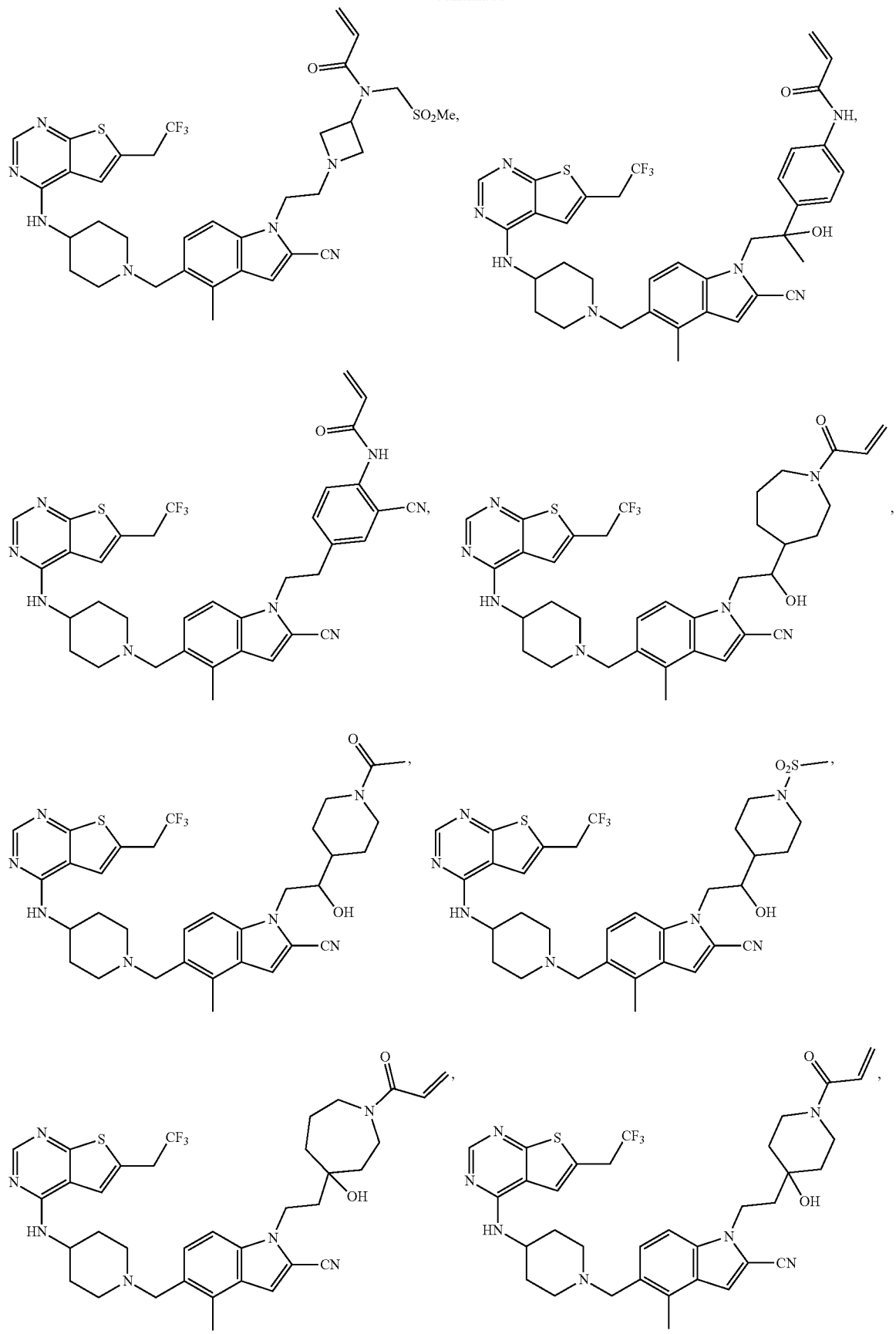

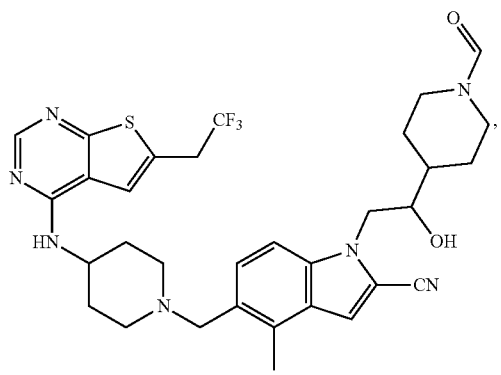
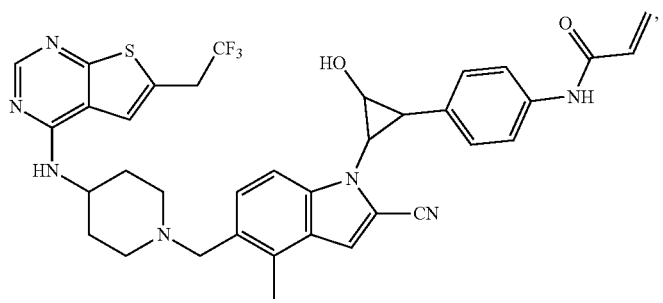
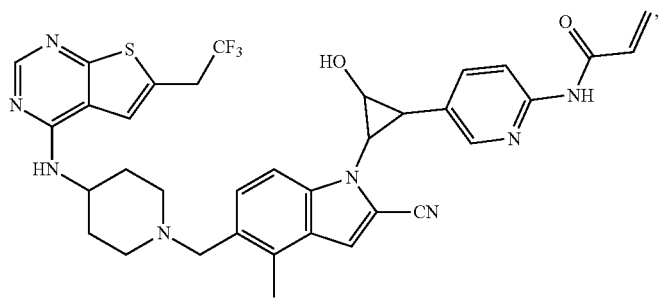
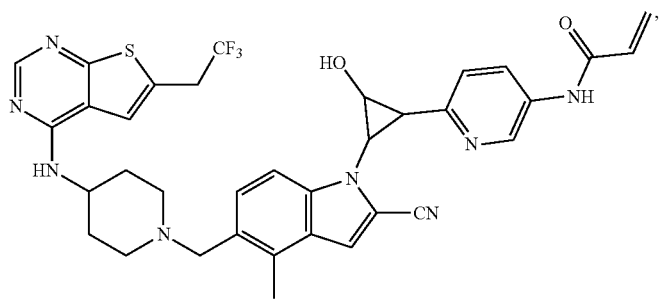
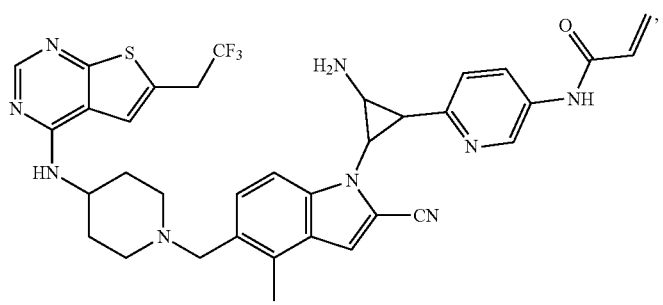

401
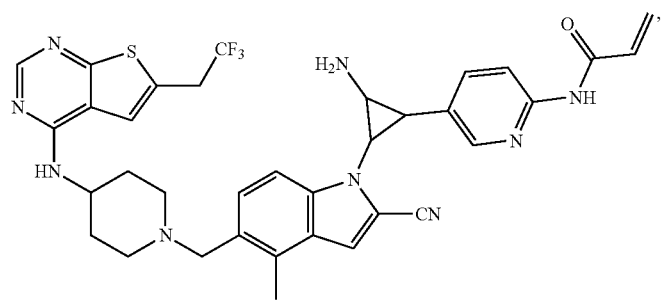
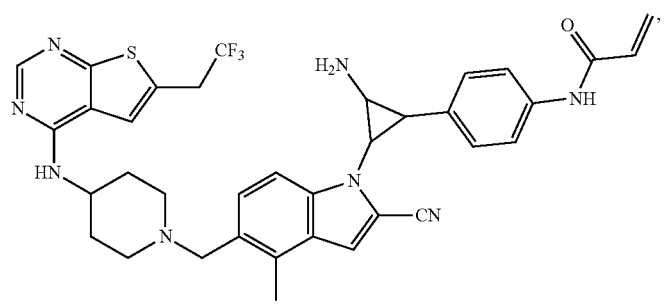
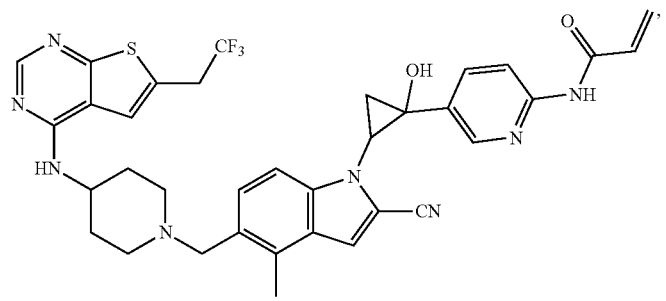
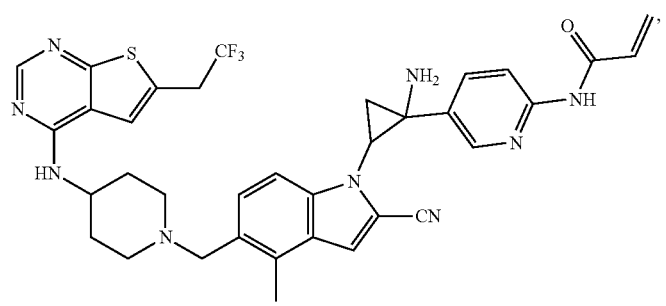
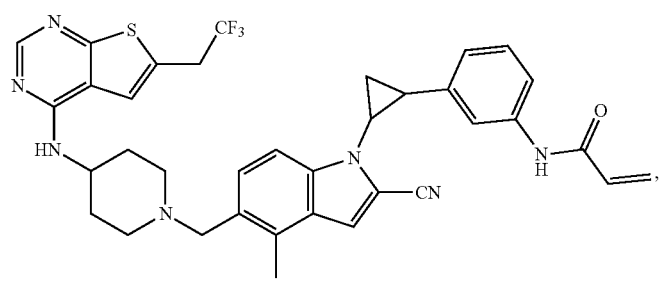
402
-continued

403
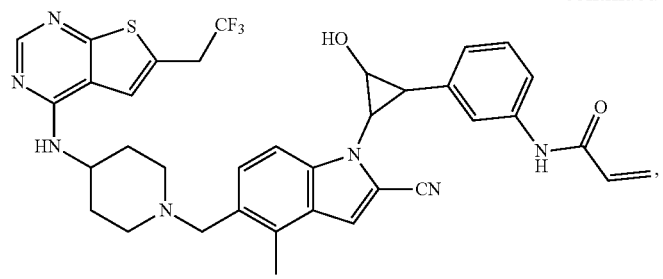
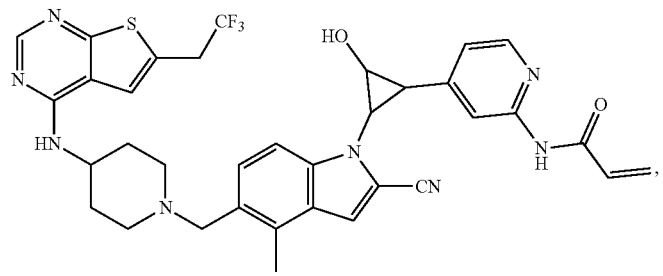
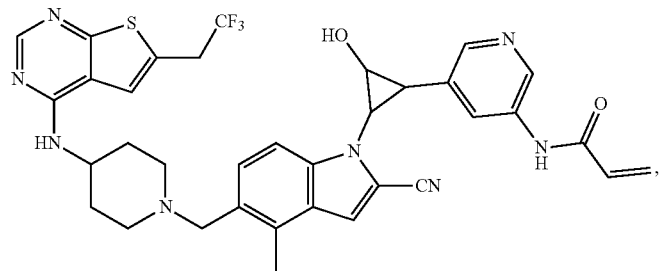
404
-continued
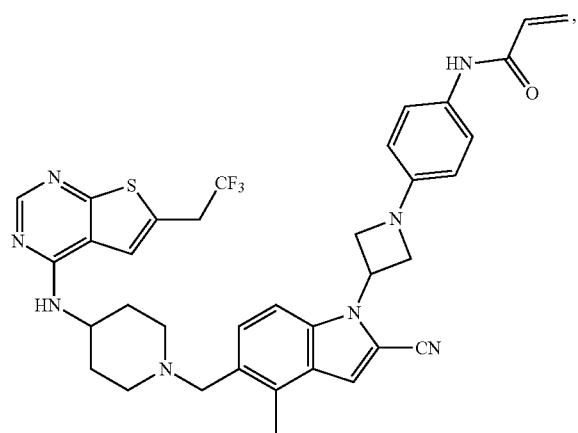
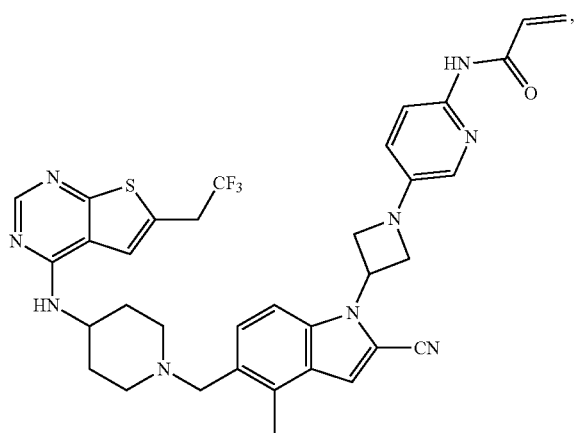
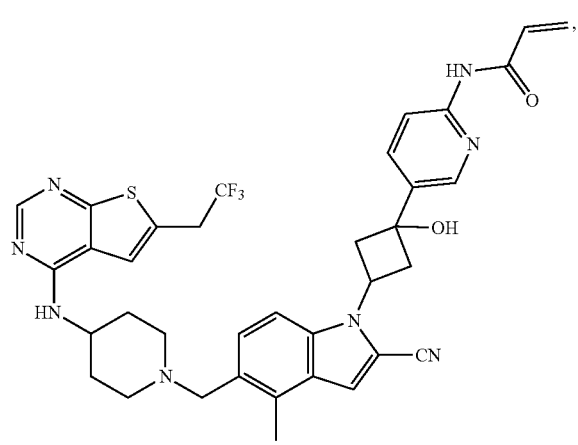
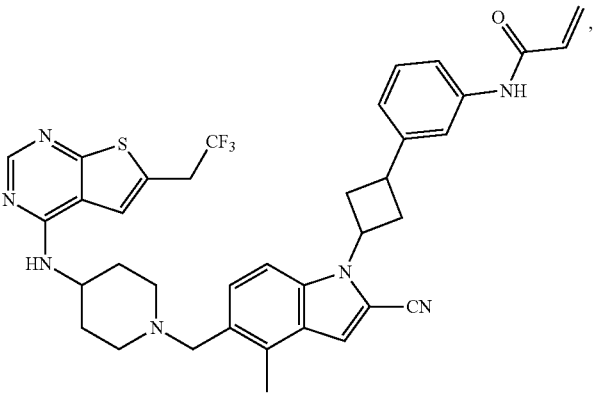

-continued
405 406
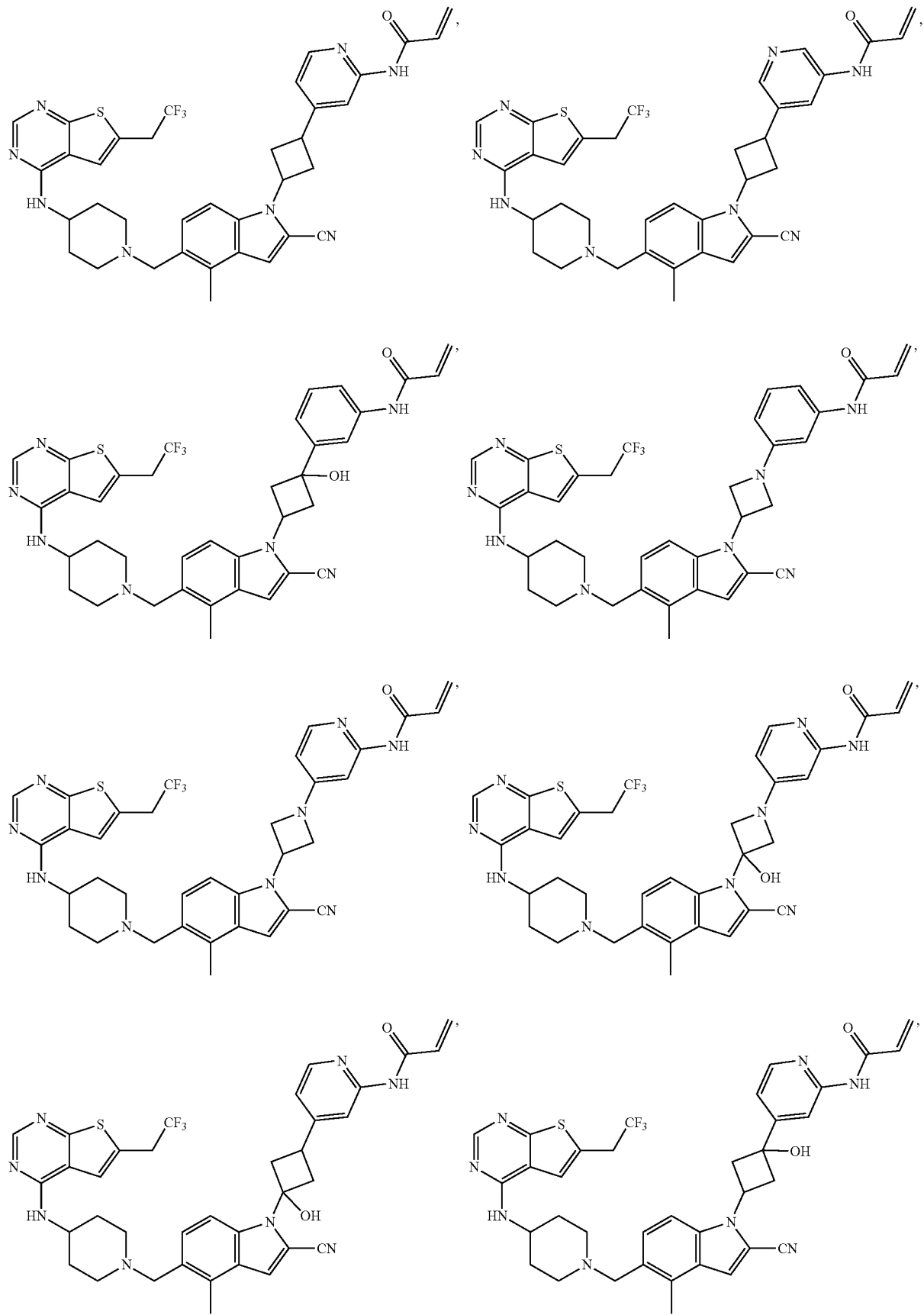

407
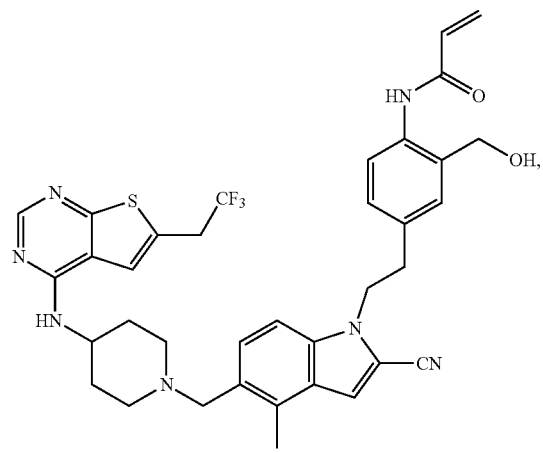
408
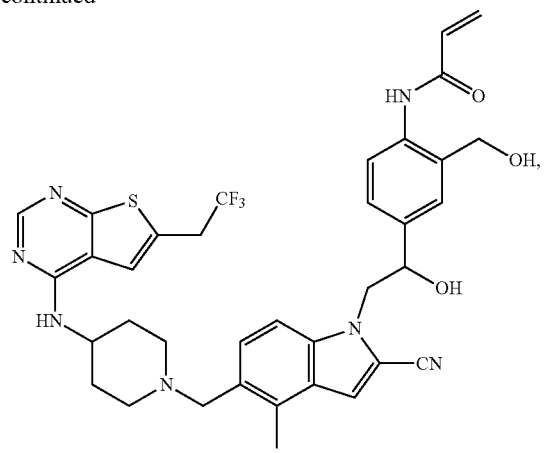
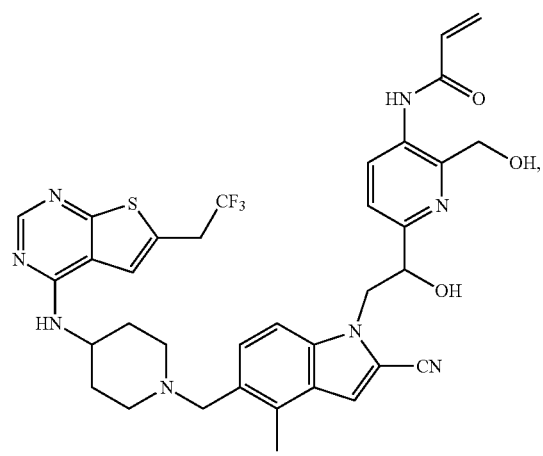
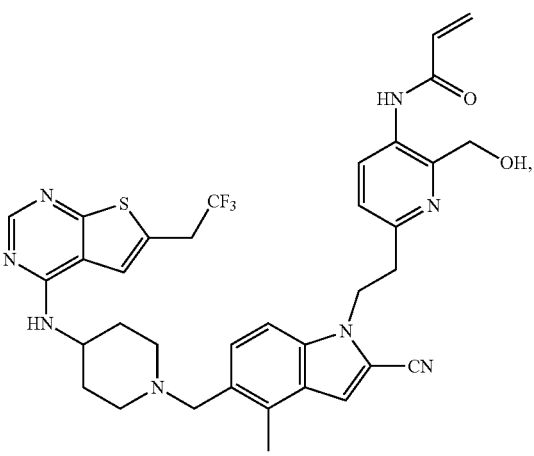
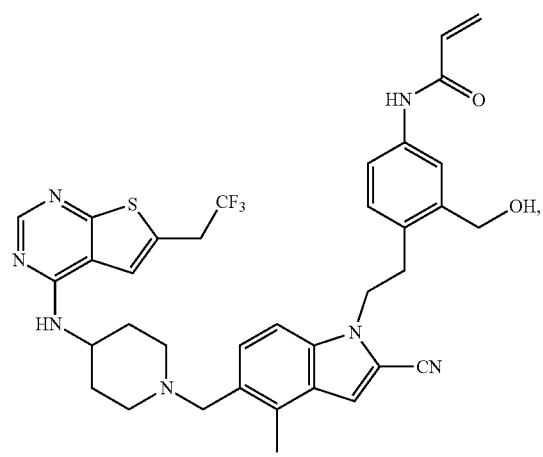
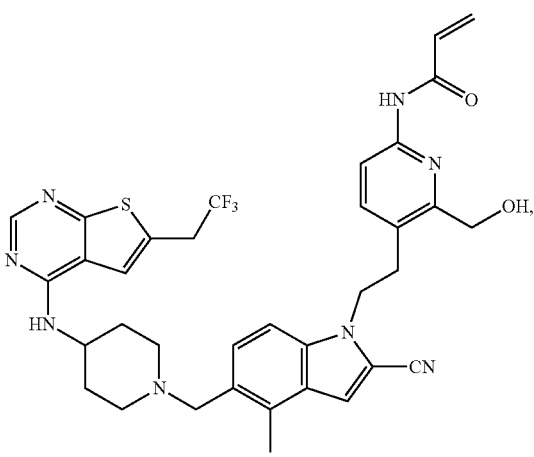

409
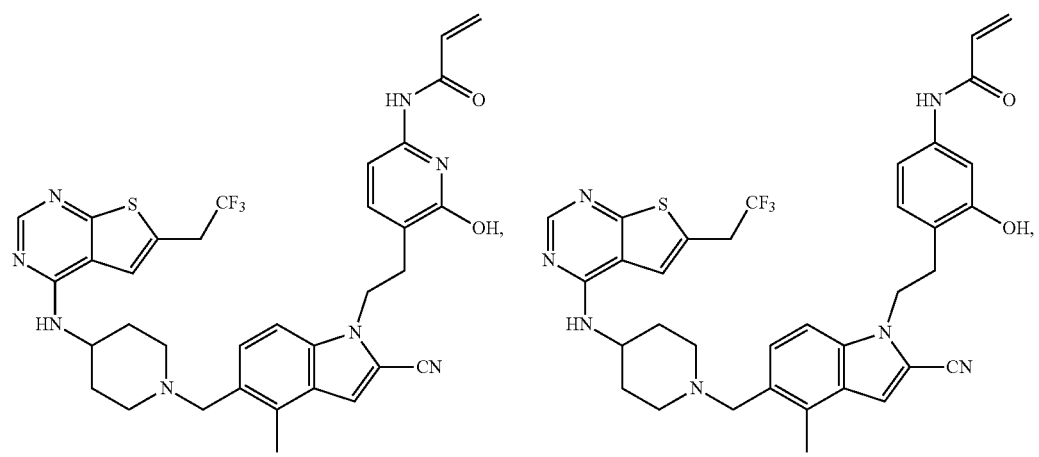
410
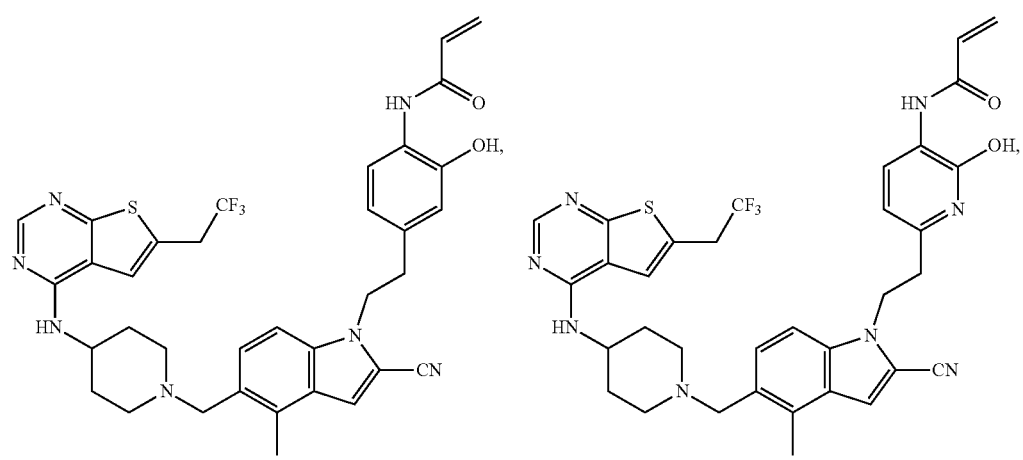
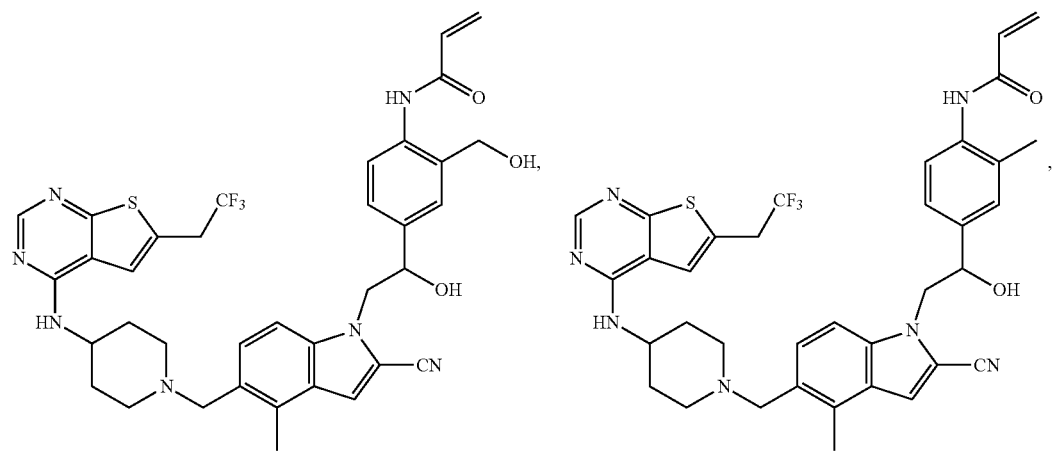

411
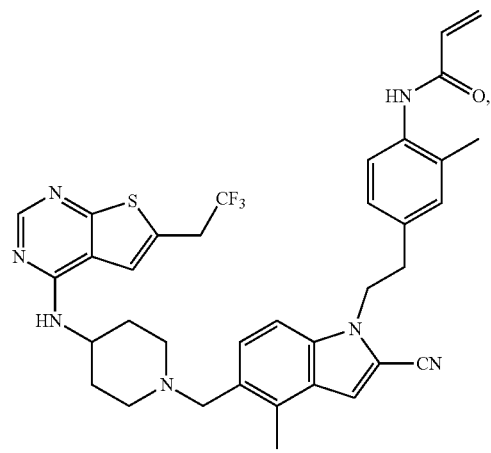
412
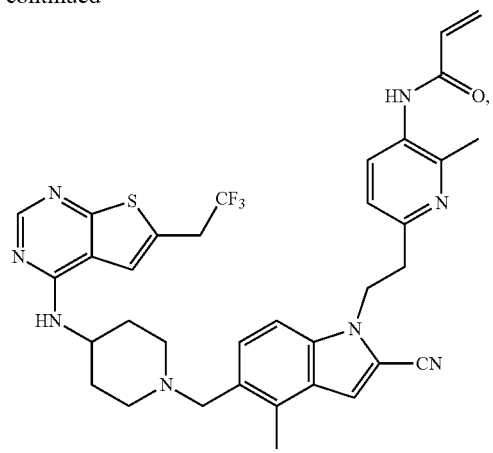
-continued
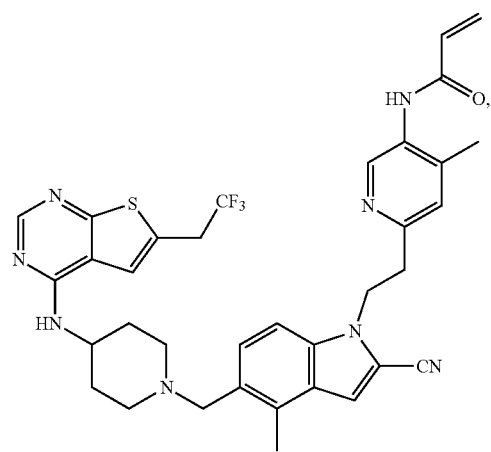
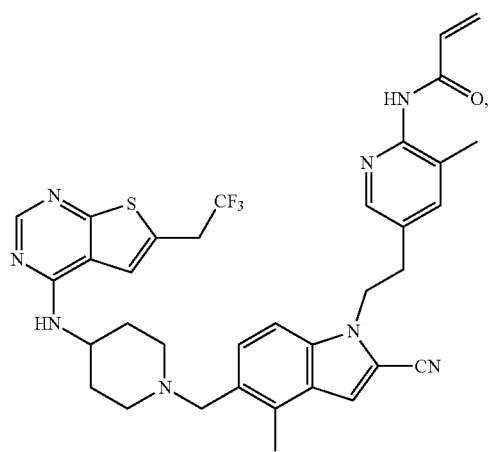
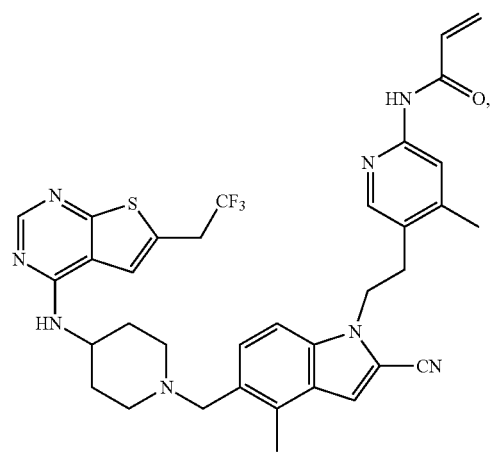
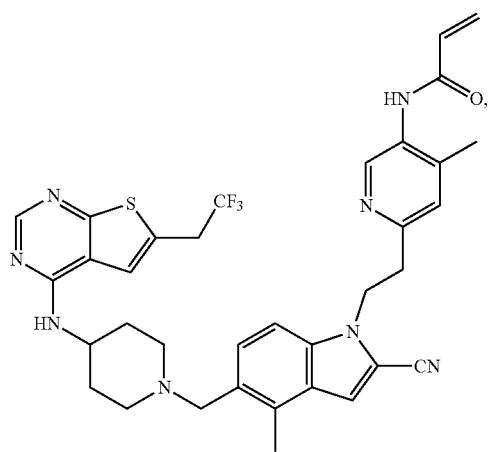

413
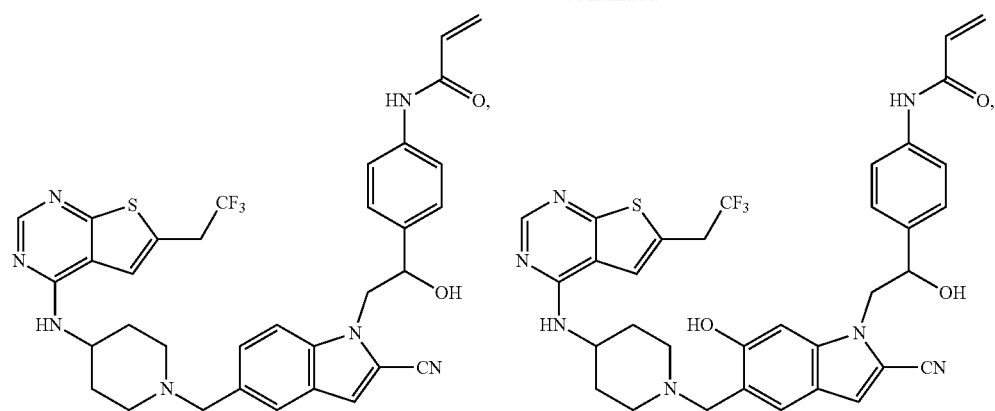
414
-continued
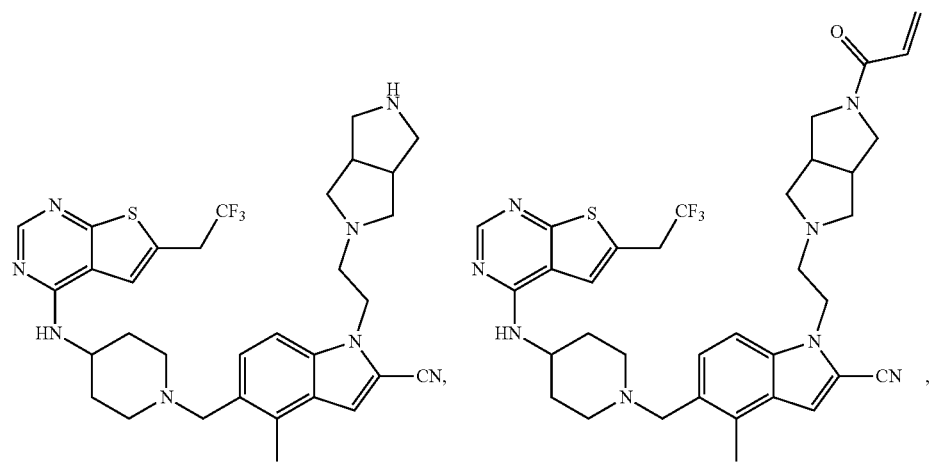
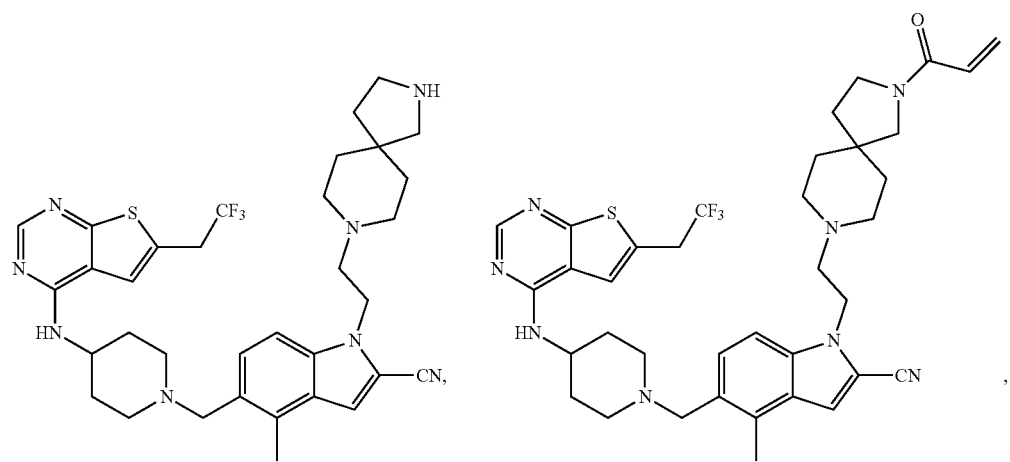

415
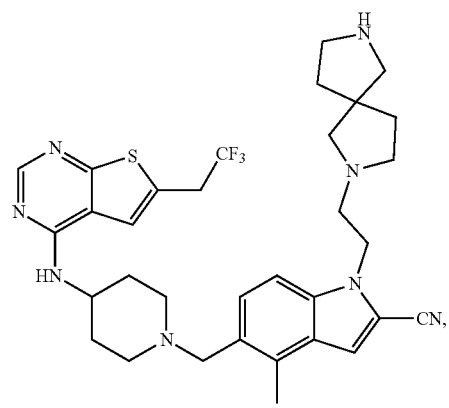
416
-continued
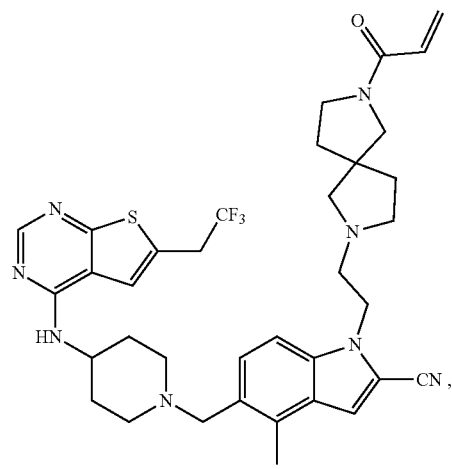
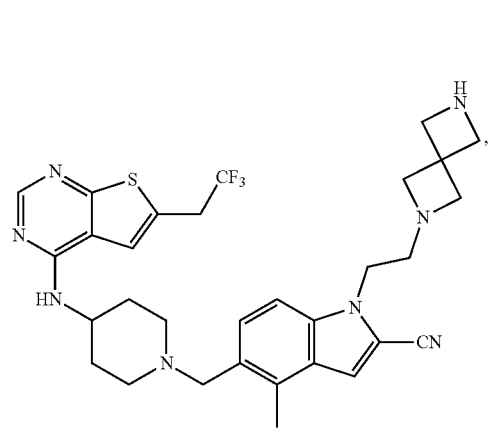
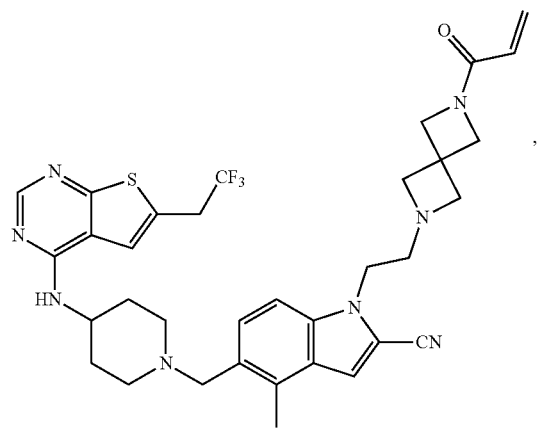
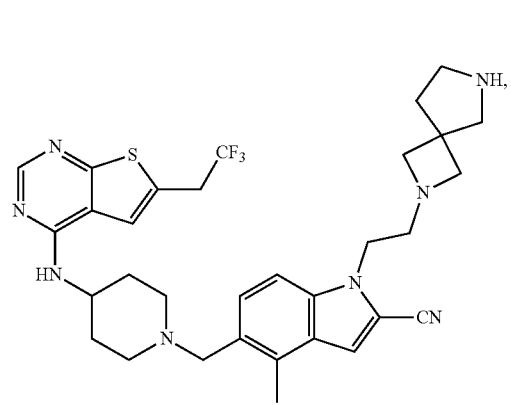
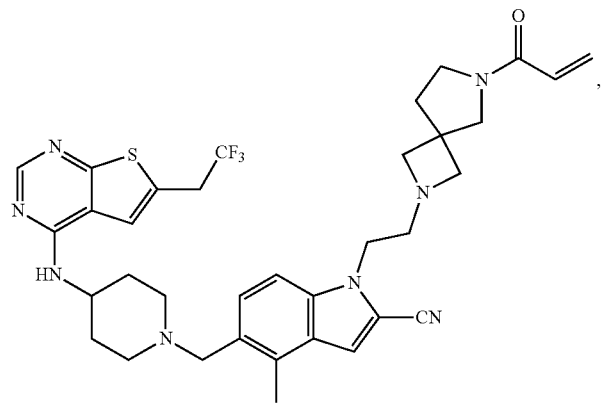

417
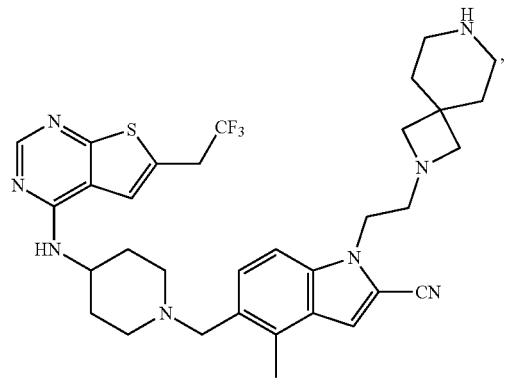
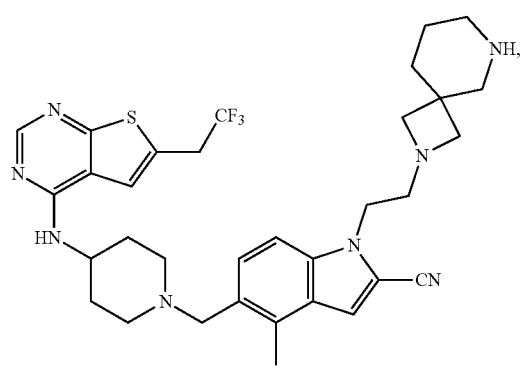
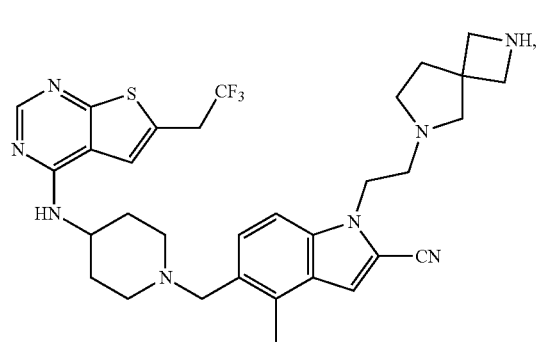
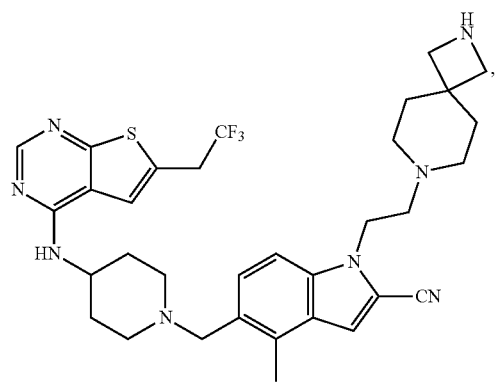
418
-continued
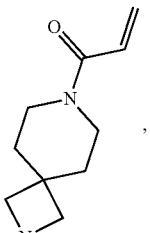
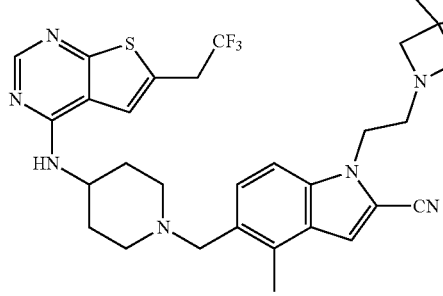
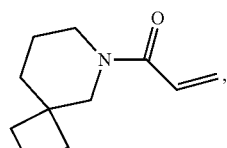
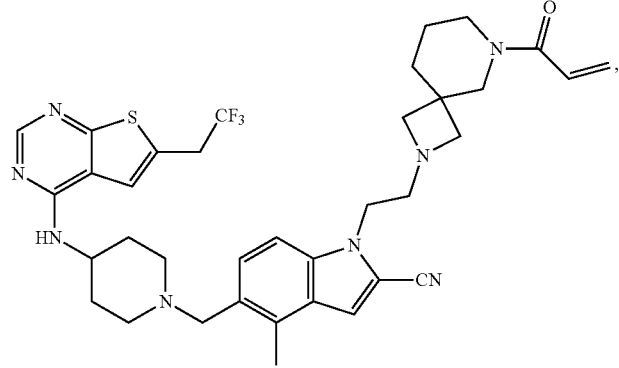
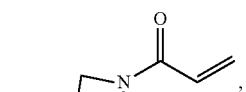
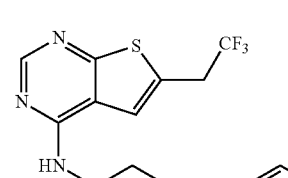
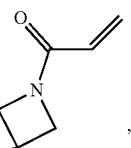
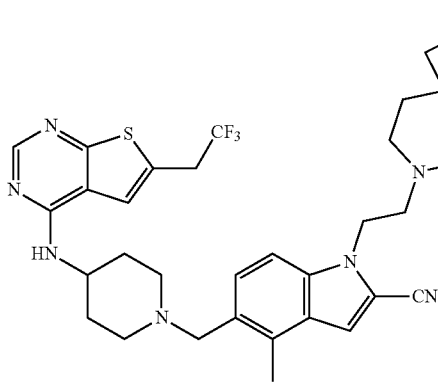

419
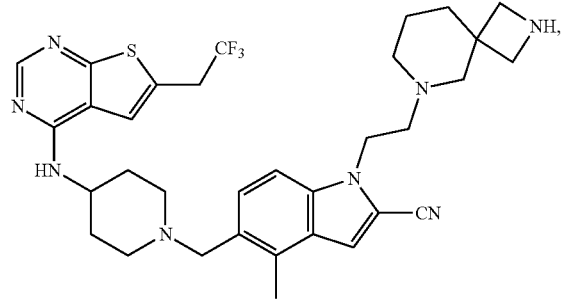
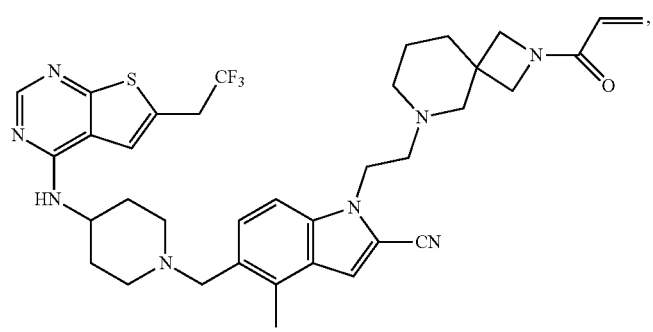
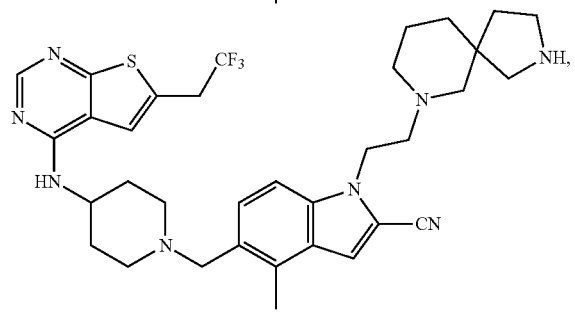
-continued
420
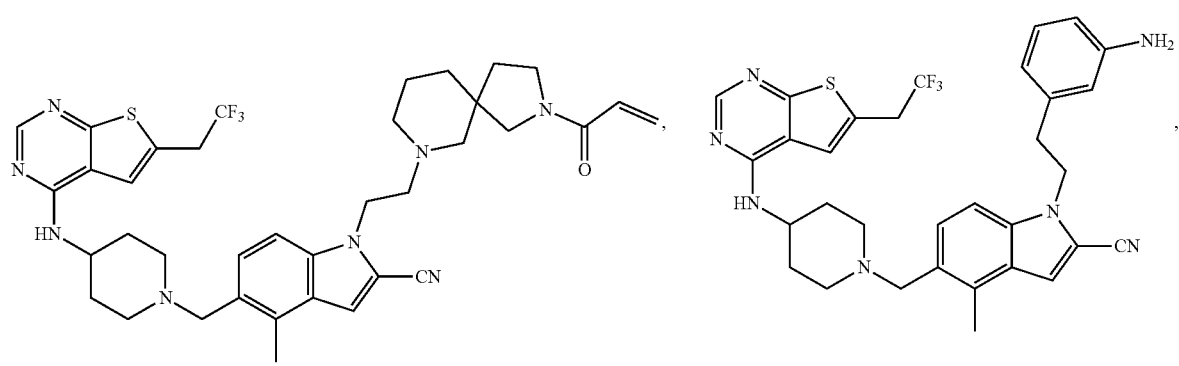
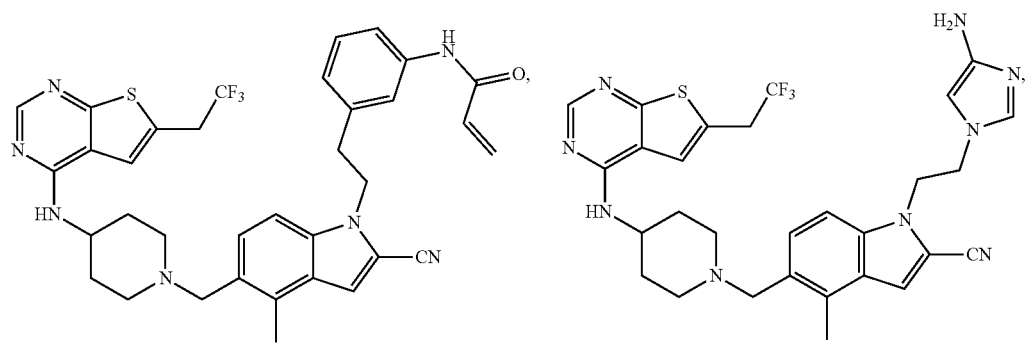

421 422
-continued
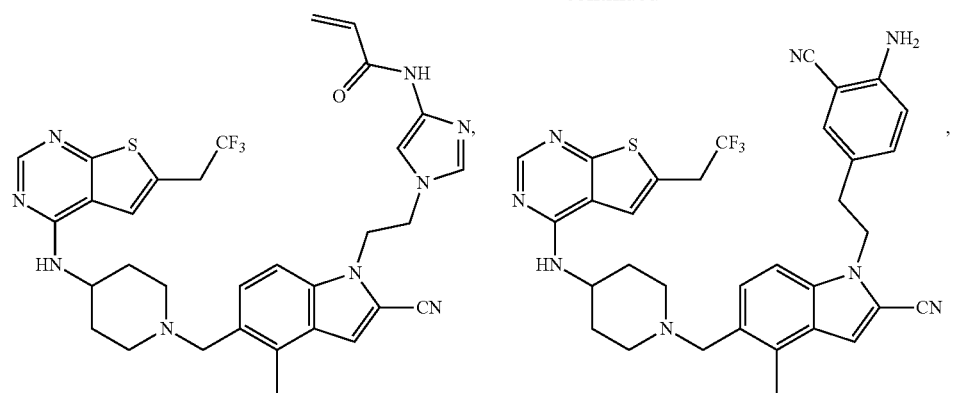
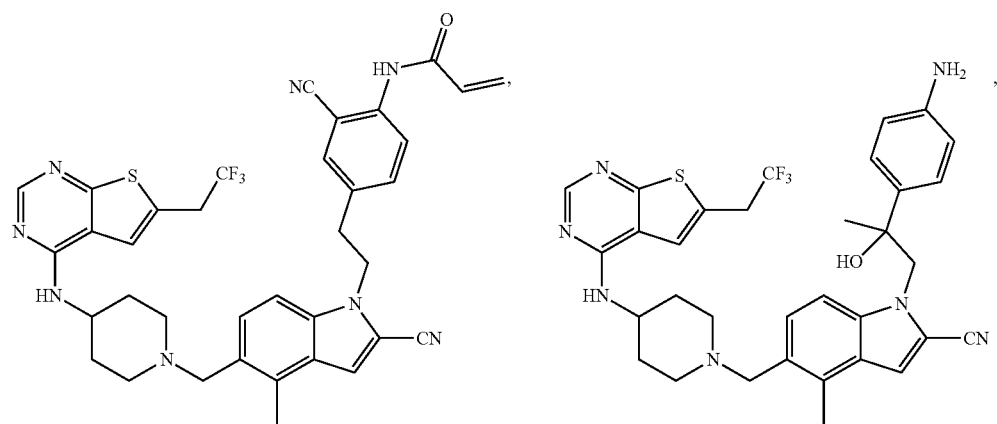
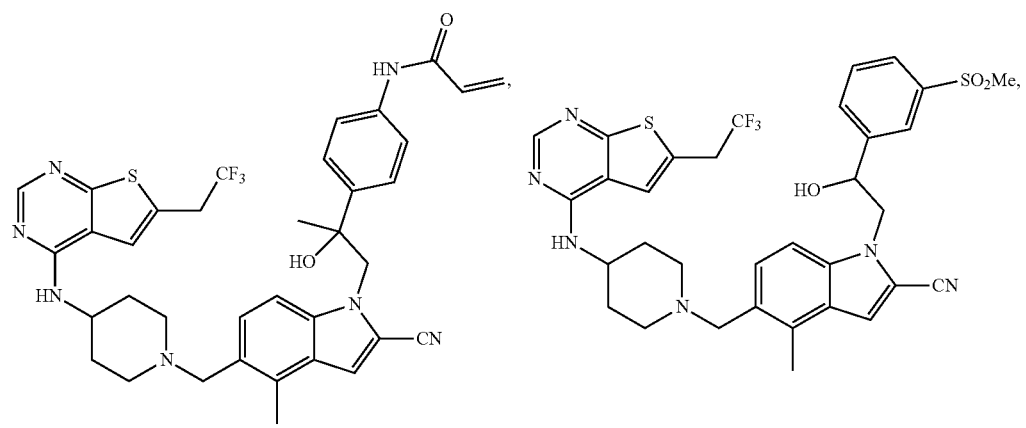
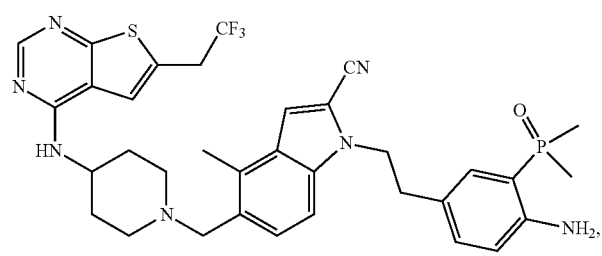

-continued
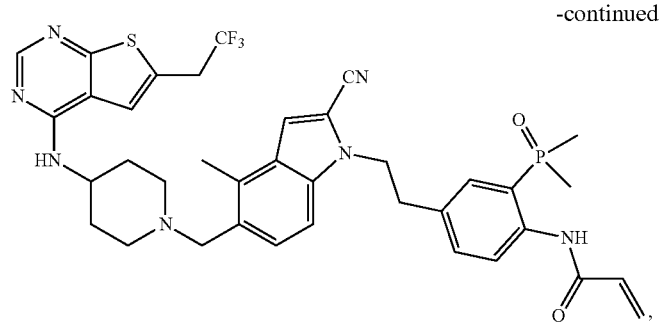
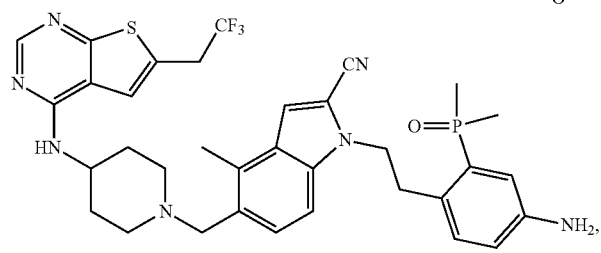
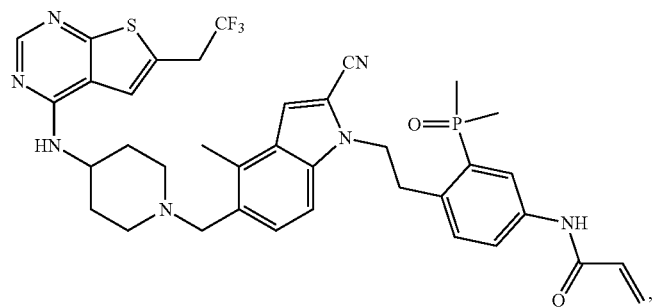
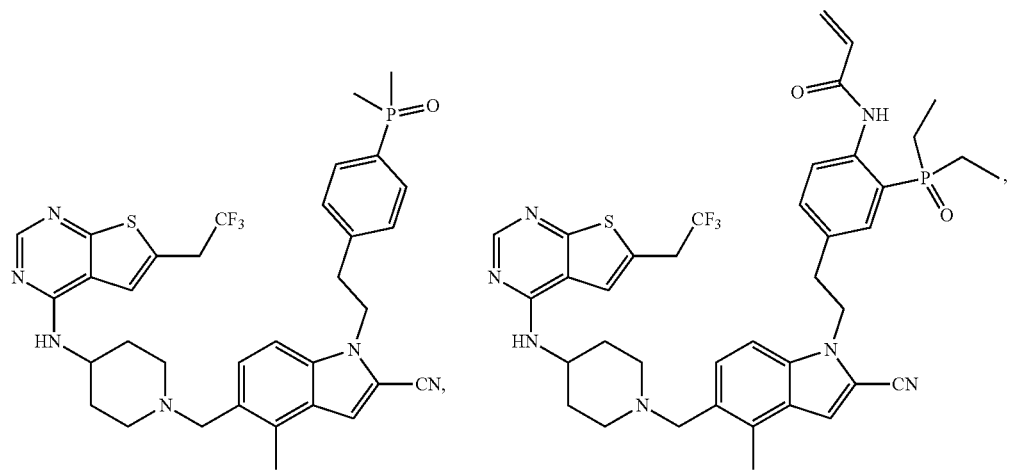
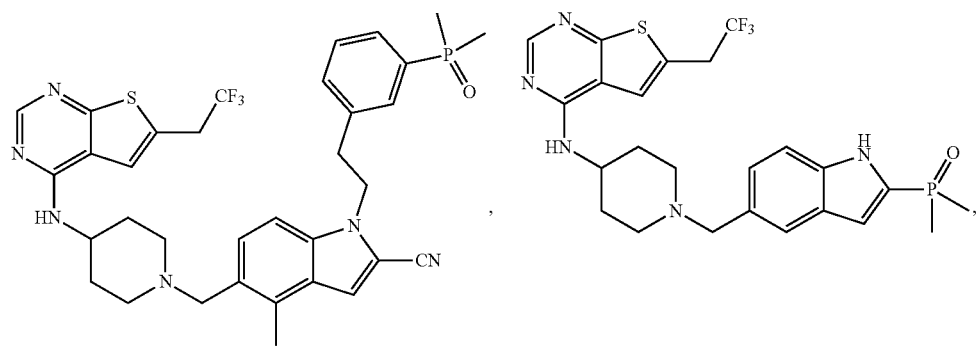

425
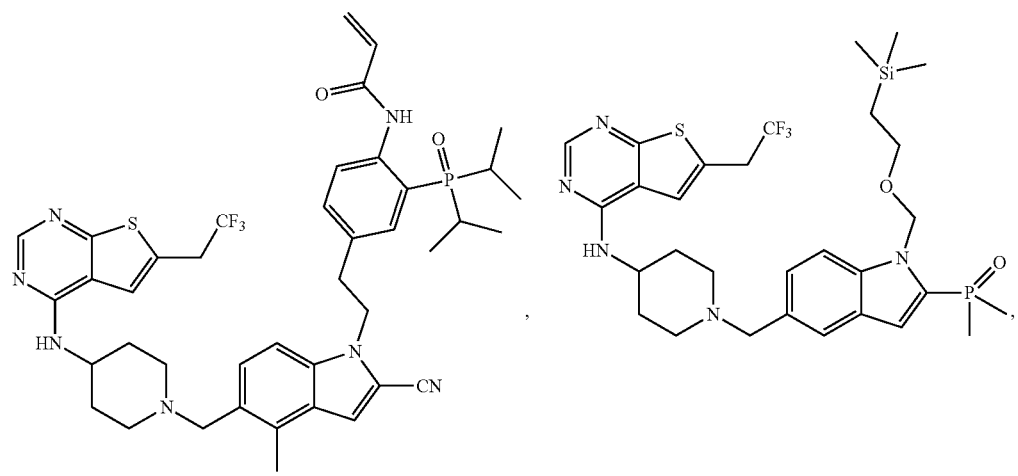
426
-continued
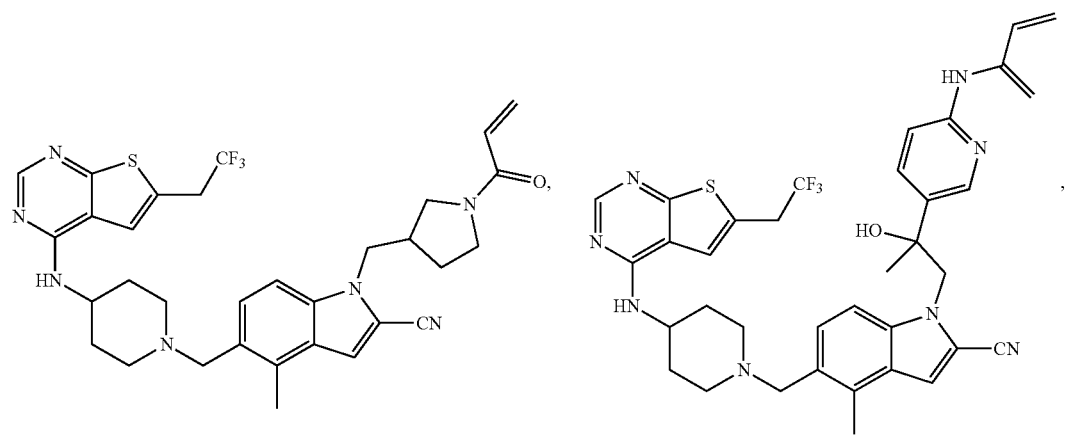
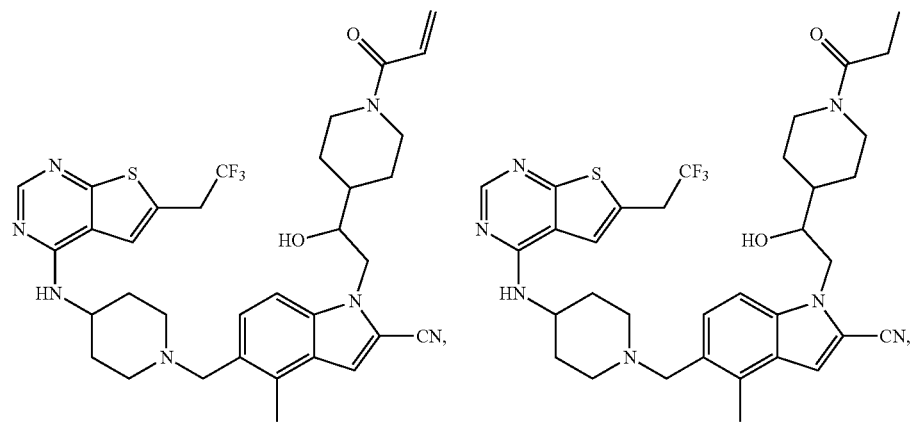

427
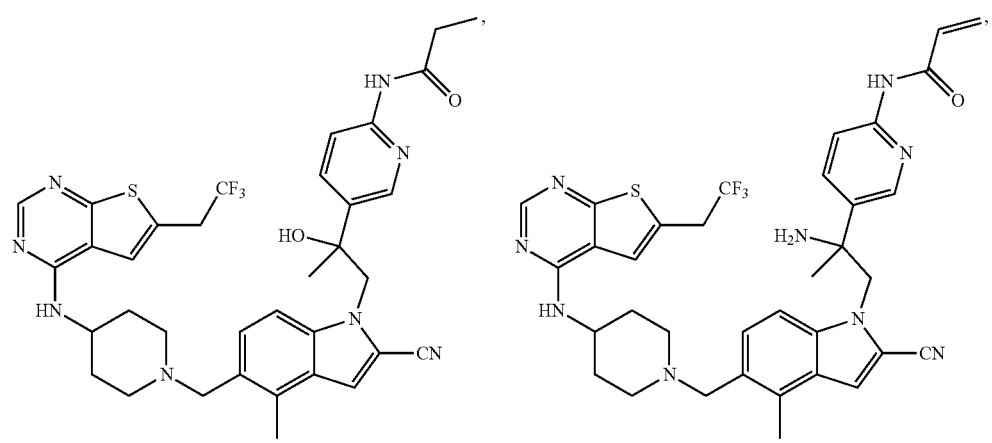
428
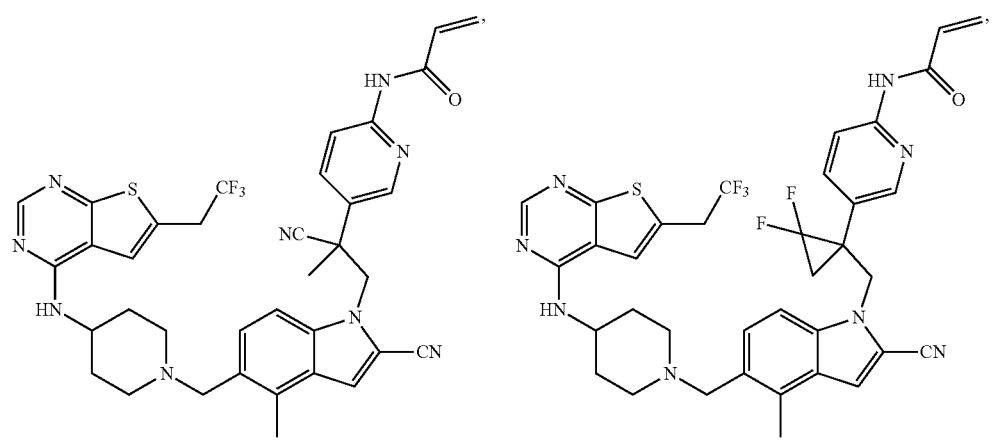
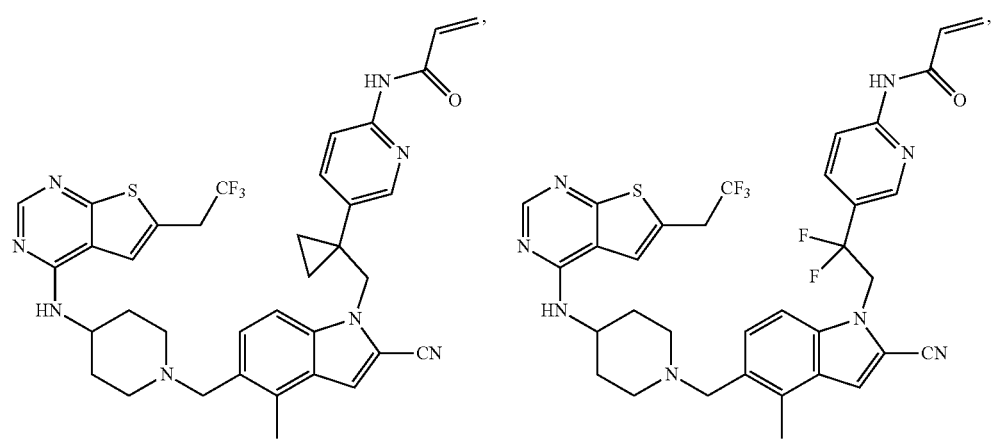
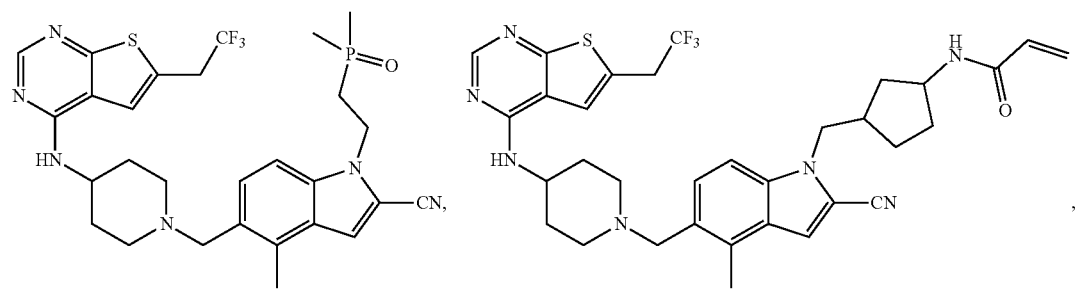

-continued
429        430
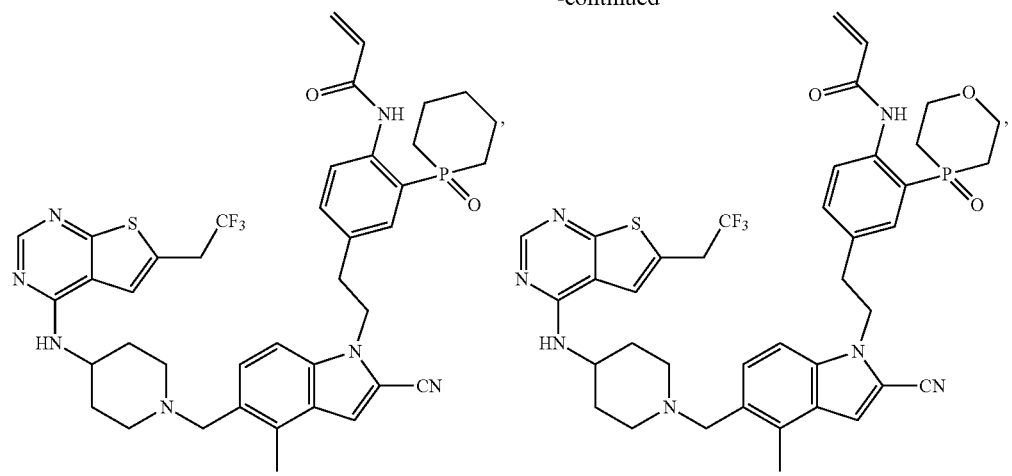
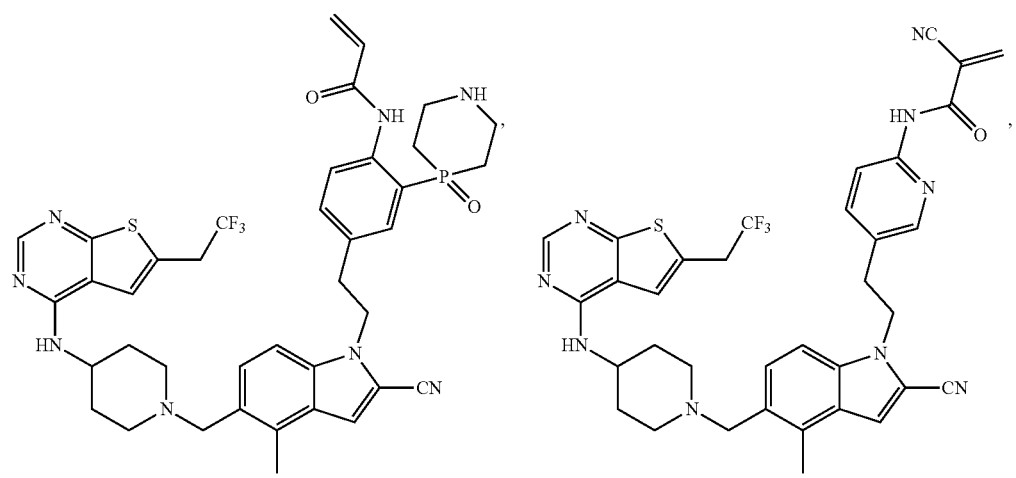
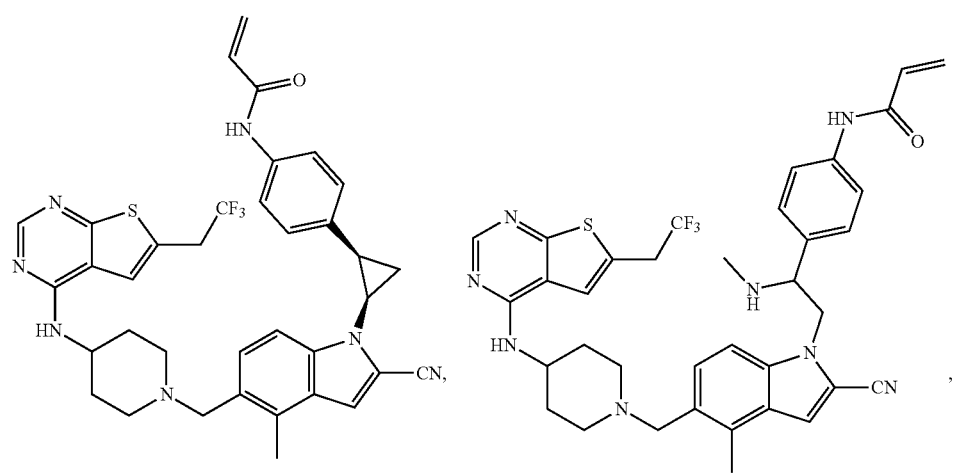

-continued
431
432
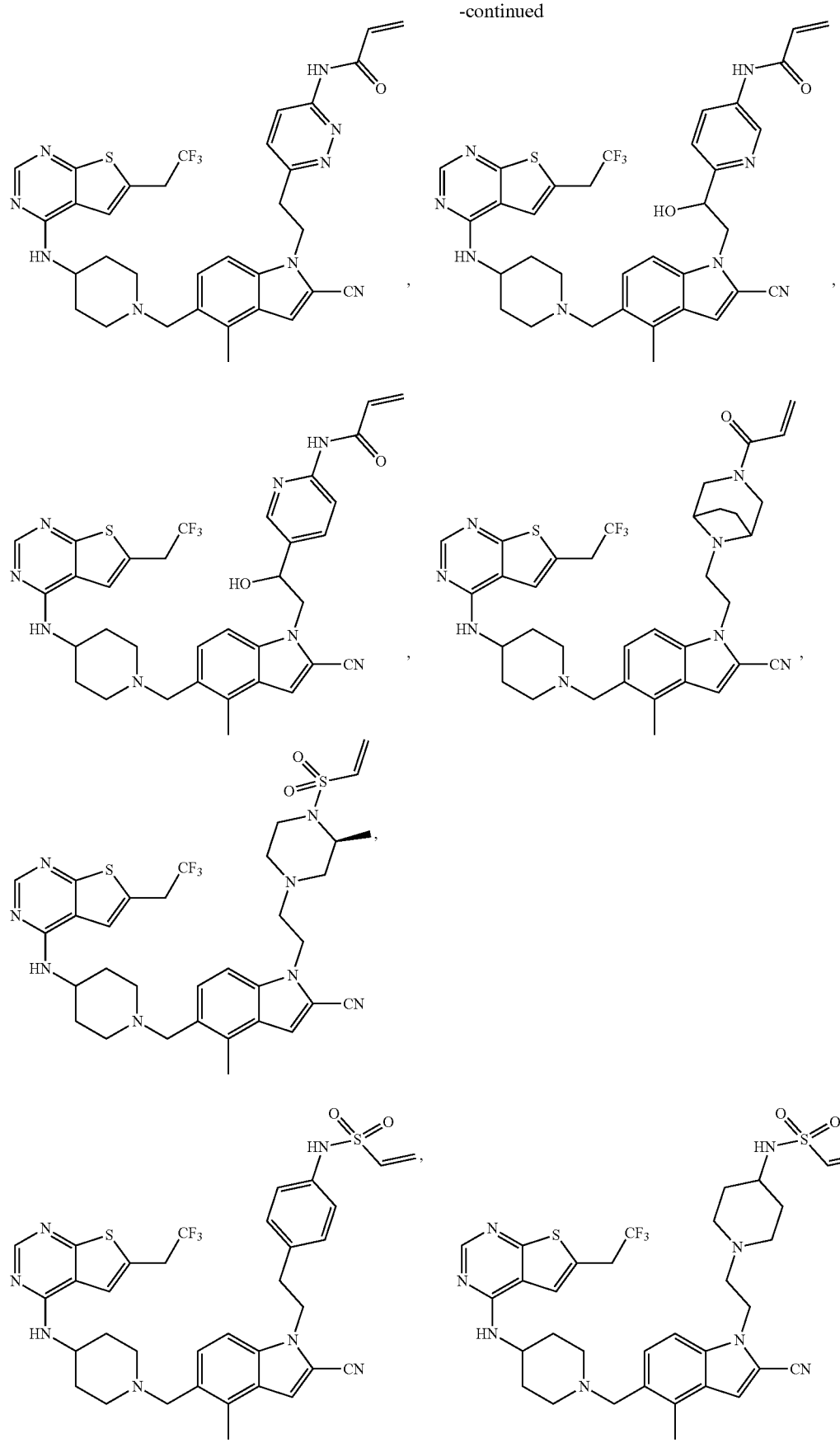

-continued
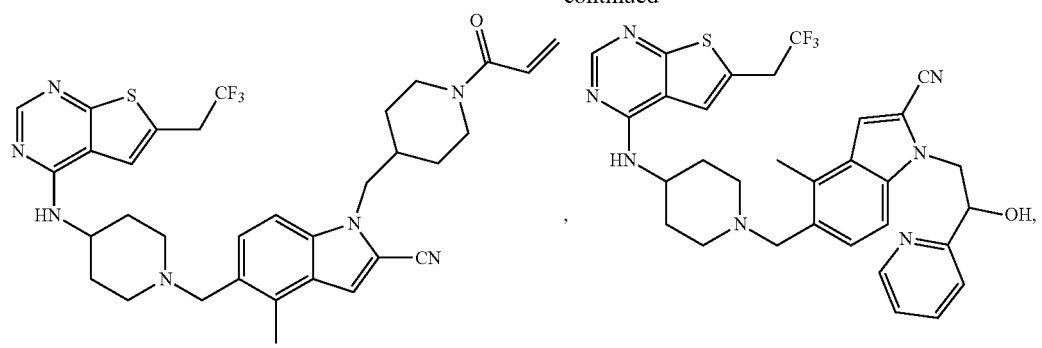
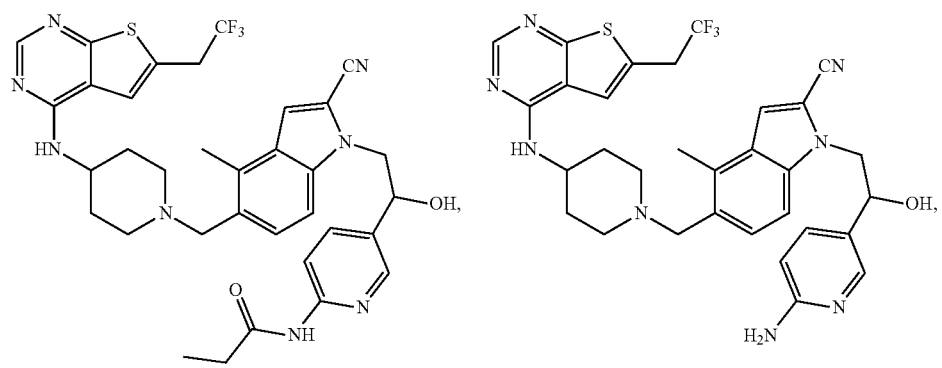
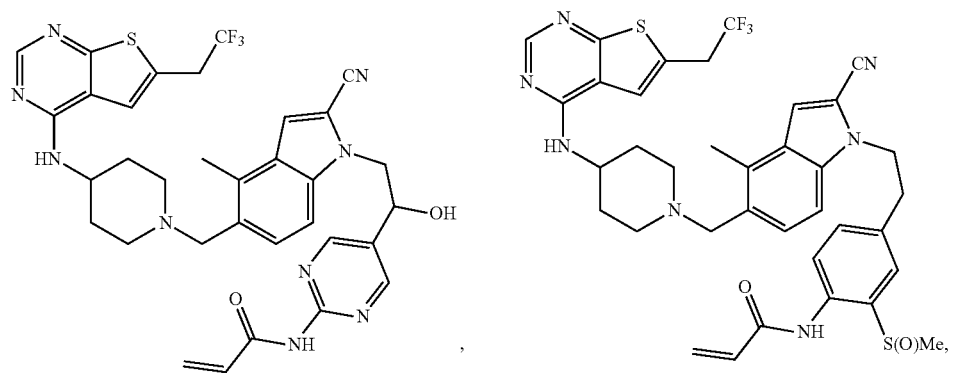
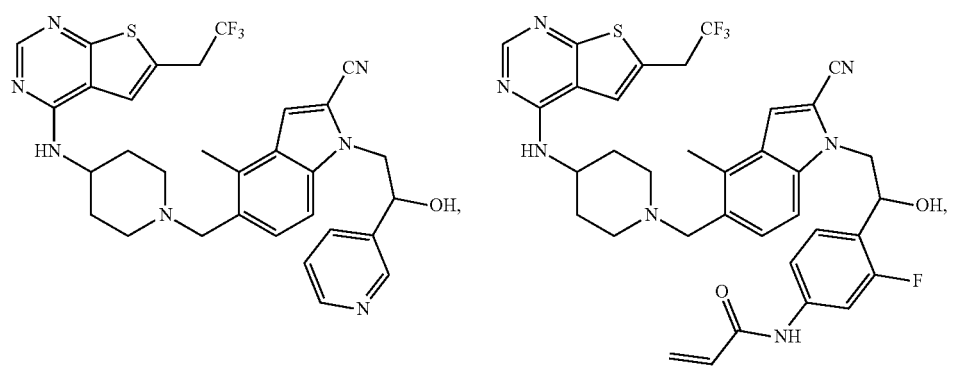

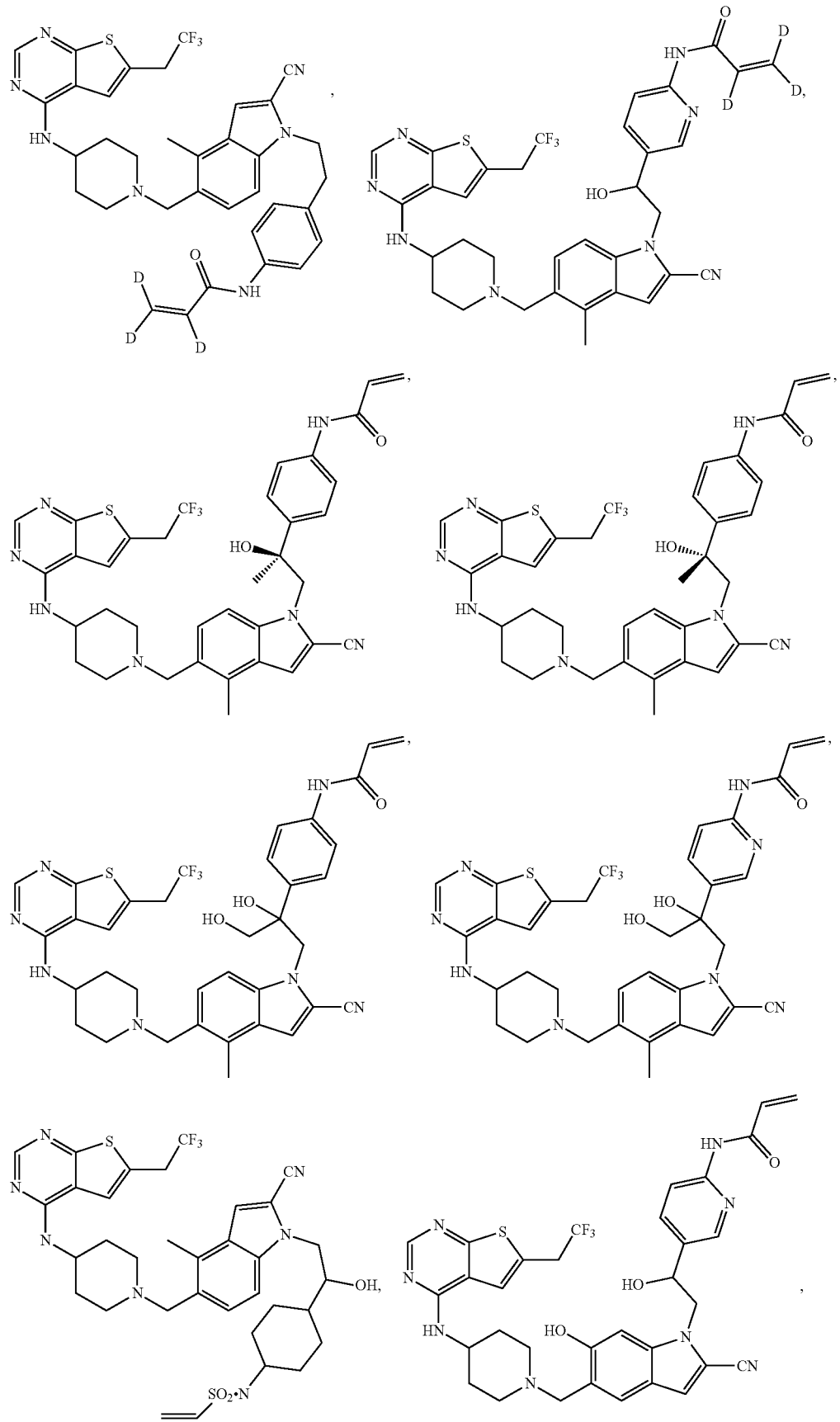

-continued
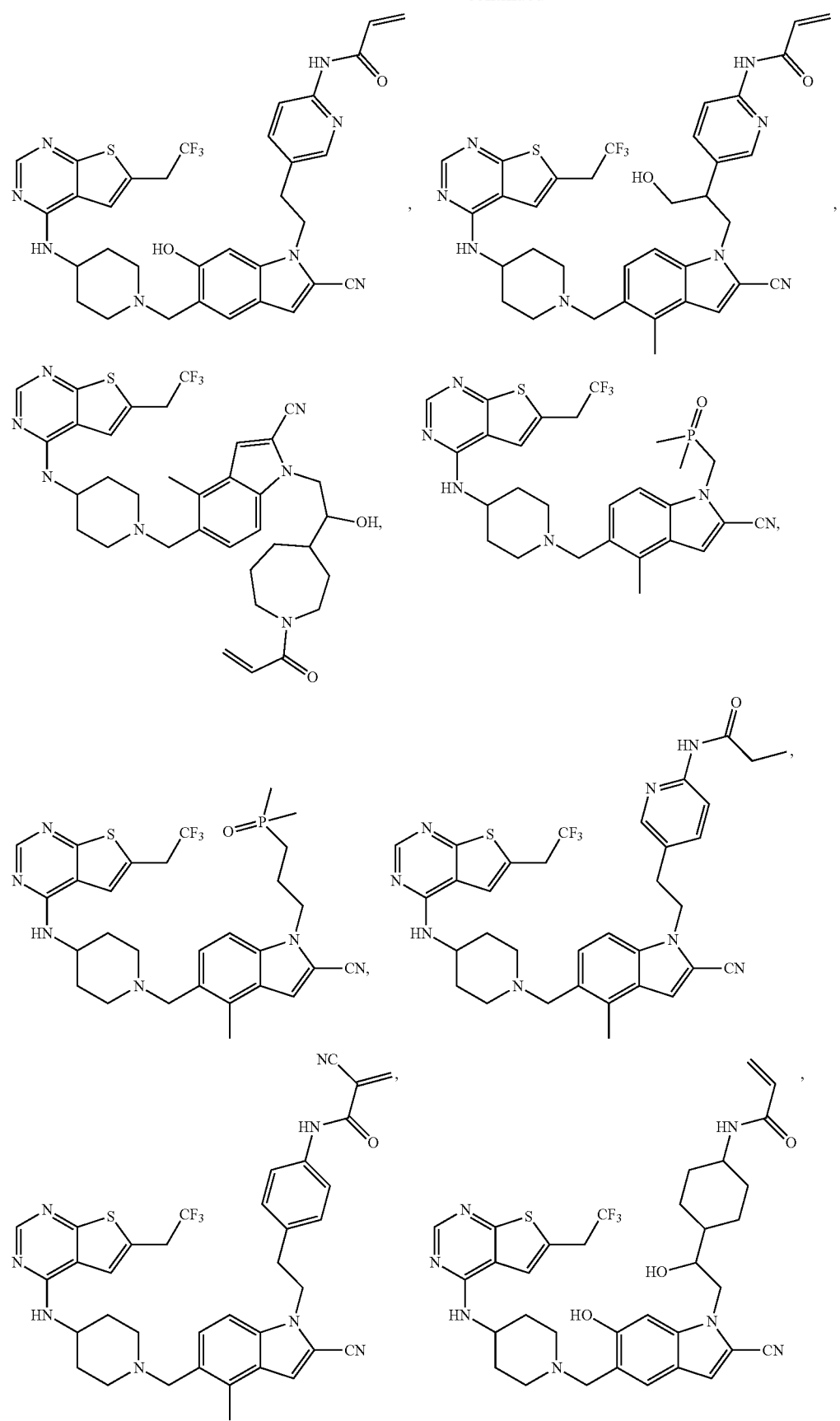

439
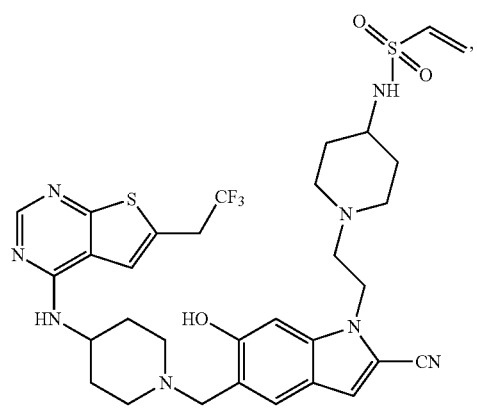
440
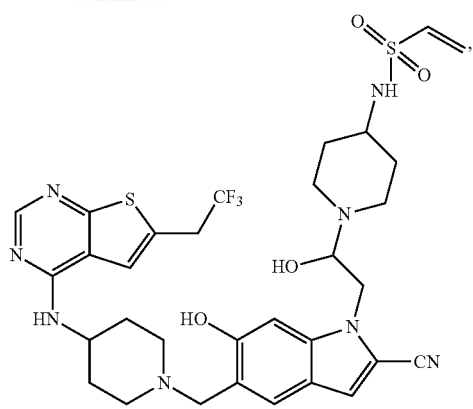
-continued
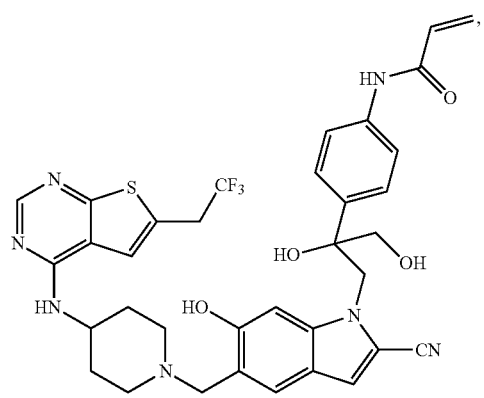
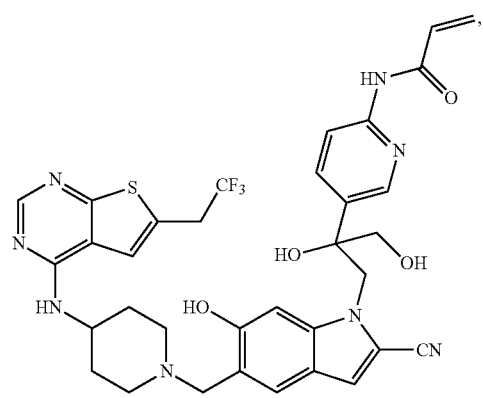
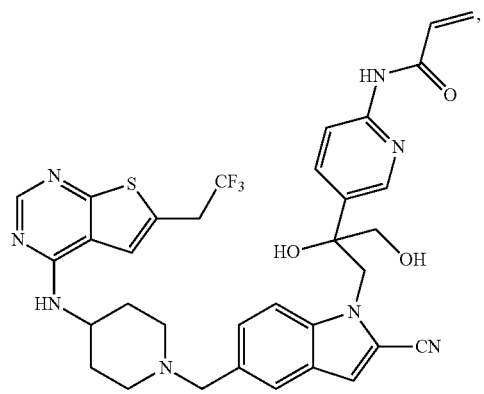
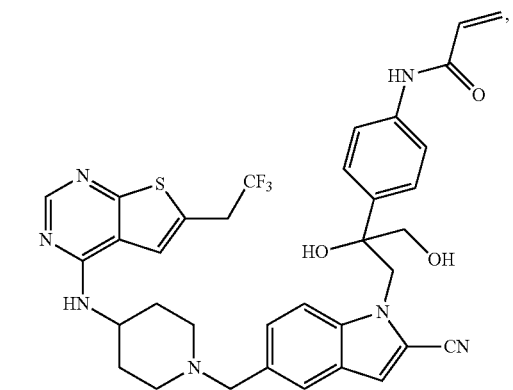

441

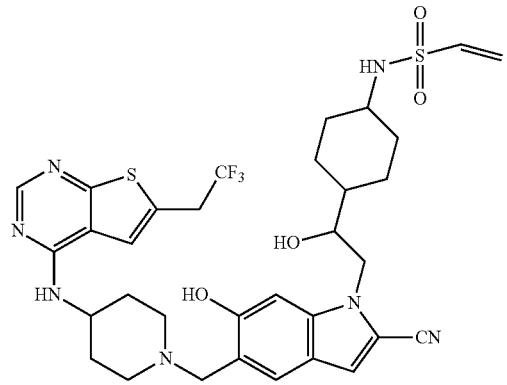

or a salt thereof.

19. A pharmaceutical composition, comprising a compound of claim 1, or a salt thereof, and a pharmaceutically acceptable carrier or excipient.

-continued

442

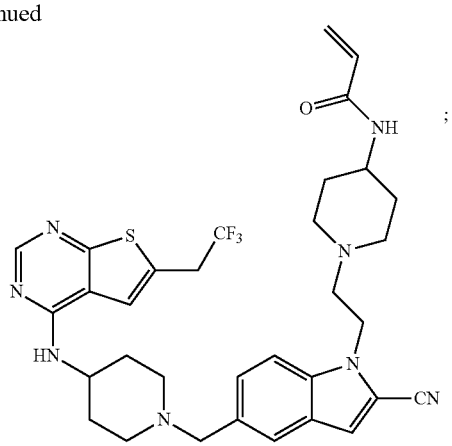

20. A method for the treatment of a disease, comprising administering a compound of claim 1, or a salt thereof, to a subject suffering from said disease, wherein said disease is leukemia, hematologic malignancies, solid tumor cancer, glioma, or diabetes.

* * * * *

SEQUENCE LISTING

<160> NUMBER OF SEQ ID NOS: 3

<210> SEQ ID NO 1
<211> LENGTH: 615
<212> TYPE: PRT
<213> ORGANISM: Homo sapiens

<400> SEQUENCE: 1

| | | | | | | | | | | | | | | |
|---|---|---|---|---|---|---|---|---|---|---|---|---|---|---|
| Met | Gly | Leu | Lys | Ala | Ala | Gln | Lys | Thr | Leu | Phe | Pro | Leu | Arg | Ser | Ile |
| 1 | | | | 5 | | | | | 10 | | | | | 15 | |
| Asp | Asp | Val | Val | Arg | Leu | Phe | Ala | Ala | Glu | Leu | Gly | Arg | Glu | Glu | Pro |
| | | | 20 | | | | | 25 | | | | | 30 | | |
| Asp | Leu | Val | Leu | Leu | Ser | Leu | Val | Leu | Gly | Phe | Val | Glu | His | Phe | Leu |
| | | | | 35 | | | | | 40 | | | | | 45 | |
| Ala | Val | Asn | Arg | Val | Ile | Pro | Thr | Asn | Val | Pro | Glu | Leu | Thr | Phe | Gln |
| | | 50 | | | | | 55 | | | | | 60 | | | |
| Pro | Ser | Pro | Ala | Pro | Asp | Pro | Pro | Gly | Gly | Leu | Thr | Tyr | Phe | Pro | Val |
| 65 | | | | | 70 | | | | | 75 | | | | | 80 |
| Ala | Asp | Leu | Ser | Ile | Ile | Ala | Ala | Leu | Tyr | Ala | Arg | Phe | Thr | Ala | Gln |
| | | | | 85 | | | | | 90 | | | | | 95 | |
| Ile | Arg | Gly | Ala | Val | Asp | Leu | Ser | Leu | Tyr | Pro | Arg | Glu | Gly | Gly | Val |
| | | | | 100 | | | | | 105 | | | | | 110 | |
| Ser | Ser | Arg | Glu | Leu | Val | Lys | Lys | Val | Ser | Asp | Val | Ile | Trp | Asn | Ser |
| | | | | 115 | | | | | 120 | | | | | 125 | |
| Leu | Ser | Arg | Ser | Tyr | Phe | Lys | Asp | Arg | Ala | His | Ile | Gln | Ser | Leu | Phe |
| | | 130 | | | | | 135 | | | | | 140 | | | |
| Ser | Phe | Ile | Thr | Gly | Trp | Ser | Pro | Val | Gly | Thr | Lys | Leu | Asp | Ser | Ser |
| 145 | | | | | 150 | | | | | 155 | | | | | 160 |
| Gly | Val | Ala | Phe | Ala | Val | Val | Gly | Ala | Cys | Gln | Ala | Leu | Gly | Leu | Arg |
| | | | | 165 | | | | | 170 | | | | | 175 | |
| Asp | Val | His | Leu | Ala | Leu | Ser | Glu | Asp | His | Ala | Trp | Val | Val | Phe | Gly |
| | | | 180 | | | | | 185 | | | | | 190 | | |
| Pro | Asn | Gly | Glu | Gln | Thr | Ala | Glu | Val | Thr | Trp | His | Gly | Lys | Gly | Asn |
| | | | | 195 | | | | | 200 | | | | | 205 | |
| Glu | Asp | Arg | Arg | Gly | Gln | Thr | Val | Asn | Ala | Gly | Val | Ala | Glu | Arg | Ser |
| | | 210 | | | | | 215 | | | | | 220 | | | |
| Trp | Leu | Tyr | Leu | Lys | Gly | Ser | Tyr | Met | Arg | Cys | Asp | Arg | Lys | Met | Glu |
| 225 | | | | | 230 | | | | | 235 | | | | | 240 |
| Val | Ala | Phe | Met | Val | Cys | Ala | Ile | Asn | Pro | Ser | Ile | Asp | Leu | His | Thr |
| | | | | 245 | | | | | 250 | | | | | 255 | |
| Asp | Ser | Leu | Glu | Leu | Leu | Gln | Leu | Gln | Gln | Lys | Leu | Leu | Trp | Leu | Leu |
| | | | 260 | | | | | 265 | | | | | 270 | | |
| Tyr | Asp | Leu | Gly | His | Leu | Glu | Arg | Tyr | Pro | Met | Ala | Leu | Gly | Asn | Leu |
| | | | | 275 | | | | | 280 | | | | | 285 | |
| Ala | Asp | Leu | Glu | Glu | Leu | Glu | Pro | Thr | Pro | Gly | Arg | Pro | Asp | Pro | Leu |
| | | 290 | | | | | 295 | | | | | 300 | | | |
| Thr | Leu | Tyr | His | Lys | Gly | Ile | Ala | Ser | Ala | Lys | Thr | Tyr | Tyr | Arg | Asp |
| 305 | | | | | 310 | | | | | 315 | | | | | 320 |
| Glu | His | Ile | Tyr | Pro | Tyr | Met | Tyr | Leu | Ala | Gly | Tyr | His | Cys | Arg | Asn |
| | | | | 325 | | | | | 330 | | | | | 335 | |
| Arg | Asn | Val | Arg | Glu | Ala | Leu | Gln | Ala | Trp | Ala | Asp | Thr | Ala | Thr | Val |
| | | | 340 | | | | | 345 | | | | | 350 | | |
| Ile | Gln | Asp | Tyr | Asn | Tyr | Cys | Arg | Glu | Asp | Glu | Ile | Tyr | Lys | Glu |
| | | | | 355 | | | | | 360 | | | | | 365 |

```
Phe Phe Glu Val Ala Asn Asp Val Ile Pro Asn Leu Leu Lys Glu Ala
    370                 375                 380

Ala Ser Leu Leu Glu Ala Gly Glu Arg Pro Gly Glu Gln Ser Gln
385                 390                 395                 400

Gly Thr Gln Ser Gln Gly Ser Ala Leu Gln Asp Pro Glu Cys Phe Ala
                405                 410                 415

His Leu Leu Arg Phe Tyr Asp Gly Ile Cys Lys Trp Glu Glu Gly Ser
            420                 425                 430

Pro Thr Pro Val Leu His Val Gly Trp Ala Thr Phe Leu Val Gln Ser
            435                 440                 445

Leu Gly Arg Phe Glu Gly Gln Val Arg Gln Lys Val Arg Ile Val Ser
450                 455                 460

Arg Glu Ala Glu Ala Ala Glu Ala Glu Pro Trp Gly Glu Ala
465                 470                 475                 480

Arg Glu Gly Arg Arg Gly Pro Arg Glu Ser Lys Pro Glu Glu
                485                 490                 495

Pro Pro Pro Pro Lys Lys Pro Ala Leu Asp Lys Gly Leu Gly Thr Gly
                500                 505                 510

Gln Gly Ala Val Ser Gly Pro Pro Arg Lys Pro Pro Gly Thr Val Ala
            515                 520                 525

Gly Thr Ala Arg Gly Pro Glu Gly Gly Ser Thr Ala Gln Val Pro Ala
530                 535                 540

Pro Thr Ala Ser Pro Pro Glu Gly Pro Val Leu Thr Phe Gln Ser
545                 550                 555                 560

Glu Lys Met Lys Gly Met Lys Glu Leu Leu Val Ala Thr Lys Ile Asn
                565                 570                 575

Ser Ser Ala Ile Lys Leu Gln Leu Thr Ala Gln Ser Gln Val Gln Met
            580                 585                 590

Lys Lys Gln Lys Val Ser Thr Pro Ser Asp Tyr Thr Leu Ser Phe Leu
        595                 600                 605

Lys Arg Gln Arg Lys Gly Leu
610                 615

<210> SEQ ID NO 2
<211> LENGTH: 610
<212> TYPE: PRT
<213> ORGANISM: Homo sapiens

<400> SEQUENCE: 2

Met Gly Leu Lys Ala Ala Gln Lys Thr Leu Phe Pro Leu Arg Ser Ile
1               5                   10                  15

Asp Asp Val Val Arg Leu Phe Ala Ala Glu Leu Gly Arg Glu Glu Pro
                20                  25                  30

Asp Leu Val Leu Leu Ser Leu Val Leu Gly Phe Val Glu His Phe Leu
            35                  40                  45

Ala Val Asn Arg Val Ile Pro Thr Asn Val Pro Glu Leu Thr Phe Gln
        50                  55                  60

Pro Ser Pro Ala Pro Asp Pro Pro Gly Gly Leu Thr Tyr Phe Pro Val
65                  70                  75                  80

Ala Asp Leu Ser Ile Ile Ala Ala Leu Tyr Ala Arg Phe Thr Ala Gln
                85                  90                  95

Ile Arg Gly Ala Val Asp Leu Ser Leu Tyr Pro Arg Glu Gly Gly Val
            100                 105                 110

Ser Ser Arg Glu Leu Val Lys Lys Val Ser Asp Val Ile Trp Asn Ser
        115                 120                 125
```

```
Leu Ser Arg Ser Tyr Phe Lys Asp Arg Ala His Ile Gln Ser Leu Phe
130                 135                 140

Ser Phe Ile Thr Gly Thr Lys Leu Asp Ser Ser Gly Val Ala Phe Ala
145                 150                 155                 160

Val Val Gly Ala Cys Gln Ala Leu Gly Leu Arg Asp Val His Leu Ala
                165                 170                 175

Leu Ser Glu Asp His Ala Trp Val Val Phe Gly Pro Asn Gly Glu Gln
            180                 185                 190

Thr Ala Glu Val Thr Trp His Gly Lys Gly Asn Glu Asp Arg Arg Gly
        195                 200                 205

Gln Thr Val Asn Ala Gly Val Ala Glu Arg Ser Trp Leu Tyr Leu Lys
210                 215                 220

Gly Ser Tyr Met Arg Cys Asp Arg Lys Met Glu Val Ala Phe Met Val
225                 230                 235                 240

Cys Ala Ile Asn Pro Ser Ile Asp Leu His Thr Asp Ser Leu Glu Leu
                245                 250                 255

Leu Gln Leu Gln Gln Lys Leu Leu Trp Leu Leu Tyr Asp Leu Gly His
            260                 265                 270

Leu Glu Arg Tyr Pro Met Ala Leu Gly Asn Leu Ala Asp Leu Glu Glu
        275                 280                 285

Leu Glu Pro Thr Pro Gly Arg Pro Asp Pro Leu Thr Leu Tyr His Lys
290                 295                 300

Gly Ile Ala Ser Ala Lys Thr Tyr Tyr Arg Asp Glu His Ile Tyr Pro
305                 310                 315                 320

Tyr Met Tyr Leu Ala Gly Tyr His Cys Arg Asn Arg Asn Val Arg Glu
                325                 330                 335

Ala Leu Gln Ala Trp Ala Asp Thr Ala Thr Val Ile Gln Asp Tyr Asn
            340                 345                 350

Tyr Cys Arg Glu Asp Glu Glu Ile Tyr Lys Glu Phe Phe Glu Val Ala
        355                 360                 365

Asn Asp Val Ile Pro Asn Leu Leu Lys Glu Ala Ala Ser Leu Leu Glu
370                 375                 380

Ala Gly Glu Glu Arg Pro Gly Glu Gln Ser Gln Gly Thr Gln Ser Gln
385                 390                 395                 400

Gly Ser Ala Leu Gln Asp Pro Glu Cys Phe Ala His Leu Leu Arg Phe
                405                 410                 415

Tyr Asp Gly Ile Cys Lys Trp Glu Glu Gly Ser Pro Thr Pro Val Leu
            420                 425                 430

His Val Gly Trp Ala Thr Phe Leu Val Gln Ser Leu Gly Arg Phe Glu
        435                 440                 445

Gly Gln Val Arg Gln Lys Val Arg Ile Val Ser Arg Glu Ala Glu Ala
450                 455                 460

Ala Glu Ala Glu Glu Pro Trp Gly Glu Glu Ala Arg Glu Gly Arg Arg
465                 470                 475                 480

Arg Gly Pro Arg Arg Glu Ser Lys Pro Glu Glu Pro Pro Pro Pro Lys
                485                 490                 495

Lys Pro Ala Leu Asp Lys Gly Leu Gly Thr Gly Gln Gly Ala Val Ser
            500                 505                 510

Gly Pro Pro Arg Lys Pro Pro Gly Thr Val Ala Gly Thr Ala Arg Gly
        515                 520                 525

Pro Glu Gly Gly Ser Thr Ala Gln Val Pro Ala Pro Thr Ala Ser Pro
530                 535                 540
```

```
Pro Pro Glu Gly Pro Val Leu Thr Phe Gln Ser Glu Lys Met Lys Gly
545                 550                 555                 560

Met Lys Glu Leu Leu Val Ala Thr Lys Ile Asn Ser Ser Ala Ile Lys
                565                 570                 575

Leu Gln Leu Thr Ala Gln Ser Gln Val Gln Met Lys Lys Gln Lys Val
            580                 585                 590

Ser Thr Pro Ser Asp Tyr Thr Leu Ser Phe Leu Lys Arg Gln Arg Lys
        595                 600                 605

Gly Leu
    610

<210> SEQ ID NO 3
<211> LENGTH: 575
<212> TYPE: PRT
<213> ORGANISM: Homo sapiens

<400> SEQUENCE: 3

Met Gly Leu Lys Ala Ala Gln Lys Thr Leu Phe Pro Leu Arg Ser Ile
1               5                   10                  15

Asp Asp Val Val Arg Leu Phe Ala Ala Glu Leu Gly Arg Glu Glu Pro
            20                  25                  30

Asp Leu Val Leu Leu Ser Leu Val Leu Gly Phe Val Glu His Phe Leu
        35                  40                  45

Ala Val Asn Arg Val Ile Pro Thr Asn Val Pro Glu Leu Thr Phe Gln
    50                  55                  60

Pro Ser Pro Ala Pro Asp Pro Gly Gly Leu Thr Tyr Phe Pro Val
65                  70                  75                  80

Ala Asp Leu Ser Ile Ile Ala Ala Leu Tyr Ala Arg Phe Thr Ala Gln
                85                  90                  95

Ile Arg Gly Ala Val Asp Leu Ser Leu Tyr Pro Arg Glu Gly Gly Val
            100                 105                 110

Ser Ser Arg Glu Leu Val Lys Lys Val Ser Asp Val Ile Trp Asn Ser
        115                 120                 125

Leu Ser Arg Ser Tyr Phe Lys Asp Arg Ala His Ile Gln Ser Leu Phe
130                 135                 140

Ser Phe Ile Thr Gly Thr Lys Leu Asp Ser Ser Gly Val Ala Phe Ala
145                 150                 155                 160

Val Val Gly Ala Cys Gln Ala Leu Gly Leu Arg Asp Val His Leu Ala
                165                 170                 175

Leu Ser Glu Asp His Ala Trp Ser Trp Leu Tyr Leu Lys Gly Ser Tyr
            180                 185                 190

Met Arg Cys Asp Arg Lys Met Glu Val Ala Phe Met Val Cys Ala Ile
        195                 200                 205

Asn Pro Ser Ile Asp Leu His Thr Asp Ser Leu Glu Leu Leu Gln Leu
210                 215                 220

Gln Gln Lys Leu Leu Trp Leu Leu Tyr Asp Leu Gly His Leu Glu Arg
225                 230                 235                 240

Tyr Pro Met Ala Leu Gly Asn Leu Ala Asp Leu Glu Glu Leu Glu Pro
                245                 250                 255

Thr Pro Gly Arg Pro Asp Pro Leu Thr Leu Tyr His Lys Gly Ile Ala
            260                 265                 270

Ser Ala Lys Thr Tyr Tyr Arg Asp Glu His Ile Tyr Pro Tyr Met Tyr
        275                 280                 285

Leu Ala Gly Tyr His Cys Arg Asn Arg Asn Val Arg Glu Ala Leu Gln
290                 295                 300
```

-continued

```
Ala Trp Ala Asp Thr Ala Thr Val Ile Gln Asp Tyr Asn Tyr Cys Arg
305             310             315             320

Glu Asp Glu Glu Ile Tyr Lys Glu Phe Phe Glu Val Ala Asn Asp Val
            325             330             335

Ile Pro Asn Leu Leu Lys Glu Ala Ala Ser Leu Leu Glu Ala Gly Glu
            340             345             350

Glu Arg Pro Gly Glu Gln Ser Gln Gly Thr Gln Ser Gln Gly Ser Ala
            355             360             365

Leu Gln Asp Pro Glu Cys Phe Ala His Leu Leu Arg Phe Tyr Asp Gly
            370             375             380

Ile Cys Lys Trp Glu Glu Gly Ser Pro Thr Pro Val Leu His Val Gly
385             390             395             400

Trp Ala Thr Phe Leu Val Gln Ser Leu Gly Arg Phe Glu Gly Gln Val
            405             410             415

Arg Gln Lys Val Arg Ile Val Ser Arg Glu Ala Glu Ala Ala Glu Ala
            420             425             430

Glu Glu Pro Trp Gly Glu Glu Ala Arg Glu Gly Arg Arg Arg Gly Pro
            435             440             445

Arg Arg Glu Ser Lys Pro Glu Glu Pro Pro Pro Lys Lys Pro Ala
450             455             460

Leu Asp Lys Gly Leu Gly Thr Gly Gln Gly Ala Val Ser Gly Pro Pro
465             470             475             480

Arg Lys Pro Pro Gly Thr Val Ala Gly Thr Ala Arg Gly Pro Glu Gly
            485             490             495

Gly Ser Thr Ala Gln Val Pro Ala Pro Thr Ala Ser Pro Pro Pro Glu
            500             505             510

Gly Pro Val Leu Thr Phe Gln Ser Glu Lys Met Lys Gly Met Lys Glu
            515             520             525

Leu Leu Val Ala Thr Lys Ile Asn Ser Ser Ala Ile Lys Leu Gln Leu
530             535             540

Thr Ala Gln Ser Gln Val Gln Met Lys Lys Gln Lys Val Ser Thr Pro
545             550             555             560

Ser Asp Tyr Thr Leu Ser Phe Leu Lys Arg Gln Arg Lys Gly Leu
            565             570             575
```